(12) United States Patent
Wein et al.

(10) Patent No.: US 11,241,435 B2
(45) Date of Patent: Feb. 8, 2022

(54) USES OF SALT-INDUCIBLE KINASE (SIK) INHIBITORS FOR TREATING OSTEOPOROSIS

(71) Applicants: The General Hospital Corporation, Boston, MA (US); The Broad Institute, Inc., Cambridge, MA (US); Dana-Farber Cancer Institute, Inc., Boston, MA (US)

(72) Inventors: Marc Wein, Boston, MA (US); Henry Kronenberg, Boston, MA (US); Thomas Sundberg, Boston, MA (US); Ramnik Xavier, Brookline, MA (US); Nathanael S. Gray, Stanford, CA (US); Yanke Liang, Belmont, MA (US); Hwan Geun Choi, Chestnut Hill, MA (US); Alykhan Shamji, Somerville, MA (US)

(73) Assignees: The General Hospital Corporation, Boston, MA (US); The Broad Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 120 days.

(21) Appl. No.: 16/333,546

(22) PCT Filed: Sep. 16, 2017

(86) PCT No.: PCT/US2017/051937
§ 371 (c)(1),
(2) Date: Mar. 14, 2019

(87) PCT Pub. No.: WO2018/053373
PCT Pub. Date: Mar. 22, 2018

(65) Prior Publication Data
US 2020/0179387 A1    Jun. 11, 2020

Related U.S. Application Data

(60) Provisional application No. 62/396,089, filed on Sep. 16, 2016.

(51) Int. Cl.
*A61K 31/519* (2006.01)
*A61P 19/10* (2006.01)

(52) U.S. Cl.
CPC ............ *A61K 31/519* (2013.01); *A61P 19/10* (2018.01)

(58) Field of Classification Search
CPC .... A61K 31/519; A61K 31/5377; A61P 19/10
See application file for complete search history.

(56) References Cited

U.S. PATENT DOCUMENTS 6,150,373 A    11/2000    Harris et al.
6,217,875 B1    4/2001    Murai et al.
(Continued)

FOREIGN PATENT DOCUMENTS

CN    104 482 860 A    4/2015
EP    1 544 295 A1    6/2005
(Continued)

OTHER PUBLICATIONS

Extended European Search Report for EP 18760857.5, dated Nov. 12, 2020.
(Continued)

*Primary Examiner* — San Ming R Hui
(74) *Attorney, Agent, or Firm* — Wolf, Greenfield & Sacks, P.C.

(57) ABSTRACT

The present disclosure provides methods of treating and/or preventing osteoporosis using salt-inducible kinase (SIK) inhibitors. Also provided are methods of using SIK inhibitors for increasing the function of osteocytes, increasing the (Continued)

number of osteoblasts, increasing the activity of osteoblasts, inhibiting the resorption of a bone, decreasing the number of osteoclasts, inhibiting the activity of osteoclasts, increasing the mass of a bone, down-regulating the expression of the gene SOST, and/or inhibiting the activity of sclerostin. The SIK inhibitors may be combined with Src inhibitors or CSF I R inhibitors. Exemplary SIK inhibitors include the compounds of the formula: (I), (II), (III), (IV), (V) or (VI).

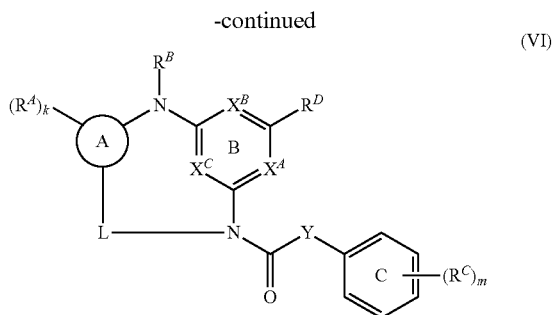

27 Claims, 70 Drawing Sheets

(56) References Cited

U.S. PATENT DOCUMENTS

| | | | |
|---|---|---|---|
| 6,451,804 B1 * | 9/2002 | Dunn | A61P 13/12 514/262.1 |
| 7,084,270 B2 | 8/2006 | Chen et al. | |
| 7,112,676 B2 | 9/2006 | Dermatakis et al. | |
| 7,312,225 B2 | 12/2007 | Luecking et al. | |
| 8,921,336 B2 | 12/2014 | Gray et al. | |
| 9,586,936 B2 | 3/2017 | Sim et al. | |
| 9,663,524 B2 | 5/2017 | Barrague et al. | |
| 9,670,165 B2 | 6/2017 | Cohen et al. | |
| 9,783,504 B2 | 10/2017 | Gray et al. | |
| 9,925,188 B2 | 3/2018 | Charifson et al. | |
| 10,233,157 B2 | 3/2019 | Cohen et al. | |
| 10,265,321 B2 | 4/2019 | Shamji et al. | |
| 10,287,268 B2 | 5/2019 | Gray et al. | |
| 10,457,691 B2 | 10/2019 | Gray et al. | |
| 10,954,242 B2 | 3/2021 | Gray et al. | |
| 10,975,058 B2 | 4/2021 | Gray et al. | |
| 2004/0204427 A1 | 10/2004 | Chen et al. | |
| 2005/0026914 A1 | 2/2005 | Buchanan et al. | |
| 2005/0202001 A1 | 9/2005 | Shen et al. | |
| 2006/0258687 A1 | 11/2006 | Boehm et al. | |
| 2007/0225286 A1 | 9/2007 | Ren et al. | |
| 2008/0221098 A1 | 9/2008 | You et al. | |
| 2008/0249079 A1 | 10/2008 | Chen et al. | |
| 2009/0137804 A1 | 5/2009 | Ding et al. | |
| 2010/0056524 A1 | 3/2010 | McIver et al. | |
| 2011/0086858 A1 | 4/2011 | Wang et al. | |
| 2011/0207711 A1 | 8/2011 | Katz et al. | |
| 2017/0204082 A1 | 7/2017 | Gray et al. | |
| 2017/0204116 A1 | 7/2017 | Gray et al. | |
| 2017/0224700 A1 | 8/2017 | Shamji et al. | |
| 2017/0342036 A1 | 11/2017 | Cohen et al. | |
| 2018/0221379 A1 | 8/2018 | Shamji et al. | |
| 2019/0315752 A1 | 10/2019 | Gray et al. | |
| 2019/0343842 A1 | 11/2019 | Shamji et al. | |
| 2019/0367487 A1 | 12/2019 | Gray et al. | |
| 2020/0253981 A1 | 8/2020 | Fisher et al. | |
| 2020/0317675 A9 | 10/2020 | Gray et al. | |
| 2021/0147425 A1 | 5/2021 | Gray et al. | |

FOREIGN PATENT DOCUMENTS

EP 2 746 283 A1 6/2014
WO WO 2000/024744 A1 5/2000

(56) References Cited

FOREIGN PATENT DOCUMENTS

| WO | WO 2004/041821 A1 | 5/2004 |
|---|---|---|
| WO | WO 2004/041822 A1 | 5/2004 |
| WO | WO 2004/048343 A1 | 6/2004 |
| WO | WO 2005/009443 A1 | 2/2005 |
| WO | WO 2005/009978 A1 | 2/2005 |
| WO | WO 2005/011597 A2 | 2/2005 |
| WO | WO 2005/123719 A1 | 12/2005 |
| WO | WO 2006/000420 A1 | 1/2006 |
| WO | WO 2006/024545 A1 | 3/2006 |
| WO | WO 2007/071752 A2 | 6/2007 |
| WO | WO 2007/136465 A2 | 11/2007 |
| WO | WO 2008/060248 A1 | 5/2008 |
| WO | WO 2009/073153 A2 | 6/2009 |
| WO | WO 2009/122180 A1 | 10/2009 |
| WO | WO 2009/152027 A1 | 12/2009 |
| WO | WO 2013/045653 A1 | 4/2013 |
| WO | WO 2013/074986 A1 | 5/2013 |
| WO | WO 2013/136070 A1 | 9/2013 |
| WO | WO 2014/093383 A1 | 6/2014 |
| WO | WO 2014/140313 A1 | 9/2014 |
| WO | WO 2014/144737 A1 | 9/2014 |
| WO | WO 2015/006492 A1 | 1/2015 |
| WO | WO 2016/014542 A1 | 1/2016 |
| WO | WO 2016/014551 A1 | 1/2016 |
| WO | WO 2016/023014 A2 | 2/2016 |
| WO | WO 2018/009544 A1 | 1/2018 |

OTHER PUBLICATIONS

U.S. Appl. No. 16/953,984, filed Nov. 20, 2020, Gray et al.
EP 18760857.5, Nov. 12, 2020, Extended European Search Report.
U.S. Appl. No. 15/327,690, filed Jan. 20, 2017, Gray et al.
U.S. Appl. No. 15/327,705, filed Jan. 20, 2017, Gray et al.
U.S. Appl. No. 15/502,287, filed Feb. 7, 2017, Shamji et al.
U.S. Appl. No. 15/847,856, filed Dec. 19, 2017, Shamji et al.
U.S. Appl. No. 14/385,077, filed Sep. 12, 2014, Cohen et al.
U.S. Appl. No. 15/606,970, filed May 26, 2017, Cohen et al.
U.S. Appl. No. 16/489,462, filed Aug. 28, 2019, Fisher et al.
PCT/US2017/040722, Oct. 18, 2017, Invitation to Pay Additional Fees.
PCT/US2017/040722, Dec. 12, 2017, International Search Report and Written Opinion.
PCT/US2017/040722, Jan. 17, 2019, International Preliminary Report on Patentability.
EP 15824907.8, Jan. 2, 2018, Extended European Search Report.
PCT/US2015/041360, Sep. 24, 2015, Invitation to Pay Additional Fees.
PCT/US2015/041360, Dec. 15, 2015, International Search Report and Written Opinion.
PCT/US2015/041360, Feb. 2, 2017, International Preliminary Report on Patentability.
EP 15824975.5, Nov. 27, 2017, Extended European Search Report.
PCT/US2015/41348, Oct. 28, 2015, International Search Report and Written Opinion.
PCT/US2015/41348, Feb. 2, 2017, International Preliminary Report on Patentability.
EP 15829427.2, Feb. 8, 2018, Partial Supplementary European Search Report.
EP 15829427.2, May 14, 2018, Extended European Search Report.
EP 19164054.9, Jul. 31, 2019, Extended European Search Report.
PCT/US2015/04438, Jan. 28, 2016, Invitation to Pay Additional Fees.
PCT/US2015/04438, Mar. 25, 2016, International Search Report and Written Opinion.
PCT/US2015/04438, Feb. 23, 2017, International Preliminary Report on Patentability.
PCT/GB2013/050618, May 17, 2013, International Search Report and Written Opinion.
PCT/GB2013/050618, Sep. 25, 2014, International Preliminary Report on Patentability.
PCT/US2018/020335, May 17, 2018, International Search Report and Written Opinion.
PCT/US2018/020335, Sep. 12, 2019, International Preliminary Report on Patentability.
PCT/US2017/051937, Dec. 28, 2017, International Search Report and Written Opinion.
PCT/US2017/051937, Mar. 28, 2019, International Preliminary Report on Patentability.
Extended European Search Report for EP 15824907.8, dated Jan. 2, 2018.
Invitation to Pay Additional Fees for PCT/US2015/041360 dated Sep. 24, 2015.
International Search Report and Written Opinion for PCT/US2015/041360 dated Dec. 15, 2015.
International Preliminary Report on Patentability for PCT/US2015/041360 dated Feb. 2, 2017.
Extended European Search Report for EP 15824975.5, dated Nov. 27, 2017.
International Search Report and Written Opinion for PCT/US2015/41348 dated Oct. 28, 2015.
International Preliminary Report on Patentability for PCT/US2015/41348 dated Feb. 2, 2017.
Partial Supplementary European Search Report for EP 15829427.2, dated Feb. 8, 2018.
Extended European Search Report for EP 15829427.2, dated May 15, 2018.
Invitation to Pay Additional Fees for PCT/US2015/044387, dated Jan. 28, 2016.
International Search Report and Written Opinion for PCT/US2015/044387, dated Mar. 25, 2016.
International Preliminary Report on Patentability for PCT/US2015/044387, dated Feb. 23, 2017.
International Preliminary Report on Patentability for PCT/GB2013/050618, dated Sep. 25, 2014.
International Search Report and Written Opinion for PCT/GB2013/050618, dated May 17, 2013.
Invitation to Pay Additional Fees for PCT/US2017/040722, dated Oct. 18, 2017.
International Search Report and Written Opinion for PCT/US2017/040722, dated Dec. 12, 2017.
International Preliminary Report on Patentability for PCT/US2017/040722, dated Jan. 17, 2019.
International Search Report and Written Opinion for PCT/US2018/020335, dated May 17, 2018.
Extended European Search Report for EP 19164054.9, dated July 31, 2019.
International Preliminary Report on Patentability for PCT/US2018/020335, dated Sep. 12, 2019.
International Search Report and Written Opinion for PCT/US2017/051937, dated Dec. 28, 2017.
International Preliminary Report on Patentability for PCT/US2017/051937, dated Mar. 28, 2019.
Altarejos et al., CREB and the CRTC co-activators: sensors for hormonal and metabolic signals. Nat Rev Mol Cell Biol. Mar. 2011;12(3):141-51. doi: 10.1038/nrm3072.
Ananieva et al., The kinases MSK1 and MSK2 act as negative regulators of Toll-like receptor signaling. Nat Immunol. Sep. 2008;9(9):1028-36. doi: 10.1038/ni.1644.
Antiga et al., Serum levels of the regulatory cytokines transforming growth factor-β and interleukin-10 are reduced in patients with discoid lupus erythematosus. Lupus. May 2011;20(6):556-60. doi: 10.1177/0961203310392424. Epub Mar. 3, 2011.
Armstrong et al., The epidemiology of UV induced skin cancer. J Photochem Photobiol B. Oct. 2001;63(1-3):8-18.
Baertschi et al., Class I and IIa histone deacetylases have opposite effects on sclerostin gene regulation. J Biol Chem. Sep. 5, 2014;289(36):24995-5009. doi: 10.1074/jbc.M114.564997. Epub Jul. 10, 2014.
Bain et al., The selectivity of protein kinase inhibitors: a further update. Biochem J. Dec. 15, 2007;408(3):297-315.
Baron et al., WNT signaling in bone homeostasis and disease: from human mutations to treatments. Nat Med. Feb. 2013;19(2):179-92. doi: 10.1038/nm.3074. Epub Feb. 6, 2013.

(56) References Cited

OTHER PUBLICATIONS

Benoit et al., Macrophage polarization in bacterial infections. J Immunol. Sep. 15, 2008;181(6):3733-9.

Berdesux et al., SIK1 is a class II HDAC kinase that promotes survival of skeletal myocytes. Nat Med. May 2007;13(5):597-603. Epub Apr. 29, 2007.

Bergwitz et al., Regulation of phosphate homeostasis by PTH, vitamin D, and FGF23. Annu Rev Med. 2010;61:91-104. doi: 10.1146/annurev.med.051308.111339.

Bertolotto et al., Microphthalmia gene product as a signal transducer in cAMP-induced differentiation of melanocytes. J Cell Biol. Aug. 10, 1998;142(3):827-35.

Bettencourt-Dias et al., Genome-wide survey of protein kinases required for cell cycle progression. Nature. Dec. 23, 2004;432(7020):980-7.

Bonewald, The amazing osteocyte. J Bone Miner Res. Feb. 2011;26(2):229-38. doi: 10.1002/jbmr.320.

Bonnet et al., Regulation of beta catenin signaling and parathyroid hormone anabolic effects in bone by the matricellular protein periostin. Proc Natl Acad Sci U S A. Sep. 11, 2012;109(37):15048-53. doi: 10.1073/pnas.1203085109. Epub Aug. 27, 2012.

Bos et al., The 500 Dalton rule for the skin penetration of chemical compounds and drugs. Exp Dermatol. Jun. 2000;9(3):165-9.

Bouxsein et al., Guidelines for assessment of bone microstructure in rodents using micro-computed tomography. J Bone Miner Res. Jul. 2010;25(7):1468-86. doi: 10.1002/jbmr.141.

Chang et al., Histone deacetylases 5 and 9 govern responsiveness of the heart to a subset of stress signals and play redundant roles in heart development. Mol Cell Biol. Oct. 2004;24(19):8467-76.

Cheloha et al., PTH receptor-1 signalling-mechanistic insights and therapeutic prospects. Nat Rev Endocrinol. Dec. 2015;11(12):712-24. doi: 10.1038/nrendo.2015.139. Epub Aug. 25, 2015.

Clark et al., Novel cross-talk within the IKK family controls innate immunity. Biochem J. Feb. 15, 2011;434(1):93-104. doi: 10.1042/BJ20101701.

Clark et al., Phosphorylation of CRTC3 by the salt-inducible kinases controls the interconversion of classically activated and regulatory macrophages. Proc Natl Acad Sci U S A. Oct. 16, 2012;109(42):16986-91. doi: 10.1073/pnas.1215450109. Epub Oct. 2, 2012. With Supporting Information.

Clark et al., The TRAF-associated protein TANK facilitates crosstalk within the IkappaB kinase family during Toll-like receptor signaling. Proc Natl Acad Sci U S A. Oct. 11, 2011;108(41):17093-8. doi: 10.1073/pnas.1114194108. Epub Sep. 23, 2011.

Clark et al., Use of the pharmacological inhibitor BX795 to study the regulation and physiological roles of TBK1 and IkappaB kinase epsilon: a distinct upstream kinase mediates Ser-172 phosphorylation and activation. J Biol Chem. May 22, 2009;284(21):14136-46. doi: 10.1074/jbc.M109.000414. Epub Mar. 22, 2009.

Collette et al., Targeted deletion of Sost distal enhancer increases bone formation and bone mass. Proc Natl Acad Sci U S A. Aug. 28, 2012;109(35):14092-7. doi: 10.1073/pnas.1207188109. Epub Aug. 10, 2012.

Cui et al., Central role of p53 in the suntan response and pathologic hyperpigmentation. Cell. Mar. 9, 2007;128(5):853-64.

Cummings et al., Denosumab for prevention of fractures in postmenopausal women with osteoporosis. N Engl J Med. Aug. 20, 2009;361(8):756-65. doi: 10.1056/NEJMoa0809493. Epub Aug. 11, 2009.

Dempster et al., Standardized nomenclature, symbols, and units for bone histomorphometry: a 2012 update of the report of the ASBMR Histomorphometry Nomenclature Committee. J Bone Miner Res. Jan. 2013;28(1):2-17. doi: 10.1002/jbmr.1805.

Dentin et al., Insulin modulates gluconeogenesis by inhibition of the coactivator TORC2. Nature. Sep. 20, 2007;449(7160):366-9. Epub Sep. 5, 2007.

D'Orazto et al., Topical drug rescue strategy and skin protection based on the role of Mc1r in UV-induced tanning. Nature. Sep. 21, 2006;443(7109):340-4.

Ewald et al., Nucleic acid sensing Toll-like receptors in autoimmunity. Curr Opin Immunol. Feb. 2011;23(1):3-9. doi: 10.1016/j.coi.2010.11.006. Epub Dec. 14, 2010.

Eyers et al., Conversion of SB 203580-insensitive MAP kinase family members to drug-sensitive forms by a single amino-acid substitution. Chem Biol. Jun. 1998;5(6):321-8.

Fitzgerald et al., IKKepsilon and TBK1 are essential components of the IRF3 signaling pathway. Nat Immunol. May 2003;4(5):491-6.

Fleming et al., Regulatory macrophages: setting the threshold for therapy. Eur J Immunol. Sep. 2011;41(9):2498-502. doi: 10.1002/eji.201141717.

Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.

Fu et al., Parathyroid hormone controls receptor activator of NF-kappaB ligand gene expression via a distant transcriptional enhancer. Mol Cell Biol. Sep. 2006;26(17):6453-68.

Fu et al., Parathyroid hormone stimulates receptor activator of NFkappa B ligand and inhibits osteoprotegerin expression via protein kinase A activation of cAMP-response element-binding protein. J Biol Chem. Dec. 13, 2002;277(50):48868-75. Epub Oct. 2, 2002.

Fulzele et al., Myelopoiesis is regulated by osteocytes through Gsα-dependent signaling. Blood. Feb. 7, 2013;121(6):930-9. doi: 10.1182/blood-2012-06-437160. Epub Nov. 16, 2012.

Galli et al., Targeted deletion of a distant transcriptional enhancer of the receptor activator of nuclear factor-kappaB ligand gene reduces bone remodeling and increases bone mass. Endocrinology. Jan. 2008;149(1):146-53. Epub Oct. 11, 2007.

Garcia-Gomez et al., Dasatinib as a bone-modifying agent:anabolic and anti-resorptive effects. PLoS One. 2012;7(4):e34914. doi:10.1371/journal.pone.0034914. Epub Apr. 23, 2012.

Gendini et al., Meta-analysis of risk factors for cutaneous melanoma: III. Family history, actinic damage and phenotypic factors. Eur J Cancer. Sep. 2005;41(14):2040-59.

Ghoreschi et al., Janus kinases in immune cell signaling. Immunol Rev. Mar. 2009;228(1):273-87. doi: 10.1111/j.1600-065X.2008.00754.x.

Grozinger et al., Regulation of histone deacetylase 4 and 5 and transcriptional activity by 14-3-3-dependent cellular localization. Proc Natl Acad Sci U S A. Jul. 5, 2000;97(14):7835-40.

Haberland et al., Regulation of HDAC9 gene expression by MEF2 establishes a negative-feedback loop in the transcriptional circuitry of muscle differentiation. Mol Cell Biol. Jan. 2007;27(2):518-25. Epub Nov. 13, 2006.

Haberland et al., The many roles of histone deacetylases in development and physiology: implications for disease and therapy. Nat Rev Genet. Jan. 2009;10(1):32-42. doi: 10.1038/nrg2485.

Hadgraft et al., The selection and design of topical and transdermal agents: a review. J Investig Dermatol Symp Proc. Aug. 1998;3(2):131-5.

Hahn et al., Targeted therapies in systemic lupus erythematosus: successes, failures and future. Ann Rheum Dis. Mar. 2011;70 Suppl 1:i64-i66. doi: 10.1136/ard.2010.142208.

Harms et al., Mitigating photosensitivity of erythropoietic protoporphyria patients by an agonistic analog of alpha-melanocyte stimulating hormone. Photochem Photobiol. Nov.-Dec. 2009;85(6):1434-9. doi: 10.1111/j.1751-1097.2009.00595.x.

Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.

Hemmi et al., The roles of two IkappaB kinase-related kinases in lipopolysaccharide and double stranded RNA signaling and viral infection. J Exp Med. Jun. 21, 2004;199(12):1641-50.

Henriksson et al., SIK2 regulates CRTCs, HDAC4 and glucose uptake in adipocytes. J Cell Sci. Feb. 1, 2015;128(3):472-86.

Henriksson et al., The AMPK-related kinase SIK2 is regulated by cAMP via phosphorylation at Ser358 in adipocytes. Biochem J. Jun. 15, 2012;444(3):503-14. doi: 10.1042/BJ20111932.

(56) References Cited

OTHER PUBLICATIONS

Heppner et al., Immune attack: the role of inflammation in Alzheimer disease. Nat Rev Neurosci. Jun. 2015;16(6):358-72. doi: 10.1038/nrn3880.

Horike et al., Downregulation of SIK2 expression promotes the melanogenic program in mice. Pigment Cell Melanoma Res. Dec. 2010;23(6):809-19. doi: 10.1111/j.1755-148X.2010.00760.x. Epub Aug. 31, 2010.

Jansson et al., Glucose controls CREB activity in islet cells via regulated phosphorylation of TORC2. Proc Natl Acad Sci U S A. Jul. 22, 2008;105(29):10161-6. doi: 10.1073/pnas.0800796105. Epub Jul. 14, 2008.

Kantarjian et al., Dasatinib versus imatinib in newly diagnosed chronic-phase chronic myeloid leukemia. N Engl J Med. Jun. 17, 2010;362(24):2260-70.

Kawai et al., The role of pattern-recognition receptors in innate immunity: update on Toll-like receptors. Nat Immunol. May 2010;11(5):373-84. doi: 10.1038/ni.1863. Epub Apr. 20, 2010.

Keller et al., SOST is a target gene for PTH in bone. Bone. Aug. 2005;37(2):148-58.

Kennedy et al., The influence of painful sunburns and lifetime sun exposure on the risk of actinic keratoses, seborrheic warts, melanocytic nevi, atypical nevi, and skin cancer. J Invest Dermatol. Jun. 2003;120(6):1087-93.

Khaled et al., Control of melanocyte differentiation by a MITF-PDE4D3 homeostatic circuit. Genes Dev. Oct. 15, 2010;24(20):2276-81. doi: 10.1101/gad.1937710.

Kim et al., Activation of receptor activator of NF-kappaB ligand gene expression by 1,25-dihydroxyvitamin D3 is mediated through multiple long-range enhancers. Activation of receptor activator of NF-kappaB ligand gene expression by 1,25-dihydroxyvitamin D3 is mediated through multiple long-range enhancers. Mol Cell Biol. Sep. 2006;26(17):6469-86.

Kim et al., An essential role for histone deacetylase 4 in synaptic plasticity and memory formation. J Neurosci. Aug. 8, 2012;32(32):10879-86. doi: 10.1523/JNEUROSCI.2089-12.2012.

Kim et al., Transcriptional control of receptor activator of nuclear factor-kappaB ligand by the protein kinase A activator forskolin and the transmembrane glycoprotein 130-activating cytokine, oncostatin M, is exerted through multiple distal enhancers. Mol Endocrinol. Jan. 2007;21(1):197-214. Epub Oct. 19, 2006.

Kir et al., Tumour-derived PTH-related protein triggers adipose tissue browning and cancer cachexia. Nature. Sep. 4, 2014;513(7516):100-4. doi: 10.1038/nature13528. Epub Jul. 13, 2014.

Kobayashi et al., Supranuclear melanin caps reduce ultraviolet induced DNA photoproducts in human epidermis. J Invest Dermatol. May 1998;110(5):806-10.

Kopf et al., Averting inflammation by targeting the cytokine environment. Nat Rev Drug Discov. Sep. 2010;9(9):703-18. doi: 10.1038/nrd2805.

Kozhemyakina et al., Parathyroid hormone-related peptide represses chondrocyte hypertrophy through a protein phosphatase 2A/histone deacetylase 4/MEF2 pathway. Mol Cell Biol. Nov. 2009;29(21):5751-62. doi: 10.1128/MCB.00415-09. Epub Aug. 24, 2009.

Kramer et al., Mef2c deletion in osteocytes results in increased bone mass. J Bone Miner Res. Feb. 2012;27(2):360-73. doi: 10.1002/jbmr.1492.

Kramer et al., Parathyroid hormone (PTH)-induced bone gain is blunted in SOST overexpressing and deficient mice. J Bone Miner Res. Feb. 2010;25(2):178-89. doi: 10.1359/jbmr.090730.

Kronenberg et al., Developmental regulation of the growth plate. Nature. May 15, 2003;423(6937):332-6.

Kuhn et al., Interleukin-10-deficient mice develop chronic enterocolitis. Cell. Oct. 22, 1993;75(2):263-74.

Kumagai et al., A potent inhibitor of SIK2, 3, 3', 7-trihydroxy-4'-methoxyflavon (4'-O-methylfisetin), promotes melanogenesis in B16F10 melanoma cells. PLoS One. 2011;6(10):e26148. doi: 10.1371/journal.pone.0026148. Epub Oct. 13, 2011.

Kunisada et al., Murine cutaneous mastocytosis and epidermal melanocytosis induced by keratinocyte expression of transgenic stem cell factor. J Exp Med. May 18, 1998;187(10):1565-73.

Langendonk et al., Afamelanotide for Erythropoietic Protoporphyria. N Engl J Med. Jul. 2, 2015;373(1):48-59. doi: 10.1056/NEJMoa1411481.

Leupin et al., Control of the SOST bone enhancer by PTH using MEF2 transcription factors. J Bone Miner Res. Dec. 2007;22(12):1957-67.

Li et al., Lipoprotein receptor-related protein 6 is required for parathyroid hormone-induced Sost suppression. Ann N Y Acad Sci. Jan. 2016;1364:62-73. doi: 10.1111/nyas.12750. Epub Apr. 2, 2015.

Liu et al., Engineering Src family protein kinases with unnatural nucleotide specificity. Chem Biol. Feb. 1998;5(2):91-101.

Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.

Lizcano et al., LKB1 is a master kinase that activates 13 kinases of the AMPK subfamily, including MARK/PAR-1. EMBO J. Feb. 25, 2004;23(4):833-43. Epub Feb. 19, 2004.

Loots et al., Genomic deletion of a long-range bone enhancer misregulates sclerostin in Van Buchem disease. Genome Res. Jul. 2005;15(7):928-35. Epub Jun. 17, 2005.

Lu et al., DMP1-targeted Cre expression in odontoblasts and osteocytes. J Dent Res. Apr. 2007;86(4):320-5.

Maier et al., Development of N-4,6-pyrimidine-N-alkyl-N'-phenyl ureas as orally active inhibitors of lymphocyte specific tyrosine kinase. Bioorg Med Chem Lett. Jul. 15, 2006;16(14):3646-50. Epub May 8, 2006.

Mair et al., Lifespan extension induced by AMPK and calcineurin is mediated by CRTC-1 and CREB. Nature. Feb. 17, 2011;470(7334):404-8. doi: 10.1038/nature09706.

Mallison et al., Macrocycles in new drug discovery. Future Med Chem. Jul. 2012;4(11):1409-38. doi: 10.4155/fmc.12.93.

Manthey et al., JNJ-28312141, a novel orally active colony-stimulating factor-1 receptor/FMS-related receptor tyrosine kinase-3 receptor tyrosine kinase inhibitor with potential utility in solid tumors, bone metastases, and acute myeloid leukemia. Mol Cancer Ther. Nov. 2009;8(11):3151-61. doi:10.1158/1535-7163.MCT-09-0255. Epub Nov. 3, 2009.

Martin et al., Novel 2-aminopyrimidine carbamates as potent and orally active inhibitors of Lck: synthesis, SAR, and in vivo antiinflammatory activity. J Med Chem. Aug. 10, 2006;49(16):4981-91.

Martowicz et al., The mouse RANKL gene locus is defined by a broad pattern of histone H4 acetylation and regulated through distinct distal enhancers. J Cell Biochem. Aug. 2011;112(8):2030-45. doi: 10.1002/jcb.23123.

Mcclung et al., Romosozumab in postmenopausal women with low bone mineral density. N Engl J Med. Jan. 30, 2014;370(5):412-20. doi: 10.1056/NEJMoa1305224. Epub Jan. 1, 2014.

Mckinsey et al., Signal-dependent nuclear export of a histone deacetylase regulates muscle differentiation. Nature. Nov. 2, 2000;408(6808):106-11.

Mcwhirter et al., IFN-regulatory factor 3-dependent gene expression is defective in Tbk1-deficient mouse embryonic fibroblasts. Proc Natl Acad Sci U S A. Jan. 6, 2004;101(1):233-8. Epub Dec. 16, 2003.

Mosser et al., Interleukin-10: new perspectives on an old cytokine. Immunol Rev. Dec. 2008;226:205-18. doi: 10.1111/j.1600-065X.2008.00706.x.

Nakashima et al., Evidence for osteocyte regulation of bone homeostasis through RANKL expression. Nat Med. Sep. 11, 2011;17(10):1231-4. doi: 10.1038/nm.2452.

Navarro et al., Phosphoproteomic analysis reveals an intrinsic pathway for the regulation of histone deacetylase 7 that controls the function of cytotoxic T lymphocytes. Nat Immunol. Apr. 2011;12(4):352-61. doi: 10.1038/ni.2008. Epub Mar. 13, 2011.

Newton et al., Activation of the cAMP pathway by variant human MC1R alleles expressed in HEK and in melanoma cells. Peptides. Oct. 2005;26(10):1818-24.

(56) References Cited

OTHER PUBLICATIONS

Oancea et al., TRPM1 forms ion channels associated with melanin content in melanocytes. Sci Signal. May 12, 2009;2(70):ra21. doi: 10.1126/scisignal.2000146.

Obri et al., HDAC4 integrates PTH and sympathetic signaling in osteoblasts. J Cell Biol. Jun. 23, 2014;205(6):771-80. doi: 10.1083/jcb.201403138. Epub Jun. 16, 2014.

O'Garra et al., Strategies for use of IL-10 or its antagonists in human disease. Immunol Rev. Jun. 2008;223:114-31. doi: 10.1111/j.1600-065X.2008.00635.x.

Onal et al., Deletion of the Distal Tnfsf11 RL-D2 Enhancer That Contributes to PTH-Mediated RANKL Expression in Osteoblast Lineage Cells Results in a High Bone Mass Phenotype in Mice. J Bone Miner Res. Feb. 2016;31(2):416-29. doi: 10.1002/jbmr.2698.

Pacifici et al., Role of T cells in the modulation of PTH action: physiological and clinical significance. Endocrine. Dec. 2013;44(3):576-82. doi: 10.1007/s12020-013-9960-8. Epub Jun. 2, 2013.

Park et al., A long-term time course of colorimetric evaluation of ultraviolet light-induced skin reactions. Clin Exp Dermatol. Jul. 1999;24(4):315-20.

Park et al., SIK2 is critical in the regulation of lipid homeostasis and adipogenesis in vivo. Diabetes. Nov. 2014;63(11):3659-73. doi: 10.2337/db13-1423. Epub Jun. 4, 2014.

Parra et al., Regulatory signal transduction pathways for class IIa histone deacetylases. Curr Opin Pharmacol. Aug. 2010;10(4):454-60. doi: 10.1016/j.coph.2010.04.004. Epub May 4, 2010.

Patel et al., The LKB1-salt-inducible kinase pathway functions as a key gluconeogenic suppressor in the liver. Nat Commun. Aug. 4, 2014;5:4535. doi: 10.1038/ncomms5535.

Pennello et al., Association of surface ultraviolet B radiation levels with melanoma and nonmelanoma skin cancer in United States blacks. Cancer Epidemiol Biomarkers Prev. Mar. 2000;9(3):291-7.

Perry et al., Differential requirement for TANK-binding kinase-1 in type I interferon responses to toll-like receptor activation and viral infection. J Exp Med. Jun. 21, 2004;199(12):1651-8.

Pethe et al., A chemical genetic screen in *Mycobacterium tuberculosis* identifies carbon-source-dependent growth inhibitors devoid of in vivo efficacy. Nature Communications 2010;1:57. doi:10.1038/ncomms1060.

Pfeifer et al., Mutations induced by ultraviolet light. Mutat Res. Apr. 1, 2005;571(1-2):19-31. Epub Jan. 20, 2005.

Popov et al., Lack of salt-inducible kinase 2 (SIK2) prevents the development of cardiac hypertrophy in response to chronic high-salt intake. PLoS One. Apr. 21, 2014;9(4):e95771. doi: 10.1371/journal.pone.0095771. eCollection 2014.

Price et al., alpha-Melanocyte-stimulating hormone signaling regulates expression of microphthalmia, a gene deficient in Waardenburg syndrome. J Biol Chem. Dec. 4, 1998;273(49):33042-7.

Rhee et al., PTH receptor signaling in osteocytes governs periosteal bone formation and intracortical remodeling. J Bone Miner Res. May 2011;26(5):1035-46. doi: 10.1002/jbmr.304.

Saidak et al., Low-dose PTH increases osteoblast activity via decreased Mef2c/Sost in senescent osteopenic mice. J Endocrinol. Oct. 2014;223(1):25-33. doi: 10.1530/JOE-14-0249. Epub Jul. 23, 2014.

Saini et al., Parathyroid hormone (PTH)/PTH-related peptide type 1 receptor (PPR) signaling in osteocytes regulates anabolic and catabolic skeletal responses to PTH. J Biol Chem. Jul. 12, 2013;288(28):20122-34. doi: 10.1074/jbc.M112.441360. Epub Jun. 2, 2013.

Sakamaki et al., Role of the SIK2-p35-PJA2 complex in pancreatic B-cell functional compensation. Nat Cell Biol. Mar. 2014;16(3):234-44. doi: 10.1038/ncb2919.

Santegoets et al., Toll-like receptors in rheumatic diseases: are we paying a high price for our defense against bugs? FEBS Lett. Dec. 1, 2011;585(23):3660-6. doi: 10.1016/j.febslet.2011.04.028. Epub Apr. 16, 2011.

Saraiva et al., The regulation of IL-10 production by immune cells. Nat Rev Immunol. Mar. 2010;10(3):170-81. doi: 10.1038/nri2711. Epub Feb. 15, 2010.

Sasagawa et al., SIK3 is essential for chondrocyte hypertrophy during skeletal development in mice. Development. Mar. 2012;139(6):1153-63. doi: 10.1242/dev.072652. Epub Feb. 8, 2012.

Sasaki et al., SIK2 is a key regulator for neuronal survival after ischemia via TORC1-CREB. Neuron. Jan. 13, 2011;69(1):106-19. doi: 10.1016/j.neuron.2010.12.004.

Screaton et al., The CREB coactivator TORC2 functions as a calcium- and cAMP-sensitive coincidence detector. Cell. Oct. 1, 2004;119(1):61-74.

Sharma et al., Triggering the interferon antiviral response through an IKK-related pathway. Science. May 16, 2003;300(5622):1148-51. Epub Apr. 17, 2003.

Shimizu et al., HDAC4 represses matrix metalloproteinase-13 transcription in osteoblastic cells, and parathyroid hormone controls this repression. J Biol Chem. Mar. 26, 2010;285(13):9616-26. doi: 10.1074/jbc.M109.094862. Epub Jan. 22, 2010.

Soriano et al., Targeted disruption of the c-src proto-oncogene leads to osteopetrosis in mice. Cell. Feb. 22, 1991;64(4):693-702.

Spatz et al., The Wnt Inhibitor Sclerostin Is Up-regulated by Mechanical Unloading in Osteocytes in Vitro. J Biol Chem. Jul. 3, 2015;290(27):16744-58. doi: 10.1074/jbc.M114.628313. Epub May 7, 2015.

St John et al., Analysis of SOST expression using large minigenes reveals the MEF2C binding site in the evolutionarily conserved region (ECR5) enhancer mediates forskolin, but not 1,25-dihydroxyvitamin D3 or TGFβ1 responsiveness. J Steroid Biochem Mol Biol. Nov. 2016;164:277-280. doi: 10.1016/j.jsbmb.2015.09.005. Epub Sep. 7, 2015.

Sundberg et al., Development of Chemical Probes for Investigation of Salt-Inducible Kinase Function in Vivo. ACS Chem Biol. Aug. 19, 2016;11(8):2105-11. doi: 10.1021/acschembio.6b00217. Epub Jun. 6, 2016.

Sundberg et al., Small-molecule screening identifies inhibition of salt-inducible kinases as a therapeutic strategy to enhance immunoregulatory functions of dendritic cells. Proc Natl Acad Sci U S A. Aug. 26, 2014;111(34):12468-73. doi: 10.1073/pnas.1412308111. Epub Aug. 11, 2014.

Takemori et al., Inactivation of HDAC5 by SIK1 in AICAR-treated C2C12 myoblasts. Endocr J. 2009;56(1):121-30. Epub Oct. 22, 2008.

Taniguchi et al., Histone deacetylase 5 limits cocaine reward through cAMP-induced nuclear import. Neuron. Jan. 12, 2012;73(1):108-20. doi: 10.1016/j.neuron.2011.10.032.

Tella et al., Prevention and treatment of postmenopausal osteoporosis. J Steroid Biochem Mol Biol. Jul. 2014;142:155-70. doi:10.1016/j.jsbmb.2013.09.008. Epub Oct. 29, 2013.

Triantafillidis et al., Current and emerging drugs for the treatment of inflammatory bowel disease. Drug Des Devel Ther. Apr. 6, 2011;5:185-210. doi: 10.2147/DDDT.S11290.

Tsai et al., Teriparatide and denosumab, alone or combined, in women with postmenopausal osteoporosis: the DATA study randomised trial. Lancet. Jul. 6, 2013;382(9886):50-6. doi: 10.1016/S0140-6736(13)60856-9. Epub May 15, 2013.

Tsatmalia et al., Skin POMC peptides. Their binding affinities and activation of the human MC1 receptor. Ann N Y Acad Sci. Oct. 20, 1999;885:466-9.

Tu et al., Sost downregulation and local Wnt signaling are required for the osteogenic response to mechanical loading. Bone. Jan. 2012;50(1):209-17. doi: 10.1016/j.bone.2011.10.025. Epub Oct. 30, 2011.

Valverde et al., Variants of the melanocyte-stimulating hormone receptor gene are associated with red hair and fair skin in humans. Nat Genet. Nov. 1995;11(3):328-30.

Wakamatsu et al., Advanced chemical methods in melanin determination. Pigment Cell Res. Jun. 2002;15(3):174-83.

Walkinshaw et al., The tumor suppressor kinase LKB1 activates the downstream kinases SIK2 and SIK3 to stimulate nuclear export of class IIa histone deacetylases. J Biol Chem. Mar. 29, 2013;288(13):9345-62. doi: 10.1074/jbc.M113.456996. Epub Feb. 7, 2013.

Wang et al. Cloning of a novel kinase (SIK) of the SNF1/AMPK family from high salt diet-treated rat adrenal. FEBS Lett. Jun. 18, 1999;453(1-2):135-9.

(56) References Cited

OTHER PUBLICATIONS

Wang et al., A hormone-dependent module regulating energy balance. Cell. May 13, 2011;145(4):596-606. doi: 10.1016/j.cell.2011.04.013.
Wein et al., HDAC5 controls MEF2C-driven sclerostin expression in osteocytes. J Bone Miner Res. Mar. 2015;30(3):400-11. doi: 10.1002/jbmr.2381.
Weir et al., Targeted overexpression of parathyroid hormone-related peptide in chondrocytes causes chondrodysplasia and delayed endochondral bone formation. Proc Natl Acad Sci U S A. Sep. 17, 1996;93(19):10240-5.
Wu et al., Cumulative ultraviolet radiation flux in adulthood and risk of incident skin cancers in women. Br J Cancer. Apr. 2, 2014;110(7):1855-61. doi: 10.1038/bjc.2014.43. Epub Mar. 4, 2014.
Wu et al., Exploring the selectivity of PI3Kα and mTOR inhibitors by 3D-QSAR, molecular dynamics simulations and MM/GBSA binding free energy decomposition. Med. Chem. Commun., 2013;4:1482-1496. DOI: 10.1039/C3MD00157A.
Wu et al., Gsα enhances commitment of mesenchymal progenitors to the osteoblast lineage but restrains osteoblast differentiation in mice. J Clin Invest. Sep. 2011;121(9):3492-504. doi: 10.1172/JCI46406. Epub Aug. 1, 2011.
Xiong et al., Matrix-embedded cells control osteoclast formation. Nat Med. Sep. 11, 2011;17(10):1235-41. doi: 10.1038/nm.2448.
Yahara et al., Pterosin B prevents chondrocyte hypertrophy and osteoarthritis in mice by inhibiting Sik3. Nat Commun. Mar. 24, 2016;7:10959. doi: 10.1038/ncomms10959.
Yang et al., CBP/p300-interacting protein CITED1 modulates parathyroid hormone regulation of osteoblastic differentiation. Endocrinology. Apr. 2008;149(4):1728-35. doi: 10.1210/en.2007-0826. Epub Jan. 10, 2008.
Yasumoto et al., Microphthalmia-associated transcription factor as a regulator for melanocyte-specific transcription of the human tyrosinase gene. Mol Cell Biol. Dec. 1994;14(12):8058-70.
CAPLUS Accession No. 2015:690395. 2 pages. Reynolds et al., N-Aryl-heteroarylamines as FGFR4 inhibitors and their Preparation.
CAPLUS Accession No. 2015:453874. 12 pages. Ding et al., Pyrimido-heterocyclic compounds as EGFR protease inhibitors and their preparation, pharmaceutical compositions and use in the treatment of cancer.
CAPLUS Accession No. 2015:76117. 2 pages. Gray et al., Preparation of functionalized pyrimidine compounds as kinase inhibitors for the treatment of proliferative diseases.
CAPLUS Accession No. 2014:1815213. 3 pages. Tan et al., Development of covalent inhibitors that can overcome resistance to first-generation FGFR kinase inhibitors.
CAPLUS Accession No. 2014:1753550. 1 page. Huang et al., DFG-out Mode of Inhibition by an Irreversible Type-1 Inhibitor Capable of Overcoming Gate-Keeper Mutations.
CAPLUS Accession No. 2014:1558688. 10 pages. D'Agostino et al., Preparation of heteroaryl compounds as inhibitors of protein kinases.
CAPLUS Accession No. 2013:1609048. 10 pages. Xu et al., Design, Synthesis, and Biological Evaluation of 2-Oxo-3,4-dihydropyrimido[4,5 d]pyrimidinyl Derivatives as New Irreversible Epidermal Growth Factor Receptor Inhibitors with Improved Pharmacokinetic Properties.
CAPLUS Accession No. 2013:82305. 2 pages. Zender et al., Pharmaceutical compositions comprising sorafenib in combination with MAPK14 inhibitors for the treatment and prevention of liver cancer.
CAPLUS Accession No. 2013:51064. 2 pages. Zender et al., Pharmaceutical compositions comprising sorafenib in combination with MAPK14 inhibitors for the treatment and prevention of liver cancer.
CAPLUS Accession No. 2012:1832180. 2 pages. Ding et al., Pyrimidopyrimidone derivatives as EGFR inhibitors and their preparation, pharmaceutical compositions and use in the treatment of cancers.
CAPLUS Accession No. 2012:1816780. 5 pages. Ding et al., Pyrimidopyrimidone derivatives as EGFR inhibitors and their preparation, pharmaceutical compositions and use in the treatment of cancers.
CAPLUS Accession No. 2012:1191791. 1 page. Wan et al., Discovery of novel Bruton's tyrosine kinase inhibitors using a hybrid protocol of virtual screening approaches based on SVM model, pharmacophore and molecular docking.
CAPLUS Accession No. 2012:235081. 3 pages. Chang et al., Design, Synthesis, and Biological Evaluation of Novel Conformationally Constrained Inhibitors Targeting Epidermal Growth Factor Receptor Threonine790® Methionine790 Mutant.
CAPLUS Accession No. 2011:391484. 1 page. Kuglstatter et al., Insights into the conformational flexibility of Bruton's tyrosine kinase from multiple ligand complex structures.
CAPLUS Accession No. 2007:1363959. 4 page. Ren et al., Preparation of pyrimidopyrimidinones and analogs as FGF receptor kinases inhibitors.
CAPLUS Accession No. 2006:333232. 17 pages. Engh et al., Preparation of amide derivatives of 3-phenyl-dihydropyrimido[4,5-d]pyrimidinones as antitumor agents.
CAPLUS Accession No. 2005:120672. 22 pages. Sim et al., Preparation of pyrimidopyrimidines as protein kinase inhibitors.
CAPLUS Accession No. 2004:412945. 5 pages. Luk et al., Preparation of pyrimido Src tyrosine kinase inhibitors as anti-proliferative agents for the treatment of cancer.
CAPLUS Accession No. 2000:291041. 11 pages. Harris et al., Preparation of pyrimidopyrimidinones as T-cell tyrosine kinase inhibitors.
CAPLUS Accession No. 1999:764041. 5 pages. Dobrusin et al., Preparation of oxopyrido- and -pyrimidopyrimidines as cellular proliferation inhibitors.
Mattox et al., Ed:KUBINYI, 3D QSAR in Drug Design: Theory Methods and Applications. 1994. 243-244.
Rodríguez-Spong et al., General principles of pharmaceutical solid polymorphism: a supramolecular perspective. Adv Drug Deliv Rev. Feb. 23, 2004;56(3):241-74. doi: 10.1016/j.addr.2003.10.005. PMID: 14962581.
Terfloth et al., Electronic Screening: Lead Finding from Databse Mining. Practice of Medicinal Chemistry. 2003. 131-157.

\* cited by examiner

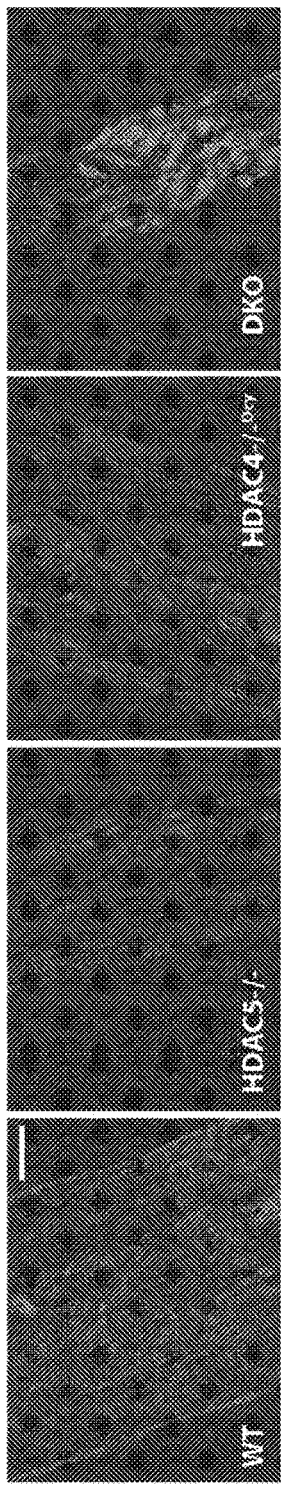
Figure 1D
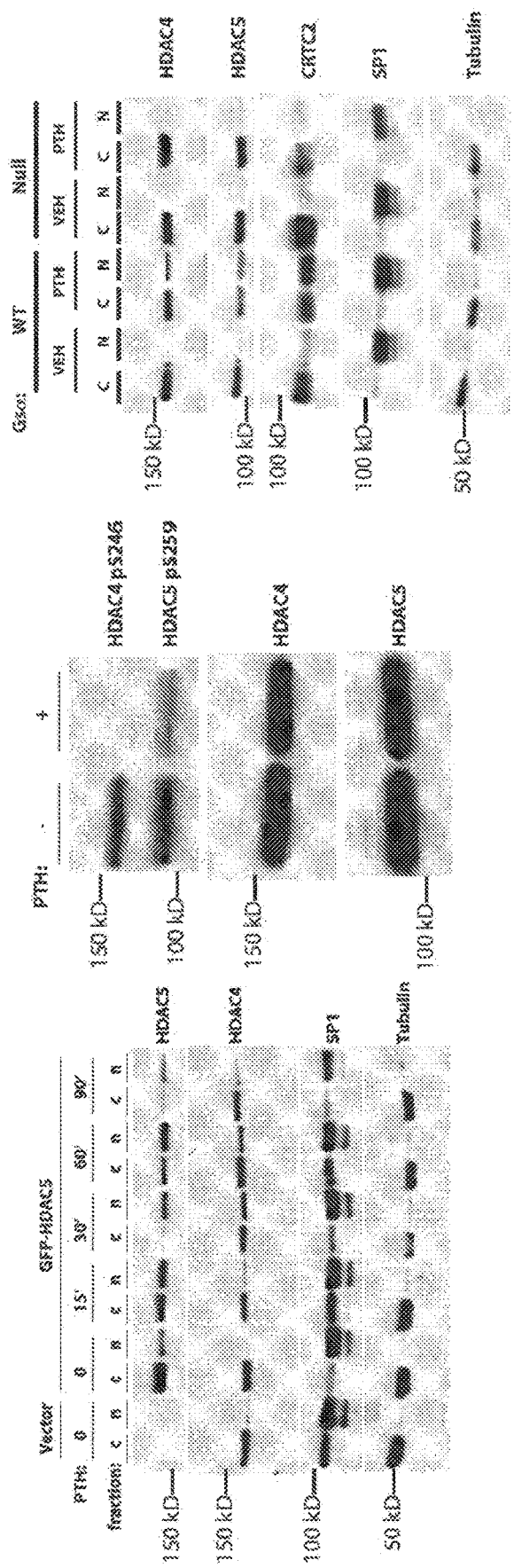
Figure 2C
Figure 2B
Figure 2A

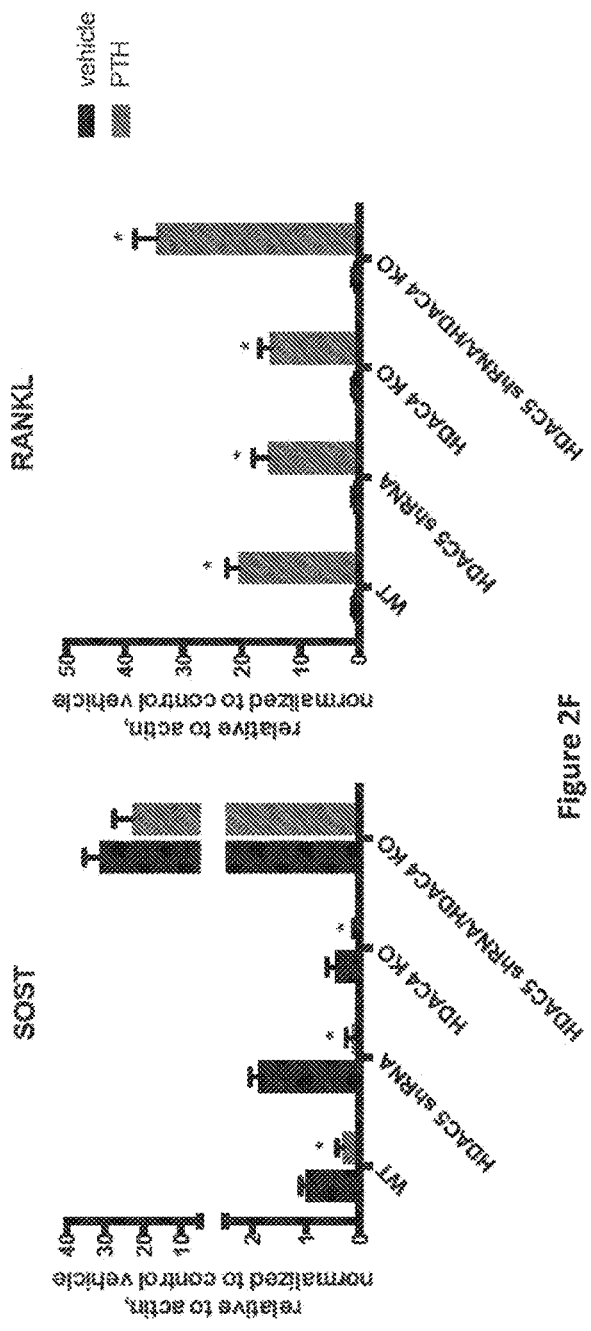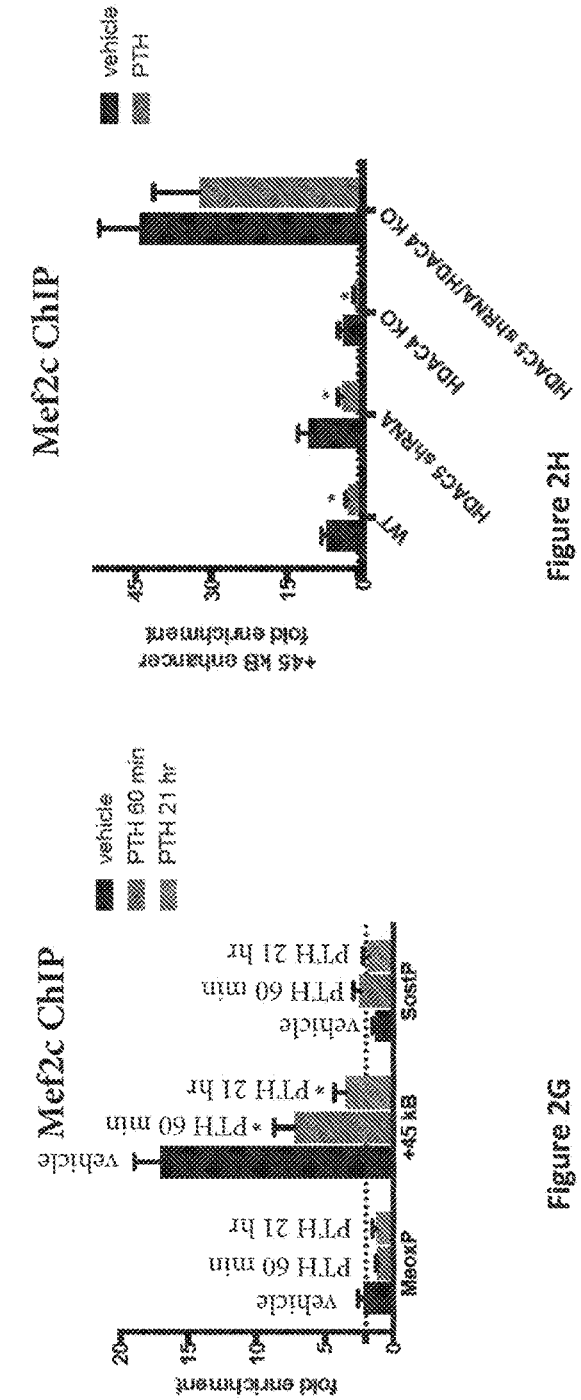

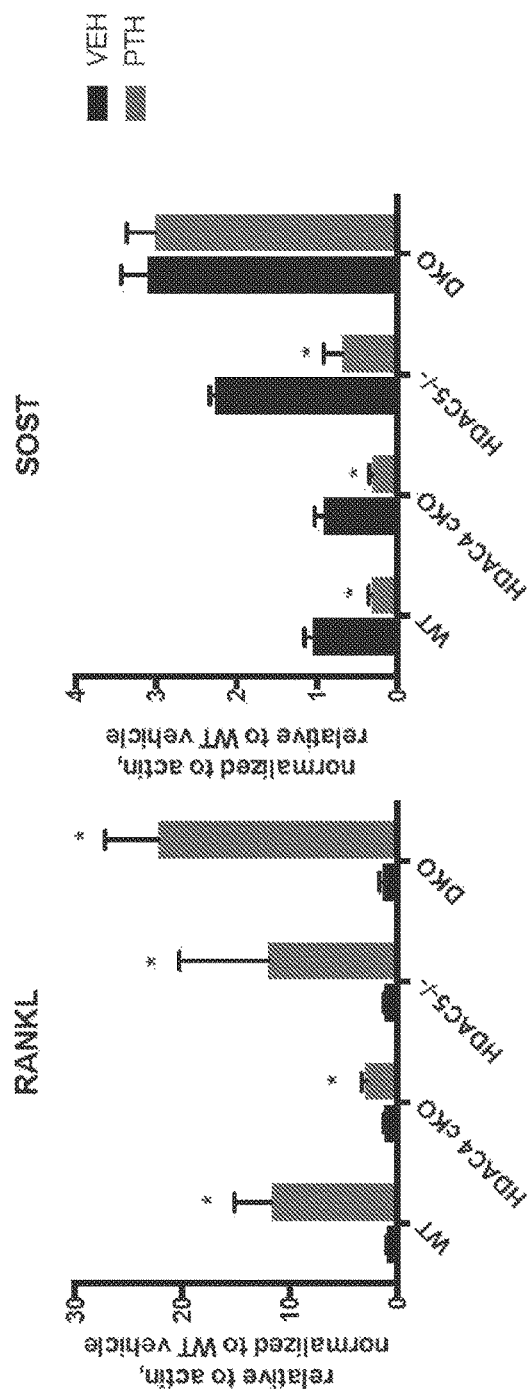
Figure 3A
Figure 3B
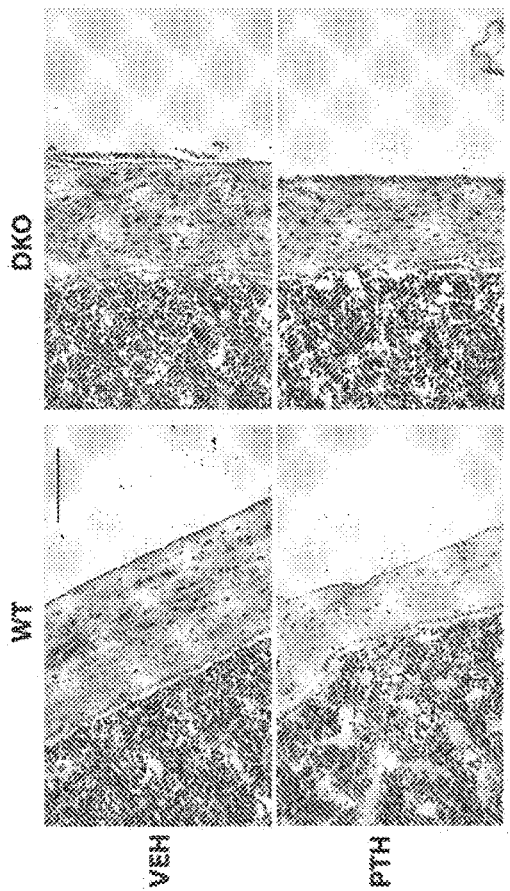
Figure 3C
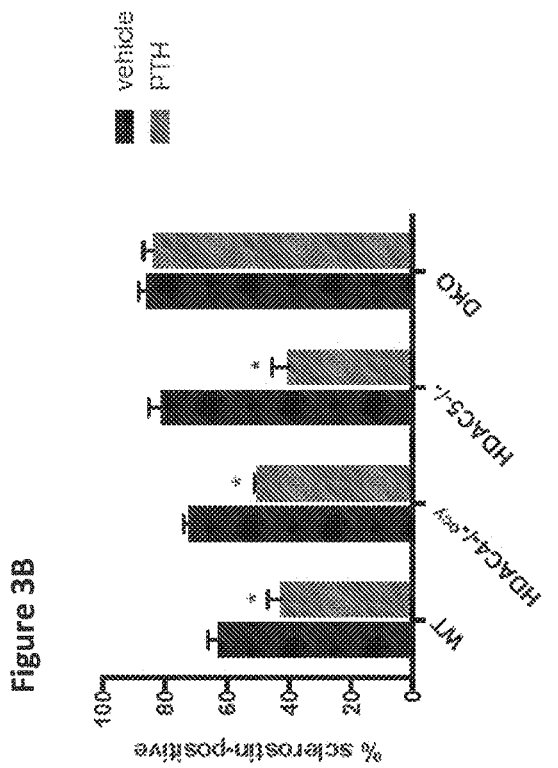
Figure 3D

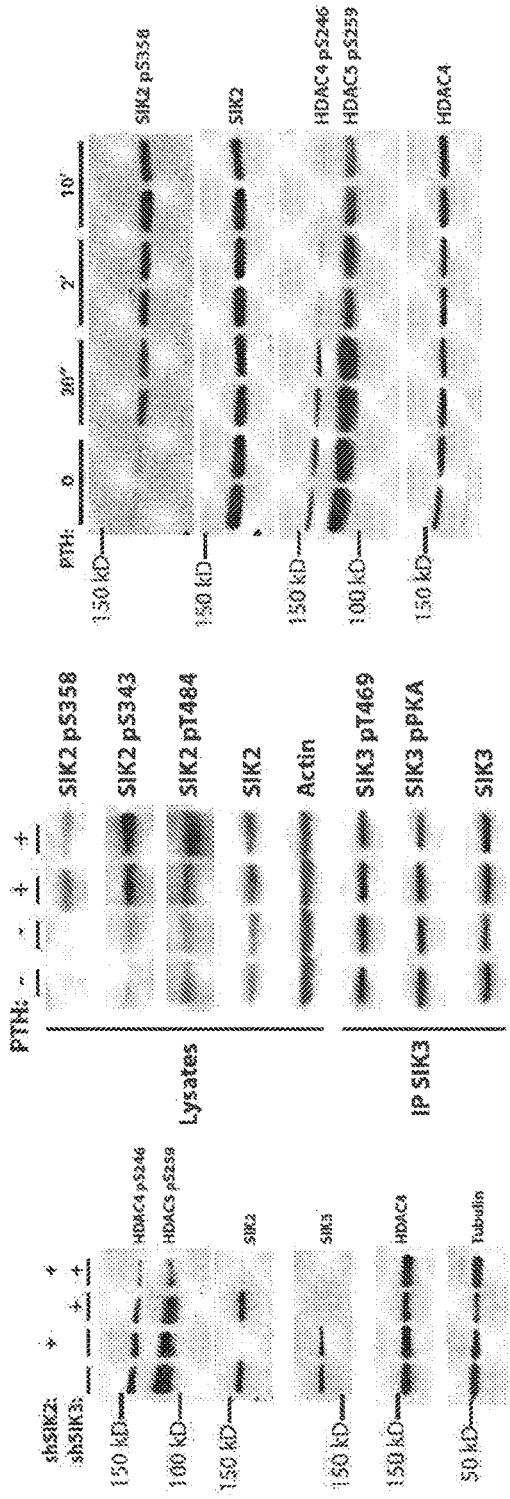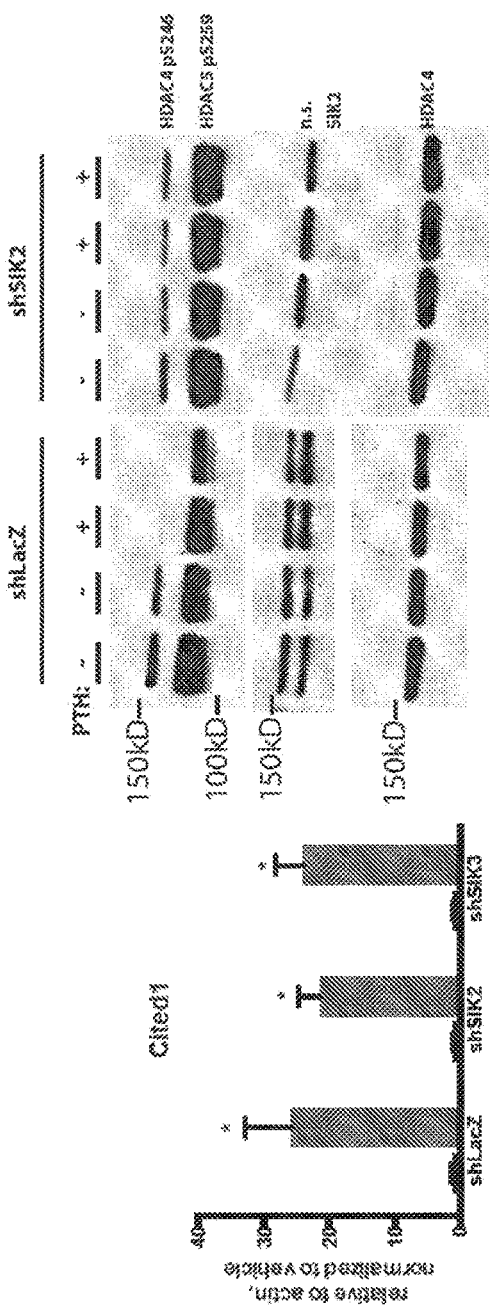

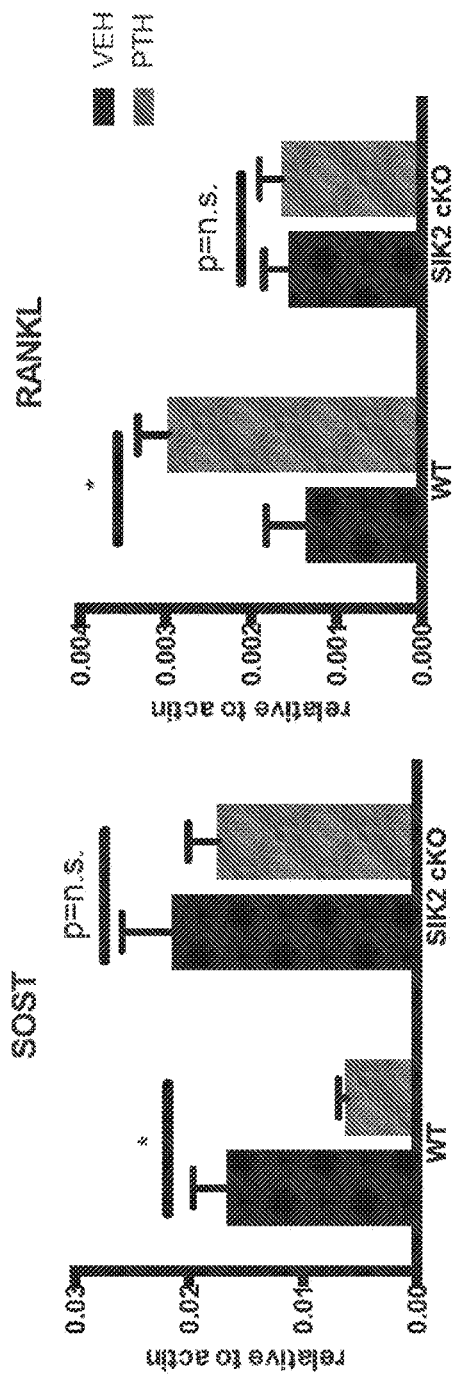
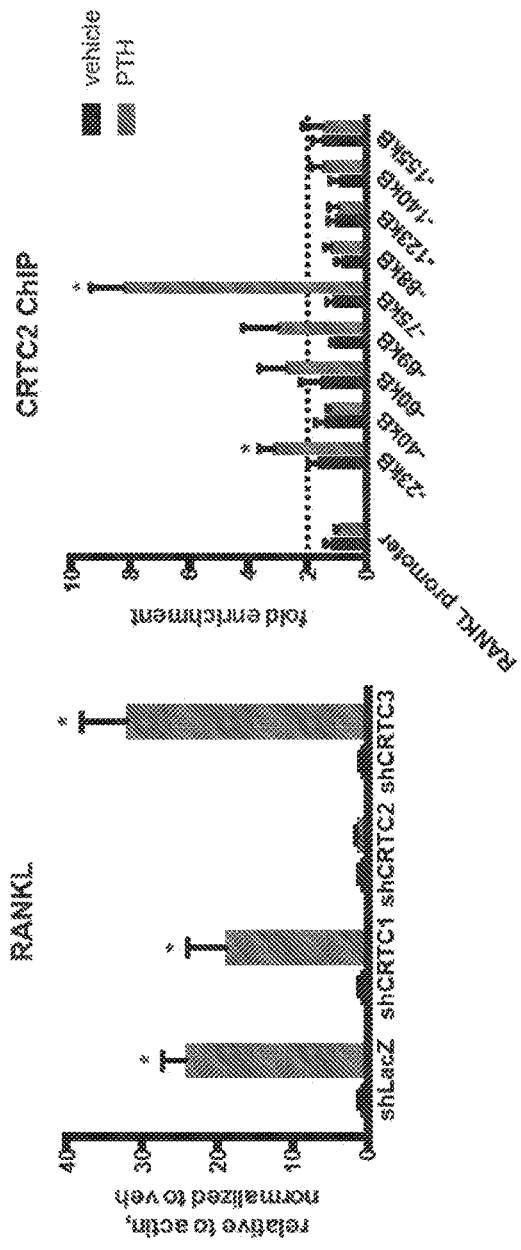
Figure 4K
Figure 4L
Figure 4M

YKL-04-114  YKL-05-093

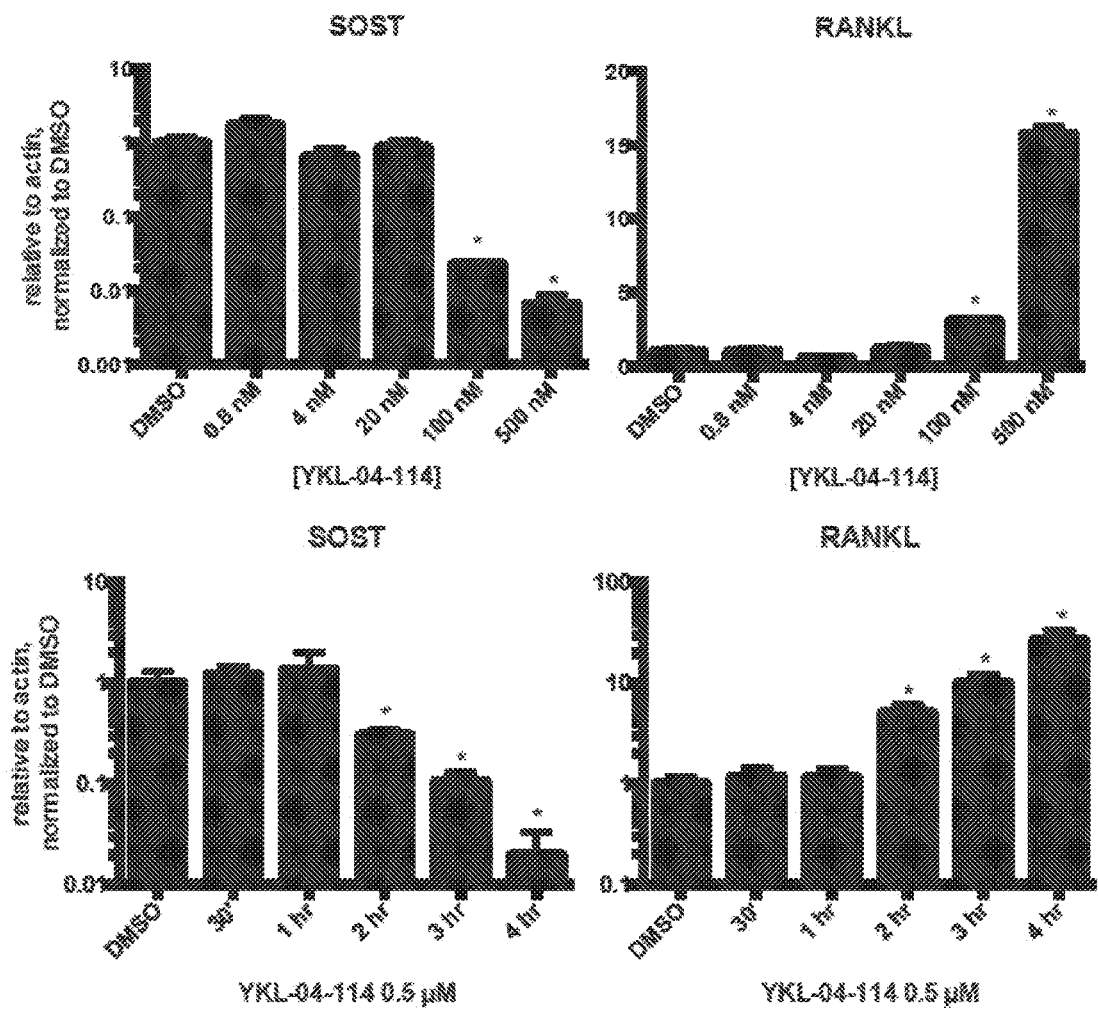
Figure 5E
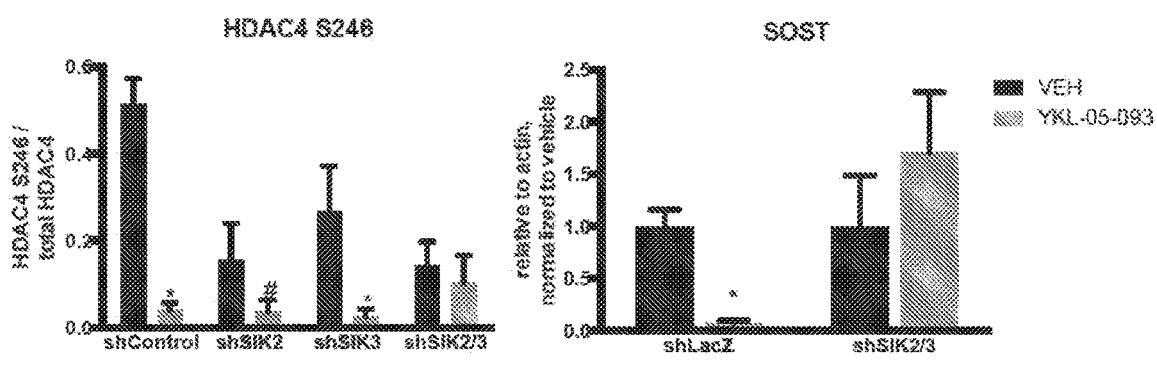
Figure 5F
Figure 5G

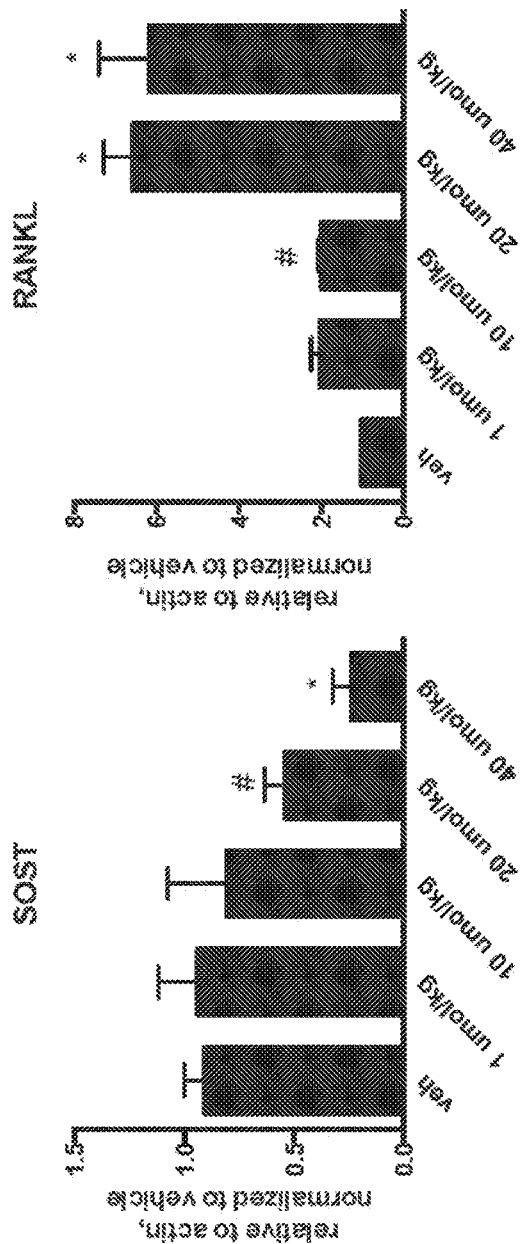
Figure 7A
Figure 7B
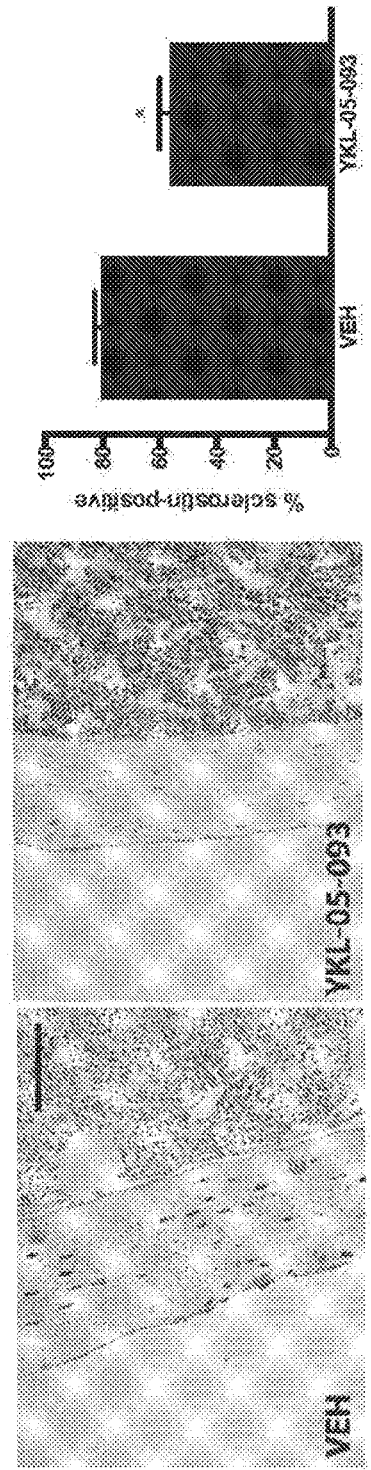
Figure 7C

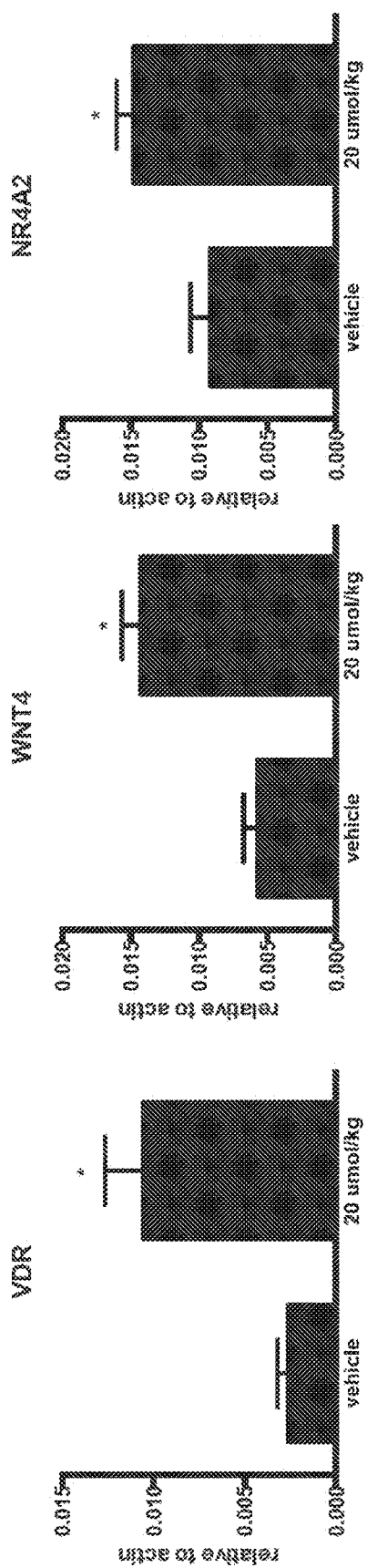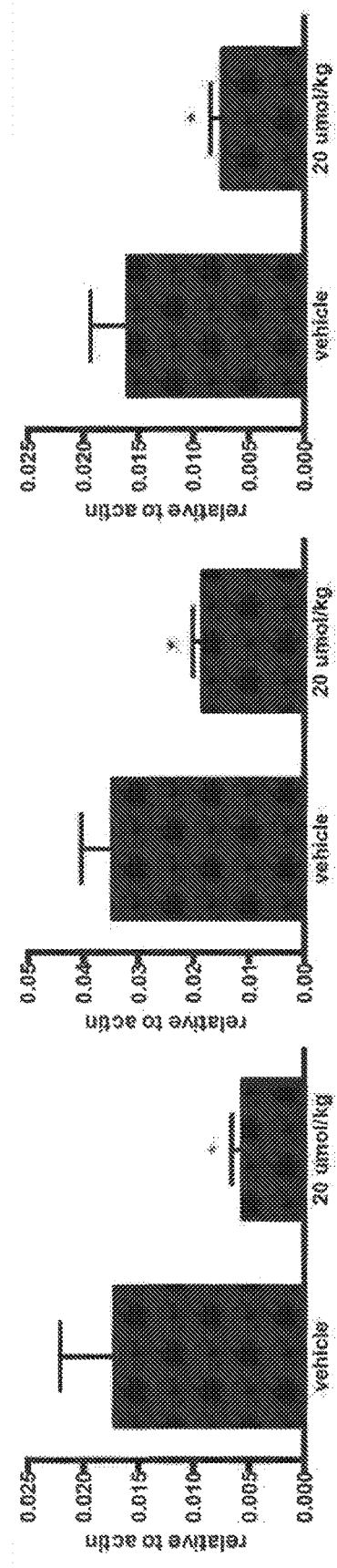

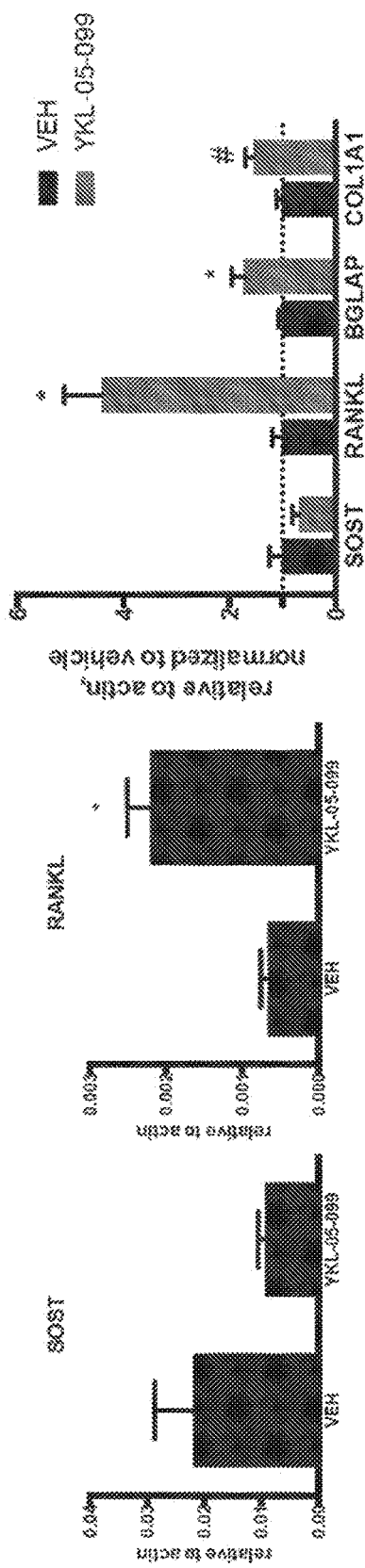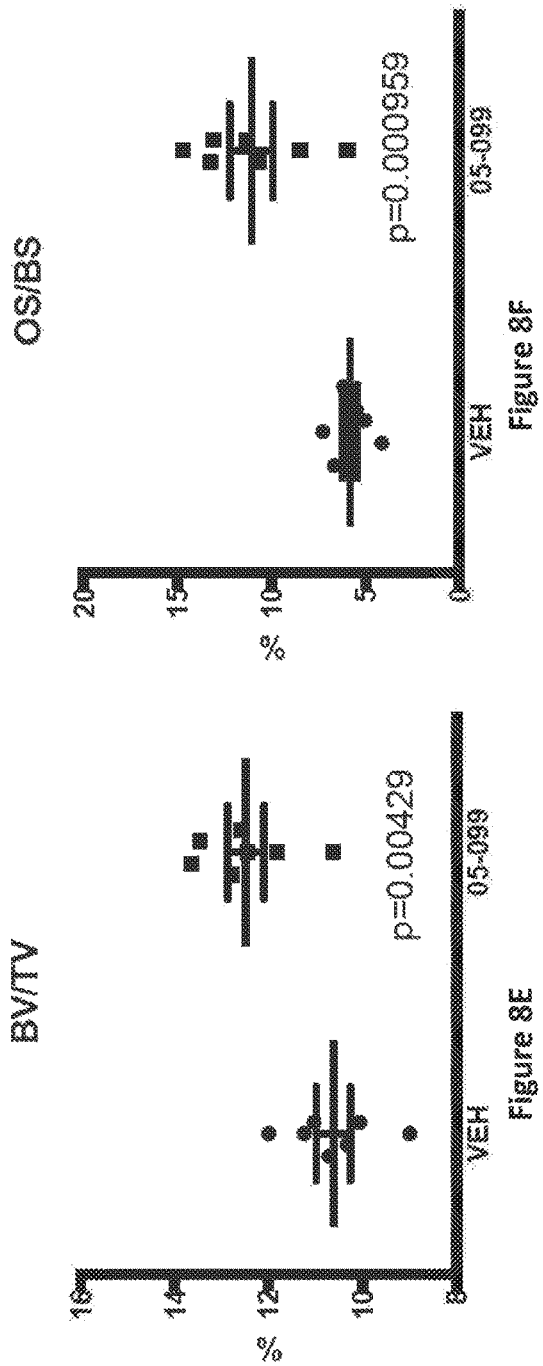
Figure 8C, Figure 8D, Figure 8E, Figure 8F

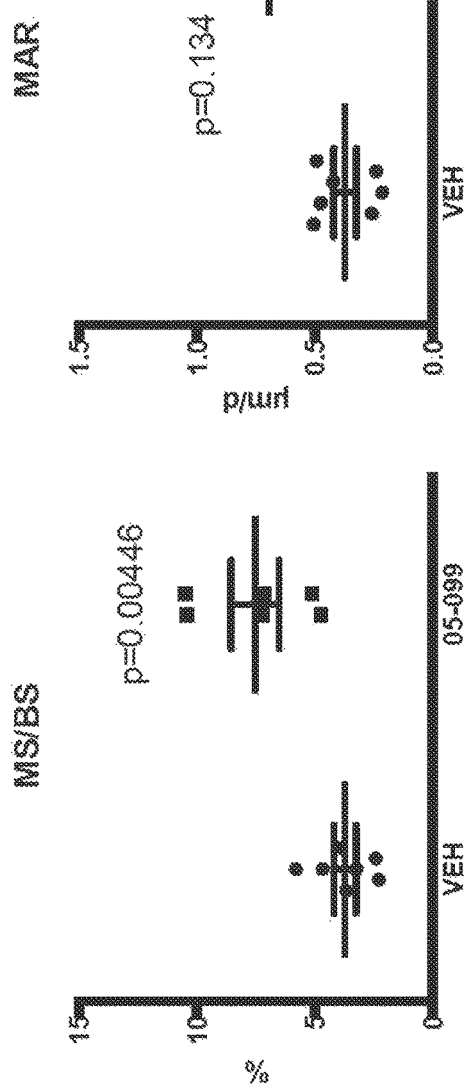
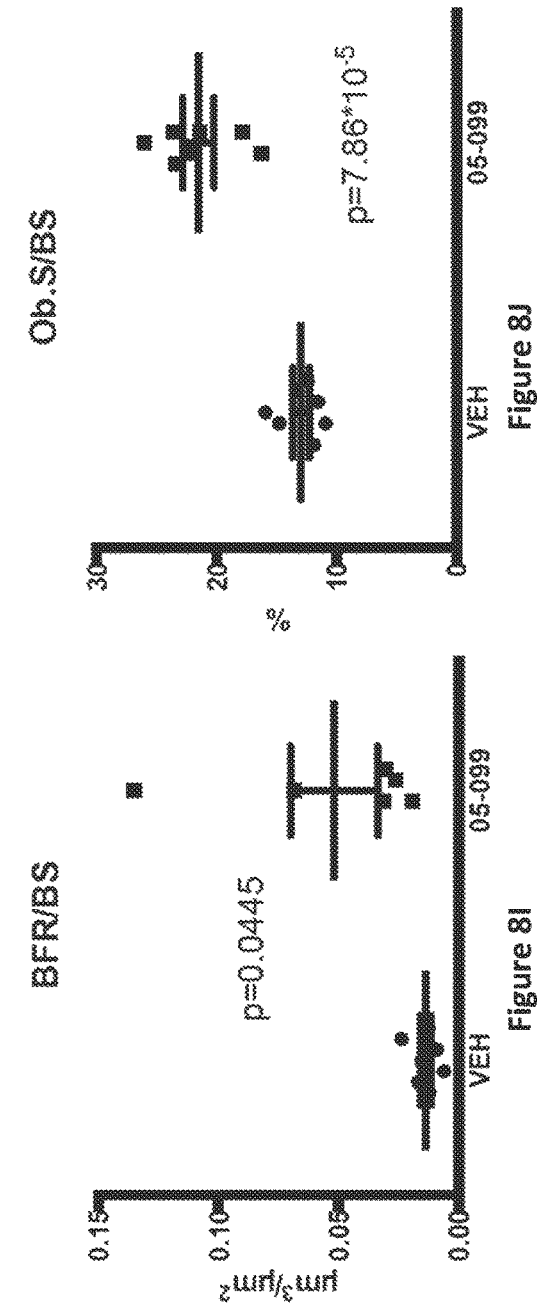
Figure 8G, Figure 8H, Figure 8I, Figure 8J

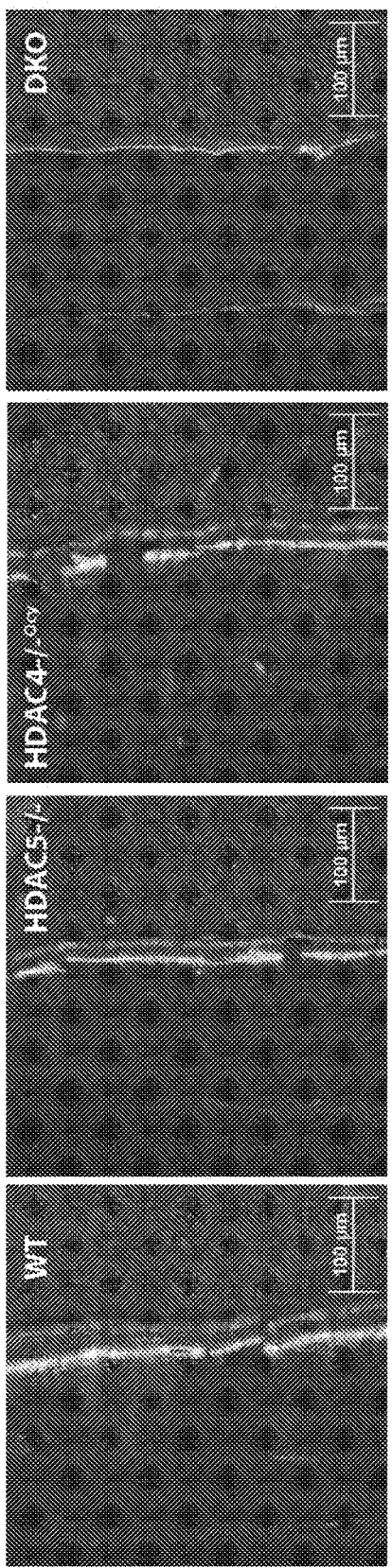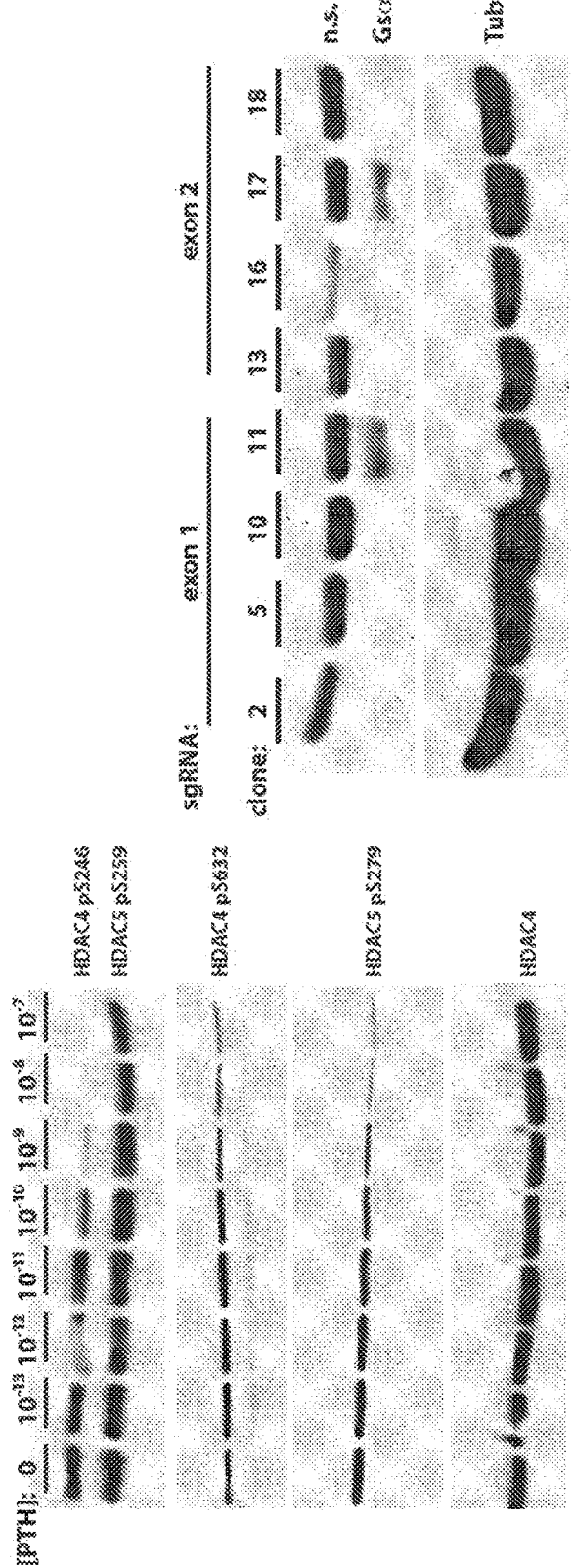
Figure 10E
Figure 11A
Figure 11B

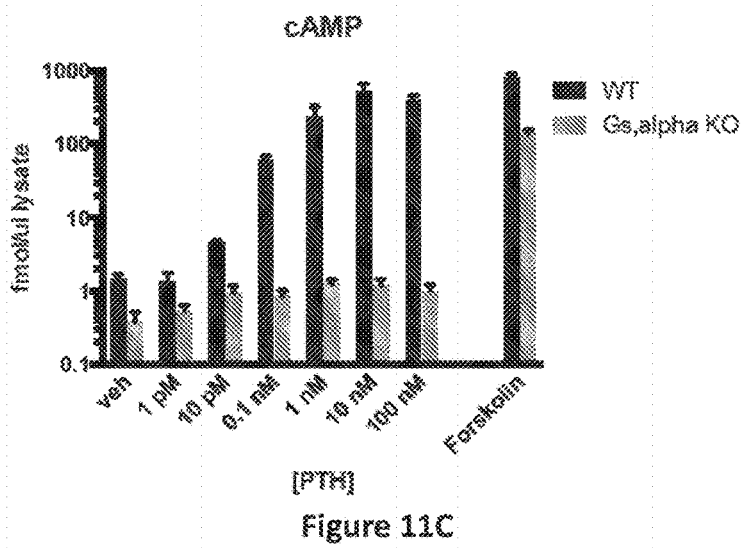
Figure 11C
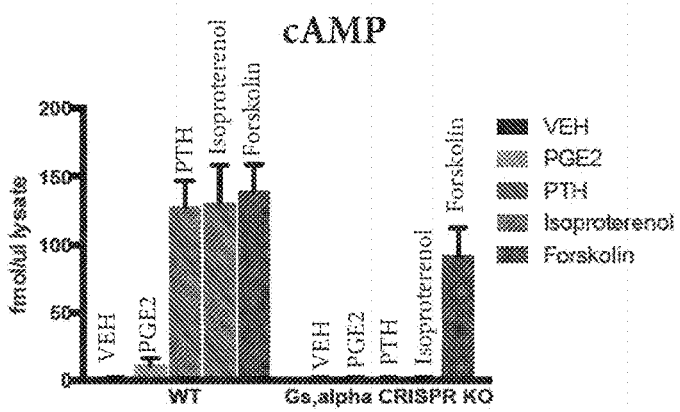
Figure 11D
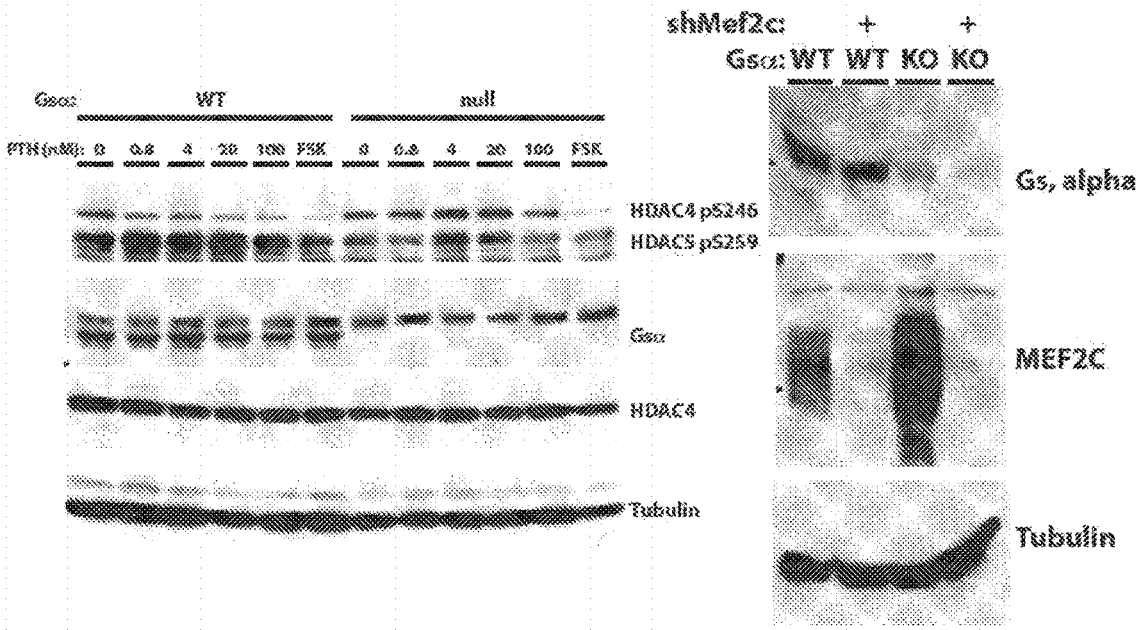
Figure 11E
Figure 11F

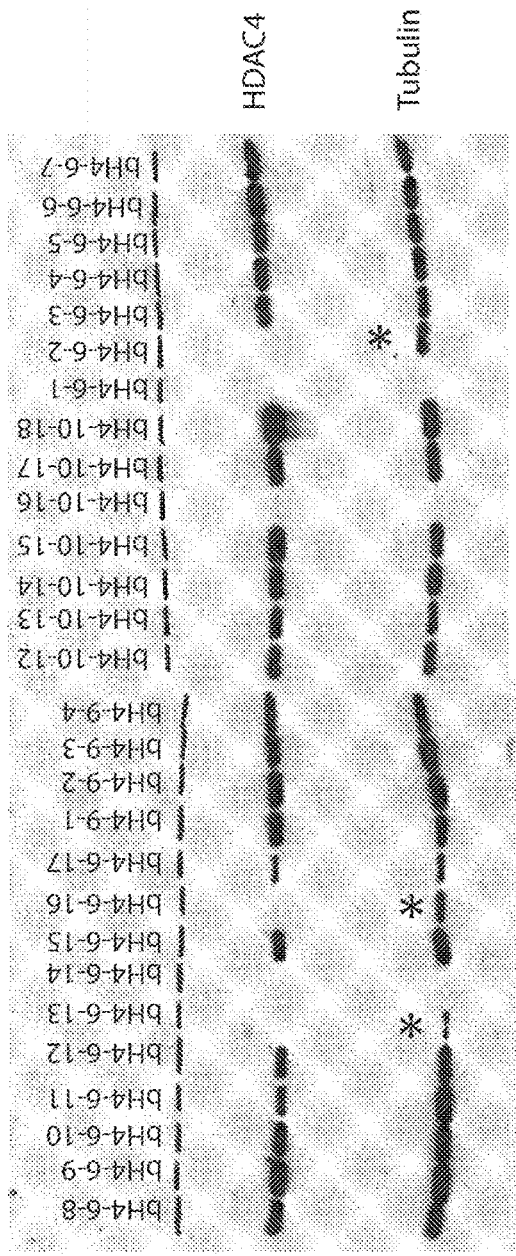

| GO Term | FDR value (coverage) |
|---|---|
| Cell chemotaxis | 2.04e-5 (10/174) |
| Blood vessel morphogenesis | 2.04e-5 (12/278) |
| Ossification | 8.99e-5 (11/275) |
| Muscle organ development | 1.54e-4 (11/298) |
| Relaxation of cardiac muscle | 2.1e-4 (4/10) |

Figure 15C

| GO Term | FDR value (coverage) |
|---|---|
| Skeletal muscle tissue development | 6.052e-6 (9/166) |
| Blood vessel morphogenesis | 1.69e-5 (10/278) |
| Muscle organ development | 2.2e-5 (10/298) |
| Skeletal muscle cell differentiation | 2.35e-3 (5/61) |
| Regulation of muscle tissue development | 2.78e-2 (5/113) |

Figure 15D

Half life in 1 mg/ml hepatic microsomes

| Compound ID | Mouse |
|---|---|
| YKL-04-114 | 13.8 |
| YKL-05-093 | 22.7 |
| HG-9-91-01 | 13.0 |

Femur, distal metaphysis μ-CT

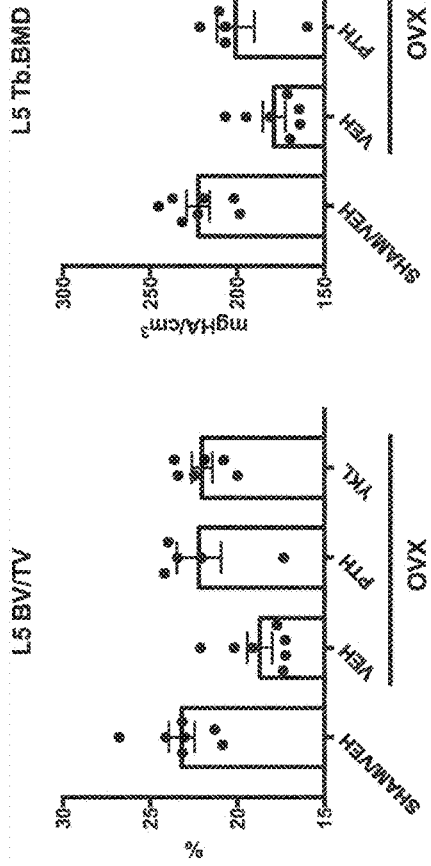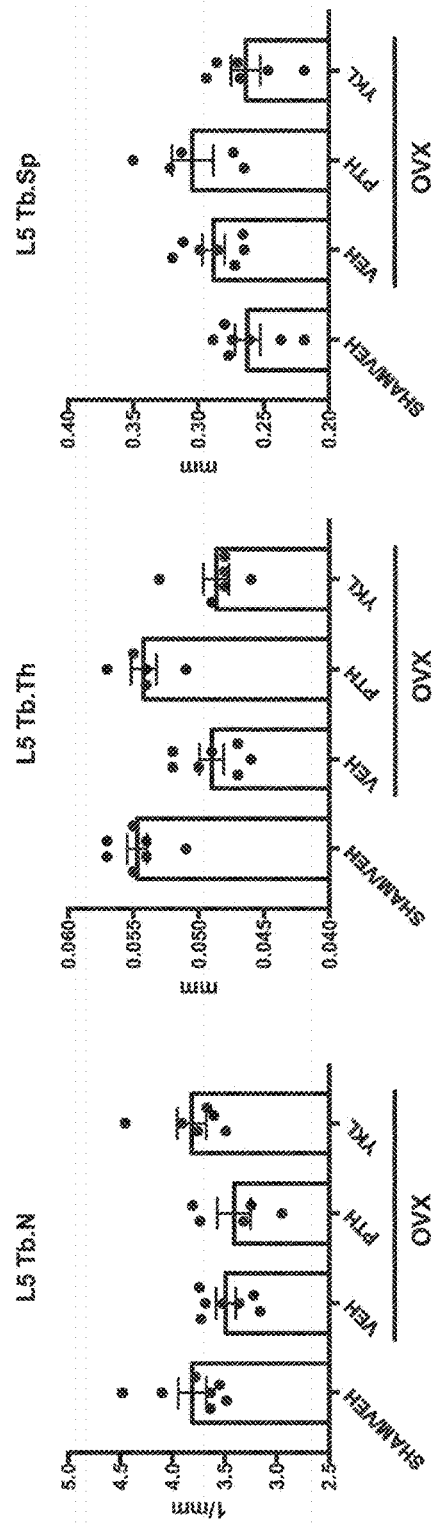
Figure 31A, Figure 31B, Figure 31C, Figure 31D, Figure 31E

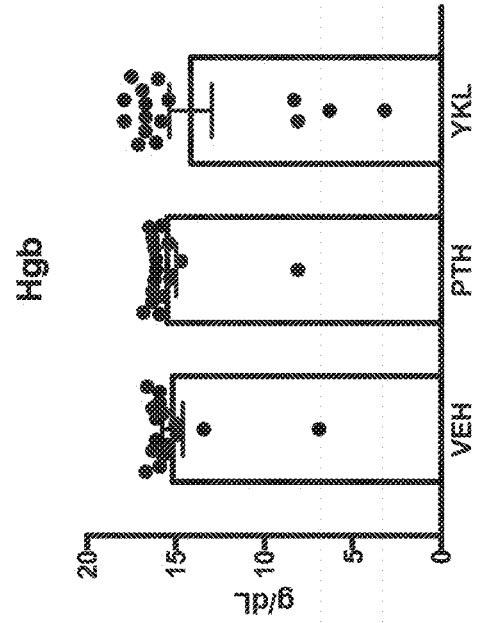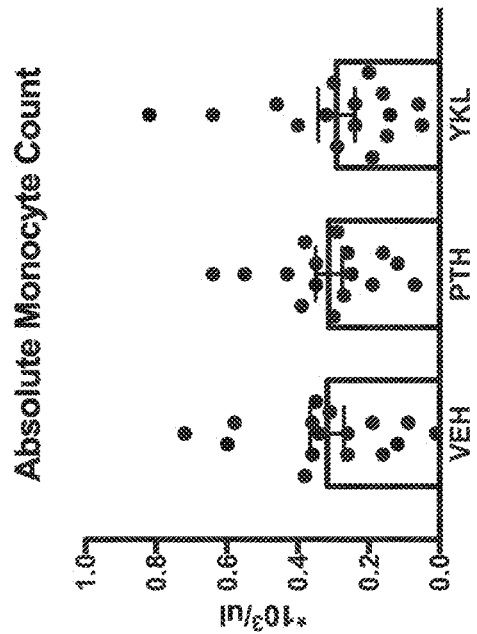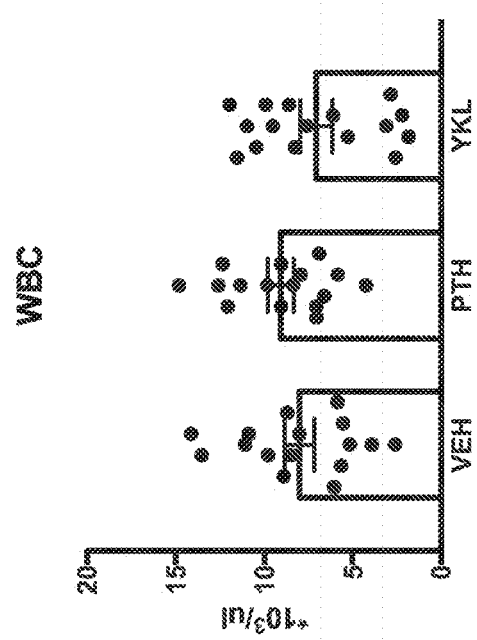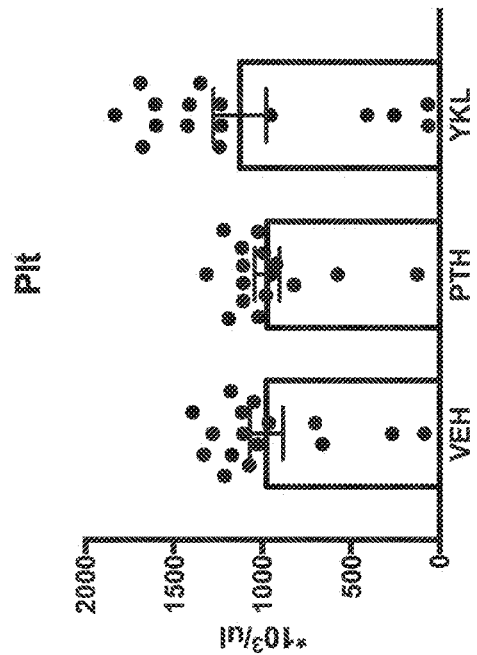
Figure 36A
Figure 36B
Figure 36C
Figure 36D

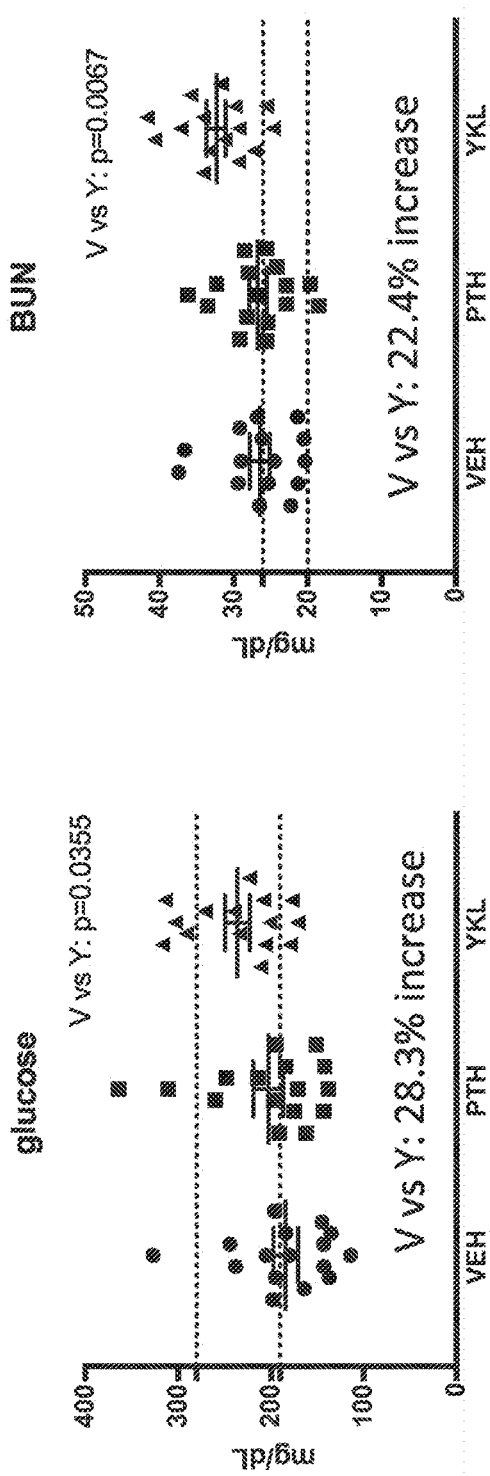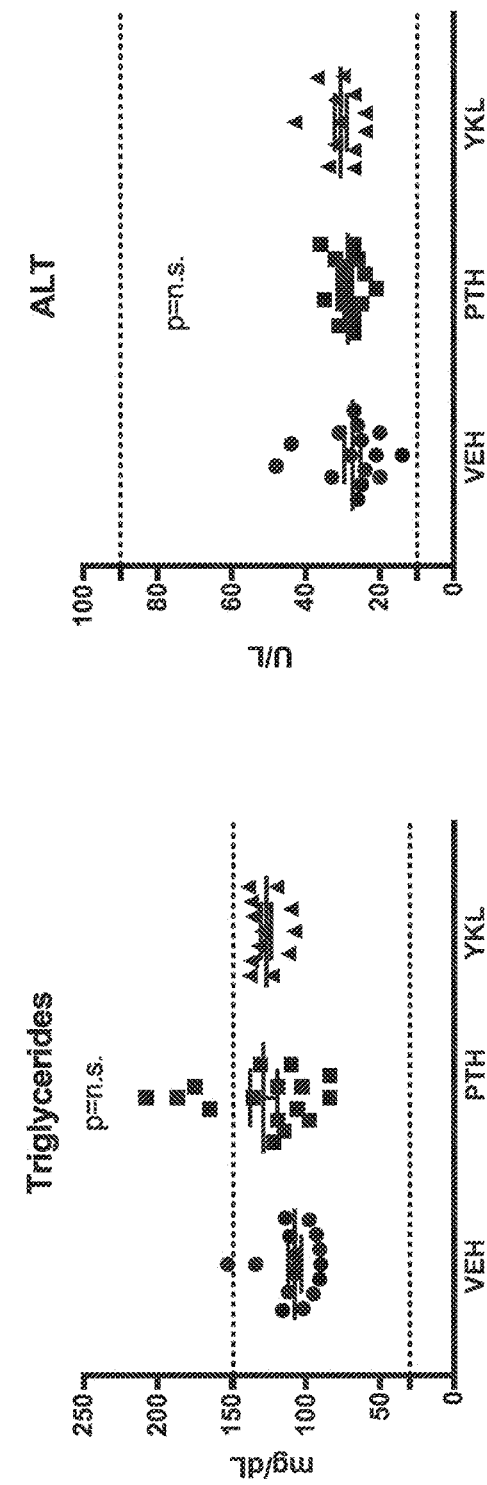
Figure 37A, Figure 37B, Figure 37C, Figure 37D

USES OF SALT-INDUCIBLE KINASE (SIK) INHIBITORS FOR TREATING OSTEOPOROSIS

RELATED APPLICATIONS

The present application is a national stage filing under 35 U.S.C. § 371 of international PCT application, PCT/US2017/051937, filed Sep. 16, 2017, which claims priority under 35 U.S.C. § 119(e) to U.S. provisional patent application, U.S. Ser. No. 62/396,089, filed Sep. 16, 2016, the entire contents of each of which are which is incorporated herein by reference.

GOVERNMENT SUPPORT

This invention was made with government support under grant numbers AR067285, DK011794, and AR066261 awarded by the National institutes of Health. The government has certain rights in the invention.

BACKGROUND OF THE INVENTION

Osteoporosis is a serious problem in our aging population, with fragility fractures costing $25 billion annually (1). Novel treatments are needed to boost bone mass. Osteocytes, cells buried within bone, orchestrate bone remodeling by secreting endocrine and paracrine factors (2). Central amongst these are RANKL (encoded by the TNFSF11 gene), the major osteocyte-derived osteoclastogenic cytokine (3, 4) and an FDA-approved osteoporosis drug target (5), and sclerostin (encoded by the SOST gene), an osteocyte-derived WNT pathway inhibitor that blocks bone formation by osteoblasts (6) and current osteoporosis drug target (7).

When given once daily, parathyroid hormone (PTH), is the only approved osteoporosis treatment agent that stimulates new bone formation. The proximal signaling events downstream of Gsα-coupled PTH receptor signaling in bone cells are well-characterized (8), but how cAMP generation in osteocytes is linked to gene expression changes remains unknown. SOST and RANKL are well-established target genes important for the physiological effects of PTH on osteocytes. Among the mechanisms through which PTH stimulates new bone formation, down-regulation of SOST expression in osteocytes plays an important role (9-11). PTH also stimulates bone catabolism, in large part through stimulation of osteoclastogenesis via inducing RANKL (12-15), which may limit its therapeutic efficacy (16). Therefore, there is a need for the treatment of osteoporosis.

SUMMARY OF THE INVENTION

The present invention is based on the discovery that inhibitors of salt-inducible kinases (SIK) are useful in the treatment and/or prevention of osteoporosis. SIK inhibitors may be able to treat osteoporosis, prevent osteoporosis, increase the function of osteocytes, increase the number of osteoblasts, increase the activity of osteoblasts, inhibit the resorption of a bone, decrease the number of osteoclasts, inhibit the activity of osteoclasts, increase the mass of a bone, down-regulate the expression of the gene SOST, and/or inhibit the activity of sclerostin, in a subject in need thereof. In certain embodiments, the SIK is salt-inducible kinase 1 (SIK1). In certain embodiments, the SIK is salt-inducible kinase 2 (SIK2). In certain embodiments, the SIK is salt-inducible kinase 3 (SIK3).

Without being bound by any theory, SIK inhibitors may be able to down-regulate the expression of the gene SOST. Down-regulation of the expression of SOST in osteocytes may increase bone formation, e.g., by osteoblasts. The SIK inhibitors may also be able to inhibit the resorption of a bone, e.g., by osteoclasts. The SIK inhibitors may inhibit (e.g., directly inhibit) osteoclasts. The SIK inhibitors may also inhibit proto-oncogene tyrosine-protein kinase Src (Src) and/or colony stimulating factor 1 receptor (CSF1R; macrophage colony stimulating factor (M-CSF) receptor). Src and/or CSF may be associated with osteoclast function. The SIK inhibitors may be beneficial as being anabolic agents that also block the resorption of a bone.

In one aspect, the present disclosure provides methods of treating osteoporosis in a subject in need thereof comprising administering to the subject in need thereof a therapeutically effective amount of a SIK inhibitor.

In another aspect, the present disclosure provides methods of preventing osteoporosis in a subject in need thereof comprising administering to the subject in need thereof a prophylactically effective amount of a SIK inhibitor.

In another aspect, the present disclosure provides methods of increasing the function of osteocytes in a subject in need thereof comprising administering to the subject in need thereof an effective amount of a SIK inhibitor.

In another aspect, the present disclosure provides methods of increasing the number of osteoblasts in a subject in need thereof comprising administering to the subject in need thereof an effective amount of a SIK inhibitor.

In another aspect, the present disclosure provides methods of increasing the activity of osteoblasts in a subject in need thereof comprising administering to the subject in need thereof an effective amount of a SIK inhibitor.

In another aspect, the present disclosure provides methods of inhibiting the resorption of a bone in a subject in need thereof comprising administering to the subject in need thereof an effective amount of a SIK inhibitor.

In another aspect, the present disclosure provides methods of decreasing the number of osteoclasts in a subject in need thereof comprising administering to the subject in need thereof an effective amount of a SIK inhibitor.

In another aspect, the present disclosure provides methods of inhibiting the activity of osteoclasts in a subject in need thereof comprising administering to the subject in need thereof an effective amount of a SIK inhibitor.

In another aspect, the present disclosure provides methods of increasing the mass of a bone in a subject in need thereof comprising administering to the subject in need thereof an effective amount of a SIK inhibitor.

In another aspect, the present disclosure provides methods of down-regulating the expression of the gene SOST in a subject in need thereof comprising administering to the subject in need thereof an effective amount of a SIK inhibitor.

In another aspect, the present disclosure provides methods of inhibiting the activity of sclerostin in a subject in need thereof comprising administering to the subject in need thereof an effective amount of a SIK inhibitor.

In another aspect, the present disclosure provides methods of reducing the production of sclerostin in a subject in need thereof comprising administering to the subject in need thereof an effective amount of a SIK inhibitor.

The SIK inhibitors useful in the invention include, but are not limited to, bicyclic urea compounds of any one of Formulae (I), (II), and (III), imidazolyl compounds of Formula (IV), urea and carbamate compounds of Formula (V), macrocyclic compounds of Formula (VI), and pharmaceutically acceptable salts, solvates, hydrates, polymorphs, co-crystals, tautomers, stereoisomers, isotopically labeled derivatives, and prodrugs thereof.

In certain embodiments, the SIK inhibitor for use in the invention described herein is a compound of Formula (I):

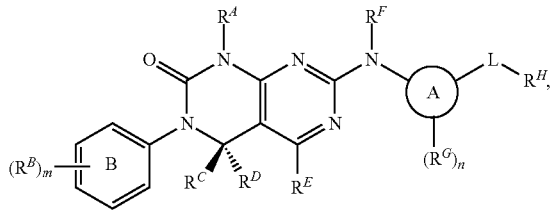

or a pharmaceutically acceptable salt, solvate, hydrate, polymorph, co-crystal, tautomer, stereoisomer, isotopically labeled derivative, or prodrug thereof, wherein Ring A, Ring B, $R^A$, $R^B$, $R^C$, $R^D$, $R^E$, $R^F$, $R^G$, $R^H$, L, m, and n are as described herein for Formula (I).

In certain embodiments, the SIK inhibitor for use in the invention described herein is a compound of Formula (II):

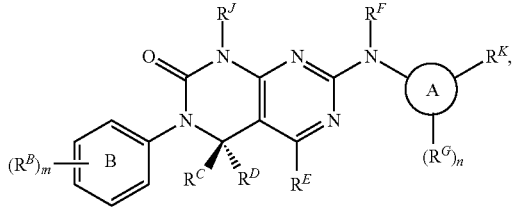

or a pharmaceutically acceptable salt, solvate, hydrate, polymorph, co-crystal, tautomer, stereoisomer, isotopically labeled derivative, or prodrug thereof, wherein Ring A, Ring B, $R^J$, $R^B$, $R^C$, $R^D$, $R^E$, $R^F$, $R^G$, $R^K$, m, and n are as described herein for Formula (II).

In certain embodiments, the SIK inhibitor for use in the invention described herein is a compound of Formula (III):

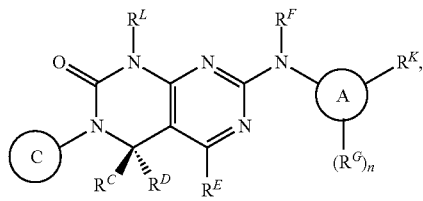

or a pharmaceutically acceptable salt, solvate, hydrate, polymorph, co-crystal, tautomer, stereoisomer, isotopically labeled derivative, or prodrug thereof, wherein Ring A, Ring C, $R^L$, $R^C$, $R^D$, $R^E$, $R^F$, $R^G$, $R^K$, m, and n are as described herein for Formula (III).

In certain embodiments, the SIK inhibitor for use in the invention described herein is a compound of Formula (IV):

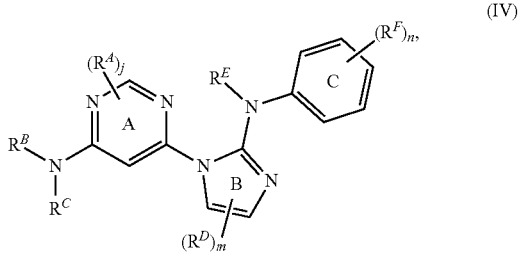

or a pharmaceutically acceptable salt, solvate, hydrate, polymorph, co-crystal, tautomer, stereoisomer, isotopically labeled derivative, or prodrug thereof, wherein $R^A$, $R^B$, $R^C$, $R^D$, $R^E$, $R^F$, j, m, and n are as described herein for Formula (IV).

In certain embodiments, the SIK inhibitor for use in the invention described herein is a compound of Formula (V):

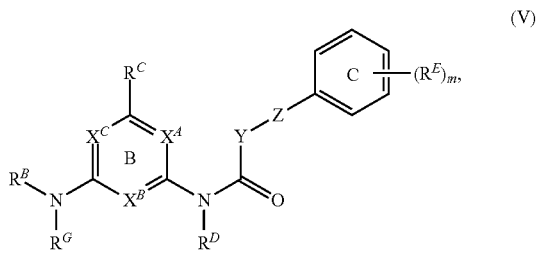

or a pharmaceutically acceptable salt, solvate, hydrate, polymorph, co-crystal, tautomer, stereoisomer, isotopically labeled derivative, or prodrug thereof, wherein $X^A$, $X^B$, $X^C$, Y, Z, $R^B$, $R^C$, $R^D$, $R^E$, $R^G$, and m are as described herein for Formula (V).

In certain embodiments, the SIK inhibitor for use in the invention described herein is a compound of Formula (VI):

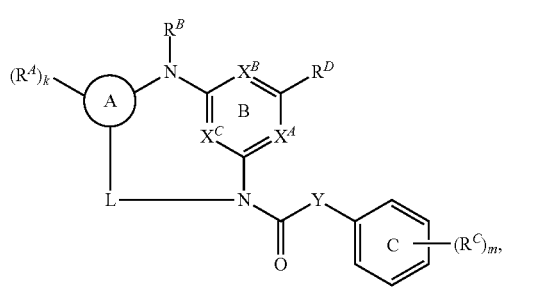

or a pharmaceutically acceptable salt, solvate, hydrate, polymorph, co-crystal, tautomer, stereoisomer, isotopically labeled derivative, or prodrug thereof, wherein Ring A, $X^A$, $X^B$, $X^C$, L, Y, $R^A$, $R^B$, $R^C$, $R^D$, k, and m are as described herein for Formula (VI).

In another aspect, the present disclosure provides pharmaceutical compositions comprising:
a SIK inhibitor;
a Src inhibitor; and
optionally a pharmaceutically acceptable excipient.

In another aspect, the present disclosure provides pharmaceutical compositions comprising:

a SIK inhibitor;

a CSF1R inhibitor; and optionally a pharmaceutically acceptable excipient.

In another aspect, the present disclosure provides uses of the SIK inhibitors in a method described herein.

In another aspect, the present disclosure provides uses of the pharmaceutical compositions in a method described herein.

The present disclosure refers to various issued patents, published patent applications, journal articles, and other publications, all of which are incorporated herein by reference.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, — is absent or a single bond, and ═══ or ≡≡≡ is a single or double bond. In a formula, ∼∼∼ is a single bond where the stereochemistry of the moieties immediately attached thereto is not specified. Such a ∼∼∼ bond may be ◄━━ or ·····.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tort-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is unspecified (e.g., —CH=CHCH$_3$ or 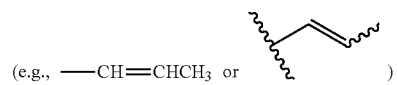)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an un substituted heteroC$_{2-10}$ alkenyl. In certain embodiments, the heteroalkenyl group is a substituted heteroC$_{2-10}$ alkenyl.

The term "alkynyl" refers to a radical of a straightchain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butyryl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a nonaromatic cyclic hydrocarbon group having from 3 to 14 ring carbon atoms ("$C_{3-14}$ carbocyclyl") and zero heteroatoms in the nonaromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthatenyl ($C_{10}$), spiro[4.5]decanyl ($C_{10}$), and the like. As the foregoing examples illustrate. In certain embodiments, the carbocyclyl group is either monocyclic ("monocyclic carbocyclyl") or polycyclic (e.g., containing a fused, bridged or Spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl. In certain embodiments, the carbocyclyl includes 0, 1, or 2 C=C double bonds in the carbocyclic ring system, as valency permits.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl, and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetra-hydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted. $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl), —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, fluorine, and/or chlorine atoms. In certain embodiments, a substituent comprises 0, 1, 2, or 3 hydrogen bond donors. In certain embodiments, a substituent comprises 0, 1, 2, or 3 hydrogen bond acceptors.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —$ON(R^{bb})_2$, —$OC(=O)SR^{aa}$, —$OC(=O)R^{aa}$, —$OC(=O)OR^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OSi(R^{aa})_3$, —$OP(R^{cc})_2$, —$OP(R^{cc})_3^+X^-$, —$OP(OR^{cc})_2$, —$OP(OR^{cc})_3^+X^-$, —$OP(=O)(R^{aa})_2$, —$OP(=O)(OR^{cc})_2$, and —$OP(=O)(N(R^{bb}))_2$, wherein $X^-$, $R^{aa}$, $R^{bb}$, and $R^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —$S=SR^{cc}$, —$SC(=S)SR^{aa}$, —$SC(=O)SR^{aa}$, —$SC(=O)OR^{aa}$, and —$SC(=O)R^{aa}$, wherein $R^{aa}$ and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —$NHC(=O)R^{aa}$, —$NHCO_2R^{aa}$, —$NHC(=O)N(R^{bb})_2$, —$NHC(=NR^{bb})N(R^{bb})_2$, —$NHSO_2R^{aa}$, —$NHP(=O)(OR^{cc})_2$, and —$NHP(=O)(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}C(=O)R^{aa}$, —$NR^{bb}CO_2R^{aa}$, —$NR^{bb}C(=O)N(R^{bb})_2$, —$NR^{bb}C(=NR^{bb})N(R^{bb})_2$, —$NR^{bb}SO_2R^{aa}$, —$NR^{bb}P(=O)(OR^{cc})_2$, and —$NR^{bb}P(=O)(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —$N(R^{bb})_3$ and —$N(R^{bb})_3^+X^-$, wherein $R^{bb}$ and $X^-$ are as defined herein.

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "sulfinyl" refers to the group —$S(=O)R^{aa}$, wherein $R^{aa}$ is as defined herein.

The term "carbonyl" refers a group wherein the carbon directly attached to the parent molecule is sp² hybridized, and is substituted with an oxygen, nitrogen or sulfur atom, e.g., a group selected from ketones (—$C(=O)R^{aa}$), carboxylic acids (—$CO_2H$), aldehydes (—CHO), esters (—$CO_2R^{aa}$, —$C(=O)SR^{aa}$, —$C(=S)SR^{aa}$), amides (—$C(=O)N(R^{bb})_2$, —$C(=O)NR^{bb}SO_2R^{aa}$, —$C(=S)N(R^{bb})_2$), and imines (—$C(=NR^{bb})R^{aa}$, —$C(=NR^{bb})OR^{aa}$), —$C(=NR^{bb})N(R^{bb})_2$), wherein $R^{aa}$ and $R^{bb}$ are as defined herein.

The term "silyl" refers to the group —$Si(R^{aa})_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(OR^{cc})_2$, —$P(=O)(R^{aa})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

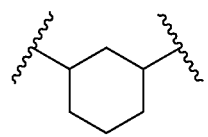 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C═C and/or C≡C bonds anywhere in the hydrocarbon chain. For instance, —CH═CH—(CH$_2$)$_2$—, —CH$_2$—C≡C—CH$_2$—, and —C≡C—CH═CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

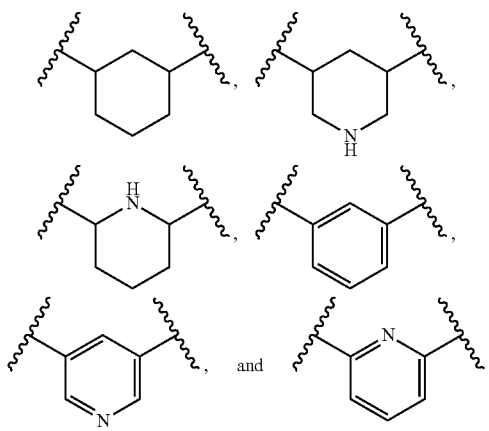 [SMILES: *C1CCCC(*)C1 ; *C1CNCC(*)C1 ; *C1CCCC(*)N1 ; *c1cccc(*)c1 ; *c1cncc(*)c1 ; *c1cccc(*)n1]

are all examples of a hydrocarbon chain. In contrast, in certain embodiments,

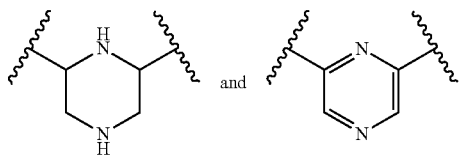 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

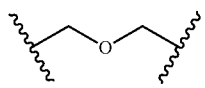

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. In certain embodiments, the leaving group is an activated substituted hydroxyl group (e.g., —OC(═O)SR$^{aa}$, —OC(═O)R$^{aa}$, —OCO$_2$R$^{aa}$, —OC(═O)N(R$^{bb}$)$_2$, —OC(═NR$^{bb}$)R$^{aa}$, —OC(═NR$^{bb}$)OR$^{aa}$, —OC(═NR$^{bb}$)N(R$^{bb}$)$_2$, —OS(═O)R$^{aa}$, —OSO$_2$R$^{aa}$, —OP(R$^{cc}$)$_2$, —OP(R$^{cc}$)$_3$, —OP(═O)$_2$R$^{aa}$, —OP(═O)(R$^{aa}$)$_2$, —OP(═O)(OR$^{cc}$)$_2$, —OP(═O)$_2$N(R$^{bb}$)$_2$, or —OP(═O)(NR$^{bb}$)$_2$, wherein R$^{aa}$, R$^{bb}$, and R$^{cc}$ are as defined herein).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertible compounds resulting from at least one thermal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are tenured "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or nonhuman animal. In certain embodiments, the nonhuman animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease described herein.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective treatment. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, salt-inducible kinase (SIK, e.g., salt-inducible kinase 1 (SIK I), salt-inducible kinase 2 (SIK2), salt-inducible kinase 3 (SIK3)).

The term "salt-inducible kinase" or "SIK" refers to a subfamily of serine/threonine protein kinases including SIK1, SIK2, and SIK3 that belong to an AMP-activated protein kinase family.

The terms "SIK inhibitor" and "inhibitor of SIK" are used interchangeably.

The term "inhibition", "inhibiting", "inhibit," or "inhibitor" refer to the ability of a compound to reduce, slow, halt, and/or prevent activity of a particular biological process (e.g., kinase activity) in a cell relative to vehicle (veh, Veh, or VEH).

When a compound, pharmaceutical composition, method, or use is referred to as "selectively" or "specifically" modulating (e.g., increasing or inhibiting) the activity of a first protein kinase, the compound, pharmaceutical composition, method, or use modulates the activity of the first protein kinase to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least a second protein kinase that is different from the first protein kinase.

BRIEF DESCRIPTION OF THE DRAWINGS

FIGS. 1A to 1D: HDAC4 and HDAC5 control osteocyte biology in vivo. (FIG. 1A) Endogenous MEF2C was immunoprecipitated from Ocy454 cells, followed by immunoblotting for the indicated proteins. Data shown in this figure is representative of n=3 independent experiments. (FIG. 1B) Osteocyte density in cortical bone 3 mm below the growth plate. 4-5 mice per genotype were analyzed, * indicates p<0.01 versus WT by Student's unpaired 2 tailed t-test. (FIG. 1C) Representative H+E section demonstrating increased osteocyte density and disorganized cortical bone in double-knockout (DKO) (HDAC4f/f; HDAC5–/–; DMP1-Cre) mice. (FIG. 1D) Sections were stained with Sirius Red and analyzed under polarized light to view collagen fiber organization. Disorganized collagen fibers are only seen in DKO sections. Error bars indicate s.e.m for all figures.

FIGS. 2A to 2H: Class IIa HDACs are required for PTH-induced SOST suppression in vitro. (FIG. 2A) Ocy454 cells were transfected with GFP-HDAC5 and then treated with PTH (50 nM) for the indicated times. Cytosolic (c) and nuclear (n) lysates were prepared and immunoblotted as indicated. (FIG. 2B) Ocy454 cells were treated with PTH (50 nM) for 30 minutes. Whole cell lysates were prepared and immunoblotted as indicated. Similar results were observed in 4 independent experiments. (FIG. 2C) Ocy454 cells with (WT, clone 17) and without (Null, clone 8) Gsα were treated with PTH (50 nM for 30 minutes) and analyzed as in FIG. 2A. (FIG. 2D) Ocy454 cells with (WT) and without (Null) Gsα were treated with either PTH (50 nM) or forskolin (5 μg/mL) for 30 minutes and analyzed as in FIG. 2B. (FIG. 2E) Ocy454 cells were exposed to the indicated combinations of HDAC4-targeting sgRNAs (with Cas9) and HDAC5 shRNA-expressing lentiviruses, and whole cell lysates were analyzed by immunoblotting as indicated. (FIG. 2F) WT, HDAC5 shRNA, HDAC4 KO, and DKO Ocy454 cells were treated with PTH (1 nM) for 4 hours, and SOST (left) and RANKL (right) mRNA transcript abundance was measured by RT-qPCR. For all cell culture experiments therein, values represent mean of n=3 biologic replicates. * indicates p<0.05 comparing the effects of PTH to vehicle for each cell line. (FIGS. 2G to 2H) MEF2C chromatin immunoprecipitation was performed, and enrichment for the +45 kB enhancer determined (relative to control IgG ChIP). * indicates p<0.05 comparing fold enrichment of PTH versus vehicle by Student's unpaired 2 tailed t-test.

FIGS. 3A to 3D: Class IIa HDACs are required for PTH-induced SOST suppression in vivo. (FIGS. 3A and 3B) 6 week old mice of the indicated genotype were treated with vehicle or PTH (1-34, 300 µg/kg) and sacrificed 90 minutes later. Bone RNA was obtained and RANKL and SOST transcript abundance was determined by RT-qPCR. * indicates p<0.05 comparing vehicle and PTH for each genotype. N=6-8 mice per group were analyzed. (FIG. 3C) Representative photomicrographs of sclerostin immunohistochemistry from WT and DKO mice treated with vehicle or PTH. (FIG. 3D) Quantification of immunohistochemistry results. Cortical osteocytes in a fixed region of bone 3 mm below the tibial growth plate were counted and scored as either sclerostin-positive or negative. N=6-8 mice per group were analyzed. * indicates p<0.01 comparing vehicle and PTH for each genotype by Student's unpaired 2 tailed t-test. In the Figures, "VEH" or "veh" denotes vehicle.

Figure 4F:
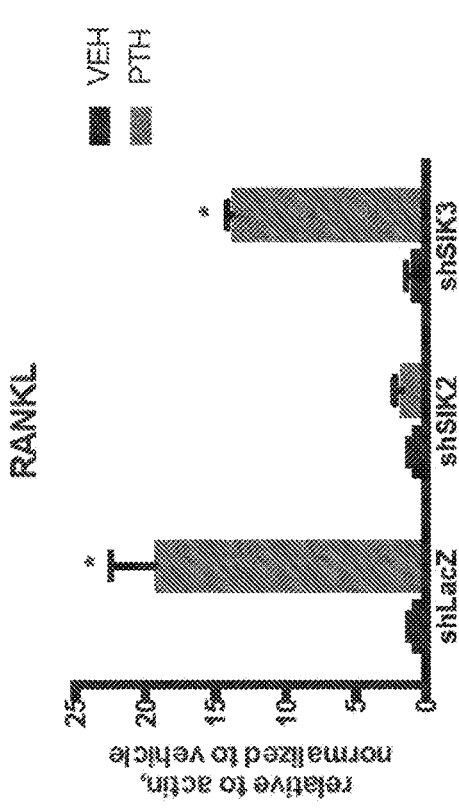
Figure 4G:
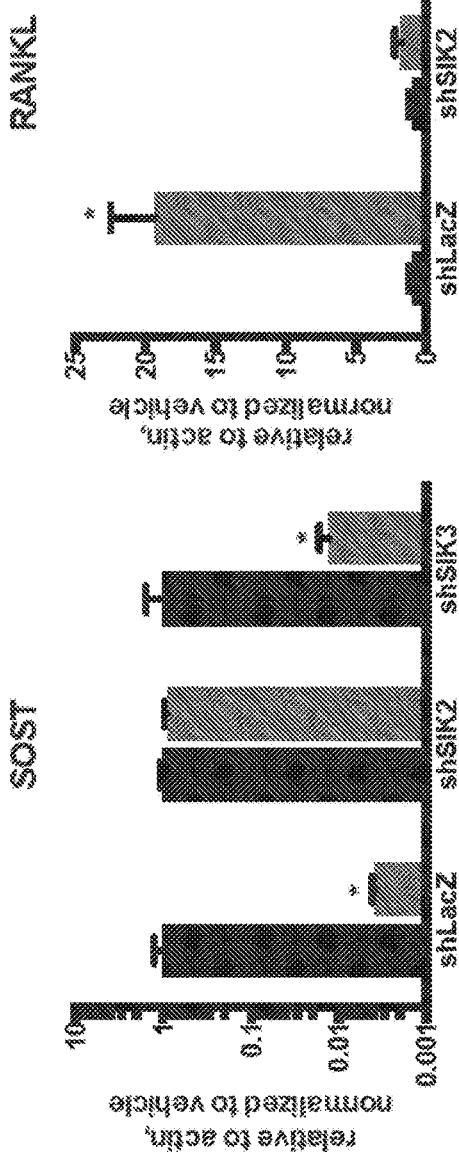

FIGS. 4A to 4M: SIK2 is an HDAC4/5 N-terminal kinases whose activity is regulated by PTH signaling. (FIG. 4A) Ocy454 cells were infected with the indicated combination of shRNA-expressing lentiviruses, and whole cell lysates were analyzed by immunoblotting as indicated. (FIG. 4B) Ocy454 cells were treated with vehicle or PTH (50 nM) for 30 minutes, and whole cell lysates were analyzed by immunoblotting using phospho-specific antibodies. In the bottom panels, SIK3 immunoprecipitation was performed first, followed by immunoblotting as indicated. pPKA is an antibody that recognizes a degenerate consensus PKA substrate motif. (FIG. 4C) Ocy454 cells were treated with PTH (50 nM) for the indicated times. Whole cell lysates were generated followed by immunoblotting as indicated. (FIG. 4D) Ocy454 cells infected with either control (shLacZ), shSIK2-, or shSIK3-expressing lentiviruses were treated with PTH (1 nM) for 4 hours. RNA was isolated and Cited1 RNA transcript abundance was measured by RT-qPCR. * indicates p<0.05 comparing vehicle and PTH for each cell line. In FIG. 4D, for each cell line, the left bar refers to vehicle, and the right bar refers to PTH. (FIG. 4E) Control and shSIK2 cells were treated with PTH (50 nM for 30 minutes) and then analyzed as in FIG. 4B. (FIGS. 4F to 4G) Control, shSIK2, and shSIK3 cells were treated as in FIG. 4D, and SOST and RANKL transcript abundance measured by RT-qPCR. * indicates p<0.05 comparing vehicle and PTH. In FIGS. 4F to 4G, for each cell line, the left bar refers to vehicle, and the right bar refers to PTH. (FIG. 4H) Left, control and shSIK2 cells were treated with vehicle, PTH (25 nM), or forskolin (FSK, 5 µg/mL) for 30 minutes followed by cAMP radioimmunoassay. Middle/right, cells were treated with PTH (2.5 nM) or forskolin (500 ng/mL) for 4 hours, gene expression was analyzed by RT-qPCR. * indicates p<0.05 comparing vehicle and treatment. (FIG. 4I) RNA from femurae of 5 week old WT (SIK2 f/f) or SIK2$^{OcyKO}$ (SIK2 f/f; DMP1-Cre) mice (n=3/group) was isolated and SIK2 and PTH receptor (PPR) transcripts were measured by RT-qPCR. * indicates p<0.001 comparing WI and SIK2 cKO mice. (FIGS. 4J to 4K) Mice as in FIG. 4I were treated with a single dose of PTH (1 mg/kg) and sacrificed 2 hours later. Bone RNA was isolated from bilateral femurae and expression of Cited1, SOST, and RANKL was determined by RT-qPCR. * indicates p<0.05 comparing vehicle and PTH within a given genotype. (FIG. 4L) Ocy454 cells were infected with shRNA-expressing lentiviruses targeting CRTC1, CRTC2, or CRTC3. Cells were then treated with PTH (1 nM for 4 hours) and RANKL transcript abundance was measured by RT-qPCR. In FIG. 4L, for each cell line, the left bar refers to vehicle, and the right bar refers to PTH. (FIG. 4M) Ocy454 cells were treated with vehicle or PTH (20 nM for 60 minutes) followed by chromatin immunoprecipitation for CRTC2. Recovered DNA was quantified by qPCR using primer pairs detecting the indicated regions of the RANKL enhancer (based on enhancers described by (44)) and data are expressed as fold enrichment versus control IgG ChIP. * indicates p<0.05 comparing vehicle and PTH. The −23 kB and −75 kB enhancers correspond to the previously-described "D2" and "D5" enhancers. In FIG. 4D, the left bars correspond to vehicle, and the right bars correspond to PTH.

Figure 5A:
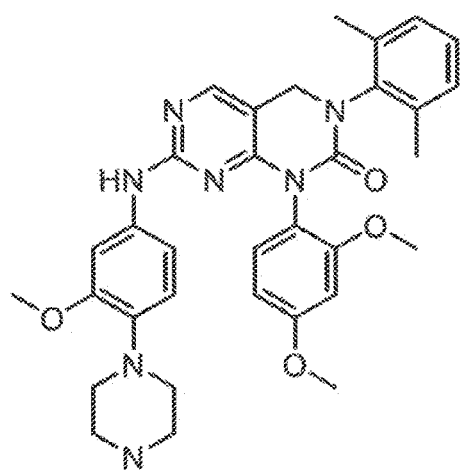
Figure 5A:
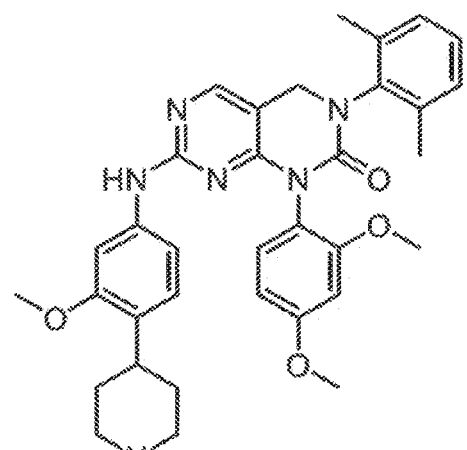
Figure 5A:
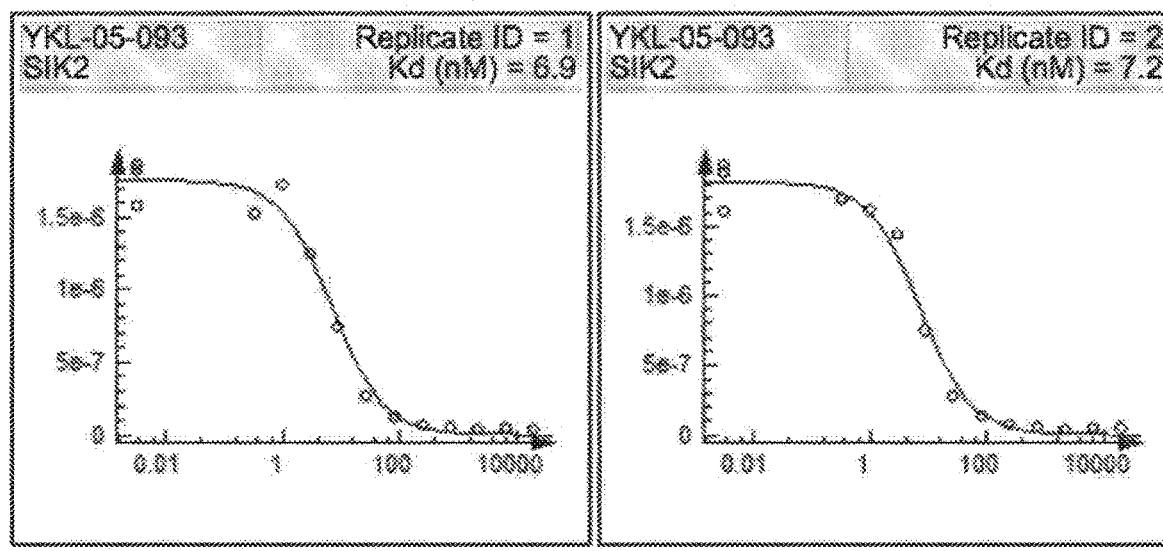
Figure 5B:
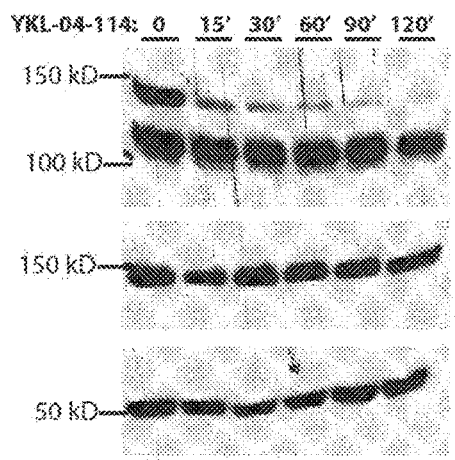
Figure 5C:
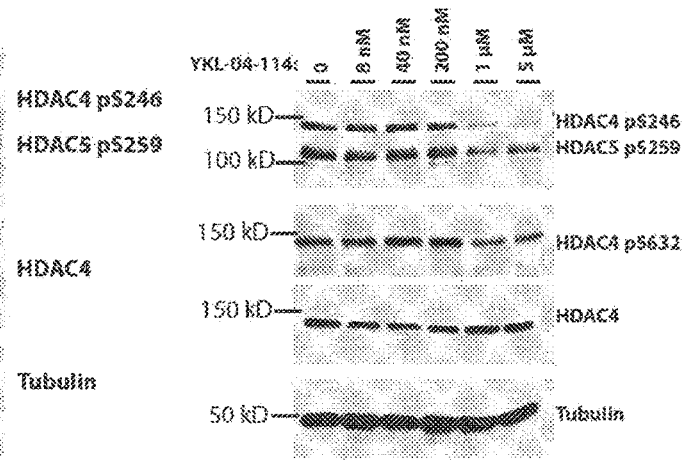

FIGS. 5A to 5J: Small molecule SIK inhibitors regulate SOST and RANKL expression by osteocytes. (FIG. 5A) Structure of YKL-04-114 (top panel, left), YKL-05-093 (top panel, right), and YKL-05-093 $K_d$ determination curves for SIK2 (bottom panels). For the $K_d$ determination curves, the y-axis represents the amount of bound kinase measured by qPCR (see methods), and the x-axis represents the corresponding compound concentration in nM. (FIG. 5B) Ocy454 cells were treated with YKL-04-114 (10 µM) for the indicated times, followed by immunoblotting of whole cell lysates as indicated, (FIG. 5C) Ocy454 cells were treated with the indicated concentrations of YKL-04-114 for 60 minutes, followed by immunoblotting of whole cell lysates as indicated. (FIG. 5D) Left: Ocy454 cells were treated with vehicle, PTH (50 nM), or YKL-05-093 (10 µM) for 60 minutes. Cytosol and nuclear fractions were then generated, followed by immunoblotting as indicated. Right: quantification of nuclear fraction (defined as nuclear/total) of HDAC4 or CRTC2. * indicates p<0.01 comparing treatment vs vehicle. (FIG. 5E) Top: Ocy454 cells were treated with the indicated concentrations of YKL-04-114 for 4 hours, followed by RT-qPCR. Bottom: Cells were treated with YKL-04-114 (0.5 µM) for the indicated times. * indicates p<0.05 comparing treatment vs vehicle. (FIG. 5F) Cells lacking SIK2, SIK3 or both were treated with YKL-05-093 (10 µM for 45 minutes). Quantification of HDAC4 S246 phosphorylation, as assessed by densitometric analysis of immunoblots, is shown. * indicates p<0.01 comparing treatment vs vehicle, # indicates p<0.05 for the same comparison. In FIG. 5F, for each cell line, the left bar refers to vehicle, and the right bar refers to YKL-05-093. (FIG. 5G) Control and SIK2/3 deficient cells were treated with YKL-05-093 (0.5 µM) for 4 hours and SOST transcript abundance was measured by RT-qPCR. (FIG. 5H) Control and CRTC2 shRNA cells were treated with PTH (1 nM) or YKL-05-093 (0.5 µM) for 4 hours and RANKL transcript abundance was measured by RT-qPCR. (FIG. 5I) Control and Gsα-deficient Ocy454 cells were treated with PTH (1 nM), YKL-05-093 (0.5 µM), or forskolin (5 µg/mL) and SOST and RANKL transcript abundance was determined by RT-qPCR. For FIGS. 5H and 5I, * indicates p<0.05 comparing treatment and vehicle. (FIG. 5J) Control and Gsα-deficient Ocy454 cells were treated with PTH (50 nM), YKL-05-093 (10 µM), or forskolin (5 mg/mL) for 30 minutes. Whole cell lysates were generated and immunoblotted as indicated.

Figure 6A:
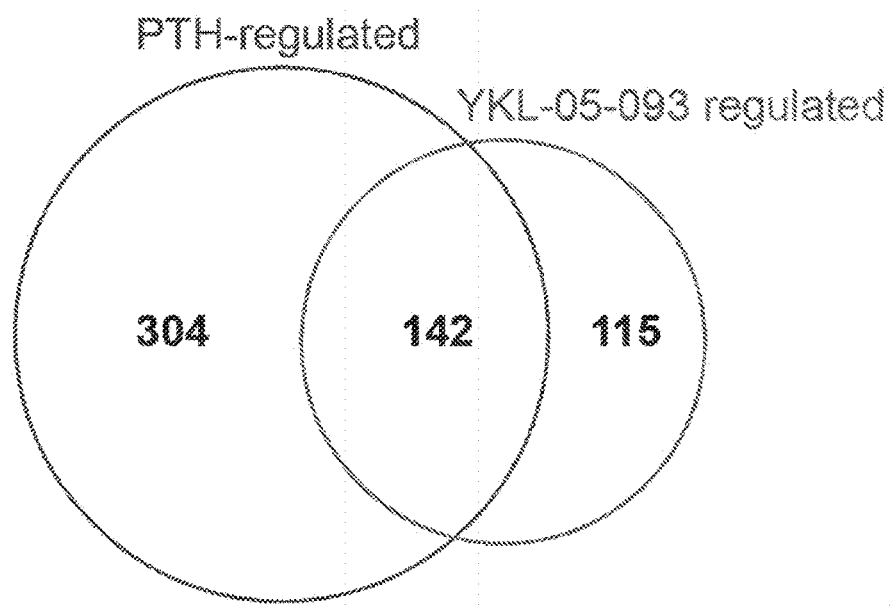
Figure 6B:
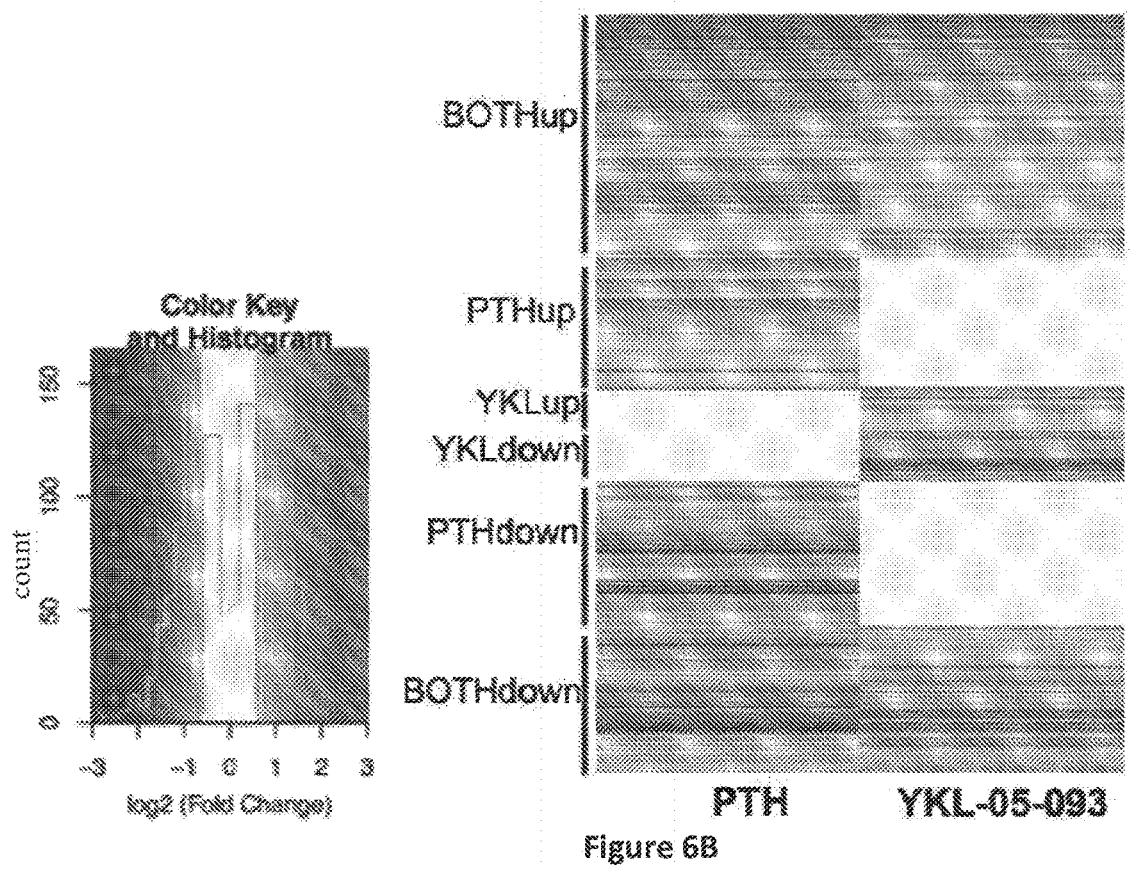
Figure 6C:
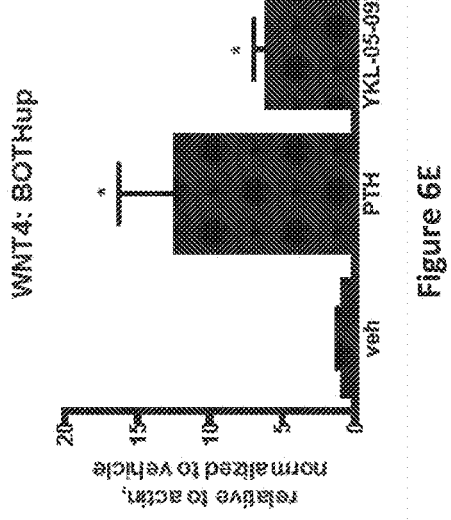
Figure 6D:
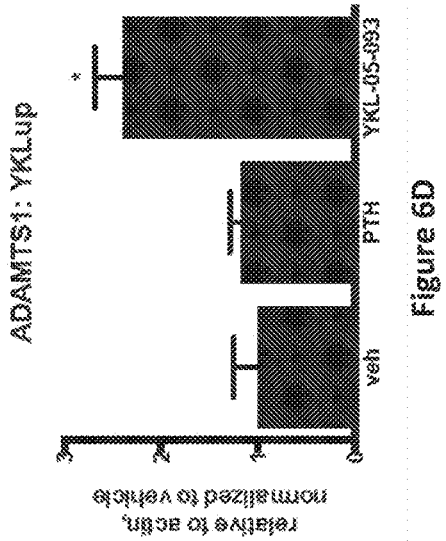
Figure 6E:
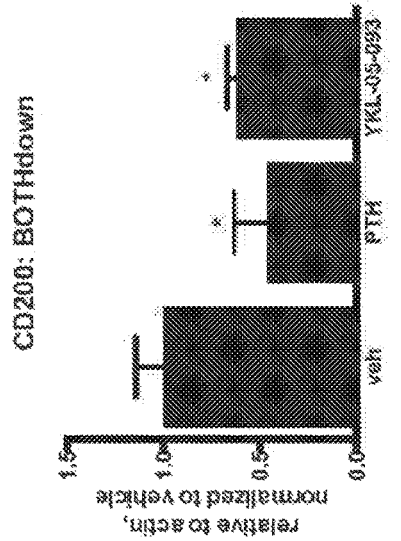
Figure 6F:
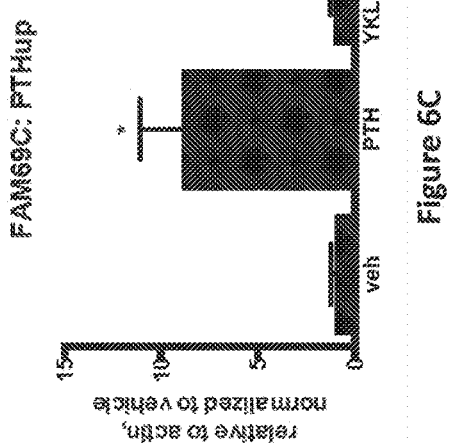
Figure 6G:
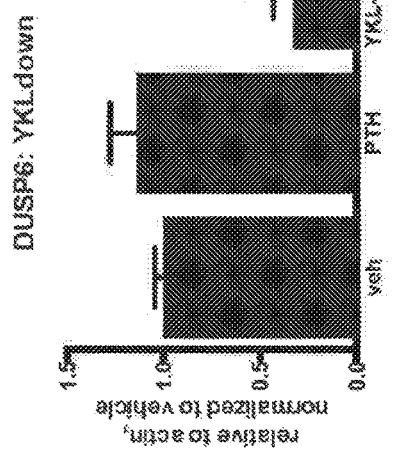
Figure 6H:
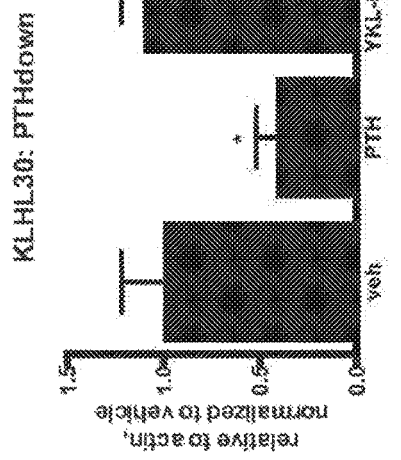
Figures 6I, 6J:
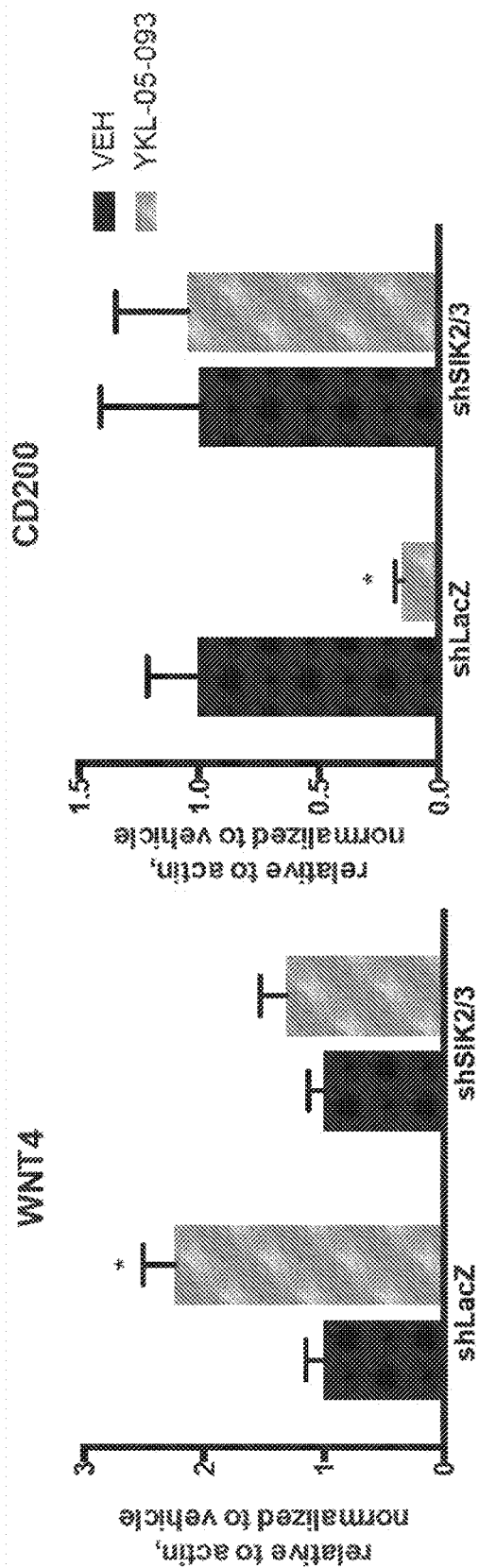

FIGS. 6A to 6J: YKL-05-093 effects on gene expression significantly overlap with PTH. (FIG. 6A) Venn diagram showing overlap between differentially-expressed genes (fold chance>2, FDR<0.05) determined by RNA-Seq from Ocy454 cells treated with vehicle, PTH (1 nM), or YKL-05-093 (0.5 µM) for 4 hours. (FIG. 6B) Heat map showing 6 different clusters of differentially expressed genes. Each row corresponds to a single differentially expressed gene. Color coding is with respect to the average log 2 (fold change) for each gene comparing treatment to vehicle. Genes were ordered by the strength of the significance of the fold change comparing PTH and vehicle. (FIGS. 6C to 6H) Ocy454 cells were treated with vehicle, PTH (1 nM), and YKL-05-093 (0.5 μM) for 4 hours, and RT-qPCR was performed for the indicated gene. FAM69C and KLHL30 are regulated by PTH alone, ADAMTS1 and DUSP6 are regulated by YKL-05-093 alone, and WNT4 and CD200 are regulated by both PTH and YKL-05-093. (FIGS. 6I to 6J) Control and SIK2/3 deficient cells were treated with vehicle or YKL-05-093 (0.5 μM) for 4 hours, and WNT4 and CD200 transcript abundance determined by RT-qPCR. For all panels, * indicates p<0.05 comparing vehicle and compound or PTH treatment by Student's unpaired 2 tailed t-test. In FIGS. 6I to 6J, for each cell line, the left bar refers to vehicle, and the right bar refers to YKL-05-093.

FIGS. 7A to 7I: Effects of YKL-05-093 administration on bone gene expression in vivo. (FIGS. 7A and 7B) 8 week old C57B/6 mice (n=4/group) were treated with the indicated dose of YKL-05-093 via intraperitoneal injection. 2 hours later, bone RNA was isolated and transcript abundance was measured by RT-qPCR. # indicates p<0.05 versus vehicle, and * indicates p<0.01 versus vehicle by Student's unpaired 2 tailed t-test. (FIG. 7C) Left: sclerostin immunohistochemistry was performed 2 hours after intraperitoneal injection with either vehicle or YKL-05-093 (20 μmol/kg). Right: quantification of sclerostin-positive cortical osteocytes, n=4 mice per treatment group, * indicated p<0.01 versus vehicle. (FIGS. 7D to 7I) Genes regulated by PTH and YKL-05-093 in vitro are also regulated by YKL-05-093 in vivo. Mice were treated with YKL-05-093 (20 μmol/kg) and bone RNA collected 2 hours later as in FIG. 7A. * indicates p<0.05 versus vehicle. In FIGS. 7A, 7B, and 7D to 7I, "umol" denotes μmol. In FIGS. 7D to 7I, each of the right bars corresponds to YKL-05-093.

Figure 8A:
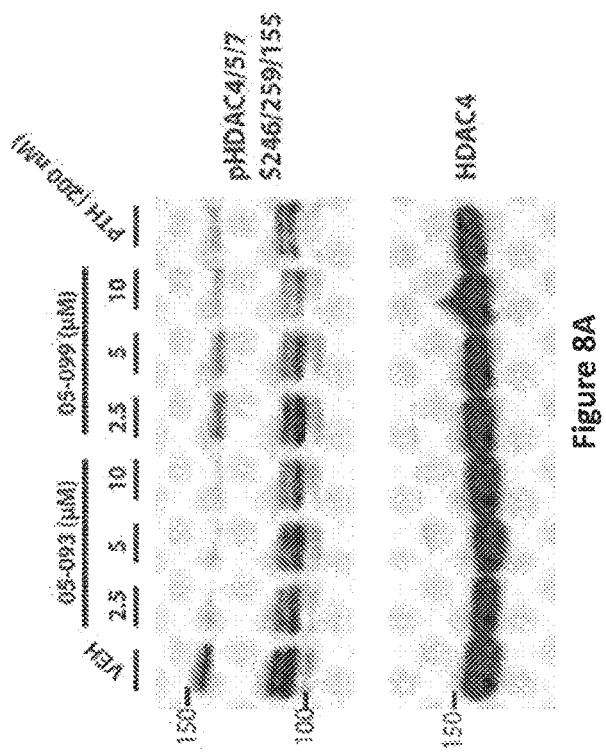
Figure 8B:
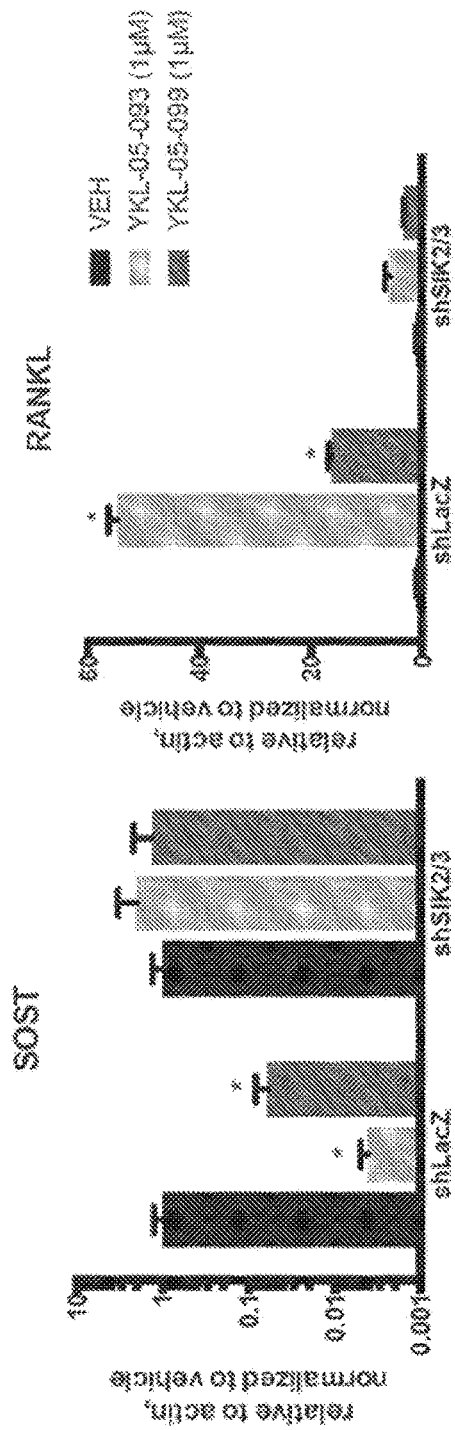
Figure 8K:
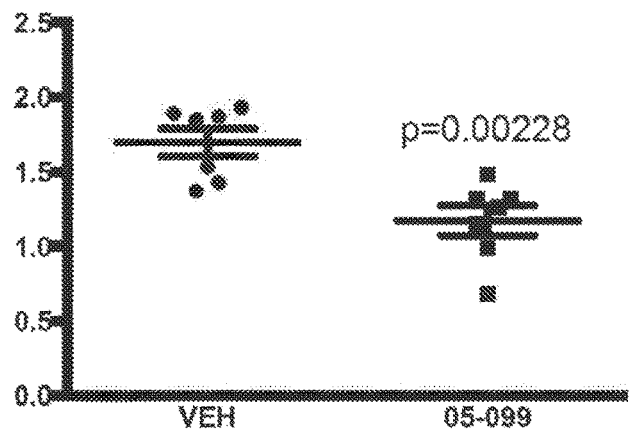
Figure 8L:
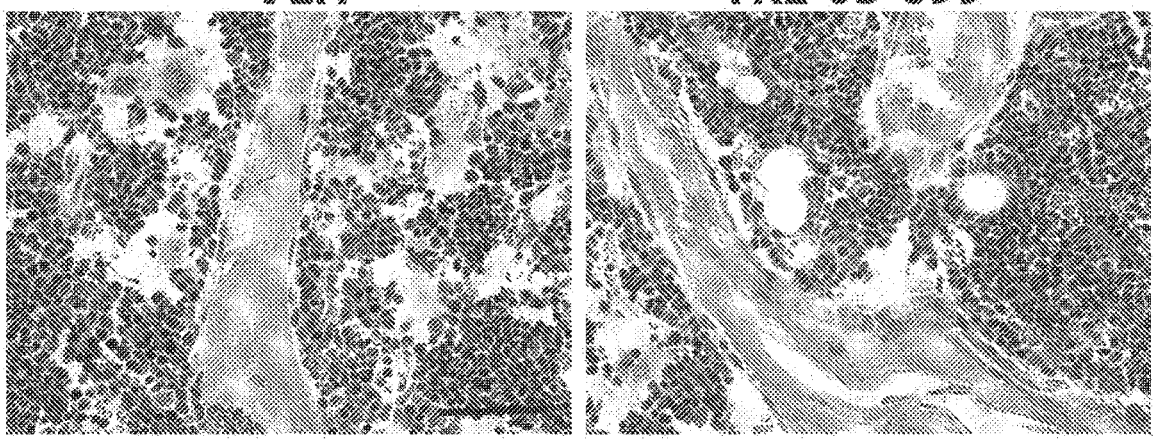
Figure 8M:
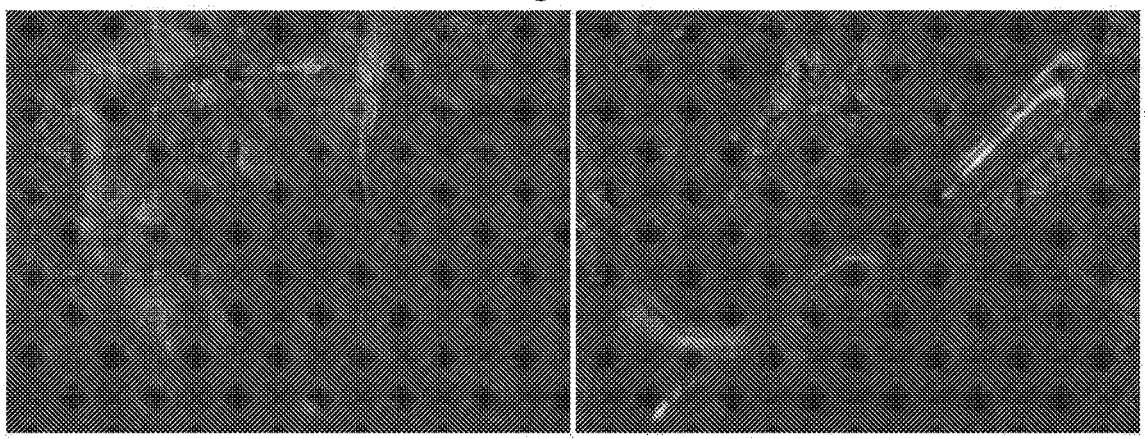

FIGS. 8A to 8M: YKL-05-099 (05-099) increases bone formation and bone mass in vivo. (FIG. 8A) Ocy454 cells were treated with the indicated doses of YKL-05-093 (05-093), YKL-05-099, or PTH for 20 minutes. Whole cell extracts were generated, followed by immunoblotting. (FIG. 8B) Control or shSIK2/3 Ocy454 cells were treated with YKL-05-093 or YKL-05-099 (1 μM) for 4 hours. RNA was prepared, and gene expression analyzed by RI-qPCR. Both YKL-05-093 and YKL-05-099 regulate SOST and RANKL expression in control, but not SIK2/3-deficient cells. (FIG. 8C) 8 week old male mice (n=5/group) were treated with a single I.P. dose of YKL-05-099 (20 μmol/kg) or vehicle. 2 hours later, animals were sacrificed, RNA was prepared from femurs, and gene expression analyzed by RT-qPCR. SOST down-regulation was observed in response to YKL-05-099, but the p value for this difference was 0.105. * indicates p<0.01. (FIG. 8D) 8 week old male mice were treated with vehicle (n=8) or YKL-05-099 (n=7, 10 μmol/kg, I.P.) once daily 5 days per week for 2 weeks. Animals were sacrificed 2 hours after the final dose, and RNA from femurs analyzed for the indicated genes. BGLAP encodes osteocalcin. * indicated p<0.01 versus vehicle, # indicates p<0.05 versus vehicle. (FIGS. 8E to 8K), static and dynamic histomorphometry were performed on the tibia from the same mice as in FIG. 8D. Each data point represents an individual mouse, p values for each difference are shown on the graph. (FIG. 8L) Representative photomicrograph showing increased osteoblasts on cancellous bone surfaces from YKL-05-099-treated mice. (FIG. 8M) Dual calcein/demeclocycline images demonstrating increased mineralizing surface in YKL-05-099-treated mice. In FIG. 8M, the left panel corresponds to vehicle, and the right panel corresponds to YKL-05-099.

Figure 9:
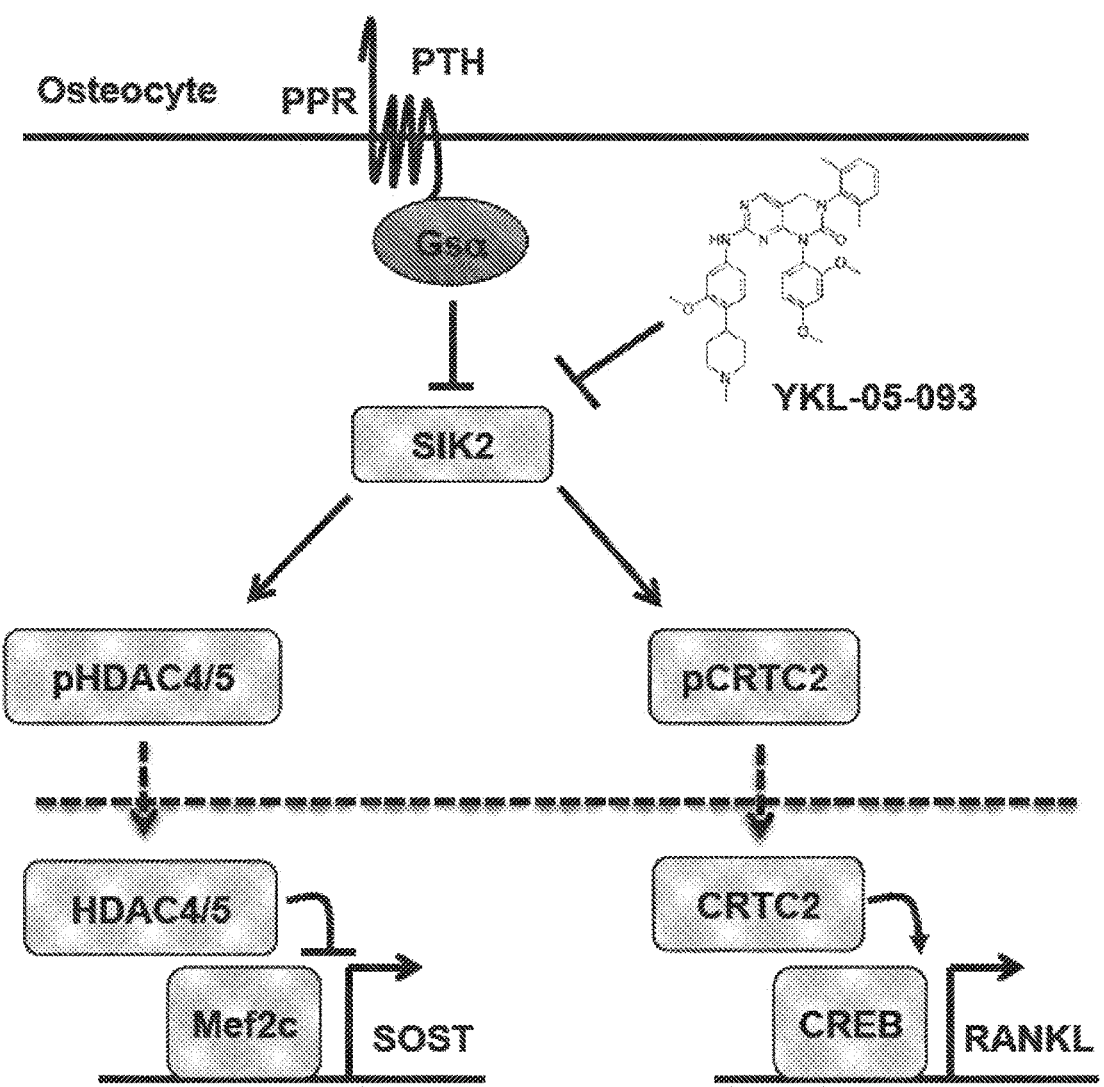

FIG. 9: Model showing PTH signaling via inhibition of SIK2 in osteocytes. In the absence of PTH signaling, SIK2 tonically phosphorylates its substrates HDAC4/5 and CRTC2, leading to their cytoplasmic retention. PTH signaling leads to PKA-mediated phosphorylation of SIK2 which inhibits its cellular activity. This in turn reduces phosphorylation of HDAC4/5 and CRTC2, leading to their nuclear translocation. In the nucleus, HDAC4/5 block MEF2C-driven SOST expression, while CRTC2 enhances CREB-mediated RANKL gene transcription.

FIGS. 10A to 10E. (FIG. 10A) Cortical and (FIG. 10B) trabecular micro-CT results from 8 week old mice of the indicated compound heterozygous genotype. The high bone mass observed in SOST+/− mice is not observed in SOST/HDAC5 compound heterozygotes. (FIG. 10C) Representative sagittal images from mice analyzed in FIGS. 10A and 10B. (FIG. 10D) Male WT (n=5), HDAC4$^{OcyKO}$ (n=6), HDAC5−/− (n=5), and DKO (n=6) mice were treated with anti-sclerostin antibody (50 mg/kg) twice weekly from 2 to 8 weeks of age. Distal femur BV/TV was determined by micro-CT. 2 way ANOVA analysis revealed a significant interaction between genotype and Scl-Ab treatment, therefore post-hoc t tests were performed to determine effects of Scl Ab treatment within each genotype. Individual p values for each comparison are noted on the graph. (FIG. 10E) Dual calcein/demeclocycline images showing reduced endocortical bone formation in DKO mice.

FIGS. 11A to 11I. (FIG. 11A) Ocy454 cells were treated with the indicated concentrations (in molar) of PTH for 30 minutes, followed by immunoblotting as indicated. (FIG. 11B) Immunoblots from individual single cell clones isolated after exposure to Gsα sgRNA/Cas9 targeting the indicated GNAS exon. Clones 11 and 17 show intact Gsα expression, while the other clones show no detectable Gsα protein. Clone 8, not shown here, also was isolated after exposure to the sgRNA sequence targeting GNAS exon 1. (FIG. 11C) WT and Gsα KO cells were treated with the indicated concentrations of PTH and cAMP levels were measured by RIA 20 minutes later. No detectable PTH-induced increases in cAMP were observed in cells lacking Gsα. (FIG. 11D) As in FIG. 11C, except cells were treated with other agents known to stimulate cAMP production. (FIG. 11E) WT and Gsα null cells were treated with the indicated concentrations of PTH and analyzed by immunoblotting as in FIG. 11A. (FIG. 11F) Cells lacking Gsα were infected with control or MEF2C shRNA lentiviruses, followed by immunoblotting as indicated. (FIG. 11G) Cells from FIG. 11F were allowed to differentiate for the indicated times at 37° C., and sclerostin ELISAs were then performed from the conditioned medium. While Gsα KO cells showed increased sclerostin secretion, MEF2C shRNA abrogates this effect. (FIG. 11H) Cells lacking Gsα were infected with lentiviruses to over-express HDAC5 S/A (S259/498A) and analyzed by immunoblotting. (FIG. 11I) Cells from FIG. 11H were analyzed as in FIG. 11G. HDAC5 S/A overexpression dramatically reduces sclerostin secretion by Gsα deficient cells.

FIGS. 12A to 12F. (FIG. 12A) Immunoblot showing Ocy454 cells uninfected with lentivirus, infected with control lentivirus (LV-GFP), or infected with lentivirus overexpressing FLAG-tagged Cas9. (FIG. 12B) Sclerostin ELISA demonstrating no effect of Cas9 expression on Ocy454 cell sclerostin secretion in the absence of sgRNA co-expression. (FIG. 12C) Ocy454 cells were transfected with PX458 plasmid which co-expresses a sgRNA of interest, Cas9, and eGFP. 48 hours later, eGFP positive cells were sorted by flow cytometry into 96 well plates at a density of 1 cell per well. Clones were identified, expanded, and analyzed by immunoblotting. (FIG. 12D) Representative immunoblot of single cell clones isolated after exposure to an sgRNA targeting HDAC4. Starred clones show no detectable HDAC4 protein. (FIG. 12E) Genomic DNA was isolated from individual HDAC4 deficient clones followed by allele-specific sequencing. As shown in the example here, cells without HDAC4 protein show bi-allelic HDAC4 insertion/deletions resulting in frameshift mutations. N17 refers to the 17$^{th}$ nucleotide within the 20mer sgRNA sequence, where insertions/deletions are most likely to occur. The sequences, from top to bottom and left to right, correspond to SEQ ID NOs: 1-4. (FIG. 12F) Ocy454 cells were treated with PTH (1 nM) for the indicated times, and MEF2C transcript abundance was measured by RT-qPCR. # indicates p<0.05, and * indicates p<0.01 vs vehicle.

FIGS. 13A to 13J. (FIG. 13A) 8 week old female mice of the indicated genotypes were treated with vehicle or hPTH (1-34, 100 mcg/kg) once daily, 5 days per week, for 4 weeks. Micro-CT analysis of bone volume fraction of the primary spongiosa is shown. 2 way ANOVA revealed a significant (p<0.01) interaction between genotype and drug treatment. Therefore, posthoc t tests were performed comparing effects of vehicle and PTH within each genotype. * indicates p<0.01. (FIG. 13B) Ocy454 cells were treated with vehicle, PTH (50 nM), okadaic acid (OA, 300 nM), staurosporine (sts, 1 µM), or PTH plus okadaic acid. When okadaic acid was used, cells were pre-treated with this agent for 20 minutes. 30 minutes later, whole cell lysates were obtained followed by immunoblotting as indicated. Okadaic acid does not block the ability of PTH to induce HDAC4/5 dephosphorylation. (FIG. 13C) Ocy454 cells were treated with okadaic acid (300 nM), PTH (1 nM), and both. 4 hours later, RNA was isolated and SOST transcript abundance was analyzed by RT-qPCR. (FIG. 13D) Ocy454 cells were infected with control (shLacZ) or PP2A catalytic subunit (c.s.) shRNA-expressing lentiviruses. Cells were then treated with the indicated concentrations of PTH for 30 minutes followed by immunoblotting as indicated. (FIG. 13E) Cells from FIG. 13D were treated with the indicated concentrations of PTH and SOST transcript abundance was measured by RT-qPCR 4 hours later, (FIG. 13F) Control, shSIK2, and shSIK3 Ocy454 cells were subjected to subcellular fractionation followed by immunoblotting for the indicated proteins. (FIG. 13G) Control (shLacZ) and shSIK2 cells were treated with the indicated concentrations of PTH or isoproterenol (iso), and cAMP levels were determined by RIA. While shSIK2 cells show reduced cAMP levels at all doses compared to control cells, significant upregulation (versus vehicle) in these cells is noted at doses above 4 nM. (FIG. 13H) Ocy454 cells were infected with shRNAs targeting CRTC1, CRTC2, and CRTC3. Knockdown efficiency and specificity for each gene was then measured by RT-qPCR. (FIG. 13I) CRTC2 shRNAs effectively reduce CRTC2 protein levels. "1-1", "2-1", "2-2", "3-1", and "3-2" denote the gene CRTC targeted for shRNA-mediated knockdown. (FIG. 13J) CRTC2 knockdown cells show normal PTH-induced cAMP generation as measured by radioimmunoassay.

Figure 14A:
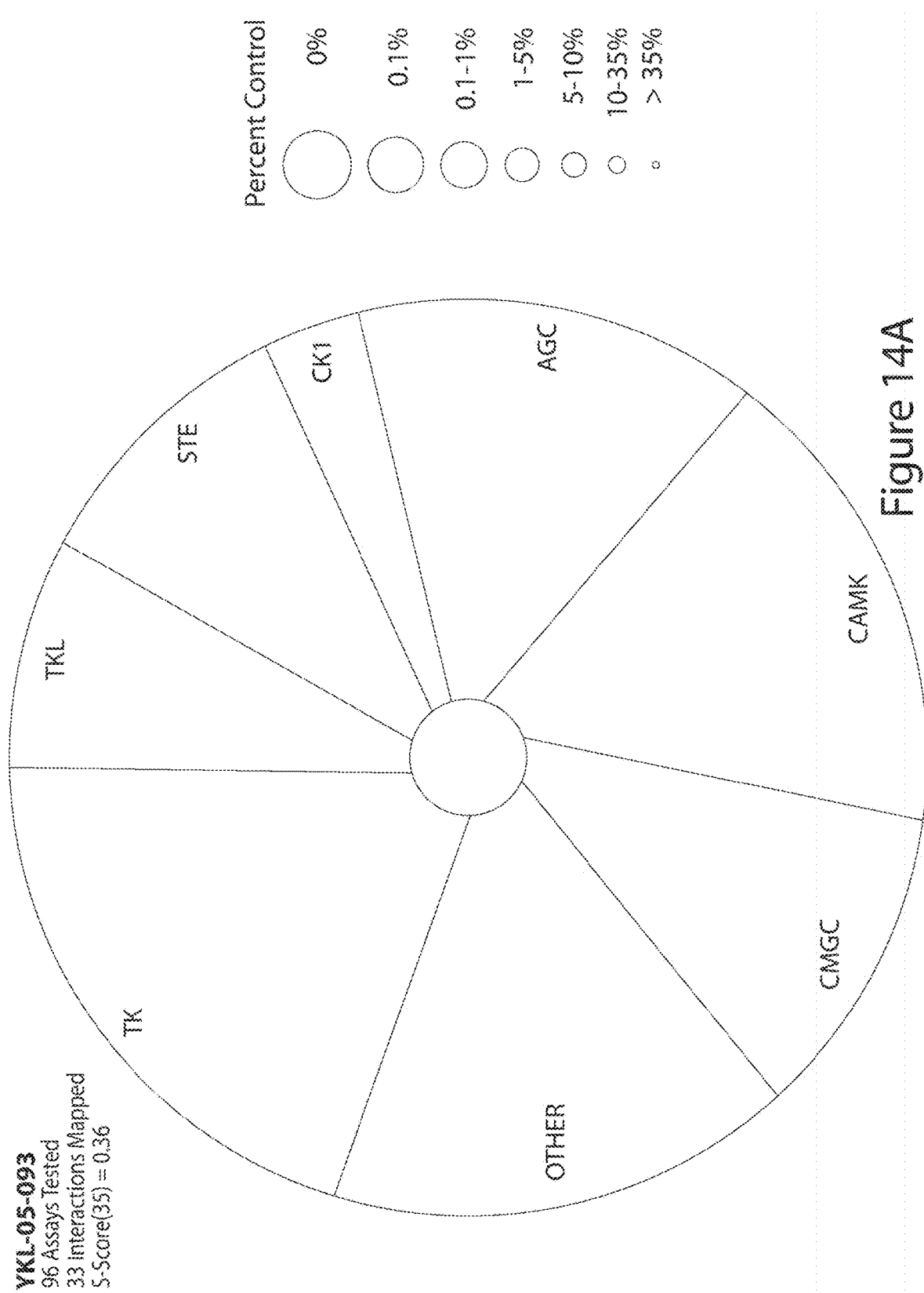
Figure 14A:
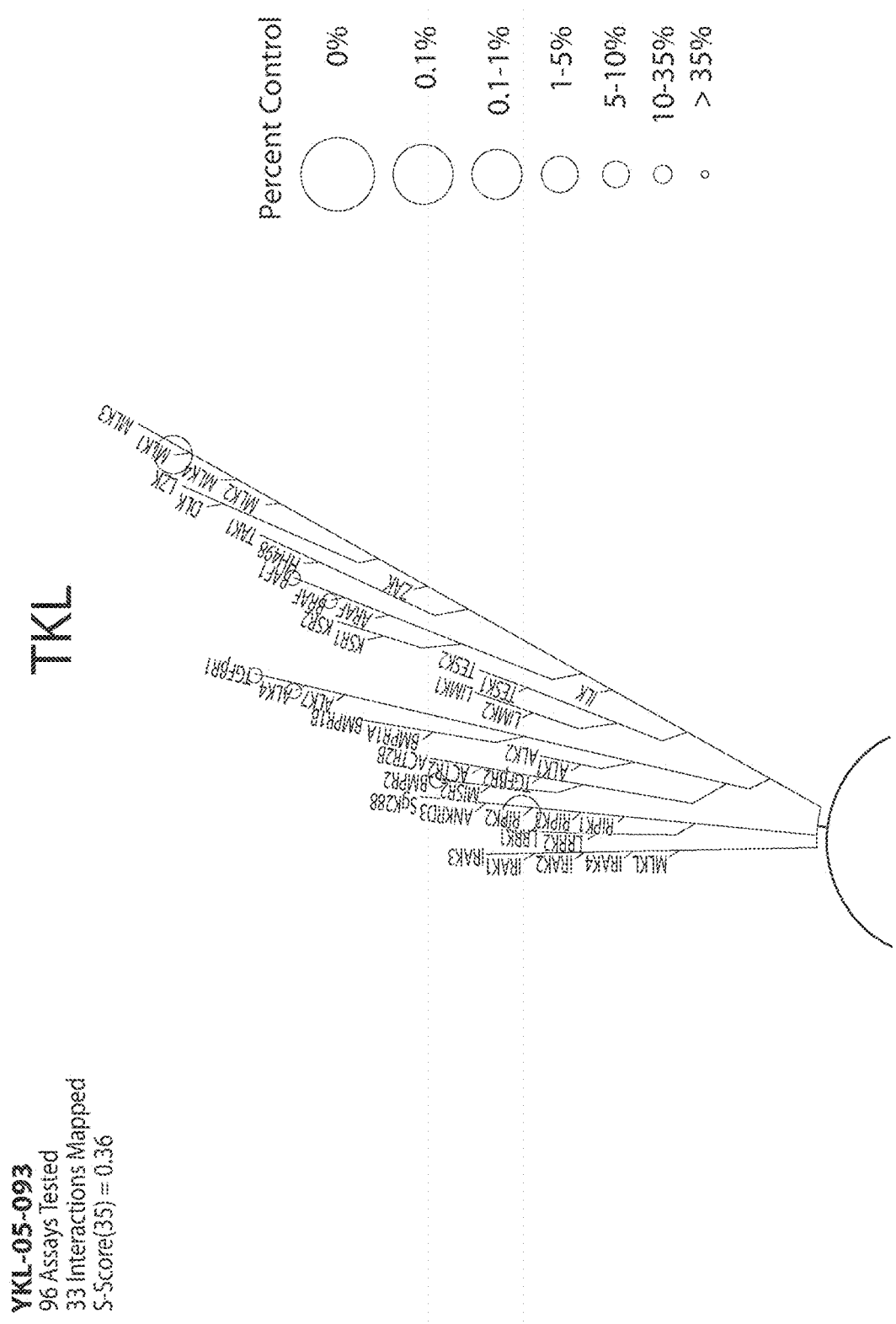
Figure 14A:
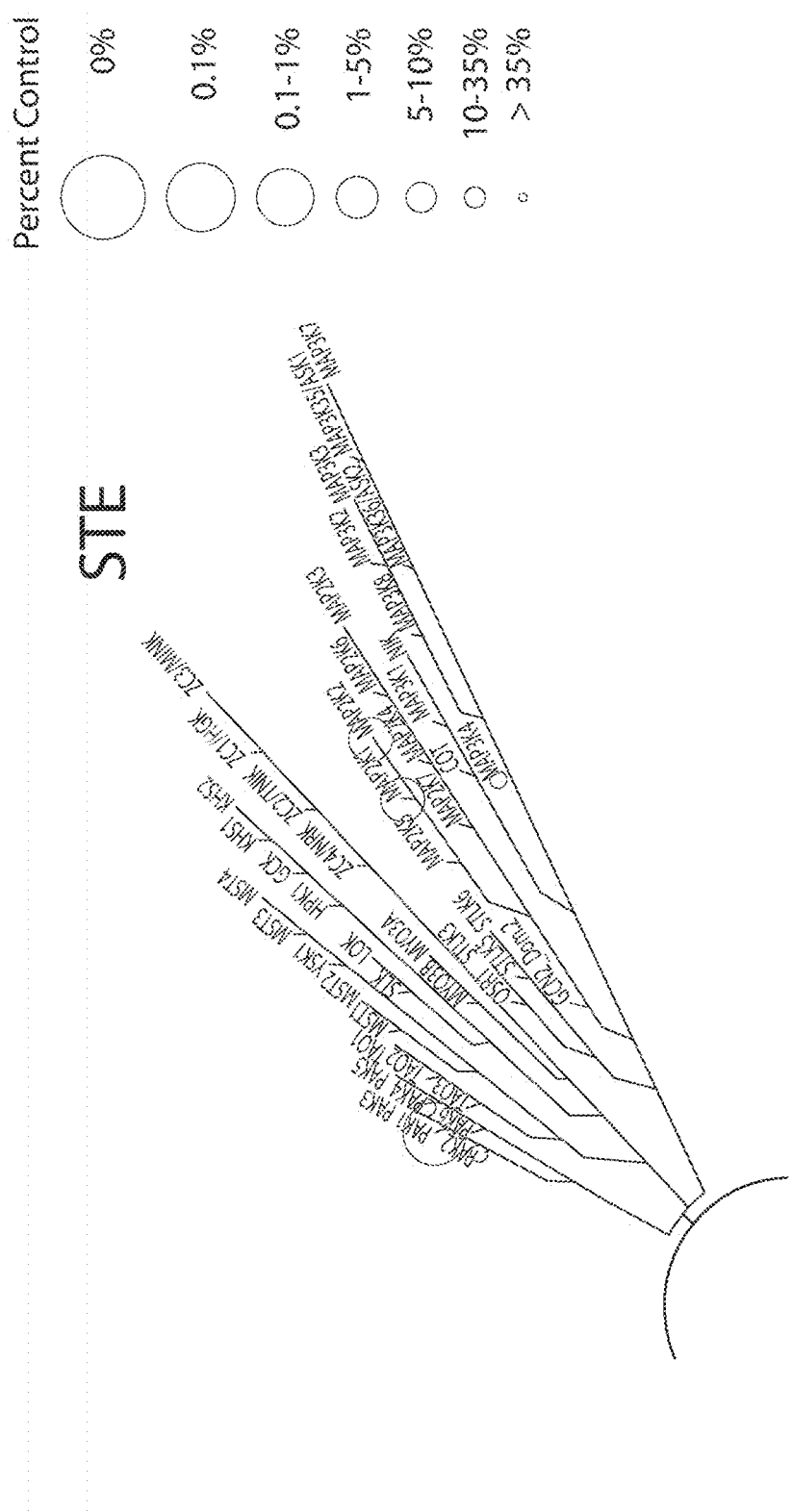
Figure 14A:
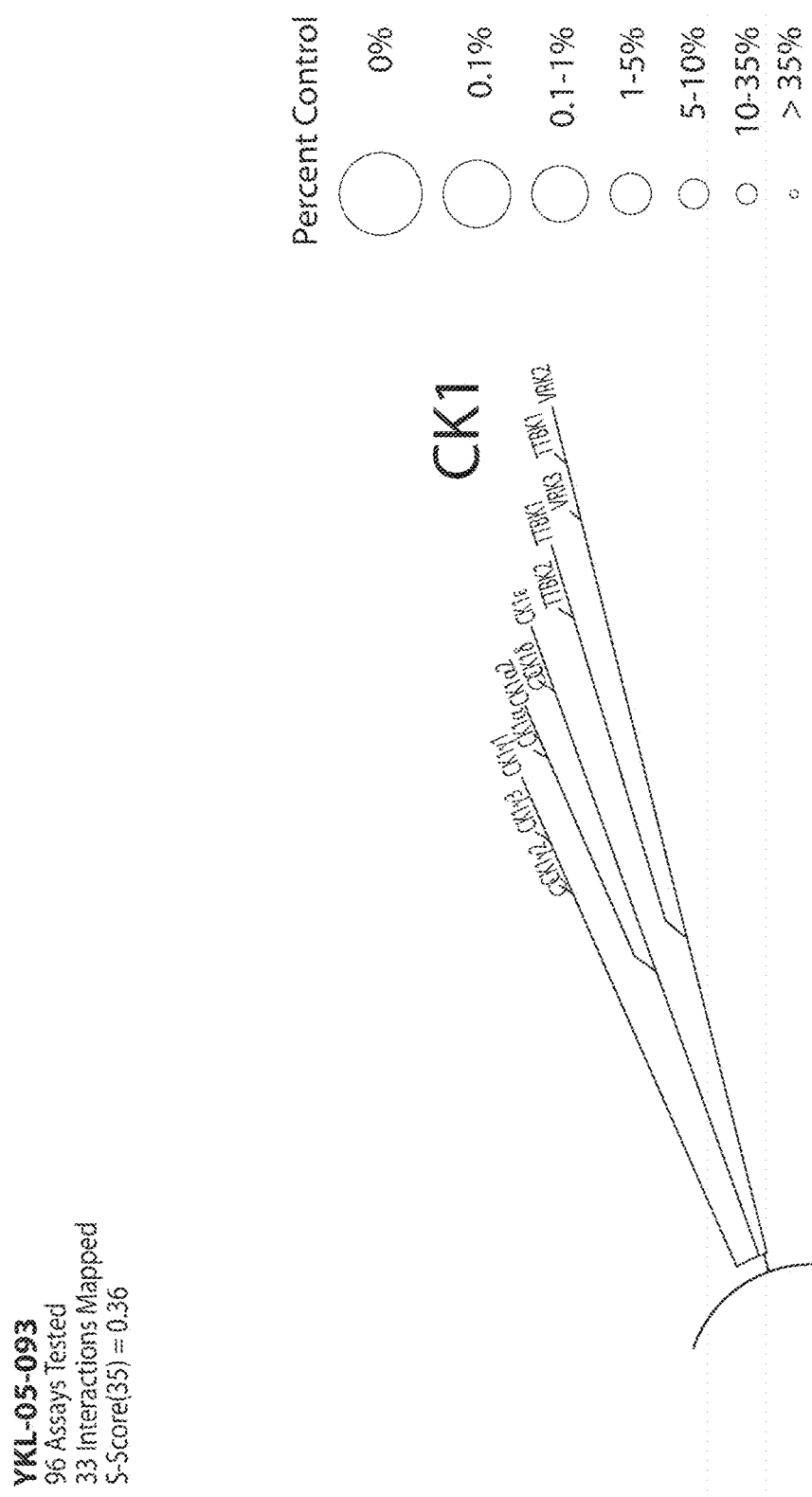
Figure 14A:
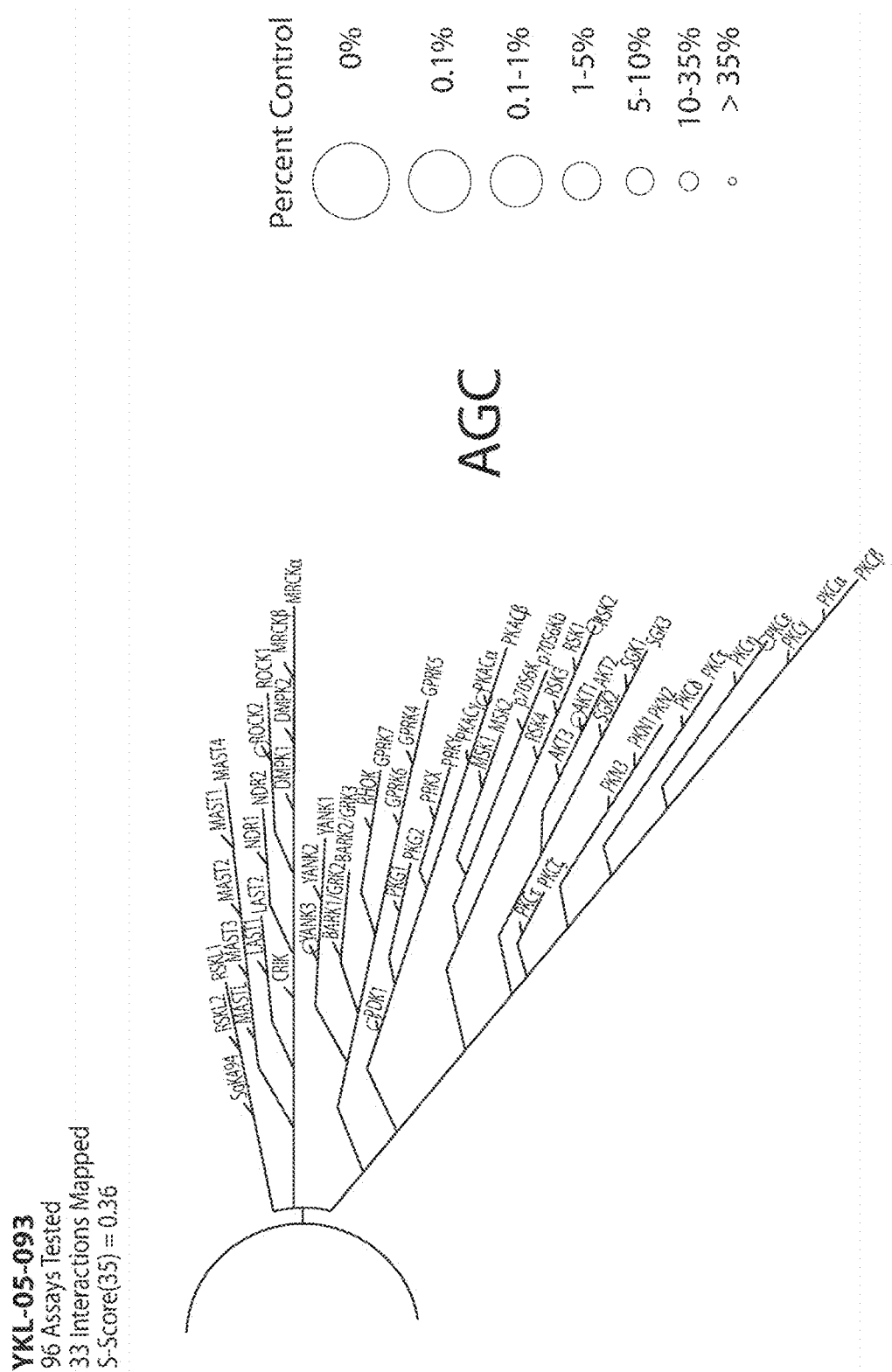
Figure 14A:
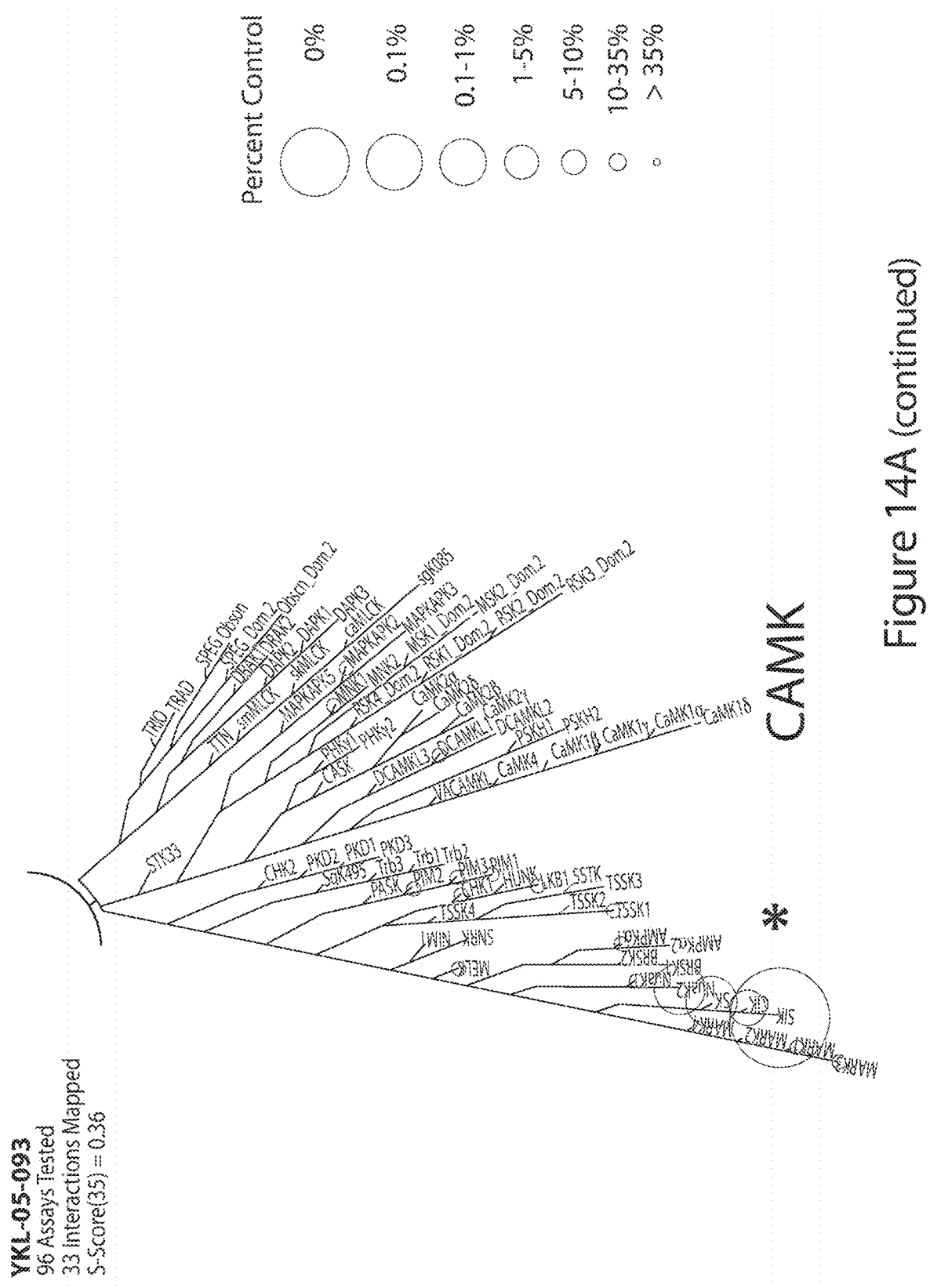
Figure 14A:
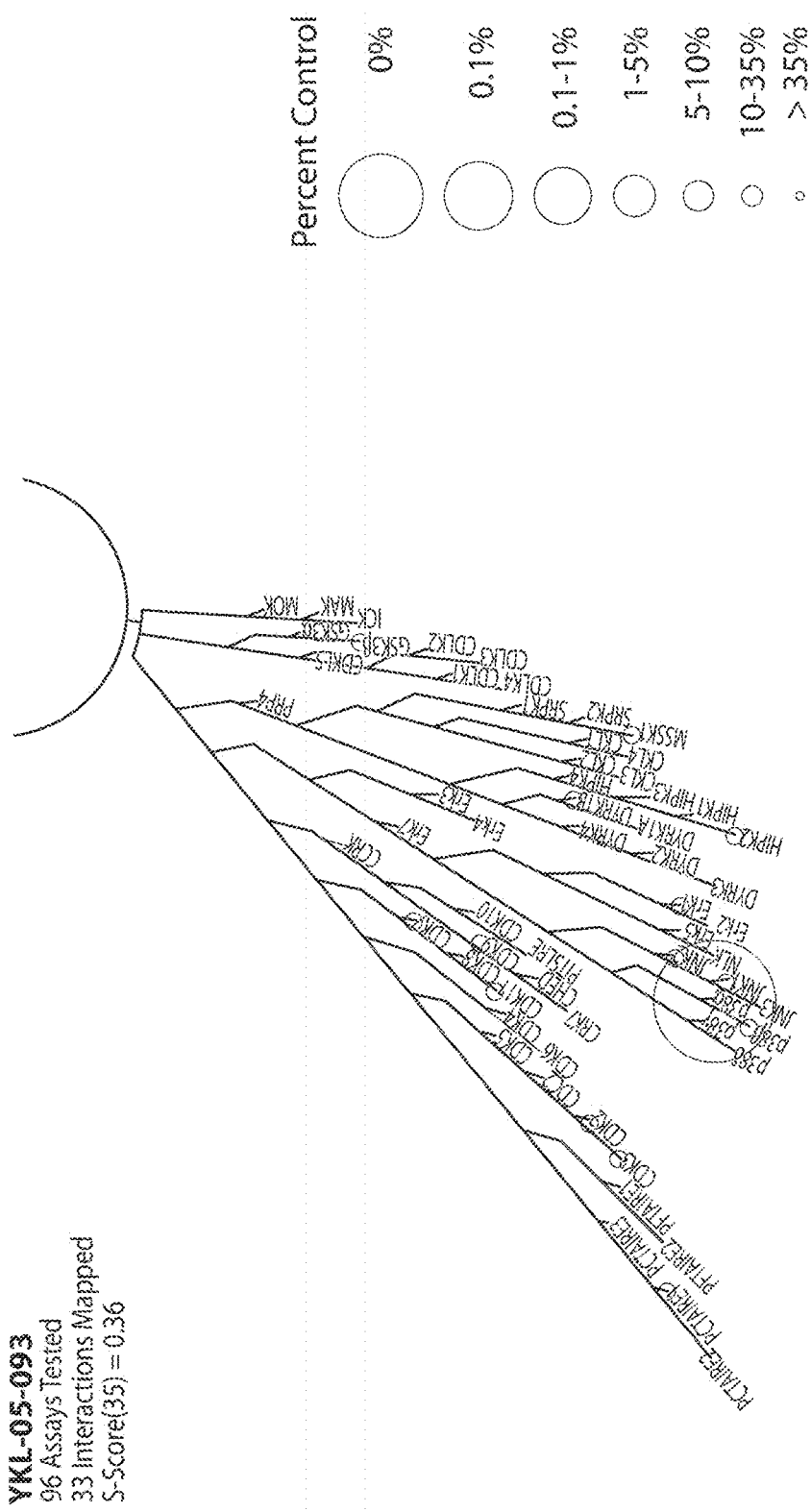
Figure 14A:
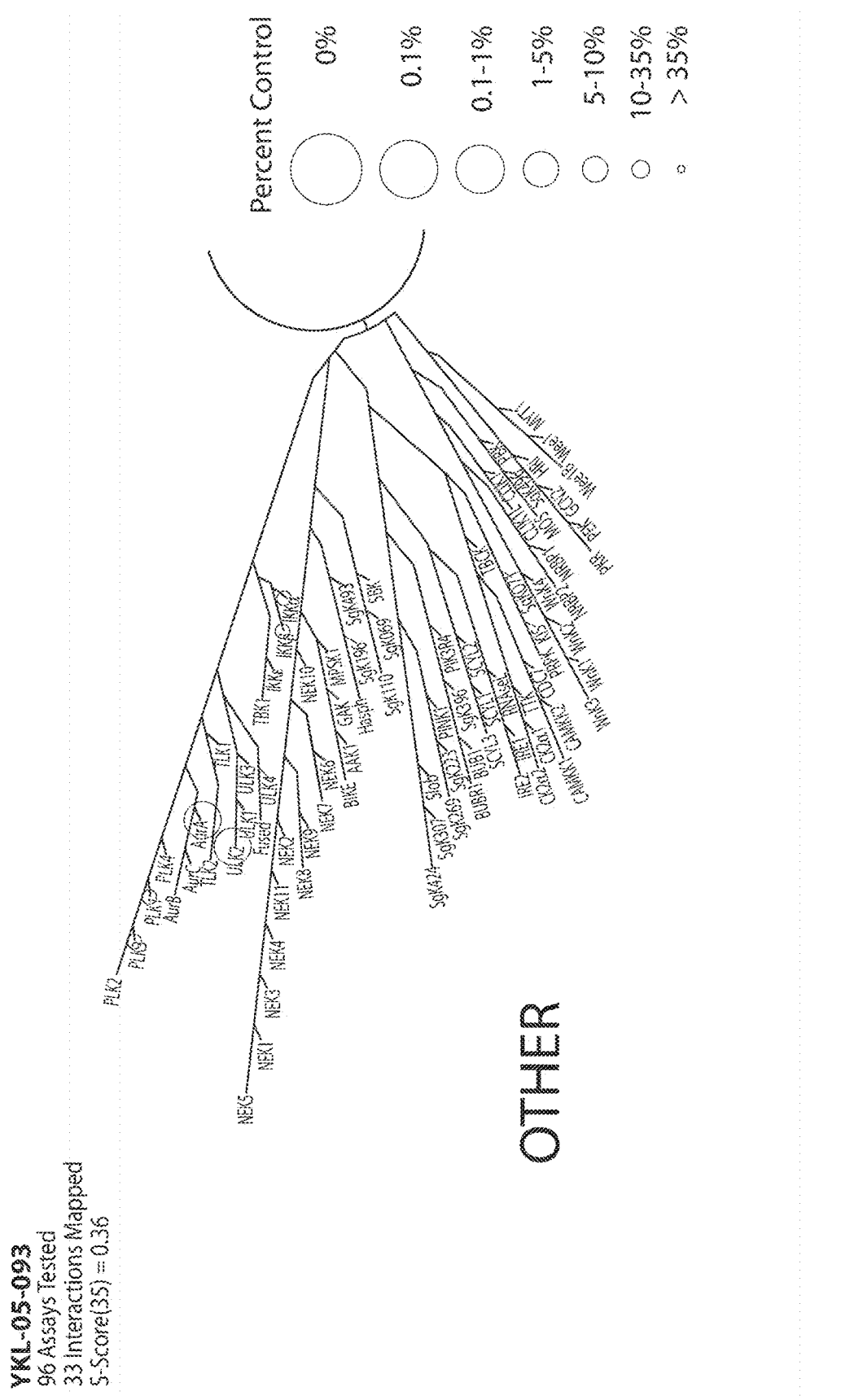
Figure 14A:
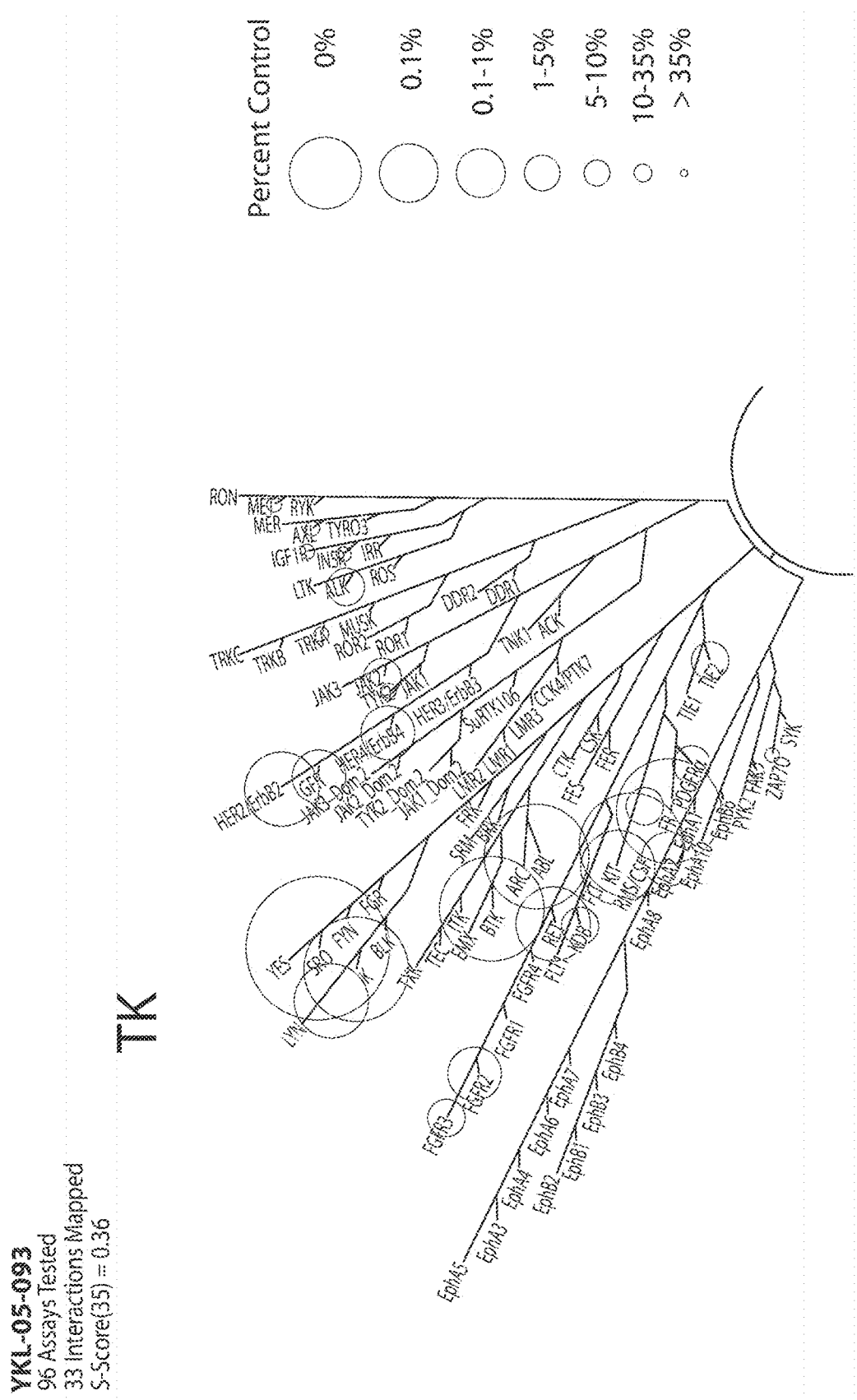
Figure 14B:
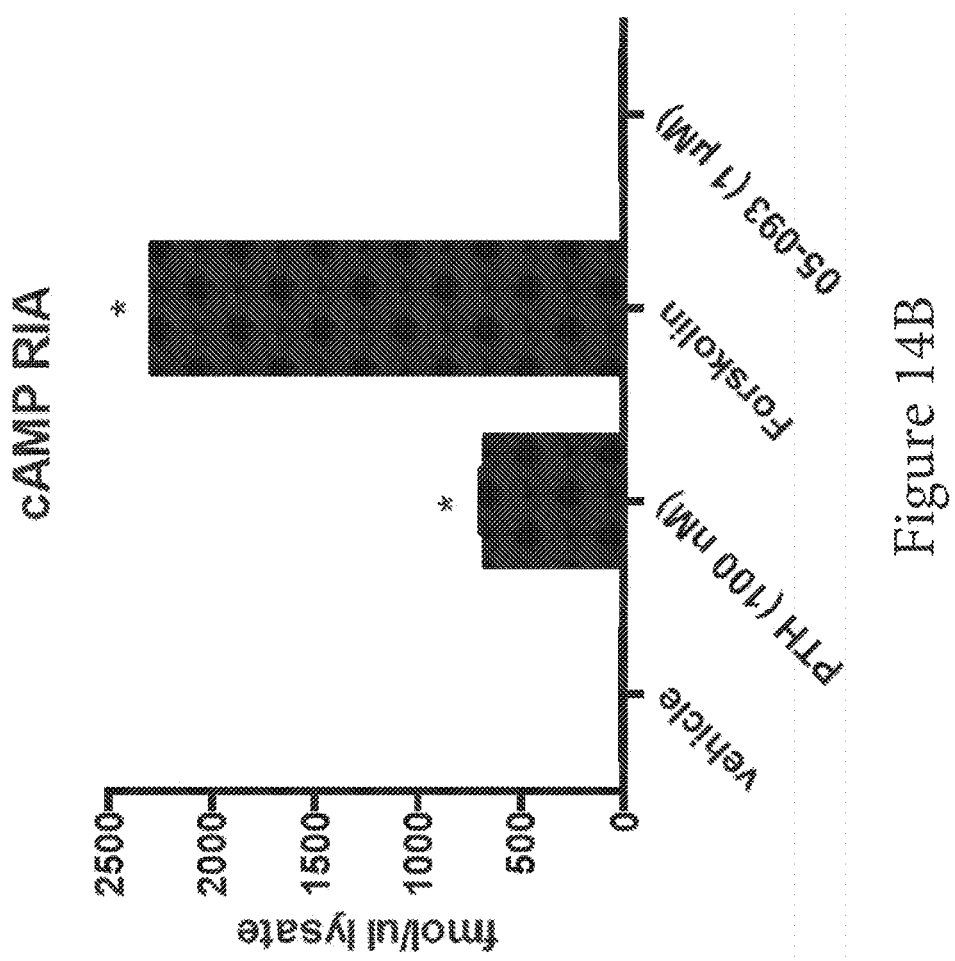

FIGS. 14A to 14B. (FIG. 14A) Dendrogram showing effects of YKL-05-093 on different classes of kinases. The location of SIK kinases is denoted with an asterix. SIK refers to SIK1, and QSK refers to SIK3 in these assays. See Table 3 for more details. Kinase group names follow standard nomenclature: AGC (containing PKA, PKG, PKC families), CAMK (calcium/calmodulin-dependent protein kinases), CK1 (casein kinase 1), CMGC (containing CDK, MAPK, GSK3, CLK families), STE (homologs of yeast sterile 7, sterile 11, and sterile 20 kinases), TK. (tyrosine kinase), and TKL (tyrosine kinase-like). Image generated using TREEspot™ Software Tool and reprinted with permission from KINOMEscan®, a division of DiscoveRx Corporation, © DISCOVER$^X$ CORPORATION 2010. (FIG. 14B) Ocy454 cells were treated with PTH, forskolin, or YKL-05-093 (05-093), and cAMP levels were measured by RIA 20 minutes later. YKL-05-093 does not induce cAMP generation.

Figure 15A:
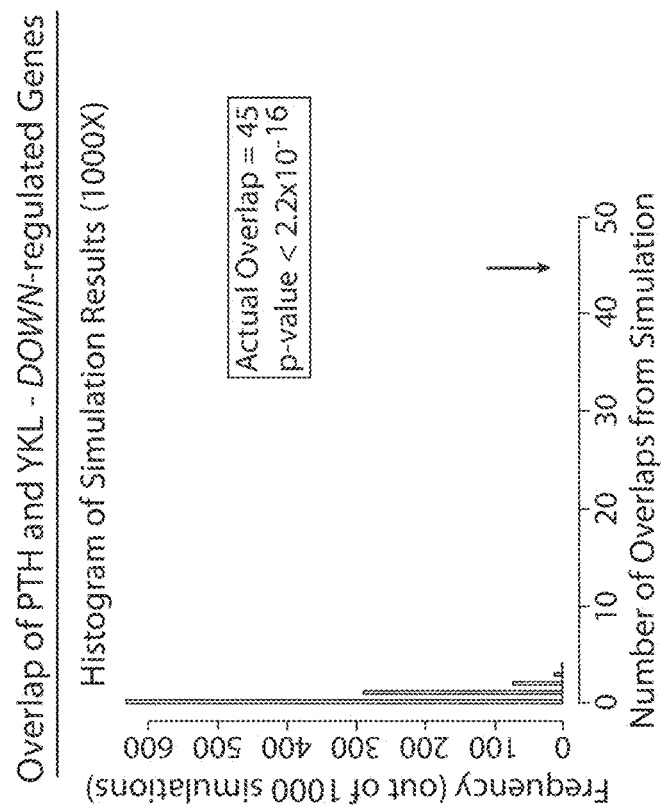
Figure 15B:
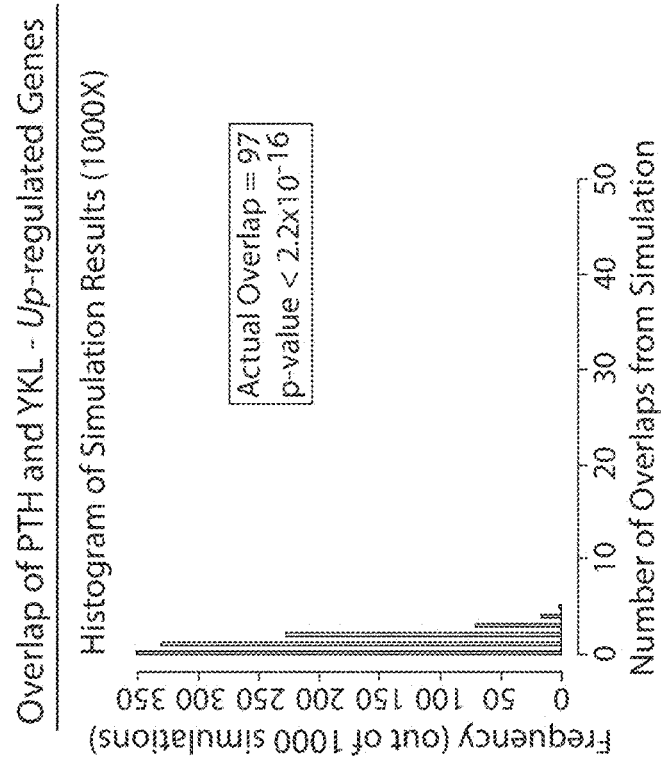
Figures 15E, 16:
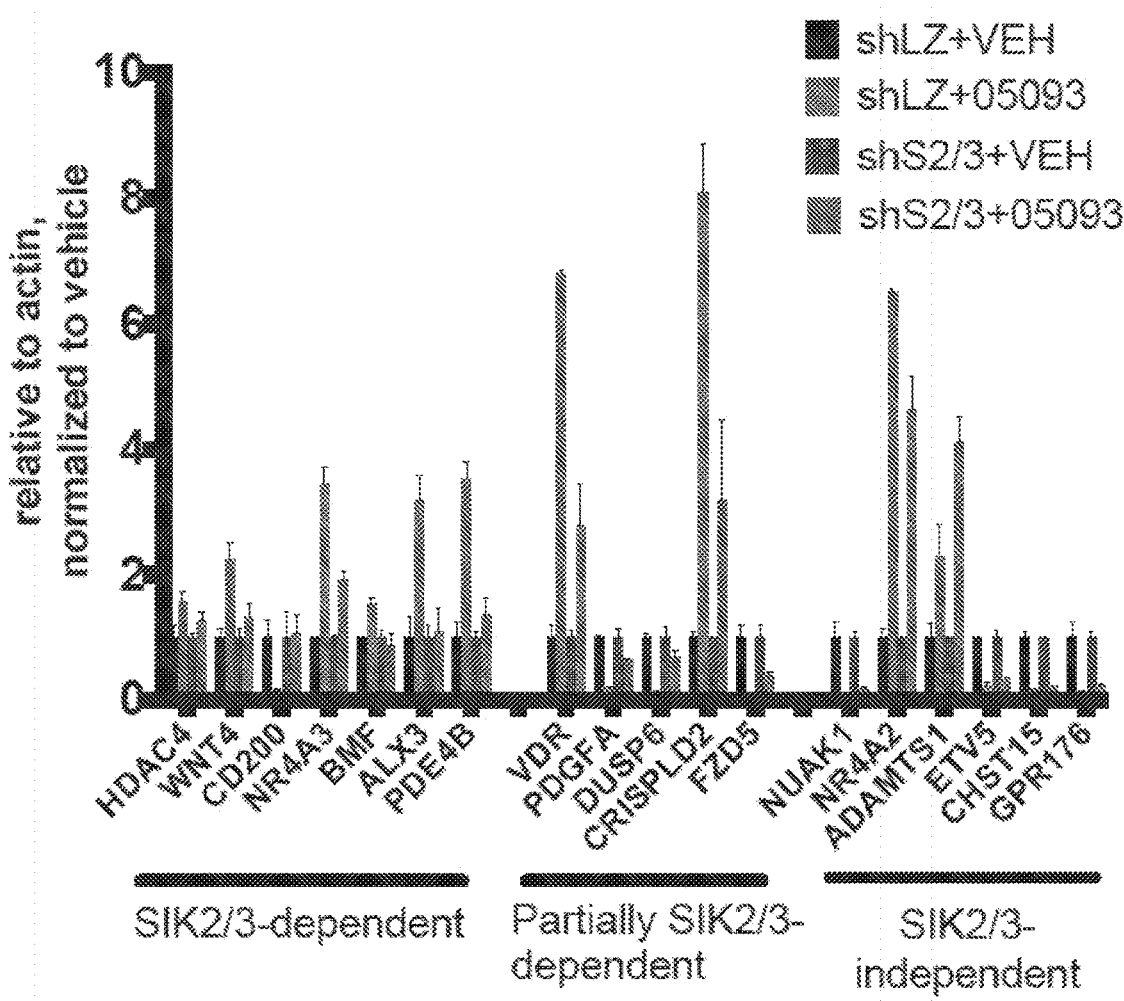

FIGS. 15A to 15E. (FIGS. 15A and 15B) Simulation results demonstrating that the overlap between the group of genes co-regulated in the same direction by PTH and YKL-05-093 (YKL) is not due to random chance. (FIGS. 15C and 15D) Gene ontology analysis of genes up- or down-regulated by both PTH and YKL-05-093. (FIG. 15E) Control and shSIK2/3 cells were treated with vehicle or YKL-05-093 (0.5 µM) for 4 hours, and the indicated genes were measured by RT-ciPCR. In FIG. 15E, for each gene, the four bars from left to right refer to shLZ+VEH, shLZ+05093, shS2/3+VEH, and shS2/3+05093, respectively. Genes are categorized based on the dependence of SIK2/3 for the ability of YKL-05-093 to regulate their expression. Genes that are SIK2/3-dependent show no YKL-05-093-induced regulation in SIK2/3-deficient cells. Genes that are partially SIK2/3-dependent show blunted regulation by YKL-05-093 in SIK2/3-deficient cells. Genes that are SIK2/3-independent show normal YKL-05-093-induced regulation in SIK2/3-deficient cells. Therefore, the regulation of these genes is likely due to cellular targets of YKL-05-093 other than SIK2/3.

FIG. 16: The half-life (in minute) of the indicated compound was measured in murine hepatic microsomes. Note the improved half-life of YKL-05-093 compared to YKL-04-114 and HG-9-91-01.

Figure 17:
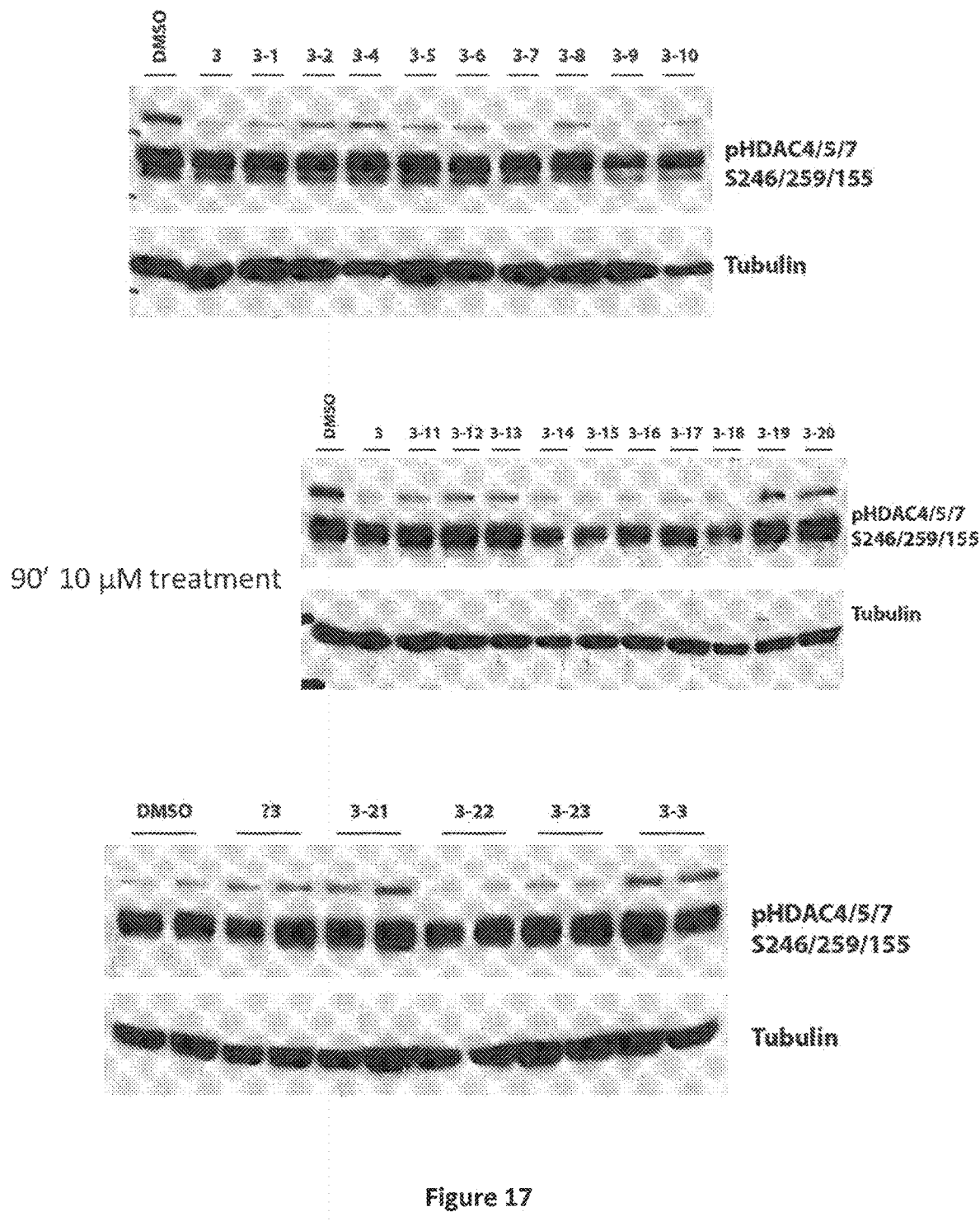

FIG. 17: Western blots showing the results of the Ocy454 osteocyte cell line treated for 90 minutes with a 10 µM dose of the indicated compound.

Figure 18:
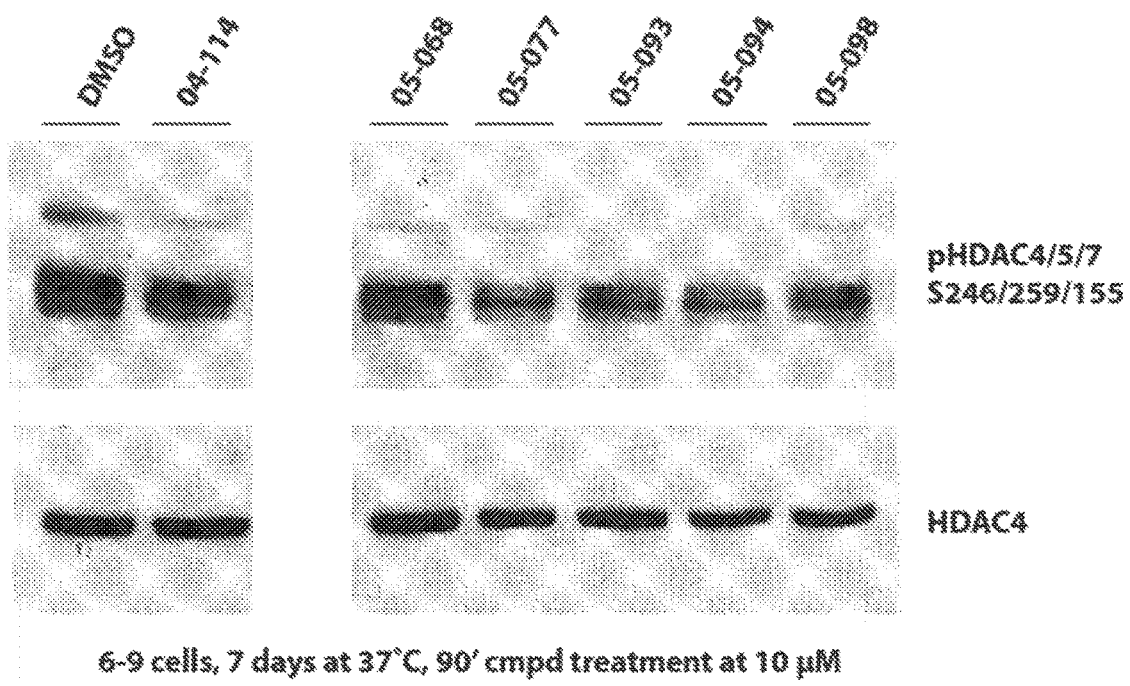

FIG. 18: Western blot showing the results exemplary analogs of YKL-04-114. "04-114" denotes YKL-04-114. "05-068" denotes YKL-05-068. "05-077" denotes YKL-05-077. "05-093" denotes YKL-05-093, "05-094" denotes YKL-05-094. "05-098" denotes YKL-05-098. "cmpd" denotes compound. "90" denotes 90 minutes.

Figure 19:
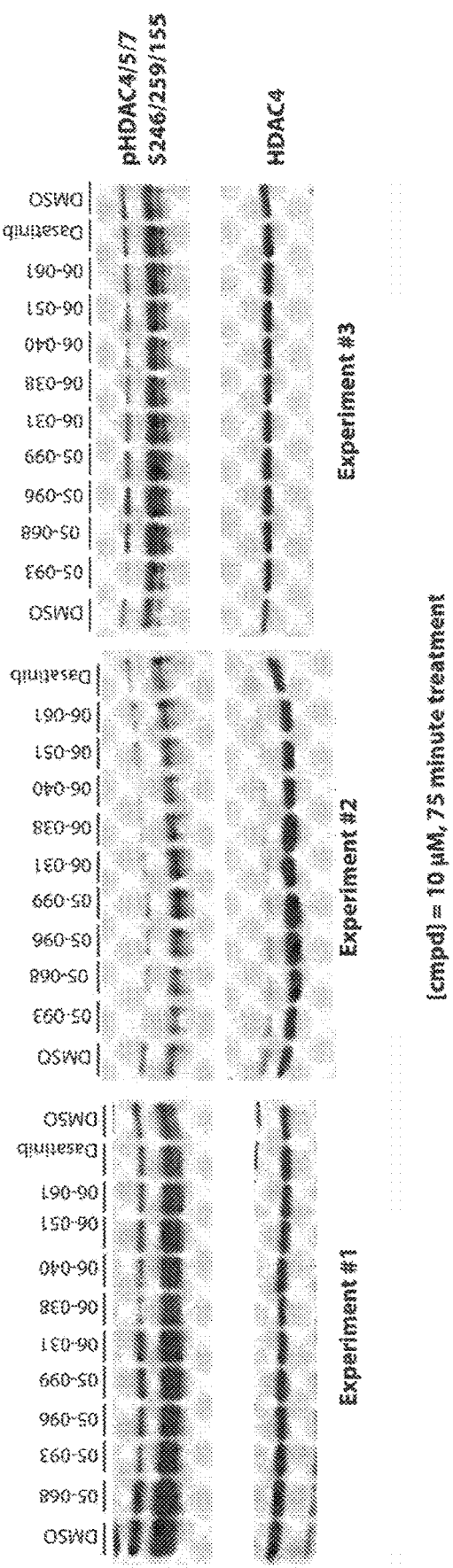

FIG. 19: Western blots showing the results of exemplary analogs of YKL-05-093. "05-068" denotes YKL-05-068. "05-093" denotes YKL-05-093. "05-096" denotes YKL-05-096. "05-099" denotes YKL-05-099. "06-031" denotes YKL-06-031. "06-038" denotes YKL-06-038. "06-040" denotes YKL-06-040. "06-051" denotes YKL-06-051. "06-061" denotes YKL-06-061. "cmpd" denotes compound.

Figure 20:
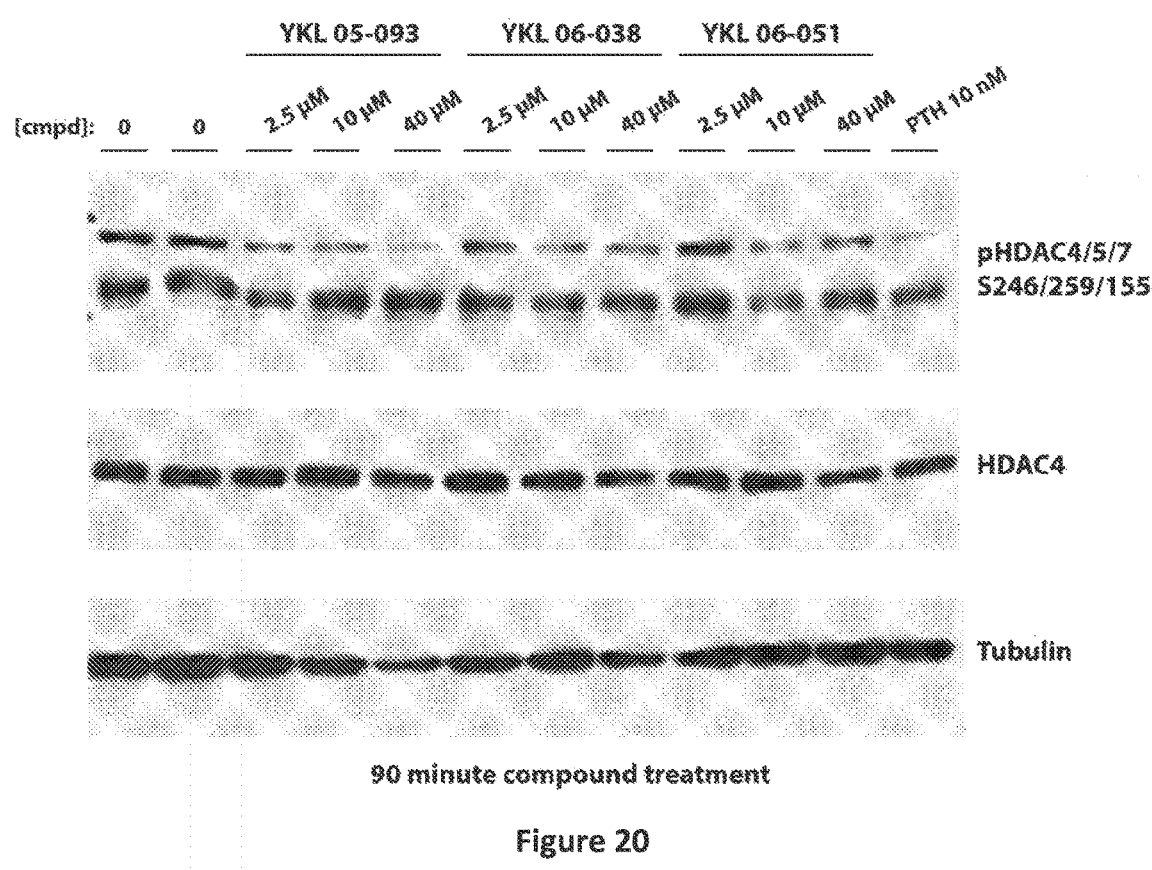

FIG. 20: Western blot showing the effect of YKL-05-093, and exemplary analogs thereof, on HDAC4 S246 phosphorylation. "cmpd" denotes compound.

Figure 21:
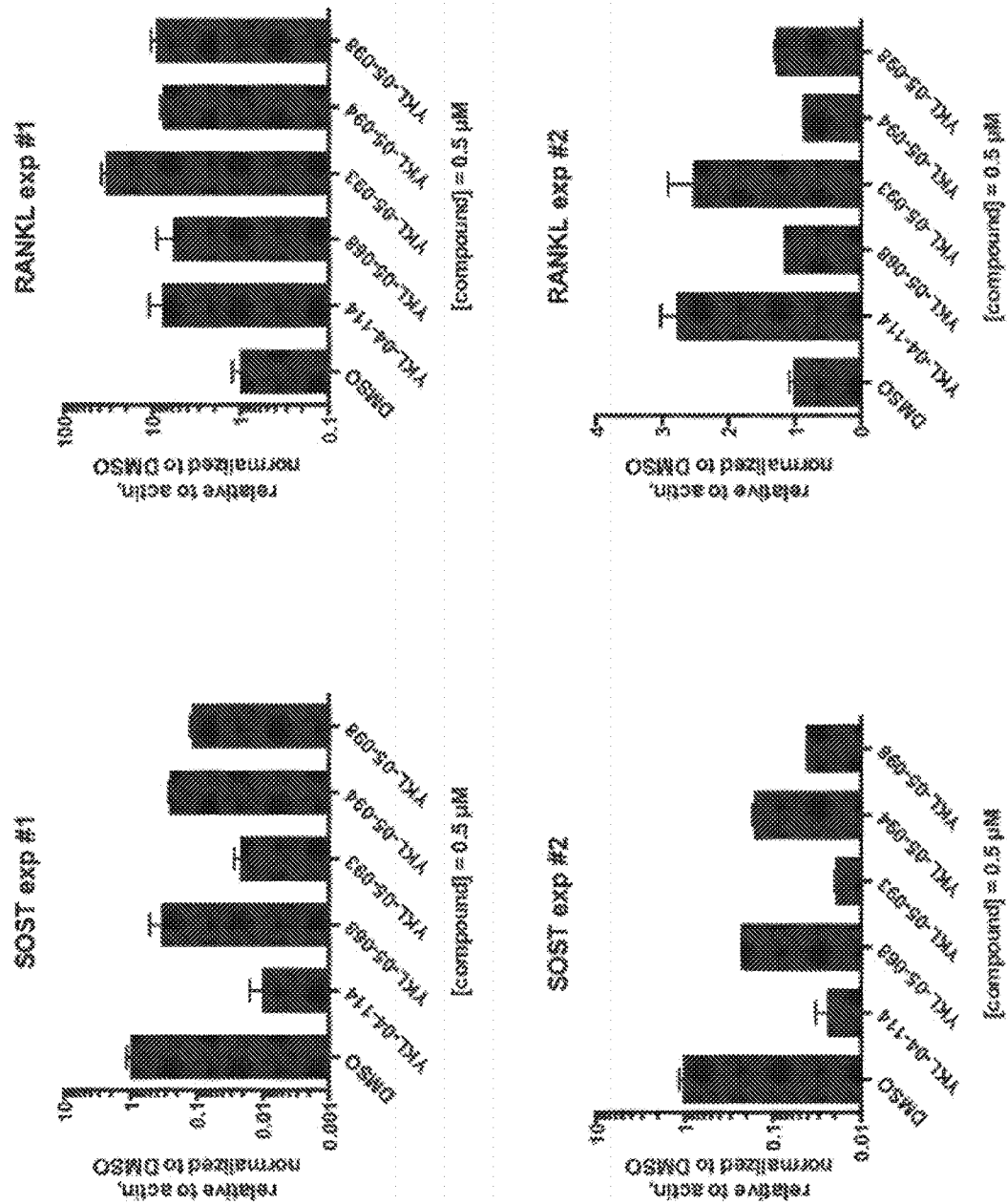

FIG. 21: Graphs showing gene expression of Ocy454 cells treated with the indicated compounds analyzed by RT-qPCR. "exp" denotes expression.

Figures 22A, 22B:
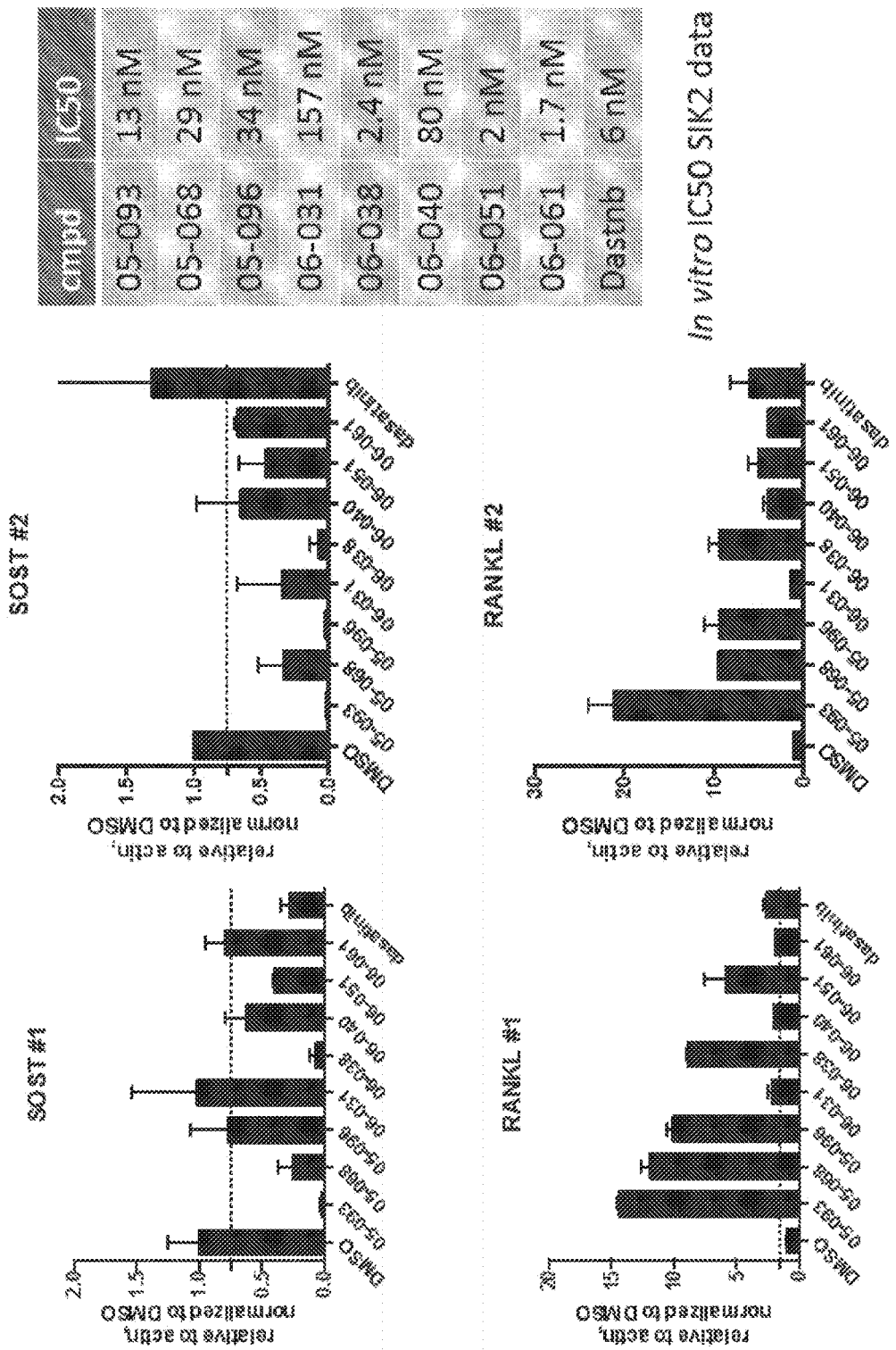

FIG. 22A: Graphs showing gene expression YKL-05-093 analogs treated with the indicated compounds was analyzed by RT-qPCR.

FIG. 22B: SIK2 IC$_{50}$ data generated from an in vitro kinase assay. In FIGS. 22A and 22B: "05-093" denotes YKL-05-093; "05-068" denotes YKL-05-068; "05-096" denotes YKL-05-096; "06-031" denotes YKL-06-031; "06-

038" denotes YKL-06-038; "06-040" denotes YKL-06-040; "06-051" denotes YKL-06-051; "06-061" denotes YKL-06-061; "Dastnb" denotes dasatinib; and "cmpd" denotes compound.

Figure 23:
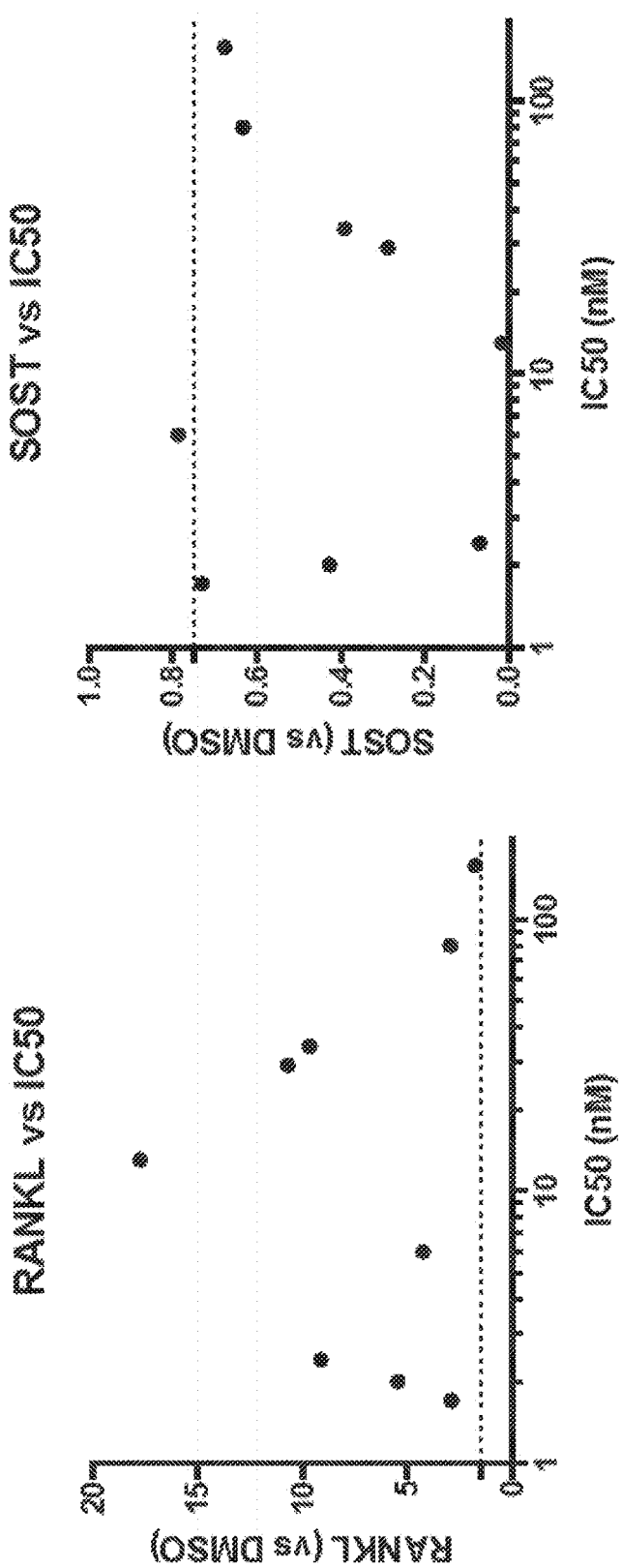

FIG. 23: Graphs showing the gene expression of YKL-05-093, and exemplary analogs thereof, versus SIK2 $IC_{50}$.

Figure 24:
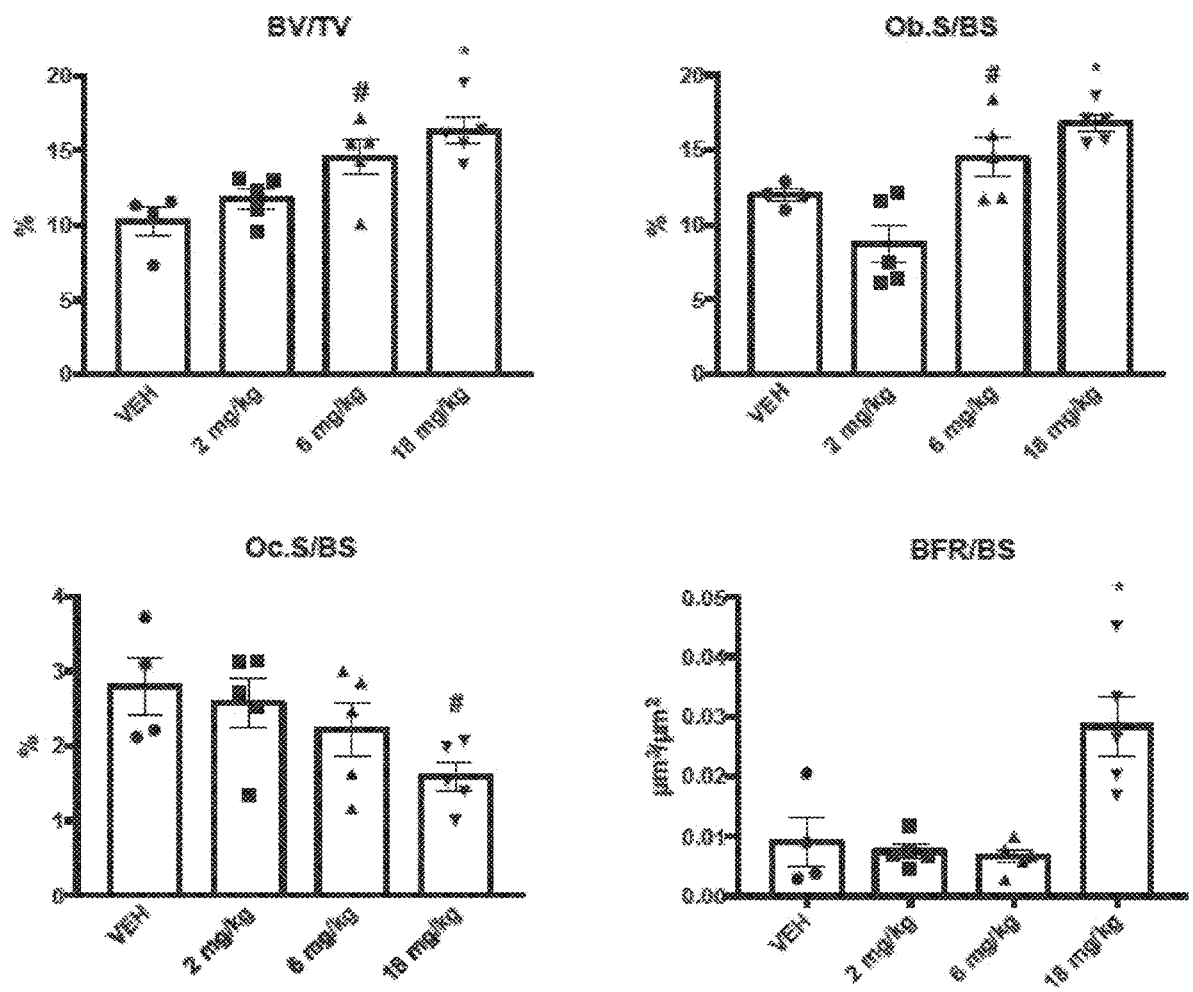

FIG. 24: 8 week old male mice were treated for 2 weeks with the indicated doses of YKL-05-099. Histomorphometry of the proximal tibia was performed.

Figure 25:
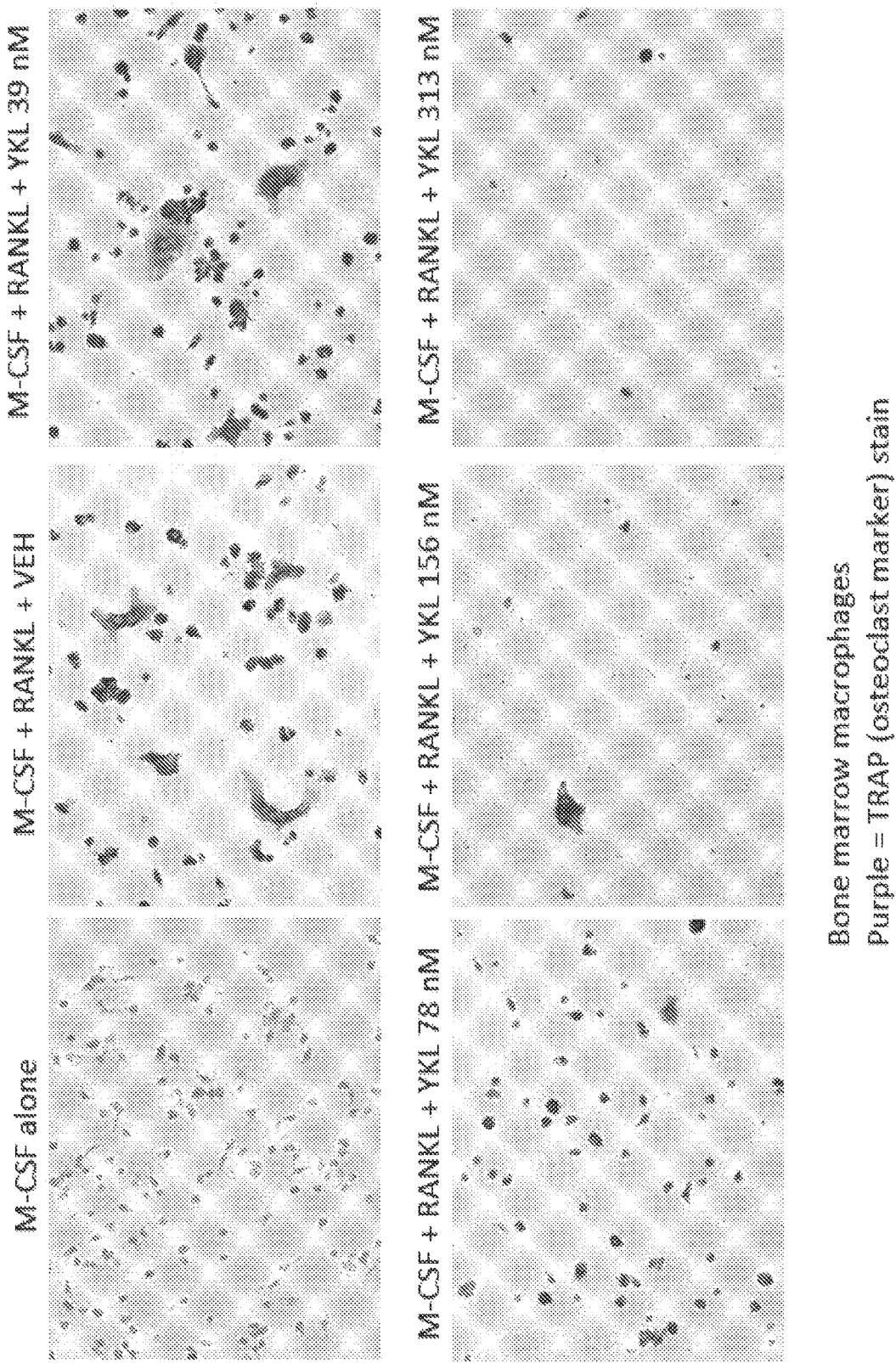

FIG. 25: Bone marrow macrophages were differentiated into osteoclasts in the prescence of the indicated doses of YKL-05-099.

Figure 26:
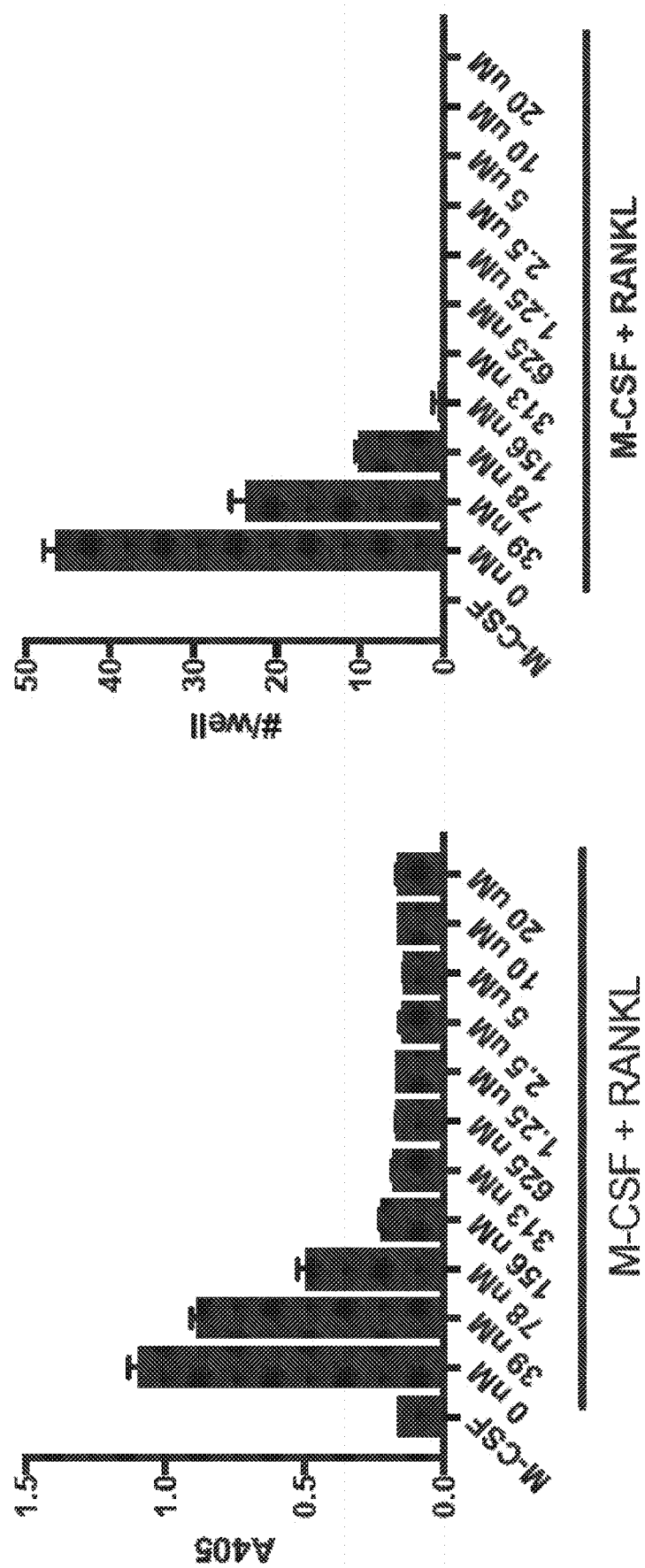

FIG. 26: Quantification of tartrate resistant acid phosphatase (TRAP) secretion (see left panel) and TRAP+ multinucleated cells (see right panel). "uM" refers to µM.

Figure 27:
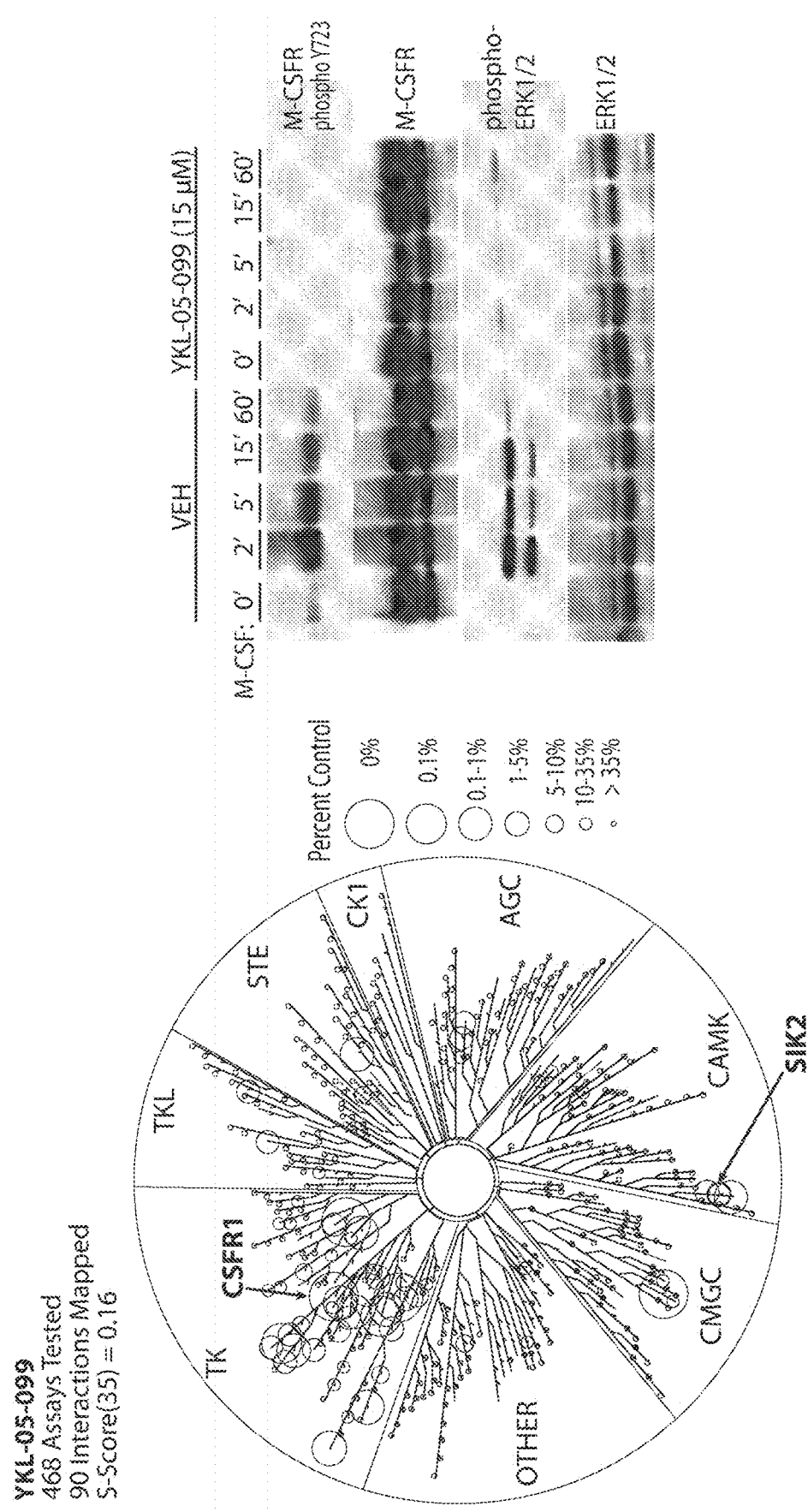

FIG. 27: DiscoverX profiling data revealed that YKL-05-099 inhibited multiple tyrosine kinases in vitro, including CSFR1 (see left panel). Bone marrow macrophages were pre-treated with either vehicle or YKL-05-099. 60 minutes later, cells were treated with M-CSF for the indicated time. YKL-05-099 pre-treatment blocked M-CSF induced receptor auto-phosphorylation and downstream ERK1/2 phosphorylation (see right panel).

Figure 28:
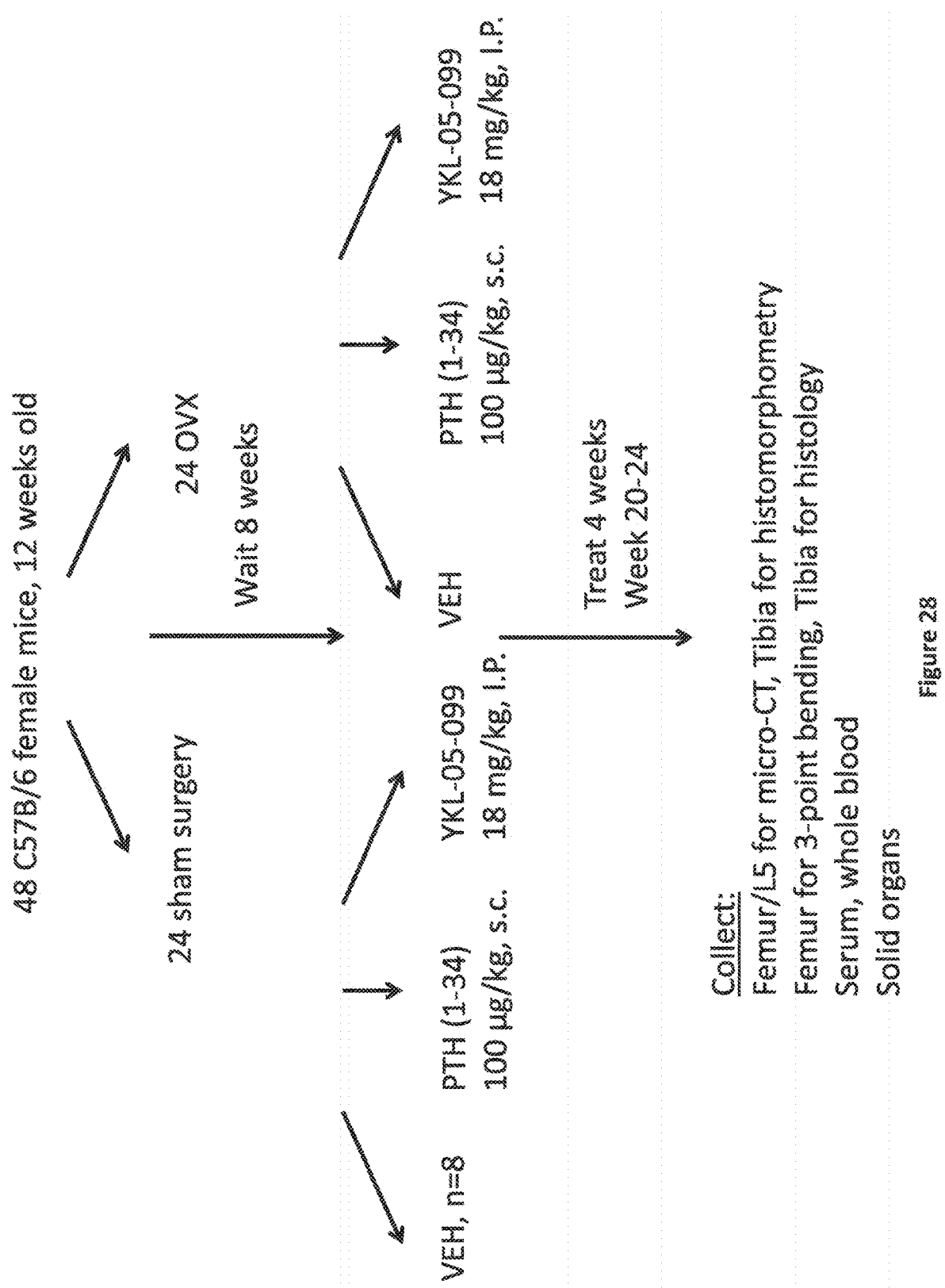
Figure 29A:
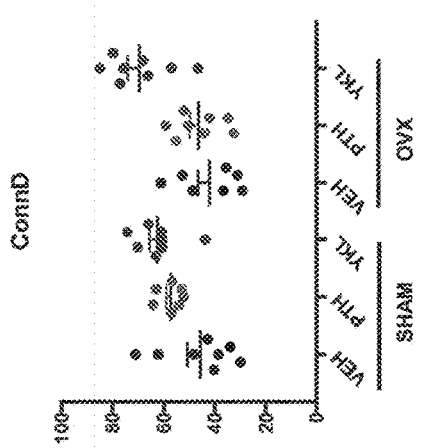
Figure 29B:
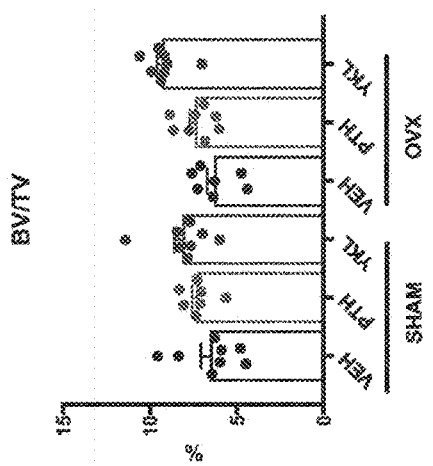
Figure 29C:
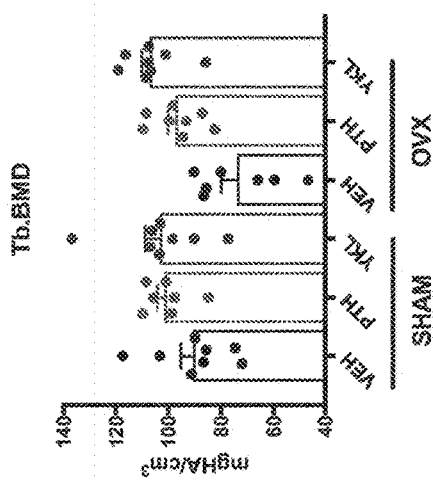
Figure 29D:
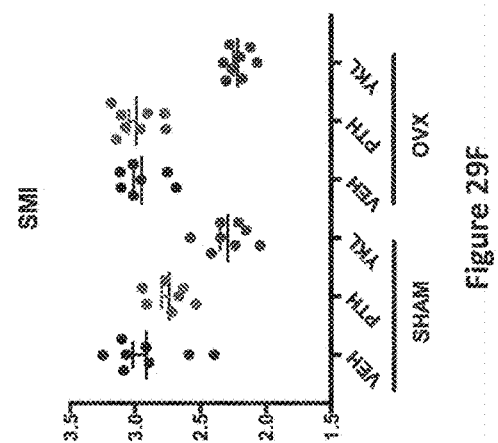
Figure 29E:
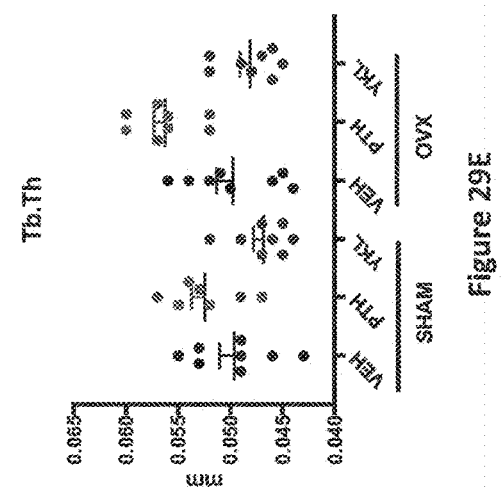
Figure 29F:
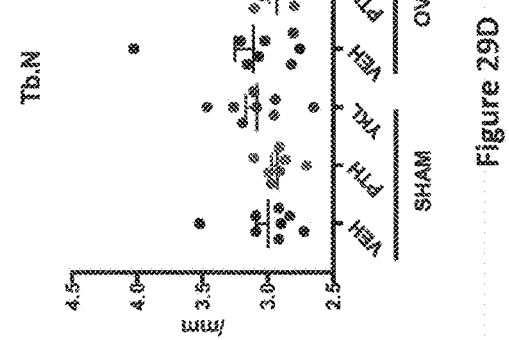

FIG. 28: Overview of the experimental conditions employed for FIGS. 29A to 35.

FIGS. 29A to 29F: Graphs showing effects of OVX and drug (PTH or YKL) treatments assessed by of micro-CT of the distal femur metaphysis. OVX had no effect on BV/TV, but led to reduced Tb.BMD.

Figure 30:
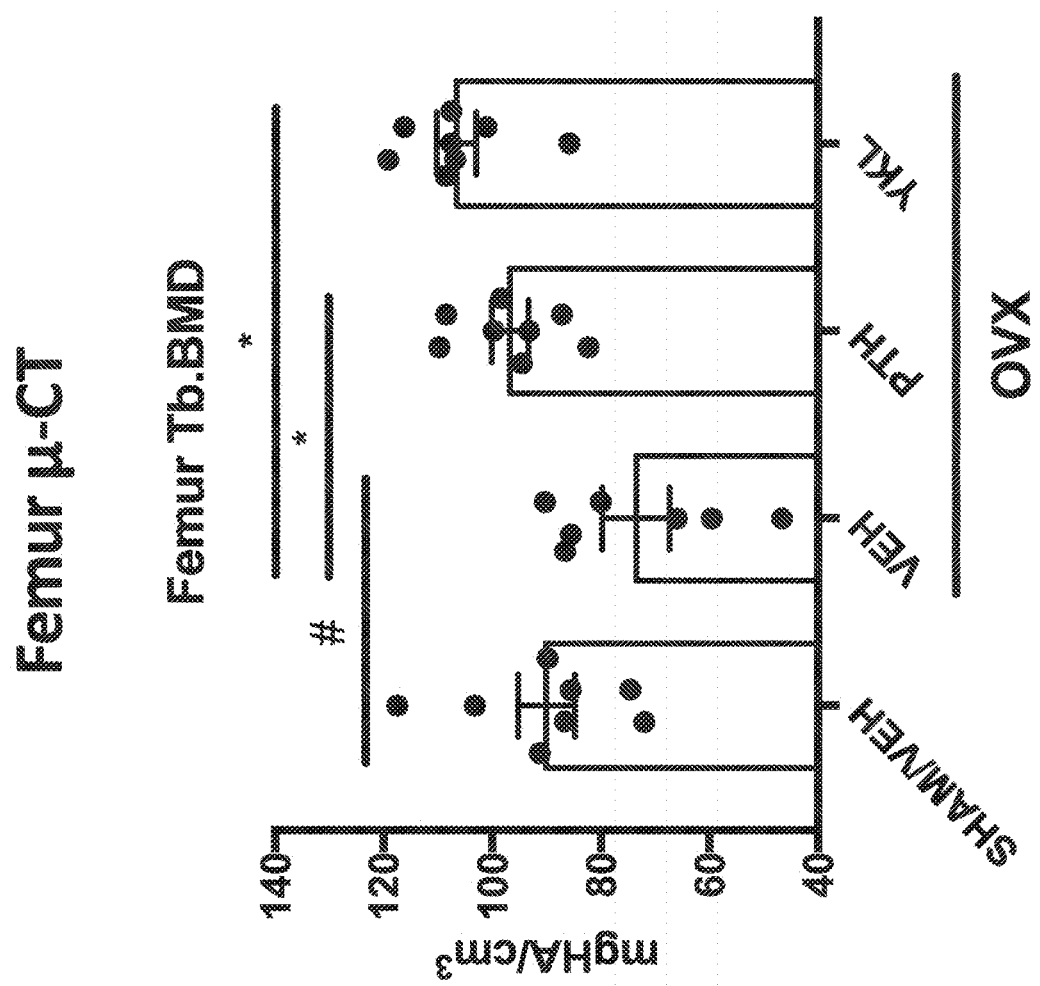

FIG. 30: Graph showing effects of OVX and drug (PTH or YKL) treatments assessed by of micro-CT of the femur. OVX: 18.4% bone loss, p=0.041 vs SHAM; PTH: 31.5% bone gain, p=0.0047 vs OVX/VEH; YKL: 44.9% bone gain, p=0.00036 vs OVX/VEH.

FIGS. 31A to 31E: Graphs showing effects of OVX and drug (PTH or YKL) treatments assessed by micro-CT of the L5 vertebrae. OVX: 19.6% bone loss, p=0.00043 vs SHAM; PTH: 12.4% bone gain, p=0.084 vs OVX/VEH; YKL: 11.9% bone gain, p=0.036 vs OVX/VEH.

Figures 32A, 32B, 32C:
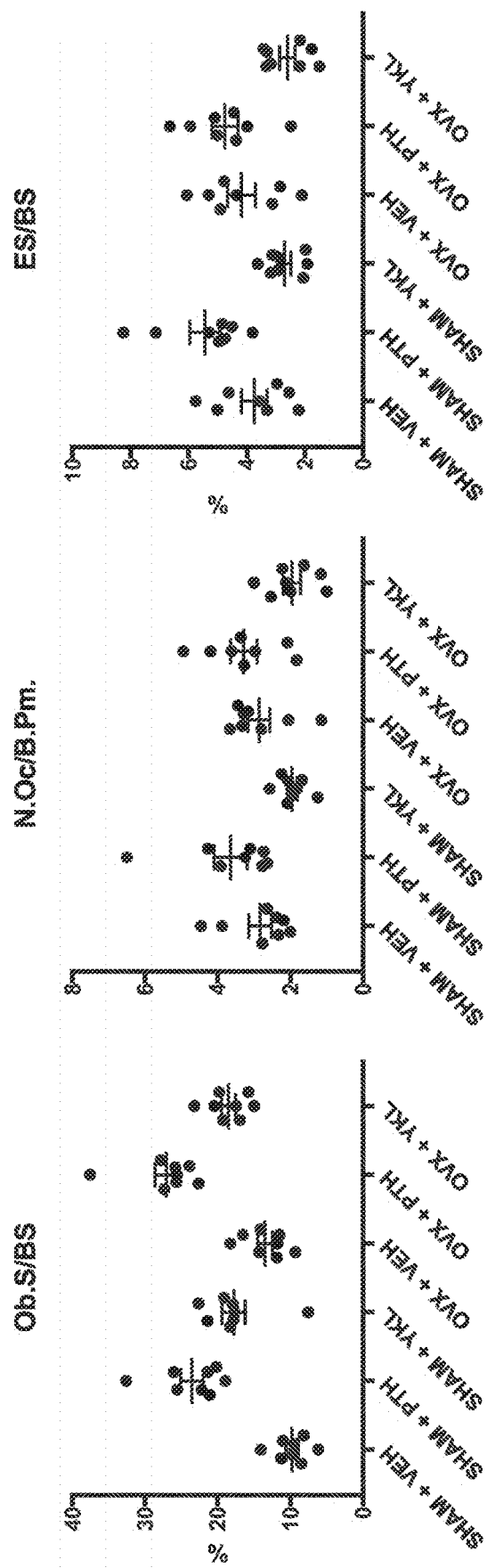

FIGS. 32A to 32C: Graphs showing that both treatments (treatment comprising PTH and treatment comprising YKL) increased osteoblasts, but showed different effects on osteoclasts.

FIGS. 33A to 33D: Histomorphometry: both treatments (treatment comprising PTH and treatment comprising YKL) increased BFR, but only PTH increases osteoid.

Figure 34B:
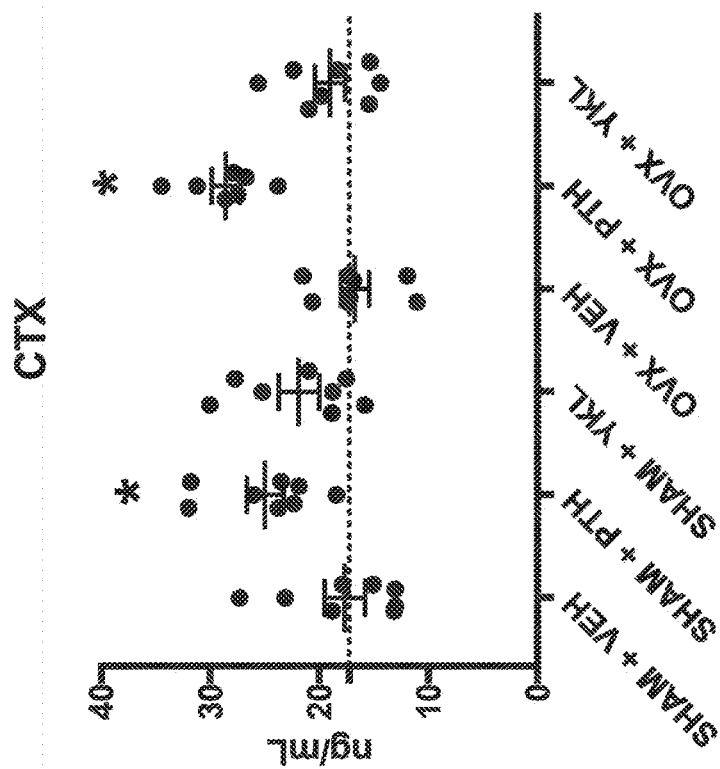
Figure 34A:
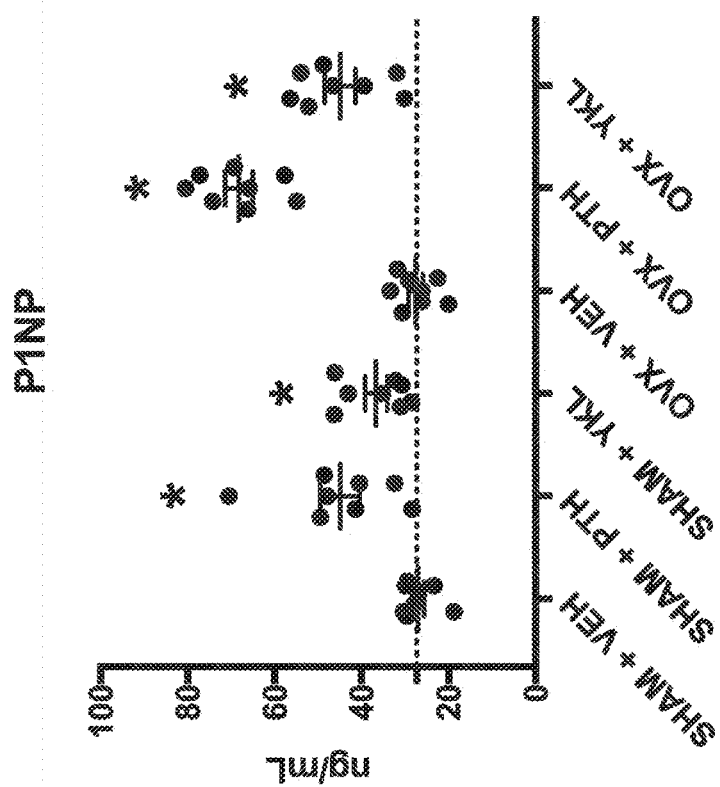

FIGS. 34A to 34B: Bone turnover markers: both treatments (treatment comprising PTH and treatment comprising YKL) increased P1NP, only the treatment comprising PTH increased CTX.

Figure 35:
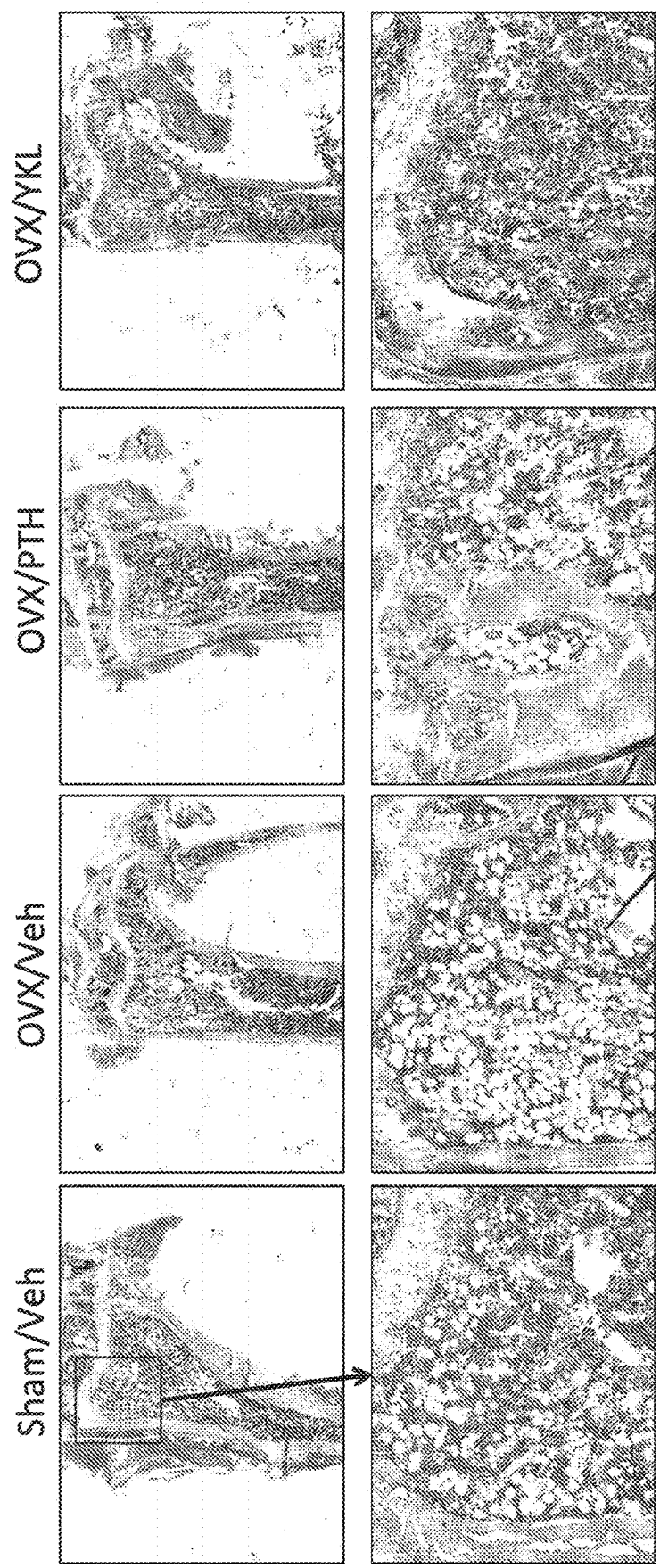

FIG. 35: Tibial histomorphometry results. YKL treatment may have reduced marrow adiposity.

FIGS. 36A to 36D: the hematology data showed no signal.

FIGS. 37A to 37D: Serum toxicology data showed increased glucose and BUN.

DETAILED DESCRIPTION OF CERTAIN EMBODIMENTS OF THE INVENTION

Described herein are uses of SIK inhibitors (e.g., SIK1 inhibitors, SIK2 inhibitors, SIK3 inhibitors) and pharmaceutical compositions that include SIK inhibitors in the treatment and/or prevention of osteoporosis. SIK inhibitors may be able to treat osteoporosis, prevent osteoporosis, increase the function of osteocytes, increase the number of osteoblasts, increase the activity of osteoblasts, inhibit the resorption of a bone, decrease the number of osteoclasts, inhibit the activity of osteoclasts, increase the mass of a bone, down-regulate the expression of the gene SOST, inhibit the activity of sclerostin, and/or reduce the production of sclerostin in a subject in need thereof.

Osteocytes orchestrate bone formation and resorption. Parathyroid hormone (PTH) activates receptors on osteocytes to accomplish both goals. PTH inhibition of SOST, a WNT antagonist, may require HDAC4 and HDAC5, while PTH stimulation of RANKL, a stimulator of bone resorption, may require CRTC2. Salt inducible kinases (SIKs) may control subcellular localization of both HDAC4/5 and CRTC2. PTH may regulate both HDAC4/5 and CRTC2 localization via phosphorylation and inhibition of SIK2. Like PTH, SIK inhibitors may cause dephosphorylation and nuclear translocation of HDAC4/5 and CRTC2. SIK inhibition may mimic many of the effects of PTH in osteocytes as assessed by RNA-seq in cultured osteocytes and following in vivo administration. Once daily treatment with the SIK inhibitor YKL-05-099 increased bone formation and bone mass. Therefore, a major arm of PTH signaling in osteocytes may involve SIK inhibition, and SIK inhibitors may be a useful strategy to mimic skeletal effects of PTH.

Compounds for Use in the Invention
Compounds of Formula (I)

In one aspect, the present disclosure provides bicyclic urea compounds of Formula (I) for use in the present disclosure:

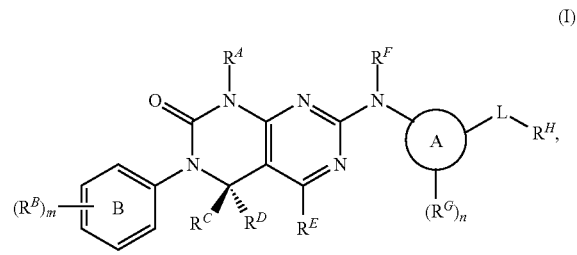

(I)

and pharmaceutically acceptable salts, solvates, hydrates, polymorphs, co-crystals, tautomers, stereoisomers, isotopically labeled derivatives, and prodrugs thereof, wherein:

$R^A$ is substituted or unsubstituted alkenyl, substituted or unsubstituted alkynyl,

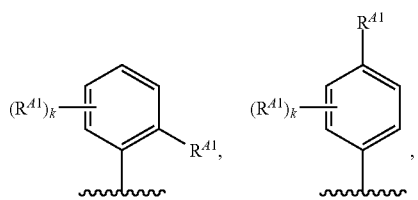

substituted or unsubstituted heteroaryl, or substituted or unsubstituted heterocyclyl, provided that the substituted or unsubstituted heterocyclyl is not substituted or un substituted 3-pyrrolidinyl;

each instance of $R^{A1}$ is independently halogen, substituted or unsubstituted alkyl, substituted or unsubstituted alkenyl, substituted or unsubstituted alkynyl, substituted or un substituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N (R$^b$)$_2$, —C(=O)R$^a$, —C(=O)OR$^a$, —C(=O)N(R$^b$)$_2$, —NO$_2$, —NR$^b$C(=O)R$^a$, —NR$^b$C(=O)OR$^a$, —NR$^b$C(=O)N(R$^b$)$_2$, —OC(=O)R$^a$, —OC(=O)OR$^a$, or —OC(=O)N(R$^b$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

each instance of R$^b$ is independently hydrogen, substituted or unsubstituted, C$_{1-6}$ alkyl, or a nitrogen protecting group, or optionally two instances of R$^b$ are taken together with their intervening atoms to form a substituted or unsubstituted heterocyclic or substituted or unsubstituted heteroaryl ring;

k is 0, 1, 2, 3, or 4;

each instance of R$^D$ is independently halogen, substituted or un substituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or un substituted heteroaryl, —OR$^a$, —N(R$^b$)$_2$, —SR$^a$, —CN, —SCN, —C(=NR$^b$)R$^a$, —C(=NR$^b$)OR$^a$, —C(=NR$^b$)N(R$^b$)$_2$, —C(=O)R$^a$, —C(=O)OR$^a$, —C(=O)N(R$^b$)$_2$, —NO$_2$, —NR$^b$C(=O)R$^a$, —NR$^b$C(=O)OR$^a$, —NR$^b$C(=O)N(R$^b$)$_2$, —OC(=O)R$^a$, —OC(=O)OR$^a$, or —OC(=O)N(R)$_2$;

m is 0, 1, 2, 3, 4, or 5;

R$^C$ is hydrogen, halogen, or substituted or unsubstituted, C$_{1-6}$ alkyl;

R$^D$ is hydrogen, halogen, or substituted or unsubstituted, C$_{1-6}$ alkyl;

R$^E$ is hydrogen, halogen, or substituted or unsubstituted, C$_{1-6}$ alkyl;

R$^F$ is hydrogen, substituted or unsubstituted, C$_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of R$^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, —SR$^a$, —CN, —SCN, —C(=NR$^b$)R$^a$, —C(=NR$^b$)OR$^a$, —C(=NR$^b$)N(R$^b$)$_2$, —C(=O)R$^a$, —C(=O)OR$^a$, —C(=O)N(R$^b$)$_2$, —NO$_2$, —NR$^b$C(=O)R$^a$, —NR$^b$C(=O)OR$^a$, —NR$^b$C(=O)N(R$^b$)$_2$, —OC(=O)R$^a$, —OC(=O)OR$^a$, or —OC(=O)N(R$^b$)$_2$;

n is 0, 1, 2, 3, or 4, as valency permits;

L is a bond or a substituted or unsubstituted, C$_{1-6}$ hydrocarbon chain, optionally wherein one or more chain atoms of the hydrocarbon chain are independently replaced with —C(=O)—, —O—, —S—, —NR$^b$—, —N=, or =N—; and R$^H$ is substituted or unsubstituted, C$_{1-6}$ alkyl, substituted or unsubstituted heterocyclyl, —OH, or —N(R$^c$)$_2$, wherein each instance of R$^c$ is independently hydrogen, substituted or unsubstituted, C$_{1-6}$ alkyl, or a nitrogen protecting group, or optionally two instances of R$^a$ are taken together with their intervening atoms to form a substituted or unsubstituted heterocyclic or substituted or unsubstituted heteroaryl ring.

Unless expressly provided otherwise, the moieties and variables described in the subsection Compounds of Formula (I) apply only to Formula (I).

Formula (I) includes substituent R$^A$. In certain embodiments, R$^A$ is substituted alkenyl. In certain embodiments, R$^A$ is unsubstituted alkenyl. In certain embodiments, R$^A$ is substituted alkynyl. In certain embodiments, R$^A$ is unsubstituted alkynyl. In certain embodiments, R$^A$ is substituted phenyl. In certain embodiments, R$^A$ is of the formula:

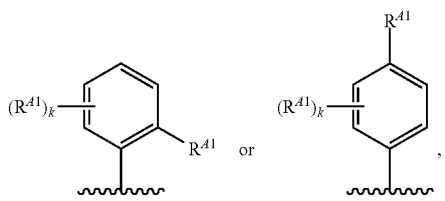

In certain embodiments, k is 0. In certain embodiments, R$^A$ is of the formula:

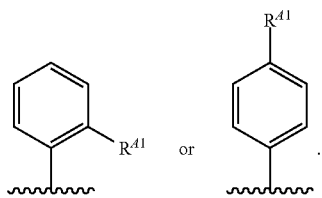

In certain embodiments, k is 1. In certain embodiments, R$^A$ is of the formula:

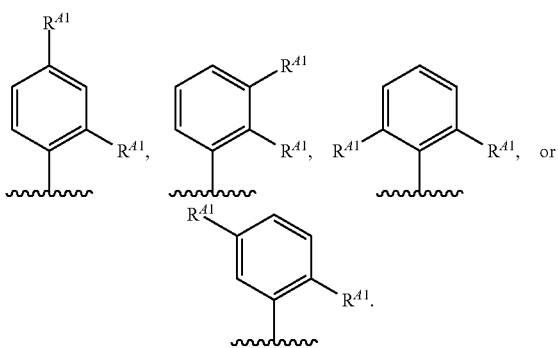

In certain embodiments, R$^A$ is of the formula:

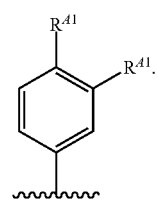

In certain embodiments, $R^A$ is

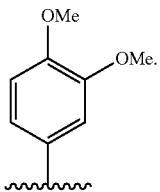 [SMILES: *c1ccc(OC)c(OC)c1]

In certain embodiments, k is 2. In certain embodiments, $R^A$ is of the formula:

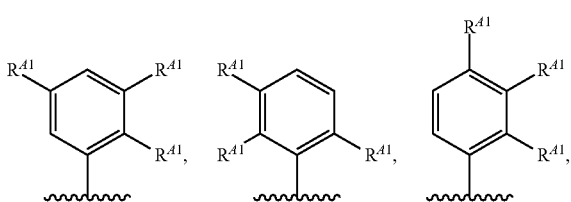

In certain embodiments, k is 3. In certain embodiments, $R^A$ is of the formula:

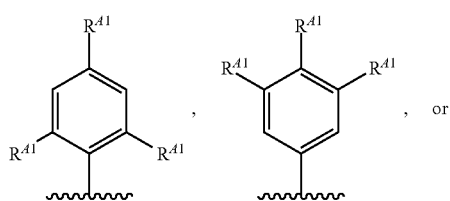

In certain embodiments, k is 4. In certain embodiments, $R^A$ is of the formula:

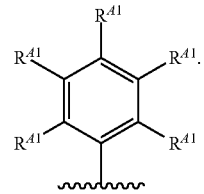

In certain embodiments, when $R^A$ is substituted phenyl, $R^A$ includes one or more $R^{A1}$ substituents. In certain embodiments, at least one instance of $R^{A1}$ is halogen (e.g., F, Cl, Br, or I). In certain embodiments, at least one $R^{A1}$ is substituted or unsubstituted alkyl (e.g., substituted or unsubstituted, $C_{1-6}$ alkyl). In certain embodiments, at least one instance of $R^{A1}$ is substituted or unsubstituted methyl. In certain embodiments, at least one instance of $R^{A1}$ is substituted or unsubstituted ethyl. In certain embodiments, at least one instance of $R^{A1}$ is substituted or unsubstituted propyl. In certain embodiments, at least one instance of $R^{A1}$ is substituted or unsubstituted alkenyl (e.g., substituted or unsubstituted, $C_{2-6}$ alkenyl). In certain embodiments, at least one instance of $R^{A1}$ is substituted or unsubstituted alkynyl (e.g., substituted or unsubstituted, $C_{2-6}$ alkynyl). In certain embodiments, at least one instance of $R^{A1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{A1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{A1}$ is substituted or unsubstituted aryl (e.g., substituted or unsubstituted, 6- to 10-membered aryl). In certain embodiments, at least one instance of $R^{A1}$ is benzyl. In certain embodiments, at least one instance of $R^{A1}$ is substituted or unsubstituted phenyl. In certain embodiments, at least one instance of $R^{A1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A1}$ is —$OR^a$ (e.g., —OH or —OMe). In certain embodiments, at least one instance of $R^{A1}$ is —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$.

In certain embodiments, at least one instance of $R^a$ is hydrogen. In certain embodiments, at least one instance of $R^a$ is halogen (e.g., F, Cl, Br, or I). In certain embodiments, at least one instance of $R^a$ is substituted or unsubstituted alkyl (e.g., substituted or unsubstituted, $C_{1-6}$ alkyl). In certain embodiments, at least one instance of $R^a$ is substituted or unsubstituted methyl. In certain embodiments, at least one instance of $R^a$ is substituted or unsubstituted ethyl. In certain embodiments, at least one instance of $R^a$ is substituted or unsubstituted propyl. In certain embodiments, at least one instance of $R^a$ is substituted or unsubstituted alkenyl (e.g., substituted or unsubstituted, $C_{2-6}$ alkenyl). In certain embodiments, at least one instance of $R^a$ is substituted or unsubstituted alkynyl (e.g., substituted or unsubstituted, $C_{2-6}$ alkynyl). In certain embodiments, at least one instance of $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^a$ is substituted or unsubstituted aryl (e.g, substituted or unsubstituted, 6- to 10-membered aryl). In certain embodiments, at least one instance of $R^{41}$ is benzyl. In certain embodiments, at least one instance of $R^a$ is substituted or unsubstituted phenyl. In certain embodiments, at least one instance of $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^a$ is an oxygen protecting group when attached to an oxygen atom. In certain embodiments, at least one instance of $R^a$ is a sulfur protecting group when attached to a sulfur atom.

In certain embodiments, at least one instance of $R^b$ is hydrogen. In certain embodiments, at least one instance of $R^b$ is substituted or unsubstituted, $C_{1-6}$ alkyl (e.g., substituted or unsubstituted methyl, ethyl, or propyl). In certain embodiments, at least one instance of $R^b$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^b$ are taken together with their intervening atoms to form a substituted or unsubstituted heterocyclic or substituted or unsubstituted heteroaryl ring (e.g., substituted or unsubstituted, 5- to 10-membered monocyclic or bicyclic heterocyclic ring, wherein one or two atoms in the heterocyclic ring are independently nitrogen, oxygen, or sulfur; or substituted or unsubstituted, 5- to 6-membered, monocyclic heteroaryl, wherein one, two, three, or four atoms in the heteroaryl ring system are independently nitrogen, oxygen, or sulfur). In certain embodiments, two instances of $R^b$ are taken together with their intervening atoms to form substituted or unsubstituted piperazinyl. In certain embodiments, two instances of $R^b$ are taken together with their intervening atoms to form

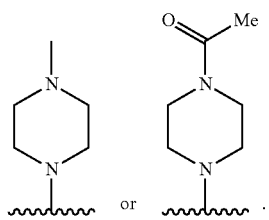

In certain embodiments, $R^A$ is substituted or unsubstituted heteroaryl. In certain embodiments, $R^A$ is substituted or unsubstituted, 5- to 6-membered, monocyclic heteroaryl, wherein one, two, three, or four atoms in the heteroaryl ring system are independently nitrogen, oxygen, or sulfur (e.g., furanyl, thiophenyl, pyridinyl, or pyrimidinyl, etc.) In certain embodiments, $R^A$ is substituted or unsubstituted furanyl. In certain embodiments, $R^A$ is substituted or unsubstituted thiophenyl. In certain embodiments, $R^A$ is substituted or unsubstituted pyridinyl. In certain embodiments, $R^A$ is of the formula:

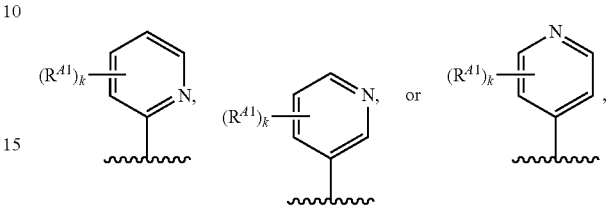

In certain embodiments, k is 0. In certain embodiments, $R^A$ is of the formula:

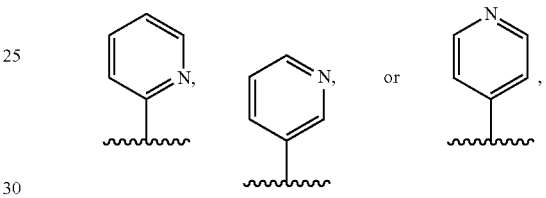

In certain embodiments, k is 1. In certain embodiments, $R^A$ is of the formula:

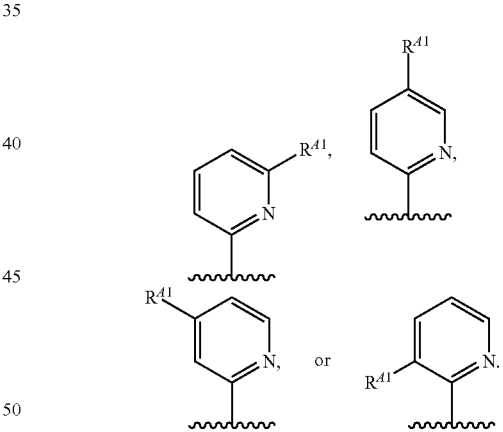

In certain embodiments, $R^A$ is of the formula:

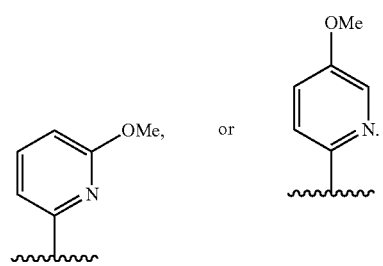 [SMILES: *c1cccc(OC)n1 ; "or" ; *c1ccc(OC)cn1]

In certain embodiments, $R^A$ is of the formula:
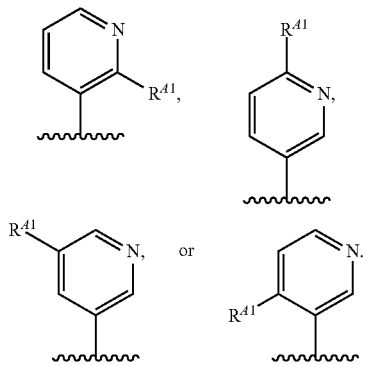
In certain embodiments, $R^A$ is of the formula:
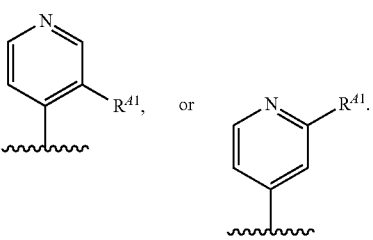
In certain embodiments, k is 2. In certain embodiments, $R^A$ is of the formula:
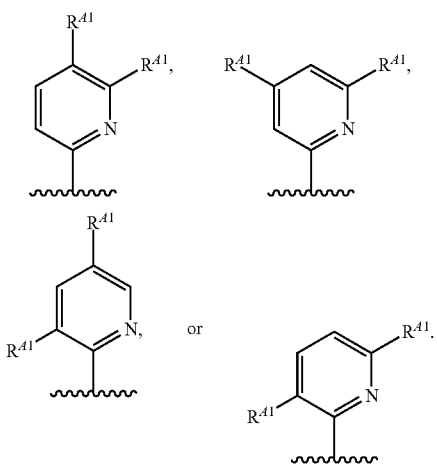
In certain embodiments, $R^A$ is of the formula:
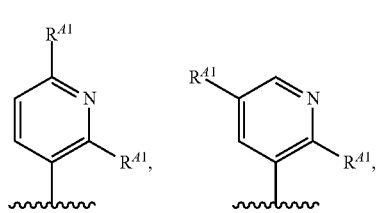
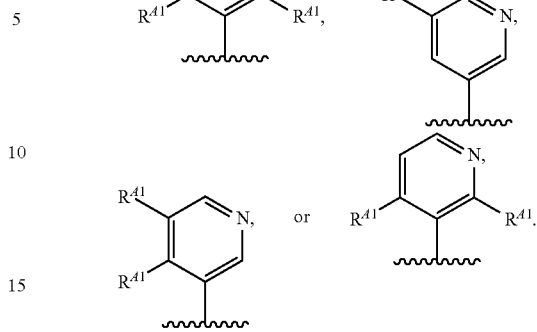
In certain embodiments, $R^A$ is of the formula:
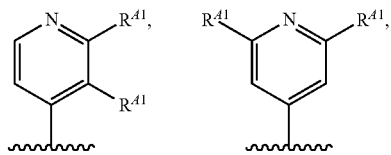
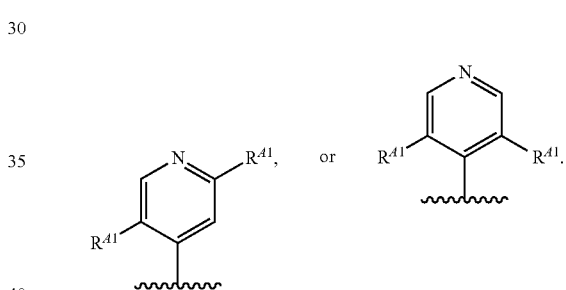
In certain embodiments, k is 3. In certain embodiments, $R^A$ is of the formula:
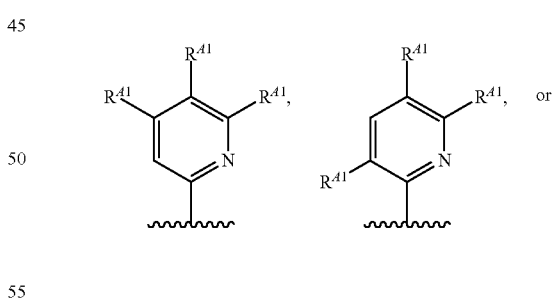
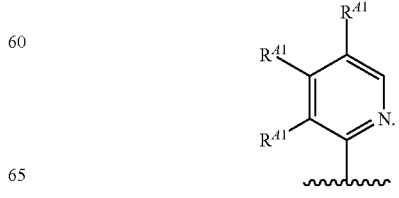

In certain embodiments, $R^A$ is of the formula:

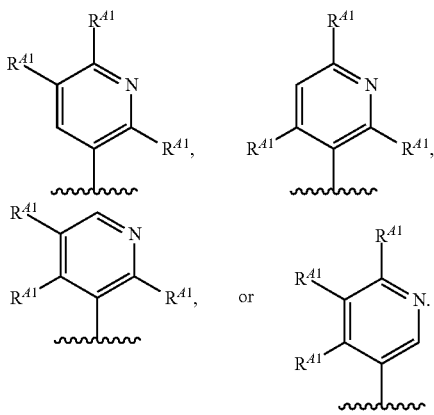

In certain embodiments, $R^A$ is of the formula:

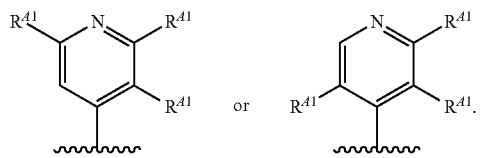

In certain embodiments, k is 4. In certain embodiments, $R^A$ is of the formula:

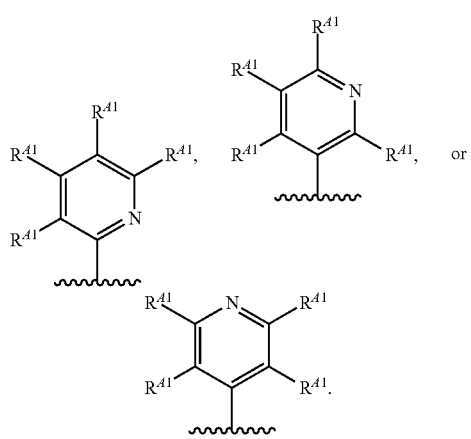

In certain embodiments, $R^A$ is not substituted or unsubstituted pyridinyl. In certain embodiments, $R^A$ is not substituted or unsubstituted 2-pyridinyl. In certain embodiments, $R^A$ is not substituted 2-pyridinyl. In certain embodiments, $R^A$ is substituted or unsubstituted pyrimidinyl. In certain embodiments, $R^A$ is substituted or unsubstituted pyrazinyl. In certain embodiments, $R^A$ is substituted or unsubstituted triazinyl. In certain embodiments, $R^A$ is substituted or unsubstituted, 9- to 10-membered, bicyclic heteroaryl, wherein one, two, three, or four atoms in the heteroaryl ring system are independently nitrogen, oxygen, or sulfur). In certain embodiments, $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur), provided that the substituted or unsubstituted heterocyclyl is not substituted or unsubstituted 3-pyrrolidinyl. In certain embodiments, $R^A$ is substituted or unsubstituted tetrahydropyranyl. In certain embodiments, $R^A$ is unsubstituted tetrahydropyranyl. In certain embodiments, $R^A$ is piperidinyl. In certain embodiments, $R^A$ is substituted or unsubstituted morpholinyl. In certain embodiments, $R^A$ is substituted or unsubstituted piperazinyl.

Formula (I) includes Ring B. Ring B is as described herein for Formula (II).

Formula (I) includes substituents $R^C$, $R^D$, $R^E$, and $R^F$, $R^C$, $R^D$, $R^E$, and $R^F$ are as described herein for Formula (III).

Formula (I) includes Ring A and one or more instances of substituent $R^G$. Ring A and substituent $R^G$ are as described herein for Formula (III).

Formula (I) includes linker L that connects Ring A to substituent $R^H$. In certain embodiments, L is a substituted or unsubstituted, $C_{1-6}$ hydrocarbon chain. In certain embodiments, one or more (e.g., 2, 3, 4, 5, or 6) chain atoms of the hydrocarbon chain of L are independently replaced with —C(=O)—, —O—, —S—, —$NR^b$—, —N=, or =N—. In certain embodiments, L is an unsubstituted $C_{1-3}$ hydrocarbon chain.

In certain embodiments, L is of the formula:

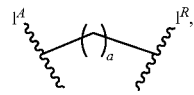

wherein a is 0, 1, 2, 3, 4, 5, or 6. In certain embodiments, a is 0. In certain embodiments, L is a bond. In certain embodiments, a is 1. In certain embodiments, a is 2. In certain embodiments, a is 3. In certain embodiments, a is 4. In certain embodiments, a is 5. In certain embodiments, a is 6. In certain embodiments, L is of the formula:

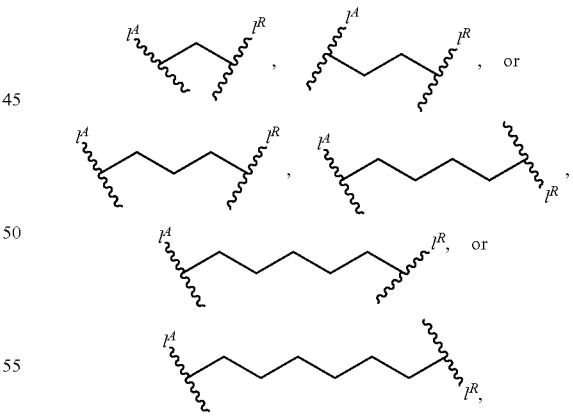

wherein $l^A$ indicates the point of attachment to Ring A, and $l^R$ indicates the point of attachment to $R^H$.

In certain embodiments, L is an unsubstituted $C_{1-3}$ hydrocarbon chain, wherein one or more (e.g., 2, 3, 4, 5, or 6) chain atoms of the hydrocarbon chain are independently replaced with —O— or —$NR^b$—. In certain embodiments, L is an unsubstituted $C_{1-3}$ hydrocarbon chain, wherein one chain atom of the hydrocarbon chain is replaced with —O—. In certain embodiments, L is of the formula:

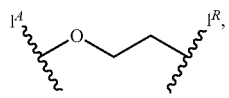

wherein l$^A$ indicates the point of attachment to Ring A, and l$^R$ indicates the point of attachment to R$^A$. In certain embodiments, L is of the formula:

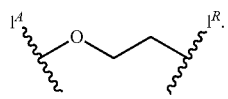

In certain embodiments, L is a substituted C$_{1-6}$ hydrocarbon chain, wherein one chain atom of the hydrocarbon chain is replaced with —N—. In certain embodiments, L is of the formula:

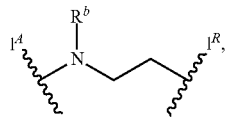

wherein l$^A$ indicates the point of attachment to Ring A, and l$^R$ indicates the point of attachment to R$^H$. In certain embodiments, L is of the formula:

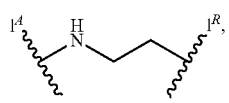

In certain embodiments, L is of the formula:

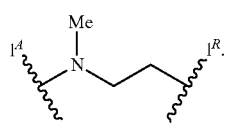

In certain embodiments, L is of the formula:

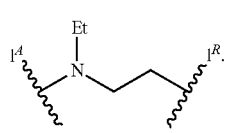

In certain embodiments, L is an unsubstituted C$_{1-3}$ hydrocarbon chain, wherein one chain atom of the hydrocarbon chain is replaced with —C(=O)—. In certain embodiments, L is an unsubstituted C$_{1-3}$ hydrocarbon chain, wherein one chain atom of the hydrocarbon chain is replaced with —S—. In certain embodiments, L is an unsubstituted C$_{1-3}$ hydrocarbon chain, wherein one chain atom of the hydrocarbon chain is replaced with —NR$^b$—. In certain embodiments, L is an unsubstituted C$_{1-3}$ hydrocarbon chain, wherein one chain atom of the hydrocarbon chain is replaced with —N=. In certain embodiments, L is an unsubstituted C$_{1-3}$ hydrocarbon chain, wherein one chain atom of the hydrocarbon chain is replaced with =N—.

Formula (I) includes substituent R$^H$. In certain embodiments, R$^H$ is substituted or unsubstituted, C$_{1-6}$ alkyl (e.g., methyl, ethyl, or propyl). In certain embodiments, R$^H$ is methyl. In certain embodiments, R$^H$ is ethyl. In certain embodiments, R$^H$ is propyl. In certain embodiments, R$^H$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^H$ is substituted or unsubstituted tetrahydropyranyl, substituted or unsubstituted piperidinyl, substituted or unsubstituted morpholinyl, or substituted or unsubstituted piperazinyl. In certain embodiments, R$^H$ is of the formula:

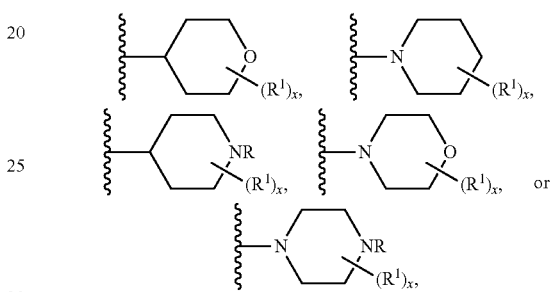

wherein R$^1$ is substituted or unsubstituted, C$_{1-6}$ alkyl or —O$^{x1}$, wherein R is hydrogen, substituted or unsubstituted, C$_{1-6}$ alkyl or nitrogen protecting group; R$^{x1}$ is hydrogen or substituted or unsubstituted, C$_{1-6}$ alkyl; and x is 0, 1, 2, or 3. In certain embodiments, R$^H$ is of the formula:

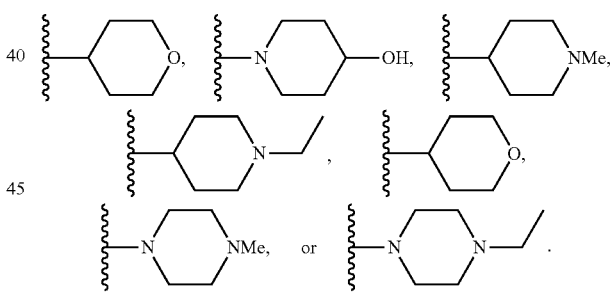

In certain embodiments, R$^H$ is —OH. In certain embodiments, R$^H$ is —N(R$^c$)$_2$.

R$^H$ may include substituent R$^c$. In certain embodiments, R$^c$ is hydrogen. In certain embodiments, R$^c$ is substituted or unsubstituted, C$_{1-6}$ alkyl. In certain embodiments, R$^c$ is substituted or unsubstituted, C$_{1-3}$ alkyl. In certain embodiments, R$^c$ is substituted or unsubstituted methyl. In certain embodiments, R$^c$ is methyl. In certain embodiments, R$^c$ is substituted or unsubstituted ethyl. In certain embodiments, R$^c$ is substituted or unsubstituted methyl. In certain embodiments, R$^c$ is a nitrogen protecting group. In certain embodiments, R$^H$ is —NMe$_2$. In certain embodiments, two instances of R$^c$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two instances of $R^c$ are taken together with their intervening atoms to form a substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, Ring A with linker L and substituent $R^H$ is of the formula:

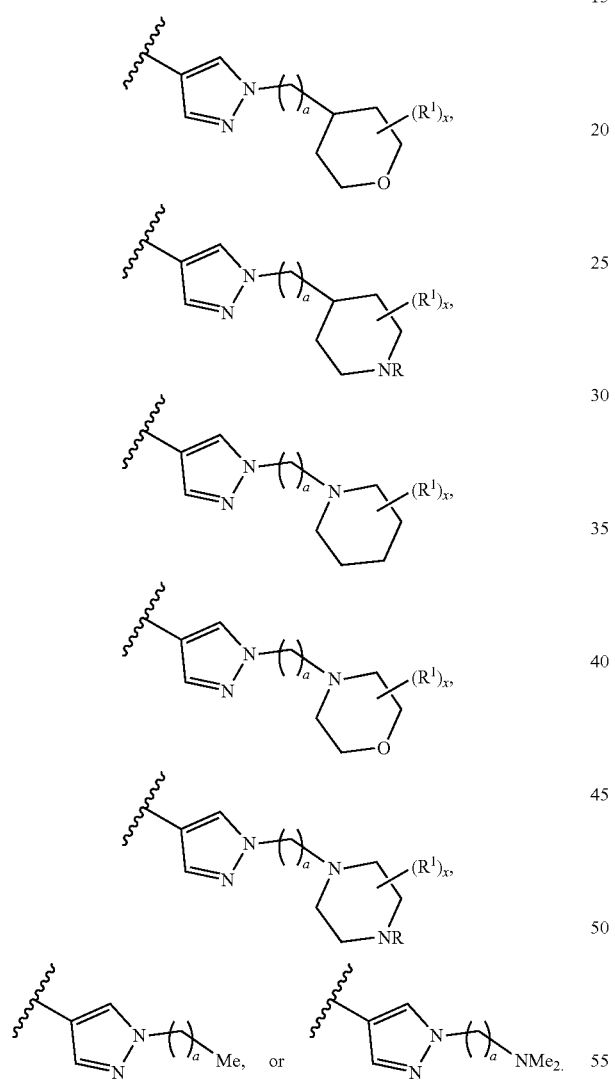

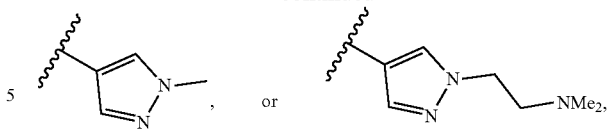

In certain embodiments, Ring A with linker L and substituent $R^H$ is of the formula:

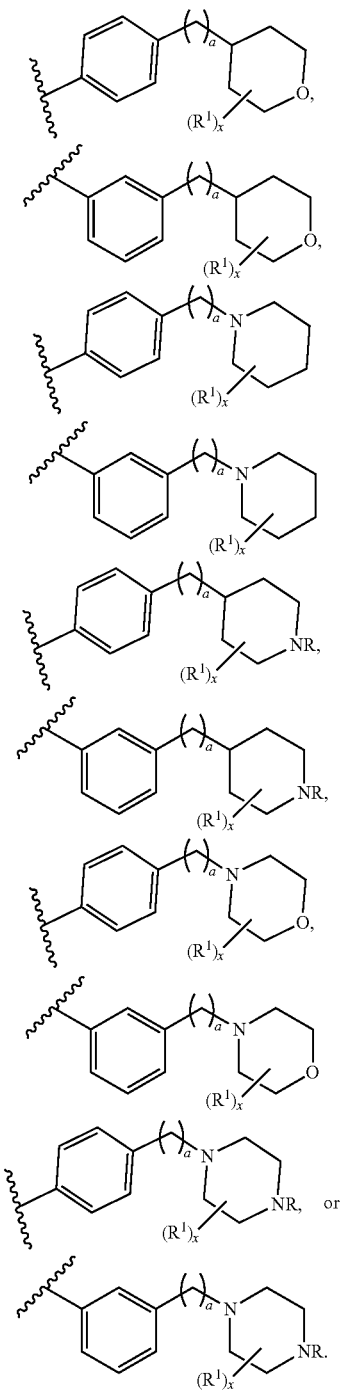

In certain embodiments, Ring A with linker L and substituent $R^H$ is of the formula:

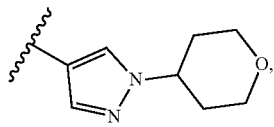

In certain embodiments, Ring A with linker L and substituent $R^H$ is not of the formula:

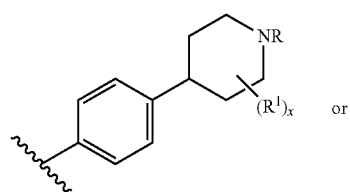
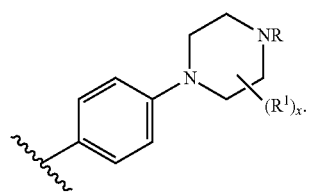
In certain embodiments, Ring A with linker L and substituent $R^H$ is of the formula:
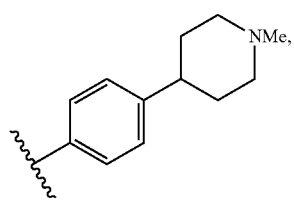
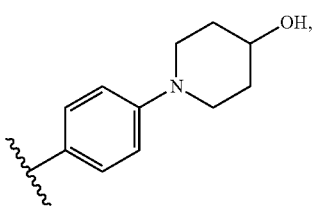
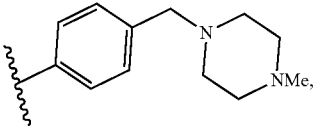
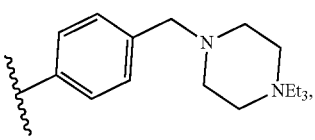
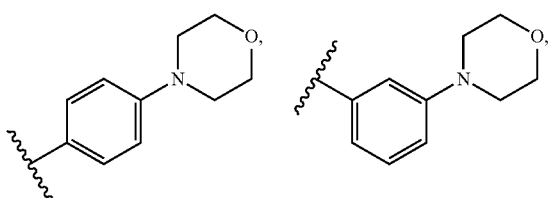
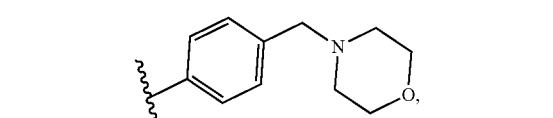
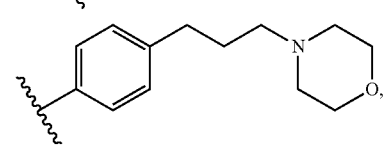
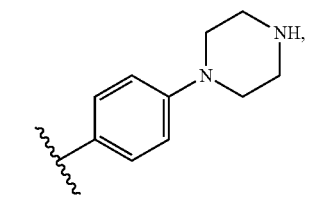
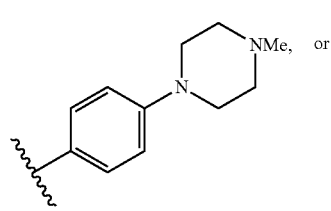
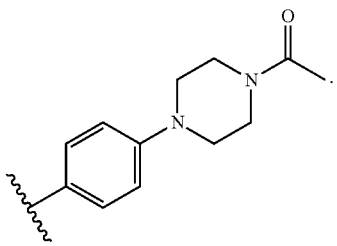
In certain embodiments, Ring A with linker L and substituent $R^H$ is not of the formula:
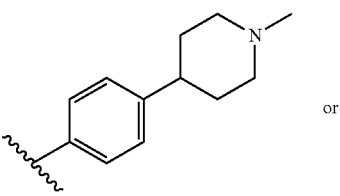
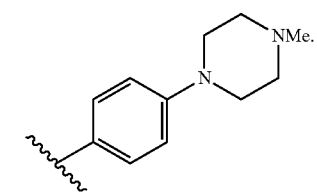
In certain embodiments, Ring A with linker L and substituent $R^H$ is of the formula:
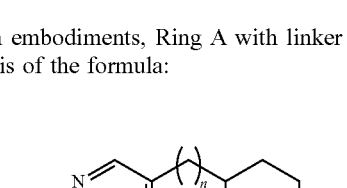
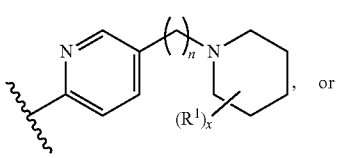

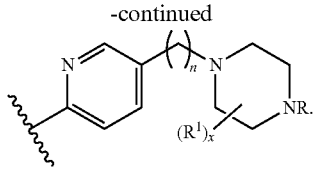

In certain embodiments, Ring A with linker L and substituent R$^H$ is of the formula:

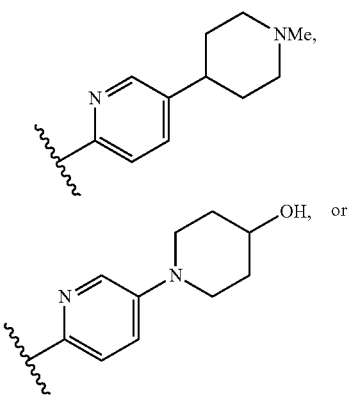

In certain embodiments, Ring A with linker L and substituent R$^H$ is of the formula:

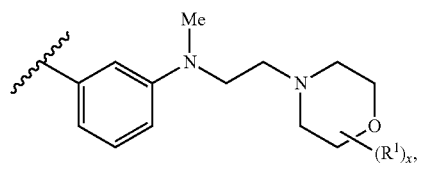

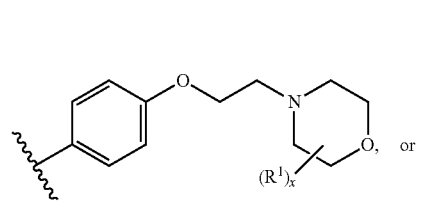

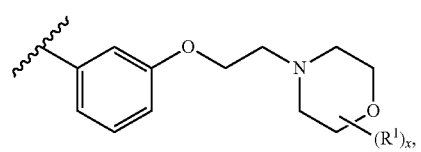

In certain embodiments, Ring A with linker L and substituent R$^H$ is of the formula:

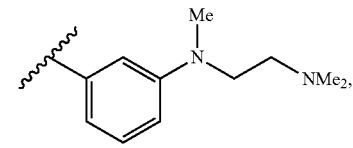

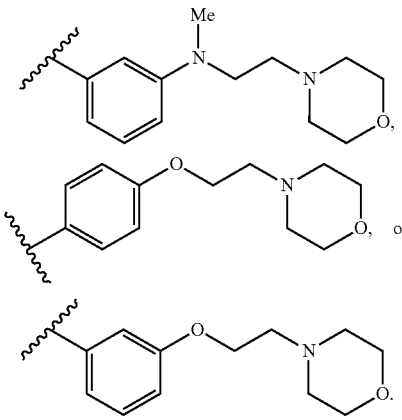

In certain embodiments, the compound of Formula (I) is of the formula:

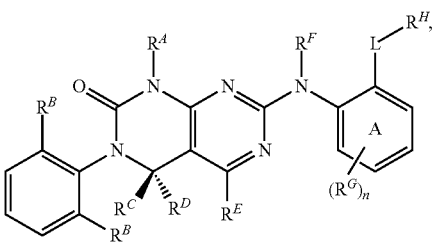

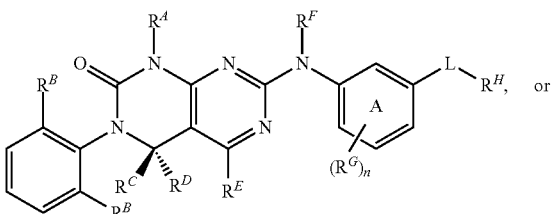

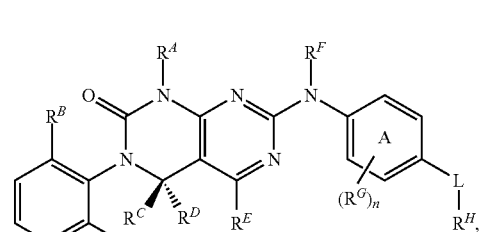

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

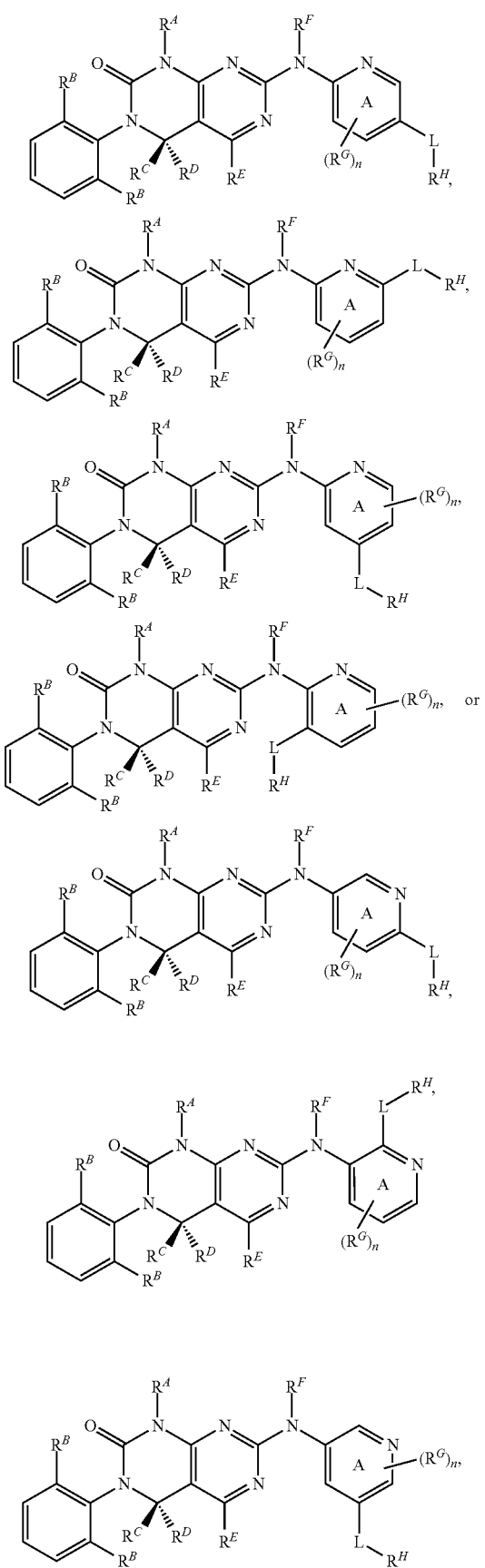

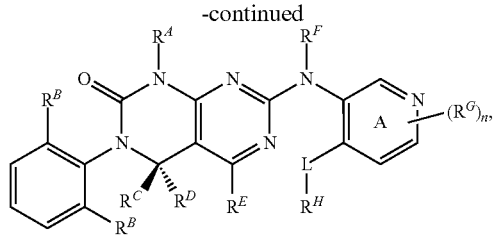

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

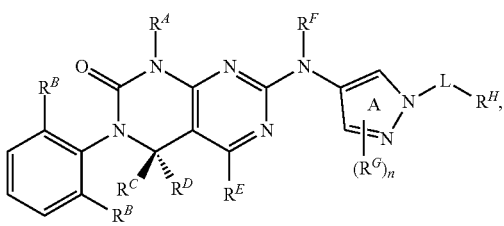

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

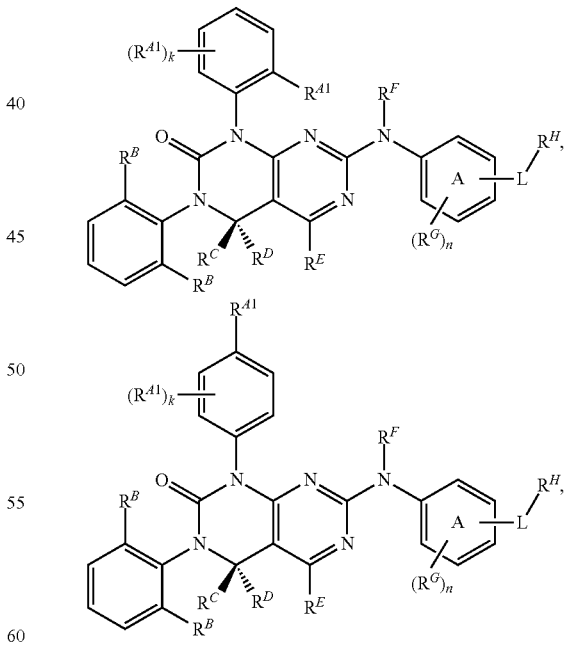

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

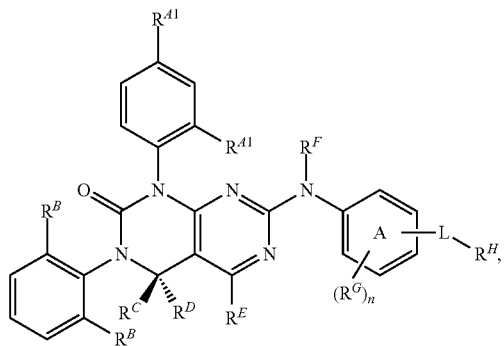

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

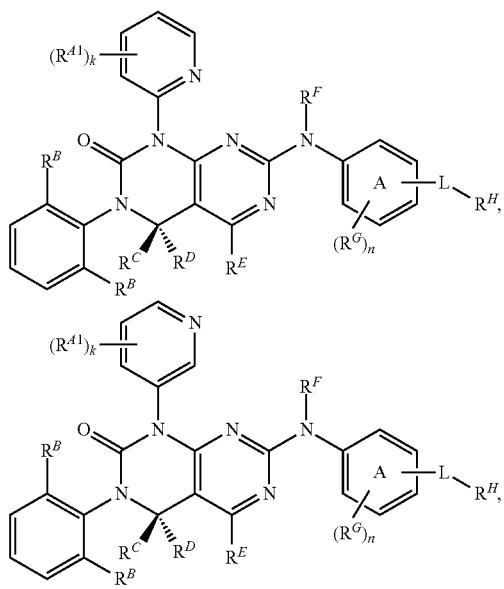

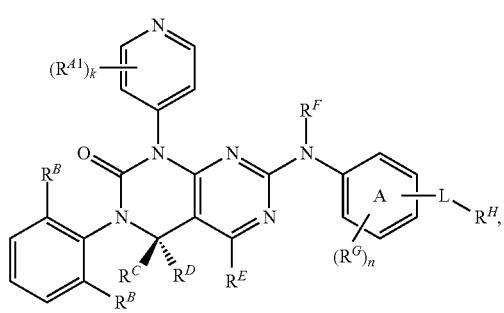

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

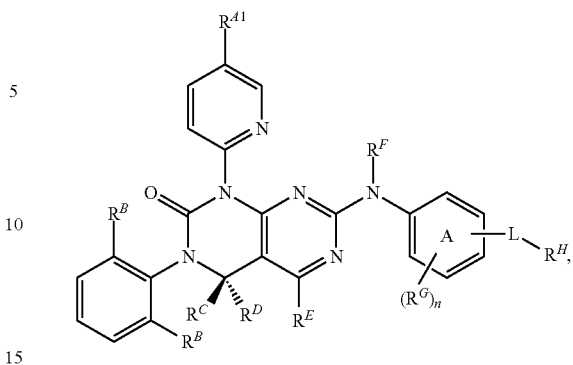

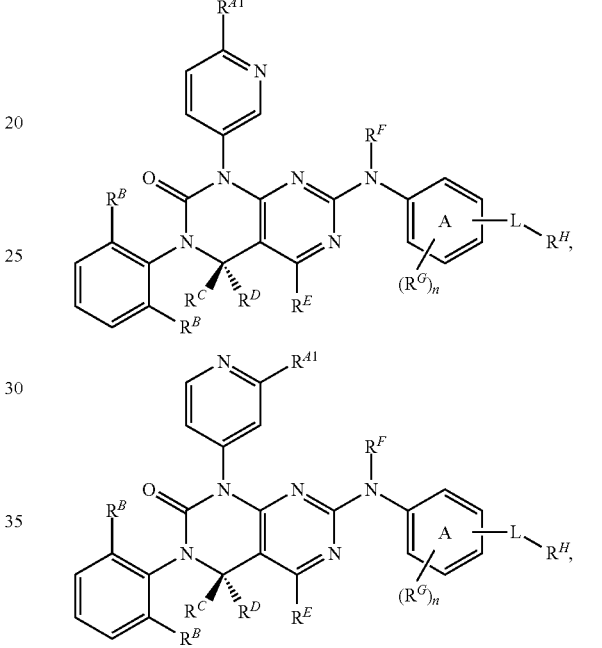

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

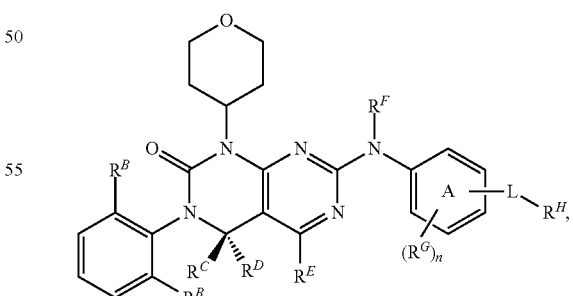

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

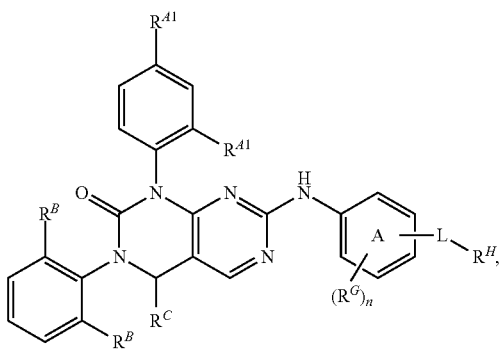

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

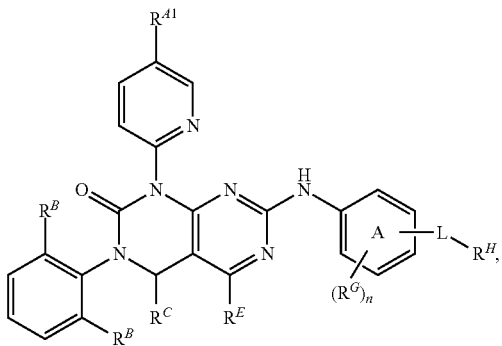

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

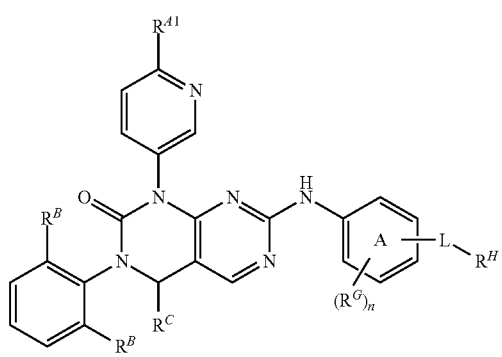

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

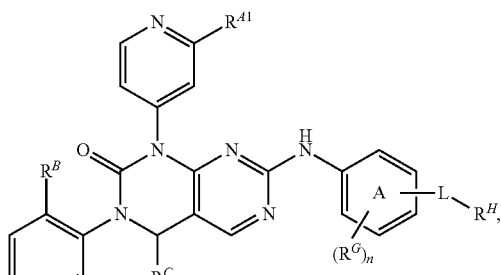

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

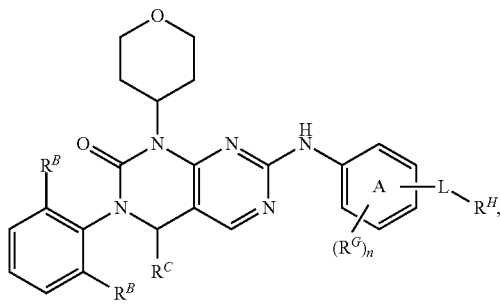

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

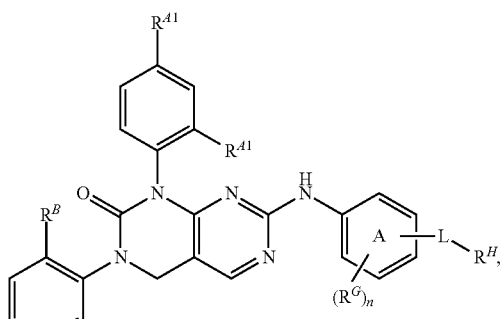

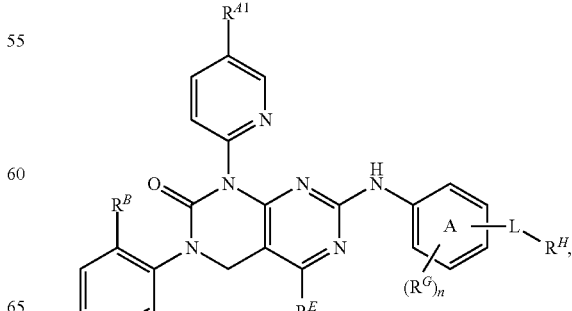

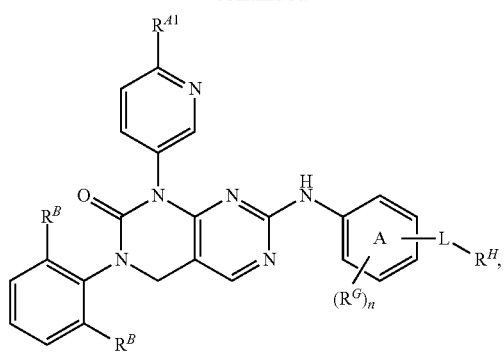
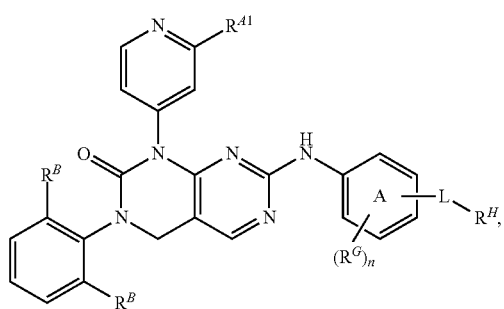
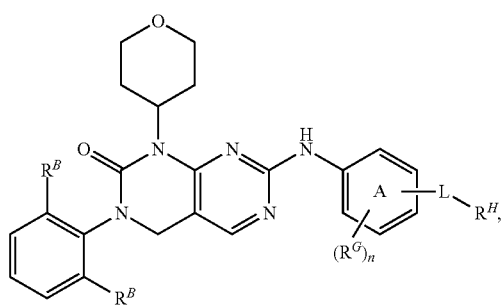
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
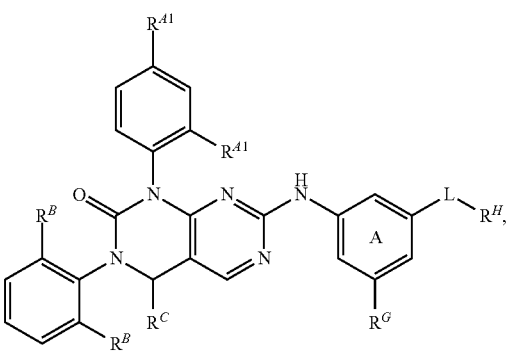
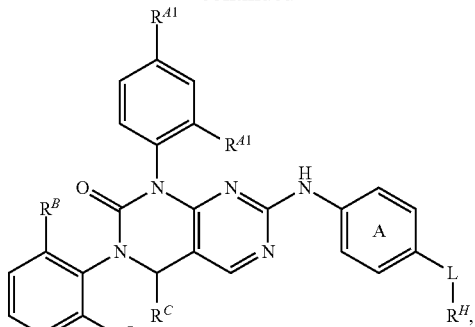
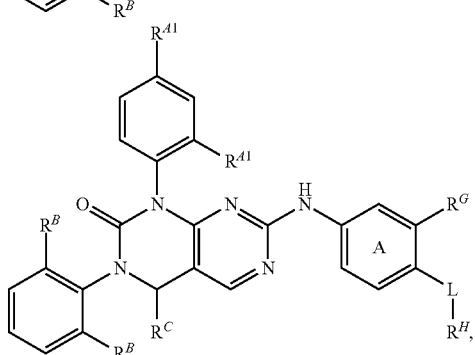
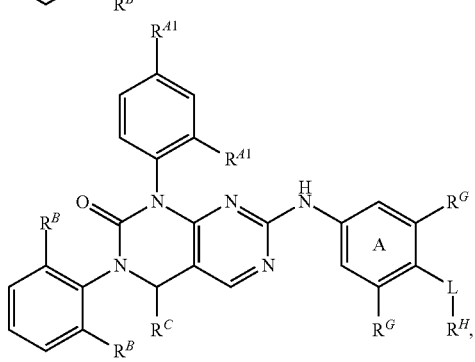
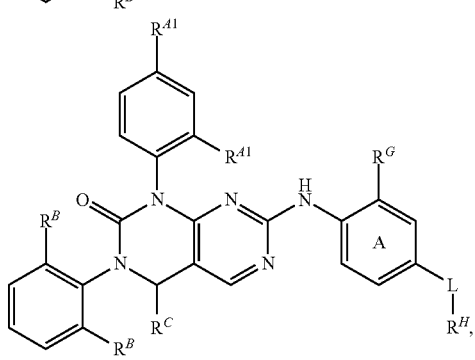
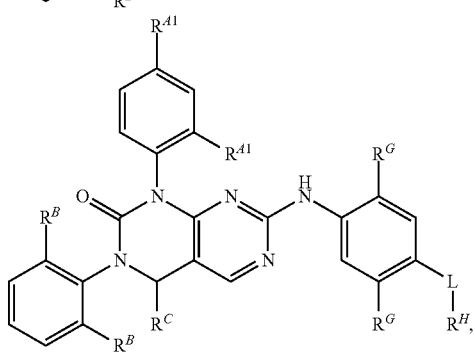

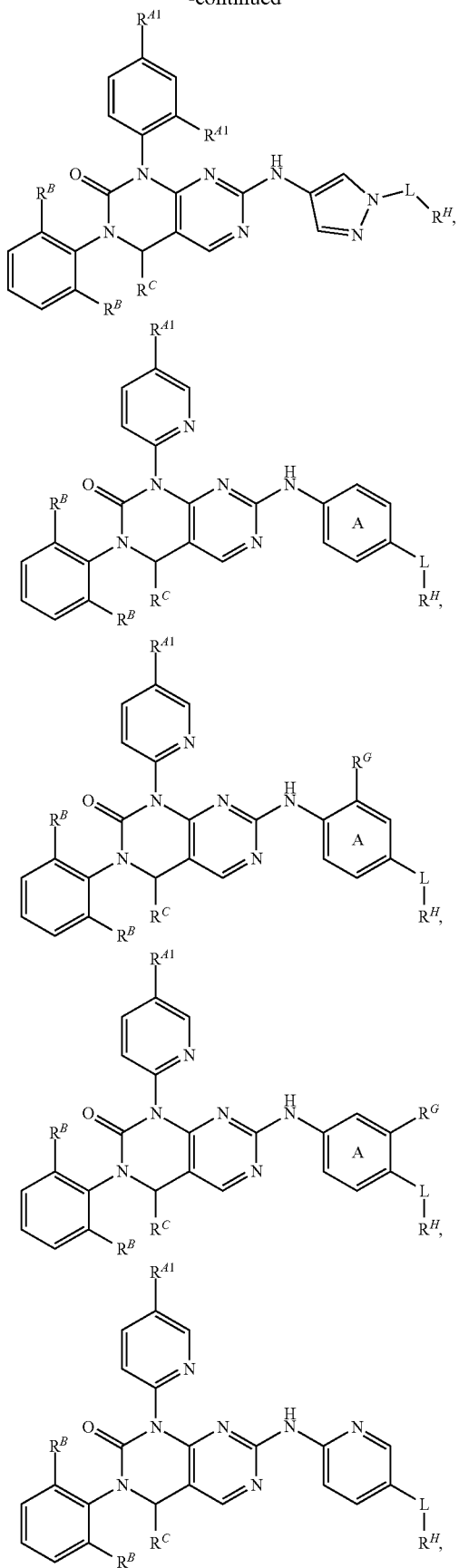
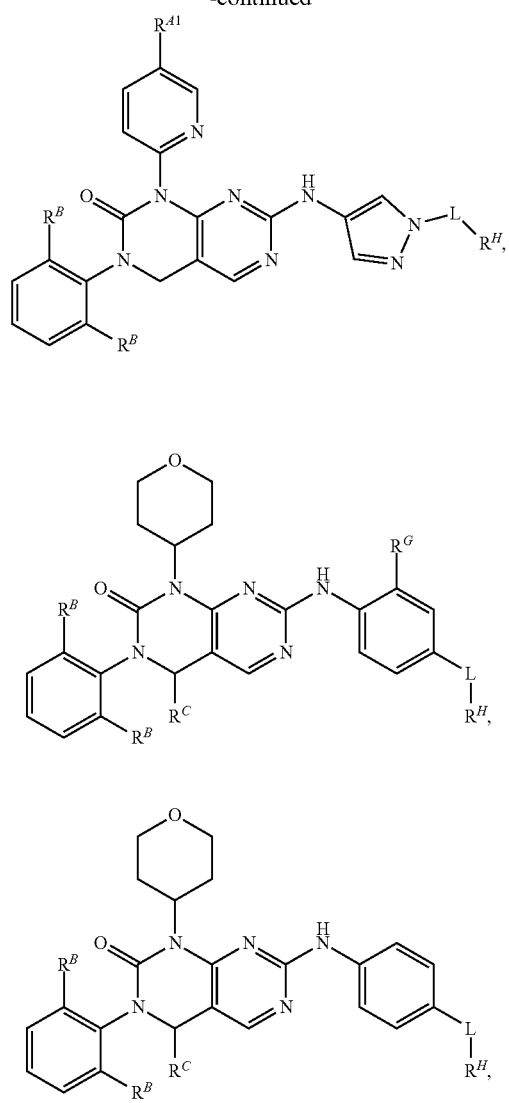
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
(YKL-05-57)
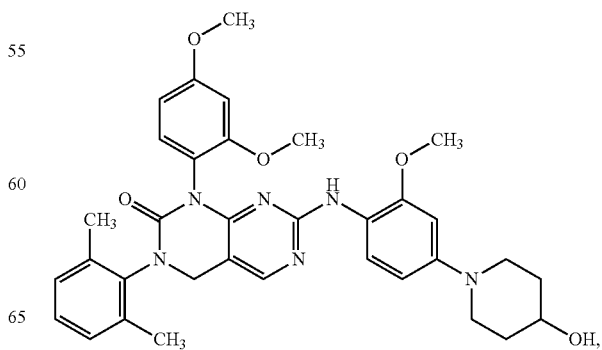

-continued
(YKL-05-58)
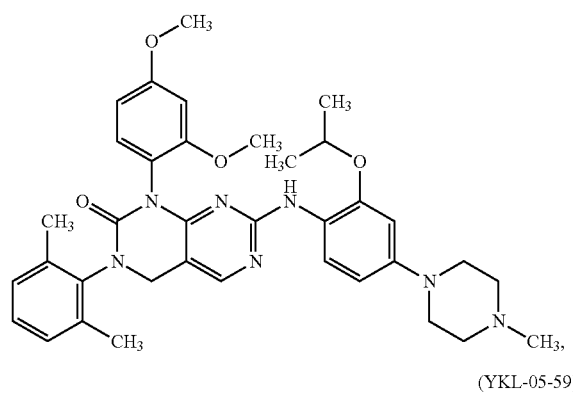
(YKL-05-59)
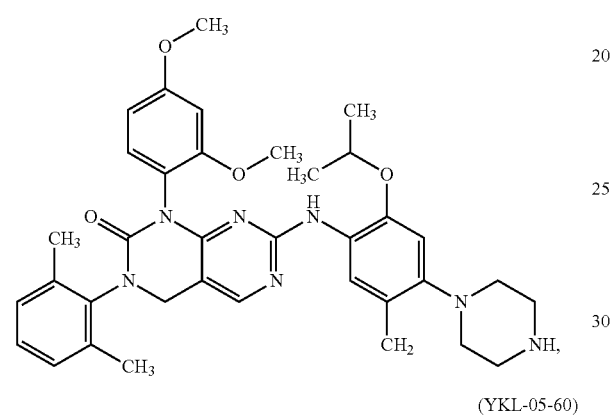
(YKL-05-60)
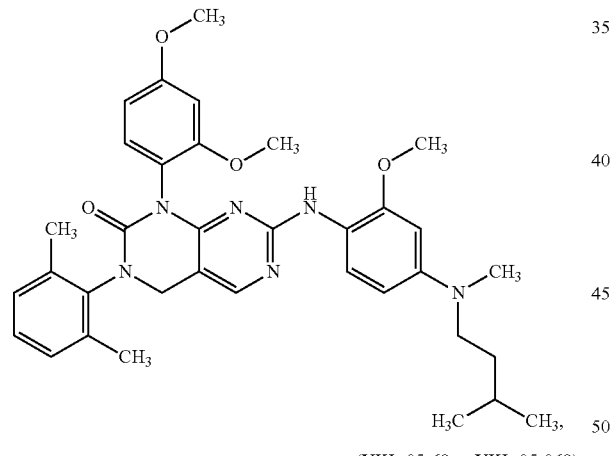
(YKL-05-68 or YKL-05-068)
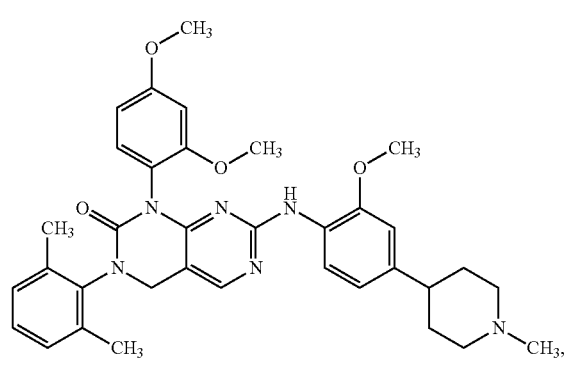
(YKL-05-69)
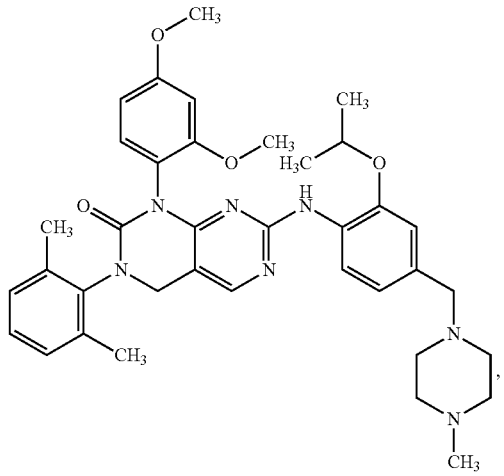
(YKL-05-70)
(YKL-05-74)
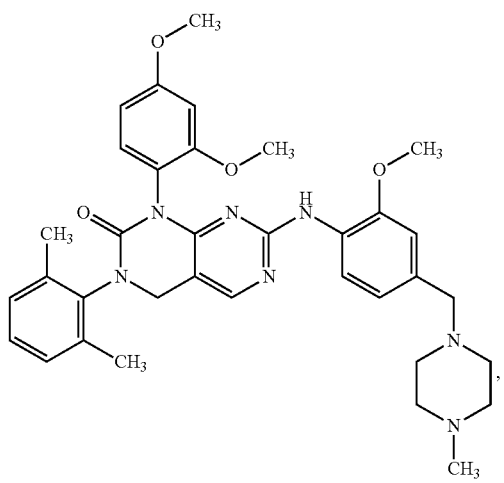

(YKL-05-76)
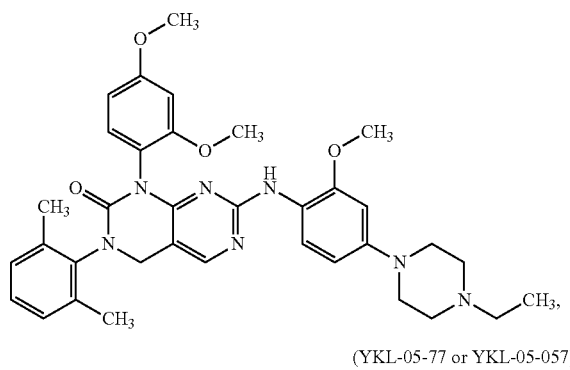
(YKL-05-77 or YKL-05-057)
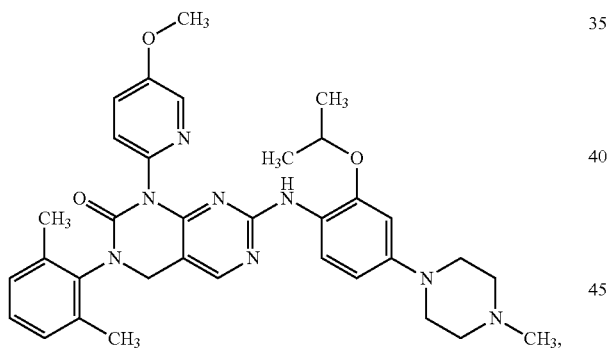
(YKL-05-88)
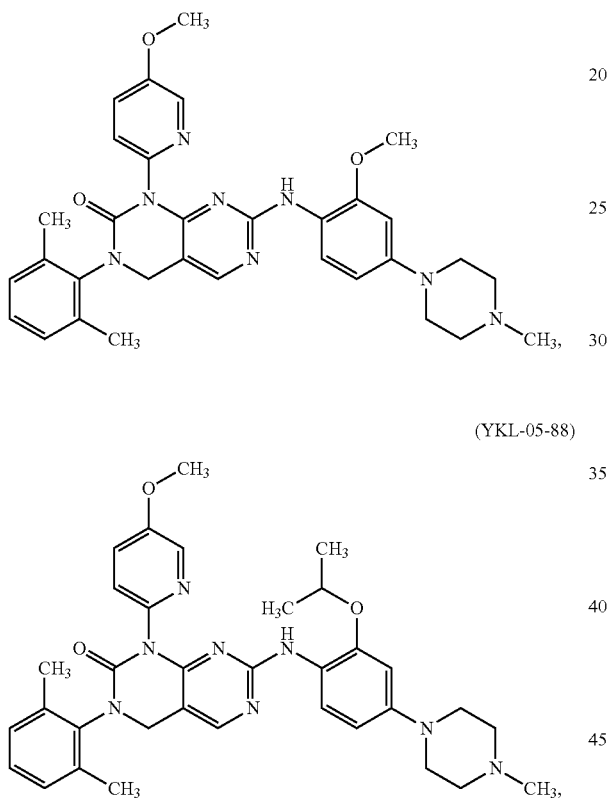
(YKL-05-89)
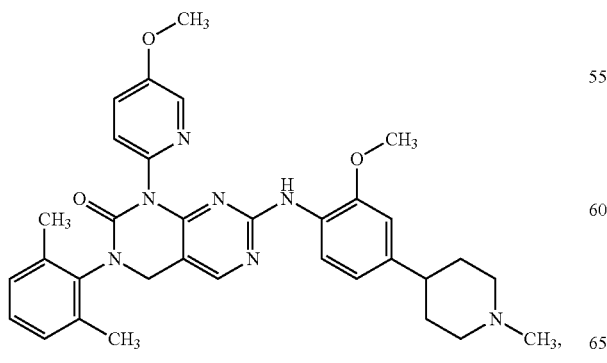
(YKL-05-90)
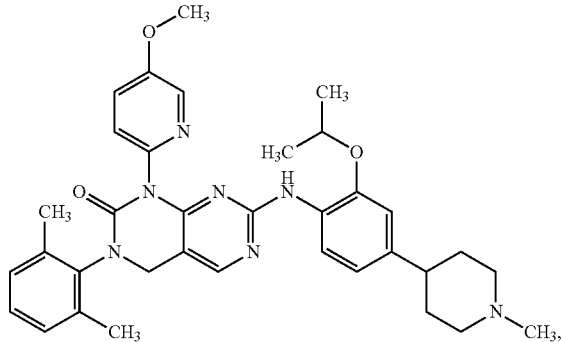
(YKL-05-91)
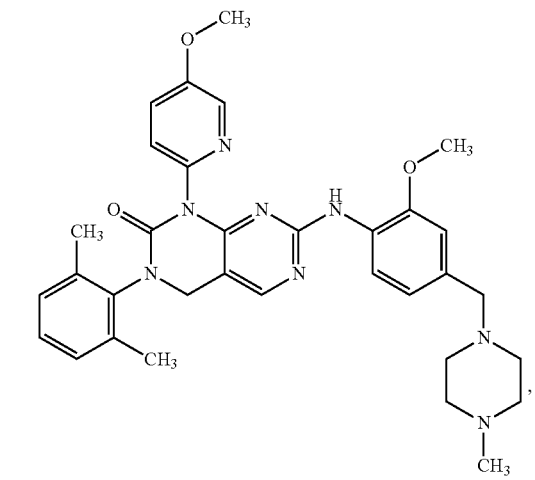
(YKL-05-92)
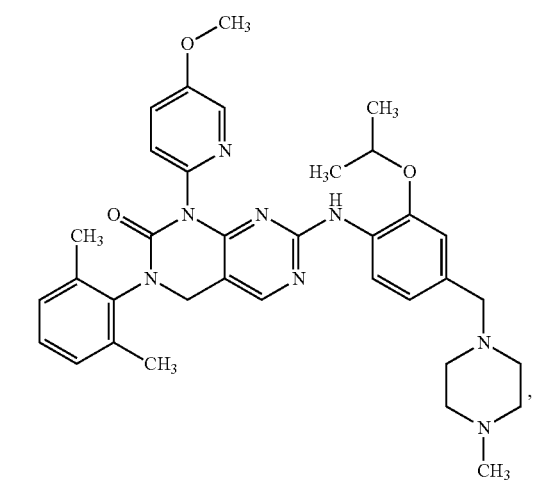

(YKL-05-93 or YKL-05-093)
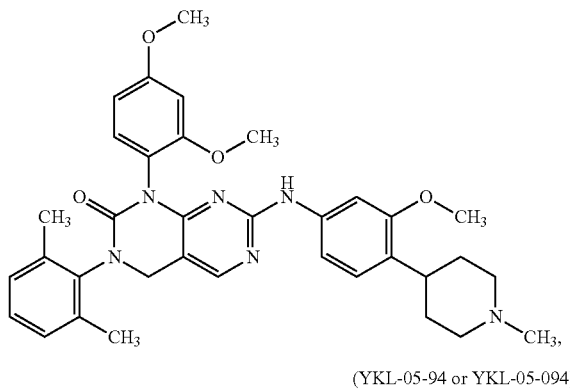
(YKL-05-94 or YKL-05-094)
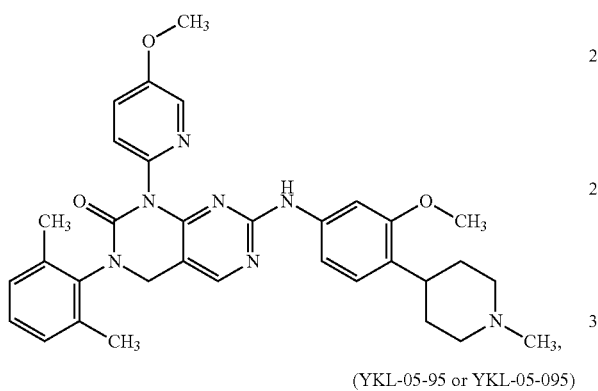
(YKL-05-95 or YKL-05-095)
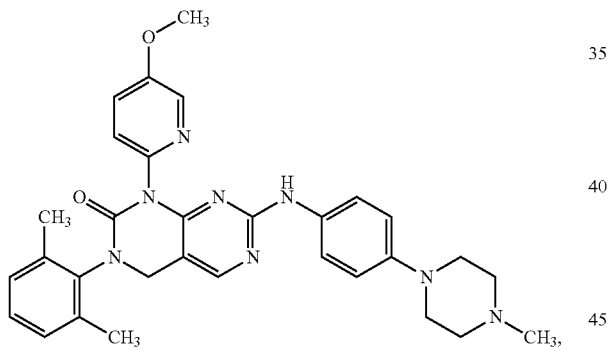
(YKL-05-96 or YKL-05-096)
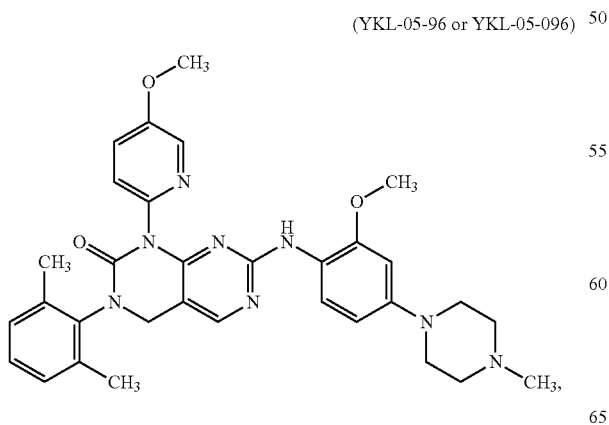
(YKL-05-97 or YKL-05-097)
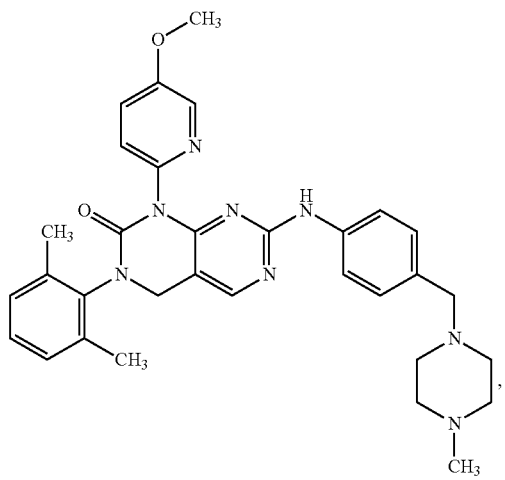
(YKL-05-98 or YKL-05-098)
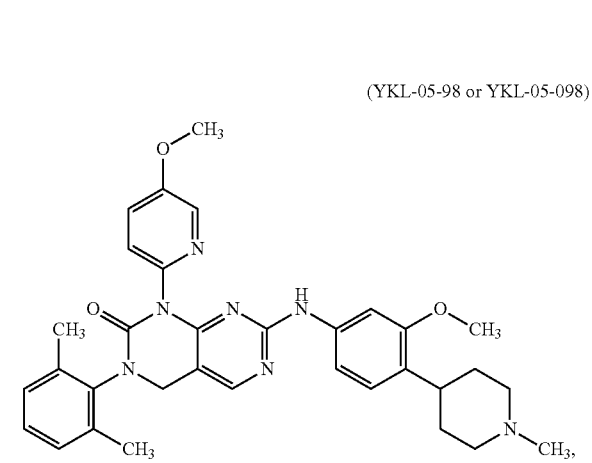
(YKL-05-99 or YKL-05-099)
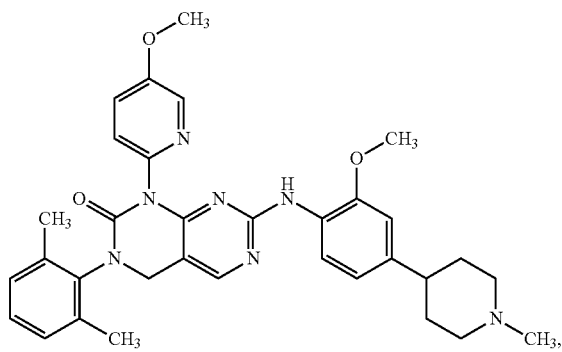

(YKL-05-100)
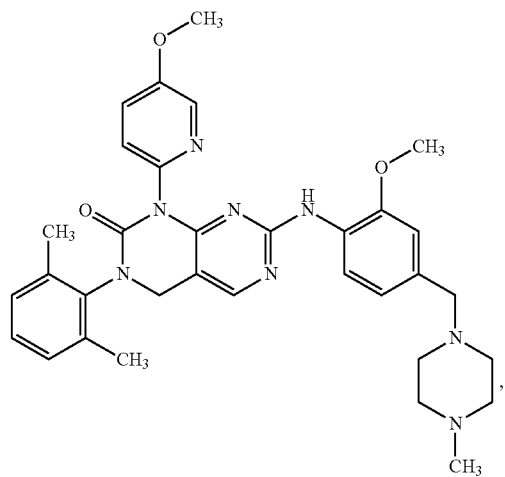
(YKL-05-151)
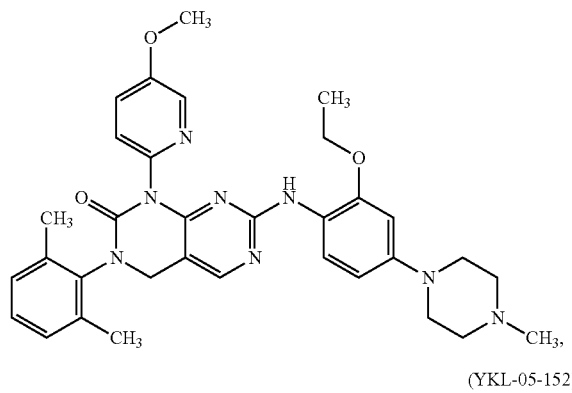
(YKL-05-152)
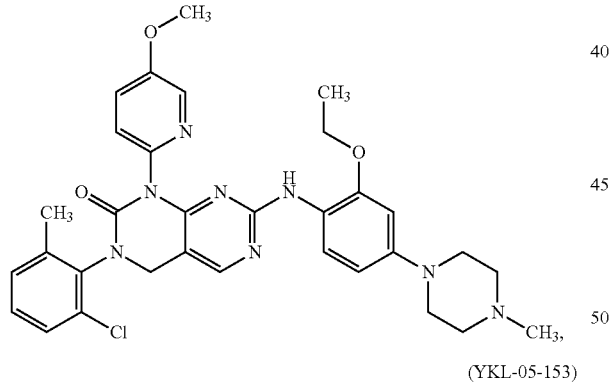
(YKL-05-153)
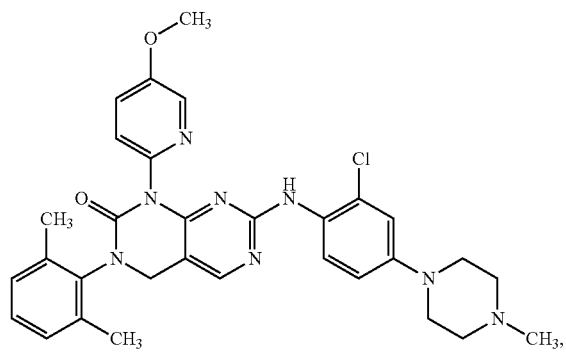
(YKL-05-154)
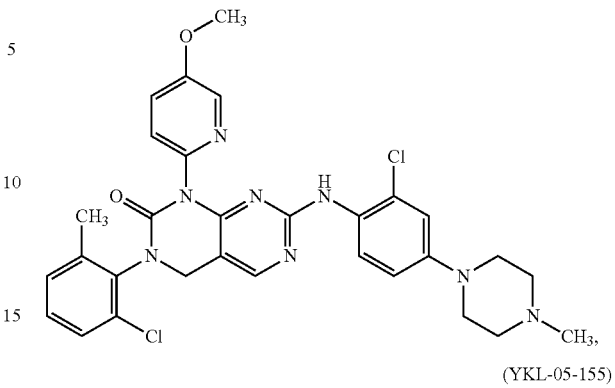
(YKL-05-155)
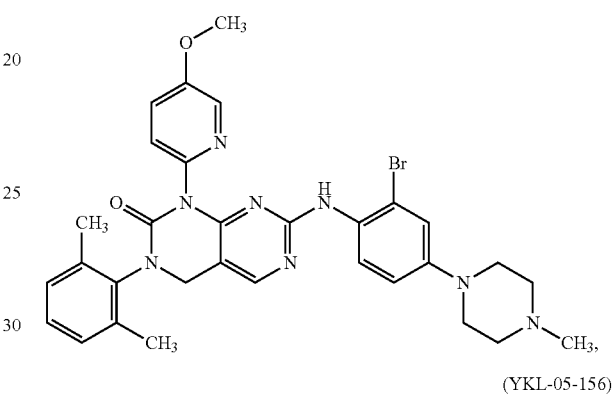
(YKL-05-156)
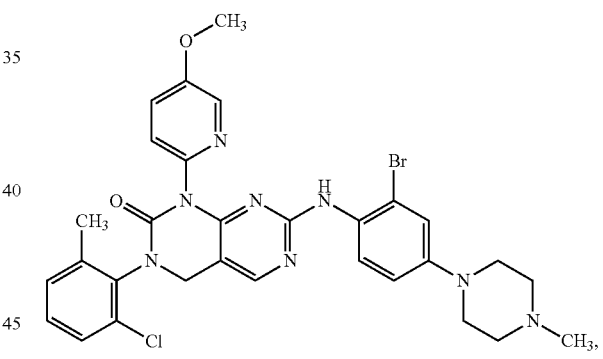
(YKL-05-163)
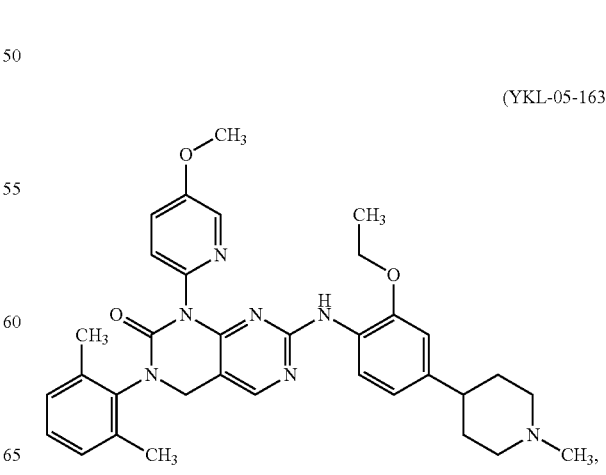

(YKL-05-164)
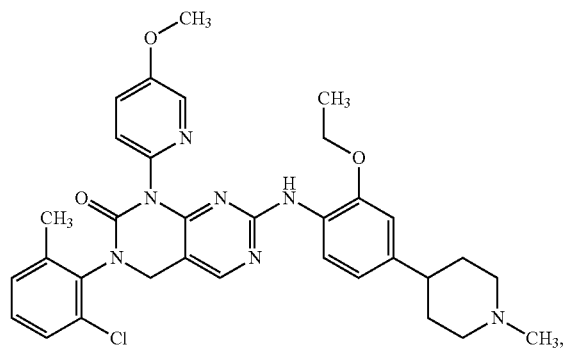
(YKL-05-179)
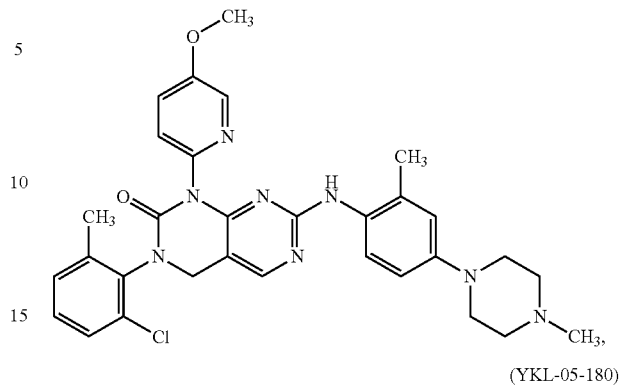
(YKL-05-165)
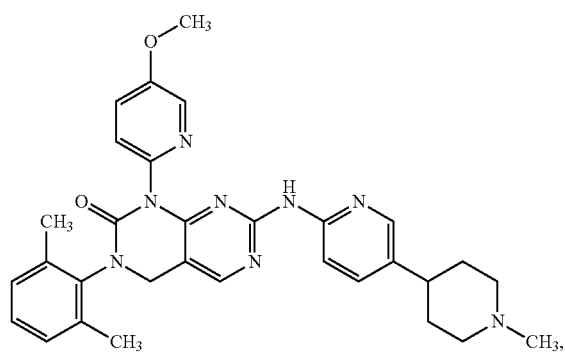
(YKL-05-180)
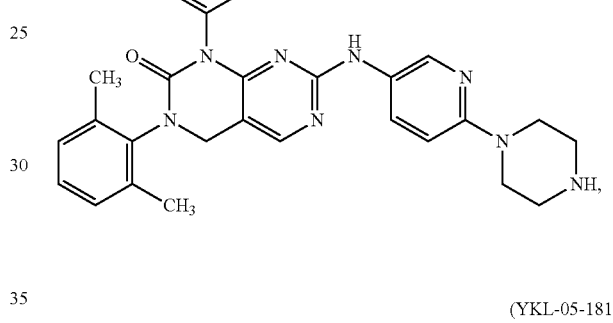
(YKL-05-166)
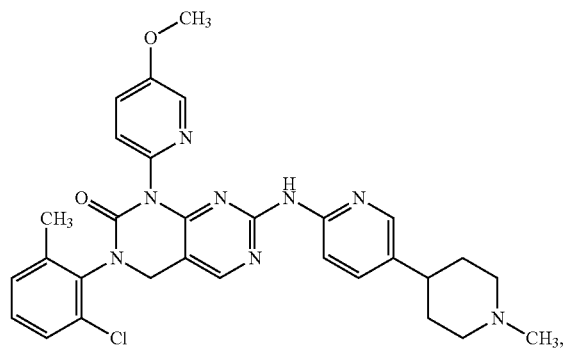
(YKL-05-181)
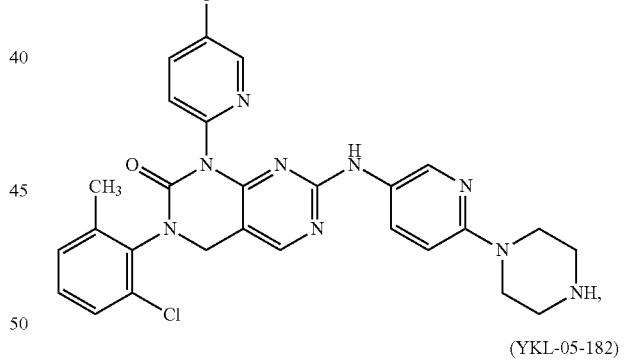
(YKL-05-178)
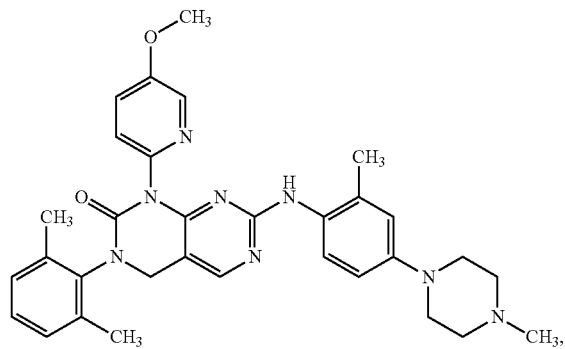
(YKL-05-182)
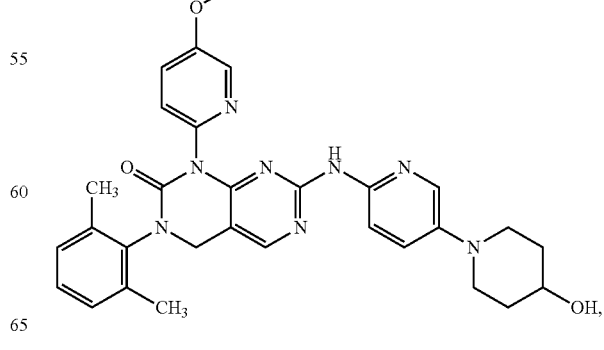

-continued
(YKL-05-183)
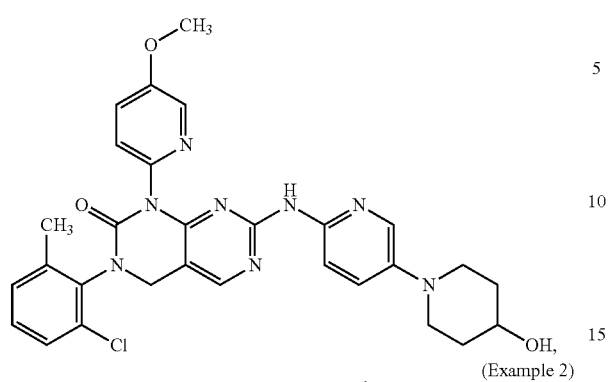
(Example 2)
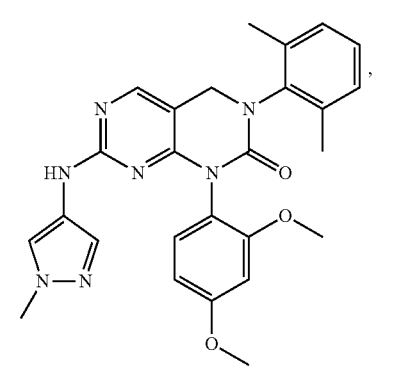
(YKL-04-136-1 or SB1-D-01)
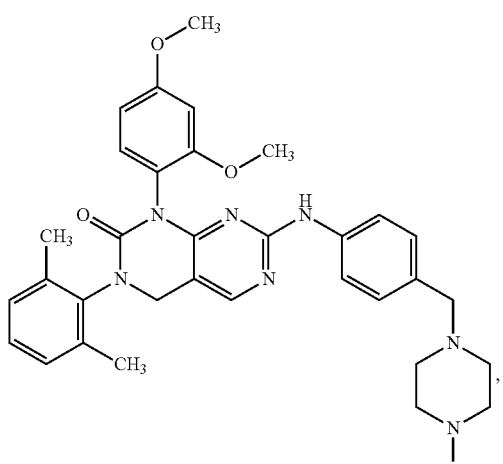
(YKL-04-136-2 or SB1-D-02)
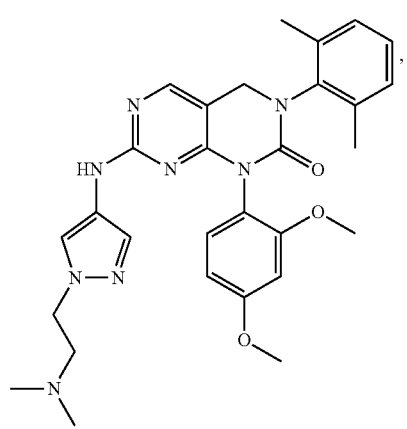
-continued
(YKL-04-136-3 or SB1-D-03)
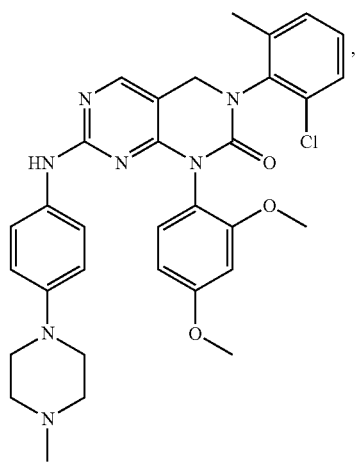
(YKL-04-136-9 or SB1-D-04)
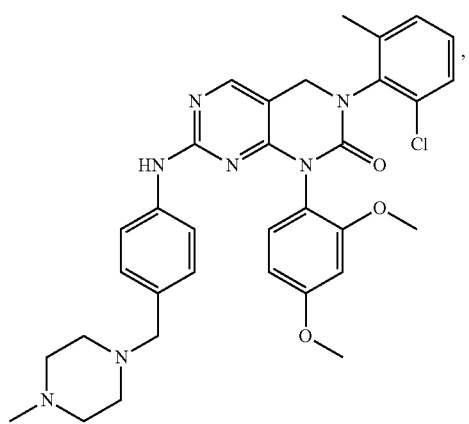
(YKL-04-136-4 or SB1-D-05)
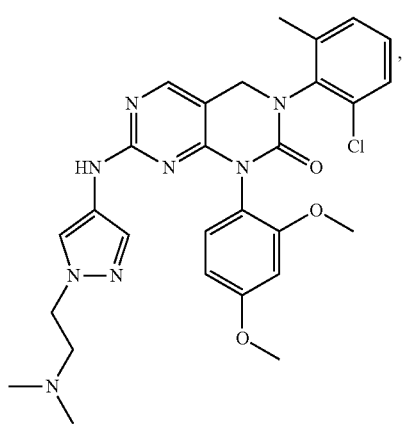

77
-continued
(YKL-04-136-5 or SB1-D-06)
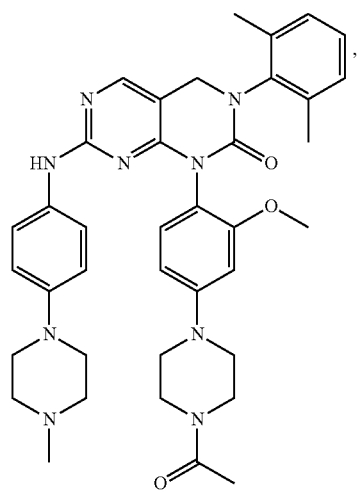
(YKL-04-136-4 or SB1-D-05)
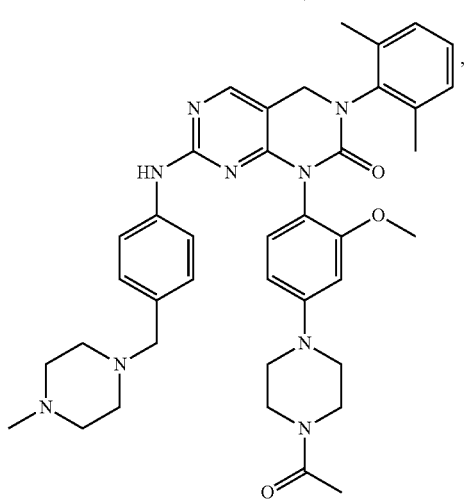
(YKL-04-136-7 or SB1-D-08)
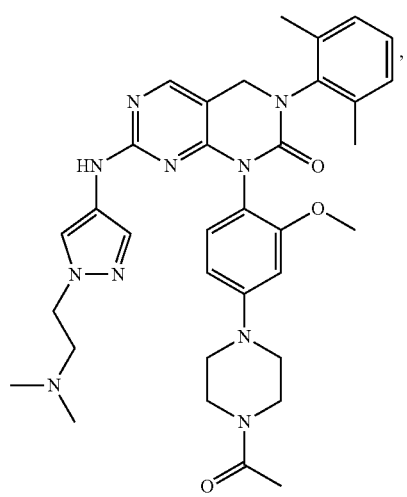
78
-continued
(YKL-04-136-6 or SB1-D-09)
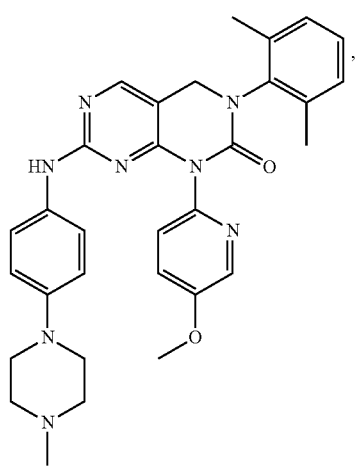
(YKL-04-136-10 or SB1-D-10)
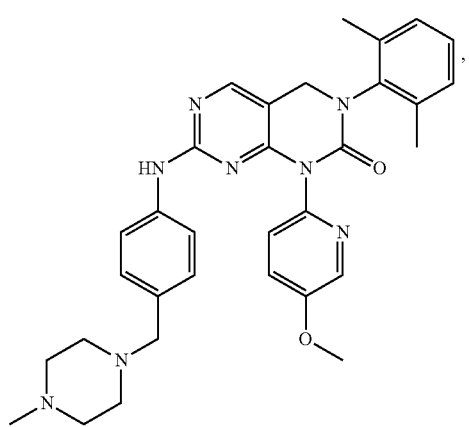
(YKL-04-136-8 or SB1-D-11)
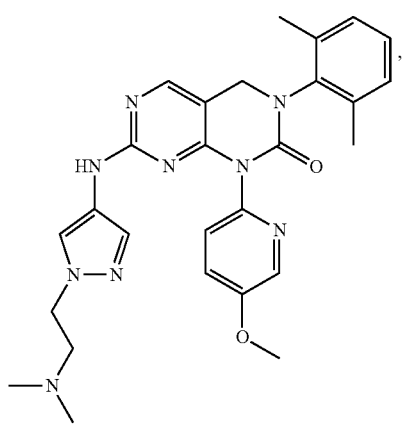

(YKL-04-103)
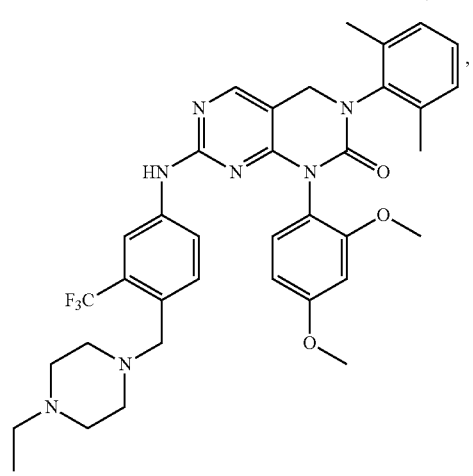
(YKL-04-104)
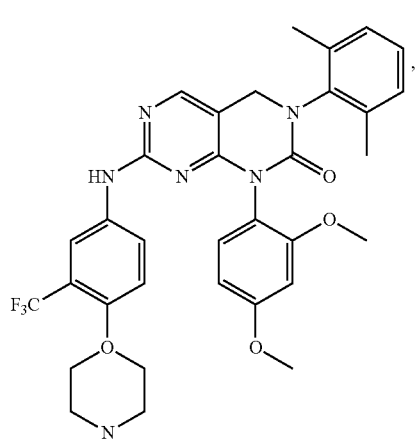
(YKL-04-105)
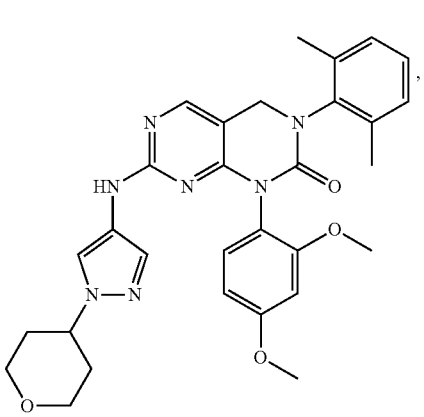
(YKL-04-106)
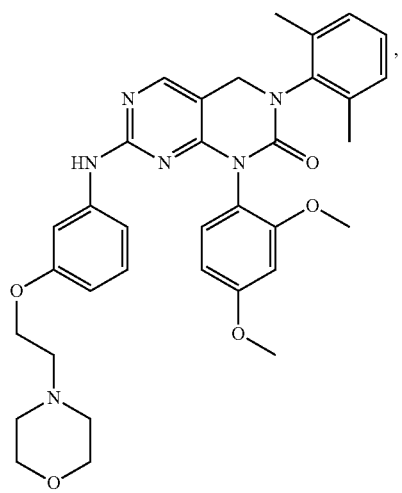
(YKL-04-107)
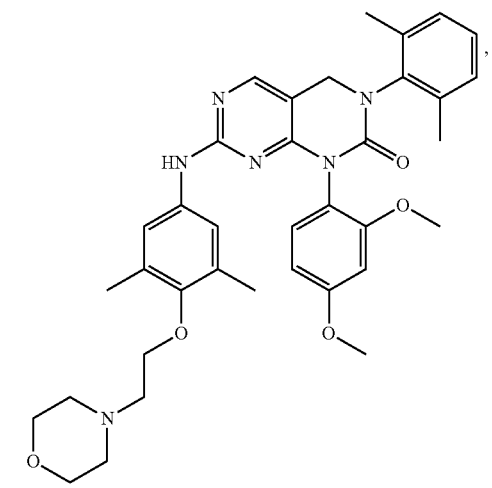
(YKL-04-108)
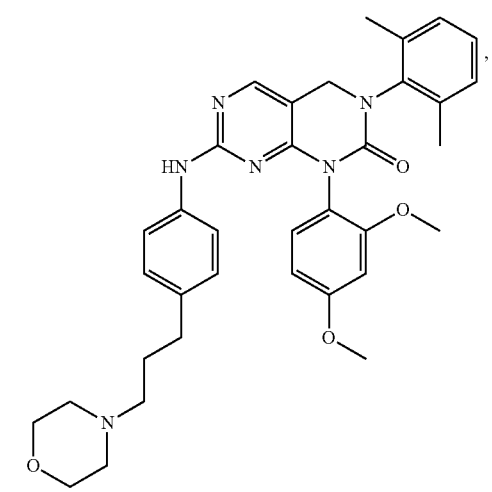

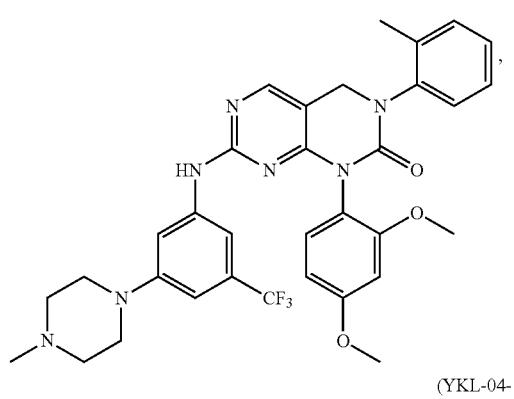
(YKL-04-112)
(YKL-04-113)
(YKL-04-114)
(YKL-04-115)
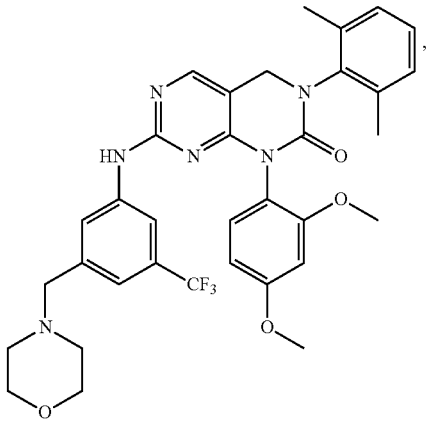
(YKL-04-118)
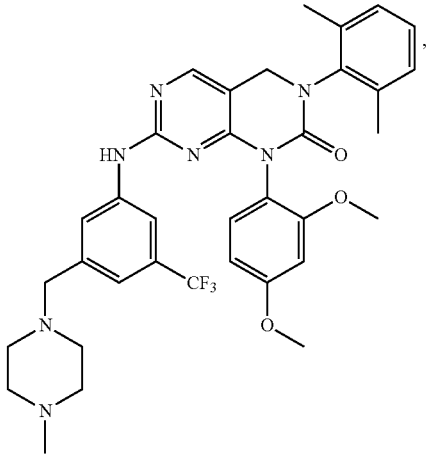
(YKL-04-125)
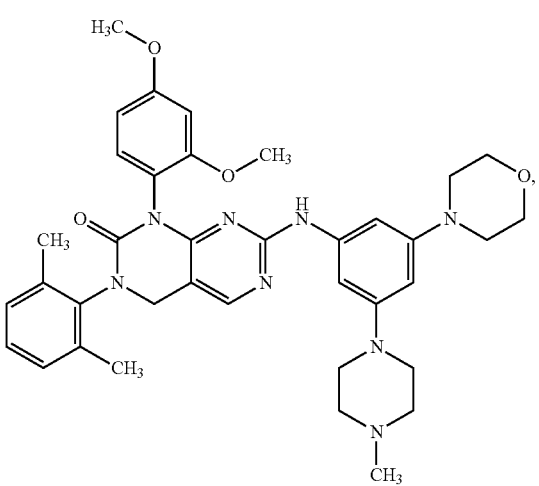
(HG-11-143-01)

83
-continued
(HG-11-136-01)
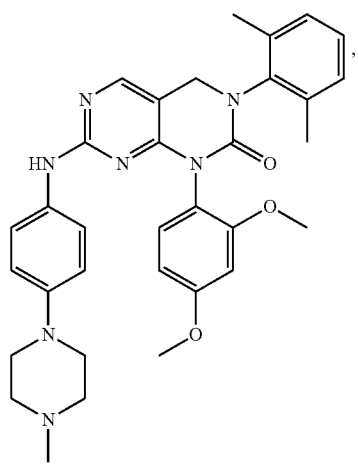
(HG-11-139-01)
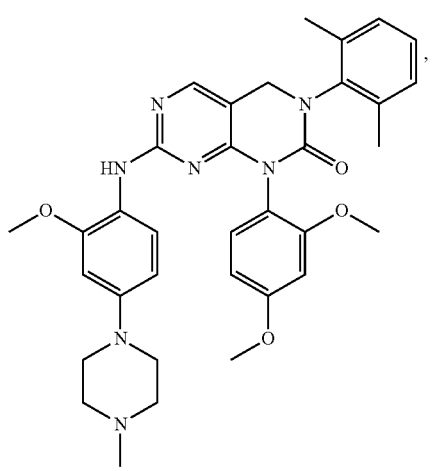
(YKL-06-038, YKL 06-038, or SBI-D-40)
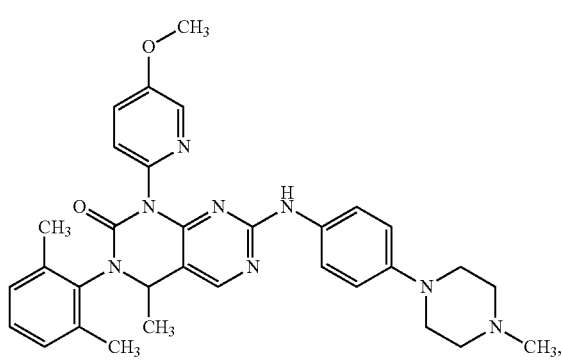
84
-continued
(YKL-06-039 or SB1-D-42)
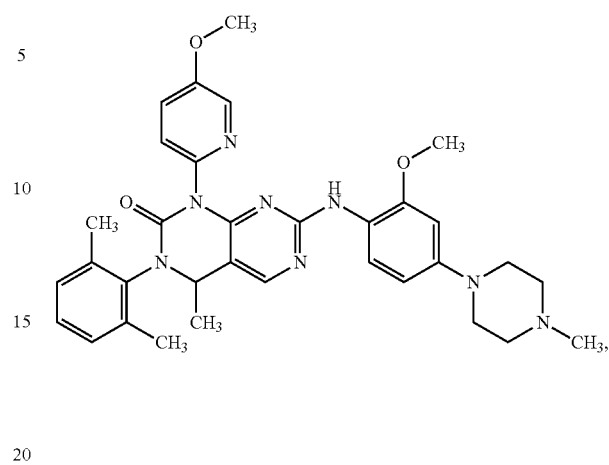
(YKL-06-040)
(YKL-06-044)
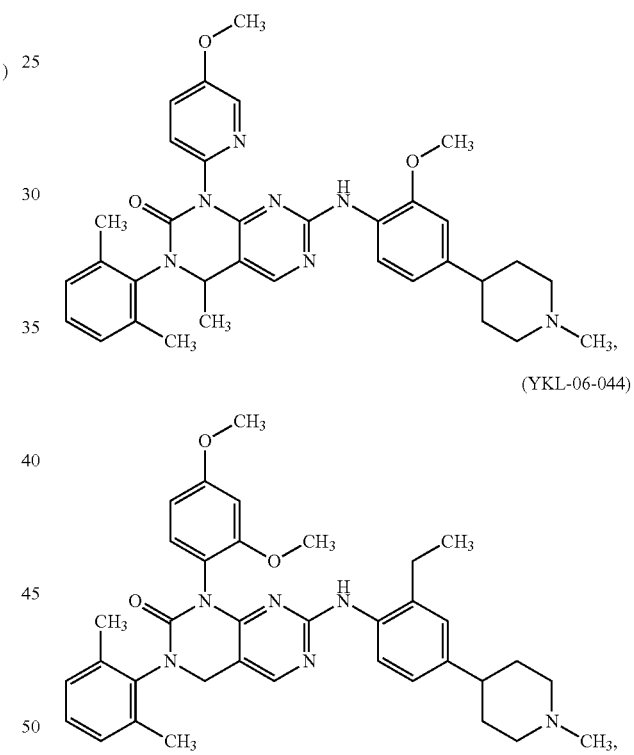
(YKL-06-045)
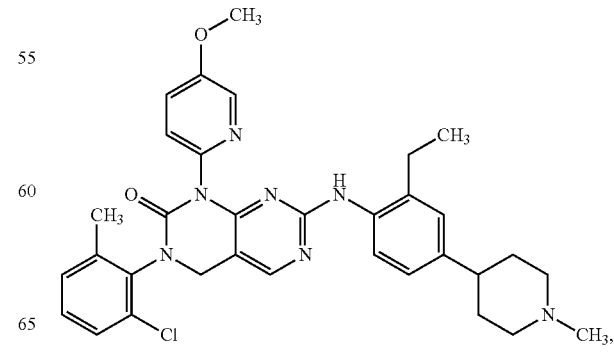

-continued
(YKL-06-051)
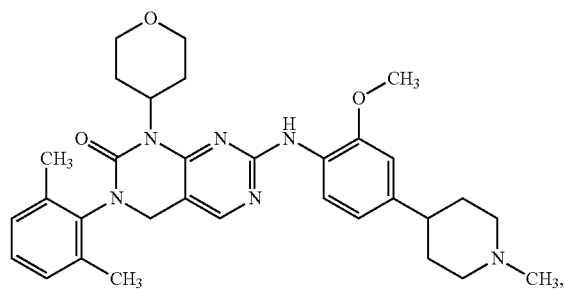
(YKL-06-054)
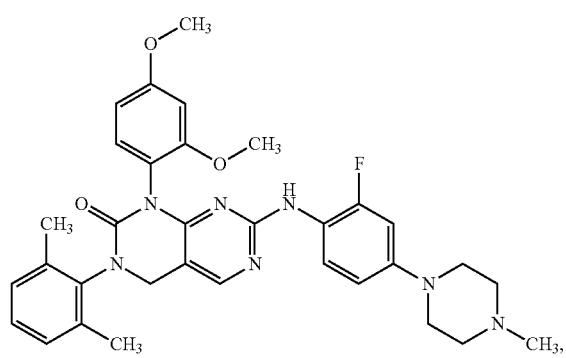
(YKL-06-055)
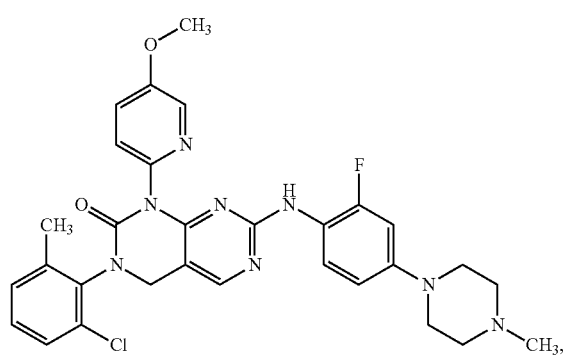
(YKL-06-056)
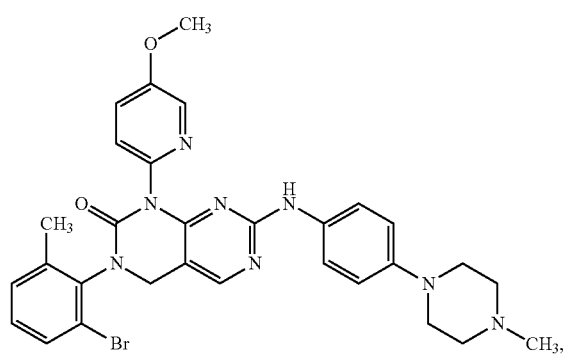
-continued
(YKL-06-057 or SB1-D-43)
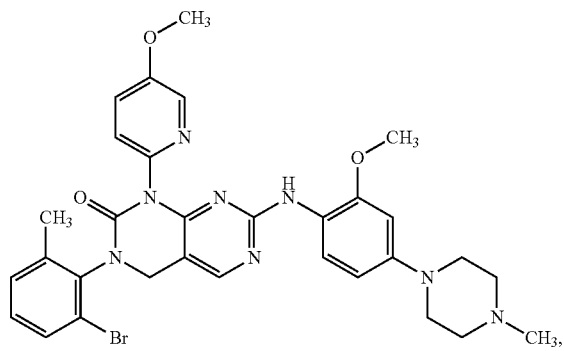
(YKL-06-077 or SB1-D-57)
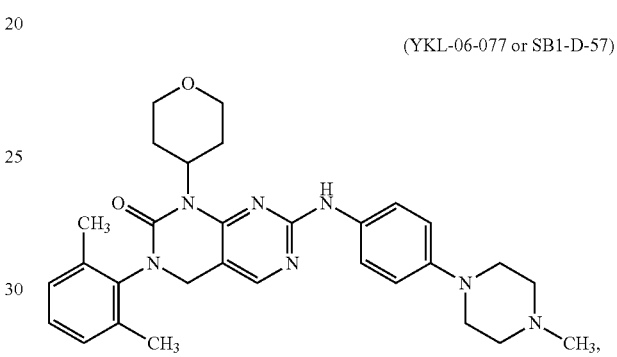
(YKL-06-078 or SB1-D-58)
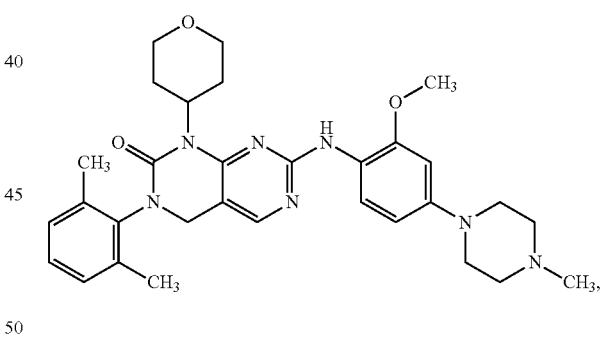
(YKL-06-080 or SB1-D-60)
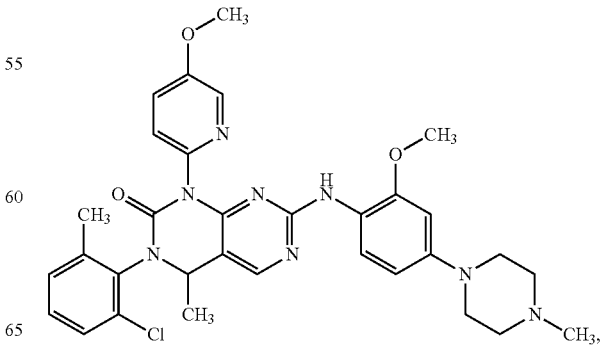

(YKL-06-081-1 or SB1-D-61)
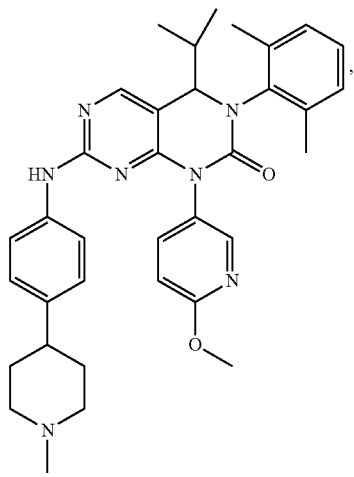
(YKL-06-082 or SB1-D-62)
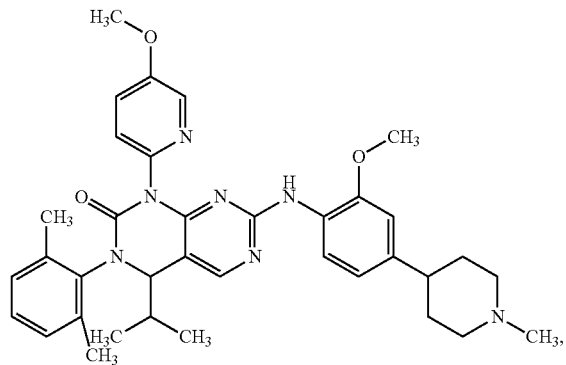
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of the formula:
(HG-11-136-01)
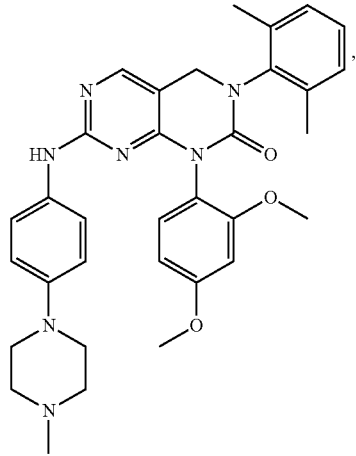
(HG-11-139-01)
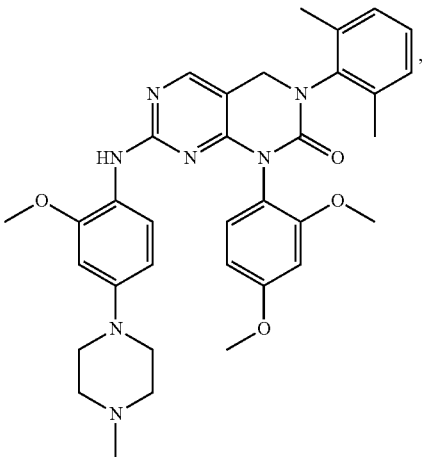
(HG-11-143-01)
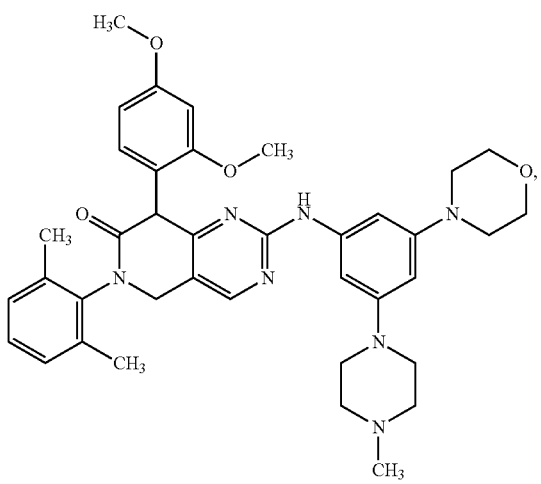
(YKL-04-103)
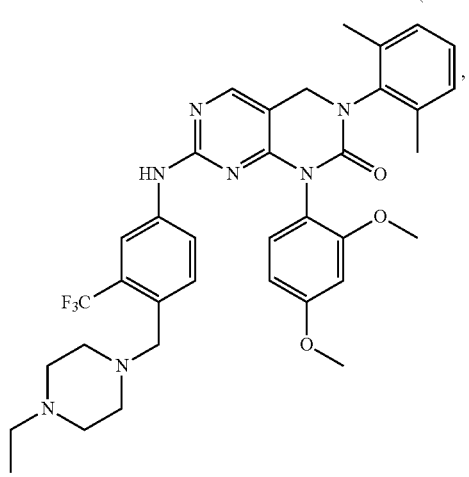

(YKL-04-104)
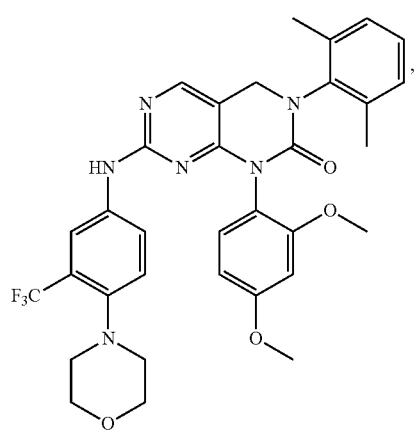
(YKL-04-107)
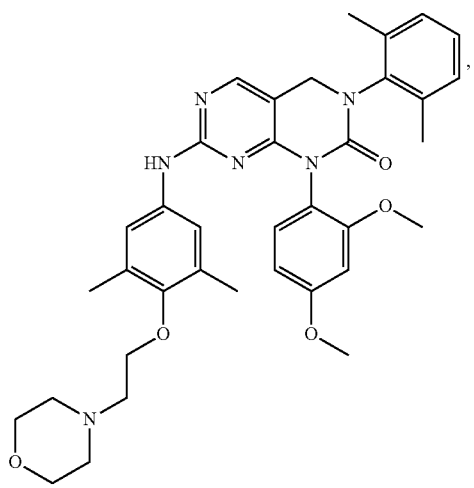
(YKL-04-105)
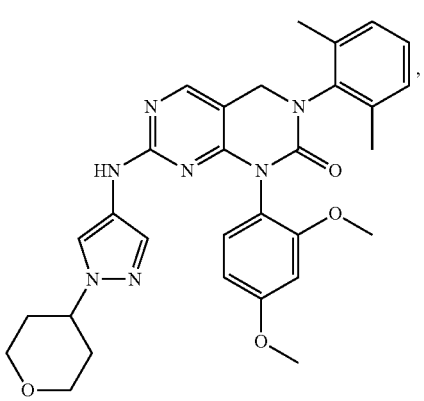
(YKL-04-108)
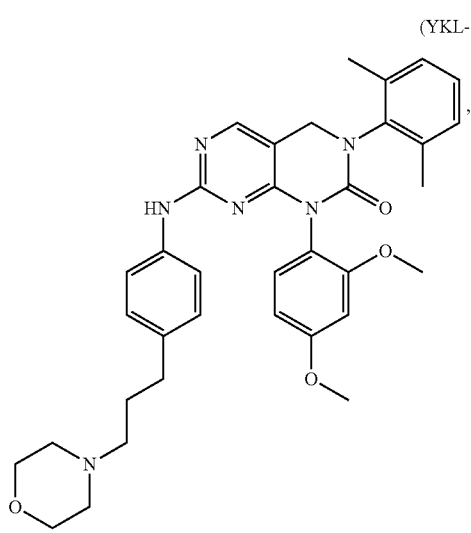
(YKL-04-106)
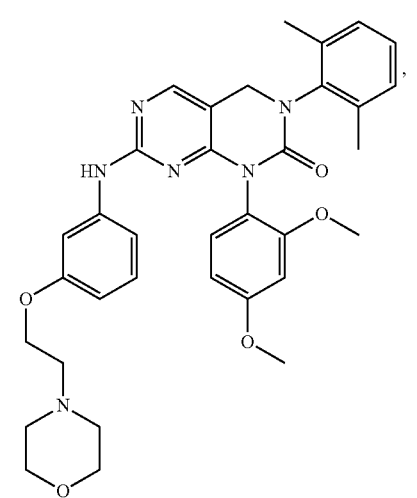
(YKL-04-112)
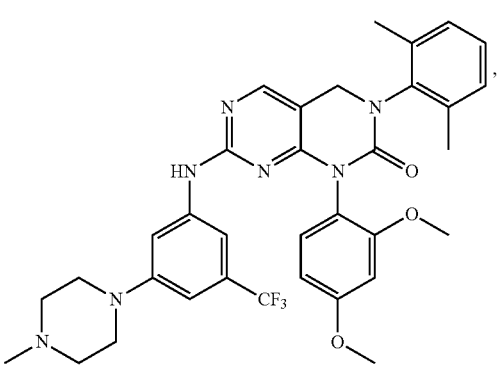

-continued
(YKL-04-113)
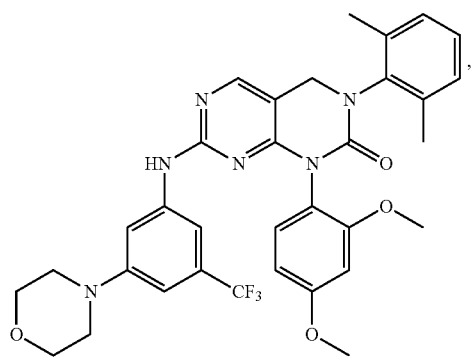
(YKL-04-114)
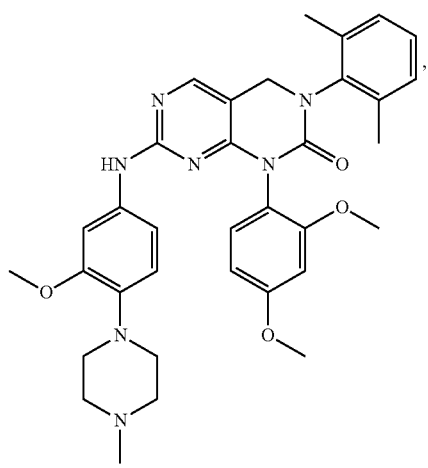
(YKL-04-115)
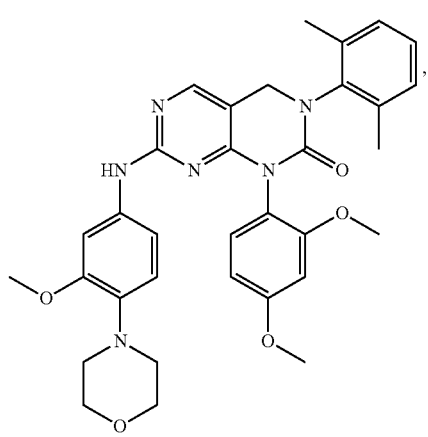
-continued
(YKL-04-118)
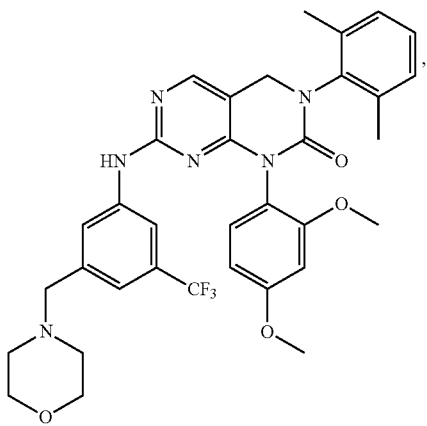
(YKL-04-125)
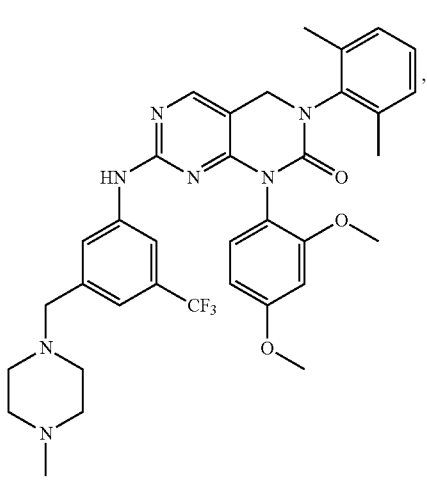
(YKL-04-136-1)
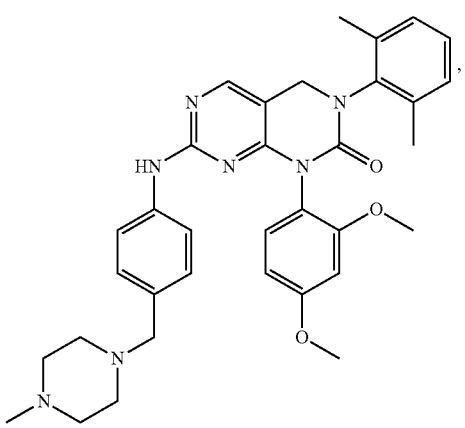

93
-continued
(YKL-04-136-2)
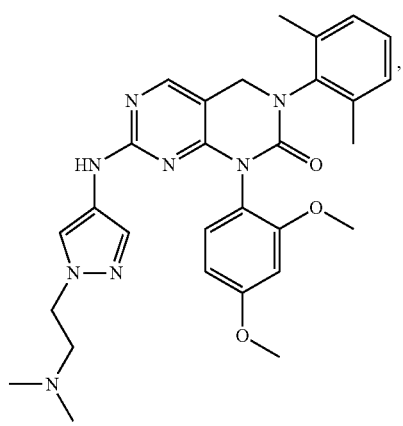
(YKL-04-136-3)
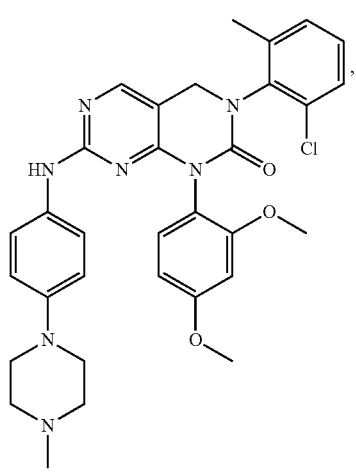
(YKL-04-136-4)
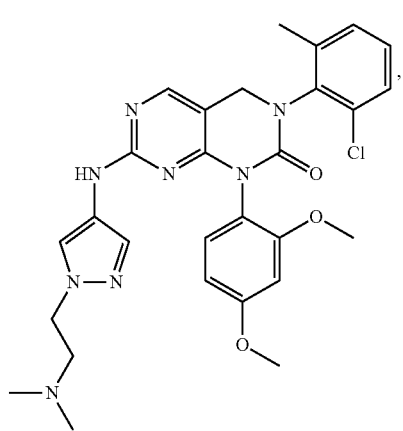
94
-continued
(YKL-04-136-5)
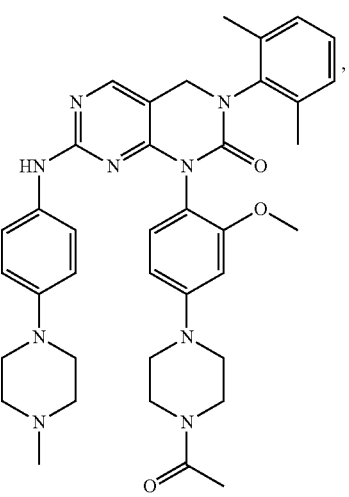
(YKL-04-136-6)
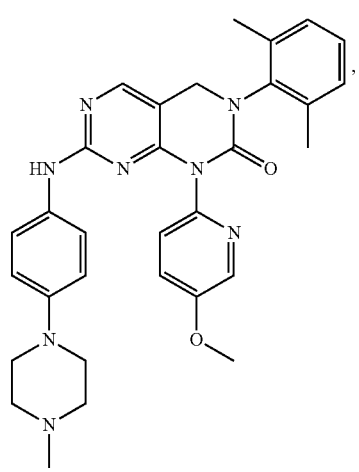
(YKL-04-136-7)
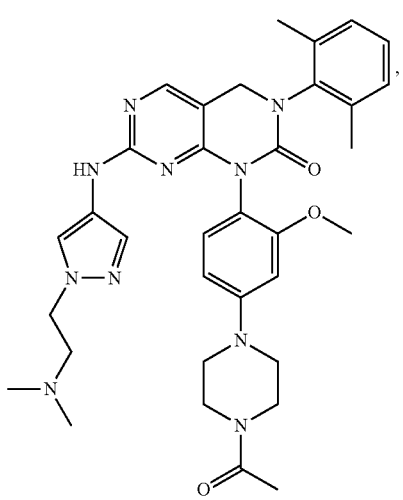

-continued
(YKL-04-136-8)
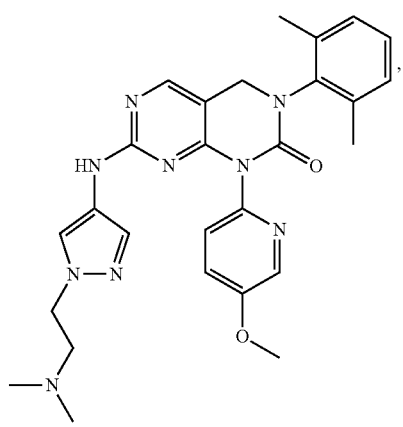
(YKL-04-136-11)
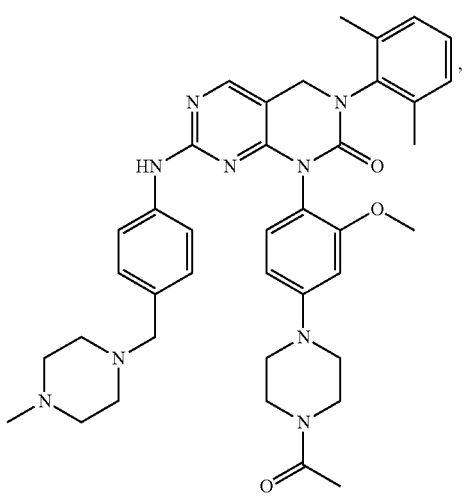
(YKL-04-136-9)
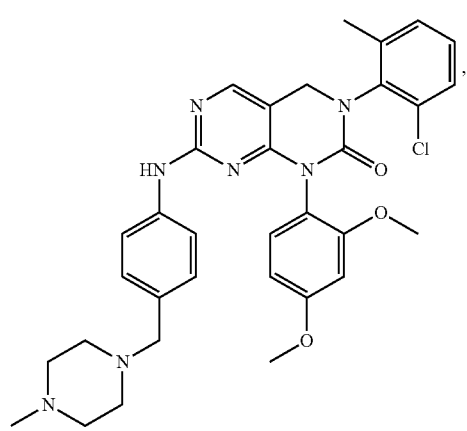
(YKL-05-068)
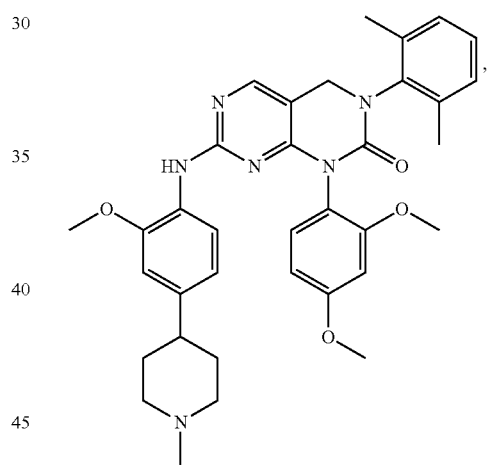
(YKL-04-136-10)
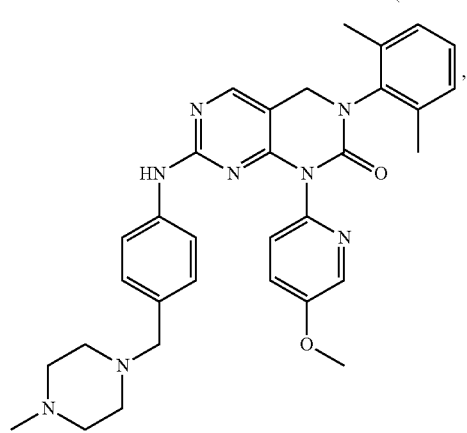
(YKL-05-077)
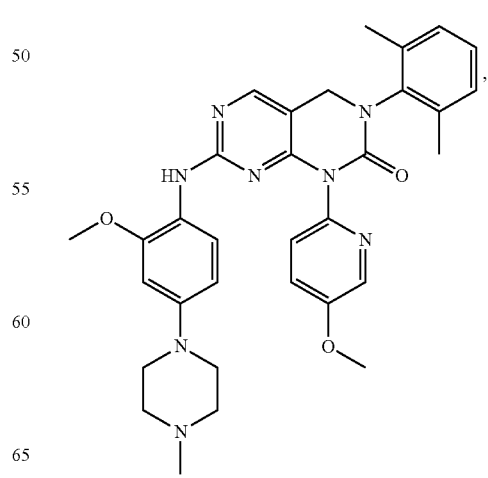

(YKL-05-093 or YKL 05-093)
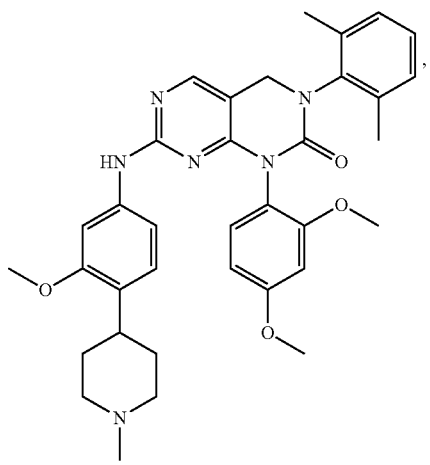
(YKL-05-094)
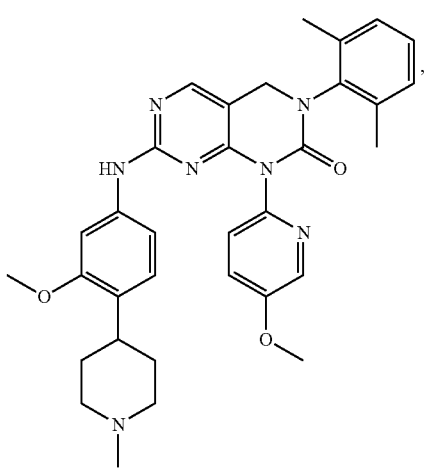
(YKL-05-098)
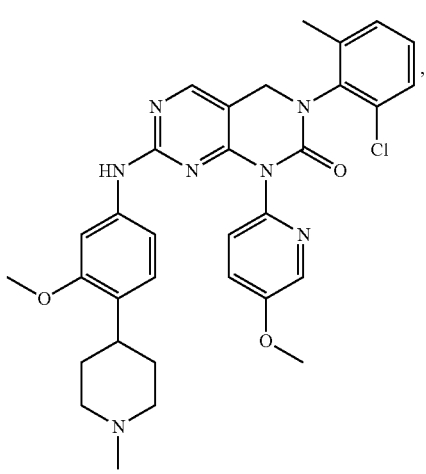
(YKL-05-99 or YKL-05-099)
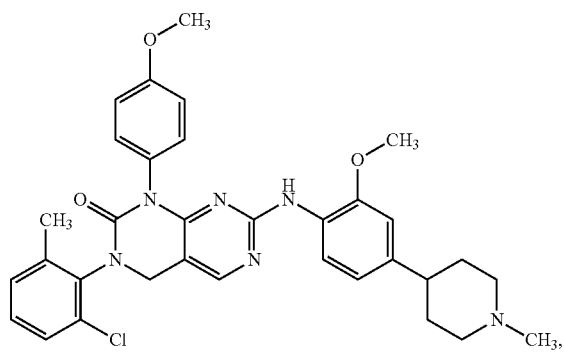
(YKL-05-096)
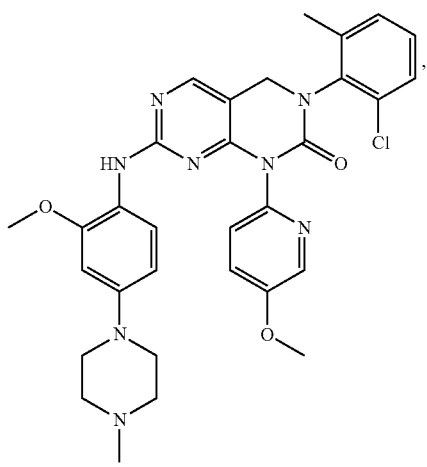
(YKL-06-038)
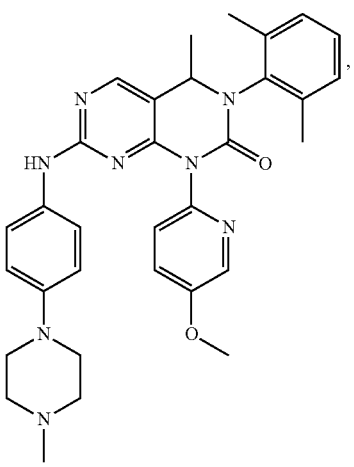

-continued (YKL-06-040)

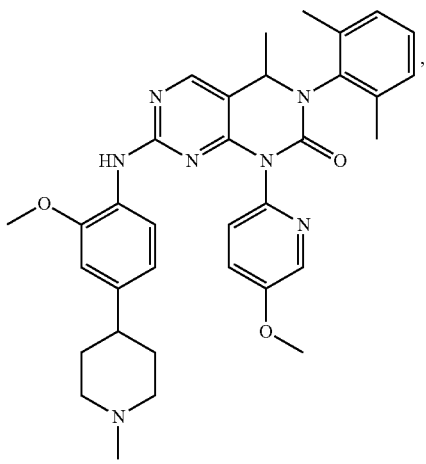

(YKL-06-051 or YKL 06-051)

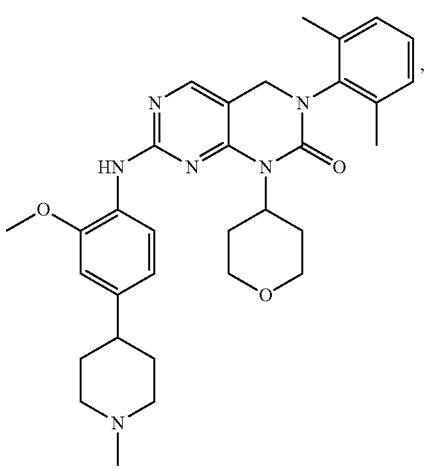

or a pharmaceutically acceptable salt, solvate, hydrate, polymorph, co-crystal, tautomer, stereoisomer, isotopically labeled derivative, or prodrug thereof.

In certain embodiments, the compound of Formula (I) is YKL-05-99, or a pharmaceutically acceptable salt, solvate, hydrate, polymorph, co-crystal, tautomer, stereoisomer, isotopically labeled derivative, or prodrug thereof (e.g., a pharmaceutically acceptable salt thereof). In certain embodiments, the compound of Formula (I) is YKL-05-093, or a pharmaceutically acceptable salt, solvate, hydrate, polymorph, co-crystal, tautomer, stereoisomer, isotopically labeled derivative, or prodrug thereof (e.g., a pharmaceutically acceptable salt thereof). In certain embodiments, the compound of Formula (I) is YKL-04-114, or a pharmaceutically acceptable salt, solvate, hydrate, polymorph, co-crystal, tautomer, stereoisomer, isotopically labeled derivative, or prodrug thereof (e.g, a pharmaceutically acceptable salt thereof).

Compounds of Formula (II)

In another aspect, the present disclosure provides bicyclic urea compounds of Formula (II) for use in the present disclosure:

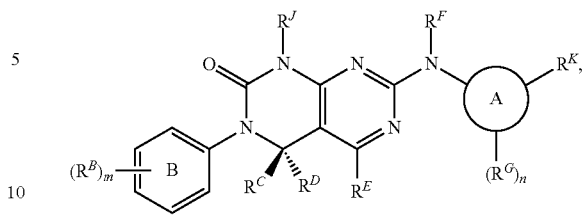

(II)

and pharmaceutically acceptable salts, solvates, hydrates, polymorphs, co-crystals, tautomers, stereoisomers, isotopically labeled derivatives, and prodrugs thereof, wherein:

$R^J$ is substituted or unsubstituted carbocyclyl;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^bC$(=O)$R^a$, —$NR^bC$(=O)$OR^a$, —$NR^bC$(=O)N($R^b$)$_2$, —OC(=O)$R^a$, —OC(=O)$OR^a$, or —OC(=O)N($R^b$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted, $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring;

m is 0, 1, 2, 3, 4, or 5;

$R^C$ is hydrogen, halogen, or substituted or unsubstituted, $C_{1-6}$ alkyl;

$R^D$ is hydrogen, halogen, or substituted or unsubstituted, $C_{1-6}$ alkyl;

$R^E$ is hydrogen, halogen, or substituted or unsubstituted, $C_{1-6}$ alkyl;

$R^F$ is hydrogen, substituted or unsubstituted, $C_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^bC$(=O)$R^a$, —$NR^bC$(=O)$OR^a$, —$NR^bC$(=O)N($R^b$)$_2$, —OC(=O)$R^a$, —OC(=O)$OR^a$, or —OC(=O)N($R^b$)$_2$;

n is 0, 1, 2, 3, or 4, as valency permits; and $R^K$ is unsubstituted methyl, substituted or unsubstituted heterocyclyl, —$OR^a$, or —$N(R^c)_2$, wherein each instance of $R^c$ is independently hydrogen, substituted or unsubstituted, $C_{1-6}$ alkyl, or a nitrogen protecting group, or optionally two instances of are taken together with their intervening atoms to form a substituted or unsubstituted heterocyclic or substituted or unsubstituted heteroaryl ring.

Unless expressly provided otherwise, the moieties and variables described in the subsection Compounds of Formula (II) apply only to Formula (II). The moieties and variables included but not described in detail in the subsection Compounds of Formula (II) are as described in detail in other subsections.

Formula (II) includes substituent $R^J$. In certain embodiments, $R^J$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^J$ is substituted or unsubstituted, $C_{3-6}$ carbocyclyl. In certain embodiments, $R^J$ is substituted or unsubstituted cyclopropyl. In certain embodiments, $R^J$ is substituted or unsubstituted cyclobutyl. In certain embodiments, $R^J$ is cyclobutyl. In certain embodiments, $R^J$ is substituted or unsubstituted cyclopentyl. In certain embodiments, $R^J$ is cyclopentyl. In certain embodiments, $R^J$ is substituted or unsubstituted cyclohexyl. In certain embodiments, $R^J$ is cyclohexyl.

In Formulae (I) and (II), Ring B is an unsubstituted phenyl ring (e.g., when m is 0) or a phenyl ring substituted with one or more substituents $R^B$ (e.g., when m is 1, 2, 3, 4, or 5). In certain embodiments, at least two instances of $R^B$ are different. In certain embodiments, all instances of $R^B$ are the same. In certain embodiments, m is 0. In certain embodiments, m is 1. In certain embodiments, m is 2. In certain embodiments, m is 3. In certain embodiments, m is 4. In certain embodiments, m is 5. In certain embodiments, Ring B is of the formula:

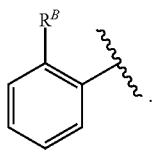

In certain embodiments, Ring B is of the formula:

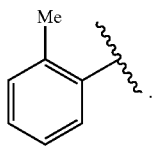 [SMILES: *c1ccccc1C]

In certain embodiments, Ring B is of the formula:

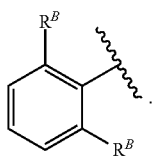

In certain embodiments, Ring B is of the formula:

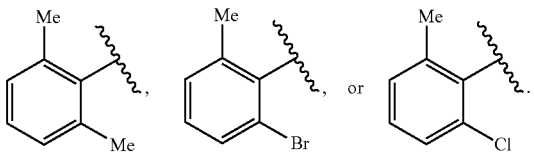 [SMILES: *c1c(C)cccc1C ; *c1c(C)cccc1Br ; *c1c(C)cccc1Cl]

In certain embodiments, Ring B is not of the formula:

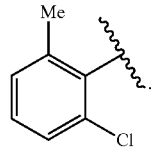 [SMILES: *c1c(C)cccc1Cl]

In certain embodiments, Ring B is of the formula:

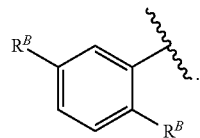

In certain embodiments, Ring B is of the formula:

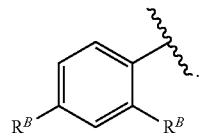

In certain embodiments, Ring B is of the formula:

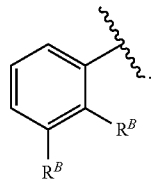

In certain embodiments, at least one instance of $R^B$ is halogen (e.g., F, Cl, Br, or I). In certain embodiments, at least one instance of $R^B$ is F. In certain embodiments, at least one instance of $R^B$ is Cl. In certain embodiments, at least one instance of $R^B$ is Br. In certain embodiments, at least one instance of $R^B$ is I. In certain embodiments, at least one $R^B$ is substituted or unsubstituted alkyl (e.g., substituted or unsubstituted, $C_{1-6}$ alkyl). In certain embodiments, at least one instance of $R^B$ is substituted or unsubstituted methyl. In certain embodiments, at least one instance of $R^B$ is methyl. In certain embodiments, m is 2, and both instances of $R^B$ are methyl. In certain embodiments, m is 2, and one instance of $R^B$ is halogen, and the other instance of $R^B$ is methyl. In certain embodiments, m is 2, and one instance of $R^B$ is Cl, and the other instance of $R^B$ is methyl. In certain embodiments, at least one instance of $R^B$ is substituted or unsubstituted ethyl. In certain embodiments, at least one instance of $R^B$ is substituted or unsubstituted propyl. In certain embodiments, at least one instance of $R^B$ is substituted or unsubstituted alkenyl (e.g., substituted or unsubstituted, $C_{2-6}$ alkenyl). In certain embodiments, at least one instance of $R^B$ is substituted or unsubstituted alkynyl (e.g., substituted or unsubstituted, $C_{2-6}$ alkynyl). In certain embodiments, at least one instance of $R^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^B$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^B$ is substituted or unsubstituted aryl (e.g., substituted or unsubstituted, 6- to 10-membered aryl). In certain embodiments, at least one instance of $R^B$ is benzyl. In certain embodiments, at least one instance of $R^B$ is substituted or unsubstituted phenyl. In certain embodiments, at least one instance of $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^B$ is —$OR^a$ (e.g., —OH or —OMe). In certain embodiments, at least one instance of $R^B$ is —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^b$C(=O)$R^a$, —$NR^b$C(=O)$OR^a$, —$NR^b$C(=O)N($R^b$)$_2$, —OC(=O)$R^a$, —OC(=O)$OR^a$, or —OC(=O)N($R^b$)$_2$.

Formula (II) includes substituents $R^C$, $R^D$, $R^E$, and $R^F$. $R^C$, $R^D$, $R^E$, and $R^F$ are as described herein for Formula (III).

Formula (II) includes Ring A and one or more instances of substituent $R^G$. Ring A and substituent $R^G$ are as described herein for Formula (III).

Formula (II) includes substituent $R^K$ attached to Ring A. $R^K$ is as described herein for Formula (III).

In certain embodiments, Ring A with substituent $R^K$ is of the formula:

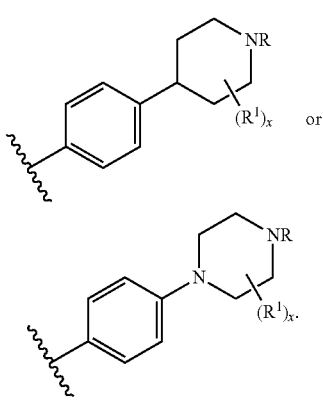

In certain embodiments, Ring A with substituent $R^K$ is of the formula

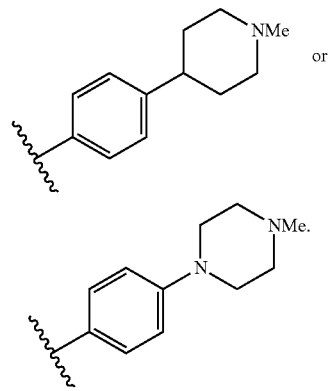

In certain embodiments, Ring B is of the formula:

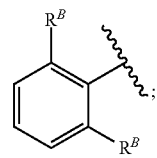

$R^C$, $R^D$, $R^E$, and $R^F$ are each hydrogen; $R^G$ is —$OR^a$; $R^J$ is substituted or unsubstituted, 4- to 6-membered carbocyclyl; and $R^K$ is substituted or unsubstituted piperidinyl, or substituted or unsubstituted piperazinyl.

In certain embodiments, Ring B is of the formula:

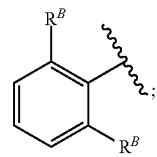

$R^C$, $R^D$, $R^E$, and $R^F$ are each hydrogen; n is 0; $R^J$ is substituted or unsubstituted, 4- to 6-membered carbocyclyl; and $R^K$ is substituted or unsubstituted piperidinyl, or substituted or unsubstituted piperazinyl.

In certain embodiments, the compound of Formula (II) is of the formula:

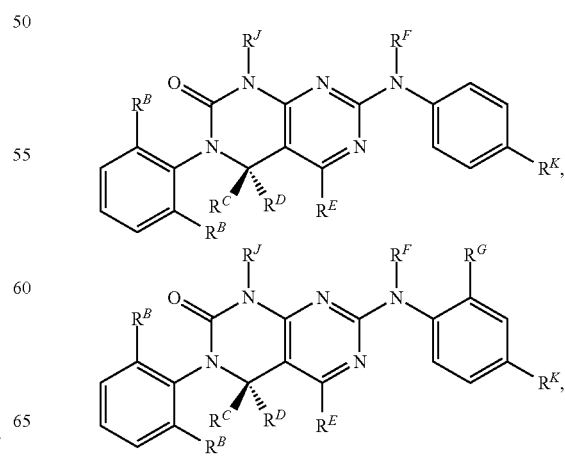

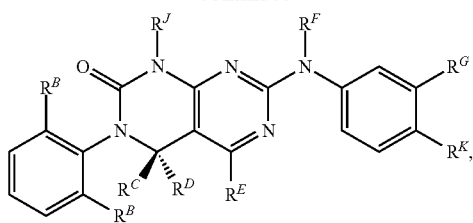

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

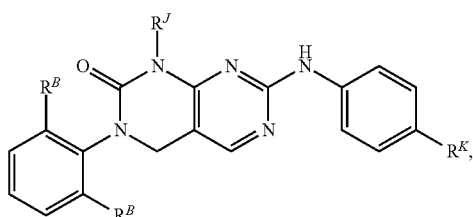

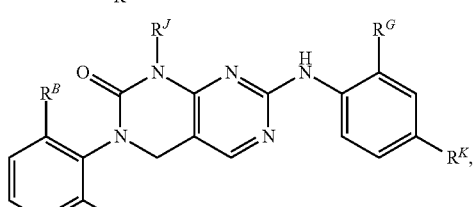

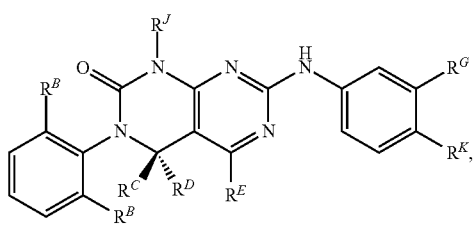

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

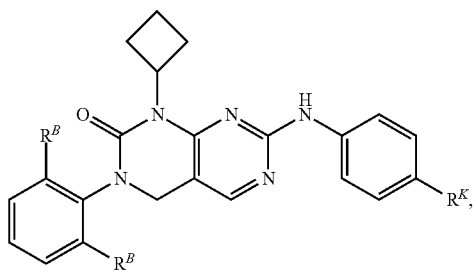

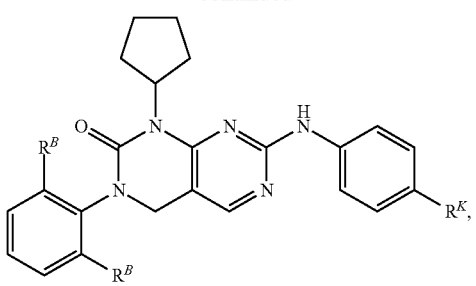

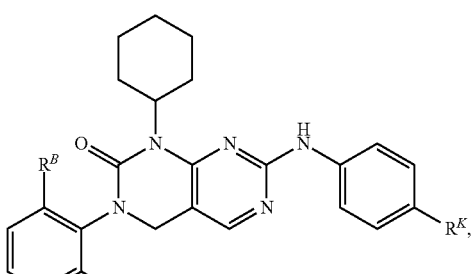

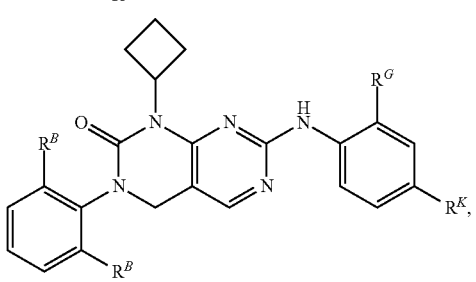

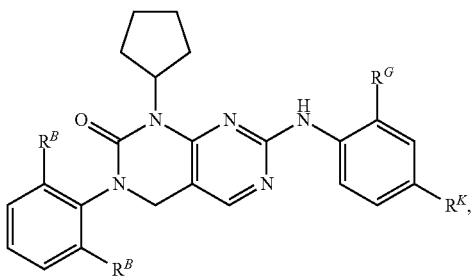

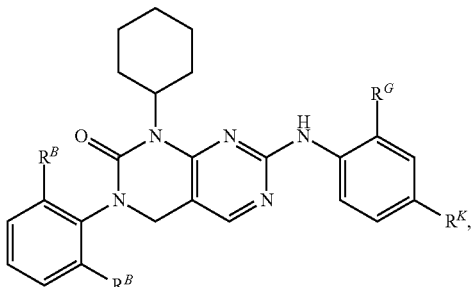

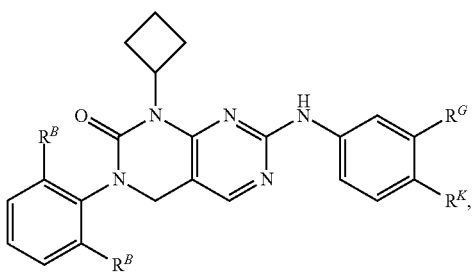

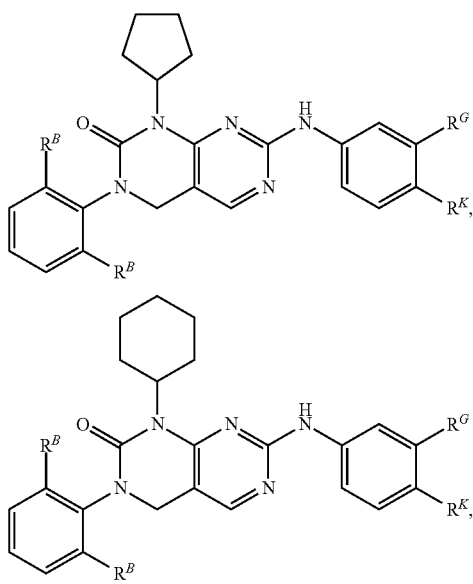

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

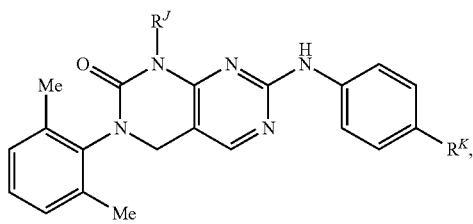

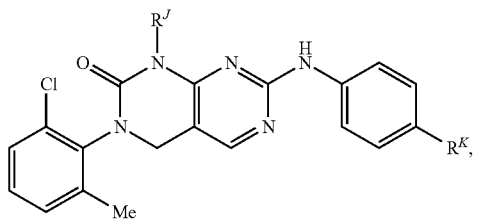

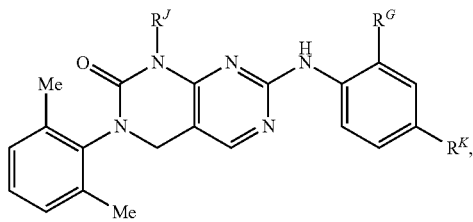

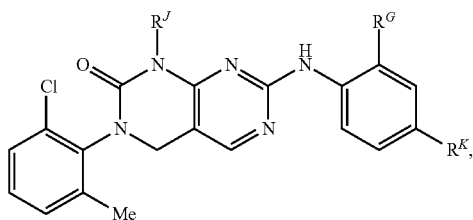

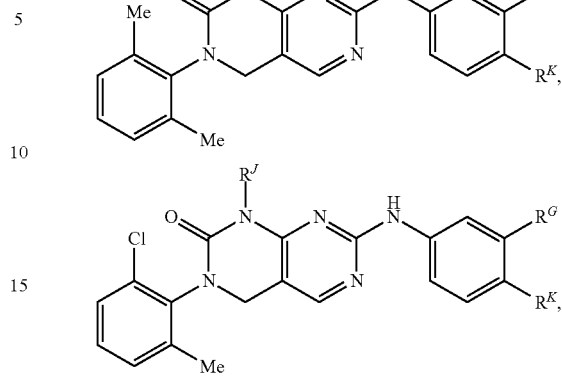

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

(YKL-06-050)

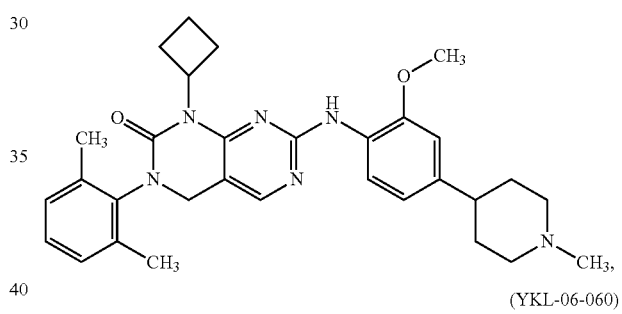

(YKL-06-060)

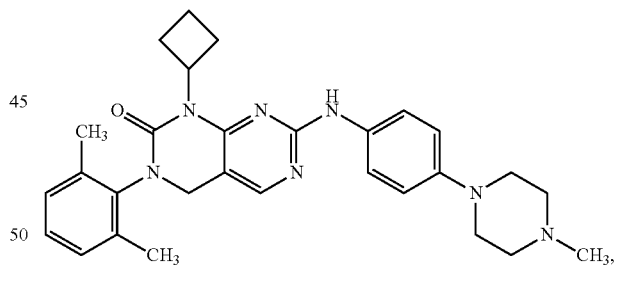

(YKL-06-061)

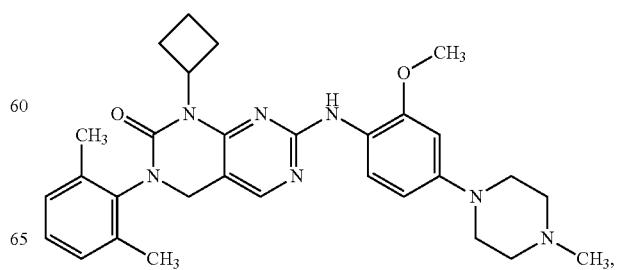

(YKL-06-062)
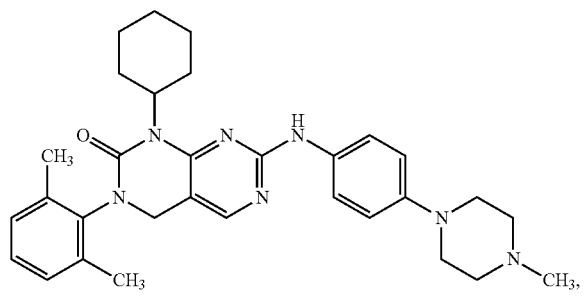
(YKL-06-063)

(YKL-06-064)

(YKL-06-075)
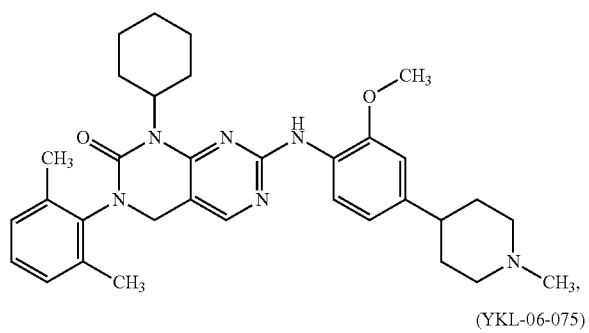

(YKL-06-076)
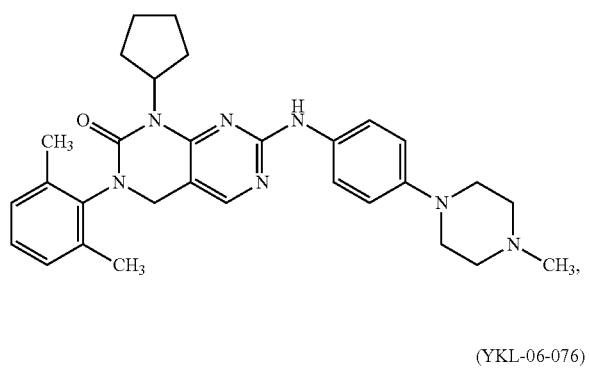

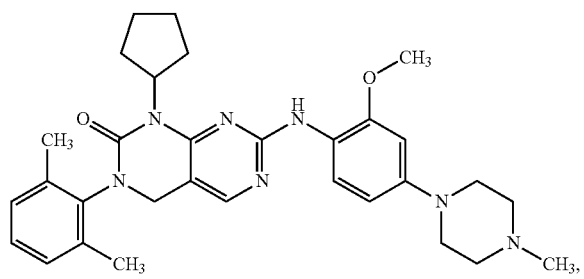

(YKL-06-088)
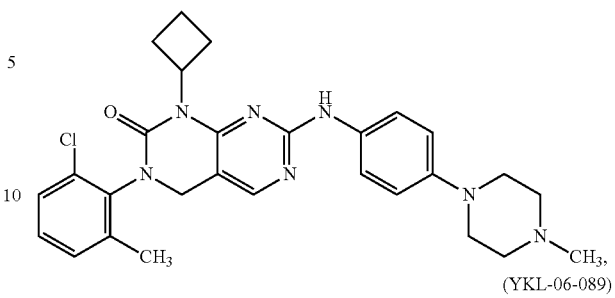
(YKL-06-089)

(YKL-06-090)
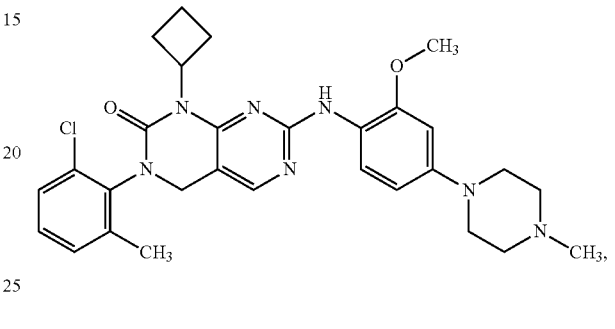

(YKL-06-091)
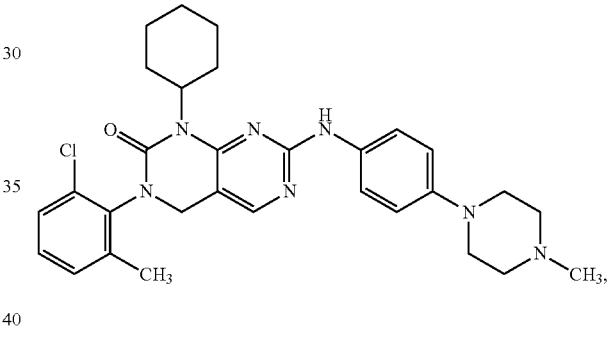

or a pharmaceutically acceptable salt, solvate, hydrate, polymorph, co-crystal, tautomer, stereoisomer, isotopically labeled derivative, or prodrug thereof.

In certain embodiments, the compound of Formula (II) is YKL-06-061, or a pharmaceutically acceptable salt, solvate, hydrate, polymorph, co-crystal, tautomer, stereoisomer, isotopically labeled derivative, or prodrug thereof.

Compounds of Formula (III)

In another aspect, the present disclosure provides bicyclic urea compounds of Formula (III) for use in the present disclosure:

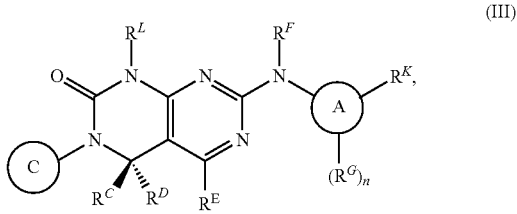

(III)

and pharmaceutically acceptable salts, solvates, hydrates, polymorphs, co-crystals, tautomers, stereoisomers, isotopically labeled derivatives, and prodrugs thereof, wherein:

$R^L$ is substituted or unsubstituted alkyl;

Ring C is unsubstituted phenyl or of the formula:

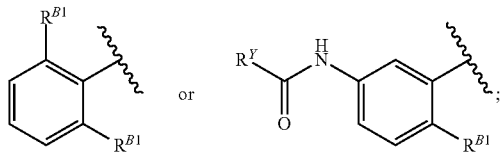

each instance of $R^{B1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^d$)$_2$, —SR$^a$, —CN, —SCN, —C(=NR$^d$)R$^a$, —C(=NR$^d$)OR$^a$, —C(=NR$^d$)N(R$^d$)$_2$, —C(=O)R$^a$, —C(=O)OR$^a$, —C(=O)N(R$^d$)$_2$, —NO$_2$, —NR$^d$C(=O)R$^a$, —NR$^d$C(=O)OR$^a$, —NR$^d$C(=O)N(R$^a$)$_2$, —OC(=O)R$^a$, —OC(=O)OR$^a$, or —OC(=O)N(R$^d$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of R$^d$ is independently hydrogen, —C(=O)R$^a$, substituted or unsubstituted, C$_{1-6}$ alkyl, or a nitrogen protecting group, or optionally two instances of R$^d$ are taken together with their intervening atoms to form a substituted or unsubstituted heterocyclic or substituted or unsubstituted heteroaryl ring;

R$^C$ is hydrogen, halogen, or substituted or unsubstituted, C$_{1-6}$ alkyl;

R$^D$ is hydrogen, halogen, or substituted or unsubstituted, C$_{1-6}$ alkyl;

R$^E$ is hydrogen, halogen, or substituted or unsubstituted, C$_{1-6}$ alkyl;

R$^F$ is hydrogen, substituted or unsubstituted, C$_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of R$^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, —SR$^a$, —CN, —SCN, —C(=NR$^b$)R$^a$, —C(=NR$^b$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^b$C(=O)R$^a$, —NR$^b$C(=O)OR$^a$, —NR$^b$C(=O)N(R$^a$)$_2$, —OC(=O)R$^a$, —OC(=O)OR$^a$, or —OC(=O)N(R$^b$)$_2$;

each instance of R$^b$ is independently hydrogen, substituted or unsubstituted C$_{1-6}$ alkyl, or a nitrogen protecting group, or optionally two instances of R$^b$ are taken together with their intervening atoms to form a substituted or unsubstituted heterocyclic or substituted or unsubstituted heteroaryl ring;

n is 0, 1, 2, 3, or 4, as valency permits;

R$^K$ is unsubstituted methyl, substituted or unsubstituted heterocyclyl, —OR$^a$, or —N(R$^c$)$_2$, wherein each instance of R$^c$ is independently hydrogen, substituted or unsubstituted, C$_{1-6}$ alkyl, or a nitrogen protecting group, or optionally two instances of R$^c$ are taken together with their intervening atoms to form a substituted or unsubstituted heterocyclic or substituted or unsubstituted heteroaryl ring; and R$^Y$ is substituted phenyl.

Unless expressly provided otherwise, the moieties and variables described in the subsection Compounds of Formula (III) apply only to Formula (III). The moieties and variables included but not described in detail in the subsection Compounds of Formula (III) are as described in detail in other subsections.

Formula (III) includes Ring C. In certain embodiments, Ring C is unsubstituted phenyl. In certain embodiments, Ring C is of the formula:

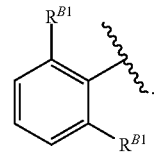

In certain embodiments, at least one instance of R$^{B1}$ is halogen. In certain embodiments, at least one instance of R$^{B1}$ is halogen. In certain embodiments, at least one instance of R$^{B1}$ is F. In certain embodiments, at least one instance of R$^{B1}$ is Cl. In certain embodiments, at least one instance of R$^{B1}$ is Br. In certain embodiments, at least one instance of R$^{B1}$ is I (iodine). In certain embodiments, at least one instance of R$^{B1}$ is substituted or unsubstituted, C$_{1-6}$ alkyl (e.g., methyl, ethyl, or propyl). In certain embodiments, at least one instance of R$^{B1}$ is substituted or unsubstituted methyl. In certain embodiments, at least one instance of R$^{B1}$ is methyl. In certain embodiments, at least one instance of R$^{B1}$ is —N(R$^d$)$_2$, wherein each instance of R$^d$ is hydrogen or —C(=O)R$^a$. In certain embodiments, at least one instance of R$^{B1}$ is —NH(C(=O)R$^a$). In certain embodiments, at least one instance of R$^{B1}$ is —OR$^a$ (e.g., —OH or —OMe). In certain embodiments, at least one instance of R$^{B1}$ is —SR$^a$, —CN, —SCN, —C(=NR$^d$)R$^a$, —C(=NR$^d$)OR$^a$, —C(=NR$^d$)N(R$^d$)$_2$, —C(=O)R$^a$, —C(=O)OR$^a$, —C(=O)N(R$^d$)$_2$, —NO$_2$, —NR$^d$C(=O)R$^a$, —NR$^d$C(=O)OR$^a$, —NR$^d$C(=O)N(R$^a$)$_2$, —OC(=O)R$^a$, —OC(=O)OR$^a$, or —OC(=O)N(R$^d$)$_2$. In certain embodiments, Ring C is of the formula:

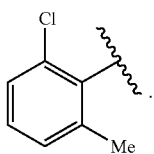

In certain embodiments, Ring C is of the formula:

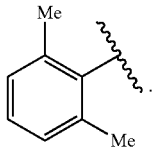 [SMILES: *c1c(C)cccc1C]

In certain embodiments, Ring C is of the formula:

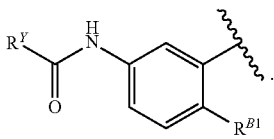

In certain embodiments, $R^Y$ is substituted phenyl. In certain embodiments, $R^Y$ is substituted phenyl. In certain embodiments, $R^Y$ is of the formula:

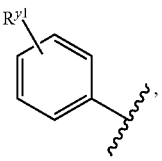

wherein $R^{y1}$ is halogen or substituted or unsubstituted, $C_{1-6}$ alkyl. In certain embodiments, $R^{y1}$ is halogen (e.g., Br, Cl, F). In certain embodiments, $R^{y1}$ is substituted or unsubstituted, $C_{1-6}$ alkyl (e.g., substituted or unsubstituted, methyl, ethyl, or propyl). In certain embodiments, $R^{y1}$ is substituted or unsubstituted methyl. In certain embodiments, $R^{y1}$ is substituted methyl. In certain embodiments, $R^{y1}$ is methyl. In certain embodiments, $R^{y1}$ is —$CF_3$. In certain embodiments, Ring C is of the formula:

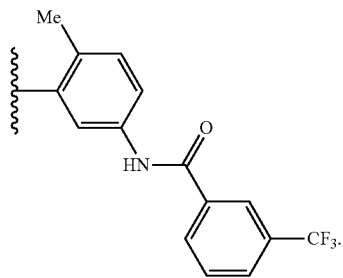 [SMILES: *c1cc(NC(=O)c2cccc(C(F)(F)F)c2)ccc1C]

In certain embodiments, Ring C is of the formula:

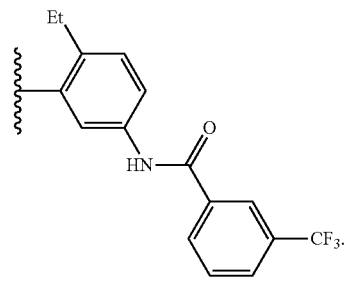 [SMILES: *c1cc(NC(=O)c2cccc(C(F)(F)F)c2)ccc1CC]

Formula (III) includes substituent $R^L$. In certain embodiments, $R^L$ is substituted or unsubstituted alkyl (e.g., substituted or unsubstituted, $C_{1-6}$ alkyl). In certain embodiments, $R^L$ is substituted or unsubstituted methyl. In certain embodiments, $R^L$ is methyl. In certain embodiments, $R^L$ is substituted or unsubstituted ethyl. In certain embodiments, $R^L$ is ethyl. In certain embodiments, $R^L$ is substituted or unsubstituted propyl. In certain embodiments, $R^L$ is propyl. In certain embodiments, $R^L$ is isopropyl. In certain embodiments, $R^L$ is substituted or unsubstituted butyl.

Formula (II) and (III) include substituent $R^K$ attached to Ring A. In certain embodiments, $R^K$ is unsubstituted methyl. In certain embodiments, $R^K$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^K$ is substituted or unsubstituted tetrahydropyranyl. In certain embodiments, $R^K$ is substituted or unsubstituted piperidinyl. In certain embodiments, $R^K$ is substituted or unsubstituted morpholinyl. In certain embodiments, $R^K$ is substituted or unsubstituted piperazinyl. In certain embodiments, $R^K$ is of the formula:

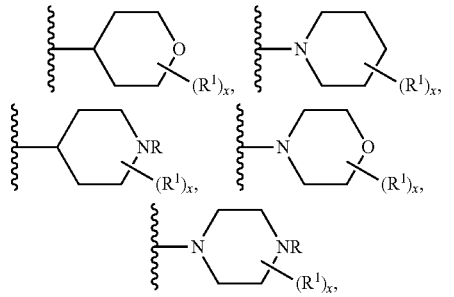

wherein $R^1$ is substituted or unsubstituted, $C_{1-6}$ alkyl or —$OR^{x1}$, wherein R is hydrogen, substituted or unsubstituted, $C_{1-6}$ alkyl, or nitrogen protecting group; $R^{x1}$ is hydrogen or substituted or unsubstituted, $C_{1-6}$ alkyl; and x is 0, 1, 2, or 3. In certain embodiments, $R^K$ is of the formula:

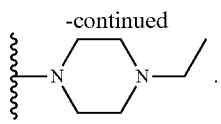

In certain embodiments, $R^K$ is —$OR^a$ (e.g., —OH or —OMe). In certain embodiments, $R^K$ is —$N(R^c)_2$. In certain embodiments, two instances of $R^c$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two instances of $R^c$ are taken together with their intervening atoms to form a substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^K$ is —$NMe_2$. In certain embodiments, $R^K$ is —$SR^a$, —CN, —SCN, —C(=$NR^b$)$R^a$, —C(=$NR^b$)$OR^a$, —C(=$NR^b$)$N(R^b)_2$, —C(=O)$R^a$, —C(=O)$OR^a$, —C(=O)$N(R^b)_2$, —$NO_2$, —$NR^b$C(=O)$R^a$, —$NR^b$C(=O)$OR^a$, —$NR^b$C(=O)$N(R^b)_2$, —OC(=O)$R^a$, —OC(=O)$OR^a$, or —OC(=O)$N(R^b)_2$.

Formulae (I), (II), and (III) include substituent $R^C$. In certain embodiments, $R^C$ is hydrogen. In certain embodiments, $R^C$ is halogen (e.g., F, Cl, Br, or I). In certain embodiments, $R^C$ is substituted or unsubstituted, $C_{1-6}$ alkyl (e.g., methyl, ethyl, or propyl). In certain embodiments, $R^C$ is substituted or unsubstituted methyl. In certain embodiments, $R^C$ is methyl. In certain embodiments, $R^C$ is substituted or unsubstituted ethyl. In certain embodiments, $R^C$ is ethyl. In certain embodiments, $R^C$ is substituted or unsubstituted propyl. In certain embodiments, $R^C$ is unsubstituted isopropyl.

Formulae (I), (II), and (III) include substituent $R^D$. In certain embodiments, $R^D$ is hydrogen. In certain embodiments, $R^D$ is halogen (e.g., F, Cl, Br, or I). In certain embodiments, $R^D$ is substituted or unsubstituted, $C_{1-6}$ alkyl (e.g., methyl, ethyl, or propyl). In certain embodiments, $R^D$ is substituted or unsubstituted methyl. In certain embodiments, $R^D$ is methyl. In certain embodiments, $R^D$ is substituted or unsubstituted ethyl. In certain embodiments, $R^D$ is ethyl. In certain embodiments, $R^D$ is substituted or unsubstituted propyl. In certain embodiments, $R^D$ is isopropyl.

Formulae (I), (II), and (III) include substituent $R^E$. In certain embodiments, $R^E$ is hydrogen. In certain embodiments, $R^E$ is halogen (e.g., F, Cl, Br, or I). In certain embodiments, $R^E$ is substituted or unsubstituted, $C_{1-6}$ alkyl (e.g., methyl, ethyl, or propyl). In certain embodiments, $R^E$ is substituted or unsubstituted methyl. In certain embodiments, $R^E$ is methyl. In certain embodiments, $R^E$ is substituted or unsubstituted ethyl. In certain embodiments, $R^E$ is ethyl. In certain embodiments, $R^E$ is substituted or unsubstituted propyl. In certain embodiments, $R^E$ is isopropyl.

Formulae (I), (II), and (III) include substituent $R^F$. In certain embodiments, $R^F$ is hydrogen. In certain embodiments, $R^E$ is substituted or unsubstituted, $C_{1-6}$ alkyl (e.g., methyl, ethyl, or propyl). In certain embodiments, $R^F$ is substituted or unsubstituted methyl. In certain embodiments, $R^F$ is methyl. In certain embodiments, $R^F$ is substituted or unsubstituted ethyl. In certain embodiments, $R^F$ is ethyl. In certain embodiments, $R^F$ is substituted or unsubstituted propyl. In certain embodiments, $R^F$ is isopropyl. In certain embodiments, $R^F$ is a nitrogen protecting group (e.g., a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, $R^C$, $R^D$, $R^E$, and $R^F$ are each hydrogen. In certain embodiments, at least one substituent selected from the group consisting of $R^C$, $R^D$, $R^E$, and $R^F$ is substituted or unsubstituted, $C_{1-6}$ alkyl. In certain embodiments, $R^C$ is substituted or unsubstituted, $C_{1-6}$ alkyl; and $R^D$, $R^E$, and $R^F$ are each hydrogen. In certain embodiments, $R^C$ is unsubstituted methyl; and $R^D$, $R^E$, and $R^F$ are each hydrogen. In certain embodiments, $R^C$ is unsubstituted isopropyl; and $R^D$, $R^E$, and $R^F$ are each hydrogen. In certain embodiments, $R^D$ is substituted or unsubstituted, $C_{1-6}$ alkyl; and $R^C$, $R^E$, and $R^F$ are each hydrogen. In certain embodiments, $R^E$ is substituted or unsubstituted, $C_{1-6}$ alkyl; and $R^C$, $R^D$, and $R^F$ are each hydrogen. In certain embodiments, $R^F$ is substituted or unsubstituted, $C_{1-6}$ alkyl; and $R^C$, $R^D$, and $R^E$ are each hydrogen.

Formulae (I), (II), and (III) include Ring A. In certain embodiments, Ring A is substituted or unsubstituted phenyl. In certain embodiments, Ring A is not substituted or unsubstituted phenyl. In certain embodiments, Ring A is not substituted phenyl. In certain embodiments, Ring A is not unsubstituted phenyl. In certain embodiments, Ring A is unsubstituted phenyl. In certain embodiments, Ring A is phenyl, and includes one or more $R^G$ substituents. In certain embodiments, Ring A includes one $R^G$ substituent. In certain embodiments, Ring A includes two $R^G$ substituents. In certain embodiments, Ring A is substituted or unsubstituted polycyclic aryl (e.g., naphthalene or anthracene). In certain embodiments, Ring A is substituted or unsubstituted, 5- or 6-membered, monocyclic heteroaryl substituted or unsubstituted, 5- to 6-membered, monocyclic heteroaryl, wherein one, two, three, or four atoms in the heteroaryl ring system are independently nitrogen, oxygen, or sulfur). In certain embodiments, Ring A is substituted or unsubstituted furan. In certain embodiments, Ring A is substituted or unsubstituted thiophene. In certain embodiments, Ring A is substituted or unsubstituted pyrrole. In certain embodiments, Ring A is substituted or unsubstituted pyrazole. In certain embodiments, Ring A is pyrazole. In certain embodiments, Ring A is substituted or unsubstituted pyridinyl. In certain embodiments, Ring A is pyridinyl. In certain embodiments, Ring A is substituted or unsubstituted polycyclic heteroaryl (e.g., substituted or unsubstituted, 9- to 10-membered, bicyclic heteroaryl, wherein one, two, three, or four atoms in the heteroaryl ring system are independently nitrogen, oxygen, or sulfur).

Formulae (I), (II), and (III) include one or more instances of substituent $R^G$. In certain embodiments, n is 0. In certain embodiments, n is 1. In certain embodiments, n is 2. In certain embodiments, n is 3. In certain embodiments, n is 4. In certain embodiments, at least one instance of $R^G$ is halogen (e.g., F, Cl, Br, or I). In certain embodiments, at least one instance of $R^G$ is F. In certain embodiments, at least one instance of $R^G$ is Cl. In certain embodiments, at least one instance of $R^G$ is Br. In certain embodiments, at least one instance of $R^G$ is I. In certain embodiments, at least one $R^G$ is substituted or unsubstituted alkyl (e.g., substituted or unsubstituted, $C_{1-6}$ alkyl). In certain embodiments, at least one instance of $R^G$ is substituted or unsubstituted, $C_{1-3}$ alkyl. In certain embodiments, at least one instance of $R^G$ is substituted or unsubstituted methyl. In certain embodiments, at least one instance of $R^G$ is unsubstituted methyl. In certain embodiments, at least one instance of $R^G$ is substituted methyl. In certain embodiments, at least one instance of $R^G$ is —CF$_3$. In certain embodiments, at least one instance of $R^G$ is substituted or unsubstituted ethyl. In certain embodiments, at least one instance of $R^G$ is substituted ethyl. In certain embodiments, at least one instance of $R^G$ is unsubstituted ethyl. In certain embodiments, at least one instance of $R^G$ is substituted or unsubstituted propyl. In certain embodiments, at least one instance of $R^G$ is substituted or unsubstituted alkenyl (e.g., substituted or unsubstituted, $C_{2-6}$ alkenyl). In certain embodiments, at least one instance of $R^G$ is substituted or unsubstituted alkynyl (e.g., substituted or unsubstituted, $C_{2-6}$ alkynyl). In certain embodiments, at least one instance of $R^G$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^G$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^G$ is substituted or unsubstituted morpholinyl. In certain embodiments, at least one instance of $R^G$ is of the formula:

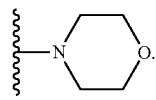

In certain embodiments, at least one instance of $R^G$ is substituted or unsubstituted piperazinyl. In certain embodiments, at least one instance of $R^G$ is of the formula:

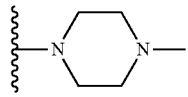

In certain embodiments, at least one instance of $R^G$ is substituted or unsubstituted aryl (e.g., substituted or unsubstituted, 6- to 10-membered aryl). In certain embodiments, at least one instance of $R^G$ is benzyl. In certain embodiments, at least one instance of $R^G$ is substituted or unsubstituted phenyl. In certain embodiments, at least one instance of $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^G$ is —OR$^a$, wherein $R^a$ is hydrogen or substituted or unsubstituted, $C_{1-6}$ alkyl (e.g., —OH or —OMe). In certain embodiments, at least one instance of $R^G$ is —OMe. In certain embodiments, at least one instance of $R^G$ is —OEt. In certain embodiments, at least one instance of $R^G$ is —O(Pr). In certain embodiments, at least one instance of $R^G$ is —O(iPr). In certain embodiments, at least one instance of $R^G$ is —N(R$^b$)$_2$, —SR$^a$, —CN, —SCN, —C(=NR$^b$)R$^a$, —C(=NR$^b$)OR$^a$, —C(=NR$^b$)N(R$^b$)$_2$, —C(=O)R$^a$, —C(=O)OR$^a$, —C(=O)N(R$^b$)$_2$, —NO$_2$, —NR$^b$C(=O) R$^a$, —NR$^b$C(=O)OR$^a$, —NR$^b$C(=O)N(R$^b$)$_2$, —OC(=O) R$^a$, —OC(=O)OR$^a$, or —OC(=O)N(R$^b$)$_2$.

In certain embodiments, Ring A with substituent $R^K$ is of the formula:

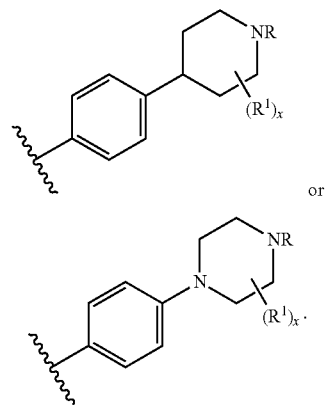

In certain embodiments, Ring A with substituent $R^K$ is of the formula:

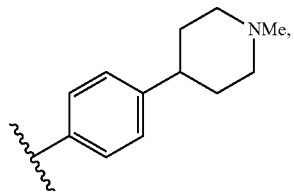

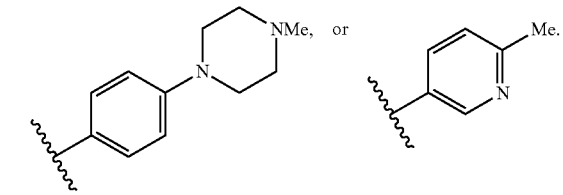

In certain embodiments, Ring C is unsubstituted phenyl; $R^C$, $R^D$, $R^E$, and $R^F$ are each hydrogen; n is 0; $R^L$ is substituted or unsubstituted, $C_{1-6}$ alkyl; and $R^K$ is substituted or unsubstituted piperidinyl, or substituted or unsubstituted piperazinyl.

In certain embodiments, Ring C is of the formula:

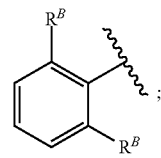

$R^C$, $R^D$, $R^E$, and $R^F$ are each hydrogen; $R^G$ is —OR$^a$, —CH$_3$, or —C$_2$H$_5$; $R^L$ is substituted or unsubstituted, $C_{1-6}$ alkyl; and $R^K$ is substituted or unsubstituted piperidinyl, or substituted or unsubstituted piperazinyl.

In certain embodiments, the compound of Formula (III) is of the formula:

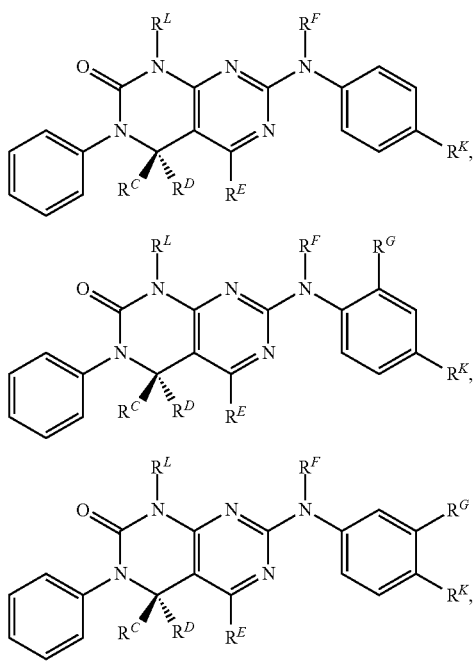

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

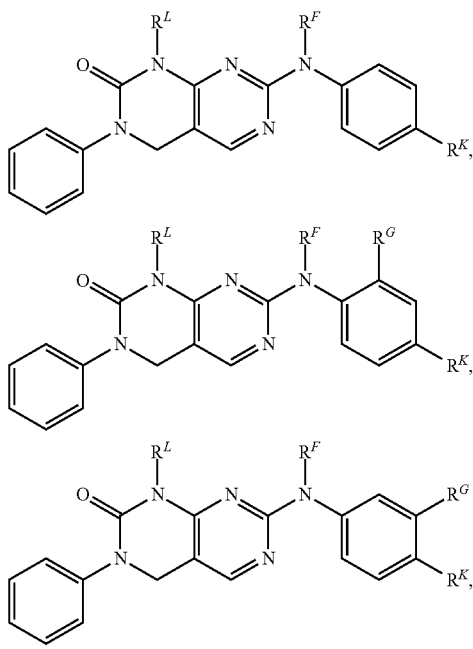

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

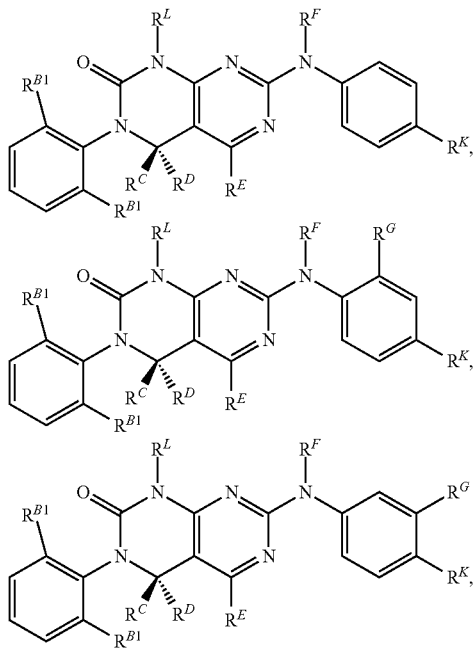

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

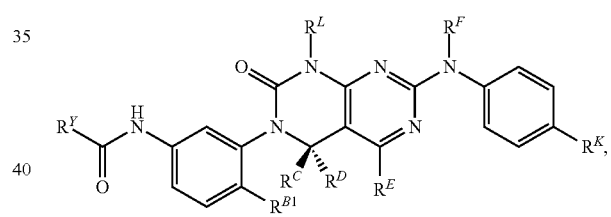

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

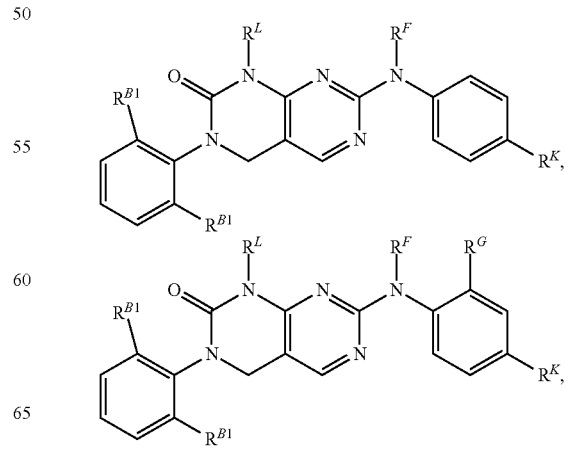

121

-continued

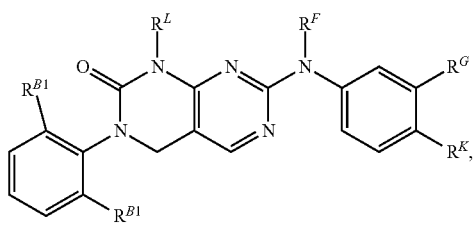

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

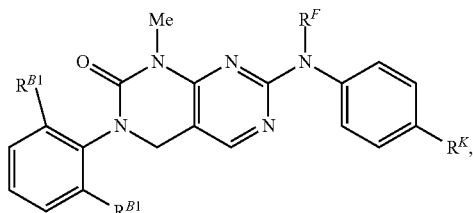

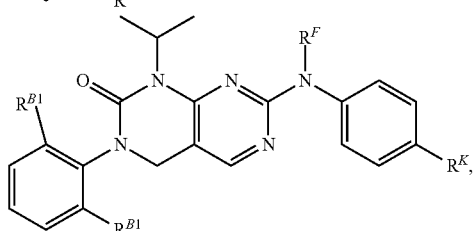

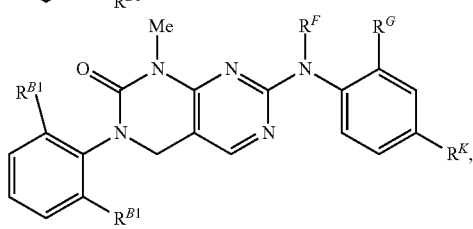

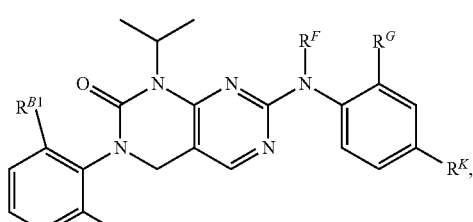

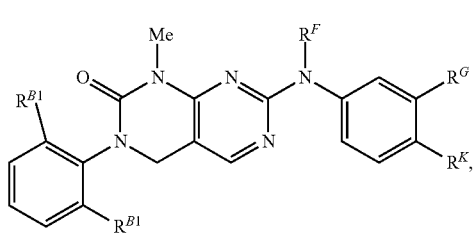

122

-continued

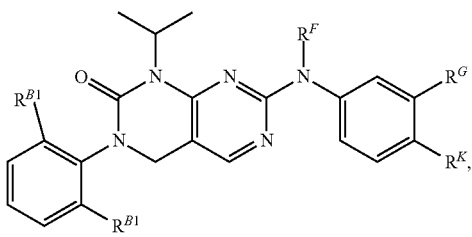

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

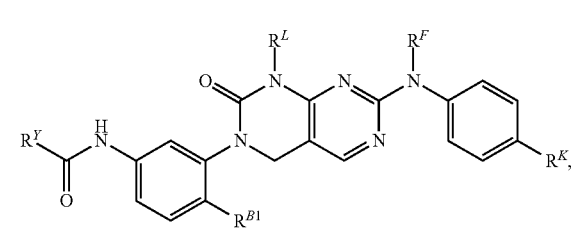

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

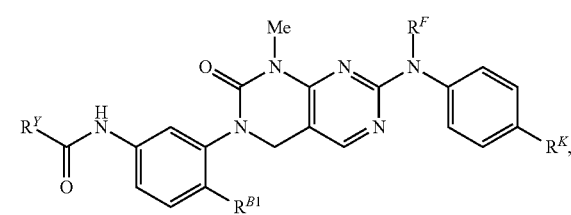

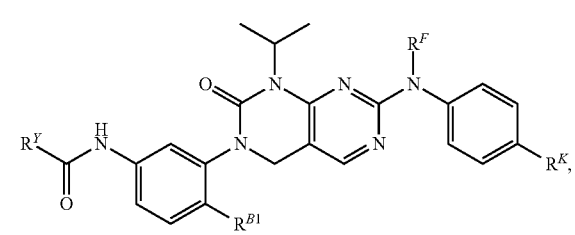

or a pharmaceutically acceptable salt, solvate, hydrate, polymorph, co-crystal, tautomer, stereoisomer, isotopically labeled derivative, or prodrug thereof.

In certain embodiments, the compound of Formula (III) is of the formula:

(HG-11-137-01)
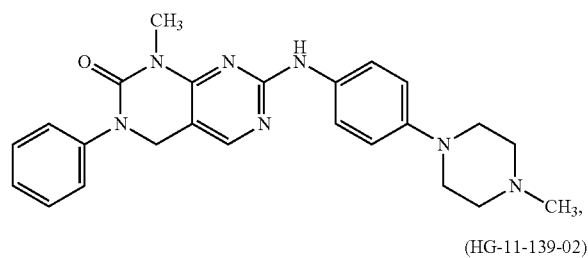
(HG-11-139-02)
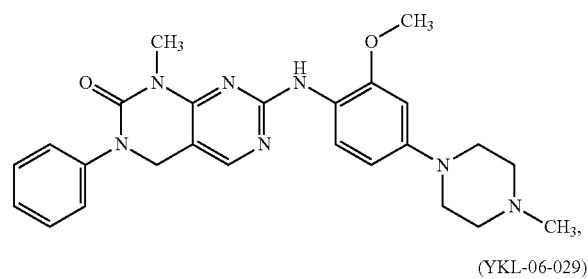
(YKL-06-029)
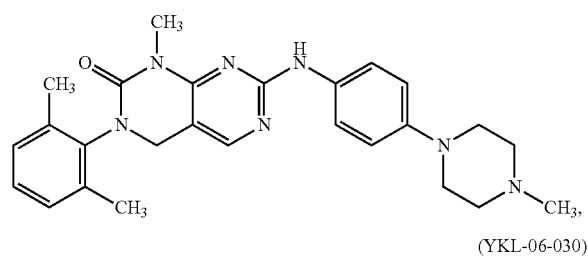
(YKL-06-030)
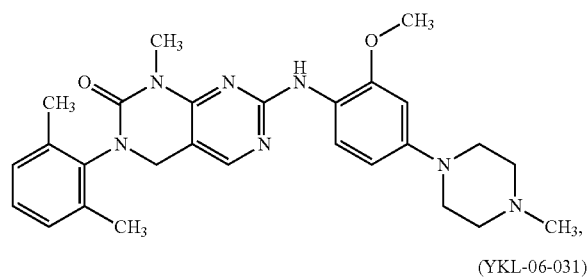
(YKL-06-031)
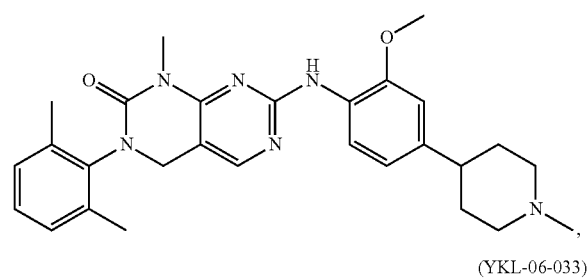
(YKL-06-033)
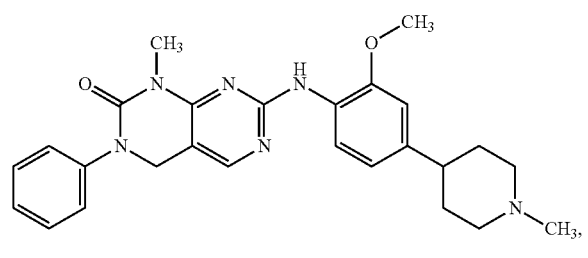
-continued
(YKL-06-046)
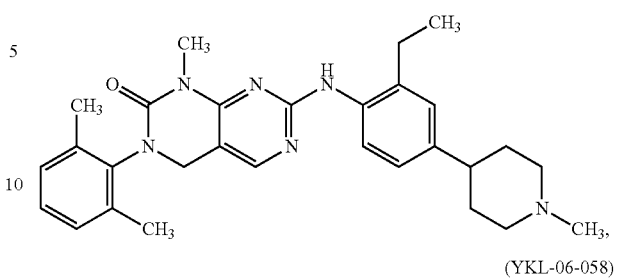
(YKL-06-058)
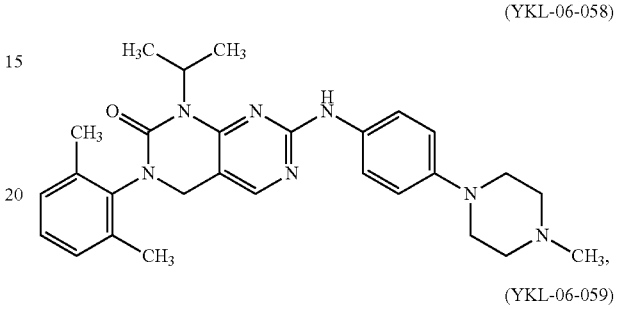
(YKL-06-059)
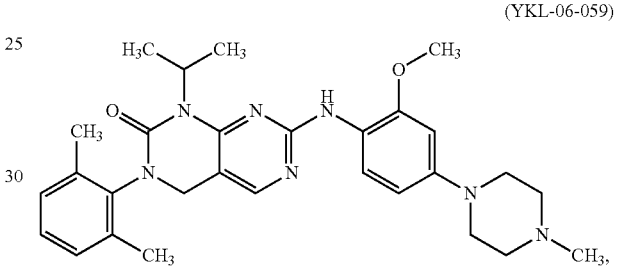
(YKL-06-084)
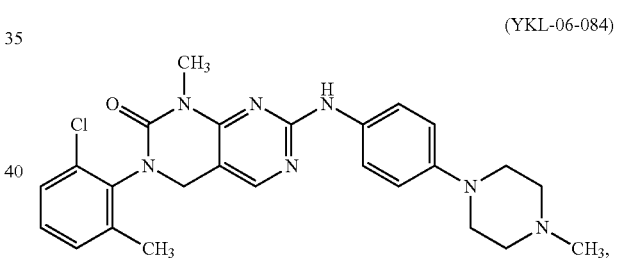
(YKL-06-085)
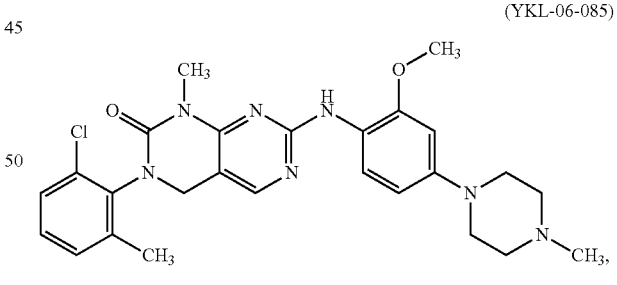
(YKL-06-086)
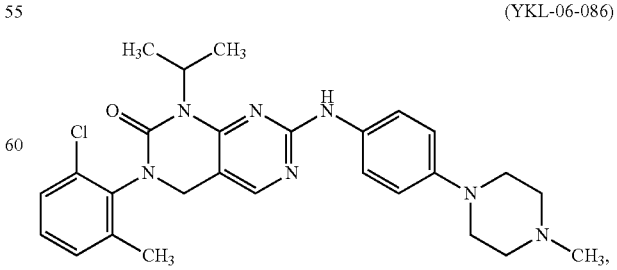

-continued (YKL-06-087)

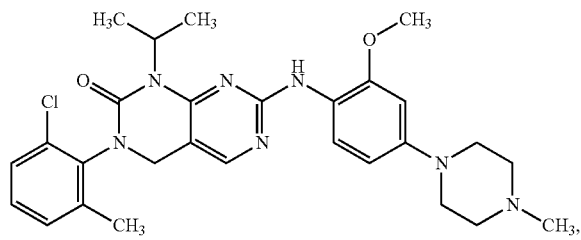

(HG-11-23-01)

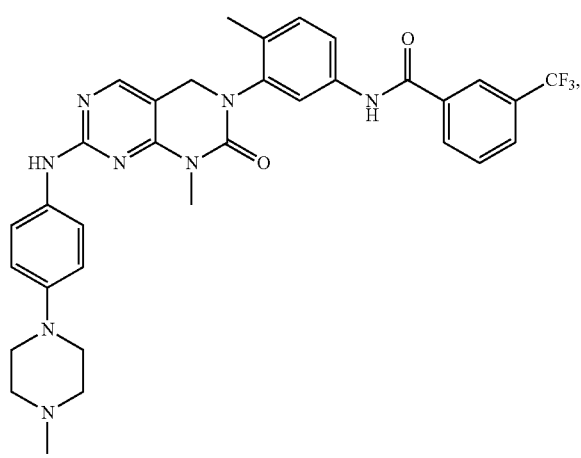

(HG-4-34-01)

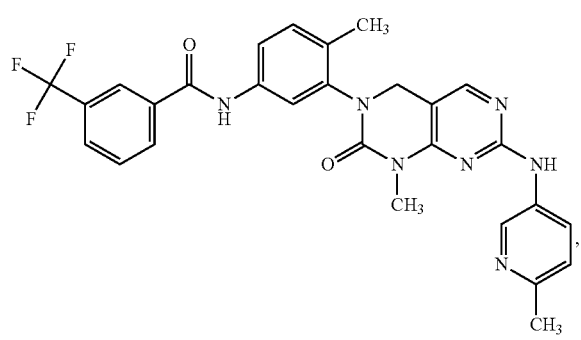

or a pharmaceutically acceptable salt, solvate, hydrate, polymorph, co-crystal, tautomer, stereoisomer, isotopically labeled derivative, or prodrug thereof.

In certain embodiments, the compound of Formula (III) is YKL-06-031, or a pharmaceutically acceptable salt, solvate, hydrate, polymorph, co-crystal, tautomer, stereoisomer, isotopically labeled derivative, or prodrug thereof.

Compounds of Formula (IV)

In another aspect, the present disclosure provides imidazolyl compounds of Formula (IV) for use in the invention:

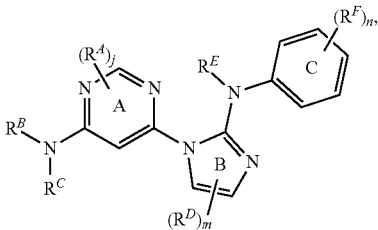

(IV)

and pharmaceutically acceptable salts, solvates, hydrates, polymorphs, co-crystals, tautomers, stereoisomers, isotopically labeled derivatives, and prodrugs thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

j is 0, 1, or 2;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^C$ is hydrogen, substituted or unsubstituted acyl, substituted or unsubstituted, $C_{1-6}$ alkyl, or a nitrogen protecting group;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

m is 0, 1, or 2;

$R^E$ is hydrogen, substituted or unsubstituted acyl, substituted or unsubstituted, $C_{1-6}$ alkyl, or a nitrogen protecting group;

each instance of $R^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and n is 0, 1, 2, 3, 4, or 5.

Unless expressly provided otherwise, the moieties and variables described in the subsection Compounds of Formula (IV) apply only to Formula (IV). The moieties and variables included but not described in detail in the subsection Compounds of Formula (IV) are as described in detail in other subsections.

Formula (IV) includes as Ring A a pyrimidinyl ring that is unsubstituted (e.g., when j is 0) or substituted with one or two substituents R$^A$ (e.g., when j is 1 or 2). In certain embodiments, the two instances of R$^A$ are different. In certain embodiments, both instances of R$^A$ are the same. In certain embodiments, at least one instance of R$^A$ is halogen. In certain embodiments, at least one instance of R$^A$ is F. In certain embodiments, at least one instance of R$^A$ is Cl. In certain embodiments, at least one instance of R$^A$ is Br. In certain embodiments, at least one instance of R$^A$ is I (iodine). In certain embodiments, at least one instance of R$^A$ is substituted alkyl. In certain embodiments, at least one instance of R$^A$ is unsubstituted alkyl. In certain embodiments, at least one instance of R$^A$ is unsubstituted C$_{1-6}$ alkyl. In certain embodiments, both instances of R$^A$ are unsubstituted C$_{1-6}$ alkyl. In certain embodiments, at least one instance of R$^A$ is substituted C$_{1-6}$ alkyl. In certain embodiments, at least one instance of R$^A$ is C$_{1-6}$ alkyl substituted with at least one halogen. In certain embodiments, at least one instance of R$^A$ is —CH$_3$. In certain embodiments, at least one instance of R$^A$ is substituted methyl. In certain embodiments, at least one instance of R$^A$ is —CH$_2$F. In certain embodiments, at least one instance of R$^A$ is —CHF$_2$. In certain embodiments, at least one instance of R$^A$ is —CF$_3$. In certain embodiments, at least one instance of R$^A$ is ethyl. In certain embodiments, at least one instance of R$^A$ is propyl. In certain embodiments, at least one instance of R$^A$ is butyl. In certain embodiments, at least one instance of R$^A$ is pentyl. In certain embodiments, at least one instance of R$^A$ is hexyl. In certain embodiments, at least one instance of R$^A$ is Bn. In certain embodiments, at least one instance of R$^A$ is halogen or substituted or unsubstituted, C$_{1-6}$ alkyl. In certain embodiments, at least one instance of R$^A$ is substituted alkenyl. In certain embodiments, at least one instance of R$^A$ is unsubstituted alkenyl. In certain embodiments, at least one instance of R$^A$ is substituted alkynyl. In certain embodiments, at least one instance of R$^A$ is unsubstituted alkynyl. In certain embodiments, at least one instance of R$^A$ is substituted carbocyclyl. In certain embodiments, at least one instance of R$^A$ is unsubstituted carbocyclyl. In certain embodiments, at least one instance of R$^A$ is saturated carbocyclyl. In certain embodiments, at least one instance of R$^A$ is unsaturated carbocyclyl. In certain embodiments, at least one instance of R$^A$ is monocyclic carbocyclyl. In certain embodiments, at least one instance of R$^A$ is 3- to 7-membered, monocyclic carbocyclyl. In certain embodiments, at least one instance of R$^A$ is substituted heterocyclyl. In certain embodiments, at least one instance of R$^A$ is unsubstituted heterocyclyl. In certain embodiments, at least one instance of R$^A$ is saturated heterocyclyl. In certain embodiments, at least one instance of R$^A$ is unsaturated heterocyclyl. In certain embodiments, at least one instance of R$^A$ is heterocyclyl, wherein one, two, or three atoms of the heterocyclic ring system are independently selected from the group consisting of nitrogen, oxygen, and sulfur. In certain embodiments, at least one instance of R$^A$ is monocyclic heterocyclyl. In certain embodiments, at least one instance of R$^A$ is 3- to 7-membered, monocyclic heterocyclyl. In certain embodiments, at least one instance of R$^A$ is substituted aryl. In certain embodiments, at least one instance of R$^A$ is unsubstituted aryl. In certain embodiments, at least one instance of R$^A$ is 6- to 10-membered aryl. In certain embodiments, at least one instance of R$^A$ is substituted phenyl. In certain embodiments, at least one instance of R$^A$ is unsubstituted phenyl. In certain embodiments, at least one instance of R$^A$ is substituted heteroaryl. In certain embodiments, at least one instance of R$^A$ is unsubstituted heteroaryl. In certain embodiments, at least one instance of R$^A$ is heteroaryl, wherein one, two, three, or four atoms of the heteroaryl ring system are independently selected from the group consisting of nitrogen, oxygen, and sulfur. In certain embodiments, at least one instance of R$^A$ is monocyclic heteroaryl. In certain embodiments, at least one instance of R$^A$ is 5-membered, monocyclic heteroaryl. In certain embodiments, at least one instance of R$^A$ is 6-membered, monocyclic heteroaryl. In certain embodiments, at least one instance of R$^a$ is bicyclic heteroaryl, wherein the point of attachment may be on any atom of the bicyclic heteroaryl ring system, as valency permits. In certain embodiments, at least one instance of R$^A$ is 9- or 10-membered, bicyclic heteroaryl. In certain embodiments, at least one instance of R$^A$ is —OR$^a$. In certain embodiments, at least one instance of R$^A$ is —OH. In certain embodiments, at least one instance of R$^A$ is —O(substituted or unsubstituted, C$_{1-6}$ alkyl). In certain embodiments, at least one instance of R$^A$ is —OMe. In certain embodiments, at least one instance of R$^A$ is —OEt. In certain embodiments, at least one instance of R$^A$ is —OPr. In certain embodiments, at least one instance of R$^A$ is —OBu. In certain embodiments, at least one instance of R$^A$ is —OBn. In certain embodiments, at least one instance of R$^A$ is —OPh. In certain embodiments, at least one instance of R$^A$ is —SR$^a$. In certain embodiments, at least one instance of R$^A$ is —SH. In certain embodiments, at least one instance of R$^A$ is —SMe. In certain embodiments, at least one instance of R$^A$ is —N(R$^a$)$_2$. In certain embodiments, at least one instance of R$^A$ is —NH$_2$. In certain embodiments, at least one instance of R$^A$ is —NHMe. In certain embodiments, at least one instance of R$^A$ is —NMe$_2$. In certain embodiments, at least one instance of R$^A$ is —CN. In certain embodiments, at least one instance of R$^A$ is —SCN. In certain embodiments, at least one instance of R$^A$ is —C(=NR$^a$)R$^a$, —C(=NR$^a$)OR$^a$, or —C(=NR$^a$)N(R$^a$)$_2$. In certain embodiments, at least one instance of R$^A$ is —C(=O)R$^a$ or —C(=O)OR$^a$. In certain embodiments, at least one instance of R$^A$ is —C(=O)N(R$^a$)$_2$. In certain embodiments, at least one instance of R$^A$ is —C(=O)NMe$_2$, —C(=O)NHMe, or —C(=O)NH$_2$. In certain embodiments, at least one instance of R$^A$ is —NO$_2$. In certain embodiments, at least one instance of R$^A$ is —NR$^a$C(=O)R$^a$, —NR$^a$C(=O)OR$^a$, or —NR$^a$C(=O)N(R$^a$)$_2$. In certain embodiments, at least one instance of R$^A$ is —OC(=O)R$^a$, —OC(=O)OR$^a$, or —OC(=O)N(R$^a$)$_2$.

Each instance of R$^A$, R$^D$, R$^F$, R$^G$, R$^J$, and R$^K$ may independently include one or more substituents R$^a$. In certain embodiments, all instances of R$^a$ are the same. In certain embodiments, at least two instances of R$^a$ are different. In certain embodiments, at least one instance of R$^a$ is H. In certain embodiments, each instance of R$^a$ is H. In certain embodiments, at least one instance of R$^a$ is substituted acyl. In certain embodiments, at least one instance of R$^a$ is unsubstituted acyl. In certain embodiments, at least one instance of $R^a$ is acetyl. In certain embodiments, at least one instance of $R^a$ is substituted alkyl. In certain embodiments, at least one instance of $R^a$ is unsubstituted alkyl. In certain embodiments, at least one instance of $R^a$ is unsubstituted $C_{1-6}$ alkyl. In certain embodiments, at least one instance of $R^a$ is methyl. In certain embodiments, at least one instance of $R^a$ is ethyl. In certain embodiments, at least one instance of $R^a$ is propyl. In certain embodiments, at least one instance of $R^a$ is butyl. In certain embodiments, at least one instance of $R^a$ is pentyl. In certain embodiments, at least one instance of $R^a$ is hexyl. In certain embodiments, at least one instance of $R^a$ is Bn. In certain embodiments, at least one instance of $R^a$ is substituted alkenyl. In certain embodiments, at least one instance of $R^a$ is unsubstituted alkenyl. In certain embodiments, at least one instance of $R^a$ is substituted alkynyl. In certain embodiments, at least one instance of $R^a$ is unsubstituted alkynyl. In certain embodiments, at least one instance of $R^a$ is substituted or unsubstituted carbocyclyl. In certain embodiments, at least one instance of $R^a$ is saturated carbocyclyl. In certain embodiments, at least one instance of $R^a$ is unsaturated carbocyclyl. In certain embodiments, at least one instance of $R^a$ is 3- to 7-membered, monocyclic carbocyclyl. In certain embodiments, at least one instance of $R^a$ is substituted or unsubstituted heterocyclyl. In certain embodiments, at least one instance of $R^a$ is saturated heterocyclyl. In certain embodiments, at least one instance of $R^a$ is unsaturated heterocyclyl. In certain embodiments, at least one instance of $R^a$ is heterocyclyl, wherein one, two, or three atoms of the heterocyclic ring system are independently selected from the group consisting of nitrogen, oxygen, and sulfur. In certain embodiments, at least one instance of $R^a$ is 3- to 7-membered, monocyclic heterocyclyl. In certain embodiments, at least one instance of $R^a$ is substituted or unsubstituted aryl. In certain embodiments, at least one instance of $R^a$ is 6- to 10-membered aryl. In certain embodiments, at least one instance of $R^a$ is monocyclic aryl. In certain embodiments, at least one instance of $R^a$ is substituted phenyl. In certain embodiments, at least one instance of $R^a$ is unsubstituted phenyl. In certain embodiments, at least one instance of $R^a$ is bicyclic aryl. In certain embodiments, at least one instance of $R^a$ is substituted or unsubstituted heteroaryl. In certain embodiments, at least one instance of $R^a$ is heteroaryl, wherein one, two, three, or four atoms of the heteroaryl ring system are independently selected from the group consisting of nitrogen, oxygen, and sulfur. In certain embodiments, at least one instance of $R^a$ is monocyclic heteroaryl. In certain embodiments, at least one instance of $R^a$ is 5- or 6-membered, monocyclic heteroaryl. In certain embodiments, at least one instance of $R^a$ is bicyclic heteroaryl, wherein the point of attachment may be on any atom of the bicyclic heteroaryl ring system, as valency permits. In certain embodiments, at least one instance of $R^a$ is a nitrogen protecting group when attached to a nitrogen atom. In certain embodiments, at least one instance of $R^a$ is Bn, Boc, Cbz, Fmoc, trifluoroacetyl, triphenylmethyl, acetyl, or Ts when attached to a nitrogen atom. In certain embodiments, $R^a$ is an oxygen protecting group when attached to an oxygen atom. In certain embodiments, $R^a$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^a$ is a sulfur protecting group when attached to a sulfur atom. In certain embodiments, $R^a$ is acetamidomethyl, t-Bu, 3-nitro-2-pyridine sulfenyl, 2-pyridine-sulfenyl, or triphenylmethyl when attached to a sulfur atom. In certain embodiments, two instances of $R^a$ are joined to form a substituted or unsubstituted heterocyclic ring. In certain embodiments, two instances of $R^a$ are joined to form a saturated or unsaturated heterocyclic ring. In certain embodiments, two instances of $R^a$ are joined to form a heterocyclic ring, wherein one, two, or three atoms of the heterocyclic ring system are independently selected from the group consisting of nitrogen, oxygen, and sulfur. In certain embodiments, two instances of $R^a$ are joined to form a 3- to 7-membered, monocyclic heterocyclic ring. In certain embodiments, two instances of $R^a$ are joined to form a substituted or unsubstituted heteroaryl ring. In certain embodiments, two instances of $R^a$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, j is 0. In certain embodiments, j is 1. In certain embodiments, j is 2.

Formula (IV) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is substituted alkyl. In certain embodiments, $R^B$ is unsubstituted alkyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is —$CH_3$. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is Bn. In certain embodiments, $R^B$ is —$(CH_2)_{1-4}$-(Ring F), wherein Ring F is a substituted or unsubstituted, 3- to 7-membered, monocyclic heterocyclic ring. In certain embodiments, $R^B$ is —$(CH_2)_{1-4}$-(substituted or unsubstituted pyrrolidinyl). In certain embodiments, $R^B$ is of the formula:

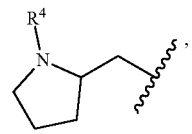

wherein $R^4$ is H, substituted or unsubstituted, $C_{1-6}$ alkyl, or a nitrogen protecting group. In certain embodiments, $R^B$ is of the formula:

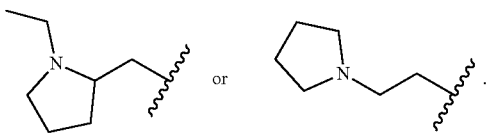

In certain embodiments, $R^B$ is —$(CH_2)_{1-4}$-(Ring F), wherein Ring F is a substituted or unsubstituted oxetanyl, substituted or unsubstituted azetidinyl, substituted or unsubstituted tetrahydrofuranyl, substituted or unsubstituted tetrahydropyranyl, substituted or unsubstituted piperidinyl, substituted or unsubstituted piperazinyl, or substituted or unsubstituted morpholinyl ring. In certain embodiments, $R^B$ is substituted alkenyl. In certain embodiments, $R^B$ is unsubstituted alkenyl. In certain embodiments, $R^B$ is substituted alkynyl. In certain embodiments, $R^B$ is unsubstituted alkynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is monocyclic carbocyclyl. In certain embodiments, $R^B$ is 3- to 7-membered, monocyclic carbocyclyl. In certain embodiments, $R^B$ is unsubstituted cyclopropyl. In certain embodiments, $R^B$ is substituted cyclopropyl. In certain embodiments, $R^B$ is substituted heterocyclyl. In certain embodiments, $R^B$ is unsubstituted heterocyclyl. In certain embodiments, $R^B$ is saturated heterocyclyl. In certain embodiments, $R^B$ is unsaturated heterocyclyl. In certain embodiments, $R^B$ is heterocyclyl, wherein one, two, or three atoms of the heterocyclic ring system are independently selected from the group consisting of nitrogen, oxygen, and sulfur. In certain embodiments, $R^B$ is monocyclic heterocyclyl. In certain embodiments, $R^B$ is 3- to 7-membered, monocyclic heterocyclyl. In certain embodiments, $R^B$ is substituted aryl. In certain embodiments, $R^B$ is unsubstituted aryl. In certain embodiments, $R^B$ is 6- to 10-membered aryl. In certain embodiments, $R^B$ is substituted phenyl. In certain embodiments, $R^B$ is unsubstituted phenyl. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur. In certain embodiments, $R^B$ is substituted or unsubstituted pyrazolyl. In certain embodiments, $R^B$ is of the formula:

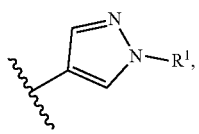

wherein $R^1$ is substituted or unsubstituted, $C_{1-6}$ alkyl, or a nitrogen protecting group. In certain embodiments, $R^B$ is of the formula:

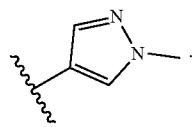 [SMILES: *c1cnn(C)c1]

In certain embodiments, $R^B$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^B$ is substituted or unsubstituted pyridyl, substituted or unsubstituted pyrazinyl, substituted or unsubstituted pyrimidinyl, or substituted or unsubstituted pyridazinyl. In certain embodiments, $R^B$ is substituted or unsubstituted, 9- to 10-membered, bicyclic heteroaryl, wherein one, two, three, or four atoms of the heteroaryl ring system are independently nitrogen, oxygen, or sulfur. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

Formula (IV) includes substituent $R^C$ on a nitrogen atom. In certain embodiments, $R^C$ is H. In certain embodiments, $R^C$ is substituted acyl. In certain embodiments, $R^C$ is unsubstituted acyl. In certain embodiments, $R^C$ is acetyl. In certain embodiments, $R^C$ is unsubstituted $C_{1-6}$ alkyl. In certain embodiments, $R^C$ is substituted $C_{1-6}$ alkyl. In certain embodiments, $R^C$ is $C_{1-6}$ alkyl substituted with at least one halogen. In certain embodiments, $R^C$ is unsubstituted methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is ethyl. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is Bn. In certain embodiments, $R^C$ is a nitrogen protecting group. In certain embodiments, $R^C$ is Bn, Boc, Cbz, Fmoc, trifluoroacetyl, triphenylmethyl, acetyl, or Ts.

In certain embodiments, $R^B$ is substituted or unsubstituted, $C_{1-6}$ alkyl, and $R^C$ is H. In certain embodiments, $R^B$ is —$(CH_2)_{1-4}$-(Ring F), wherein Ring F is a substituted or unsubstituted, 3- to 7-membered, monocyclic heterocyclic ring; and $R^C$ is H. In certain embodiments, $R^B$ is substituted or unsubstituted phenyl (e.g., para-substituted phenyl), and $R^C$ is H. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur; and $R^C$ is H. In certain embodiments, $R^B$ is substituted or unsubstituted pyrazolyl, and $R^C$ is H. In certain embodiments, $R^B$ is substituted or unsubstituted, 3- to 7-membered, monocyclic carbocyclyl; and $R^C$ is H. In certain embodiments, $R^B$ is substituted or unsubstituted cyclopropyl, and $R^C$ is H.

Formula (IV) includes as Ring B an imidazolyl ring that is unsubstituted (e.g., when m is 0) or substituted with one or two substituents $R^D$ (e.g., when m is 1 or 2). In certain embodiments, Ring B does not include substituents $R^D$, that is, m is 0. In certain embodiments, the two instances of $R^D$ are different. In certain embodiments, both instances of $R^D$ are the same. In certain embodiments, at least one instance of $R^D$ is halogen. In certain embodiments, at least one instance of $R^D$ is F. In certain embodiments, at least one instance of $R^D$ is Cl. In certain embodiments, at least one instance of $R^D$ is Br. In certain embodiments, at least one instance of $R^D$ is I (iodine). In certain embodiments, at least one instance of $R^D$ is substituted alkyl. In certain embodiments, at least one instance of $R^D$ is unsubstituted alkyl. In certain embodiments, at least one instance of $R^D$ is unsubstituted $C_{1-6}$ alkyl. In certain embodiments, both instances of $R^D$ are unsubstituted $C_{1-6}$ alkyl. In certain embodiments, at least one instance of $R^D$ is substituted $C_{1-6}$ alkyl. In certain embodiments, at least one instance of $R^D$ is $C_{1-6}$ alkyl substituted with at least one halogen. In certain embodiments, at least one instance of $R^D$ is —$CH_3$. In certain embodiments, at least one instance of $R^D$ is substituted methyl. In certain embodiments, at least one instance of $R^D$ is —$CH_2F$. In certain embodiments, at least one instance of $R^D$ is —$CHF_2$. In certain embodiments, at least one instance of $R^D$ is —$CF_3$. In certain embodiments, at least one instance of $R^D$ is ethyl. In certain embodiments, at least one instance of $R^D$ is propyl. In certain embodiments, at least one instance of $R^D$ is butyl. In certain embodiments, at least one instance of $R^D$ is pentyl. In certain embodiments, at least one instance of $R^D$ is hexyl. In certain embodiments, at least one instance of $R^D$ is Bn. In certain embodiments, at least one instance of $R^D$ is halogen or substituted or unsubstituted, $C_{1-6}$ alkyl. In certain embodiments, at least one instance of $R^D$ is substituted alkenyl. In certain embodiments, at least one instance of $R^D$ is unsubstituted alkenyl. In certain embodiments, at least one instance of $R^D$ is substituted alkynyl. In certain embodiments, at least one instance of $R^D$ is unsubstituted alkynyl. In certain embodiments, at least one instance of $R^D$ is substituted carbocyclyl. In certain embodiments, at least one instance of $R^D$ is unsubstituted carbocyclyl. In certain embodiments, at least one instance of $R^D$ is saturated carbocyclyl. In certain embodiments, at least one instance of $R^D$ is unsaturated carbocyclyl. In certain embodiments, at least one instance of $R^D$ is monocyclic carbocyclyl. In certain embodiments, at least one instance of $R^D$ is 3- to 7-membered, monocyclic carbocyclyl. In certain embodiments, at least one instance of $R^D$ is substituted heterocyclyl. In certain embodiments, at least one instance of $R^D$ is unsubstituted heterocyclyl. In certain embodiments, at least one instance of $R^D$ is saturated heterocyclyl. In certain embodiments, at least one instance of $R^D$ is unsaturated heterocyclyl. In certain embodiments, at least one instance of $R^D$ is heterocyclyl, wherein one, two, or three atoms of the heterocyclic ring system are independently selected from the group consisting of nitrogen, oxygen, and sulfur. In certain embodiments, at least one instance of $R^D$ is monocyclic heterocyclyl. In certain embodiments, at least one instance of $R^D$ is 3- to 7-membered, monocyclic heterocyclyl. In certain embodiments, at least one instance of $R^D$ is substituted aryl. In certain embodiments, at least one instance of $R^D$ is unsubstituted aryl. In certain embodiments, at least one instance of $R^D$ is 6- to 10-membered aryl. In certain embodiments, at least one instance of $R^D$ is substituted phenyl. In certain embodiments, at least one instance of $R^D$ is unsubstituted phenyl. In certain embodiments, at least one instance of $R^D$ is substituted heteroaryl. In certain embodiments, at least one instance of $R^D$ is unsubstituted heteroaryl. In certain embodiments, at least one instance of $R^D$ is heteroaryl, wherein one, two, three, or four atoms of the heteroaryl ring system are independently selected from the group consisting of nitrogen, oxygen, and sulfur. In certain embodiments, at least one instance of $R^D$ is monocyclic heteroaryl. In certain embodiments, at least one instance of $R^D$ is 5-membered, monocyclic heteroaryl. In certain embodiments, at least one instance of $R^D$ is 6-membered, monocyclic heteroaryl. In certain embodiments, at least one instance of $R^D$ is bicyclic heteroaryl, wherein the point of attachment may be on any atom of the bicyclic heteroaryl ring system, as valency permits. In certain embodiments, at least one instance of $R^D$ is 9- or 10-membered, bicyclic heteroaryl. In certain embodiments, at least one instance of $R^D$ is —$OR^a$. In certain embodiments, at least one instance of $R^D$ is —OH. In certain embodiments, at least one instance of $R^D$ is —O(substituted or unsubstituted, $C_{1-6}$ alkyl). In certain embodiments, at least one instance of $R^D$ is —OMe. In certain embodiments, at least one instance of $R^D$ is —OEt. In certain embodiments, at least one instance of $R^D$ is —OPr. In certain embodiments, at least one instance of $R^D$ is —OBu. In certain embodiments, at least one instance of $R^D$ is —OBn. In certain embodiments, at least one instance of $R^D$ is —OPh. In certain embodiments, at least one instance of $R^D$ is —$SR^a$. In certain embodiments, at least one instance of $R^D$ is —SH. In certain embodiments, at least one instance of $R^D$ is —SMe. In certain embodiments, at least one instance of $R^D$ is —$N(R^a)_2$. In certain embodiments, at least one instance of $R^D$ is —$NH_2$. In certain embodiments, at least one instance of $R^D$ is —NHMe. In certain embodiments, at least one instance of $R^D$ is —$NMe_2$. In certain embodiments, at least one instance of $R^D$ is —CN. In certain embodiments, at least one instance of $R^D$ is —SCN. In certain embodiments, at least one instance of $R^D$ is —$C(=NR^a)R^a$, —$C(=NR^a)OR^a$, or —$C(=NR^a)N(R^a)_2$. In certain embodiments, at least one instance of $R^D$ is —$C(=O)R^a$ or —$C(=O)OR^a$. In certain embodiments, at least one instance of $R^D$ is —$C(=O)N(R^a)_2$. In certain embodiments, at least one instance of $R^D$ is —$C(=O)NMe_2$, —$C(=O)NHMe$, or —$C(=O)NH_2$. In certain embodiments, at least one instance of $R^D$ is —$NO_2$. In certain embodiments, at least one instance of $R^D$ is —$NR^aC(=O)R^a$, —$NR^aC(=O)OR^a$, or —$NR^aC(=O)N(R^a)_2$. In certain embodiments, at least one instance of $R^D$ is —$OC(=O)R^a$, —$OC(=O)OR^a$, or —$OC(=O)N(R^a)_2$.

In certain embodiments, m is 0. In certain embodiments, m is 1. In certain embodiments, m is 2.

Formula (IV) includes substituent $R^E$ on a nitrogen atom. In certain embodiments, $R^E$ is H. In certain embodiments, $R^E$ is substituted acyl. In certain embodiments, $R^E$ is unsubstituted acyl. In certain embodiments, $R^E$ is acetyl. In certain embodiments, $R^E$ is unsubstituted $C_{1-6}$ alkyl. In certain embodiments, $R^E$ is substituted $C_{1-6}$ alkyl. In certain embodiments, $R^E$ is $C_{1-6}$ alkyl substituted with at least one halogen. In certain embodiments, $R^E$ is unsubstituted methyl. In certain embodiments, $R^E$ is substituted methyl. In certain embodiments, $R^E$ is —$CH_2F$. In certain embodiments, $R^E$ is —$CHF_2$. In certain embodiments, $R^E$ is —$CF_3$. In certain embodiments, $R^E$ is ethyl. In certain embodiments, $R^E$ is propyl. In certain embodiments, $R^E$ is butyl. In certain embodiments, $R^E$ is pentyl. In certain embodiments, $R^E$ is hexyl. In certain embodiments, $R^E$ is Bn. In certain embodiments, $R^E$ is a nitrogen protecting group. In certain embodiments, $R^E$ is Bn, Boc, Cbz, Fmoc, trifluoroacetyl, triphenylmethyl, acetyl, or Ts.

In certain embodiments, each of $R^C$ and $R^E$ is H.

Formula (IV) includes as Ring C a phenyl ring that is unsubstituted (e.g., when n is 0) or substituted with one or more substituents $R^F$ (e.g., when n is 1, 2, 3, 4, or 5). In certain embodiments, Ring C is of the formula:

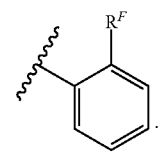

In certain embodiments, Ring C is of the formula:

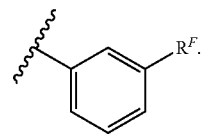

In certain embodiments, Ring C is of the formula:

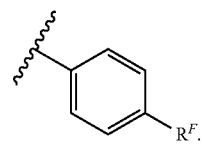

In certain embodiments, Ring C is of the formula:

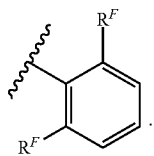

In certain embodiments, Ring C is of the formula:

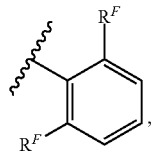

wherein each instance of $R^F$ is independently halogen or substituted or unsubstituted, $C_{1-6}$ alkyl. In certain embodiments, Ring C is of the formula:

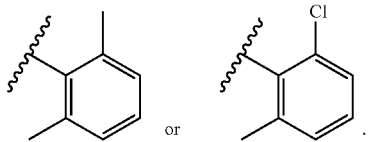

In certain embodiments, Ring C is of the formula:

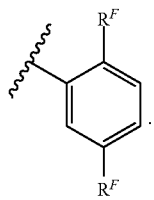

In certain embodiments, Ring C is of the formula:

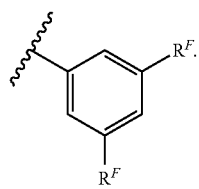

In certain embodiments, Ring C is of the formula:

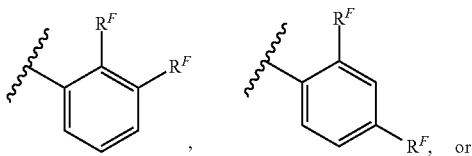

-continued

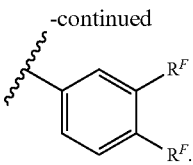

In certain embodiments, at least two instances of $R^F$ are different. In certain embodiments, all instances of $R^F$ are the same. In certain embodiments, at least one instance of $R^F$ is halogen. In certain embodiments, at least one instance of $R^F$ is F. In certain embodiments, at least one instance of $R^F$ is Cl. In certain embodiments, at least one instance of $R^F$ is Br. In certain embodiments, at least one instance of $R^F$ is I (iodine). In certain embodiments, at least one instance of $R^F$ is substituted alkyl. In certain embodiments, at least one instance of $R^F$ is unsubstituted alkyl. In certain embodiments, at least one instance of $R^F$ is unsubstituted $C_{1-6}$ alkyl. In certain embodiments, all instances of $R^F$ are unsubstituted $C_{1-6}$ alkyl. In certain embodiments, at least one instance of $R^F$ is substituted $C_{1-6}$ alkyl. In certain embodiments, at least one instance of $R^F$ is $C_{1-6}$ alkyl substituted with at least one halogen. In certain embodiments, at least one instance of $R^F$ is —$CH_3$. In certain embodiments, all instances of $R^F$ are —$CH_3$. In certain embodiments, at least one instance of $R^F$ is substituted methyl. In certain embodiments, at least one instance of $R^F$ is —$CH_2F$. In certain embodiments, at least one instance of $R^F$ is —$CHF_2$. In certain embodiments, at least one instance of $R^F$ is —$CF_3$. In certain embodiments, at least one instance of $R^F$ is ethyl. In certain embodiments, at least one instance of $R^F$ is propyl. In certain embodiments, at least one instance of $R^F$ is butyl. In certain embodiments, at least one instance of $R^F$ is pentyl. In certain embodiments, at least one instance of $R^F$ is hexyl. In certain embodiments, at least one instance of $R^F$ is Bn. In certain embodiments, at least one instance of $R^F$ is substituted alkenyl. In certain embodiments, at least one instance of $R^F$ is unsubstituted alkenyl. In certain embodiments, at least one instance of $R^F$ is substituted alkynyl. In certain embodiments, at least one instance of $R^F$ is unsubstituted alkynyl. In certain embodiments, at least one instance of $R^F$ is substituted carbocyclyl. In certain embodiments, at least one instance of $R^F$ is unsubstituted carbocyclyl. In certain embodiments, at least one instance of $R^F$ is saturated carbocyclyl. In certain embodiments, at least one instance of $R^F$ is unsaturated carbocyclyl. In certain embodiments, at least one instance of $R^F$ is monocyclic carbocyclyl. In certain embodiments, at least one instance of $R^F$ is 3- to 7-membered, monocyclic carbocyclyl. In certain embodiments, at least one instance of $R^F$ is substituted heterocyclyl. In certain embodiments, at least one instance of $R^F$ is unsubstituted heterocyclyl. In certain embodiments, at least one instance of $R^F$ is saturated heterocyclyl. In certain embodiments, at least one instance of $R^F$ is unsaturated heterocyclyl. In certain embodiments, at least one instance of $R^F$ is heterocyclyl, wherein one, two, or three atoms of the heterocyclic ring system are independently selected from the group consisting of nitrogen, oxygen, and sulfur. In certain embodiments, at least one instance of $R^F$ is monocyclic heterocyclyl. In certain embodiments, at least one instance of $R^F$ is 3- to 7-membered, monocyclic heterocyclyl. In certain embodiments, at least one instance of $R^F$ is substituted aryl. In certain embodiments, at least one instance of $R^F$ is unsubstituted aryl. In certain embodiments, at least one instance of $R^F$ is 6- to 10-membered aryl. In certain embodiments, at least one instance of $R^F$ is substituted phenyl. In certain embodiments, at least one instance of $R^F$ is unsubstituted phenyl. In certain embodiments, at least one instance of $R^F$ is substituted heteroaryl. In certain embodiments, at least one instance of $R^F$ is unsubstituted heteroaryl. In certain embodiments, at least one instance of $R^F$ is heteroaryl, wherein one, two, three, or four atoms of the heteroaryl ring system are independently selected from the group consisting of nitrogen, oxygen, and sulfur. In certain embodiments, at least one instance of $R^F$ is monocyclic heteroaryl. In certain embodiments, at least one instance of $R^F$ is 5-membered, monocyclic heteroaryl. In certain embodiments, at least one instance of $R^F$ is 6-membered, monocyclic heteroaryl. In certain embodiments, at least one instance of $R^F$ is bicyclic heteroaryl, wherein the point of attachment may be on any atom of the bicyclic heteroaryl ring system, as valency permits. In certain embodiments, at least one instance of $R^F$ is 9- or 10-membered, bicyclic heteroaryl. In certain embodiments, at least one instance of $R^F$ is —$OR^a$. In certain embodiments, at least one instance of $R^F$ is —OH. In certain embodiments, at least one instance of $R^F$ is —O(substituted or unsubstituted, $C_{1-6}$ alkyl). In certain embodiments, at least one instance of $R^F$ is —OMe. In certain embodiments, at least one instance of $R^F$ is —OEt. In certain embodiments, at least one instance of $R^F$ is —OPr. In certain embodiments, at least one instance of $R^F$ is —OBu. In certain embodiments, at least one instance of $R^F$ is —OBn. In certain embodiments, at least one instance of $R^F$ is —OPh. In certain embodiments, at least one instance of $R^F$ is —$SR^a$. In certain embodiments, at least one instance of $R^F$ is —SH. In certain embodiments, at least one instance of $R^F$ is —SMe. In certain embodiments, at least one instance of $R^F$ is —$N(R^a)_2$. In certain embodiments, at least one instance of $R^F$ is —$NH_2$. In certain embodiments, at least one instance of $R^F$ is —NHMe. In certain embodiments, at least one instance of $R^F$ is —$NMe_2$. In certain embodiments, at least one instance of $R^F$ is —CN. In certain embodiments, at least one instance of $R^F$ is —SCN. In certain embodiments, at least one instance of $R^F$ is —$C(=NR^a)R^a$, —$C(=NR^a)OR^a$, or —$C(=NR^a)N(R^a)_2$. In certain embodiments, at least one instance of $R^F$ is —$C(=O)R^a$ or —$C(=O)OR^a$. In certain embodiments, at least one instance of $R^F$ is —$C(=O)N(R^a)_2$.

In certain embodiments, at least one instance of $R^F$ is —$C(=O)N(R^a)_2$, wherein each instance of $R^a$ is independently hydrogen, substituted or unsubstituted, $C_{1-6}$ alkyl, substituted or unsubstituted phenyl, or a nitrogen protecting group. In certain embodiments, at least one instance of $R^F$ is —$C(=O)NHR^a$, wherein $R^a$ is substituted or unsubstituted phenyl. In certain embodiments, at least one instance of $R^F$ is —$C(=O)NMeR^a$, wherein $R^a$ is phenyl substituted with one, two, three, four, or five substituents independently selected from the group consisting of halogen and substituted or unsubstituted, $C_{1-6}$ alkyl. In certain embodiments, at least one instance of $R^F$ is —$C(=O)NMeR^a$, wherein $R^a$ is substituted or unsubstituted phenyl. In certain embodiments, at least one instance of $R^F$ is —$C(=O)NMeR^a$, wherein $R^a$ is phenyl substituted with one, two, three, four, or five substituents independently selected from the group consisting of halogen and substituted or unsubstituted, $C_{1-6}$ alkyl. In certain embodiments, at least one instance of $R^F$ is —$C(=O)NMe_2$, —$C(=O)NHMe$, or —$C(=O)NH_2$. In certain embodiments, at least one instance of $R^F$ is —$NO_2$. In certain embodiments, at least one instance of $R^F$ is —$NR^aC(=O)R^a$, —$NR^aC(=O)OR^a$, or —$NR^aC(=O)N(R^a)_2$. In certain embodiments, at least one instance of $R^F$ is —$OC(=O)R^a$, —$OC(=O)OR^a$, or —$OC(=O)N(R^a)_2$.

In certain embodiments, at least one instance of $R^F$ is halogen, substituted or unsubstituted, $C_{1-6}$ alkyl, or —$OR^a$. In certain embodiments, at least one instance of $R^F$ is halogen, substituted or unsubstituted, $C_{1-6}$ alkyl, or —$OR^a$, wherein $R^a$ is hydrogen, substituted or unsubstituted, $C_{1-6}$ alkyl, or an oxygen protecting group. In certain embodiments, at least one instance of $R^F$ is halogen, unsubstituted $C_{1-6}$ alkyl, or —$OR^a$, wherein $R^a$ is unsubstituted $C_{1-6}$ alkyl. In certain embodiments, at least one instance of $R^a$ is —$CH_3$ or Cl.

In certain embodiments, n is 0. In certain embodiments, n is 1. In certain embodiments, n is 2. In certain embodiments, n is 3. In certain embodiments, n is 4. In certain embodiments, n is 5.

In certain embodiments, n is 1; and $R^F$ is —$C(=O)N(R^a)_2$. In certain embodiments, n is 1; and $R^F$ is —$C(=O)N(R^a)_2$, wherein each instance of $R^a$ is independently hydrogen, substituted or unsubstituted, $C_{1-6}$ alkyl, substituted or unsubstituted phenyl, or a nitrogen protecting group. In certain embodiments, n is 2; and each instance of $R^F$ is independently halogen or substituted or unsubstituted, $C_{1-6}$ alkyl. In certain embodiments, n is 2; and each instance of $R^F$ is independently halogen or unsubstituted, $C_{1-6}$ alkyl (e.g., —$CH_3$). In certain embodiments, n is 2; and each instance of $R^F$ is independently halogen, substituted or unsubstituted, $C_{1-6}$ alkyl, —$OR^a$, or —$C(=O)N(R^a)_2$. In certain embodiments, n is 2; and each instance of $R^F$ is independently halogen, substituted or unsubstituted, $C_{1-6}$ alkyl, —$OR^a$, or —$C(=O)N(R^a)_2$, wherein each instance of $R^a$ is independently hydrogen, substituted or unsubstituted, $C_{1-6}$ alkyl, substituted or unsubstituted phenyl, an oxygen protecting group when attached to an oxygen atom, or a nitrogen protecting group when attached to a nitrogen atom.

In certain embodiments, the compound of Formula (IV) is of Formula (IV-A):

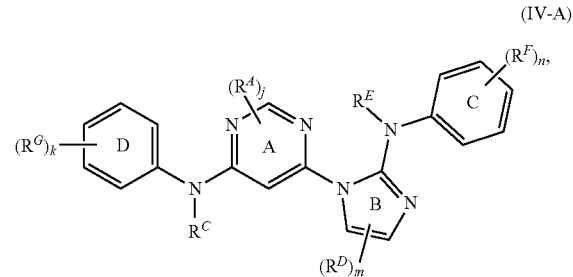

(IV-A)

or a pharmaceutically acceptable salt, solvate, hydrate, polymorph, co-crystal, tautomer, stereoisomer, isotopically labeled derivative, or prodrug thereof, wherein:

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$; and k is 0, 1, 2, 3, 4, or 5.

Formula (IV-A) includes as Ring D a phenyl ring that is unsubstituted (e.g., when k is 0) or substituted with one or more substituents $R^G$ (e.g., when k is 1, 2, 3, 4, or 5). In certain embodiments, Ring D is of the formula:

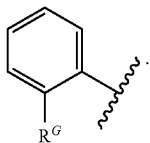

In certain embodiments, Ring D is of the formula:

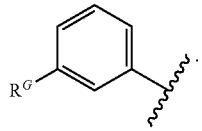

In certain embodiments, Ring D is of the formula:

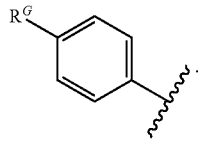

In certain embodiments, Ring D is of the formula:

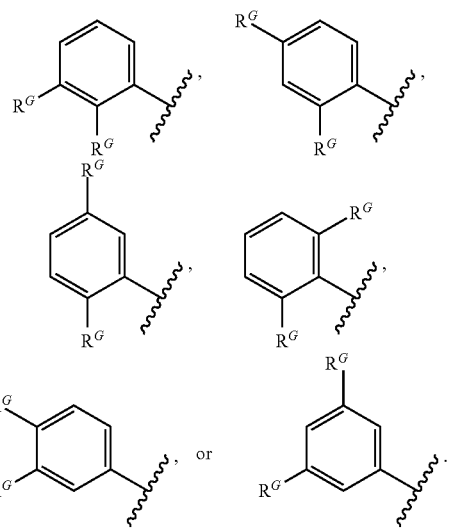

certain embodiments, at least two instances of $R^G$ are different. In certain embodiments, all instances of $R^G$ are the same. In certain embodiments, at least one instance of $R^G$ is halogen. In certain embodiments, at least one instance of $R^G$ is F. In certain embodiments, at least one instance of $R^G$ is Cl. In certain embodiments, at least one instance of $R^G$ is Br. In certain embodiments, at least one instance of $R^G$ is I (iodine). In certain embodiments, at least one instance of $R^G$ is substituted alkyl. In certain embodiments, at least one instance of $R^G$ is unsubstituted alkyl. In certain embodiments, at least one instance of $R^G$ is unsubstituted $C_{1-6}$ alkyl. In certain embodiments, all instances of $R^G$ are unsubstituted $C_{1-6}$ alkyl. In certain embodiments, at least one instance of $R^G$ is substituted $C_{1-6}$ alkyl. In certain embodiments, at least one instance of $R^G$ is $C_{1-6}$ alkyl substituted with at least one halogen. In certain embodiments, at least one instance of R2 is —$CH_3$. In certain embodiments, all instances of $R^G$ are —$CH_3$. In certain embodiments, at least one instance of $R^G$ is substituted methyl. In certain embodiments, at least one instance of $R^G$ is —$CH_2F$. In certain embodiments, at least one instance of $R^G$ is —$CHF_2$. In certain embodiments, at least one instance of $R^G$ is —$CF_3$. In certain embodiments, at least one instance of $R^G$ is ethyl. In certain embodiments, at least one instance of $R^G$ is propyl. In certain embodiments, at least one instance of $R^G$ is butyl. In certain embodiments, at least one instance of $R^G$ is pentyl. In certain embodiments, at least one instance of $R^G$ is hexyl. In certain embodiments, at least one instance of $R^G$ is Bn. In certain embodiments, at least one instance of $R^G$ is substituted alkenyl. In certain embodiments, at least one instance of $R^G$ is unsubstituted alkenyl. In certain embodiments, at least one instance of $R^G$ is substituted alkynyl. In certain embodiments, at least one instance of $R^G$ is unsubstituted alkynyl. In certain embodiments, at least one instance of $R^G$ is substituted carbocyclyl. In certain embodiments, at least one instance of $R^G$ is unsubstituted carbocyclyl. In certain embodiments, at least one instance of $R^G$ is saturated carbocyclyl. In certain embodiments, at least one instance of $R^G$ is unsaturated carbocyclyl. In certain embodiments, at least one instance of $R^G$ is monocyclic carbocyclyl. In certain embodiments, at least one instance of $R^G$ is 3- to 7-membered, monocyclic carbocyclyl. In certain embodiments, at least one instance of $R^G$ is substituted heterocyclyl. In certain embodiments, at least one instance of $R^G$ is unsubstituted heterocyclyl. In certain embodiments, at least one instance of $R^G$ is saturated heterocyclyl. In certain embodiments, at least one instance of $R^G$ is unsaturated heterocyclyl. In certain embodiments, at least one instance of $R^G$ is heterocyclyl, wherein one, two, or three atoms of the heterocyclic ring system are independently selected from the group consisting of nitrogen, oxygen, and sulfur. In certain embodiments, at least one instance of $R^G$ is monocyclic heterocyclyl. In certain embodiments, at least one instance of $R^G$ is 3- to 7-membered, monocyclic heterocyclyl. In certain embodiments, at least one instance of $R^G$ is substituted or unsubstituted piperazinyl. In certain embodiments, at least one instance of $R^G$ is of the formula:

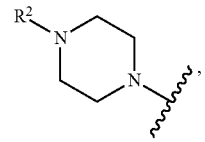

wherein $R^2$ is H, substituted or unsubstituted, $C_{1-6}$ alkyl, or a nitrogen protecting group. In certain embodiments, at least one instance of $R^G$ is of the formula:

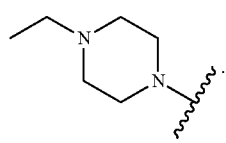 [SMILES: *N1CCN(CC)CC1]

In certain embodiments, at least one instance of $R^G$ is substituted aryl. In certain embodiments, at least one instance of $R^G$ is unsubstituted aryl. In certain embodiments, at least one instance of $R^G$ is 6- to 10-membered aryl. In certain embodiments, at least one instance of $R^G$ is substituted phenyl. In certain embodiments, at least one instance of $R^G$ is unsubstituted phenyl. In certain embodiments, at least one instance of $R^G$ is substituted heteroaryl. In certain embodiments, at least one instance of $R^G$ is unsubstituted heteroaryl. In certain embodiments, at least one instance of $R^G$ is heteroaryl, wherein one, two, three, or four atoms of the heteroaryl ring system are independently selected from the group consisting of nitrogen, oxygen, and sulfur. In certain embodiments, at least one instance of $R^G$ is monocyclic heteroaryl. In certain embodiments, at least one instance of $R^G$ is 5-membered, monocyclic heteroaryl. In certain embodiments, at least one instance of $R^G$ is 6-membered, monocyclic heteroaryl. In certain embodiments, at least one instance of $R^G$ is bicyclic heteroaryl, wherein the point of attachment may be on any atom of the bicyclic heteroaryl ring system, as valency permits. In certain embodiments, at least one instance of $R^G$ is 9- or 10-membered, bicyclic heteroaryl. In certain embodiments, at least one instance of $R^G$ is —$OR^a$. In certain embodiments, at least one instance of $R^G$ is —OH. In certain embodiments, at least one instance of $R^G$ is —O(substituted or unsubstituted, $C_{1-6}$ alkyl). In certain embodiments, at least one instance of $R^G$ is —O—$(CH_2)_{2-4}$—O-(substituted or unsubstituted, $C_{1-6}$ alkyl). In certain embodiments, at least one instance of $R^G$ is —O—$(CH_2)_2$—OMe. In certain embodiments, at least one instance of $R^G$ is —OMe. In certain embodiments, at least one instance of $R^G$ is —OEt. In certain embodiments, at least one instance of $R^G$ is OPr. In certain embodiments, at least one instance of $R^G$ is —OBu. In certain embodiments, at least one instance of $R^G$ is —OBn. In certain embodiments, at least one instance of $R^G$ is —OPh. In certain embodiments, at least one instance of $R^G$ is $SR^a$. In certain embodiments, at least one instance of $R^G$ is —SH. In certain embodiments, at least one instance of $R^G$ is —SMe. In certain embodiments, at least one instance of $R^G$ is —$N(R^a)_2$. In certain embodiments, at least one instance of $R^G$ is —$N(R^a)_2$, wherein each instance of $R^a$ is independently hydrogen, substituted or unsubstituted, $C_{1-6}$ alkyl, or a nitrogen protecting group, or two instances of $R^a$ are joined to form a substituted or unsubstituted, 3- to 7-membered, monocyclic heterocyclic ring. In certain embodiments, at least one instance of $R^G$ is —$NH_2$. In certain embodiments, at least one instance of $R^G$ is —NHMe. In certain embodiments, at least one instance of $R^G$ is —$NMe_2$. In certain embodiments, at least one instance of $R^G$ is —CN. In certain embodiments, at least one instance of $R^G$ is —SCN. In certain embodiments, at least one instance of $R^G$ is —C(=$NR^a$)$R^a$, —C(=$NR^a$)$OR^a$, or —C(=$NR^a$)$N(R^a)_2$. In certain embodiments, at least one instance of $R^G$ is —C(=O)$R^a$ or —C(=O)$OR^a$. In certain embodiments, at least one instance of $R^G$ is —C(=O)N$(R^a)_2$. In certain embodiments, at least one instance of $R^G$ is —C(=O)$NMe_2$, —C(=O)NHMe, or —C(=O)$NH_2$. In certain embodiments, at least one instance of $R^G$ is —$NO_2$. In certain embodiments, at least one instance of $R^G$ is —$NR^a$C(=O)$R^a$, —$NR^a$C(=O)$OR^a$, or —$NR^a$C(=O)N$(R^a)_2$. In certain embodiments, at least one instance of $R^G$ is —OC(=O)$R^a$, —OC(=O)$OR^a$, or —OC(=O)N$(R^a)_2$.

In certain embodiments, at least one instance of $R^G$ is —$OR^a$, —$N(R^a)_2$, or substituted or unsubstituted, 3- to 7-membered, monocyclic heterocyclyl, wherein one, two, or three atoms of the heterocyclic ring system are independently nitrogen, oxygen, or sulfur.

In certain embodiments, k is 0. In certain embodiments, k is 1. In certain embodiments, k is 2. In certain embodiments, k is 3. In certain embodiments, k is 4. In certain embodiments, k is 5.

In certain embodiments, k is 1; and $R^G$ is —$OR^a$, —$N(R^a)_2$, or substituted or unsubstituted, 3- to 7-membered, monocyclic heterocyclyl, wherein one, two, or three atoms of the heterocyclic ring system are independently nitrogen, oxygen, or sulfur. In certain embodiments, k is 1; and $R^G$ is —$OR^a$, —$N(R^a)_2$, or substituted or unsubstituted, 3- to 7-membered, monocyclic heterocyclyl, wherein one, two, or three atoms of the heterocyclic ring system are independently nitrogen, oxygen, or sulfur; and each instance of $R^a$ is independently H, substituted or unsubstituted, $C_{1-6}$ alkyl, an oxygen protecting group when attached to an oxygen atom, or a nitrogen protecting group when attached to a nitrogen group.

In certain embodiments, the compound of Formula (IV) is of the formula:

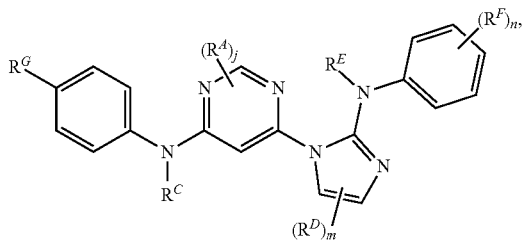

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

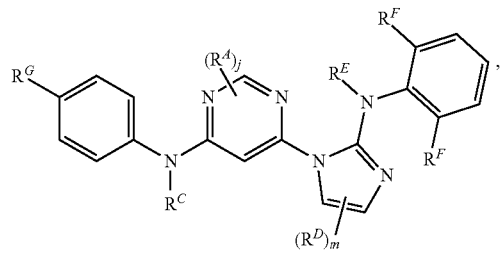

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

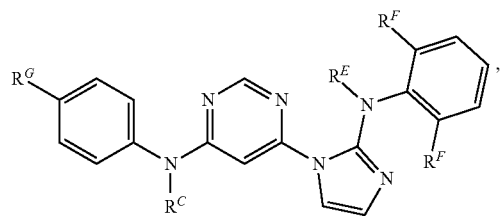

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

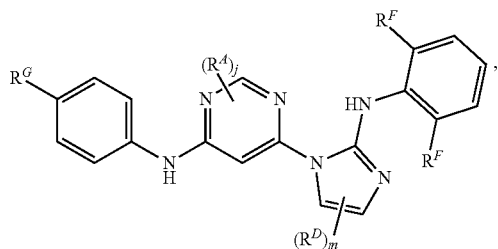

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

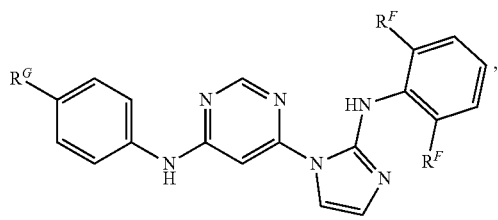

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of Formula (IV-B):

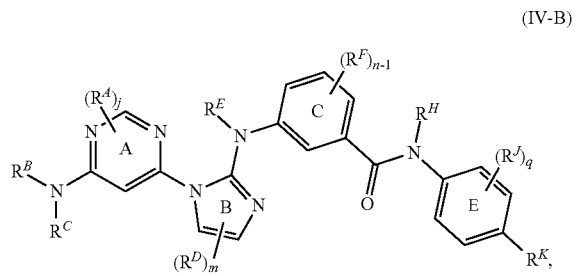

(IV-B)

or a pharmaceutically acceptable salt, solvate, hydrate, polymorph, co-crystal, tautomer, stereoisomer, isotopically labeled derivative, or prodrug thereof, wherein:

$R^H$ is hydrogen, substituted or unsubstituted acyl, substituted or unsubstituted, $C_{1-6}$ alkyl, or a nitrogen protecting group;

each instance of $R^J$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR1N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

q is 0, 1, 2, 3, or 4; and $R^K$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

In certain embodiments, a compound of Formula (IV) is of Formula (IV-B), wherein when $R^C$ is hydrogen, $R^B$ is not unsubstituted cyclopropyl or

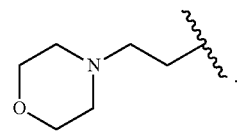 [SMILES: *CCN1CCOCC1]

Formula (IV-B) includes substituent $R^H$ on a nitrogen atom. In certain embodiments, $R^H$ is H. In certain embodiments, $R^H$ is not H. In certain embodiments, $R^H$ is substituted acyl. In certain embodiments, $R^H$ is unsubstituted acyl. In certain embodiments, $R^H$ is acetyl. In certain embodiments, $R^H$ is unsubstituted $C_{1-6}$ alkyl. In certain embodiments, $R^H$ is substituted $C_{1-6}$ alkyl. In certain embodiments, $R^H$ is $C_{1-6}$ alkyl substituted with at least one halogen. In certain embodiments, $R^H$ is unsubstituted methyl. In certain embodiments, $R^H$ is substituted methyl. In certain embodiments, $R^H$ is —CH$_2$F. In certain embodiments, $R^H$ is —CHF$_2$. In certain embodiments, $R^H$ is —CF$_3$. In certain embodiments, $R^H$ is ethyl. In certain embodiments, $R^H$ is propyl. In certain embodiments, $R^H$ is butyl. In certain embodiments, $R^H$ is pentyl. In certain embodiments, $R^H$ is hexyl. In certain embodiments, $R^H$ is Bn. In certain embodiments, $R^H$ is a nitrogen protecting group. In certain embodiments, $R^H$ is Bn, Boc, Cbz, Fmoc, trifluoroacetyl, triphenylmethyl, acetyl, or Ts. In certain embodiments, $R^H$ is hydrogen or unsubstituted, $C_{1-6}$ alkyl.

Formula (IV-B) includes as Ring E a phenyl ring that is substituted with $R^K$ and optionally one or more substituents $R^J$. In certain embodiments, Ring E is of the formula:

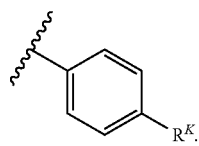

In certain embodiments, Ring E is of the formula:

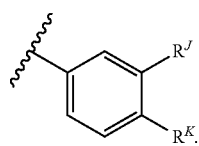

In certain embodiments, Ring E is of the formula:

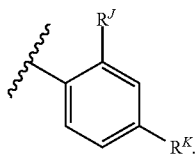

In certain embodiments, Ring E is of the formula:

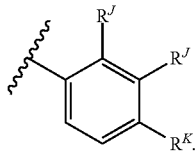

In certain embodiments, Ring E is of the formula:

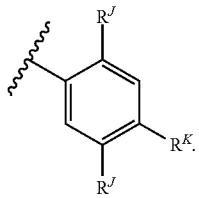

In certain embodiments, Ring E is of the formula:

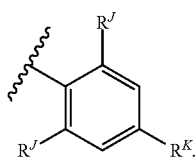

In certain embodiments, Ring E is of the formula:

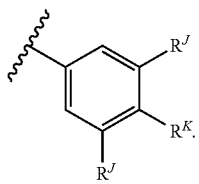

In certain embodiments, $R^K$ is H. In certain embodiments, $R^K$ is halogen. In certain embodiments, $R^K$ is F. In certain embodiments, $R^K$ is Cl. In certain embodiments, $R^K$ is Br. In certain embodiments, $R^K$ is I (iodine). In certain embodiments, $R^K$ is substituted alkyl. In certain embodiments, $R^K$ is unsubstituted alkyl. In certain embodiments, $R^K$ is unsubstituted $C_{1-6}$ alkyl. In certain embodiments, $R^K$ is substituted $C_{1-6}$ alkyl. In certain embodiments, $R^K$ is $C_{1-6}$ alkyl substituted with at least one halogen. In certain embodiments, $R^K$ is —$CH_3$. In certain embodiments, $R^K$ is substituted methyl. In certain embodiments, $R^K$ is —$CH_2F$. In certain embodiments, $R^K$ is —$CHF_2$. In certain embodiments, $R^K$ is —$CF_3$. In certain embodiments, $R^K$ is ethyl. In certain embodiments, $R^K$ is propyl. In certain embodiments, $R^K$ is butyl. In certain embodiments, $R^K$ is pentyl. In certain embodiments, $R^K$ is hexyl. In certain embodiments, $R^K$ is Bn. In certain embodiments, $R^K$ is substituted alkenyl. In certain embodiments, $R^K$ is unsubstituted alkenyl. In certain embodiments, $R^K$ is substituted alkynyl. In certain embodiments, $R^K$ is unsubstituted alkynyl. In certain embodiments, $R^K$ is substituted carbocyclyl. In certain embodiments, $R^K$ is unsubstituted carbocyclyl. In certain embodiments, $R^K$ is saturated carbocyclyl. In certain embodiments, $R^K$ is unsaturated carbocyclyl. In certain embodiments, $R^K$ is monocyclic carbocyclyl. In certain embodiments, $R^K$ is 3- to 7-membered, monocyclic carbocyclyl. In certain embodiments, $R^K$ is substituted heterocyclyl. In certain embodiments, $R^K$ is unsubstituted heterocyclyl. In certain embodiments, $R^K$ is saturated heterocyclyl. In certain embodiments, $R^K$ is unsaturated heterocyclyl. In certain embodiments, $R^K$ is heterocyclyl, wherein one, two, or three atoms of the heterocyclic ring system are independently selected from the group consisting of nitrogen, oxygen, and sulfur. In certain embodiments, $R^K$ is monocyclic heterocyclyl. In certain embodiments, $R^K$ is 3- to 7-membered, monocyclic heterocyclyl. In certain embodiments, $R^K$ is substituted aryl. In certain embodiments, $R^K$ is unsubstituted aryl. In certain embodiments, $R^K$ is 6- to 10-membered aryl. In certain embodiments, $R^K$ is substituted phenyl. In certain embodiments, $R^K$ is unsubstituted phenyl. In certain embodiments, $R^K$ is substituted heteroaryl. In certain embodiments, $R^K$ is unsubstituted heteroaryl. In certain embodiments, $R^K$ is heteroaryl, wherein one, two, three, or four atoms of the heteroaryl ring system are independently selected from the group consisting of nitrogen, oxygen, and sulfur. In certain embodiments, $R^K$ is monocyclic heteroaryl. In certain embodiments, $R^K$ is 5-membered, monocyclic heteroaryl. In certain embodiments, $R^K$ is not substituted imidazolyl. In certain embodiments, $R^K$ is 6-membered, monocyclic heteroaryl. In certain embodiments, $R^K$ is bicyclic heteroaryl, wherein the point of attachment may be on any atom of the bicyclic heteroaryl ring system, as valency permits. In certain embodiments, $R^K$ is 9- or 10-membered, bicyclic heteroaryl. In certain embodiments, $R^K$ is —$OR^a$. In certain embodiments, $R^K$ is —OH. In certain embodiments, $R^K$ is —O(substituted or unsubstituted, $C_{1-6}$ alkyl). In certain embodiments, $R^K$ is —OMe. In certain embodiments, $R^K$ is —OEt. In certain embodiments, $R^K$ is —OPr. In certain embodiments, $R^K$ is —OBu. In certain embodiments, $R^K$ is —OBn. In certain embodiments, $R^K$ is —OPh. In certain embodiments, $R^K$ is —$SR^a$. In certain embodiments, $R^K$ is —SH. In certain embodiments, $R^K$ is —SMe. In certain embodiments, $R^K$ is —$N(R^a)_2$. In certain embodiments, $R^K$ is —$NH_2$. In certain embodiments, $R^K$ is —NHMe. In certain embodiments, $R^K$ is —$NMe_2$. In certain embodiments, $R^K$ is —CN. In certain embodiments, $R^K$ is —SCN. In certain embodiments, $R^K$ is —C(=$NR^a$)$R^a$, —C(=$NR^a$)$OR^a$, or —C(=$NR^a$)$N(R^a)_2$. In certain embodiments, $R^K$ is —C(=O)$R^a$ or —C(=O)$OR^a$. In certain embodiments, $R^K$ is —C(=O)$N(R^a)_2$. In certain embodiments, $R^K$ is —C(=O)$NMe_2$, —C(=O)NHMe, or —C(=O)$NH_2$. In certain embodiments, $R^K$ is —$NO_2$. In certain embodiments, $R^K$ is —$NR^aC$(=O)$R^a$, —$NR^aC$(=O)$OR^a$, or —$NR^aC$(=O)$N(R^a)_2$. In certain embodiments, $R^K$ is —OC(=O)$R^a$, —OC(=O)$OR^a$, or —OC(=O)$N(R^a)_2$.

In certain embodiments, $R^K$, is —$(CH_2)_{1-3}$-(Ring G), wherein Ring G is a substituted or unsubstituted, 3- to 7-membered, monocyclic heterocyclic ring. In certain embodiments, $R^K$ is —$(CH_2)_{1-3}$-(substituted or unsubstituted piperazinyl). In certain embodiments, $R^K$ is of the formula:

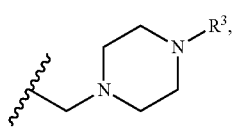

wherein R³ is H, substituted or unsubstituted, C₂₋₆ alkyl, substituted methyl, or a nitrogen protecting group. In certain embodiments, $R^K$ is of the formula:

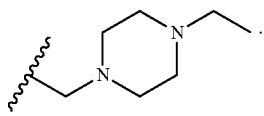 [SMILES: *CN1CCN(CC)CC1]

In certain embodiments, $R^K$ is not of the formula:

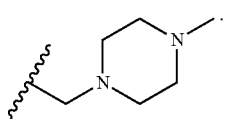 [SMILES: *CN1CCN(C)CC1]

In certain embodiments, $R^K$ is —(CH₂)₁₋₃-(Ring G), wherein Ring G is a substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, or substituted or unsubstituted morpholinyl ring.

Ring E of Formula (IV-B) may include one or more substituents $R^J$. In certain embodiments, at least two instances of $R^J$ are different. In certain embodiments, all instances of $R^J$ are the same. In certain embodiments, at least one instance of $R^J$ is halogen. In certain embodiments, at least one instance of $R^J$ is F. In certain embodiments, at least one instance of $R^J$ is Cl. In certain embodiments, at least one instance of $R^J$ is Br. In certain embodiments, at least one instance of $R^J$ is I (iodine). In certain embodiments, at least one instance of $R^J$ is substituted alkyl. In certain embodiments, at least one instance of $R^J$ is unsubstituted alkyl. In certain embodiments, at least one instance of $R^J$ is unsubstituted $C_{1-6}$ alkyl. In certain embodiments, all instances of $R^J$ are unsubstituted $C_{1-6}$ alkyl. In certain embodiments, at least one instance of $R^J$ is substituted $C_{1-6}$ alkyl. In certain embodiments, at least one instance of $R^J$ is $C_{1-6}$ alkyl substituted with at least one halogen. In certain embodiments, at least one instance of $R^J$ is —CH₃. In certain embodiments, all instances of $R^J$ are —CH₃. In certain embodiments, at least one instance of $R^J$ is substituted methyl. In certain embodiments, at least one instance of $R^J$ is —CH₂F. In certain embodiments, at least one instance of $R^J$ is —CHF₂. In certain embodiments, at least one instance of $R^J$ is —CF₃. In certain embodiments, at least one instance of $R^J$ is ethyl. In certain embodiments, at least one instance of $R^J$ is propyl. In certain embodiments, at least one instance of $R^J$ is butyl. In certain embodiments, at least one instance of $R^J$ is pentyl. In certain embodiments, at least one instance of $R^J$ is hexyl. In certain embodiments, at least one instance of $R^J$ is Bn. In certain embodiments, at least one instance of $R^J$ is halogen or substituted or unsubstituted, $C_{1-6}$ alkyl. In certain embodiments, at least one instance of $R^J$ is substituted alkenyl. In certain embodiments, at least one instance of $R^J$ is unsubstituted alkenyl. In certain embodiments, at least one instance of $R^J$ is substituted alkynyl. In certain embodiments, at least one instance of $R^J$ is unsubstituted alkynyl. In certain embodiments, at least one instance of $R^J$ is substituted carbocyclyl. In certain embodiments, at least one instance of $R^J$ is unsubstituted carbocyclyl. In certain embodiments, at least one instance of $R^J$ is saturated carbocyclyl. In certain embodiments, at least one instance of $R^J$ is unsaturated carbocyclyl. In certain embodiments, at least one instance of $R^J$ is monocyclic carbocyclyl. In certain embodiments, at least one instance of $R^J$ is 3- to 7-membered, monocyclic carbocyclyl. In certain embodiments, at least one instance of $R^J$ is substituted heterocyclyl. In certain embodiments, at least one instance of $R^J$ is unsubstituted heterocyclyl. In certain embodiments, at least one instance of $R^J$ is saturated heterocyclyl. In certain embodiments, at least one instance of $R^J$ is unsaturated heterocyclyl. In certain embodiments, at least one instance of $R^J$ is heterocyclyl, wherein one, two, or three atoms of the heterocyclic ring system are independently selected from the group consisting of nitrogen, oxygen, and sulfur. In certain embodiments, at least one instance of $R^J$ is monocyclic heterocyclyl. In certain embodiments, at least one instance of $R^J$ is 3- to 7-membered, monocyclic heterocyclyl. In certain embodiments, at least one instance of $R^J$ is substituted aryl. In certain embodiments, at least one instance of $R^J$ is unsubstituted aryl. In certain embodiments, at least one instance of $R^J$ is 6- to 10-membered aryl. In certain embodiments, at least one instance of $R^J$ is substituted phenyl. In certain embodiments, at least one instance of $R^J$ is unsubstituted phenyl. In certain embodiments, at least one instance of $R^J$ is substituted heteroaryl. In certain embodiments, at least one instance of $R^J$ is unsubstituted heteroaryl. In certain embodiments, at least one instance of $R^J$ is heteroaryl, wherein one, two, three, or four atoms of the heteroaryl ring system are independently selected from the group consisting of nitrogen, oxygen, and sulfur. In certain embodiments, at least one instance of $R^J$ is monocyclic heteroaryl. In certain embodiments, at least one instance of $R^J$ is 5-membered, monocyclic heteroaryl. In certain embodiments, no instance of $R^J$ is substituted imidazolyl. In certain embodiments, at least one instance of $R^J$ is 6-membered, monocyclic heteroaryl. In certain embodiments, at least one instance of $R^J$ is bicyclic heteroaryl, wherein the point of attachment may be on any atom of the bicyclic heteroaryl ring system, as valency permits. In certain embodiments, at least one instance of $R^J$ is 9- or 10-membered, bicyclic heteroaryl. In certain embodiments, at least one instance of $R^J$ is —OR$^a$. In certain embodiments, at least one instance of $R^J$ is —OH. In certain embodiments, at least one instance of $R^J$ is —O(substituted or unsubstituted, $C_{1-6}$ alkyl). In certain embodiments, at least one instance of $R^J$ is —OMe. In certain embodiments, at least one instance of $R^J$ is —OEt. In certain embodiments, at least one instance of $R^J$ is —OPr. In certain embodiments, at least one instance of $R^J$ is —OBu. In certain embodiments, at least one instance of $R^a$ is —OBn. In certain embodiments, at least one instance of $R^J$ is —OPh. In certain embodiments, at least one instance of $R^J$ is —SR$^a$. In certain embodiments, at least one instance of $R^J$ is —SH. In certain embodiments, at least one instance of $R^J$ is —SMe. In certain embodiments, at least one instance of $R^J$ is —N(R$^a$)₂. In certain embodiments, at least one instance of $R^J$ is —NH₂. In certain embodiments, at least one instance of $R^J$ is —NHMe. In certain embodiments, at least one instance of $R^J$ is —NMe₂. In certain embodiments, at least one instance of $R^J$ is —CN. In certain embodiments, at least one instance of $R^J$ is —SCN. In certain embodiments, at least one instance of $R^J$ is —C(=NR$^a$)R$^a$, —C(=NR$^a$)OR$^a$, or —C(=NR$^a$)N(R$^a$)$_2$. In certain embodiments, at least one instance of $R^J$ is —C(=O)R$^a$ or —C(=O)OR$^a$. In certain embodiments, at least one instance of $R^J$ is —C(=O)N(R$^a$)$_2$. In certain embodiments, at least one instance of $R^J$ is —C(=O)NMe$_2$, —C(=O)NHMe, or —C(=O)NH$_2$. In certain embodiments, at least one instance of $R^J$ is —NO$_2$. In certain embodiments, at least one instance of $R^J$ is —NR$^a$C(=O)R$^a$, —NR$^a$C(=O)OR$^a$, or —NR$^a$C(=O)N(R$^a$)$_2$. In certain embodiments, at least one instance of $R^J$ is —OC(=O)R$^a$, —OC(=O)OR$^a$, or —OC(=O)N(R$^a$)$_2$.

In certain embodiments, at least one instance of $R^J$ is halogen or substituted or unsubstituted, $C_{1-6}$ alkyl. In certain embodiments, at least one instance of $R^a$ is halogen, unsubstituted $C_{1-6}$ alkyl, or $C_{1-6}$ alkyl substituted with at least one halogen.

In certain embodiments, q is 0. In certain embodiments, q is 1. In certain embodiments, q is 2. In certain embodiments, q is 3. In certain embodiments, q is 4.

In certain embodiments, no instance of $R^J$ and $R^K$ is substituted or unsubstituted heteroaryl. In certain embodiments, no instance of $R^J$ and $R^K$ is substituted or unsubstituted imidazolyl. In certain embodiments, no instance of $R^J$ and $R^K$ is substituted imidazolyl.

In certain embodiments, the compound of Formula (IV) is of the formula:

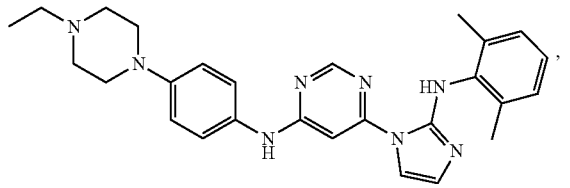
(IV-1 or HG-10-7-01)

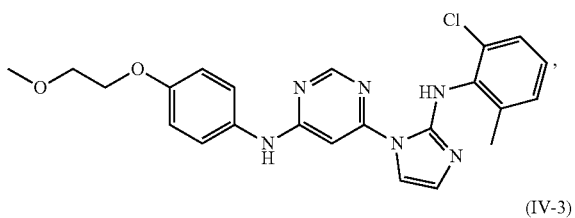
(IV-2)

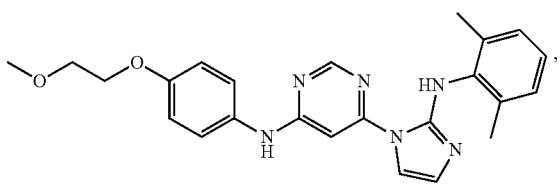
(IV-3)

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

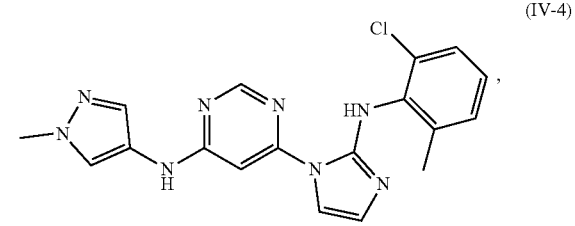 [SMILES: Cc1cccc(Cl)c1Nc1nccn1-c1cc(Nc2cnn(C)c2)ncn1]
(IV-4)

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

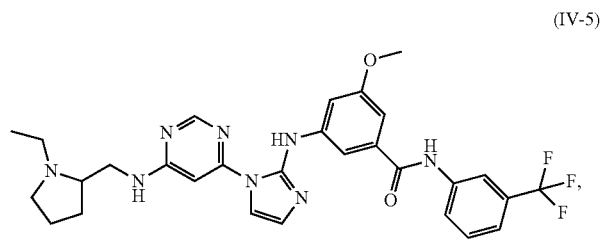
(IV-5)

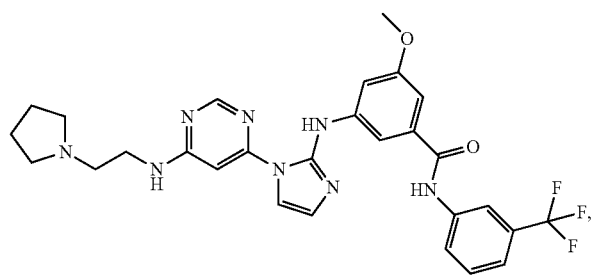
(IV-6)

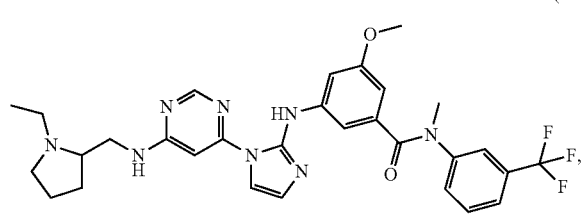
(IV-7)

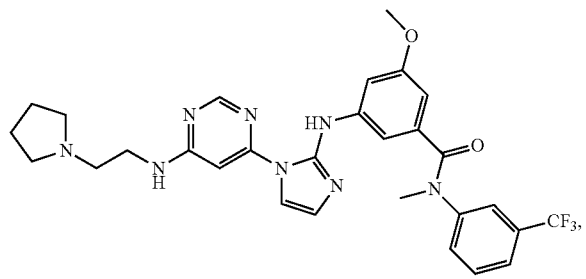
(IV-8)

-continued

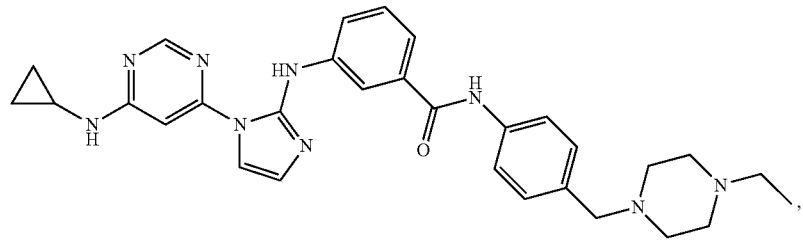
(IV-9)

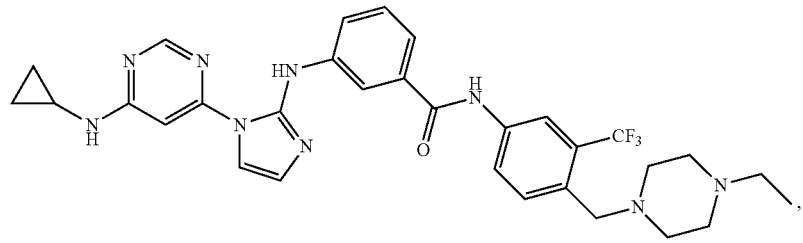
(IV-10)

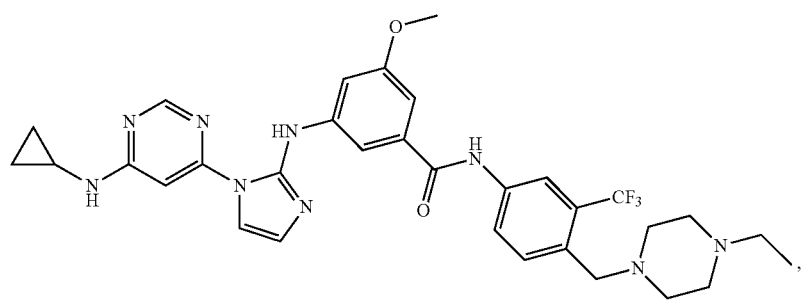
(IV-11)

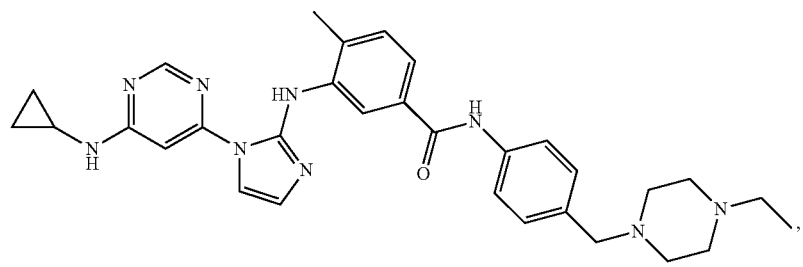
(IV-12)

or a pharmaceutically acceptable salt, solvate, hydrate, polymorph, co-crystal, tautomer, stereoisomer, isotopically labeled derivative, or prodrug thereof.

In certain embodiments, a compound of Formula (IV) is HG-10-7-01, or a pharmaceutically acceptable salt, solvate, hydrate, polymorph, co-crystal, tautomer, stereoisomer, isotopically labeled derivative, or prodrug thereof.

In certain embodiments, a compound of Formula (IV) is not of the formula:

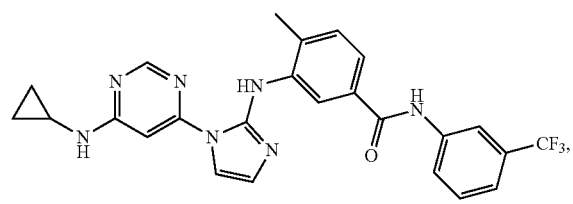

-continued
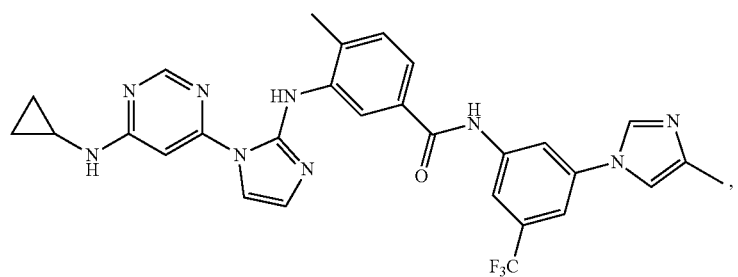
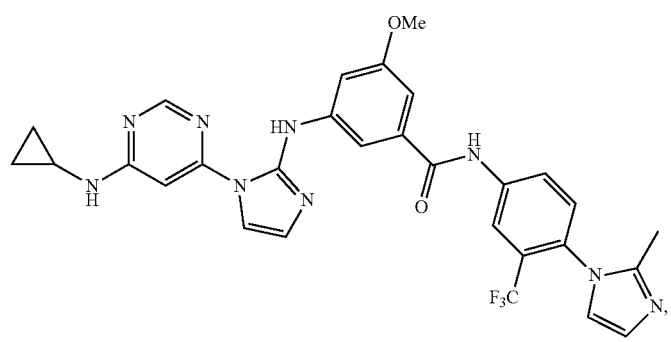
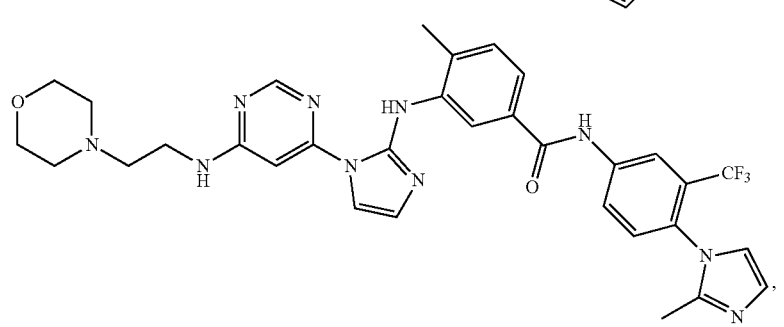
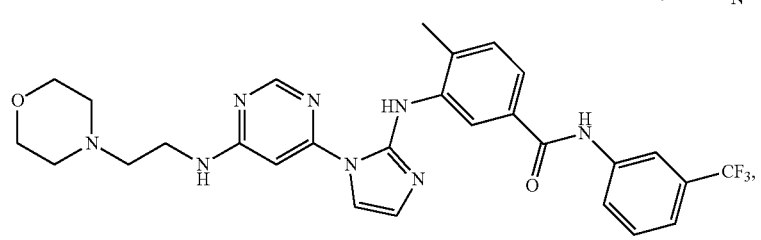
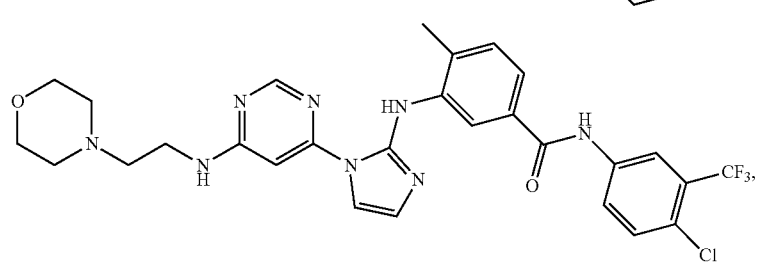
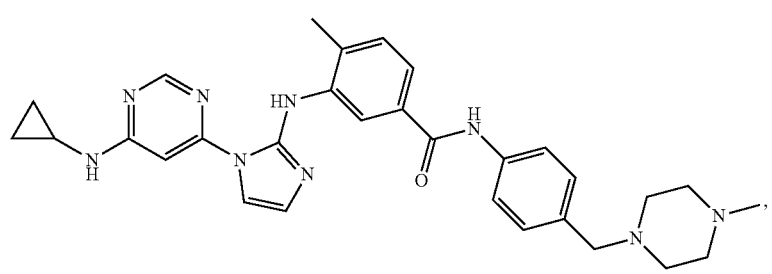

-continued

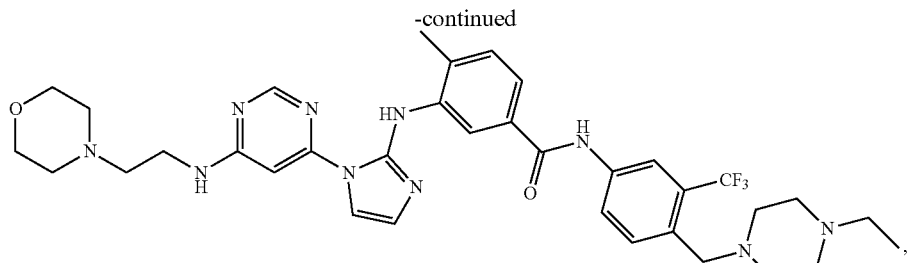

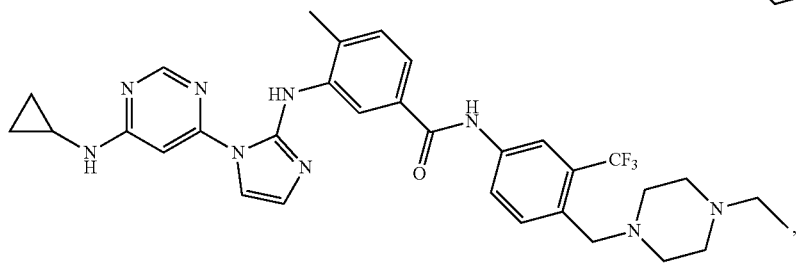

or a pharmaceutically acceptable salt, solvate, hydrate, polymorph, co-crystal, or tautomer thereof.

Compounds of Formula (V)

In another aspect, the present disclosure provides urea or carbamate compounds of Formula (V) for use in the present invention:

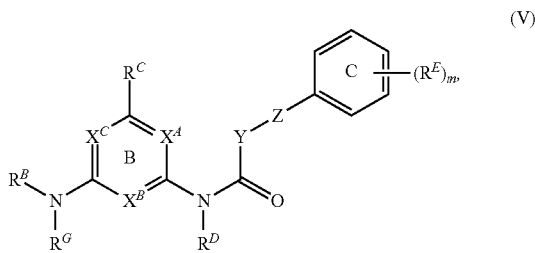

(V)

and pharmaceutically acceptable salts, solvates, hydrates, polymorphs, co-crystals, tautomers, stereoisomers, isotopically labeled derivatives, and prodrugs thereof, wherein:

$R^G$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, or of the formula:

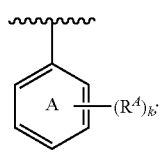

each instance of $R^A$ is independently halogen, substituted or unsubstituted alkyl, substituted or unsubstituted alkenyl, substituted or unsubstituted alkynyl, substituted or un substituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$, or two $R^A$ groups are joined to form a substituted or unsubstituted carbocyclic ring, substituted or unsubstituted heterocyclic ring, substituted or unsubstituted aryl ring, or substituted or unsubstituted heteroaryl ring;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to focus a substituted or unsubstituted heterocyclic or substituted or unsubstituted heteroaryl ring;

k is 0, 1, 2, 3, 4, or 5;

$R^B$ is hydrogen, substituted or unsubstituted acyl, substituted or unsubstituted, $C_{1-6}$ alkyl, or a nitrogen protecting group;

each of $X^A$, $X^B$, and $X^C$ is independently N or $CR^X$, wherein each instance of $R^X$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

or: $X^B$ is $CR^X$, and $R^G$ and $R^X$ of $X^B$ are joined to form a substituted or unsubstituted heterocyclic or substituted or unsubstituted heteroaryl ring;

$R^C$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^D$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

Y is —O— or —NR$^Y$—, wherein R$^Y$ is hydrogen, substituted or unsubstituted acyl, substituted or unsubstituted, C$_{1-6}$ alkyl, or a nitrogen protecting group;

Z is a bond or —C(R$^Z$)$_2$—, wherein each instance of R$^Z$ is independently hydrogen, halogen, or substituted or unsubstituted, C$_{1-6}$ alkyl; each instance of R$^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or un substituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, or —OC(=O)N(R$^a$)$_2$; and m is 0, 1, 2, 3, 4, or 5.

Unless expressly provided otherwise, the moieties and variables described in the subsection Compounds of Formula (V) apply only to Formula (V). The moieties and variables included but not described in detail in the subsection Compounds of Formula (V) are as described in detail in other subsections.

In certain embodiments, a compound of Formula (V) is of Formula (V-A):

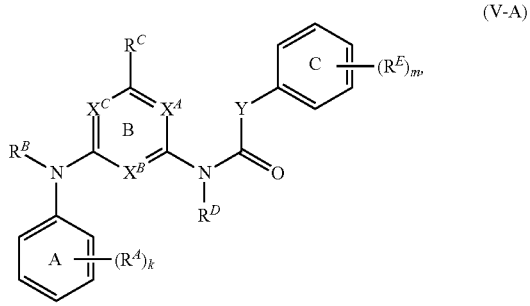

(V-A)

or a pharmaceutically acceptable salt, solvate, hydrate, polymorph, co-crystal, tautomer, stereoisomer, isotopically labeled derivative, or prodrug thereof, wherein:

each instance of R$^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^a$ groups are joined to focus a substituted or un substituted heterocyclic or substituted or unsubstituted heteroaryl ring;

k is 0, 1, 2, 3, 4, or 5;

R$^B$ is hydrogen, substituted or unsubstituted acyl, substituted or unsubstituted, C$_{1-6}$ alkyl, or a nitrogen protecting group;

each of X$^A$, X$^B$, and X$^C$ is independently N or CR$^X$, wherein each instance of R$^X$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^C$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^D$ is hydrogen, substituted or unsubstituted alkyl, substituted or unsubstituted alkenyl, substituted or un substituted alkynyl, substituted or unsubstituted carbocyclyl, substituted or unsubstituted heterocyclyl, substituted or unsubstituted aryl, substituted or unsubstituted heteroaryl, or a nitrogen protecting group;

Y is —O— or —NR$^Y$—, wherein R$^Y$ is hydrogen, substituted or unsubstituted acyl, substituted or unsubstituted, C$_{1-6}$ alkyl, or a nitrogen protecting group;

each instance of R$^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and m is 0, 1, 2, 3, 4, or 5.

Formula (V) includes substituent R$^G$. In certain embodiments, R$^G$ is hydrogen. In certain embodiments, R$^G$ is substituted or unsubstituted alkyl. In certain embodiments, R$^G$ is substituted C$_{1-6}$ alkyl (e.g., —CF$_3$, perfluoroethyl, perfluoropropyl, perfluorobutyl, Bn, or C$_{1-6}$ alkyl substituted with at least one instance of halogen and/or —OR$^a$)). In certain embodiments, R$^G$ is C$_{1-6}$ alkyl substituted with at least one instance of —OR$^a$, optionally wherein R$^a$ is hydrogen or substituted or unsubstituted, C$_{1-6}$ alkyl. In certain embodiments, R$^G$ is of the formula:

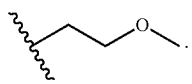 [SMILES: *CCOC]

In certain embodiments, $R^G$ is unsubstituted $C_{1-6}$ alkyl (e.g., Me, Et, Pr, or Bu). In certain embodiments, $R^G$ is substituted or unsubstituted alkenyl (e.g., substituted or unsubstituted, $C_{1-6}$ alkenyl). In certain embodiments, $R^G$ is substituted or unsubstituted alkynyl (e.g., substituted or unsubstituted, $C_{1-6}$ alkynyl). In certain embodiments, $R^G$ is substituted or unsubstituted carbocyclyl (e.g., substituted or unsubstituted, monocyclic, 3- to 7-membered carbocyclyl). In certain embodiments, $R^G$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^G$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^G$ is substituted or unsubstituted 2-pyridyl. In certain embodiments, $R^G$ is substituted or unsubstituted 3-pyridyl. In certain embodiments, $R^G$ is of the formula:

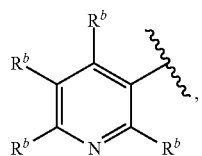

wherein $R^a$ is hydrogen, halogen, substituted or unsubstituted, $C_{1-6}$ alkyl, —OH, —O(substituted or unsubstituted, $C_{1-6}$ alkyl), or substituted or unsubstituted, monocyclic, 5- to 6-membered heterocyclyl, wherein one, two, or three atoms in the heterocyclic ring system are independently nitrogen, oxygen, or sulfur; and each instance of $R^b$ is independently hydrogen, halogen, substituted or unsubstituted, $C_{1-6}$ alkyl, —OH, or —O(substituted or unsubstituted, $C_{1-6}$ alkyl). In certain embodiments, $R^G$ is of the formula:

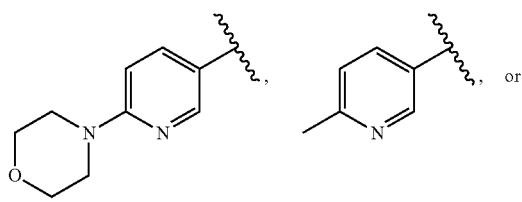

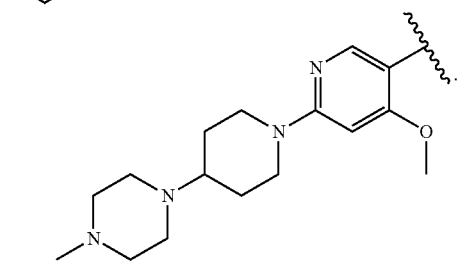

In certain embodiments, $R^G$ is substituted or unsubstituted 4-pyridyl. In certain embodiments, $R^G$ is substituted or unsubstituted 1-pyrazolyl. In certain embodiments, $R^G$ is substituted or unsubstituted 3-pyrazolyl. In certain embodiments, $R^G$ is substituted or unsubstituted 4-pyrazolyl. In certain embodiments, $R^G$ is of the formula:

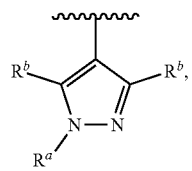

wherein $R^a$ is hydrogen, substituted or unsubstituted, $C_{1-6}$ alkyl, a nitrogen protecting group, or -(substituted or unsubstituted, $C_{1-6}$ alkylene)-(substituted or unsubstituted, monocyclic, 5- to 6-membered heterocyclyl, wherein one, two, or three atoms in the heterocyclic ring system are independently nitrogen, oxygen, or sulfur); and each instance of $R^b$ is independently hydrogen, halogen, substituted or unsubstituted, $C_{1-6}$ alkyl, —OH, or —O(substituted or unsubstituted, $C_{1-6}$ alkyl). In certain embodiments, $R^G$ is of the formula:

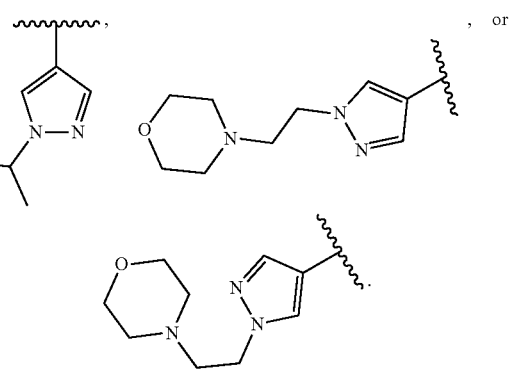

In certain embodiments, $R^G$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, substituted or unsubstituted isothiazolyl, or substituted or unsubstituted tetrazolyl. In certain embodiments, $R^G$ is substituted or unsubstituted pyrazinyl, substituted or unsubstituted pyrimidinyl, or substituted or unsubstituted pyridazinyl. In certain embodiments, $R^G$ is substituted or unsubstituted, bicyclic, 9- to 10-membered heteroaryl, wherein one, two, three, or four atoms in the heteroaryl ring system are independently nitrogen, oxygen, or sulfur.

In certain embodiments, $R^G$ is of the formula:

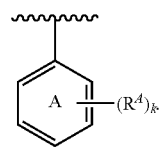

Ring A is unsubstituted (e.g., when k is 0) or substituted with one or more substituents $R^A$ (e.g., when k is 1, 2, 3, 4, or 5). In certain embodiments, Ring A is an unsubstituted phenyl ring. In certain embodiments, Ring A is a substituted phenyl ring. In certain embodiments, Ring A is of the formula:

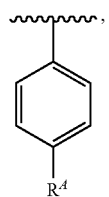

optionally wherein $R^A$ is substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

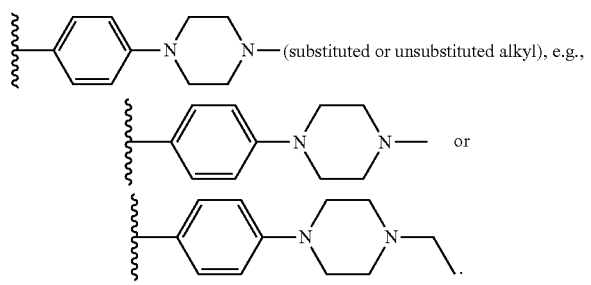

In certain embodiments, Ring A is of the formula:

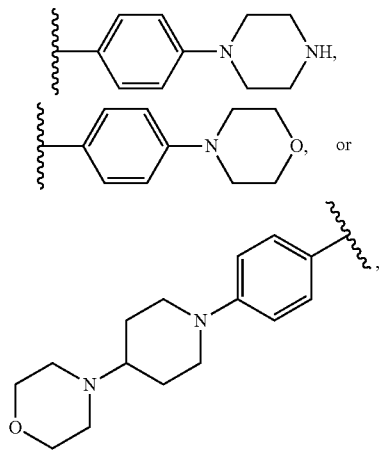

In certain embodiments, Ring A is of the formula:

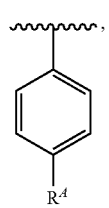

optionally wherein $R^A$ is halogen, substituted or unsubstituted, $C_{1-6}$ alkyl, or —$OR^a$. In certain embodiments, Ring A is of the formula:

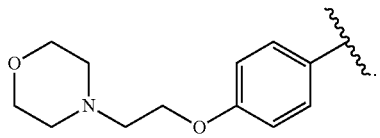 [SMILES: *c1ccc(OCCN2CCOCC2)cc1]

In certain embodiments, Ring A is of the formula:

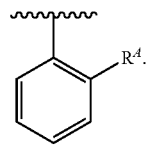

In certain embodiments, Ring A is of the formula:

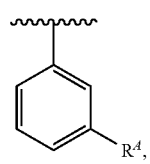

optionally wherein $R^A$ is halogen, substituted or unsubstituted, $C_{1-6}$ alkyl, or —$OR^a$. In certain embodiments, Ring A is of the formula:

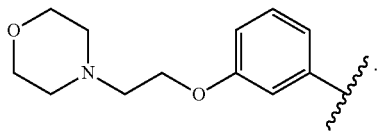 [SMILES: *c1cccc(OCCN2CCOCC2)c1]

In certain embodiments, Ring A is of the formula:

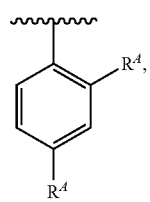

optionally wherein each instance of $R^A$ is independently halogen, substituted or unsubstituted, $C_{1-6}$ alkyl, —$OR^a$, —C(=O)$R^a$, —C(=O)O$R^a$, —C(=O)N($R^a$)$_2$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

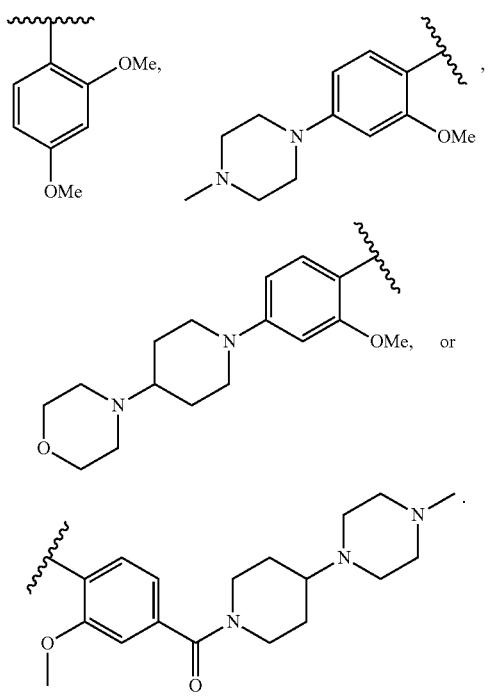

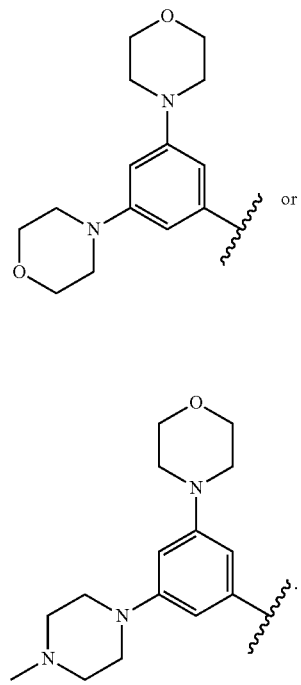

In certain embodiments, Ring A is of the formula:

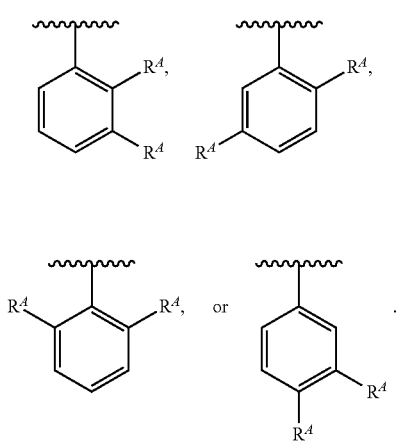

In certain embodiments, Ring A is of the formula:

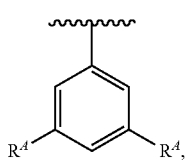

optionally wherein each instance of $R^A$ is independently halogen, substituted or unsubstituted, $C_{1-6}$ alkyl, —$OR^a$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

In certain embodiments, Ring A is of the formula:

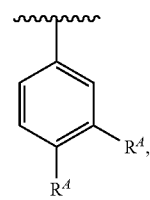

wherein the two instances of $R^A$ are joined to form a substituted or unsubstituted carbocyclic ring (e.g., substituted or unsubstituted, 3- to 7-membered, monocyclic carbocyclic ring), substituted or unsubstituted heterocyclic ring (e.g., substituted or unsubstituted, monocyclic, 5- to 6-membered heterocyclic ring, wherein one or two atoms in the heterocyclic ring system are independently nitrogen, oxygen, or sulfur), substituted or unsubstituted aryl ring (e.g., substituted or unsubstituted phenyl ring), or substituted or unsubstituted heteroaryl ring (e.g., substituted or unsubstituted, monocyclic, 5- to 6-membered heteroaryl ring, wherein one or two atoms in the heteroaryl ring system are independently nitrogen, oxygen, or sulfur). In certain embodiments, Ring A is of the formula:

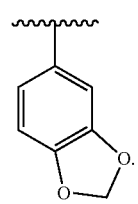

In certain embodiments, Ring A is of the formula:

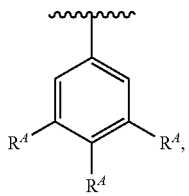

optionally wherein each instance of $R^A$ is independently halogen, substituted or unsubstituted, $C_{1-6}$ alkyl, —$OR^a$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

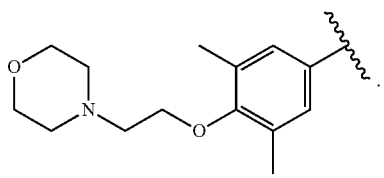 [SMILES: *c1cc(C)c(OCCN2CCOCC2)c(C)c1]

In certain embodiments, Ring A is of the formula:

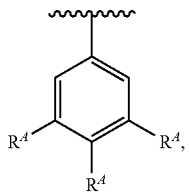

wherein each instance of $R^A$ is independently —$OR^a$. In certain embodiments, Ring A is of the formula:

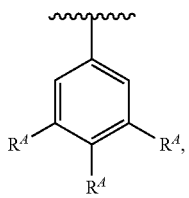

wherein each instance of $R^A$ is independently —O(substituted or unsubstituted alkyl). In certain embodiments, Ring A is of the formula:

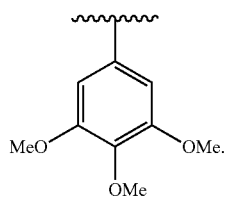

In certain embodiments, Ring A is of the formula:

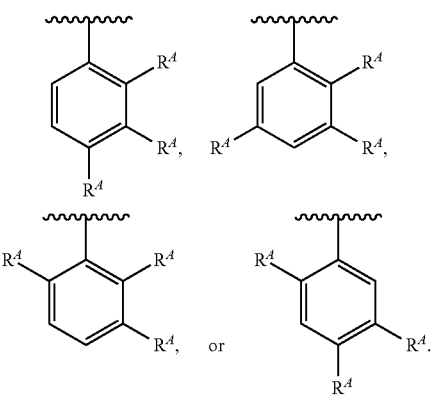

In Formula (V), Ring A may include one or more substituents $R^A$. In certain embodiments, all instances of $R^A$ are the same. In certain embodiments, at least two instances of $R^A$ are different. In certain embodiments, at least one instance of $R^A$ is halogen (e.g., F, Cl, Br, or I). In certain embodiments, at least one instance of $R^A$ is substituted or unsubstituted alkyl (e.g., substituted or unsubstituted, $C_{1-6}$ alkyl). In certain embodiments, at least one instance of $R^A$ is —$CH_3$. In certain embodiments, at least one instance of $R^A$ is $CF_3$, unsubstituted ethyl, perfluoroethyl, unsubstituted propyl, perfluoropropyl, unsubstituted butyl, perfluorobutyl, or Bn. In certain embodiments, at least one instance of $R^A$ is substituted or unsubstituted alkenyl (e.g., substituted or unsubstituted, $C_{1-6}$ alkenyl). In certain embodiments, at least one instance of $R^A$ is substituted or unsubstituted alkynyl (e.g., substituted or unsubstituted, $C_{1-6}$ alkynyl). In certain embodiments, at least one instance of $R^A$ is substituted or unsubstituted carbocyclyl (e.g., substituted or unsubstituted, monocyclic, 3- to 7-membered carbocyclyl). In certain embodiments, at least one instance of $R^A$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^A$ is of the formula:

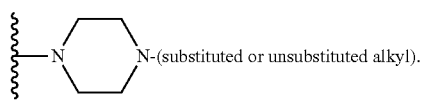

In certain embodiments, at least one instance of $R^A$ is of the formula:

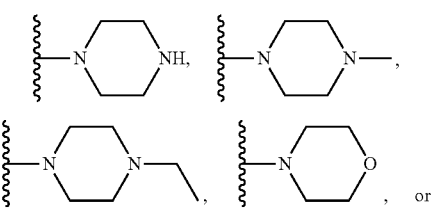

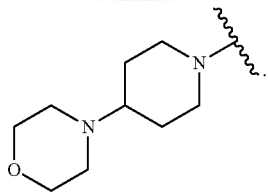

In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted phenyl. In certain embodiments, at least one instance of $R^A$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^A$ is —$OR^a$. In certain embodiments, at least one instance of $R^A$ is —OH. In certain embodiments, at least one instance of $R^A$ is —O(substituted or unsubstituted alkyl), such as —O(substituted or unsubstituted, $C_{1-6}$ alkyl) (e.g., —OMe, —OEt, —OPr, —OBu, —OBn, or

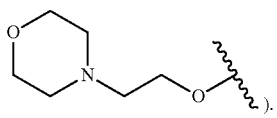 [SMILES: *OCCN1CCOCC1]

).

In certain embodiments, at least one instance of $R^A$ is —O(substituted or unsubstituted phenyl) (e.g., —OPh)). In certain embodiments, at least one instance of $R^A$ is —$SR^a$ (e.g., —SH, —S(substituted or unsubstituted, $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^A$ is —$N(R^a)_2$ (e.g., —$NH_2$, —NH(substituted or unsubstituted, $C_{1-6}$ alkyl) (e.g., —NHMe), or —N(substituted or unsubstituted, $C_{1-6}$ alkyl)-(substituted or unsubstituted, $C_{1-6}$ alkyl) (e.g., —$NMe_2$)). In certain embodiments, at least one instance of $R^A$ is —CN, —SCN, or —$NO_2$. In certain embodiments, at least one instance of $R^A$ is —C(=$NR^a$)$R^a$, —C(=$NR^a$)$OR^a$, or —C(=$NR^a$)$N(R^a)_2$. In certain embodiments, at least one instance of $R^A$ is —C(=O)$R^a$ or —C(=O)$OR^a$. In certain embodiments, at least one instance of $R^A$ is —C(=O)$N(R^a)_2$ (e.g., —C(=O)$NH_2$, —C(=O)NHMe, —C(=O)$NMe_2$, or

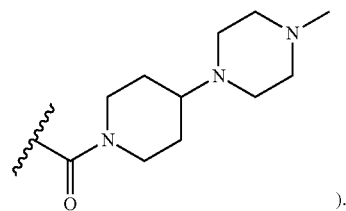 [SMILES: *C(=O)N1CCC(N2CCN(C)CC2)CC1]

).

In certain embodiments, at least one instance of $R^A$ is —$NR^a$C(=O)$R^a$, —$NR^a$C(=O)$OR^a$, or —$NR^a$C(=O)N$(R^a)_2$. In certain embodiments, at least one instance of $R^A$ is —OC(=O)$R^a$, —OC(=O)$OR^a$, or —OC(=O)$N(R^a)_2$.

Each instance of $R^A$, $R^C$, $R^E$, and $R^X$ may independently include one or more substituents $R^a$. In certain embodiments, all instances of $R^a$ are the same. In certain embodiments, at least two instances of $R^a$ are different. In certain embodiments, at least one instance of $R^a$ is H. In certain embodiments, each instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted, $C_{1-6}$ alkyl). In certain embodiments, at least one instance of $R^a$ is —$CH_3$. In certain embodiments, at least one instance of $R^a$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^a$ is substituted or unsubstituted alkenyl (e.g., substituted or unsubstituted, $C_{1-6}$ alkenyl). In certain embodiments, at least one instance of $R^a$ is substituted or unsubstituted alkynyl (e.g., substituted or unsubstituted, $C_{1-6}$ alkynyl). In certain embodiments, at least one instance of $R^a$ is substituted or unsubstituted carbocyclyl (e.g., substituted or unsubstituted, monocyclic, 3- to 7-membered carbocyclyl). In certain embodiments, at least one instance of $R^a$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, at least one instance of $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, at least one instance of $R^a$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$ are joined to form a substituted or unsubstituted heterocyclic ring (e.g., substituted or unsubstituted, monocyclic, 5- to 6-membered heterocyclic ring, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, monocyclic, 5- to 6-membered heteroaryl ring, wherein one, two, three, or four atoms in the heteroaryl ring system are independently nitrogen, oxygen, or sulfur).

In certain embodiments, k is 0. In certain embodiments, k is 1. In certain embodiments, k is 2. In certain embodiments, k is 3. In certain embodiments, k is 4. In certain embodiments, k is 5.

Formula (V) includes substituent $R^B$ on the nitrogen atom that connects Rings A and B. In certain embodiments, $R^B$ is hydrogen. In certain embodiments, $R^B$ is substituted or unsubstituted acyl (e.g., acetyl). In certain embodiments, $R^B$ is substituted or unsubstituted, $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn). In certain embodiments, $R^B$ is a nitrogen protecting group (e.g., Bn, Boc, Cbz, Fmoc, trifluoroacetyl, triphenylmethyl, acetyl, or Ts).

Formula (V) includes a heteroaryl ring as Ring B that includes moieties $X^A$, $X^B$, and $X^C$ in the heteroaryl ring system. In certain embodiments, $X^A$ is $CR^X$, and each of $X^B$ and $X^C$ is N. In certain embodiments, $X^A$ is CH, and each of $X^B$ and $X^C$ is N. In certain embodiments, $X^B$ is $CR^X$, and each of $X^A$ and $X^C$ is N. In certain embodiments, $X^B$ is CH, and each of $X^A$ and $X^C$ is N. In certain embodiments, $X^C$ is $CR^X$, and each of $X^A$ and $X^B$ is N. In certain embodiments, $X^C$ is CH, and each of $X^A$ and $X^B$ is N. In certain embodiments, $X^A$ is N, and each of $X^B$ and $X^C$ is independently $CR^X$. In certain embodiments, $X^A$ is N, and each of $X^B$ and $X^C$ is CH. In certain embodiments, $X^B$ is N, and each of $X^A$ and $X^C$ is independently $CR^C$. In certain embodiments, $X^B$ is N, and each of $X^A$ and $X^C$ is CH. In certain embodiments, $X^C$ is N, and each of $X^A$ and $X^B$ is independently $CR^X$. In certain embodiments, $X^C$ is N, and each of $X^A$ and $X^B$ is CH. In certain embodiments, each of $X^A$, $X^B$, and $X^C$ is independently $CR^X$. In certain embodiments, each of $X^A$, $X^B$, and $X^C$ is CH.

In certain embodiments, $X^B$ is $CR^X$, and $R^G$ and $R^X$ of $X^B$ are joined to form a substituted or unsubstituted heterocyclic ring (e.g., substituted or unsubstituted, monocyclic, 5- to 6-membered heterocyclic ring, wherein one or two atoms in the heterocyclic ring system are independently nitrogen, oxygen, or sulfur, further wherein at least one atom in the heterocyclic ring system is nitrogen). In certain embodiments, $X^B$ is $CR^X$, and $R^G$ and $R^X$ of $X^B$ are joined to form a substituted or unsubstituted heteroaryl ring (e.g., substituted or unsubstituted, monocyclic, 5- to 6-membered heteroaryl ring, wherein one or two atoms in the heterocyclic ring system are independently nitrogen, oxygen, or sulfur, further wherein at least one atom in the heteroaryl ring system is nitrogen). In certain embodiments, $X^B$ is $CR^X$, and $R^G$ and $R^X$ of $X^B$ are joined to form substituted or unsubstituted pyrrolyl ring.

In certain embodiments, all instances of $R^X$ are the same. In certain embodiments, at least two instances of $R^X$ are different. In certain embodiments, at least one instance of $R^X$ is hydrogen. In certain embodiments, at least one instance of $R^X$ is halogen (e.g., F, Cl, Br, or I). In certain embodiments, at least one instance of $R^X$ is substituted or unsubstituted alkyl (e.g., substituted or unsubstituted, $C_{1-6}$ alkyl). In certain embodiments, at least one instance of $R^X$ is —$CH_3$. In certain embodiments, at least one instance of $R^X$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^X$ is substituted or unsubstituted alkenyl (e.g., substituted or unsubstituted, $C_{1-6}$ alkenyl). In certain embodiments, at least one instance of $R^X$ is substituted or unsubstituted alkynyl (e.g., substituted or unsubstituted, $C_{1-6}$ alkynyl). In certain embodiments, at least one instance of $R^X$ is substituted or unsubstituted carbocyclyl (e.g., substituted or unsubstituted, monocyclic, 3- to 7-membered carbocyclyl). In certain embodiments, at least one instance of $R^X$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^X$ is substituted or unsubstituted aryl (e.g., substituted or unsubstituted, 6- to 10-membered aryl). In certain embodiments, at least one instance of $R^X$ is substituted or unsubstituted phenyl. In certain embodiments, at least one instance of $R^X$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^X$ is —$OR^a$ (e.g., —OH, —O(substituted or unsubstituted, $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^X$ is —$SR^a$ (e.g., —SH, —S(substituted or unsubstituted, $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^X$ is —$N(R^a)_2$ (e.g., —$NH_2$, —NH(substituted or unsubstituted, $C_{1-6}$ alkyl) (e.g., —NHMe), or —N(substituted or unsubstituted, $C_{1-6}$ alkyl) (substituted or unsubstituted, $C_{1-6}$ alkyl) (e.g, —$NMe_2$)). In certain embodiments, at least one instance of $R^X$ is —CN, —SCN, or —$NO_2$. In certain embodiments, at least one instance of $R^X$ is C(=$NR^a$)$R^a$, —C(=$NR^a$)$OR^a$, or —C(=$NR^a$)$N(R^a)_2$. In certain embodiments, at least one instance of $R^X$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, at least one instance of $R^X$ is —$NR^aC$(=O)$R^a$, —$NR^aC$(=O)$OR^a$, or —$NR^aC$(=O)$N(R^a)_2$. In certain embodiments, at least one instance of $R^X$ is —OC(=O)$R^a$, —OC(=O)$OR^a$, or —OC(=O)$N(R^a)_2$.

Formula (V) includes substituent $R^C$ on Ring B. In certain embodiments, $R^C$ is hydrogen. In certain embodiments, $R^C$ is halogen (e.g., F, Cl, Br, or I). In certain embodiments, $R^C$ is substituted or unsubstituted alkyl (e.g., substituted or unsubstituted, $C_{1-6}$ alkyl). In certain embodiments, $R^C$ is —$CH_3$. In certain embodiments, $R^C$ is —$CF_3$, unsubstituted ethyl, perfluoroethyl, unsubstituted propyl, perfluoropropyl, unsubstituted butyl, perfluorobutyl, or Bn. In certain embodiments, $R^C$ is substituted or unsubstituted alkenyl (e.g., substituted or unsubstituted, $C_{1-6}$ alkenyl). In certain embodiments, $R^C$ is substituted or unsubstituted alkynyl (e.g., substituted or unsubstituted, $C_{1-6}$ alkynyl). In certain embodiments, $R^C$ is substituted or unsubstituted carbocyclyl (e.g., substituted or unsubstituted, monocyclic, 3- to 7-membered carbocyclyl). In certain embodiments, $R^C$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted phenyl. In certain embodiments, $R^C$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^C$ is —$OR^a$ (e.g., —OH, —O(substituted or unsubstituted, $C_{1-6}$ alkyl) (e.g., —OMe, —OEt, —OPr, —OBu, or —OBn), or —O(substituted or unsubstituted phenyl) (e.g., —OPh)). In certain embodiments, $R^C$ is —$SR^a$ (e.g., —SH, —S(substituted or unsubstituted, $C_{1-6}$ alkyl) (e.g., —SMe, —SEt, —SPr, —SBu, or —SBn), or —S(substituted or unsubstituted phenyl) (e.g., —SPh)). In certain embodiments, $R^C$ is —$N(R^a)_2$ (e.g., —$NH_2$, —NH(substituted or unsubstituted, $C_{1-6}$ alkyl) (e.g., —NHMe), or —N(substituted or unsubstituted, $C_{1-6}$ alkyl)-(substituted or unsubstituted, $C_{1-6}$ alkyl) (e.g., —$NMe_2$)). In certain embodiments, $R^C$ is —CN, —SCN, or —$NO_2$. In certain embodiments, $R^C$ is —C(=$NR^a$)$R^a$, —C(=$NR^a$)$OR^a$, or —C(=$NR^a$)$N(R^a)_2$. In certain embodiments, $R^C$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, R$^C$ is —NR$^a$C(=O)R$^a$, —NR$^a$C(=O)OR$^a$, or —NR$^a$C(=O)N(R$^a$)$_2$. In certain embodiments, R$^C$ is —OC(=O)R$^a$, —OC(=O)OR$^a$, or —OC(=O)N(R$^a$)$_2$.

Formula (V) includes substituent R$^D$ on a nitrogen atom of the urea or carbamate moiety. In certain embodiments, R$^D$ is hydrogen. In certain embodiments, R$^D$ is substituted or unsubstituted alkyl, such as substituted or unsubstituted, C$_{1-6}$ alkyl (e.g., —CH$_3$, —CF$_3$, unsubstituted ethyl, perfluoroethyl, unsubstituted propyl, perfluoropropyl, unsubstituted butyl, perfluorobutyl, or Bn). In certain embodiments, R$^D$ is substituted or unsubstituted alkenyl (e.g., substituted or unsubstituted, C$_{1-6}$ alkenyl). In certain embodiments, R$^D$ is substituted or unsubstituted alkynyl (e.g., substituted or unsubstituted, C$_{1-6}$ alkynyl). In certain embodiments, R$^D$ is substituted or unsubstituted carbocyclyl (e.g., substituted or unsubstituted, monocyclic, 3- to 7-membered carbocyclyl). In certain embodiments, R$^D$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, R$^D$ is substituted or unsubstituted oxetanyl, substituted or unsubstituted azetidinyl, substituted or unsubstituted tetrahydrofuranyl, substituted or unsubstituted tetrahydropyranyl, substituted or unsubstituted pyrrolidinyl, substituted or unsubstituted piperidinyl, substituted or unsubstituted piperazinyl, or substituted or unsubstituted morpholinyl. In certain embodiments, R$^D$ is of the formula:

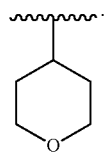

In certain embodiments, R$^D$ is substituted or unsubstituted aryl (e.g., substituted or unsubstituted, 6- to 10-membered aryl). In certain embodiments, R$^D$ is substituted or unsubstituted phenyl. In certain embodiments, R$^D$ is of the formula:

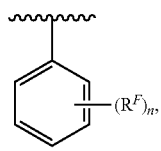

wherein each instance of R$^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and n is 0, 1, 2, 3, 4, or 5. In certain embodiments, R$^D$ is of the formula:

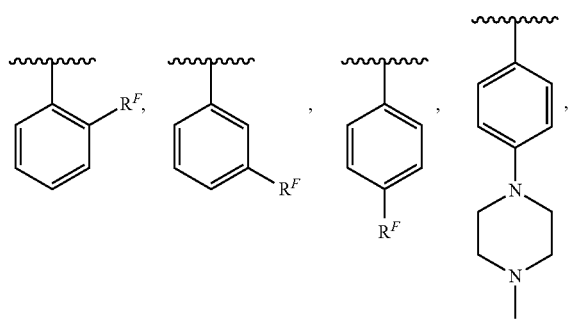

(e.g., 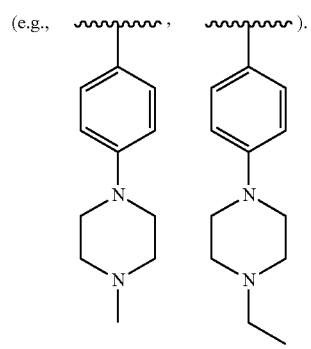).

In certain embodiments, R$^D$ is of the formula:

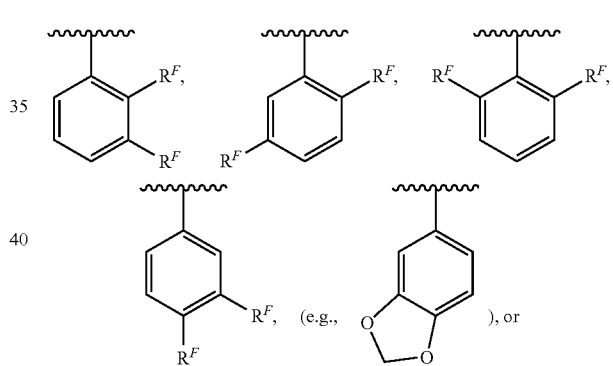

In certain embodiments, R$^D$ is of the formula:

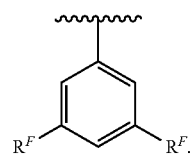

In certain embodiments, R$^D$ is of the formula:

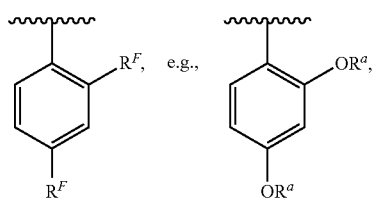

(e.g., 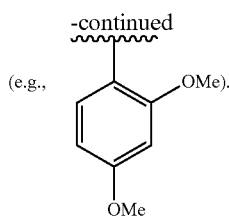).

In certain embodiments, $R^D$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^D$ is substituted or unsubstituted 1-pyrazolyl, substituted or unsubstituted 3-pyrazolyl, or substituted or unsubstituted 4-pyrazolyl (e.g., 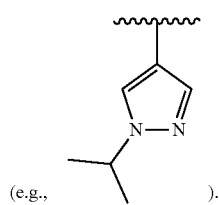).

In certain embodiments, $R^D$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, substituted or unsubstituted isothiazolyl, or substituted or unsubstituted tetrazolyl. In certain embodiments, $R^D$ is substituted or unsubstituted pyridyl, substituted or unsubstituted pyrazinyl, substituted or unsubstituted pyrimidinyl, or substituted or unsubstituted pyridazinyl.

In certain embodiments, $R^D$ is a nitrogen protecting group (e.g., Bn, Boc, Cbz, Fmoc, trifluoroacetyl, triphenylmethyl, acetyl, or Ts).

Formula (V) includes divalent moiety Y. In certain embodiments, Y is —O—. In certain embodiments, Y is —$NR^Y$—. In certain embodiments, Y is —NH—.

In certain embodiments, $R^Y$ is hydrogen. In certain embodiments, $R^Y$ is substituted or unsubstituted acyl (e.g, acetyl). In certain embodiments, $R^Y$ is substituted or unsubstituted, $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn). In certain embodiments, $R^Y$ is a nitrogen protecting group (e.g., Bn, Boc, Cbz, Fmoc, trifluoroacetyl, triphenylmethyl, acetyl, or Ts).

Formula (V) includes divalent moiety Z. In certain embodiments, Z is a bond. In certain embodiments, Z is —$C(R^Z)_2$—. In certain embodiments, Z is —$CH_2$—. In certain embodiments, Z is —CHF— or —$CF_2$—.

In certain embodiments, the two instances of $R^Z$ are the same. In certain embodiments, the two instances of $R^Z$ are not the same. In certain embodiments, at least one instance of $R^Z$ is hydrogen. In certain embodiments, each instance of $R^Z$ is hydrogen. In certain embodiments, at least one instance of $R^Z$ is halogen (e.g., F, Cl, Br, or I). In certain embodiments, at least one instance of $R^Z$ is substituted or unsubstituted, $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn).

In certain embodiments, —Y—Z— is —$N(R^Y)$—. In certain embodiments, —Y—Z— is —NH—. In certain embodiments, —Y—Z— is —N(Me)-. In certain embodiments, —Y—Z— is —O—. In certain embodiments, —Y—Z— is —$N(R^Y)$—$C(R^Z)_2$— (e.g., —$N(R^Y)$—$CH_2$—). In certain embodiments, —Y—Z— is —NH—$CH_2$—. In certain embodiments, —Y—Z— is —N(Me)-$CH_2$—. In certain embodiments, —Y—Z— is —O—$C(R^Z)_2$— (e.g., —O—$CH_2$—).

Formula (V) includes a phenyl ring as Ring C, which is unsubstituted (e.g., when m is 0) or substituted with one or more substituents $R^E$ (e.g., when m is 1, 2, 3, 4, or 5). In certain embodiments, Ring C is an unsubstituted phenyl ring. In certain embodiments, Ring C is a substituted phenyl ring. In certain embodiments, Ring C is of the formula:

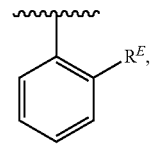

optionally wherein $R^E$ is halogen, substituted or unsubstituted, $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

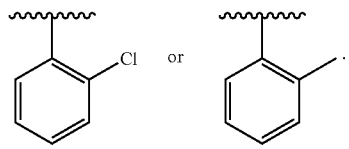

In certain embodiments, Ring C is of the formula:

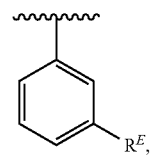

optionally wherein $R^E$ is halogen, substituted or unsubstituted, $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

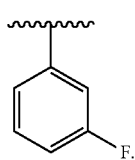 [SMILES: *c1cccc(F)c1]

In certain embodiments, Ring C is of the formula:

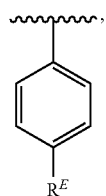

optionally wherein $R^E$ is halogen, substituted or unsubstituted, $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

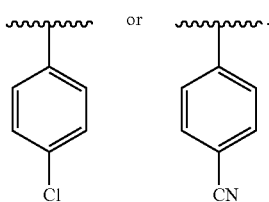 [SMILES: *c1ccc(Cl)cc1 ; *c1ccc(C#N)cc1]

In certain embodiments, Ring C is of the formula:

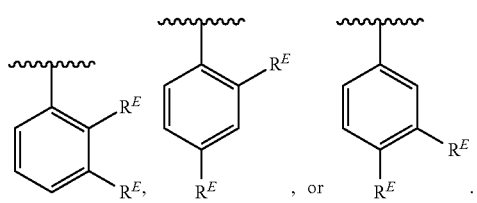

In certain embodiments, Ring C is of the formula:

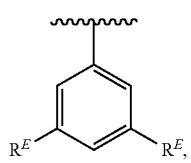

optionally wherein each instance of $R^E$ is independently halogen, substituted or unsubstituted, $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

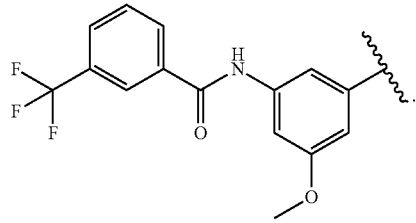 [SMILES: *c1cc(NC(=O)c2cccc(C(F)(F)F)c2)cc(OC)c1]

In certain embodiments, Ring C is of the formula:

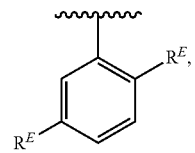

optionally wherein each instance of $R^E$ is independently halogen, substituted or unsubstituted, $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

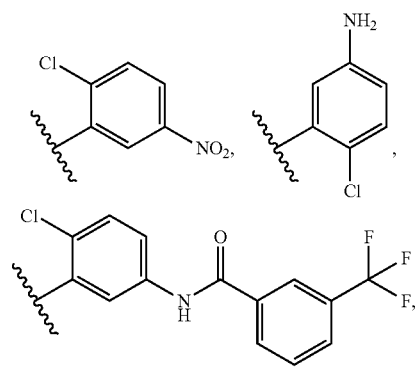

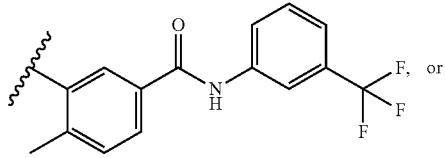

-continued

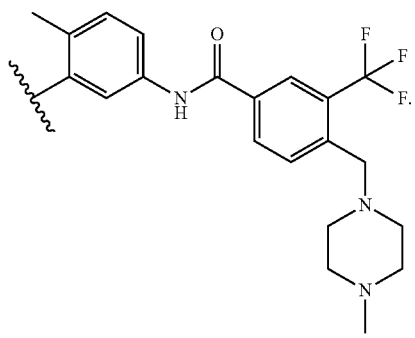

In certain embodiments, Ring C is of the formula:

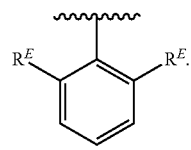

In certain embodiments, Ring C is of the formula:

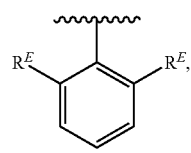

wherein each instance of $R^E$ is independently substituted or unsubstituted alkyl. In certain embodiments, Ring C is of the formula:

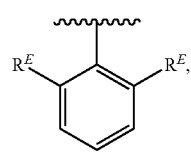

wherein each instance of $R^E$ is independently halogen, substituted or unsubstituted, $C_{1-6}$ alkyl, —$OR^a$, —$N(R^a)_2$, —C(=O)$R^a$, —C(=O)O$R^a$, —C(=O)N($R^a)_2$, —$NR^aC$(=O)$R^a$, —$NR^aC$(=O)O$R^a$, —$NR^aC$(=O)N($R^a)_2$, —$NR^aS$(=O)$R^a$, —$NR^aS$(=O)O$R^a$, —$NR^aS$(=O)N($R^a)_2$, —$NR^aS$(=O)$_2R^a$, —$NR^aS$(=O)$_2OR^a$, —$NR^aS$(=O)$_2N$($R^a)_2$, —OC(=O)$R^a$, —OC(=O)O$R^a$, —OC(=O)N$R^a)_2$, —CN, —SCN, or —$NO_2$. In certain embodiments, Ring C is of the formula:

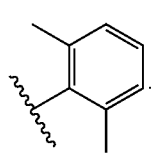

In certain embodiments, Ring C is of the formula:

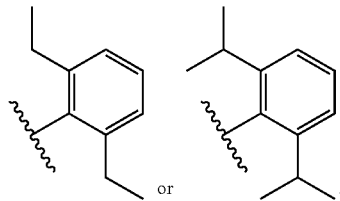

In certain embodiments, Ring C is of the formula:

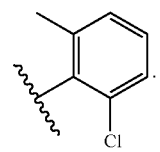

In certain embodiments, Ring C is of the formula:

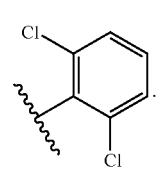

In certain embodiments, Ring C is of the formula:

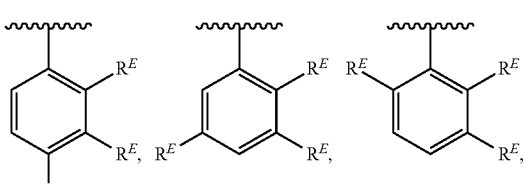

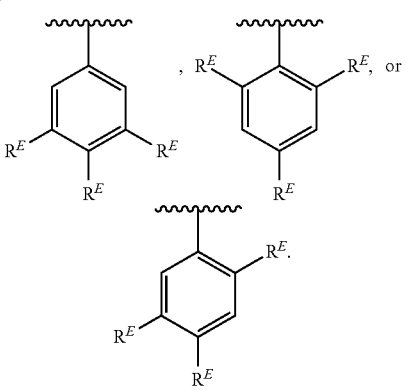

In certain embodiments, Ring C is of the formula:

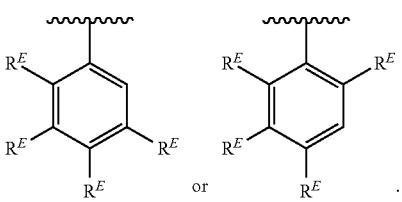

In certain embodiments, Ring C is of the formula:

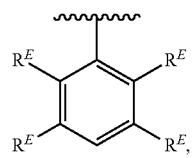

optionally wherein each instance of $R^E$ is independently halogen, substituted or unsubstituted, $C_{1-6}$ alkyl, —$OR^a$, —$N(R^a)_2$, —$C(=O)R^a$, —$C(=O)OR^a$, —$C(=O)N(R^a)_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2R^a$, —$NR^aS(=O)_2N(R^a)_2$, —$OC(=O)R^a$, —$OC(=O)OR^a$, —$OC(=O)N(R^a)_2$, —CN, —SCN, or —$NO_2$. In certain embodiments, Ring C is of the formula:

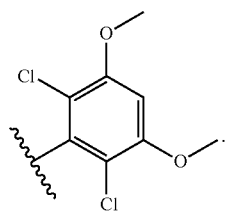 [SMILES: *c1c(Cl)c(OC)cc(OC)c1Cl]

In certain embodiments, Ring C is of the formula:

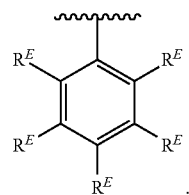

In Formula (V), Ring C may include one or more substituents $R^E$. In certain embodiments, all instances of $R^E$ are the same. In certain embodiments, at least two instances of $R^E$ are different. In certain embodiments, at least one instance of $R^E$ is halogen (e.g., F, Cl, Br, or I). In certain embodiments, at least one instance of $R^E$ is substituted or unsubstituted alkyl (e.g., substituted or unsubstituted, $C_{1-6}$ alkyl). In certain embodiments, at least one instance of $R^E$ is —$CH_3$. In certain embodiments, at least one instance of $R^E$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^E$ is substituted or unsubstituted alkenyl (e.g., substituted or unsubstituted, $C_{1-6}$ alkenyl). In certain embodiments, at least one instance of $R^E$ is substituted or unsubstituted alkynyl (e.g., substituted or unsubstituted, $C_{1-6}$ alkynyl). In certain embodiments, at least one instance of $R^E$ is substituted or unsubstituted carbocyclyl (e.g., substituted or unsubstituted, monocyclic, 3- to 7-membered carbocyclyl). In certain embodiments, at least one instance of $R^E$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^E$ is substituted or unsubstituted aryl (e.g., substituted or unsubstituted, 6- to 10-membered aryl). In certain embodiments, at least one instance of $R^E$ is substituted or unsubstituted phenyl. In certain embodiments, at least one instance of $R^E$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^E$ is —$OR^a$ (e.g., —OH, —O(substituted or unsubstituted, $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^E$ is —$SR^a$ (e.g., —SH, —S(substituted or unsubstituted, $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^E$ is —$N(R^a)_2$ (e.g., —$NH_2$, —NH(substituted or unsubstituted, $C_{1-6}$ alkyl) (e.g., —NHMe), or —N(substituted or unsubstituted, $C_{1-6}$ alkyl)(substituted or unsubstituted, $C_{1-6}$ alkyl) (e.g., —$NMe_2$)). In certain embodiments, at least one instance of $R^E$ is —CN, —SCN, or —$NO_2$. In certain embodiments, at least one instance of $R^E$ is —$C(=NR^a)R^a$, —$C(=NR^a)OR^a$, or —$C(=NR^a)N(R^a)_2$. In certain embodiments, at least one instance of $R^E$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, at least one instance of $R^E$ is —$NR^aC(=O)R^a$, optionally wherein each instance of $R^a$ is independently H, substituted or unsubstituted, $C_{1-6}$ alkyl, substituted or unsubstituted phenyl, or a nitrogen protecting group when attached to a nitrogen atom. In certain embodiments, at least one instance of $R^E$ is —$NHC(=O)R^a$, wherein $R^a$ is substituted or unsubstituted phenyl. In certain embodiments, at least one instance of $R^E$ is of the formula:

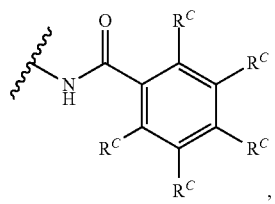

optionally wherein each instance of $R^c$ is independently H, halogen, substituted or unsubstituted, $C_{1-6}$ alkyl, —OH, or —O(substituted or unsubstituted, $C_{1-6}$ alkyl). In certain embodiments, at least one instance of $R^E$ is of the formula:

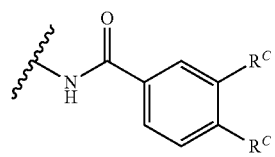

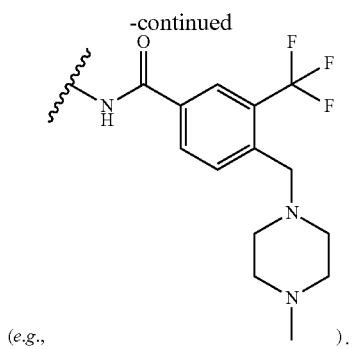

(e.g., [structure shown]).

In certain embodiments, at least one instance of $R^E$ is —$NR^aC(=O)OR^a$ or —$NR^aC(=O)N(R^a)_2$. In certain embodiments, at least one instance of $R^E$ is —$OC(=O)R^a$, —$OC(=O)OR^a$, or —$OC(=O)N(R^a)_2$. In certain embodiments, at least one instance of $R^E$ is —$NR^aS(=O)R^a$, —$NR^aS(=O)OR^a$, or —$NR^aS(=O)N(R^a)_2$, optionally wherein each instance of $R^a$ is independently H, substituted or unsubstituted, $C_{1-6}$ alkyl, nitrogen protecting group when attached to a nitrogen atom, or an oxygen protecting group when attached to an oxygen atom. In certain embodiments, at least one instance of $R^E$ is —$NR^aS(=O)_2R^a$, —$NR^aS(=O)_2OR^a$, or —$NR^aS(=O)_2N(R^a)_2$, optionally wherein each instance of $R^a$ is independently H, substituted or unsubstituted, $C_{1-6}$ alkyl, nitrogen protecting group when attached to a nitrogen atom, or an oxygen protecting group when attached to an oxygen atom. In certain embodiments, at least one instance of $R^E$ is —$NHS(=O)_2R^a$, optionally wherein $R^a$ is substituted or unsubstituted, $C_{1-6}$ alkyl. In certain embodiments, at least one instance of $R^E$ is —$NHS(=O)_2Me$.

In certain embodiments, m is 0. In certain embodiments, m is 1. In certain embodiments, m is 2. In certain embodiments, m is 3. In certain embodiments, m is 4. In certain embodiments, m is 5.

In certain embodiments, the compound of Formula (V) is of the formula:

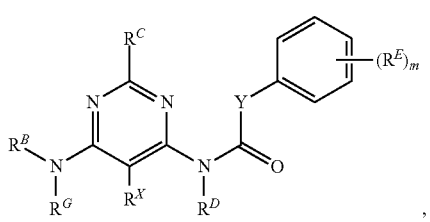

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

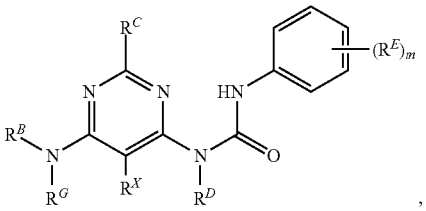

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

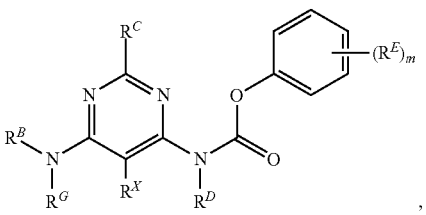

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

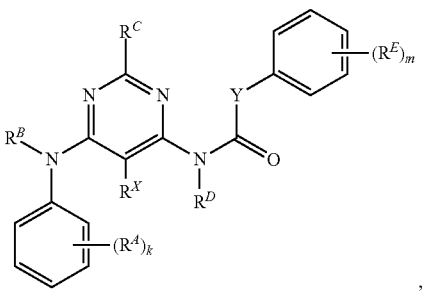

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

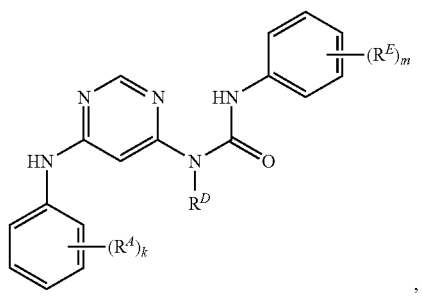

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

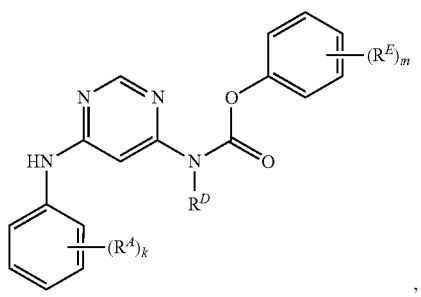

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

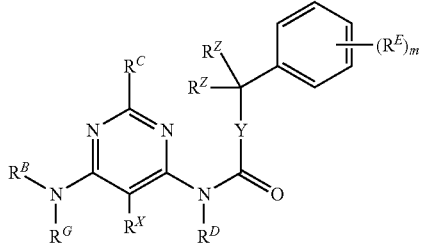

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

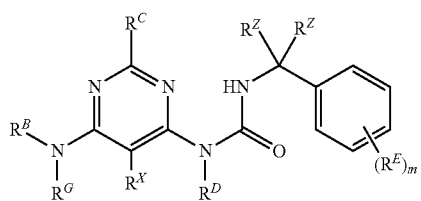

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

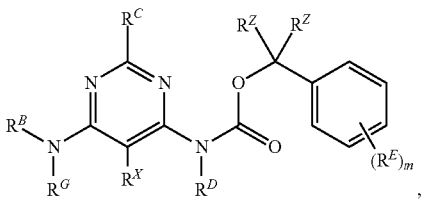

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

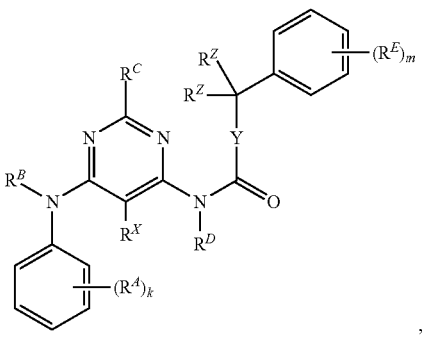

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

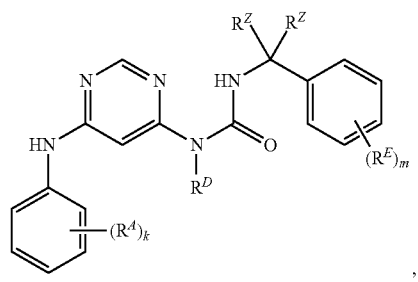

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

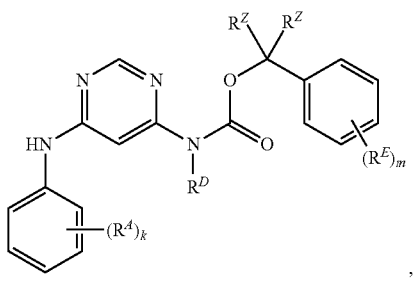

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

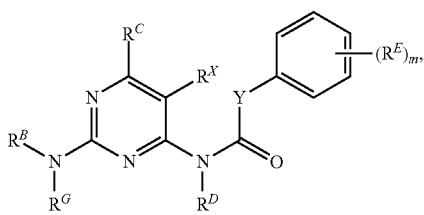

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

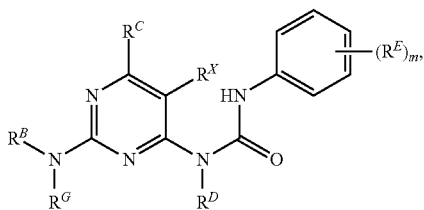

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

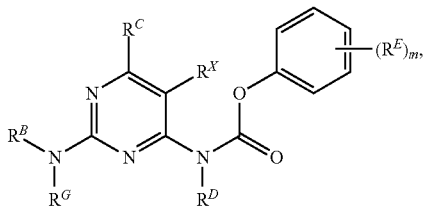

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

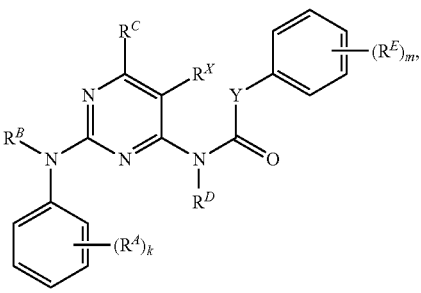

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

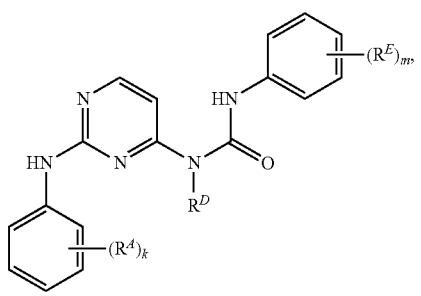

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

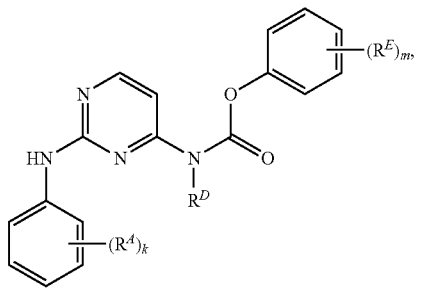

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

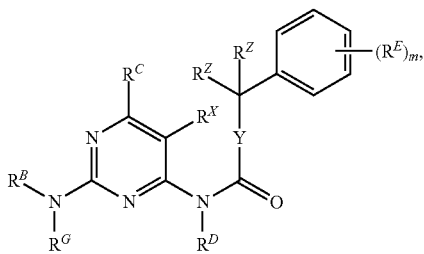

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

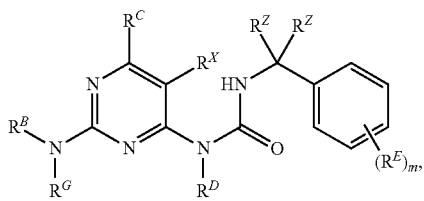

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

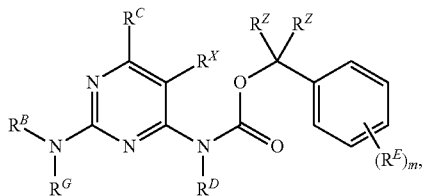

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

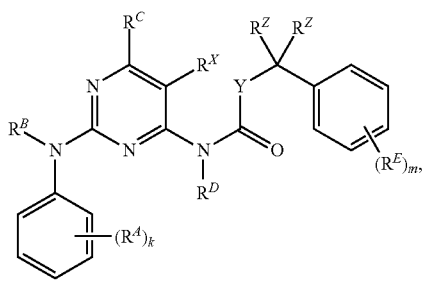

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

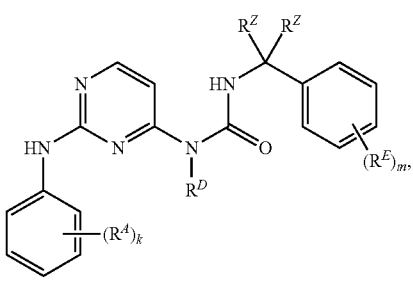

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

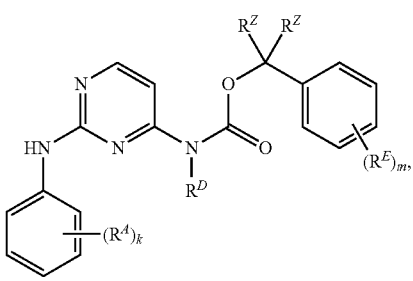

or a pharmaceutically acceptable salt, solvate, hydrate, polymorph, co-crystal, tautomer, stereoisomer, isotopically labeled derivative, or prodrug thereof.

In certain embodiments, the compound of Formula (V) is not of the formula:

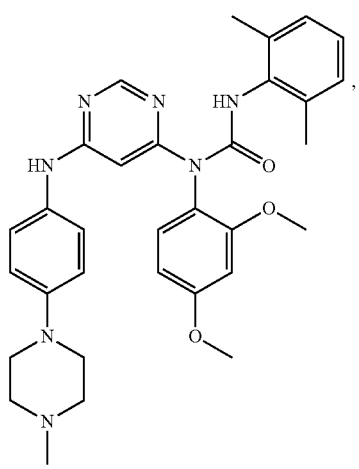 [SMILES: COc1ccc(N(C(=O)Nc2c(C)cccc2C)c2cc(Nc3ccc(N4CCN(C)CC4)cc3)ncn2)c(OC)c1]

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

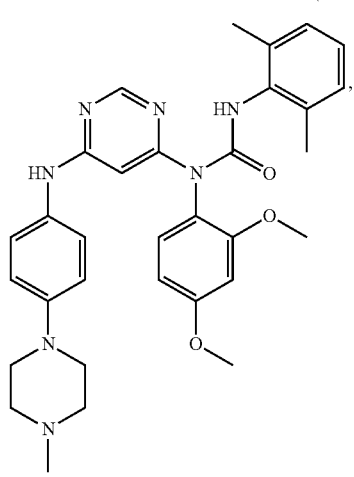

(V-1 or HG-9-91-01)

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

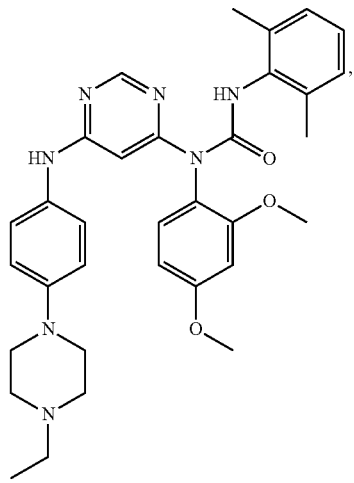

(V-2 or HG-10-11-01)

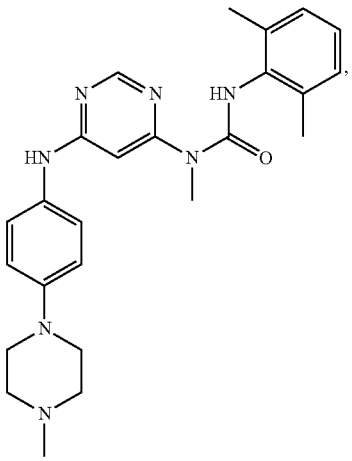

(V-3 or HG-9-148-01)

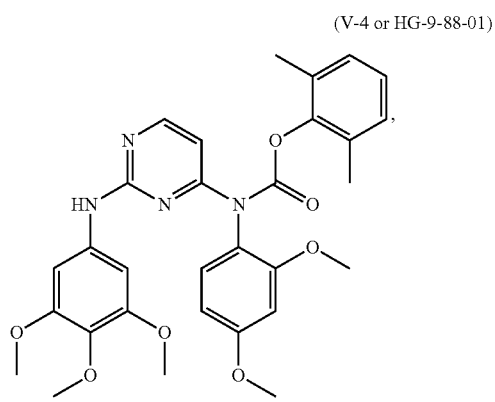

(V-4 or HG-9-88-01)

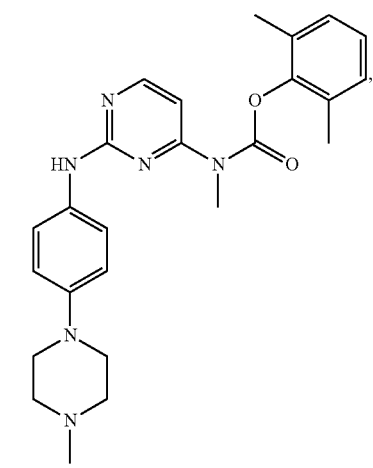

(V-5 or HG-9-150-01)

or a pharmaceutically acceptable salt, solvate, hydrate, polymorph, co-crystal, tautomer, stereoisomer, isotopically labeled derivative, or prodrug thereof.

In certain embodiments, the compound of Formula (V) is of the formula:

(HG-9-96-01)
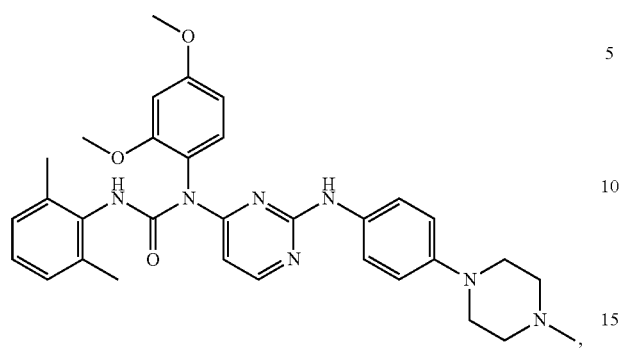
(HG-10-8-02)
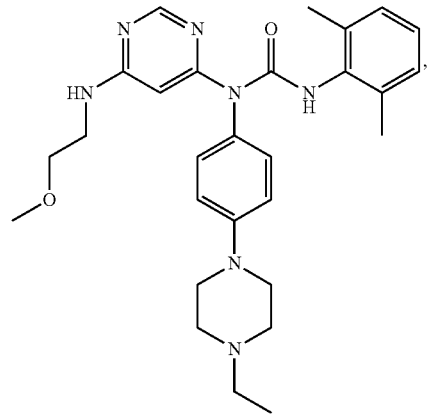
(HG-9-148-02)
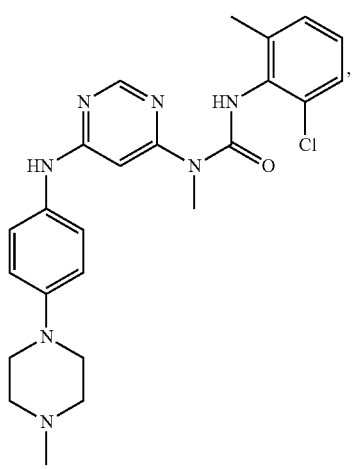
(HG-10-9-01)
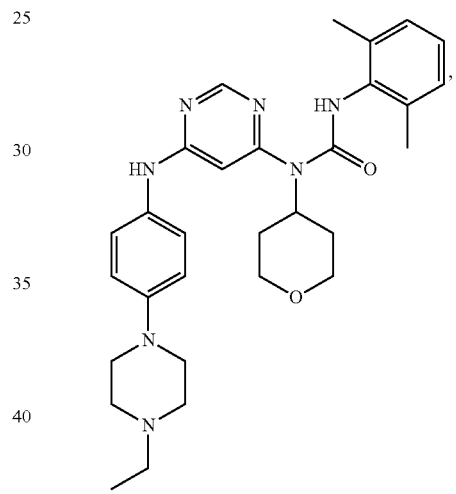
(HG-10-8-01)
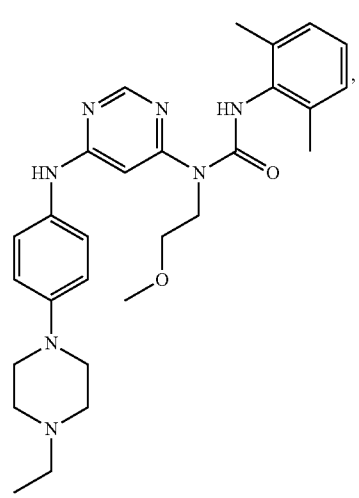
(HG-10-15-02)
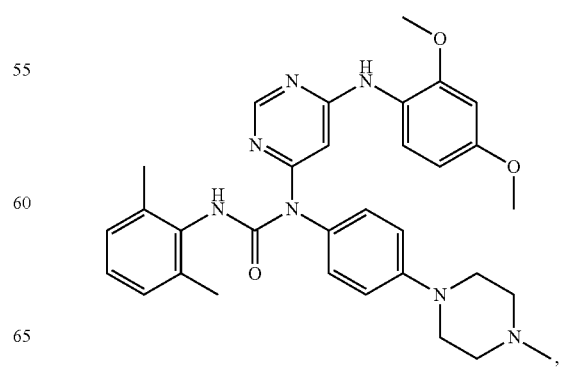

-continued
(HG-10-15-03)
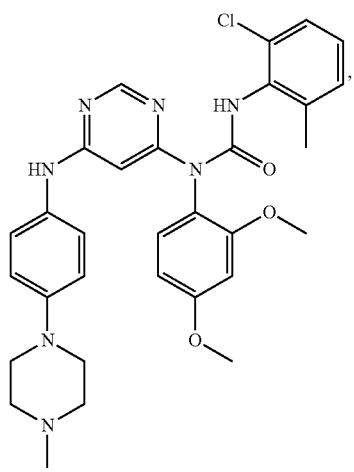
(HG-10-15-04)
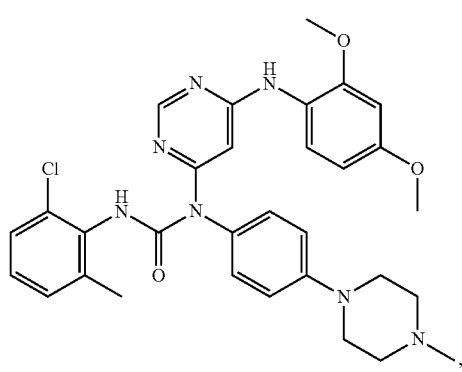
(HG-10-27-01)
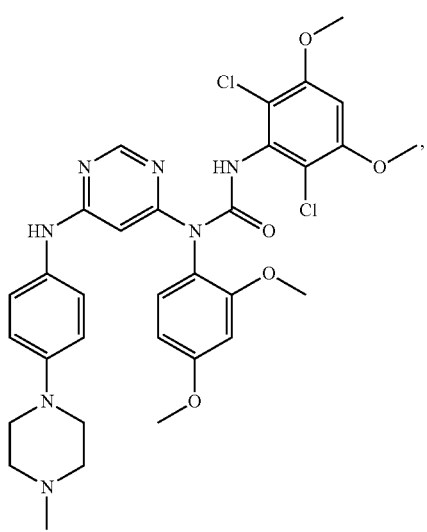
-continued
(HG-10-27-02)
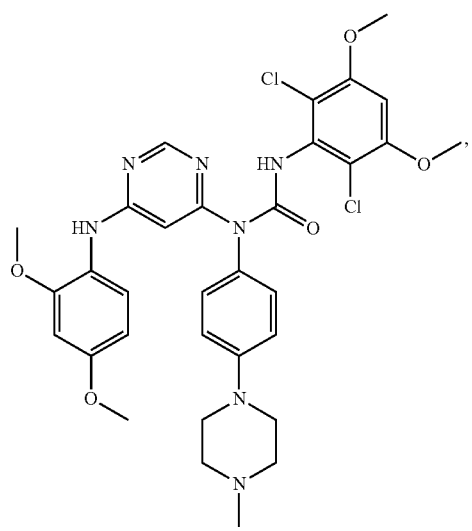
(HG-10-28-01)
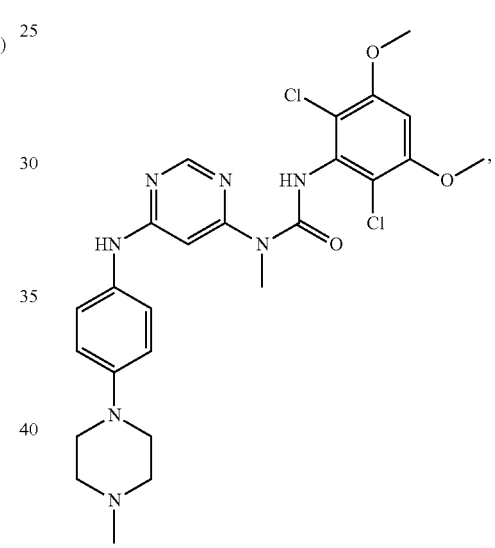
(HG-10-31-01)
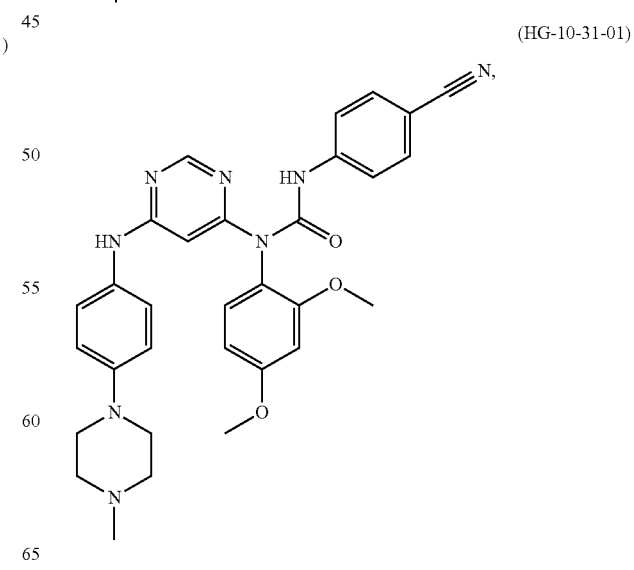

-continued
(HG-10-31-02)
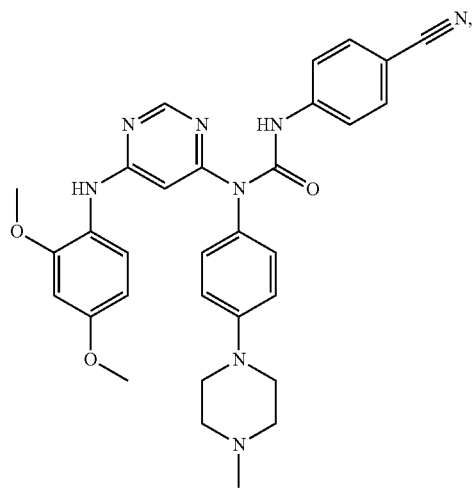
(HG-10-36-01)
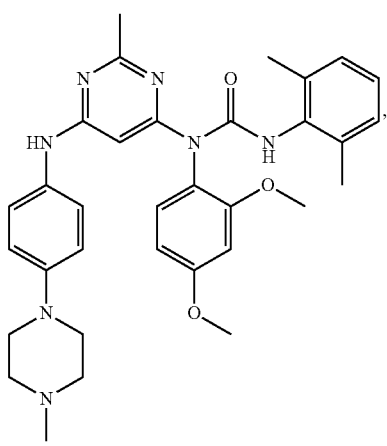
(HG-10-36-02)
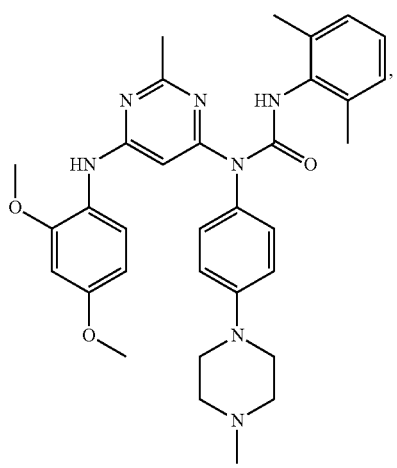
-continued
(HG 10-59-02)
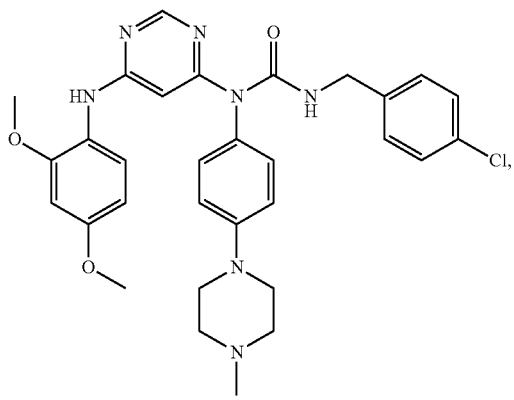
(HG 10-60-01 or HG-10-60-01)
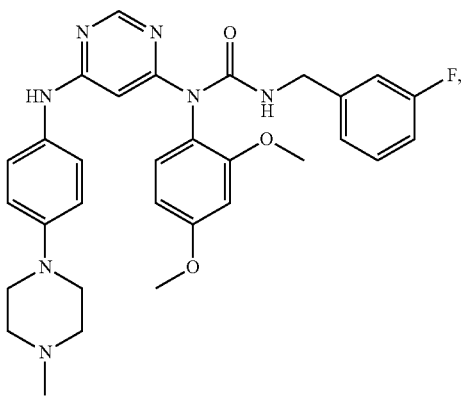
(HG 10-60-02)
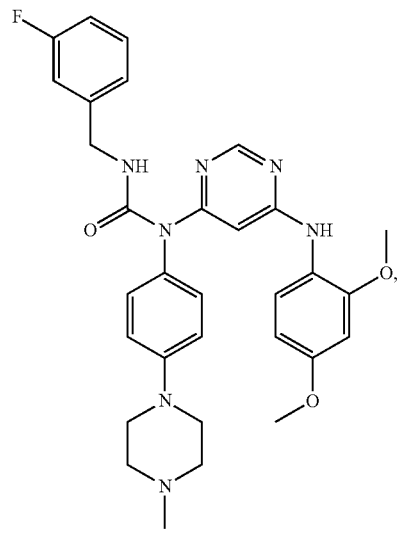

-continued
(HG 10-61-01 or HG-10-61-01)
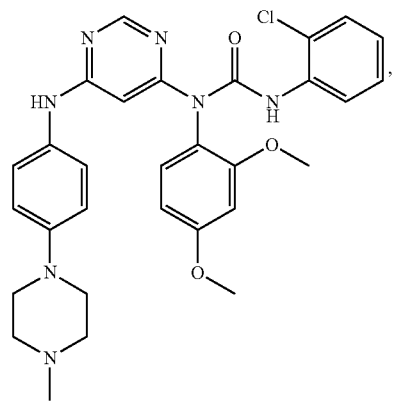
(HG 10-61-02)
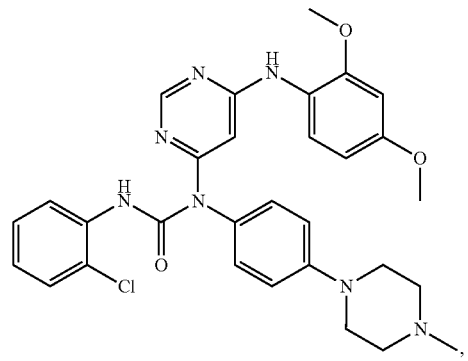
(HG 10-62-01 or HG-10-62-01)
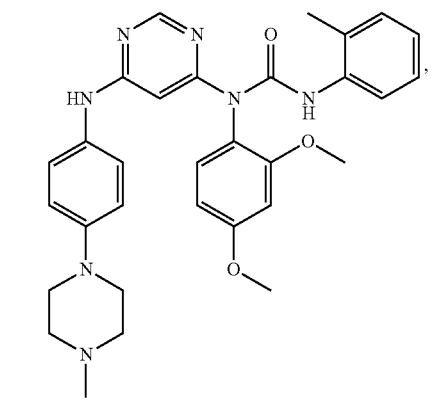
(HG 10-62-02 or HG-10-62-02)
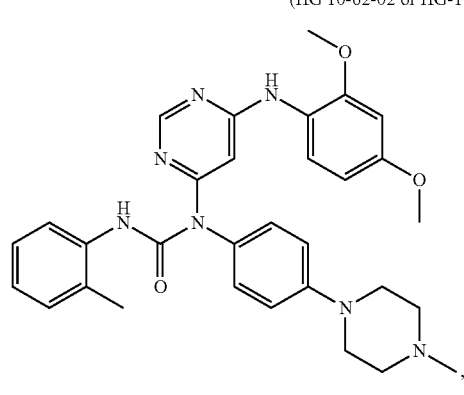
-continued
(HG 10-63-01 or HG-10-63-01)
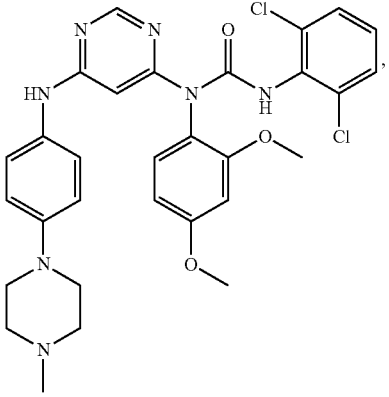
(HG 10-63-02)
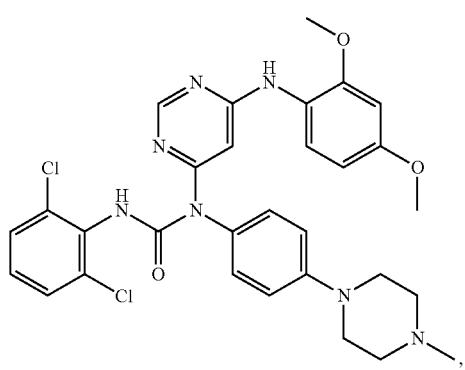
(HG 10-64-01 or HG-10-64-01)
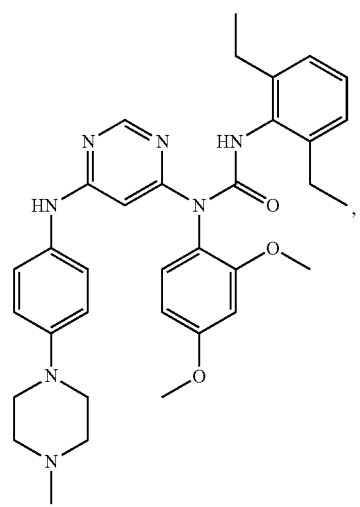

(HG 10-64-02 or HG-10-64-02)
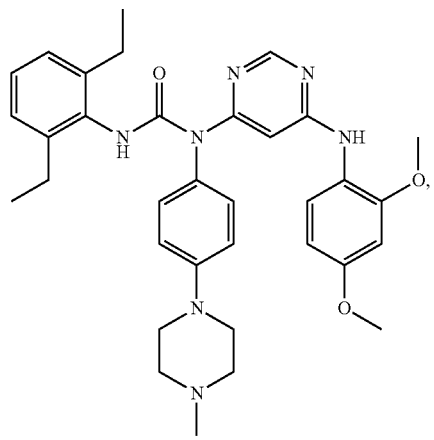
(HG 10-65-01)
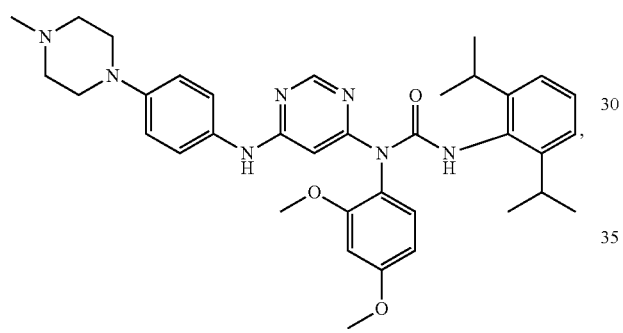
(HG 10-65-02)
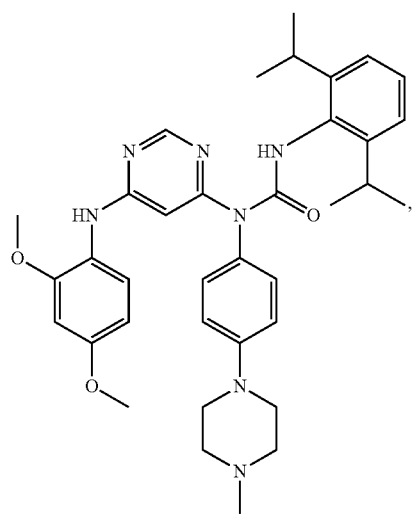
(HG-10-149-01)
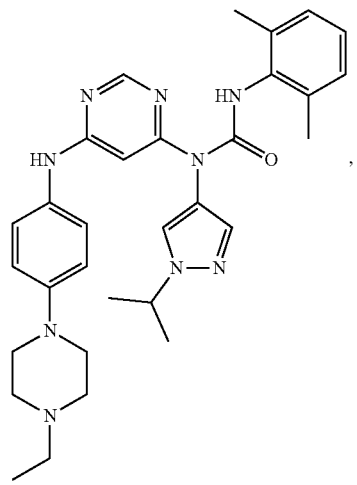
(HG-10-149-02)
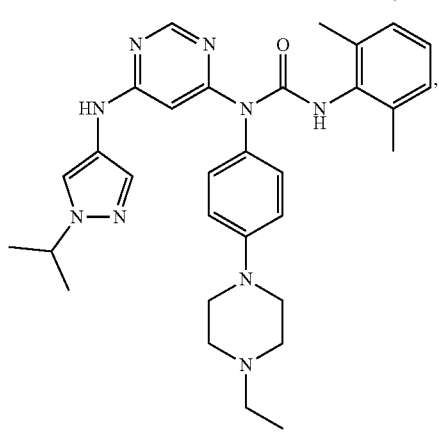
(HG-10-150-01)
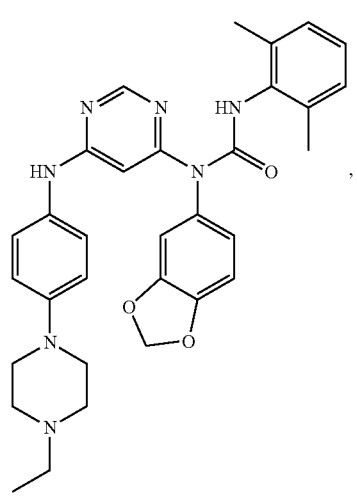

201
-continued
(HG-10-150-02)
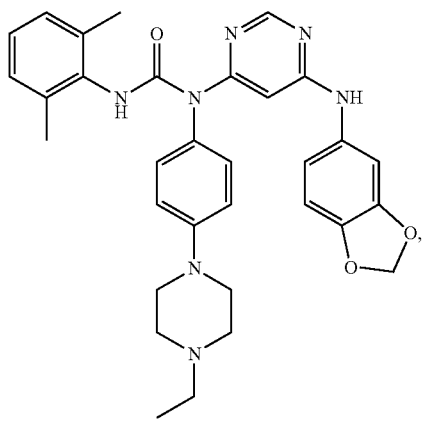
(HG-11-18-01)
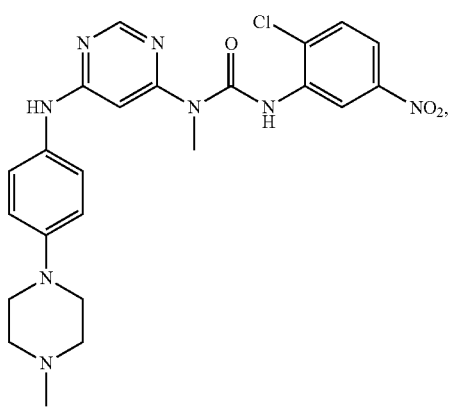
(HG-11-18-02)
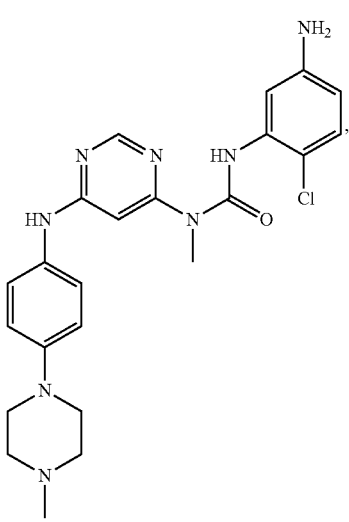
202
-continued
(HG-11-21-01)
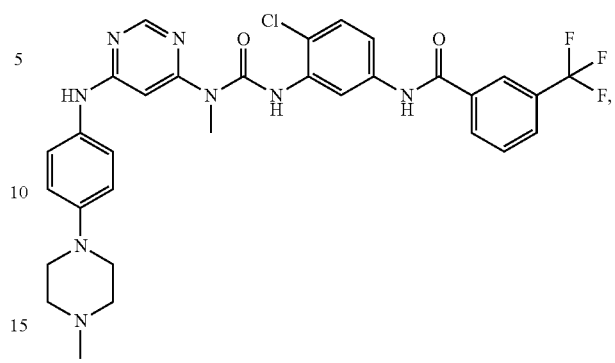
(HG-11-22-01)
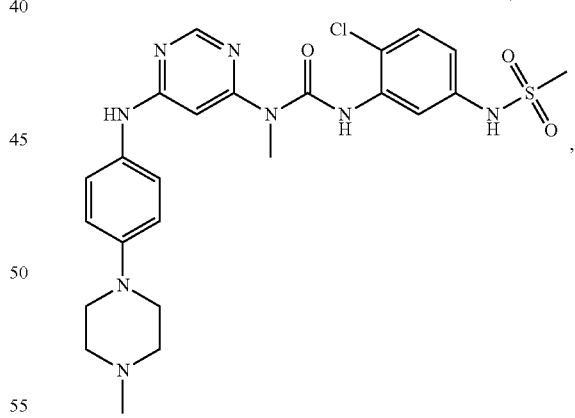
or a pharmaceutically acceptable salt, solvate, hydrate, polymorph, co-crystal, tautomer, stereoisomer, isotopically labeled derivative, or prodrug thereof.
In certain embodiments, the compound of Formula (V) is of the formula:

203 204
(HG-3-09-01)
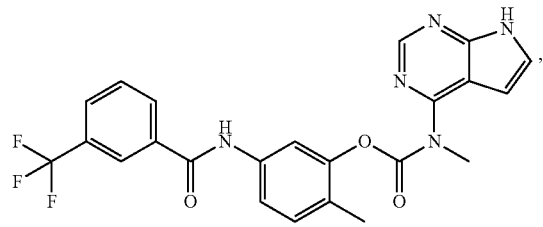
(HG-9-87-02)
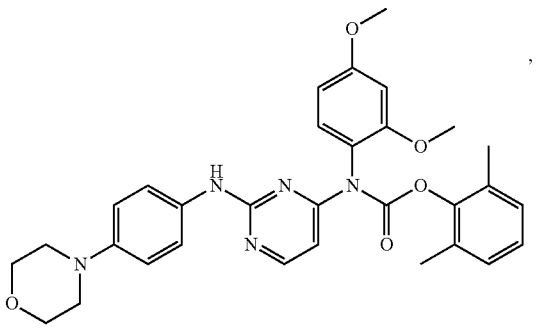
(HG-9-87-03)
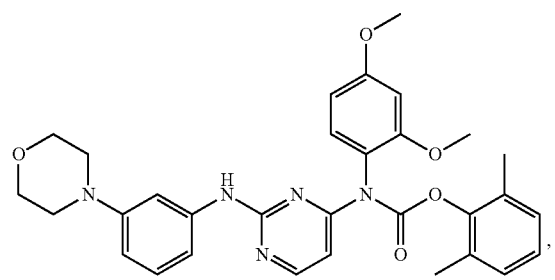
(HG-9-87-04)
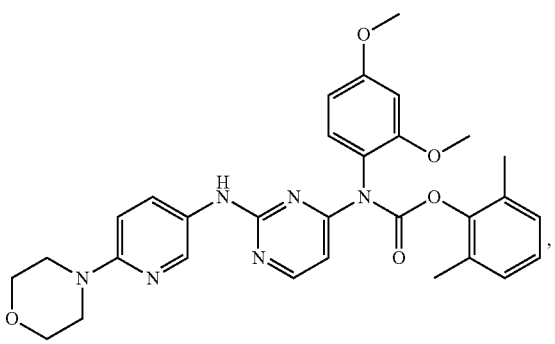
(HG-9-88-02)
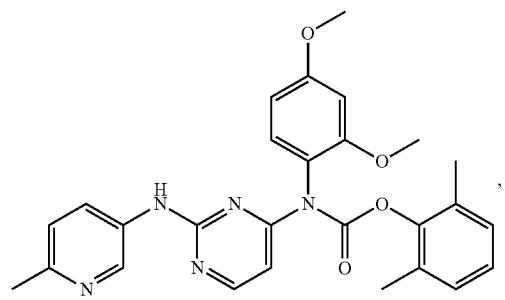
(HG-9-88-03)
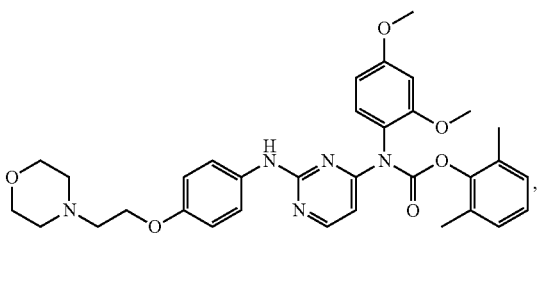
(HG-9-88-04)
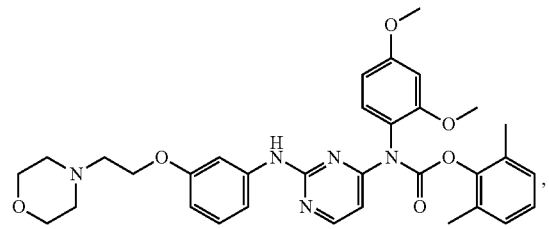
(HG-9-88-05)
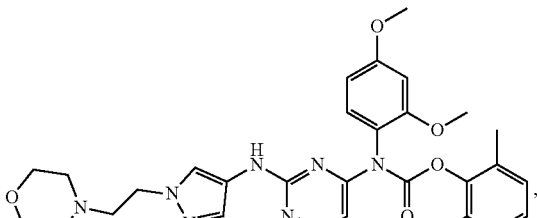
(HG-9-90-01)
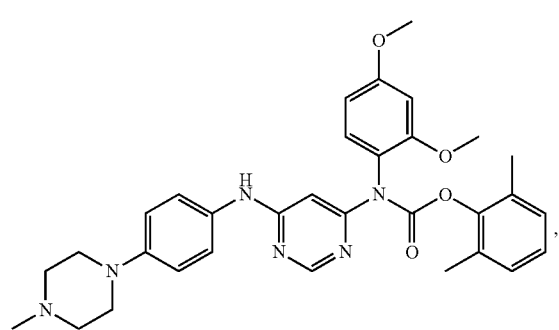
(HG-9-90-02)
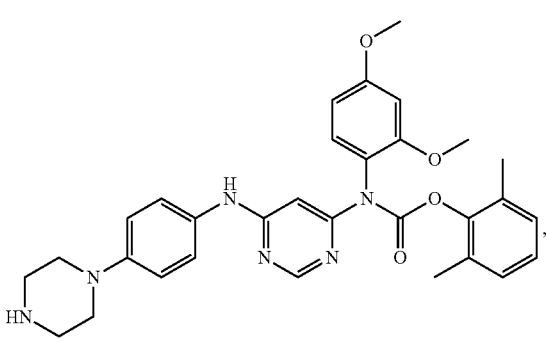

-continued
(HG-9-90-03)
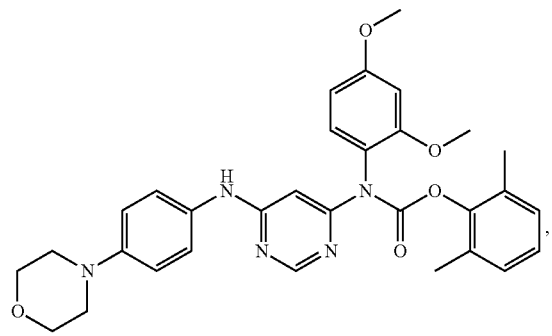
(HG-9-139-02)
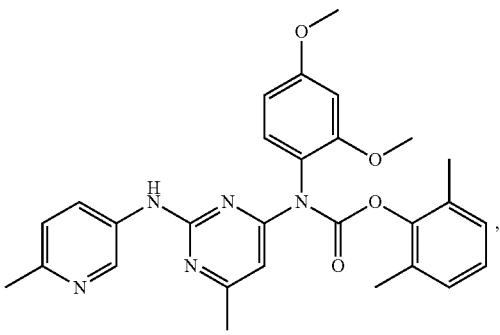
(HG-9-139-03)
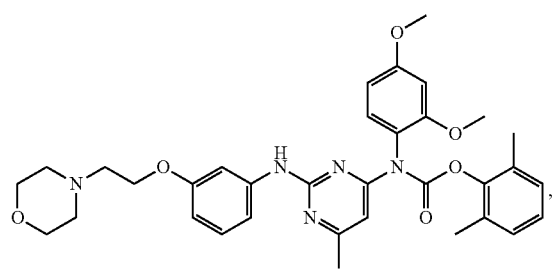
(HG-9-139-04)
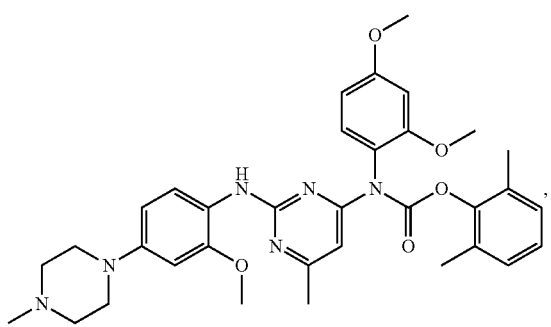
(HG-9-139-05)
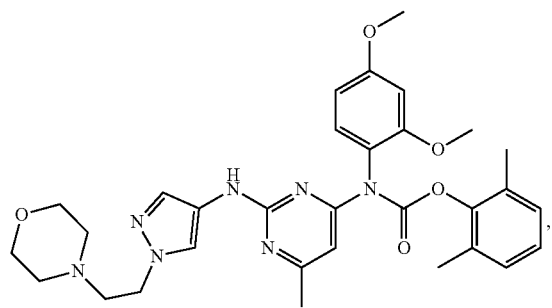
(HG-9-140-01)
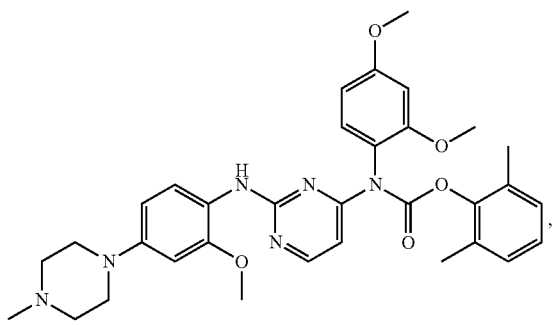
(HG-9-144-01)
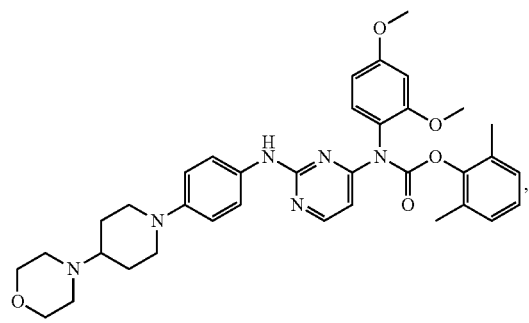
(HG-9-144-02)
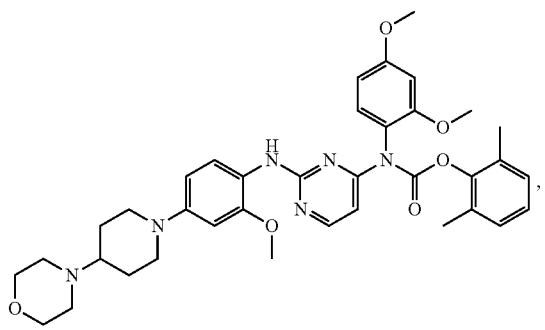

(HG-9-144-03)
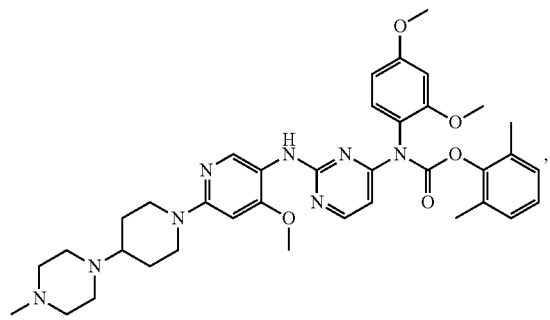
(HG-9-144-04)
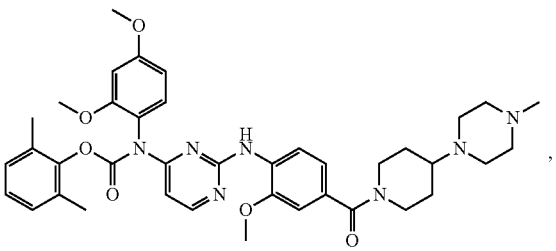
(HG-9-144-05)
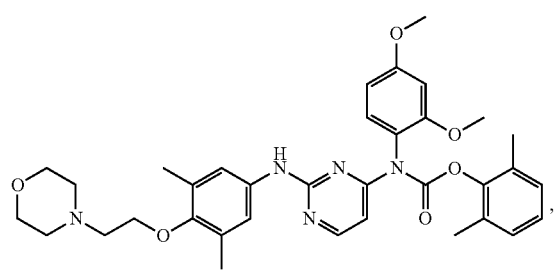
(HG-9-150-02)
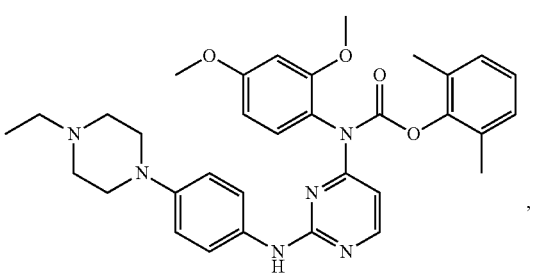
(HG-11-6-01)
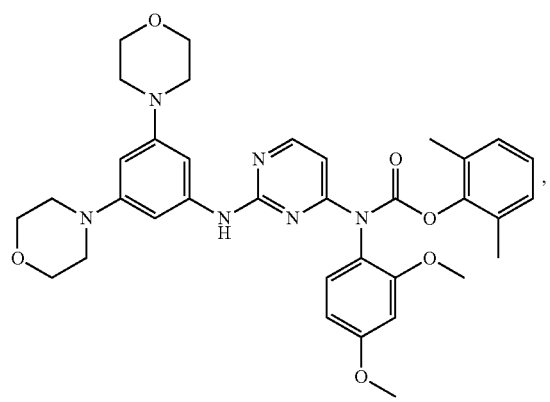
(HG-11-6-02)
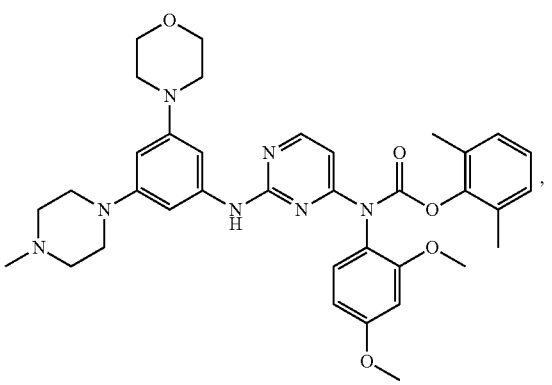
(WH-4-023)
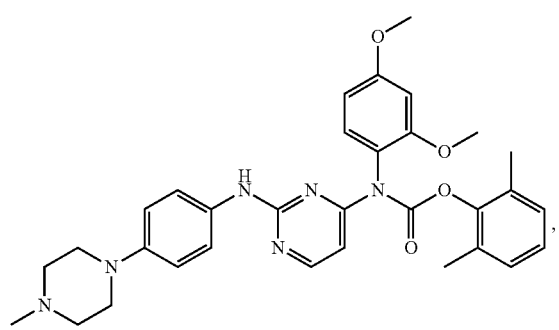

(WH-4-025)
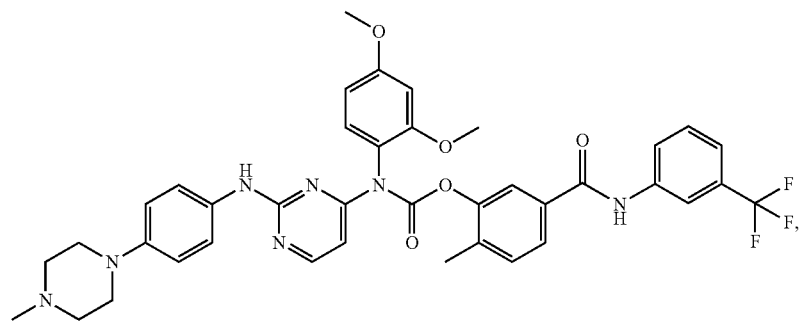
(WH4-113)
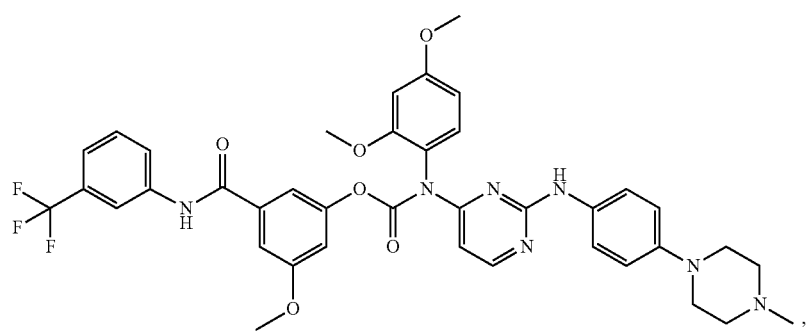
(WH4-124-1)
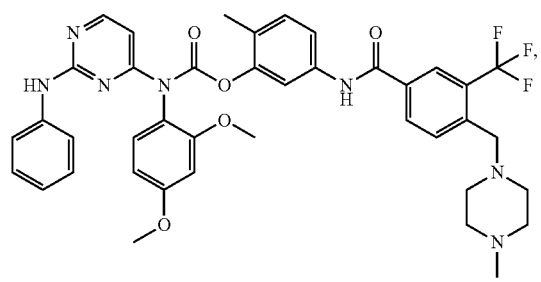
(WH4-124-2)
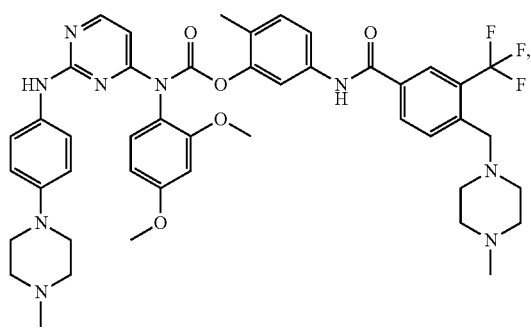
(WH4-199-1)
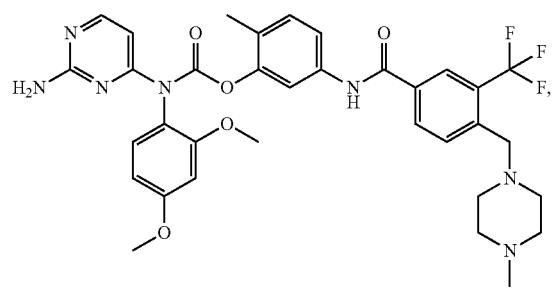
(WH4-199-2)
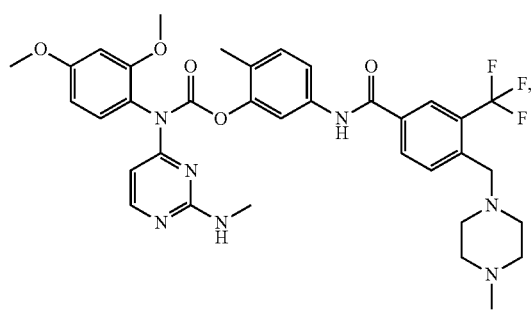

-continued (WH4-200-1)

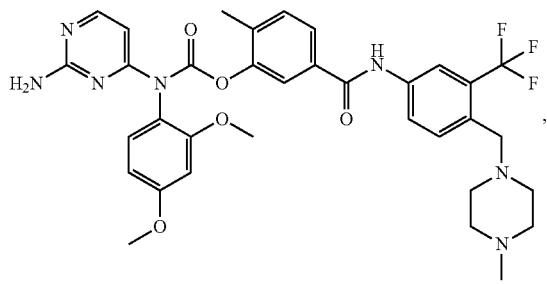

(WH4-200-2)

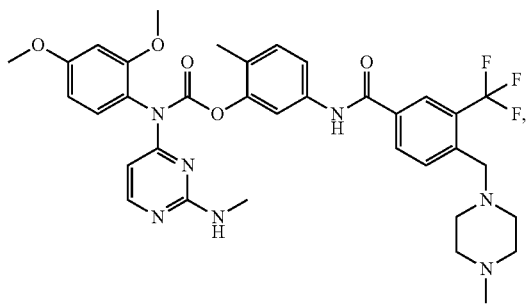

or a pharmaceutically acceptable salt, solvate, hydrate, polymorph, co-crystal, tautomer, stereoisomer, isotopically labeled derivative, or prodrug thereof.

Compounds of Formula (VI)

In one aspect, the present disclosure provides macrocyclic compounds of Formula (VI) for use in the present invention:

(VI)

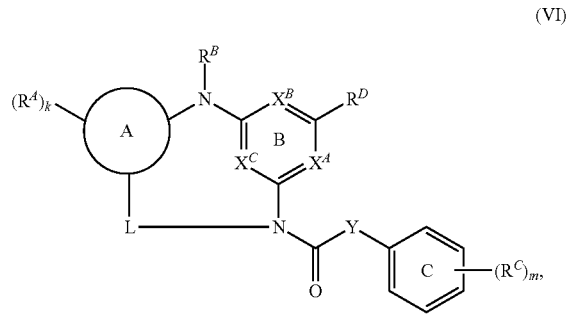

and pharmaceutically acceptable salts, solvates, hydrates, polymorphs, co-crystals, tautomers, stereoisomers, isotopically labeled derivatives, and prodrugs thereof, wherein:

Ring A is a substituted or unsubstituted phenyl ring or a substituted or unsubstituted, monocyclic, 5- to 6-membered heteroaryl ring, wherein one, two, three, or four atoms in the heteroaryl ring system are independently nitrogen, oxygen, or sulfur;

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^3$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

k is 0, 1, 2, 3, or 4;

L is a substituted or unsubstituted, saturated or unsaturated $C_{3-10}$ hydrocarbon chain, optionally wherein one or more chain atoms of the hydrocarbon chain are independently replaced with —O—, —S—, —$NR^N$—, —N=, or =N—, wherein each instance of $R^N$ is independently hydrogen, substituted or unsubstituted acyl, substituted or unsubstituted, $C_{1-6}$ alkyl, or a nitrogen protecting group;

$R^B$ is hydrogen, substituted or unsubstituted acyl, substituted or unsubstituted, $C_{1-6}$ alkyl, or a nitrogen protecting group;

each of $X^A$, $X^B$, and $X^C$ is independently N or $CR^X$, wherein $R^X$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

Y is —O— or —$NR^Y$—, wherein is hydrogen, substituted or unsubstituted acyl, substituted or unsubstituted, $C_{1-6}$ alkyl, or a nitrogen protecting group;

or when Y is —$NR^Y$— and $X^A$ is $CR^X$, $R^Y$ and $R^X$ of $X^A$ are joined to form a substituted or unsubstituted, monocyclic, 5- to 7-membered heterocyclic ring that is fused with Ring B;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

m is 0, 1, 2, 3, 4, or 5; and $R^D$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

In certain embodiments, Ring A is a substituted or unsubstituted phenyl ring or a substituted or unsubstituted, monocyclic, 5- to 6-membered heteroaryl ring, wherein one, two, three, or four atoms in the heteroaryl ring system are independently nitrogen, oxygen, or sulfur;

each instance of R$^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^a$ groups are joined to form a substituted or unsubstituted heterocyclic or substituted or unsubstituted heteroaryl ring;

k is 0, 1, 2, 3, or 4;

L is a substituted or unsubstituted, saturated or unsaturated C$_{3-10}$ hydrocarbon chain, optionally wherein one or more chain atoms of the hydrocarbon chain are independently replaced with —O—, —S—, —NR$^N$—, —N=, or =N—, wherein each instance of R$^N$ is independently hydrogen, substituted or unsubstituted acyl, substituted or unsubstituted, C$_{1-6}$ alkyl, or a nitrogen protecting group;

R$^B$ is hydrogen, substituted or unsubstituted acyl, substituted or unsubstituted, C$_{1-6}$ alkyl, or a nitrogen protecting group;

each of X$^A$, X$^B$, and X$^C$ is independently N or CR$^X$, wherein R$^X$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

Y is —O— or —NR$^Y$—, wherein R$^Y$ is hydrogen, substituted or unsubstituted acyl, substituted or unsubstituted, C$_{1-6}$ alkyl, or a nitrogen protecting group;

each instance of R$^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

m is 0, 1, 2, 3, 4, or 5; and

R$^D$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

Unless expressly provided otherwise, the moieties and variables described in the subsection Compounds of Formula (VI) apply only to Formula (VI). The moieties and variables included but not described in detail in the subsection Compounds of Formula (VI) are as described in detail in other subsections.

Formula (VI) includes Ring A that is unsubstituted (e.g., when k is 0) or substituted with one or more substituents R$^A$ (e.g., when k is 1, 2, 3, or 4). In certain embodiments, Ring A is an unsubstituted phenyl ring. In certain embodiments, Ring A is a substituted phenyl ring. In certain embodiments, Ring A is a substituted or unsubstituted, monocyclic, 5-membered heteroaryl ring (e.g., furanyl, thienyl, pyrrolyl, imidazolyl, pyrazolyl, oxazolyl, isoxazolyl, thiazolyl, or isothiazolyl ring), wherein one, two, three, or four atoms in the heteroaryl ring system are independently nitrogen, oxygen, or sulfur. In certain embodiments, Ring A is a substituted or unsubstituted, monocyclic, 6-membered heteroaryl ring (e.g., a pyridyl, pyrazinyl, pyrimidinyl, or pyridazinyl ring), wherein one, two, three, or four atoms in the heteroaryl ring system are independently nitrogen, oxygen, or sulfur. In certain embodiments, Ring A is of the formula:

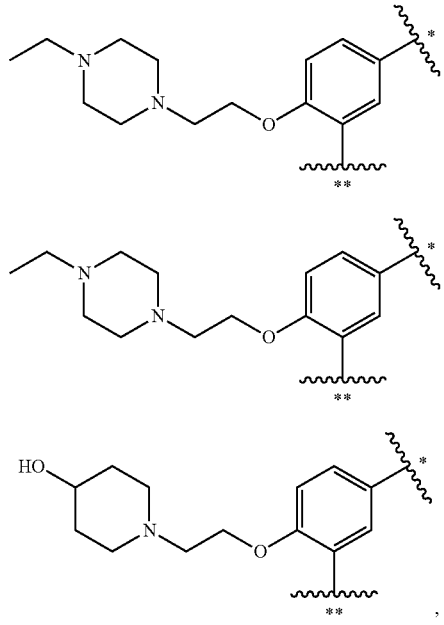

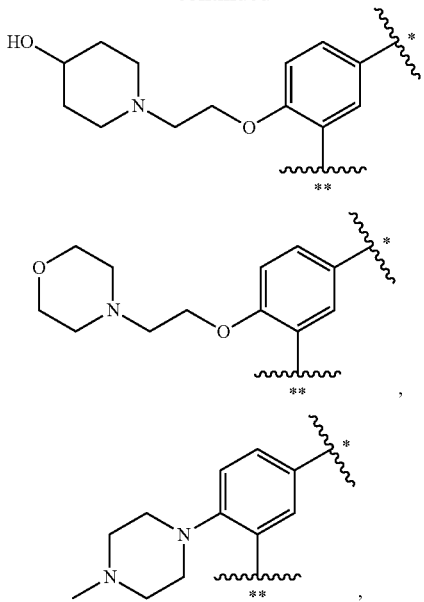

wherein the radical marked with "*" is directly attached to N(R^B), and the radical marked with "**" is directly attached to L.

In Formula (VI), Ring A may include one or more substituents $R^A$. In certain embodiments, at least two instances of $R^A$ are different. In certain embodiments, all instances of $R^A$ are the same. In certain embodiments, at least one instance of $R^A$ is halogen. In certain embodiments, at least one instance of $R^A$ is F. In certain embodiments, at least one instance of $R^A$ is Cl. In certain embodiments, at least one instance of $R^A$ is Br. In certain embodiments, at least one instance of $R^A$ is (iodine). In certain embodiments, at least one instance of $R^A$ is substituted alkyl. In certain embodiments, at least one instance of $R^A$ is unsubstituted alkyl. In certain embodiments, at least one instance of $R^A$ is unsubstituted $C_{1-6}$ alkyl. In certain embodiments, all instances of $R^A$ are unsubstituted $C_{1-6}$ alkyl. In certain embodiments, at least one instance of $R^A$ is substituted $C_{1-6}$ alkyl. In certain embodiments, at least one instance of $R^A$ is $C_{1-6}$ alkyl substituted with at least one halogen. In certain embodiments, at least one instance of $R^A$ is —$CH_3$. In certain embodiments, all instances of $R^A$ are —$CH_3$. In certain embodiments, at least one instance of $R^A$ is substituted methyl. In certain embodiments, at least one instance of $R^A$ is —$CH_2F$. In certain embodiments, at least one instance of $R^a$ is —$CHF_2$. In certain embodiments, at least one instance of $R^A$ is —$CF_3$. In certain embodiments, at least one instance of $R^A$ is ethyl. In certain embodiments, at least one instance of $R^A$ is propyl. In certain embodiments, at least one instance of $R^A$ is butyl. In certain embodiments, at least one instance of $R^A$ is pentyl. In certain embodiments, at least one instance of $R^A$ is hexyl. In certain embodiments, at least one instance of $R^A$ is Bn. In certain embodiments, at least one instance of $R^A$ is substituted alkenyl. In certain embodiments, at least one instance of $R^A$ is unsubstituted alkenyl. In certain embodiments, at least one instance of $R^A$ is substituted alkynyl. In certain embodiments, at least one instance of $R^A$ is unsubstituted alkynyl. In certain embodiments, at least one instance of $R^A$ is substituted carbocyclyl. In certain embodiments, at least one instance of $R^A$ is unsubstituted carbocyclyl. In certain embodiments, at least one instance of $R^A$ is saturated carbocyclyl. In certain embodiments, at least one instance of $R^A$ is unsaturated carbocyclyl. In certain embodiments, at least one instance of $R^A$ is monocyclic carbocyclyl. In certain embodiments, at least one instance of $R^A$ is 3- to 7-membered, monocyclic carbocyclyl. In certain embodiments, at least one instance of $R^A$ is substituted heterocyclyl. In certain embodiments, at least one instance of $R^A$ is unsubstituted heterocyclyl. In certain embodiments, at least one instance of $R^A$ is saturated heterocyclyl. In certain embodiments, at least one instance of $R^A$ is unsaturated heterocyclyl. In certain embodiments, at least one instance of $R^A$ is heterocyclyl, wherein one, two, or three atoms in the heterocyclic ring system are independently selected from the group consisting of nitrogen, oxygen, and sulfur. In certain embodiments, at least one instance of $R^A$ is monocyclic heterocyclyl. In certain embodiments, at least one instance of $R^A$ is 3- to 7-membered, monocyclic heterocyclyl. In certain embodiments, at least one instance of $R^A$ is substituted or unsubstituted, monocyclic, 3- to 7-membered heterocyclyl, wherein one, two, or three atoms in the heterocyclic ring system are independently selected from the group consisting of nitrogen, oxygen, and sulfur. In certain embodiments, at least one instance of $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^A$ is of the formula:

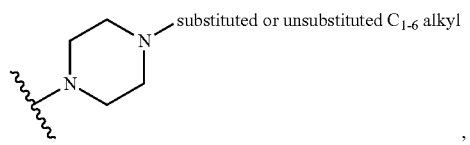

such as

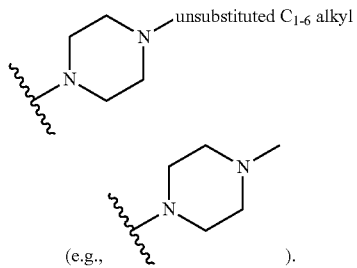

(e.g., ).

In certain embodiments, at least one instance of $R^A$ is substituted aryl. In certain embodiments, at least one instance of $R^A$ is unsubstituted aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms in the heteroaryl ring system are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9- or 10-membered, bicyclic heteroaryl. In certain embodiments, at least one instance of $R^A$ is —$OR^a$. In certain embodiments, at least one instance of $R^A$ is —OH. In certain embodiments, at least one instance of $R^A$ is —O(substituted or unsubstituted, $C_{1-6}$ alkyl). In certain embodiments, at least one instance of $R^A$ is —OMe. In certain embodiments, at least one instance of $R^A$ is —OEt. In certain embodiments, at least one instance of $R^A$ is —OPr. In certain embodiments, at least one instance of $R^A$ is —OBu. In certain embodiments, at least one instance of $R^A$ is —OBn. In certain embodiments, at least one instance of $R^A$ is —OPh. In certain embodiments, at least one instance of $R^A$ is of the formula:

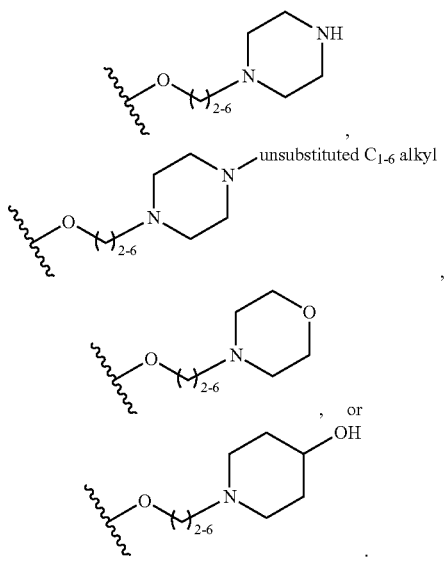

In certain embodiments, at least one instance of $R^A$ is of the formula:

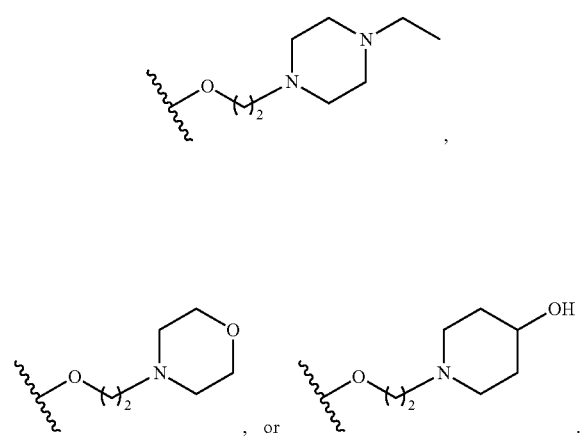

In certain embodiments, k is 1; and W is of the formula:

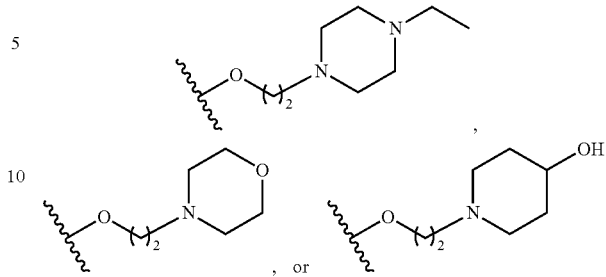

In certain embodiments, at least one instance of $R^A$ is —$SR^a$. In certain embodiments, at least one instance of $R^A$ is —SH. In certain embodiments, at least one instance of $R^A$ is —SMe. In certain embodiments, at least one instance of $R^A$ is —$N(R^a)_2$. In certain embodiments, at least one instance of $R^A$ is —$NH_2$. In certain embodiments, at least one instance of $R^A$ is —NHMe. In certain embodiments, at least one instance of $R^A$ is —$NMe_2$. In certain embodiments, at least one instance of $R^A$ is —CN. In certain embodiments, at least one instance of $R^A$ is —SCN. In certain embodiments, at least one instance of $R^A$ is —$C(=NR^a)R^a$, —$C(=NR^a)OR^a$, or —$C(=NR^a)N(R^a)_2$. In certain embodiments, at least one instance of $R^A$ is —$C(=O)R^a$ or —$C(=O)OR^a$. In certain embodiments, at least one instance of $R^A$ is —$C(=O)N(R^a)_2$. In certain embodiments, at least one instance of $R^A$ is —$C(=O)NMe_2$, —$C(=O)NHMe$, or —$C(=O)NH_2$. In certain embodiments, at least one instance of $R^A$ is —$NO_2$. In certain embodiments, at least one instance of $R^A$ is —$NR^aC(=O)R^a$, —$NR^aC(=O)OR^a$, or —$NR^aC(=O)N(R^a)_2$. In certain embodiments, at least one instance of $R^A$ is —$OC(=O)R^a$, —$OC(=O)OR^a$, or —$OC(=O)N(R^a)_2$.

Each instance of $R^A$, $R^C$, $R^D$, and $R^X$ may independently include one or more substituents $R^a$. In certain embodiments, all instances of $R^a$ are the same. In certain embodiments, at least two instances of $R^a$ are different. In certain embodiments, at least one instance of $R^a$ is H. In certain embodiments, each instance of $R^a$ is H. In certain embodiments, at least one instance of $R^a$ is substituted acyl. In certain embodiments, at least one instance of $R^a$ is unsubstituted acyl. In certain embodiments, at least one instance of $R^a$ is acetyl. In certain embodiments, at least one instance of $R^a$ is substituted alkyl. In certain embodiments, at least one instance of $R^a$ is unsubstituted alkyl. In certain embodiments, at least one instance of $R^a$ is unsubstituted $C_{1-6}$ alkyl. In certain embodiments, at least one instance of $R^a$ is methyl. In certain embodiments, at least one instance of $R^a$ is ethyl. In certain embodiments, at least one instance of $R^a$ is propyl. In certain embodiments, at least one instance of $R^a$ is butyl. In certain embodiments, at least one instance of $R^a$ is pentyl. In certain embodiments, at least one instance of $R^a$ is hexyl. In certain embodiments, at least one instance of $R^a$ is Bn. In certain embodiments, at least one instance of $R^a$ is substituted alkenyl. In certain embodiments, at least one instance of $R^a$ is unsubstituted alkenyl. In certain embodiments, at least one instance of $R^a$ is substituted alkynyl. In certain embodiments, at least one instance of $R^a$ is unsubstituted alkynyl. In certain embodiments, at least one instance of $R^a$ is substituted or unsubstituted carbocyclyl. In certain embodiments, at least one instance of $R^a$ is saturated carbocyclyl. In certain embodiments, at least one instance of $R^a$ is unsaturated carbocyclyl. In certain embodiments, at least one instance of $R^a$ is 3- to 7-membered, monocyclic carbocyclyl. In certain embodiments, at least one instance of $R^a$ is substituted or unsubstituted heterocyclyl. In certain embodiments, at least one instance of $R^a$ is saturated heterocyclyl. In certain embodiments, at least one instance of $R^a$ is unsaturated heterocyclyl. In certain embodiments, at least one instance of $R^a$ is heterocyclyl, wherein one, two, or three atoms of the heterocyclic ring system are independently selected from the group consisting of nitrogen, oxygen, and sulfur. In certain embodiments, at least one instance of $R^a$ is 3- to 7-membered, monocyclic heterocyclyl. In certain embodiments, at least one instance of $R^a$ is substituted or unsubstituted aryl. In certain embodiments, at least one instance of $R^a$ is 6- to 10-membered aryl. In certain embodiments, at least one instance of $R^a$ is monocyclic aryl. In certain embodiments, at least one instance of $R^a$ is substituted phenyl. In certain embodiments, at least one instance of $R^a$ is unsubstituted phenyl. In certain embodiments, at least one instance of $R^a$ is bicyclic aryl. In certain embodiments, at least one instance of $R^a$ is substituted or unsubstituted heteroaryl. In certain embodiments, at least one instance of $R^a$ is heteroaryl, wherein one, two, three, or four atoms of the heteroaryl ring system are independently selected from the group consisting of nitrogen, oxygen, and sulfur. In certain embodiments, at least one instance of $R^a$ is monocyclic heteroaryl. In certain embodiments, at least one instance of $R^a$ is 5- or 6-membered, monocyclic heteroaryl. In certain embodiments, at least one instance of $R^a$ is bicyclic heteroaryl, wherein the point of attachment may be on any atom of the bicyclic heteroaryl ring system, as valency permits. In certain embodiments, at least one instance of $R^a$ is a nitrogen protecting group when attached to a nitrogen atom. In certain embodiments, at least one instance of $R^a$ is Bn, Boc, Cbz, Fmoc, trifluoroacetyl, triphenylmethyl, acetyl, or Ts when attached to a nitrogen atom. In certain embodiments, $R^a$ is an oxygen protecting group when attached to an oxygen atom. In certain embodiments, $R^a$ is silyl, TBDPS, TBDMS, TIPS, TES, TMS, MOM, t-Bu, Bn, allyl, acetyl, pivaloyl, or benzoyl when attached to an oxygen atom. In certain embodiments, $R^a$ is a sulfur protecting group when attached to a sulfur atom. In certain embodiments, $R^a$ is acetamidomethyl, t-Bu, 3-nitro-2-pyridine sulfenyl, 2-pyridine-sulfenyl, or triphenylmethyl when attached to a sulfur atom. In certain embodiments, two instances of $R^a$ are joined to form a substituted or unsubstituted heterocyclic ring. In certain embodiments, two instances of $R^a$ are joined to form a saturated or unsaturated heterocyclic ring. In certain embodiments, two instances of $R^a$ are joined to form a heterocyclic ring, wherein one, two, or three atoms of the heterocyclic ring system are independently selected from the group consisting of nitrogen, oxygen, and sulfur. In certain embodiments, two instances of $R^a$ are joined to form a 3- to 7-membered, monocyclic heterocyclic ring. In certain embodiments, two instances of $R^a$ are joined to form a substituted or unsubstituted heteroaryl ring. In certain embodiments, two instances of $R^a$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, k is 0. In certain embodiments, k is 1. In certain embodiments, k is 2. In certain embodiments, k is 3. In certain embodiments, k is 4.

In certain embodiments, k is 1; and $R^A$ is —$OR^a$. In certain embodiments, k is 1; and $R^A$ is —O(substituted or unsubstituted, $C_{1-6}$ alkyl).

Formula (VI) includes divalent linker L. L consists of a chain, and optionally one or more hydrogen atoms and/or one or more substituents (e.g., =O) on the chain, where any two substituents may optionally be joined to form a ring. In certain embodiments, the molecular weight of L is not more than about 300 g/mol, not more than about 200 g/mol, not more than about 150 g/mol, not more than about 100 g/mol, or not more than 80 g/mol. In certain embodiments, the molecular weight of L is between 50 and 150 g/mol, inclusive. In certain embodiments, L consists of not more than about 70 atoms, not more than about 50 atoms, not more than about 30 atoms, not more than about 20 atoms, or not more than 15 atoms. In certain embodiments, L consists of between 10 and 30 atoms, inclusive. In certain embodiments, L does not include unsaturated bonds in the chain. In certain embodiments, L consists of one unsaturated bond in the chain. In certain embodiments, L consists of 2, 3, or 4 unsaturated bonds in the chain. In certain embodiments, L is a substituted or unsubstituted, saturated or unsaturated $C_{3-10}$ hydrocarbon chain (e.g., a $C_{5-6}$ hydrocarbon chain). In certain embodiments, L is a substituted or unsubstituted, saturated or unsaturated $C_{3-10}$ hydrocarbon chain (e.g., a $C_{5-6}$ hydrocarbon chain), wherein one chain atom of the hydrocarbon chain is replaced with —O—, —S—, —$NR^N$—, —N=, or =N—. In certain embodiments, L is a substituted or unsubstituted, saturated or unsaturated, $C_{3-10}$ hydrocarbon chain (e.g., a $C_{5-6}$ hydrocarbon chain), wherein 2, 3, 4, or 5 chain atoms of the hydrocarbon chain are independently replaced with —O—, —S—, —$NR^N$—, —N=, or =N—. In certain embodiments, L is a substituted or unsubstituted, saturated or unsaturated $C_{5-6}$ hydrocarbon chain, wherein one or two chain atoms of the hydrocarbon chain are independently replaced with —O—, —S—, or —$NR^N$—. In certain embodiments, L is of the formula:

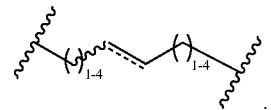

In certain embodiments, L is of the formula:

In certain embodiments, L is of the formula:

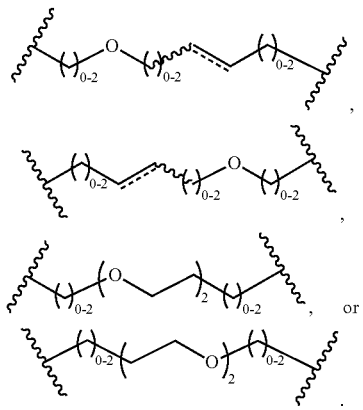

In certain embodiments, L is of the formula:

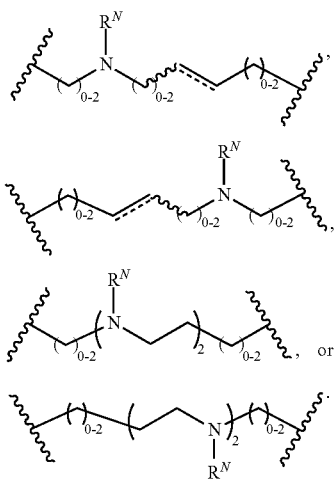

In certain embodiments, L is of the formula:

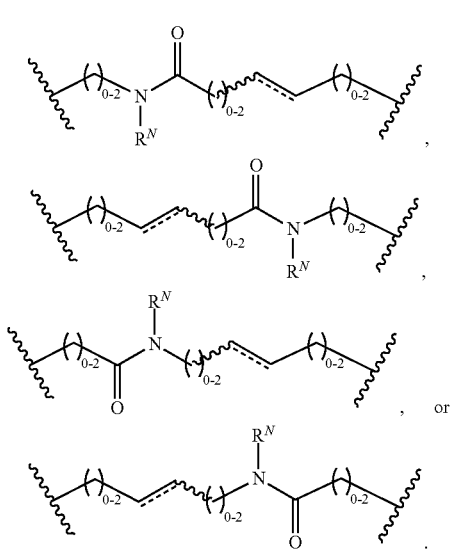

In certain embodiments, L is of the formula:

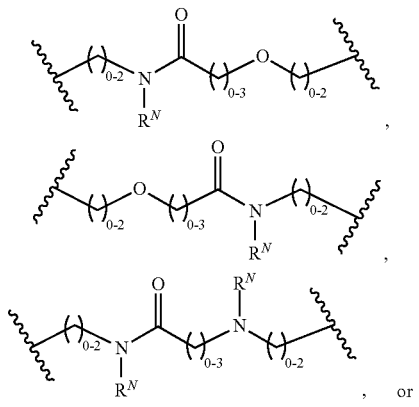

-continued

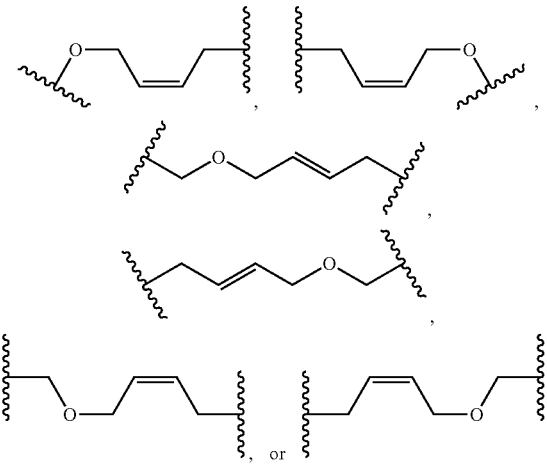

In certain embodiments, L is of the formula:

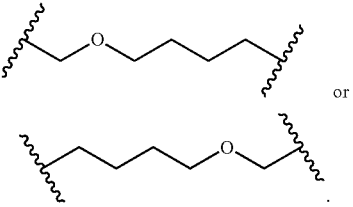

In certain embodiments, L is of the formula:

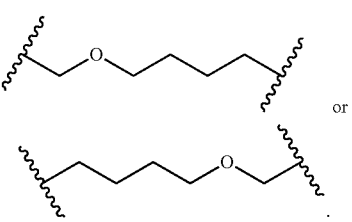

In certain embodiments, at least two instances of $R^N$ are different. In certain embodiments, all instances of $R^N$ are the same. In certain embodiments, at least one instance of $R^N$ is H. In certain embodiments, each instance of $R^N$ is H. In certain embodiments, at least one instance of $R^N$ is substituted acyl. In certain embodiments, at least one instance of $R^N$ is unsubstituted acyl. In certain embodiments, at least one instance of $R^N$ is acetyl. In certain embodiments, at least one instance of $R^N$ is unsubstituted $C_{1-6}$ alkyl. In certain embodiments, each instance of e is independently unsubstituted $C_{1-6}$ alkyl. In certain embodiments, at least one instance of $R^N$ is substituted $C_{1-6}$ alkyl. In certain embodiments, at least one instance of $R^N$ is $C_{1-6}$ alkyl substituted with at least one halogen. In certain embodiments, at least one instance of $R^N$ is unsubstituted methyl. In certain embodiments, at least one instance of $R^N$ is substituted methyl. In certain embodiments, at least one instance of $R^N$ is —CH$_2$F. In certain embodiments, at least one instance of $R^N$ is —CHF$_2$. In certain embodiments, at least one instance of $R^N$ is —CF$_3$. In certain embodiments, at least one instance of $R^N$ is ethyl. In certain embodiments, at least one instance of $R^N$ is propyl. In certain embodiments, at least one instance of $R^N$ is butyl. In certain embodiments, at least one instance of $R^N$ is pentyl. In certain embodiments, at least one instance of $R^N$ is hexyl. In certain embodiments, at least one instance of $R^N$ is Bn. In certain embodiments, at least one instance of $R^N$ is a nitrogen protecting group. In certain embodiments, at least one instance of $R^N$ is Bn, Boc, Cbz, Fmoc, trifluoroacetyl, triphenylmethyl, acetyl, or Ts.

Formula (VI) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is unsubstituted methyl. In certain embodiments, $R^B$ is substituted methyl. In certain embodiments, $R^B$ is —CH$_2$F. In certain embodiments, $R^B$ is —CHF$_2$. In certain embodiments, $R^B$ is —CF$_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is Bn. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

Formula (VI) includes Ring B that includes moieties $X^A$, $X^B$, and $X^C$ in the ring system. In certain embodiments, $X^A$ is $CR^X$, and each of $X^B$ and $X^C$ is N. In certain embodiments, $X^A$ is CH, and each of $X^B$ and $X^C$ is N. In certain embodiments, $X^B$ is $CR^X$, and each of $X^A$ and $X^C$ is N. In certain embodiments, $X^B$ is CH, and each of $X^A$ and $X^C$ is N. In certain embodiments, $X^C$ is $CR^X$, and each of $X^A$ and $X^B$ is N. In certain embodiments, $X^C$ is CH, and each of $X^A$ and $X^B$ is N. In certain embodiments, $X^A$ is N, and each of $X^B$ and $X^C$ is independently $CR^X$. In certain embodiments, $X^A$ is N, and each of $X^B$ and $X^c$ is CH. In certain embodiments, $X^B$ is N, and each of $X^A$ and $X^C$ is independently $CR^X$. In certain embodiments, $X^B$ is N, and each of $X^A$ and $X^C$ is CH. In certain embodiments, $X^C$ is N, and each of $X^A$ and $X^B$ is independently $CR^X$. In certain embodiments, $X^C$ is N, and each of $X^A$ and $X^B$ is CH. In certain embodiments, each of $X^A$, $X^B$, and $X^C$ is independently $CR^X$. In certain embodiments, each of $X^A$, $X^B$, and $X^C$ is CH.

In certain embodiments, when $X^A$, $X^B$, or $X^C$ is $CR^X$, $R^X$ is H. In certain embodiments, $R^X$ is halogen. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is substituted alkyl. In certain embodiments, $R^X$ is unsubstituted alkyl. In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —CH$_3$. In certain embodiments, $R^X$ is substituted methyl. In certain embodiments, $R^X$ is —CH$_2$F. In certain embodiments, $R^X$ is —CHF$_2$. In certain embodiments, $R^X$ is —CF$_3$. In certain embodiments, $R^X$ is ethyl. In certain embodiments, $R^X$ is propyl. In certain embodiments, $R^X$ is butyl. In certain embodiments, $R^X$ is pentyl. In certain embodiments, $R^X$ is hexyl. In certain embodiments, $R^X$ is Bn. In certain embodiments, $R^X$ is substituted alkenyl. In certain embodiments, $R^X$ is unsubstituted alkenyl. In certain embodiments, $R^X$ is substituted alkynyl. In certain embodiments, $R^X$ is unsubstituted alkynyl. In certain embodiments, $R^X$ is substituted carbocyclyl, in certain embodiments, $R^X$ is unsubstituted carbocyclyl. In certain embodiments, $R^X$ is saturated carbocyclyl. In certain embodiments, $R^X$ is unsaturated carbocyclyl. In certain embodiments, $R^X$ is monocyclic carbocyclyl. In certain embodiments, $R^X$ is 3- to 7-membered, monocyclic carbocyclyl. In certain embodiments, $R^X$ is substituted heterocyclyl. In certain embodiments, $R^X$ is unsubstituted heterocyclyl. In certain embodiments, $R^X$ is saturated heterocyclyl. In certain embodiments, $R^X$ is unsaturated heterocyclyl. In certain embodiments, $R^X$ is heterocyclyl, wherein one, two, or three atoms in the heterocyclic ring system are independently selected from the group consisting of nitrogen, oxygen, and sulfur. In certain embodiments, $R^X$ is monocyclic heterocyclyl. In certain embodiments, $R^X$ is 3- to 7-membered, monocyclic heterocyclyl. In certain embodiments, $R^X$ is substituted aryl. In certain embodiments, $R^X$ is unsubstituted aryl. In certain embodiments, $R^X$ is 6- to 10-membered aryl. In certain embodiments, $R^X$ is substituted phenyl. In certain embodiments, $R^X$ is unsubstituted phenyl. In certain embodiments, $R^X$ is substituted heteroaryl. In certain embodiments, $R^X$ is unsubstituted heteroaryl. In certain embodiments, $R^X$ is heteroaryl, wherein one, two, three, or four atoms in the heteroaryl ring system are independently selected from the group consisting of nitrogen, oxygen, and sulfur. In certain embodiments, $R^X$ is monocyclic heteroaryl. In certain embodiments, $R^X$ is 5-membered, monocyclic heteroaryl. In certain embodiments, $R^X$ is 6-membered, monocyclic heteroaryl. In certain embodiments, $R^X$ is bicyclic heteroaryl, wherein the point of attachment may be on any atom of the bicyclic heteroaryl ring system, as valency permits. In certain embodiments, $R^X$ is —OR$^a$. In certain embodiments, $R^X$ is —OH. In certain embodiments, $R^X$ is —O(substituted or unsubstituted, $C_{1-6}$ alkyl). In certain embodiments, $R^X$ is —OMe. In certain embodiments, $R^X$ is —OEt. In certain embodiments, $R^X$ is —OPr. In certain embodiments, $R^X$ is —OBu. In certain embodiments, $R^X$ is —OBn. In certain embodiments, $R^X$ is —OPh. In certain embodiments, $R^X$ is —SR$^a$. In certain embodiments, $R^X$ is —SH. In certain embodiments, $R^X$ is —SMe. In certain embodiments, $R^X$ is —N(R$^a$)$_2$. In certain embodiments, $R^X$ is —NH$_2$. In certain embodiments, $R^X$ is —NHMe. In certain embodiments, $R^X$ is —NMe$_2$. In certain embodiments, $R^X$ is —CN. In certain embodiments, $R^X$ is —SCN. In certain embodiments, $R^X$ is —C(=NR$^a$)R$^a$, —C(=NR$^a$)OR$^a$, or —C(=NR$^a$)N(R$^a$)$_2$. In certain embodiments, $R^X$ is —C(=O)R$^a$ or —C(=O)OR$^a$. In certain embodiments, $R^X$ is —C(=O)N(R$^a$)$_2$. In certain embodiments, $R^X$ is —C(=O)NMe$_2$, —C(=O)NHMe, or —C(=O)NH$_2$. In certain embodiments, $R^X$ is —NO$_2$. In certain embodiments, $R^X$ is —NR$^a$C(=O)R$^a$, —NR$^a$C(=O)OR$^a$, or —NR$^a$C(=O)N(R$^a$)$_2$. In certain embodiments, $R^X$ is —OC(=O)R$^a$, —OC(=O)OR$^a$, or —OC(=O)N(R$^a$)$_2$.

Formula (VI) includes divalent moiety Y. In certain embodiments, Y is —O—. In certain embodiments, Y is —NR$^Y$—. In certain embodiments, Y is —NH—. In certain embodiments, Y is —NR$^Y$—; $X^A$ is $CR^X$; and $R^Y$ and $R^X$ of $X^A$ are joined to form a substituted or unsubstituted, monocyclic, 5- to 7-membered heterocyclic ring that is fused with Ring B, optionally wherein there are 2 or 3 nitrogen atoms, 0 or 1 oxygen atom, and 0 or 1 sulfur atom, in the monocyclic heterocyclic ring system. The monocyclic heterocyclic ring formed by joining $R^Y$ and $R^X$ of $X^A$ is fused with Ring B to form a substituted or unsubstituted, bicyclic, 9- to 11-membered ring. In certain embodiments, Y is —$NR^Y$—; $X^A$ is $CR^X$; and $R^Y$ and $R^X$ of $X^A$ are joined to form a substituted or unsubstituted, monocyclic, 6-membered heterocyclic ring that is fused with Ring B.

In certain embodiments, when Y is —$NR^Y$—, $R^Y$ is H. In certain embodiments, $R^Y$ is substituted acyl. In certain embodiments, $R^Y$ is unsubstituted acyl. In certain embodiments, $R^Y$ is acetyl. In certain embodiments, $R^Y$ is unsubstituted $C_{1-6}$ alkyl. In certain embodiments, $R^Y$ is substituted $C_{1-6}$ alkyl. In certain embodiments, $R^Y$ is $C_{1-6}$ alkyl substituted with at least one halogen. In certain embodiments, $R^Y$ is unsubstituted methyl. In certain embodiments, $R^Y$ is substituted methyl. In certain embodiments, $R^Y$ is —$CH_2F$. In certain embodiments, $R^Y$ is —$CHF_2$. In certain embodiments, $R^Y$ is —$CF_3$. In certain embodiments, $R^Y$ is ethyl. In certain embodiments, $R^Y$ is propyl. In certain embodiments, $R^Y$ is butyl. In certain embodiments, $R^Y$ is pentyl. In certain embodiments, $R^Y$ is hexyl. In certain embodiments, $R^Y$ is Bn. In certain embodiments, $R^Y$ is a nitrogen protecting group. In certain embodiments, $R^Y$ is Bn, Boc, Cbz, Fmoc, trifluoroacetyl, triphenylmethyl, acetyl, or Ts.

In Formula (VI), Ring B includes substituent $R^D$. In certain embodiments, $R^D$ is H. In certain embodiments, $R^D$ is halogen. In certain embodiments, $R^D$ is F. In certain embodiments, $R^D$ is Cl. In certain embodiments, $R^D$ is Br. In certain embodiments, $R^D$ is I (iodine). In certain embodiments, $R^D$ is substituted alkyl. In certain embodiments, $R^D$ is unsubstituted alkyl. In certain embodiments, $R^D$ is unsubstituted $C_{1-6}$ alkyl. In certain embodiments, $R^D$ is substituted $C_{1-6}$ alkyl. In certain embodiments, $R^D$ is $C_{1-6}$ alkyl substituted with at least one halogen. In certain embodiments, $R^D$ is —$CH_3$. In certain embodiments, $R^D$ is substituted methyl. In certain embodiments, $R^D$ is —$CH_2F$. In certain embodiments, $R^D$ is —$CHF_2$. In certain embodiments, $R^D$ is —$CF_3$. In certain embodiments, $R^D$ is ethyl. In certain embodiments, $R^D$ is propyl. In certain embodiments, $R^D$ is butyl. In certain embodiments, $R^D$ is pentyl. In certain embodiments, $R^D$ is hexyl. In certain embodiments, $R^D$ is Bn. In certain embodiments, $R^D$ is substituted alkenyl. In certain embodiments, $R^D$ is unsubstituted alkenyl. In certain embodiments, $R^D$ is substituted alkynyl. In certain embodiments, $R^D$ is unsubstituted alkynyl. In certain embodiments, $R^D$ is substituted carbocyclyl. In certain embodiments, $R^D$ is unsubstituted carbocyclyl. In certain embodiments, $R^D$ is saturated carbocyclyl. In certain embodiments, $R^D$ is unsaturated carbocyclyl. In certain embodiments, $R^D$ is monocyclic carbocyclyl. In certain embodiments, $R^D$ is 3- to 7-membered, monocyclic carbocyclyl. In certain embodiments, $R^D$ is substituted heterocyclyl. In certain embodiments, $R^D$ is unsubstituted heterocyclyl. In certain embodiments, $R^D$ is saturated heterocyclyl. In certain embodiments, $R^D$ is unsaturated heterocyclyl. In certain embodiments, $R^D$ is heterocyclyl, wherein one, two, or three atoms in the heterocyclic ring system are independently selected from the group consisting of nitrogen, oxygen, and sulfur. In certain embodiments, $R^D$ is monocyclic heterocyclyl. In certain embodiments, $R^D$ is 3- to 7-membered, monocyclic heterocyclyl. In certain embodiments, $R^D$ is substituted aryl. In certain embodiments, $R^D$ is unsubstituted aryl. In certain embodiments, $R^D$ is 6- to 10-membered aryl. In certain embodiments, $R^D$ is substituted phenyl. In certain embodiments, $R^D$ is unsubstituted phenyl. In certain embodiments, $R^D$ is substituted heteroaryl. In certain embodiments, $R^D$ is unsubstituted heteroaryl. In certain embodiments, $R^D$ is heteroaryl, wherein one, two, three, or four atoms in the heteroaryl ring system are independently selected from the group consisting of nitrogen, oxygen, and sulfur. In certain embodiments, $R^D$ is monocyclic heteroaryl. In certain embodiments, $R^D$ is 5-membered, monocyclic heteroaryl. In certain embodiments, $R^D$ is 6-membered, monocyclic heteroaryl. In certain embodiments, $R^D$ is bicyclic heteroaryl, wherein the point of attachment may be on any atom of the bicyclic heteroaryl ring system, as valency permits. In certain embodiments, $R^D$ is 9- or 10-membered, bicyclic heteroaryl. In certain embodiments, $R^D$ is —$OR^a$. In certain embodiments, $R^D$ is —OH. In certain embodiments, $R^D$ is —O(substituted or unsubstituted, $C_{1-6}$ alkyl). In certain embodiments, $R^D$ is —OMe. In certain embodiments, $R^D$ is —OEt. In certain embodiments, $R^D$ is —OPr. In certain embodiments, $R^D$ is —OBu. In certain embodiments, $R^D$ is —OBn. In certain embodiments, $R^D$ is —OPh. In certain embodiments, $R^D$ is —$SR^a$. In certain embodiments, $R^D$ is —SH. In certain embodiments, $R^D$ is —SMe. In certain embodiments, $R^D$ is —$N(R^a)_2$. In certain embodiments, $R^D$ is —$NH_2$. In certain embodiments, $R^D$ is —NHMe. In certain embodiments, $R^D$ is —$NMe_2$. In certain embodiments, $R^D$ is —CN. In certain embodiments, $R^D$ is —SCN. In certain embodiments, $R^D$ is —C($=NR^a$)$R^a$, —C($=NR^a$)$OR^a$, or —C($=NR^a$)$N(R^a)_2$. In certain embodiments, $R^D$ is —C($=$O)$R^a$ or —C($=$O)$OR^a$. In certain embodiments, $R^D$ is —C($=$O)$N(R^a)_2$. In certain embodiments, $R^D$ is —C($=$O)$NMe_2$, —C($=$O)NHMe, or —C($=$O)$NH_2$. In certain embodiments, $R^D$ is —$NO_2$. In certain embodiments, $R^D$ is —$NR^aC$($=$O)$R^a$, —$NR^aC$($=$O)$OR^a$, or —$NR^aC$($=$O)$N(R^a)_2$. In certain embodiments, $R^D$ is —OC($=$O)$R^a$, —OC($=$O)$OR^a$, or —OC($=$O)$N(R^a)_2$.

Formula (VI) includes Ring C that is unsubstituted (e.g., when m is 0) or substituted with one or more substituents $R^C$ (e.g., when m is 1, 2, 3, 4, or 5). In certain embodiments, Ring C is of the formula:

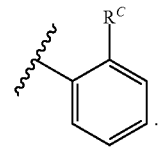

In certain embodiments, Ring C is of the formula:

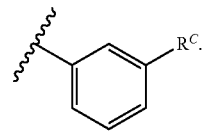

In certain embodiments, Ring C is of the formula:

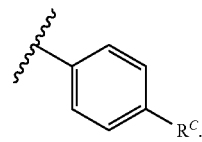

In certain embodiments, Ring C is of the formula:

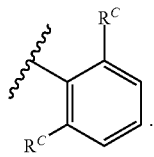

In certain embodiments, Ring C is of the formula:

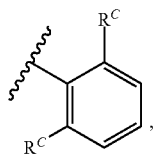

wherein each instance of $R^C$ is independently substituted or unsubstituted, $C_{1-6}$ alkyl. In certain embodiments, Ring C is of the formula:

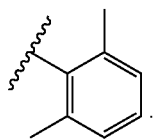 [SMILES: *c1c(C)cccc1C]

In certain embodiments, Ring C is of the formula:

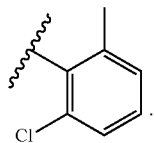 [SMILES: *c1c(C)cccc1Cl]

In certain embodiments, Ring C is of the formula:

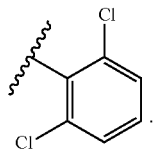

In certain embodiments, Ring C is of the formula:

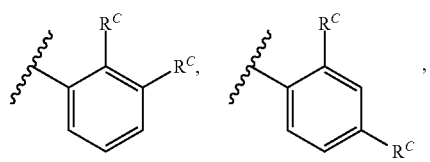

-continued

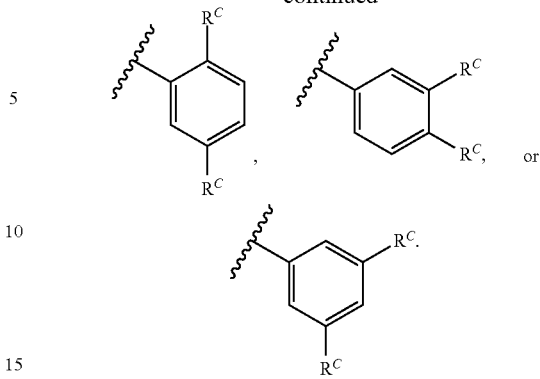

In certain embodiments, at least two instances of $R^C$ are different. In certain embodiments, all instances of $R^C$ are the same. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted alkyl. In certain embodiments, at least one instance of $R^C$ is unsubstituted alkyl. In certain embodiments, at least one instance of $R^C$ is unsubstituted $C_{1-6}$ alkyl. In certain embodiments, all instances of $R^C$ are unsubstituted $C_{1-6}$ alkyl. In certain embodiments, at least one instance of $R^C$ is substituted $C_{1-6}$ alkyl. In certain embodiments, at least one instance of $R^C$ is $C_{1-6}$ alkyl substituted with at least one halogen. In certain embodiments, at least one instance of $R^C$ is —CH$_3$. In certain embodiments, all instances of $R^C$ are —CH$_3$. In certain embodiments, at least one instance of $R^C$ is substituted methyl. In certain embodiments, at least one instance of $R^C$ is —CH$_2$F. In certain embodiments, at least one instance of $R^C$ is —CHF$_2$. In certain embodiments, at least one instance of $R^C$ is —CF$_3$. In certain embodiments, at least one instance of $R^C$ is ethyl. In certain embodiments, at least one instance of $R^C$ is propyl. In certain embodiments, at least one instance of $R^C$ is butyl. In certain embodiments, at least one instance of $R^C$ is pentyl. In certain embodiments, at least one instance of $R^C$ is hexyl. In certain embodiments, at least one instance of $R^C$ is Bn. In certain embodiments, each instance of $R^C$ is independently halogen (e.g., or substituted or unsubstituted, $C_{1-6}$ alkyl (e.g., unsubstituted $C_{1-6}$ alkyl (e.g., Me)). In certain embodiments, at least one instance of $R^C$ is substituted alkenyl. In certain embodiments, at least one instance of $R^C$ is unsubstituted alkenyl. In certain embodiments, at least one instance of $R^C$ is substituted alkynyl. In certain embodiments, at least one instance of $R^C$ is unsubstituted alkynyl. In certain embodiments, at least one instance of $R^C$ is substituted carbocyclyl. In certain embodiments, at least one instance of $R^C$ is unsubstituted carbocyclyl. In certain embodiments, at least one instance of $R^C$ is saturated carbocyclyl. In certain embodiments, at least one instance of $R^C$ is unsaturated carbocyclyl. In certain embodiments, at least one instance of $R^C$ is monocyclic carbocyclyl. In certain embodiments, at least one instance of $R^C$ is 3- to 7-membered, monocyclic carbocyclyl. In certain embodiments, at least one instance of $R^C$ is substituted heterocyclyl. In certain embodiments, at least one instance of $R^C$ is unsubstituted heterocyclyl. In certain embodiments, at least one instance of $R^C$ is saturated heterocyclyl. In certain embodiments, at least one instance of $R^C$ is unsaturated heterocyclyl. In certain embodiments, at least one instance of $R^C$ is heterocyclyl, wherein one, two, or three atoms in the heterocyclic ring system are independently selected from the group consisting of nitrogen, oxygen, and sulfur. In certain embodiments, at least one instance of $R^C$ is monocyclic heterocyclyl. In certain embodiments, at least one instance of $R^C$ is 3- to 7-membered, monocyclic heterocyclyl. In certain embodiments, at least one instance of $R^C$ is substituted aryl. In certain embodiments, at least one instance of $R^C$ is unsubstituted aryl. In certain embodiments, at least one instance of $R^C$ is 6- to 10-membered aryl. In certain embodiments, at least one instance of $R^C$ is substituted phenyl. In certain embodiments, at least one instance of $R^C$ is unsubstituted phenyl. In certain embodiments, at least one instance of $R^C$ is substituted heteroaryl. In certain embodiments, at least one instance of $R^C$ is unsubstituted heteroaryl. In certain embodiments, at least one instance of $R^C$ is heteroaryl, wherein one, two, three, or four atoms in the heteroaryl ring system are independently selected from the group consisting of nitrogen, oxygen, and sulfur. In certain embodiments, at least one instance of $R^C$ is monocyclic heteroaryl. In certain embodiments, at least one instance of $R^C$ is 5-membered, monocyclic heteroaryl. In certain embodiments, at least one instance of $R^C$ is 6-membered, monocyclic heteroaryl. In certain embodiments, at least one instance of $R^C$ is bicyclic heteroaryl, wherein the point of attachment may be on any atom of the bicyclic heteroaryl ring system, as valency permits. In certain embodiments, at least one instance of $R^C$ is 9- or 10-membered, bicyclic heteroaryl. In certain embodiments, at least one instance of $R^C$ is —$OR^a$. In certain embodiments, at least one instance of $R^C$ is —OH. In certain embodiments, at least one instance of $R^C$ is —O(substituted or unsubstituted, $C_{1-6}$ alkyl). In certain embodiments, at least one instance of $R^C$ is —OMe. In certain embodiments, at least one instance of $R^C$ is —OEt. In certain embodiments, at least one instance of $R^C$ is —OPr. In certain embodiments, at least one instance of $R^C$ is —OBu. In certain embodiments, at least one instance of $R^C$ is —OBn. In certain embodiments, at least one instance of $R^C$ is —OPh. In certain embodiments, at least one instance of $R^C$ is —$SR^a$. In certain embodiments, at least one instance of $R^C$ is —SH. In certain embodiments, at least one instance of $R^C$ is —SMe. In certain embodiments, at least one instance of $R^C$ is —N$(R^a)_2$. In certain embodiments, at least one instance of $R^C$ is —$NH_2$. In certain embodiments, at least one instance of $R^C$ is —NHMe. In certain embodiments, at least one instance of $R^C$ is —$NMe_2$. In certain embodiments, at least one instance of $R^C$ is —CN. In certain embodiments, at least one instance of $R^C$ is —SCN. In certain embodiments, at least one instance of $R^C$ is —C(=$NR^a$)$R^a$, —C(=$NR^a$)$OR^a$, or —C(=$NR^a$)N$(R^a)_2$. In certain embodiments, at least one instance of $R^C$ is —C(=O)$R^a$ or —C(=O)$OR^a$. In certain embodiments, at least one instance of $R^C$ is —C(=O)N$(R^a)_2$. In certain embodiments, at least one instance of $R^C$ is —C(=O)$NMe_2$, —C(=O)NHMe, or —C(=O)$NH_2$. In certain embodiments, at least one instance of $R^C$ is —$NO_2$. In certain embodiments, at least one instance of $R^C$ is —$NR^a$C(=O)$R^a$, —$NR^a$C(=O)$OR^a$, or —$NR^a$C(=O)N$(R^a)_2$. In certain embodiments, at least one instance of $R^C$ is —OC(=O)$R^a$, —OC(=O)$OR^a$, or —OC(=O)N$(R^a)_2$.

In certain embodiments, m is 0. In certain embodiments, m is 1. In certain embodiments, m is 2. In certain embodiments, m is 3. In certain embodiments, m is 4. In certain embodiments, m is 5.

In certain embodiments, in is 2; and each instance of $R^C$ is halogen (e.g., Cl). In certain embodiments, m is 2; and each instance of $R^C$ is substituted or unsubstituted, $C_{1-6}$ alkyl. In certain embodiments, m is 2; and each instance of $R^C$ is methyl. In certain embodiments, m is 2; and each instance of $R^C$ is independently halogen (e.g., Cl) or substituted or unsubstituted, $C_{1-6}$ alkyl (e.g., unsubstituted $C_{1-6}$ alkyl (e.g., Me)).

In certain embodiments, the compound of Formula (VI) is of the formula:

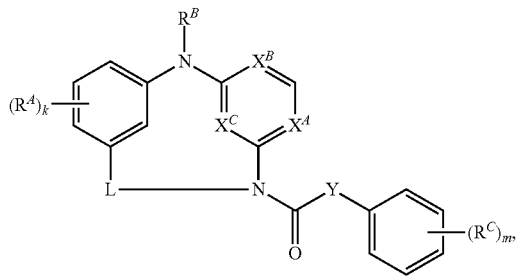

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

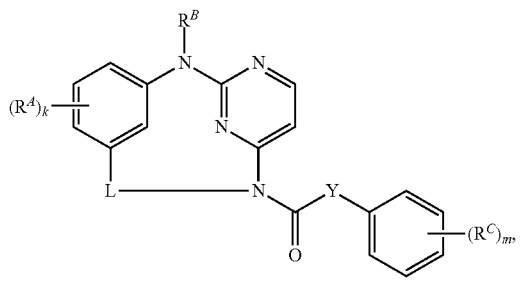

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

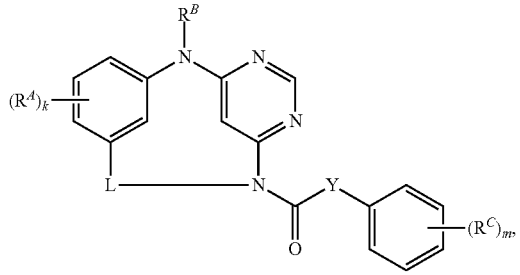

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

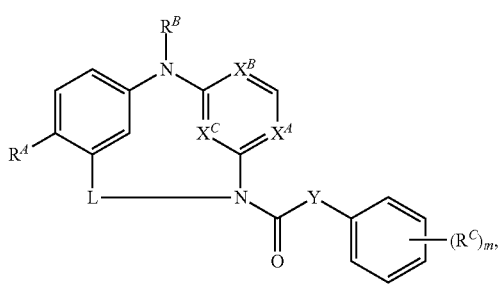

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

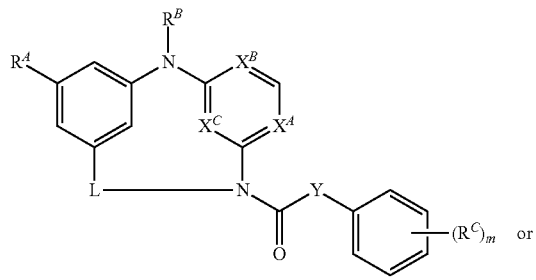  or

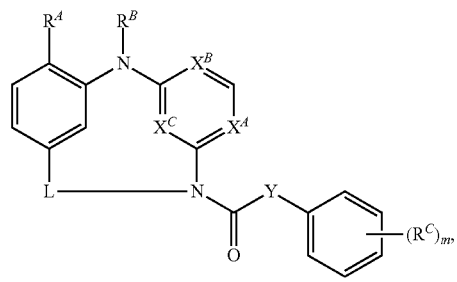

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

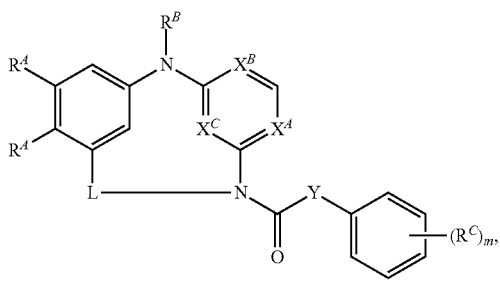

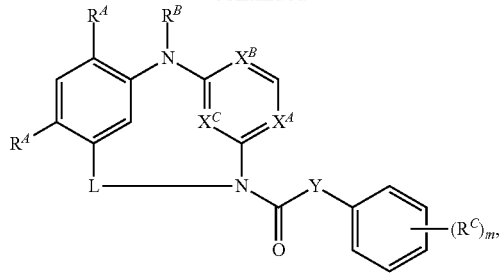

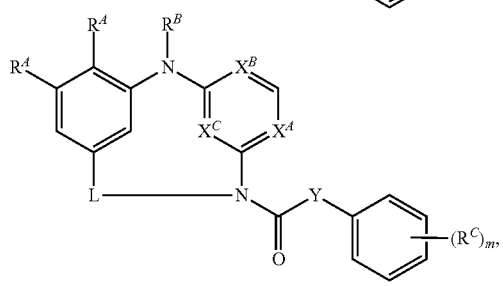

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

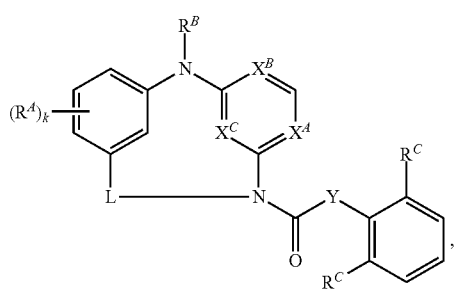

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

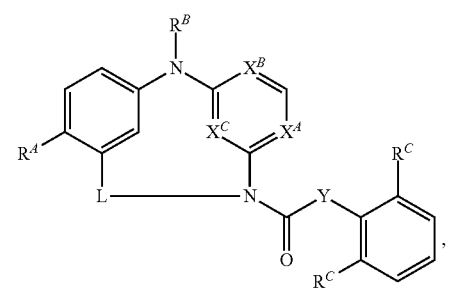

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

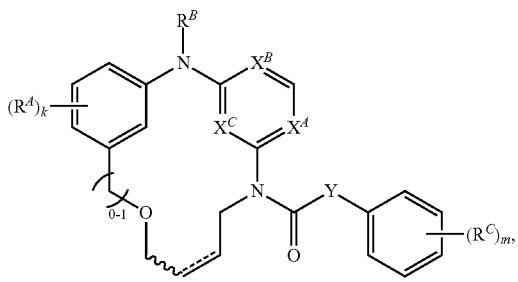

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

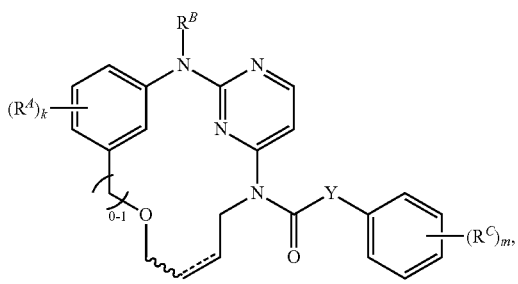

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

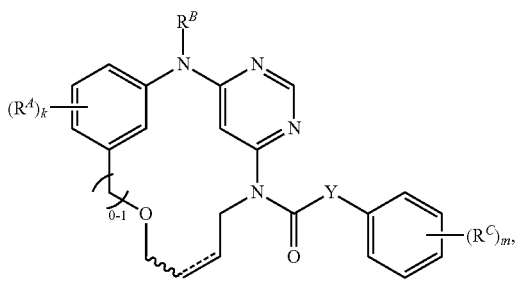

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

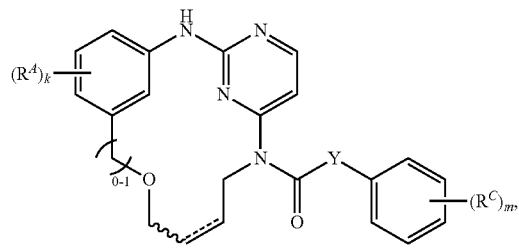

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

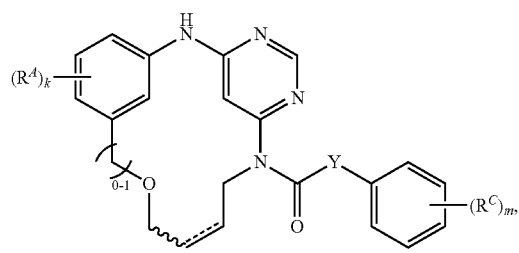

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

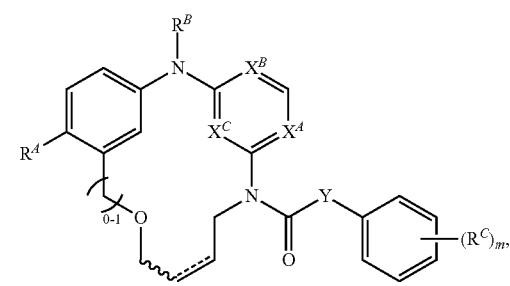

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

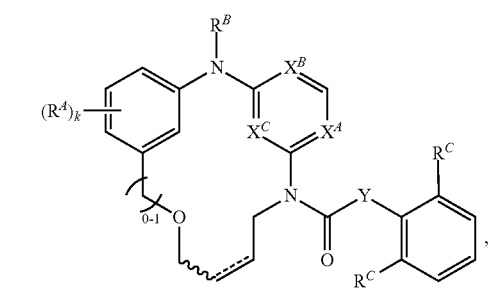

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

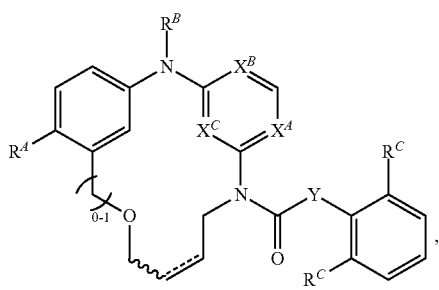

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

(VI-1 or HG-10-32-01)

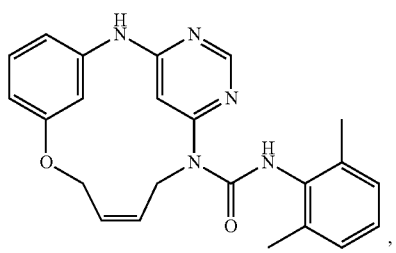

(VI-2 or HG-10-86-01)

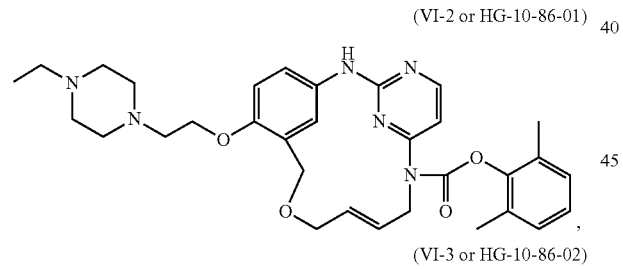

(VI-3 or HG-10-86-02)

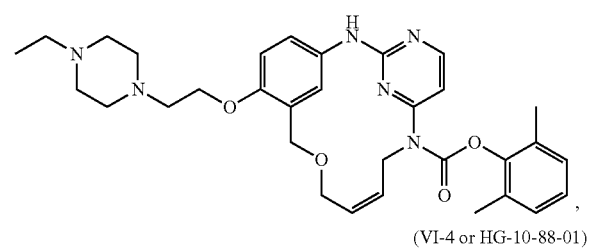

(VI-4 or HG-10-88-01)

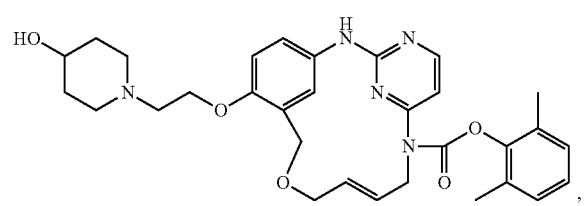

(VI-5 or HG-10-88-02)

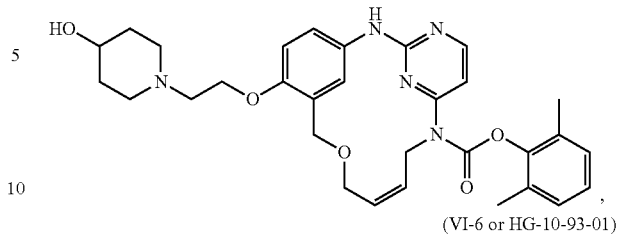

(VI-6 or HG-10-93-01)

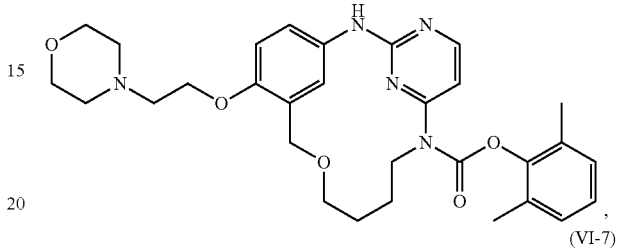

(VI-7)

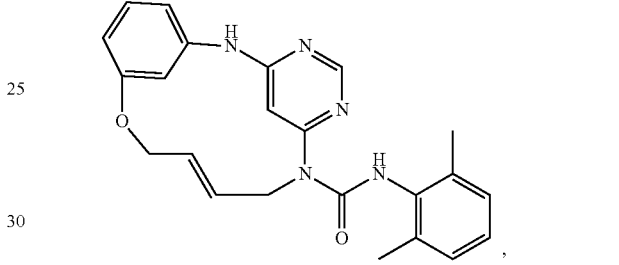

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

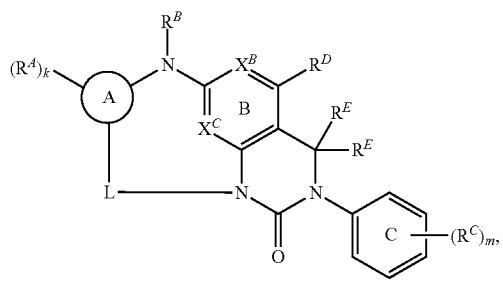

or a pharmaceutically acceptable salt, solvate, hydrate, polymorph, co-crystal, tautomer, stereoisomer, isotopically labeled derivative, or prodrug thereof; wherein each instance of $R^E$ is independently hydrogen, halogen, or substituted or unsubstituted, $C_{1-6}$ alkyl. In certain embodiments, the two instances of $R^E$ are the same. In certain embodiments, the two instances of $R^E$ are not the same. In certain embodiments, at least one instance of $R^E$ is hydrogen. In certain embodiments, each instance of $R^E$ is hydrogen. In certain embodiments, at least one instance of $R^E$ is halogen (e.g., F, Cl, Br, or I). In certain embodiments, at least one instance of $R^E$ is substituted or unsubstituted, $C_{1-6}$ alkyl. In certain embodiments, at least one instance of $R^E$ is Me. In certain embodiments, at least one instance of $R^E$ is substituted methyl (e.g., —$CF_3$ or Bn), Et, substituted ethyl (e.g., perfluoroethyl), Pr, substituted propyl (e.g., perfluoropropyl), Bu, or substituted butyl (e.g., perfluorobutyl).

In certain embodiments, the compound of Formula (VI) is of the formula:

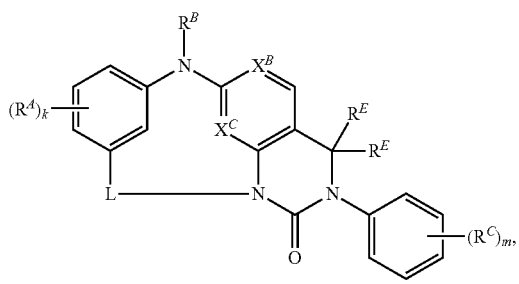

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

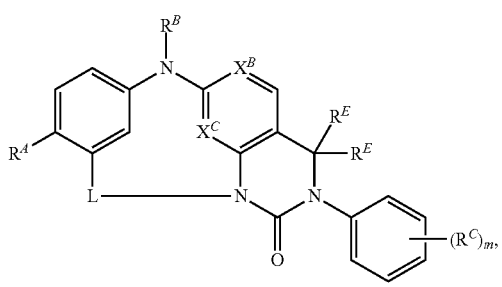

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

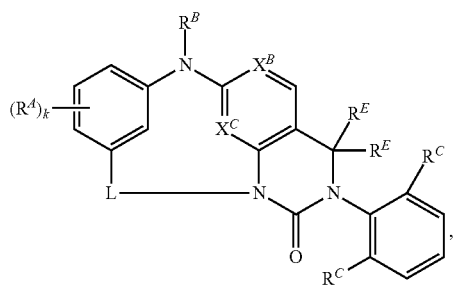

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

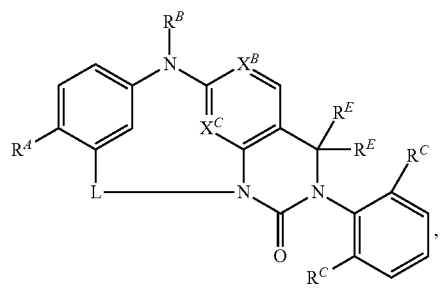

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

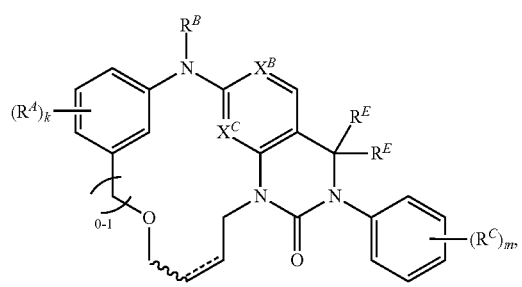

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

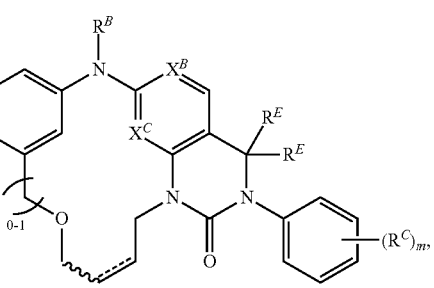

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

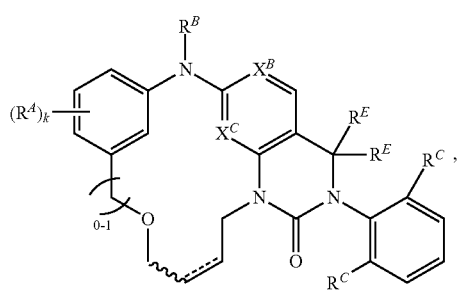

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

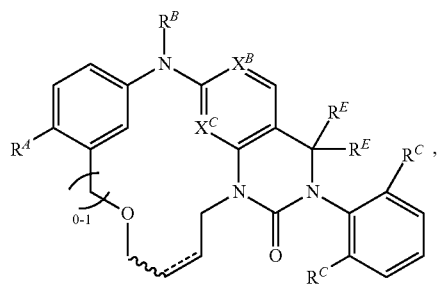

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

(YKL-05-120)

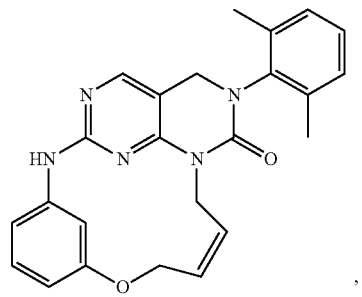

(YKL-05-200-1)

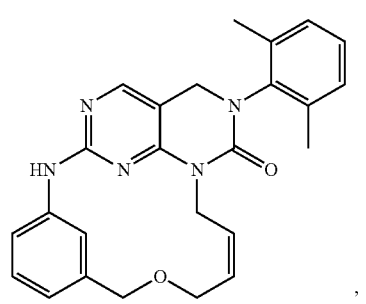

(YKL-05-200-2)

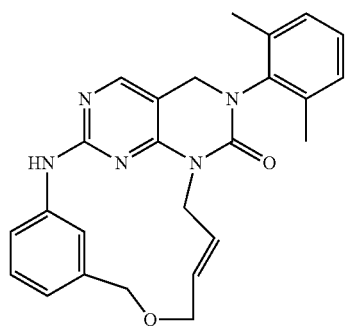

(YKL-05-201-1)

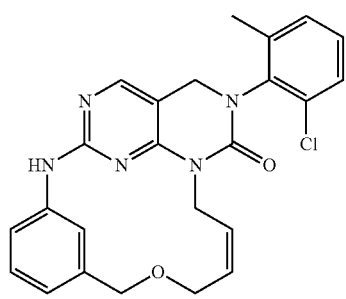

(YKL-05-201-2)

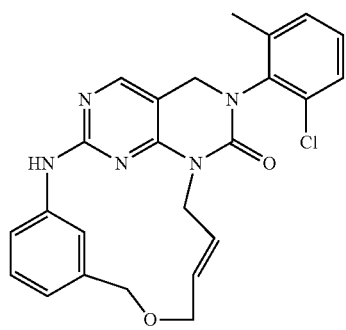

(YKL-05-202-1)

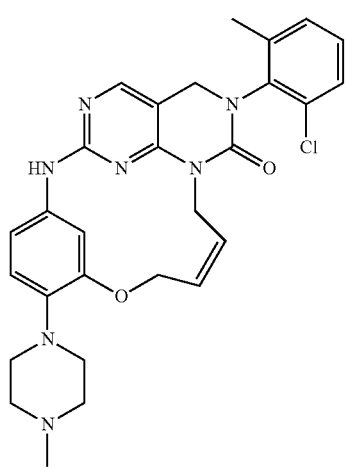

-continued (YKL-05-202-2)

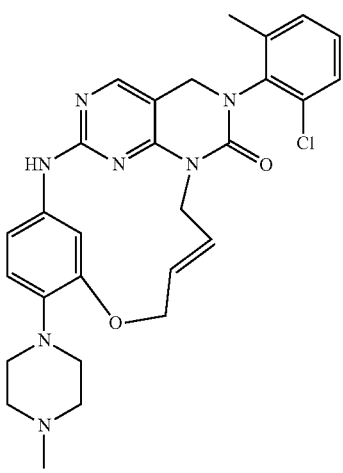

, (YKL-05-203-1)

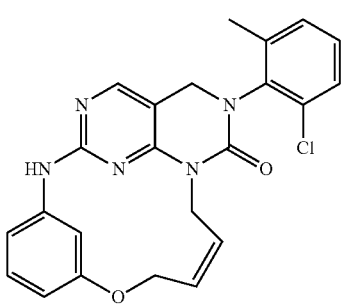

, (YKL-05-203-2)

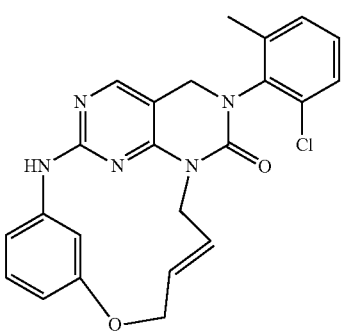

, (YKL-05-204-1)

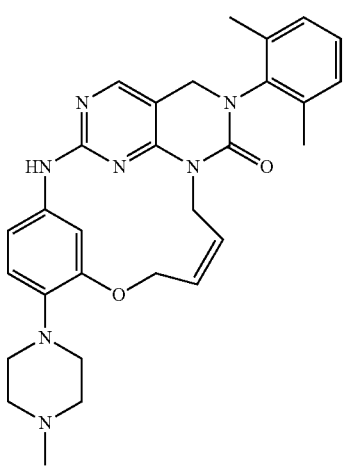

,

-continued (YKL-05-204-2)

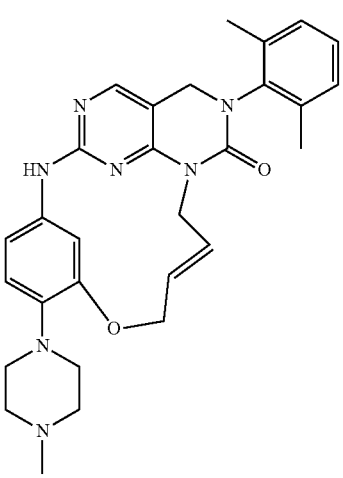

, (YKL-05-205)

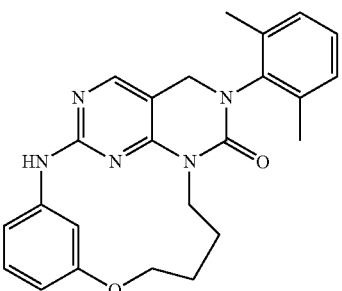

, or a pharmaceutically acceptable salt, solvate, hydrate, polymorph, co-crystal, tautomer, stereoisomer, isotopically labeled derivative, or prodrug thereof.

In certain embodiments, the compound of Formula (VI) is YKL-05-205, or a pharmaceutically acceptable salt, solvate, hydrate, polymorph, co-crystal, tautomer, stereoisomer, isotopically labeled derivative, or prodrug thereof.

In certain embodiments, a SIK inhibitor for use in the invention described herein is a compound of Formula (I), or a pharmaceutically acceptable salt, solvate, hydrate, polymorph, co-crystal, tautomer, stereoisomer, isotopically labeled derivative, or prodrug thereof (e.g., a pharmaceutically acceptable salt thereof).

In certain embodiments, a SIK inhibitor for use in the invention described herein is a compound of Formula (II), or a pharmaceutically acceptable salt, solvate, hydrate, polymorph, co-crystal, tautomer, stereoisomer, isotopically labeled derivative, or prodrug thereof (e.g., a pharmaceutically acceptable salt thereof).

In certain embodiments, a SIK inhibitor for use in the invention described herein is a compound of Formula (III), or a pharmaceutically acceptable salt, solvate, hydrate, polymorph, co-crystal, tautomer, stereoisomer, isotopically labeled derivative, or prodrug thereof (e.g., a pharmaceutically acceptable salt thereof).

In certain embodiments, a SIK inhibitor for use in the invention described herein is a compound of Formula (IV), or a pharmaceutically acceptable salt, solvate, hydrate, polymorph, co-crystal, tautomer, stereoisomer, isotopically labeled derivative, or prodrug thereof (e.g., a pharmaceutically acceptable salt thereof).

In certain embodiments, a SIK inhibitor for use in the invention described herein is a compound of Formula (V), or a pharmaceutically acceptable salt, solvate, hydrate, polymorph, co-crystal, tautomer, stereoisomer, isotopically labeled derivative, or prodrug thereof (e.g., a pharmaceutically acceptable salt thereof).

In certain embodiments, a SIK inhibitor for use in the invention described herein is a compound of Formula (VI), or a pharmaceutically acceptable salt, solvate, hydrate, polymorph, co-crystal, tautomer, stereoisomer, isotopically labeled derivative, or prodrug thereof (e.g., a pharmaceutically acceptable salt thereof).

The SIK inhibitors described herein may be able to bind a SIK. In certain embodiments, the SIK inhibitor covalently binds to a SIK. In certain embodiments, the SIK inhibitor non-covalently binds to a SIK. In certain embodiments, the SIK inhibitor reversibly binds to a SIK. In certain embodiments, the SIK inhibitor non-reversibly binds to the SIK. In certain embodiments, the SIK inhibitor modulates (e.g., inhibit) the activity (e.g., aberrant activity, such as increased activity) of a SIK. In certain embodiments, the SIK inhibitor inhibits the activity of a SIK. The inhibition of SIK may be in the context of a disease associated with aberrant or increased SIK activity.

The binding affinity of a SIK inhibitor described herein to a SIK may be measured by the dissociation constant ($K_d$) value of an adduct of the SIK inhibitor and the SIK using methods known in the art (e.g., isothermal titration calorimetry (ITC)). In certain embodiments, the adduct comprises the SIK inhibitor and the SIK, which are bound (e.g., non-covalently bound) to each other. In certain embodiments, the $K_d$ value of the adduct is not more than about 100 μM, not more than about 10 μM, not more than about 1 μM, not more than about 100 nM, not more than about 10 nM, or not more than about 1 nM. In certain embodiments, the $K_d$ value of the adduct is at least about 1 nM, at least about 10 nM, at least about 100 nM, at least about 1 μM, at least about 10 μM, or at least about 100 μM. Combinations of the above-referenced ranges are also within the scope of the disclosure.

In certain embodiments, the activity of a SIK is inhibited by a SIK inhibitor described herein. The inhibition of the activity of a SIK by a SIK inhibitor described herein may be measured by the half maximal inhibitory concentration ($IC_{50}$) value of the SIK inhibitor when the SIK inhibitor, or a pharmaceutical composition thereof, is contacted with the SIK. The $IC_{50}$ values may be obtained using methods known in the art (e.g., by a competition binding assay). In certain embodiments, the $IC_{50}$ value of a SIK inhibitor described herein is not more than about 1 mM, not more than about 100 μM, not more than about 10 μM, not more than about 1 μM, not more than about 100 nM, not more than about 10 nM, or not more than about 1 nM. In certain embodiments, the $IC_{50}$ value of a SIK inhibitor described herein is at least about 1 nM, at least about 10 nM, at least about 100 nM, at least about 1 μM, at least about 10 μM, at least about 100 μM, or at least about 1 mM. Combinations of the above-referenced ranges are also within the scope of the disclosure.

The SIK inhibitors described herein may selectively modulate the activity of a SIK. In certain embodiments, the SIK inhibitors selectively inhibit the activity of a SIK, compared to a different SIK or a protein kinase that is not a SIK.

The selectivity of a SIK inhibitor described herein in inhibiting the activity of a first SIK over a second SIK or a protein kinase that is not a SIK may be measured by the quotient of the $IC_{50}$ value of the SIK inhibitor in inhibiting the activity of the second SIK or the protein kinase that is not a SIK over the $IC_{50}$ value of the SIK inhibitor in inhibiting the activity of the first SIK. The selectivity of a SIK inhibitor described herein in modulating the activity of a first SIK over a second SIK or a protein kinase that is not a SIK may also be measured by the quotient of the $K_d$ value of an adduct of the SIK inhibitor and the second SIK or the protein kinase that is not a SIK over the $K_d$ value of an adduct of the SIK inhibitor and the first SIK. In certain embodiments, the selectivity is at least about 2-fold, at least about 3-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, the SIK inhibitors are selective for SIK2 over SIK1 and SIK3. In certain embodiments, the SIK inhibitors are selective for SIK3 over SIK1 and SIK2. In certain embodiments, the SIK inhibitors are selective for SIK2 and SIK3 over SIK1.

Pharmaceutical Compositions, Kits, and Administration

The present disclosure provides pharmaceutical compositions comprising a SIK inhibitor, or a pharmaceutically acceptable salt thereof, and optionally a pharmaceutically acceptable excipient. The pharmaceutical compositions may be useful for treating osteoporosis, preventing osteoporosis, increasing the function of osteocytes, increasing the number of osteoblasts, increasing the activity of osteoblasts, inhibiting the resorption of a bone, decreasing the number of osteoclasts, inhibiting the activity of osteoclasts, increasing the mass of a bone, down-regulating the expression of the gene SOST, inhibiting the activity of sclerostin, and/or reducing the production of sclerostin in a subject in need thereof.

In certain embodiments, the subject is an animal. The subject may be of either sex and may be at any stage of development. In certain embodiments, the subject is a human. In certain embodiments, the subject is a non-human animal. In certain embodiments, the subject is a mammal. In certain embodiments, the subject is a non-human mammal.

In certain embodiments, the osteocyte is in vitro. In certain embodiments, the osteocyte is ex vivo. In certain embodiments, the osteocyte is in vivo.

Pharmaceutical compositions described herein can be prepared by any method known in the art of pharmacology. In general, such preparatory methods include bringing the SIK inhibitor described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), polyvinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a SIK inhibitor described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the SIK inhibitor in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/vv) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

SIK inhibitors provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The SIK inhibitors and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the SIK inhibitor or pharmaceutical composition described herein is suitable for topical administration to the eye of a subject.

In certain embodiments, the SIK inhibitor described herein is provided in an effective amount in the pharmaceutical composition. In certain embodiments, the effective amount is a therapeutically effective amount. In certain embodiments, a therapeutically effective amount is an amount effective for treating osteoporosis. In certain embodiments, a therapeutically effective amount is an amount effective for both treating osteoporosis and inhibiting SIK (e.g., inhibiting the activity of SIK and/or reducing the production of SIK). In certain embodiments, a therapeutically effective amount is an amount effective for increasing the formation of a bone (e.g., increasing the mass of the bone), or inhibiting the resorption of the bone, or both. In certain embodiments, the effective amount is a prophylactically effective amount. In certain embodiments, the effective amount is an amount effective for inhibiting the activity of a SIK by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a SIK by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a SIK by a range between a percentage described in this paragraph and another percentage described in this paragraph, inclusive.

When a property (e.g., the activity of a SIK, activity of osteoclasts, activity of sclerostin, or resorption of a bone) is inhibited, the property is inhibited by at least 10%, at least 20%, at least 30%, at least 40%, at least 50%, at least 60%, at least 70%, at least 80%, at least 90%, or at least 98%.

When a production (e.g., the production of SIK or sclerostin) is reduced, the production is reduced by at least 10%, at least 20%, at least 30%, at least 40%, at least 50%, at least 60%, at least 70%, at least 80%, at least 90%, or at least 98%.

The exact amount of a SIK inhibitor required to achieve an effective amount will vary from subject to subject, depending, for example, on species, age, and general condition of a subject, severity of the side effects or disorder, identity of the particular SIK inhibitor, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A SIK inhibitor or composition, as described herein, can be administered in combination with one or more additional pharmaceutical agents (e.g., therapeutically and/or prophylactically active agents that are different from the SIK inhibitors described herein) useful in treating and/or preventing osteoporosis. The SIK inhibitors or compositions can be administered in combination with additional pharmaceutical agents. In certain embodiments, the additional pharmaceutical agents improve the activity of the SIK inhibitor (e.g., potency and/or efficacy in treating osteoporosis, preventing osteoporosis, increasing the function of osteocytes, increasing the number of osteoblasts, increasing the activity of osteoblasts, inhibiting the resorption of a bone, decreasing the number of osteoclasts, inhibiting the activity of osteoclasts, increasing the mass of a bone, down-regulating the expression of the gene SOST, inhibiting the activity of sclerostin, reducing the production of sclerostin, down-regulating the expression of the gene TNFSF11, inhibiting the activity of receptor activator of nuclear factor kappa-B ligand (RANKL), inhibiting the activity of SIK, inhibiting the activity of Src, and/or inhibiting the activity of CSF1R, in a subject in need thereof). In certain embodiments, the additional pharmaceutical agents improve bioavailability, improve safety, reduce drug resistance, reduce and/or modify metabolism, inhibit excretion, and/or modify distribution of the SIK inhibitor in a subject in need thereof. It will also be appreciated that the therapy employed may achieve a desired effect for the same disorder, and/or it may achieve different effects. In certain embodiments, a pharmaceutical composition described herein including a SIK inhibitor described herein and an additional pharmaceutical agent shows a synergistic effect that is absent in a pharmaceutical composition including one of the SIK inhibitor and the additional pharmaceutical agent, but not both.

The SIK inhibitor or composition can be administered concurrently with, prior to, or subsequent to one or more additional pharmaceutical agents, which may be useful as, e.g., combination therapies in treating osteoporosis. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing osteoporosis. In certain embodiments, the additional pharmaceutical agent is a pharmaceutical agent approved by a regulatory agency (e.g., the US FDA) for treating and/or preventing osteoporosis. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the SIK inhibitor described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is a binder or inhibitor of SIK. In certain embodiments, the additional pharmaceutical agent is a Src inhibitor (e.g., KX2-391, bosutinib, saracatinib, PP1, PP2, quercetin, dasatinib, NVP-BHG712, SU6656, or a pharmaceutically acceptable salt, solvate, hydrate, polymorph, co-crystal, tautomer, stereoisomer, isotopically labeled derivative, or prodrug thereof; or a combination thereof). In certain embodiments, the additional pharmaceutical agent is a CSF1R inhibitor (e.g., GW2580, BLZ945, pexidartinib (PLX3397), linifanib (ABT-869), OSI-930, CEP-32496, AZD6495, JNJ-28312141, or a pharmaceutically acceptable salt, solvate, hydrate, polymorph, co-crystal, tautomer, stereoisomer, isotopically labeled derivative, or prodrug thereof; or a combination thereof. Further examples of the additional pharmaceutical agents include, but are not limited to, anti-proliferative agents, anti-angiogenesis agents, cardiovascular agents, cholesterol-lowering agents, anti-diabetic agents, and anti-allergic agents. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine SIK inhibitors), modulators of protein stability (e.g., proteasome inhibitors), Hsp90 inhibitors, glucocorticoids, all-trans retinoic acids, and other agents that promote differentiation. In certain embodiments, the SIK inhibitors described herein or pharmaceutical compositions can be administered in combination with an anti-cancer therapy including, but not limited to, surgery, radiation therapy, and chemotherapy.

Also encompassed by the disclosure are kits (e.g., pharmaceutical packs). In certain embodiments, the kit comprises a pharmaceutical composition or compound (e.g., a SIK inhibitor; a SIK inhibitor and a Src inhibitor; or a SIK inhibitor and a CSF1R inhibitor) described herein, and instructions for using the pharmaceutical composition or compound. In certain embodiments, the kit further comprises a first container (e.g., a vial, ampule, bottle, syringe, and/or dispenser package, or other suitable container). In certain embodiments, the first container comprises the pharmaceutical composition or compound. In some embodiments, the kit further comprises a second container (e.g., a vial, ampule, bottle, syringe, and/or dispenser package, or other suitable container). In certain embodiments, the second container comprises a pharmaceutical excipient. In some embodiments, the pharmaceutical composition or compound described herein provided in the first container and the second container are combined to form one unit dosage form.

A kit described herein further includes instructions for using the compound or pharmaceutical composition. The kit may also include information as required by a regulatory agency, such as the U.S. Food and Drug Administration (FDA). In certain embodiments, the information included in the kits is prescribing information. In certain embodiments, the instructions include instructions for administering the SIK inhibitor to a subject in need of treatment of osteoporosis. In certain embodiments, the instructions include instructions for administering the SIK inhibitor to a subject in need of prevention of osteoporosis. In certain embodiments, the instructions include instructions for administering the SIK inhibitor to a subject in need of increasing the function of osteocytes. In certain embodiments, the instructions include instructions for administering the SIK inhibitor to a subject in need of increasing the number of osteoblasts. In certain embodiments, the instructions include instructions for administering the SIK inhibitor to a subject in need of increasing the activity of osteoblasts. In certain embodiments, the instructions include instructions for administering the SIK inhibitor to a subject in need of inhibiting the resorption of a bone. In certain embodiments, the instructions include instructions for administering the SIK inhibitor to a subject in need of decreasing the number of osteoclasts. In certain embodiments, the instructions include instructions for administering the SIK inhibitor to a subject in need of inhibiting the activity of osteoclasts. In certain embodiments, the instructions include instructions for administering the SIK inhibitor to a subject in need of increasing the mass of a bone. In certain embodiments, the instructions include instructions for administering the SIK inhibitor to a subject in need of down-regulating the expression of the gene SOST. In certain embodiments, the instructions include instructions for administering the SIK inhibitor to a subject in need of inhibiting the activity of sclerostin. In certain embodiments, the instructions include instructions for administering the SIK inhibitor to a subject in need of reducing the production of sclerostin. In certain embodiments, the instructions include instructions for administering the SIK inhibitor and Src inhibitor, the SIK inhibitor and CSF1R inhibitor, or the pharmaceutical composition to a subject in need of treatment of osteoporosis. In certain embodiments, the instructions include instructions for administering the SIK inhibitor and Src inhibitor, the SIK inhibitor and CSF1R inhibitor, or the pharmaceutical composition to a subject in need of prevention of osteoporosis. In certain embodiments, the instructions include instructions for administering the SIK inhibitor and Src inhibitor, the SIK inhibitor and CSF1R inhibitor, or the pharmaceutical composition to a subject in need of increasing the function of osteocytes. In certain embodiments, the instructions include instructions for administering the SIK inhibitor and Src inhibitor, the SIK inhibitor and CSF1R inhibitor, or the pharmaceutical composition to a subject in need of increasing the number of osteoblasts. In certain embodiments, the instructions include instructions for administering the SIK inhibitor and Src inhibitor, the SIK inhibitor and CSF1R inhibitor, or the pharmaceutical composition to a subject in need of increasing the activity of osteoblasts. In certain embodiments, the instructions include instructions for administering the SIK inhibitor and Src inhibitor, the SIK inhibitor and CSF1R inhibitor, or the pharmaceutical composition to a subject in need of inhibiting the resorption of a bone. In certain embodiments, the instructions include instructions for administering the SIK inhibitor and Src inhibitor, the SIK inhibitor and CSF1R inhibitor, or the pharmaceutical composition to a subject in need of decreasing the number of osteoclasts. In certain embodiments, the instructions include instructions for administering the SIK inhibitor and Src inhibitor, the SIK inhibitor and CSF1R inhibitor, or the pharmaceutical composition to a subject in need of inhibiting the activity of osteoclasts. In certain embodiments, the instructions include instructions for administering the SIK inhibitor and Src inhibitor, the SIK inhibitor and CSF1R inhibitor, or the pharmaceutical composition to a subject in need of increasing the mass of a bone. In certain embodiments, the instructions include instructions for administering the SIK inhibitor and Src inhibitor, the SIK inhibitor and CSF1R inhibitor, or the pharmaceutical composition to a subject in need of down-regulating the expression of the gene SOST. In certain embodiments, the instructions include instructions for administering the SIK inhibitor and Src inhibitor, the SIK inhibitor and CSF1R inhibitor, or the pharmaceutical composition to a subject in need of inhibiting the activity of sclerostin. In certain embodiments, the instructions include instructions for administering the SIK inhibitor and Src inhibitor, the SIK inhibitor and CSF1R inhibitor, or the pharmaceutical composition to a subject in need of reducing the production of sclerostin. A kit described herein may include one or more additional pharmaceutical agents described herein as a separate composition.

Methods of Treatment and Uses

The present disclosure further provides methods of using SIK inhibitors and pharmaceutical compositions for, for example, treating and/or preventing osteoporosis.

A role for the class IIa histone deacetylase HDAC5 as a negative regulator of MEF2C-driven SOST expression has been described both in vitro in Ocy454 osteocytic cells (17) and in vivo (18). Class IIa HDACs are uniquely endowed with N-terminal extensions that allow them to sense and transduce signaling information (19). When phosphorylated, class IIa HDACs are sequestered in the cytoplasm via binding to 14-3-3 proteins. When de-phosphorylated, they are able to translocate to the nucleus to inhibit MEF2-driven gene expression (20). PTH signaling in osteocytes may use both HDAC5 and the closely related family member HDAC4 to block MEF2C-driven SOST expression.

Like class IIa HDACs, cAMP-regulated transcriptional coactivators (CRTC) proteins shuttle from the cytoplasm to the nucleus where they function as CREB coactivators (21). Here, it is also shown that PTH-stimulated RANKL expression may require CRTC2. Both HDAC4/5 and CRTC2 are known substrates of SIK (21-24), and SIK3 deficiency in growth plate chondrocytes may increase nuclear HDAC4 and delays MEF2-driven chondrocyte hypertrophy (23). PTH signaling, via cAMP, may inhibit SIK2 cellular activity in osteocytes. SIK inhibition, both in vitro and in vivo, achieved via YKL-05-093, is sufficient to mimic many of the effects of PTH: HDAC4/5/CRTC2 dephosphorylation, SOST inhibition, and/or RANKL stimulation. A major arm of PTH signaling in osteocytes may involve SIK inhibition, as revealed by RNA-seq analysis of PTH− versus YKL-05-093-treated osteocytes. YKL-05-099 (25), an analog of YKL-05-093 more suitable to long-term in vivo use, was shown to boost osteoblast numbers, bone formation, and bone mass in mice. A novel PTH receptoricAMP/SIK/class IIa HDAC/CRTC axis may play a crucial role in osteocyte biology.

In one aspect, the present disclosure provides methods of treating osteoporosis in a subject in need thereof comprising administering to the subject in need thereof a therapeutically effective amount of a SIK inhibitor.

In one aspect, the present disclosure provides methods of treating osteoporosis in a subject in need thereof comprising administering to the subject in need thereof a therapeutically effective amount of a SIK inhibitor and Src inhibitor.

In one aspect, the present disclosure provides methods of treating osteoporosis in a subject in need thereof comprising administering to the subject in need thereof a therapeutically effective amount of a SIK inhibitor and CSF1R inhibitor.

In one aspect, the present disclosure provides methods of treating osteoporosis in a subject in need thereof comprising administering to the subject in need thereof a therapeutically effective amount of a pharmaceutical composition described herein.

In another aspect, the present disclosure provides methods of preventing osteoporosis in a subject in need thereof comprising administering to the subject in need thereof a prophylactically effective amount of a SIK inhibitor.

In another aspect, the present disclosure provides methods of preventing osteoporosis in a subject in need thereof comprising administering to the subject in need thereof a prophylactically effective amount of a SIK inhibitor and Src inhibitor.

In another aspect, the present disclosure provides methods of preventing osteoporosis in a subject in need thereof comprising administering to the subject in need thereof a prophylactically effective amount of a SIK inhibitor and CSF1R inhibitor.

In another aspect, the present disclosure provides methods of preventing osteoporosis in a subject in need thereof comprising administering to the subject in need thereof a prophylactically effective amount of a pharmaceutical composition described herein.

In another aspect, the present disclosure provides methods of increasing the function of osteocytes in a subject in need thereof comprising administering to the subject in need thereof an effective amount of a SIK inhibitor.

In another aspect, the present disclosure provides methods of increasing the function of osteocytes in a subject in need thereof comprising administering to the subject in need thereof an effective amount of a SIK inhibitor and Src inhibitor.

In another aspect, the present disclosure provides methods of increasing the function of osteocytes in a subject in need thereof comprising administering to the subject in need thereof an effective amount of a SIK inhibitor and CSF1R inhibitor.

In another aspect, the present disclosure provides methods of increasing the function of osteocytes in a subject in need thereof comprising administering to the subject in need thereof an effective amount of a pharmaceutical composition described herein.

In another aspect, the present disclosure provides methods of increasing the number of osteoblasts in a subject in need thereof comprising administering to the subject in need thereof an effective amount of a SIK inhibitor.

In another aspect, the present disclosure provides methods of increasing the number of osteoblasts in a subject in need thereof comprising administering to the subject in need thereof an effective amount of a SIK inhibitor and Src inhibitor.

In another aspect, the present disclosure provides methods of increasing the number of osteoblasts in a subject in need thereof comprising administering to the subject in need thereof an effective amount of a SIK inhibitor and CSF1R inhibitor.

In another aspect, the present disclosure provides methods of increasing the number of osteoblasts in a subject in need thereof comprising administering to the subject in need thereof an effective amount of a pharmaceutical composition described herein.

In another aspect, the present disclosure provides methods of increasing the activity of osteoblasts in a subject in need thereof comprising administering to the subject in need thereof an effective amount of a SIK inhibitor.

In another aspect, the present disclosure provides methods of increasing the activity of osteoblasts in a subject in need thereof comprising administering to the subject in need thereof an effective amount of a SIK inhibitor and Src inhibitor.

In another aspect, the present disclosure provides methods of increasing the activity of osteoblasts in a subject in need thereof comprising administering to the subject in need thereof an effective amount of a SIK inhibitor and CSF1R inhibitor.

In another aspect, the present disclosure provides methods of increasing the activity of osteoblasts in a subject in need thereof comprising administering to the subject in need thereof an effective amount of a pharmaceutical composition described herein.

In another aspect, the present disclosure provides methods of inhibiting the resorption of a bone in a subject in need thereof comprising administering to the subject in need thereof an effective amount of a SIK inhibitor.

In another aspect, the present disclosure provides methods of inhibiting the resorption of a bone in a subject in need thereof comprising administering to the subject in need thereof an effective amount of a SIK inhibitor and Src inhibitor.

In another aspect, the present disclosure provides methods of inhibiting the resorption of a bone in a subject in need thereof comprising administering to the subject in need thereof an effective amount of a SIK inhibitor and CSF1R inhibitor.

In another aspect, the present disclosure provides methods of inhibiting the resorption of a bone in a subject in need thereof comprising administering to the subject in need thereof an effective amount of a pharmaceutical composition described herein.

In another aspect, the present disclosure provides methods of decreasing the number of osteoclasts in a subject in need thereof comprising administering to the subject in need thereof an effective amount of a SIK inhibitor.

In another aspect, the present disclosure provides methods of decreasing the number of osteoclasts in a subject in need thereof comprising administering to the subject in need thereof an effective amount of a SIK inhibitor and Src inhibitor.

In another aspect, the present disclosure provides methods of decreasing the number of osteoclasts in a subject in need thereof comprising administering to the subject in need thereof an effective amount of a SIK inhibitor and CSF1R inhibitor.

In another aspect, the present disclosure provides methods of decreasing the number of osteoclasts in a subject in need thereof comprising administering to the subject in need thereof an effective amount of a pharmaceutical composition described herein.

In another aspect, the present disclosure provides methods of inhibiting the activity of osteoclasts in a subject in need thereof comprising administering to the subject in need thereof an effective amount of a SIK inhibitor.

In another aspect, the present disclosure provides methods of inhibiting the activity of osteoclasts in a subject in need thereof comprising administering to the subject in need thereof an effective amount of a SIK inhibitor and Src inhibitor.

In another aspect, the present disclosure provides methods of inhibiting the activity of osteoclasts in a subject in need thereof comprising administering to the subject in need thereof an effective amount of a SIK inhibitor and CSF1R inhibitor.

In another aspect, the present disclosure provides methods of inhibiting the activity of osteoclasts in a subject in need thereof comprising administering to the subject in need thereof an effective amount of a pharmaceutical composition described herein.

In another aspect, the present disclosure provides methods of increasing the mass of a bone in a subject in need thereof comprising administering to the subject in need thereof an effective amount of a SIK inhibitor.

In another aspect, the present disclosure provides methods of increasing the mass of a bone in a subject in need thereof comprising administering to the subject in need thereof an effective amount of a SIK inhibitor and Src inhibitor.

In another aspect, the present disclosure provides methods of increasing the mass of a bone in a subject in need thereof comprising administering to the subject in need thereof an effective amount of a SIK inhibitor and CSF1R inhibitor.

In another aspect, the present disclosure provides methods of increasing the mass of a bone in a subject in need thereof comprising administering to the subject in need thereof an effective amount of a pharmaceutical composition described herein.

In another aspect, the present disclosure provides methods of down-regulating the expression of the gene SOST in a subject in need thereof comprising administering to the subject in need thereof an effective amount of a SIK inhibitor.

In another aspect, the present disclosure provides methods of down-regulating the expression of the gene SOST in a subject in need thereof comprising administering to the subject in need thereof an effective amount of a SIK inhibitor and Src inhibitor.

In another aspect, the present disclosure provides methods of down-regulating the expression of the gene SOST in a subject in need thereof comprising administering to the subject in need thereof an effective amount of a SIK inhibitor and CSF inhibitor.

In another aspect, the present disclosure provides methods of down-regulating the expression of the gene SOST in a subject in need thereof comprising administering to the subject in need thereof an effective amount of a pharmaceutical composition described herein.

In another aspect, the present disclosure provides methods of inhibiting the activity of sclerostin in a subject in need thereof comprising administering to the subject in need thereof an effective amount of a SIK inhibitor.

In another aspect, the present disclosure provides methods of inhibiting the activity of sclerostin in a subject in need thereof comprising administering to the subject in need thereof an effective amount of a SIK inhibitor and Src inhibitor.

In another aspect, the present disclosure provides methods of inhibiting the activity of sclerostin in a subject in need thereof comprising administering to the subject in need thereof an effective amount of a SIK inhibitor and CSF1R inhibitor.

In another aspect, the present disclosure provides methods of inhibiting the activity of sclerostin in a subject in need thereof comprising administering to the subject in need thereof an effective amount of a pharmaceutical composition described herein.

In another aspect, the present disclosure provides methods of reducing the production of sclerostin in a subject in need thereof comprising administering to the subject in need thereof an effective amount of a SIK inhibitor.

In another aspect, the present disclosure provides methods of reducing the production of sclerostin in a subject in need thereof comprising administering to the subject in need thereof an effective amount of a SIK inhibitor and Src inhibitor.

In another aspect, the present disclosure provides methods of reducing the production of sclerostin in a subject in need thereof comprising administering to the subject in need thereof an effective amount of a SIK inhibitor and CSF1R inhibitor.

In another aspect, the present disclosure provides methods of reducing the production of sclerostin in a subject in need thereof comprising administering to the subject in need thereof an effective amount of a pharmaceutical composition described herein.

In another aspect, the present disclosure provides uses of SIK inhibitors in a method described herein.

In another aspect, the present disclosure provides uses of SIK inhibitors and Src inhibitors in a method described herein.

In another aspect, the present disclosure provides uses of SIK inhibitors and CSF1R inhibitors in a method described herein.

In another aspect, the present disclosure provides uses of a pharmaceutical composition described herein in a method described herein.

EXAMPLES

In order that the disclosure may be more fully understood, the following examples are set forth. The synthetic and biological examples described in this application are offered to illustrate the SIK inhibitors, pharmaceutical compositions, uses, and methods provided herein and are not to be construed in any way as limiting their scope.

Example 1. Preparation of the SIK Inhibitors

The SIK inhibitors described herein can be prepared according to the methods known in the art. For example, the SIK inhibitors can be prepared according to the methods described in U.S. provisional application, U.S. Ser. No. 62/358,524, filed Jul. 5, 2016, and international PCT application publications, WO 2016/014551, WO 2016/014542, and WO 2016/023014; the entire contents of each of which are incorporated herein by reference.

An exemplary synthesis of YKL-04-114 and YKL-05-093 is shown below. Commercially available trichloropyrimidine 1 was activated with sodium iodide to give iodomethyl pyrimidine 2, which was reacted with 2,6-dimethylaniline to give compound 3. Coupling of 3 with isocyanate provided compound 4 in good yield. Ring-closing reaction using tetrabutylammonium hydroxide afforded common intermediate 5 in good yield. By varying anilines and isocyanates used in the procedure described above, various analogues of 5 could be synthesized in multigram scale, which enables the generation of a focused library of inhibitors for structure-activity relationship study. Finally, acid assisted coupling of intermediate 5 with respective aniline tail gave rise to YKL-04-114 and YKL-05-093 in good yields. For in vitro studies, compounds were dissolved in DMSO at 10 mM stocks. For in vivo studies, YKL-05-093 was dissolved in PBS plus 25 mM HCl, and solvent was used as vehicle control.

Unless otherwise noted, reagents and solvents were used as received from commercial suppliers. Proton nuclear magnetic resonance spectra ($^1$H NMR) were obtained on Bruker AVANCE spectrometer at 400 MHz for proton. Spectra are given in ppm (δ) and coupling constants, J, are reported in Hertz. The solvent peak was used as the reference peak for proton spectra. LC-MS spectra were obtained on Agilent 1100 HPLC LC-MS ion trap electrospray ionization (ESI) mass spectrometer.

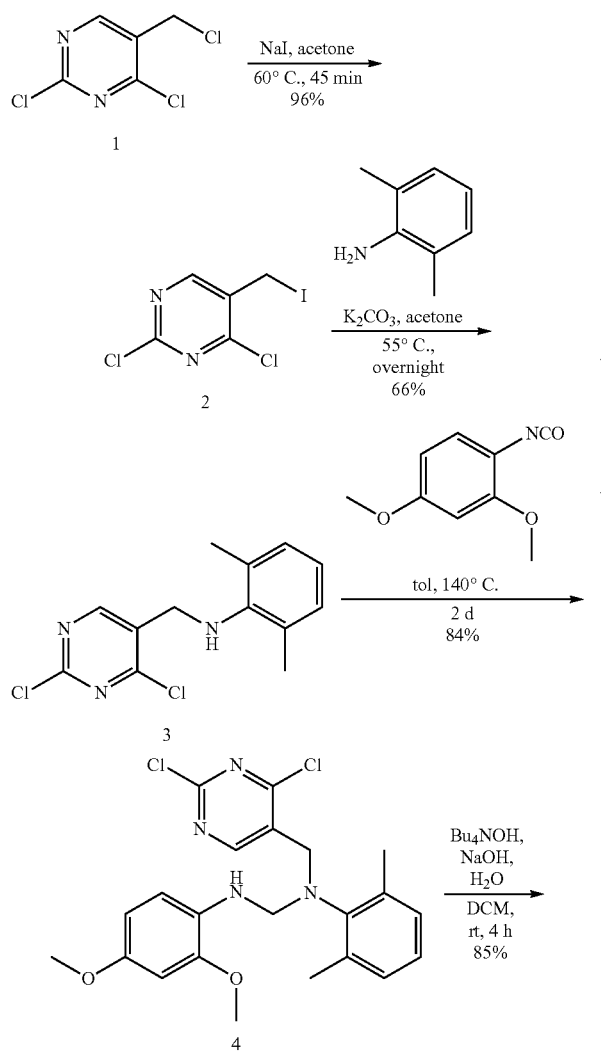

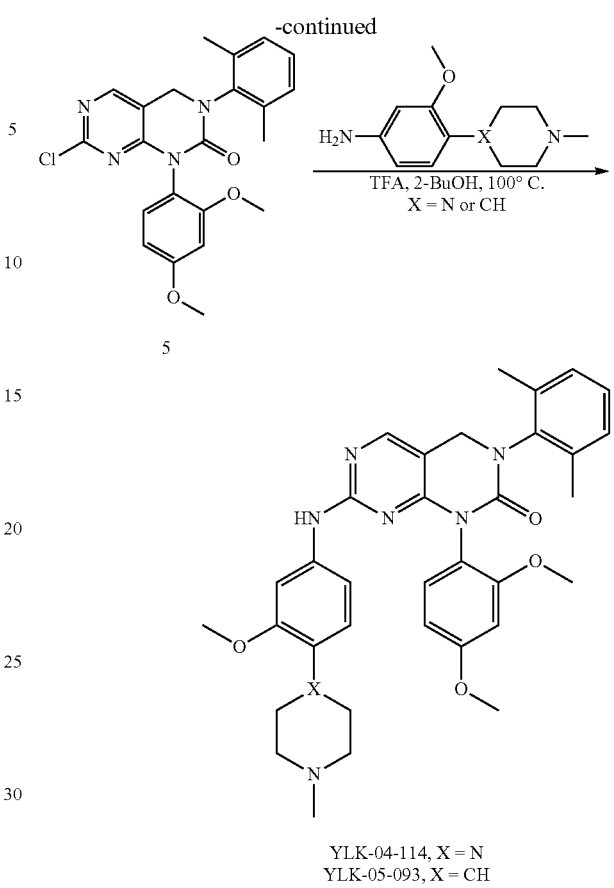

YLK-04-114, X = N
YLK-05-093, X = CH 2,4-dichloro-5-(iodomethyl)pyrimidine (2)

A mixture of 2,4-dichloro-5-(chloromethyl)pyrimidine (15.0 g, 76.0 mmol), NaI (13.7 g, 91.4 mmol) in acetone was stirred at 60° C. for 45 min. The resulting precipitate (NaCl) was removed by filtration and washed with acetone. The combined filtrate was concentrated to give light yellow solid, which was purified by column chromatography on silica gel (eluting with DCM) to obtain 2,4-dichloro-5-(iodomethyl)pyrimidine 2 as a light yellow solid (30.8 g, yield 96%). LCMS (m/z): 289.3 [M+H]$^+$.

N-((2,4-dichloropyrimidin-5-yl)methyl)-2,6-dimethylaniline (3)

A mixture of 2,4-dichloro-5-(iodomethyl)pyrimidine 2 (7.0 g, 24.2 mmol), 2,6-dimethylaniline (3.8 g, 31.4 mmol), K$_2$CO$_3$ (5.0 g, 36.2 mmol) in acetone (60 mL) was stirred at 55° C. overnight. The solvent was removed and the residue was extracted with EtOAc (150 mL×3). The combined organic phase was washed with brine (80 mL×3), dried with Na$_2$SO$_4$, filtered, and concentrated. The residue was purified by column chromatography on silica gel (petroleum ether/EtOAc=8/1, 4/1, 1/1) to get N-((2,4-dichloropyrimidin-5-yl)methyl)-2,6-dimethylaniline 3 as a light brown solid (4.5 g, yield 66%). LCMS (m/z): 282.3 [M+H]$^+$.

1-((2,4-dichloropyrimidin-5-yl)methyl)-3-(2,4-dimethoxyphenyl)-1-(2,6-dimethylphenyl)urea (4)

A round bottomed flask with a Dean-Stark apparatus was charged with N-((2,4-dichloropyrimidin-5-yl)methyl)-2,6- dimethylaniline 3 (3.0 g, 10.6 mmol), 1-isocyanato-2,4-dimethoxybenzene (2.5 g, 14.0 mmol), toluene (3 mL). The mixture was stirred at 130° C. for 2 d, cooled to rt, and concentrated. The residue was purified by column chromatography on silica gel (petroleum ether/EtOAc=4/1, 2/1, 1/1, EA) to get 1-((2,4-dichloropyrimidin-5-yl)methyl)-3-(2,4-dimethoxyphenyl)-1-(2,6-dimethylphenyl)urea 4 as a light brown solid (4.1 g, yield 84%). LCMS (m/z): 461.4 [M+H]$^+$.

7-chloro-1-(2,4-dimethoxyphenyl)-3-(2,6-dimethylphenyl)-3,4-dihydropyrimido[4,5-d]pyrimidin-2(1H)-one (5)

To the solution of 1-((2,4-dichloropyrimidin-5-yl)methyl)-3-(2,4-dimethoxyphenyl)-1-(2,6-dimethylphenyl)urea 4 (3.1 g, 6.7 mmol) in DCM (20 mL) was added Bu$_4$NOH (174 mg, 0.67 mmol), NaOH (474 mg, in 2 mL H$_2$O, 11.8 mmol). The mixture was stirred at rt for 4 h. The final mixture was diluted with H$_2$O (20 mL), extracted with DCM (80 mL×3). The combined organic phase was washed with brine (50 mL×2), dried with Na$_2$SO$_4$, filtered, and concentrated. The residue was purified by column chromatography on silica gel (eluting with DCM/MeOH=20/1) to give 7-chloro-1-(2,4-dimethoxyphenyl)-3-(2,6-dimethylphenyl)-3,4-dihydropyrimido[4,5-d]pyrimidin-2(1H)-one 5 as an off-white solid (2.4 g, yield 85%). $^1$H NMR (DMSO-d$_6$, 400 MHz): δ 8.37 (s, 1H), 7.16-7.19 (m, 4H), 6.68 (d, J=2.4 Hz, 1H), 6.58 (dd, J=8.8, 2.4 Hz, 1H), 4.74 (dd, J=5.5, 1.6 Hz, 2H), 3.81 (s, 3H), 3.70 (s, 3H), 2.25 (s, 3H), 2.20 (s, 3H); LCMS (m/z): 425.4 [M+H]$^+$.

YKL-04-114

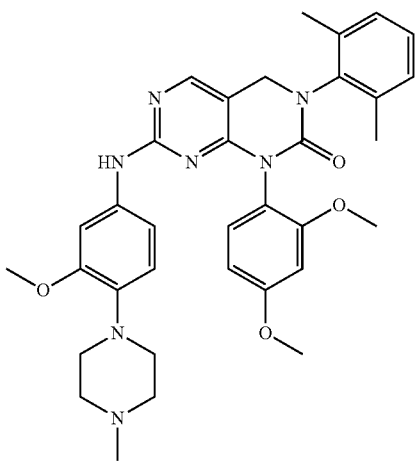

A mixture of 7-chloro-1-(2,4-dimethoxyphenyl)-3-(2,6-dimethylphenyl)-3,4-dihydropyrimido[4,5-d]pyrimidin-2(1H)-one 5 (10 mg, 0.024 mmol), 3-methoxy-4-(4-methylpiperazin-1-yl)aniline (7.8 mg, 0.035 mmol), and TFA (5.5 mg, 0.048 mmol) in 2-BuOH (0.5 mL) was stirred at 100° C. overnight. The reaction was cooled and concentrated. The residue was purified by prep-HPLC (MeOH/H$_2$O 5:95-100:0), followed by column chromatography on silica gel (0-10% MeOH in DCM) to afford YKL-04-114 as a white solid (8.0 mg, 56%). $^1$H NMR (DMSO-d$_6$, 400 MHz): δ 9.21 (s, 1H), 8.20 (s, 1H), 7.25-7.22 (m, 4H), 7.03 (d, J=8.4 Hz, 1H), 6.98 (s, 1H), 6.77 (d, J=2.8 Hz, 1H), 6.68 (dd, J=8.8, 2.8 Hz, 1H), 6.51 (d, J=8.4 Hz, 1H), 4.73 (d, J=14.4 Hz, 1H), 4.59 (d, J=14.4 Hz, 1H), 3.91 (s, 3H), 3.73 (s, 3H), 3.68 (s, 3H), 2.94 (m, 4H), 2.58 (m, 4H), 2.34 (s, 3H), 2.32 (s, 3H), 2.29 (s, 3H); LCMS (m/z): 610.7 [M+H]$^+$.

YKL-05-093

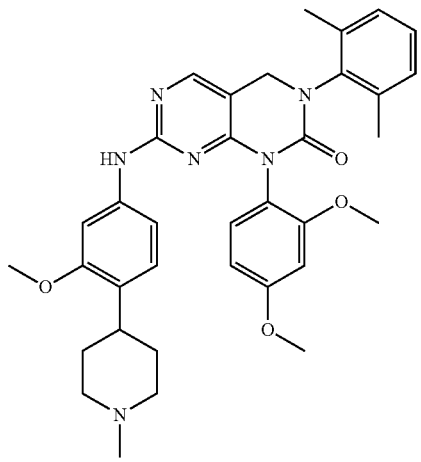

A mixture of 7-chloro-1-(2,4-dimethoxyphenyl)-3-(2,6-dimethylphenyl)-3,4-dihydropyrimido[4,5-d]pyrimidin-2(1H)-one 5 (100 mg, 0.24 mmol), 3-methoxy-4-(1-methylpiperidin-4-yl)aniline (78 mg, 0.35 mmol), and TFA (55 mg, 0.48 mmol) in 2-BuOH (5 mL) was stirred at 100° C. overnight. The reaction was cooled and concentrated. The residue was purified by prep-HPLC (MeOH/H$_2$O 5:95-100:0), followed by column chromatography on silica gel (0-10% MeOH in DCM) to afford YKL-05-093 as a white solid (127 mg, 89%). NMR (DMSO-d$_6$, 400 MHz): δ 9.16 (s, 1H), 8.09 (s, 1H), 7.12-7.09 (m, 4H), 6.95 (d, J=8.0 Hz, 1H), 6.86 (s, 1H), 6.65-6.62 (m, 2H), 6.55 (dd, J=8.4, 2.4 Hz, 1H), 4.60 (d, J=14.8 Hz, 1H), 4.47 (d, J=14.8 Hz, 1H), 3.78 (s, 3H), 3.60 (s, 3H), 3.54 (s, 3H), 2.81 (m, 2H), 2.66-2.57 (m, 1H), 2.19 (s, 3H), 2.16 (s, 3H), 2.15 (s, 3H), 1.95-1.90 (m, 2H), 1.56-1.46 (m, 4H); LCMS (m/z): 609.7 [M+H]$^+$.

Example 2. Biological Assays

Figure 10A:
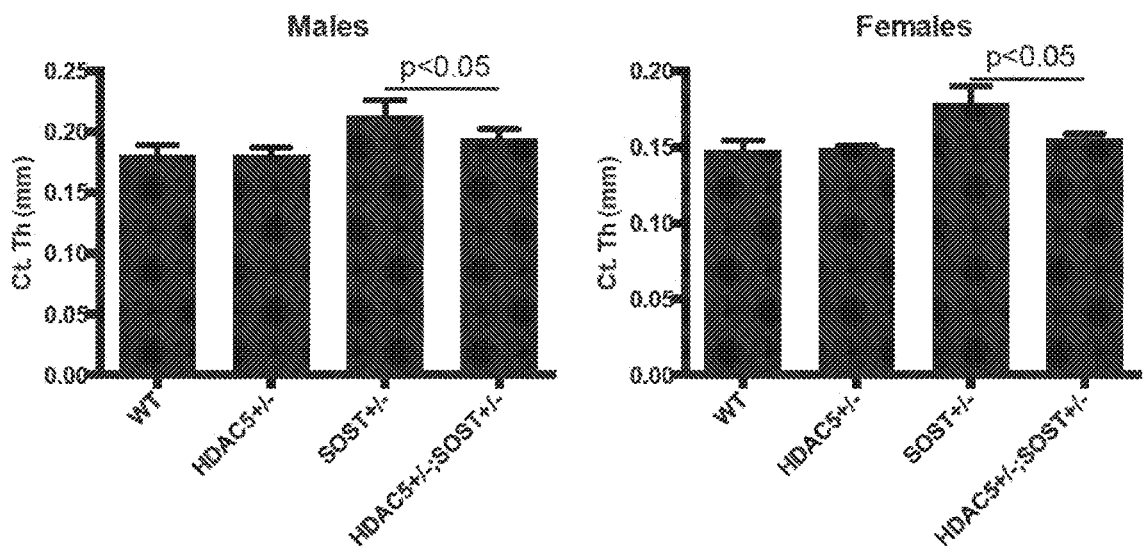
Figure 10B:
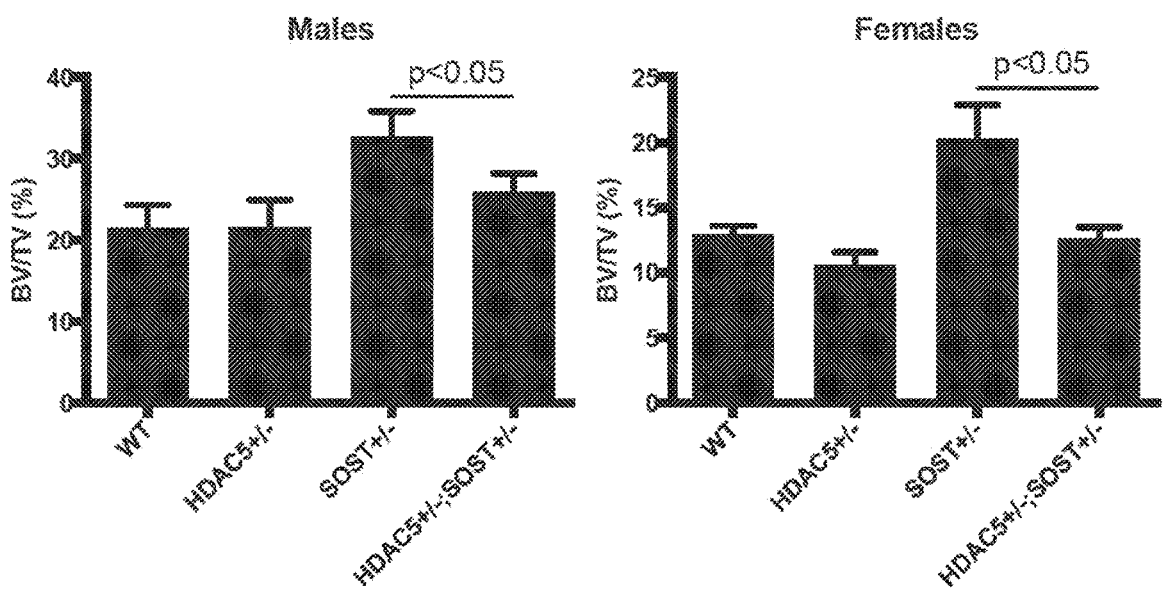
Figure 10C:
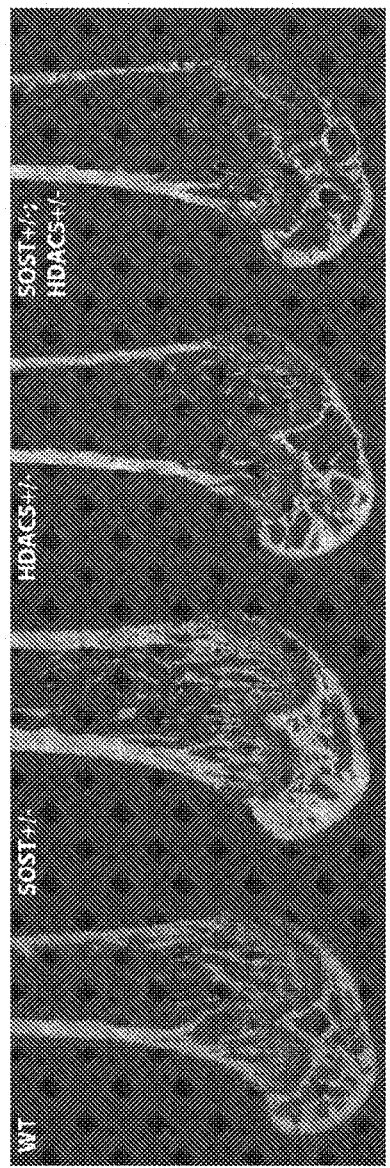
Figure 10D:
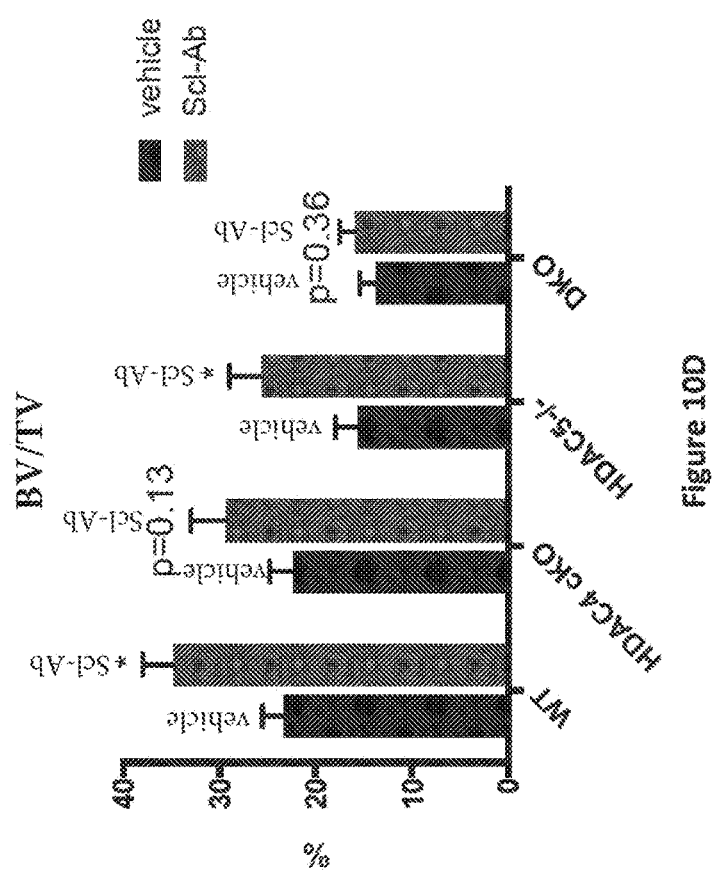
Figure 11G:
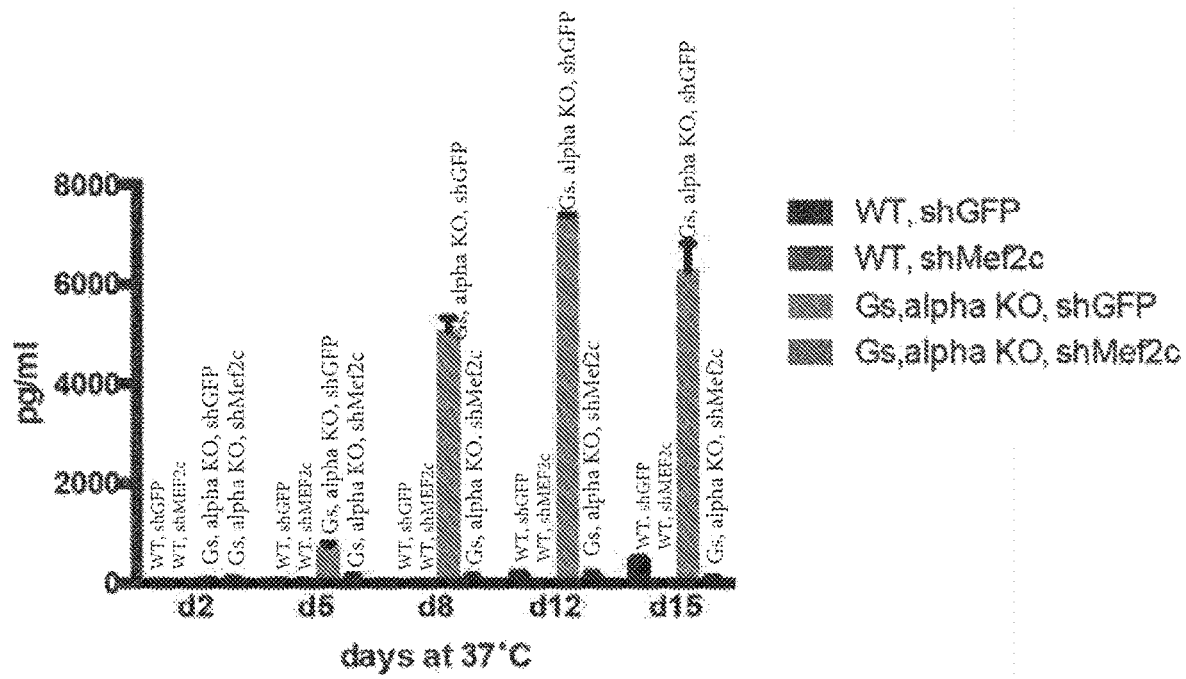
Figure 11H:
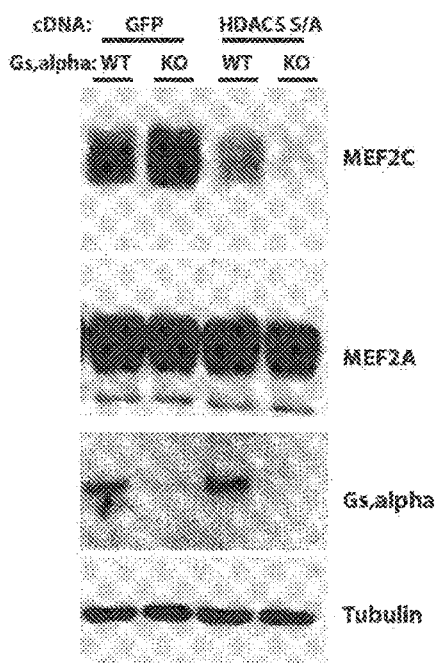
Figure 11I:
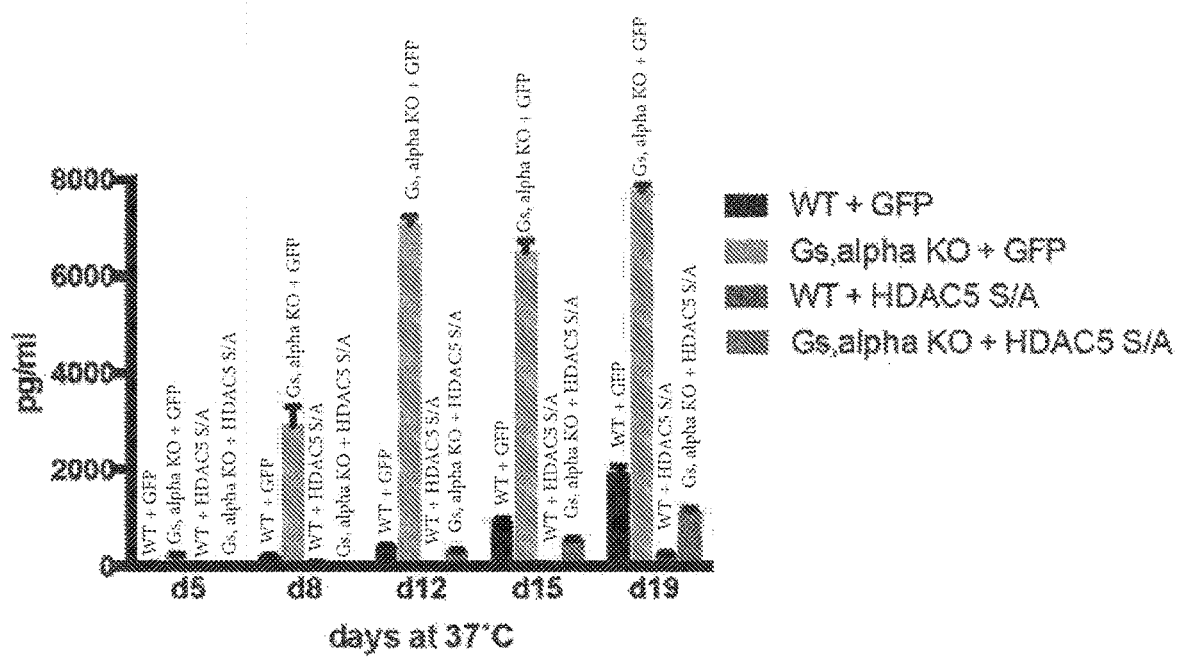
Figure 12A:
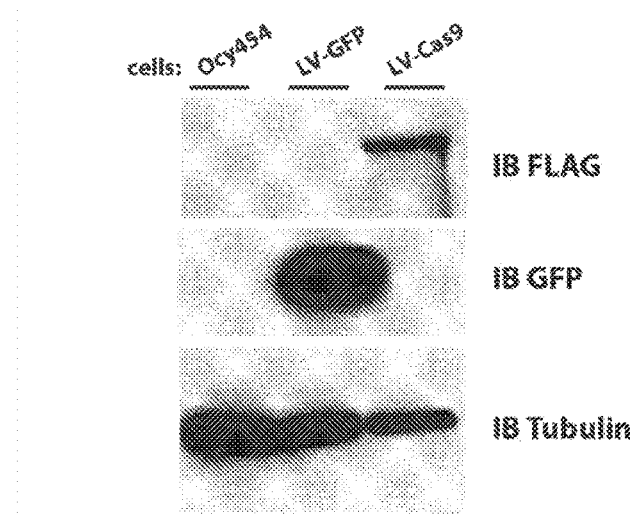
Figure 12B:
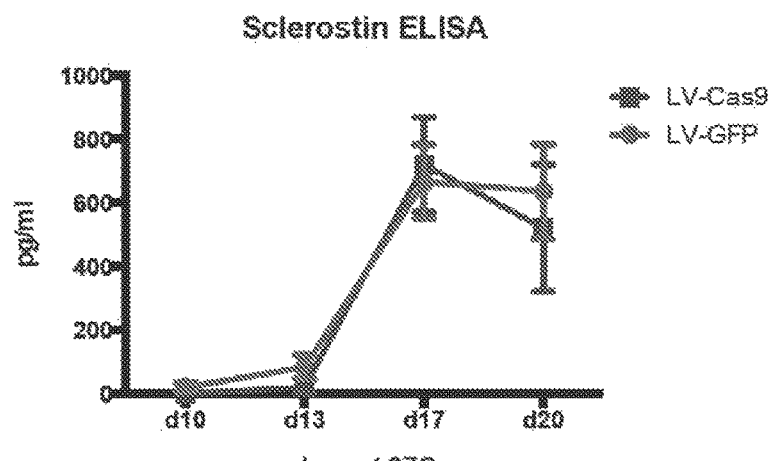
Figure 12C:
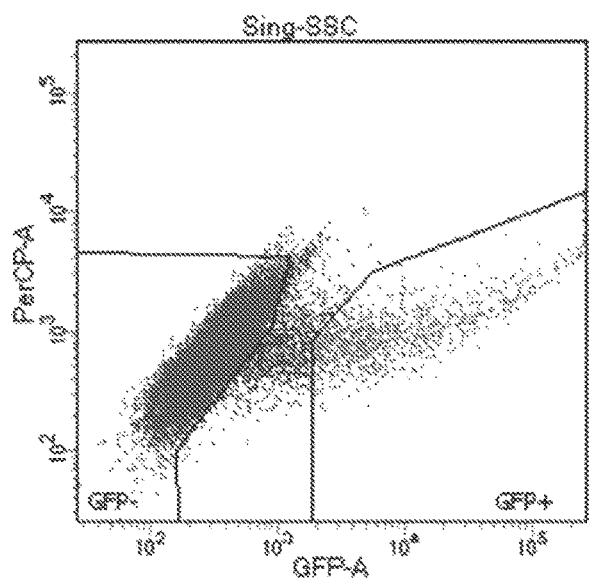
Figure 12F:
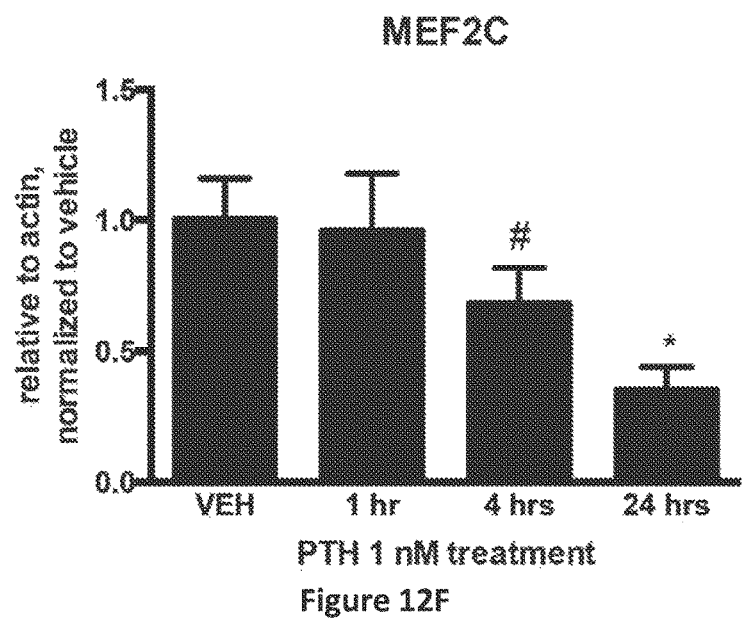

SIK Controls Osteocyte Responses to Parathyroid Hormone
Class IIa HBACs Control Bone Mass Through SOST Having previously demonstrated that HDAC5 blocks MEF2C-driven SOST expression in osteocytes (18), it was sought to determine whether HDAC5 and SOST interact in vivo to control bone mass. Two complementary approaches demonstrated that this was the case. First, compound heterozygosity of HDAC5 and SOST rescued the cortical and trabecular high bone mass phenotype of SOST+/− mice (FIGS. 10A to 10C). Second, anti-sclerostin antibody treatment rescued the trabecular osteopenia present in HDAC5−/− animals (FIG. 10D), which have high levels of SOST expression (18).

Figure 1A:
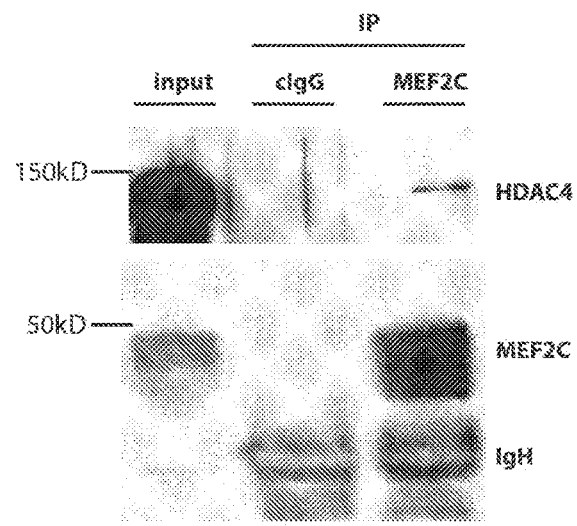
Figure 1B:
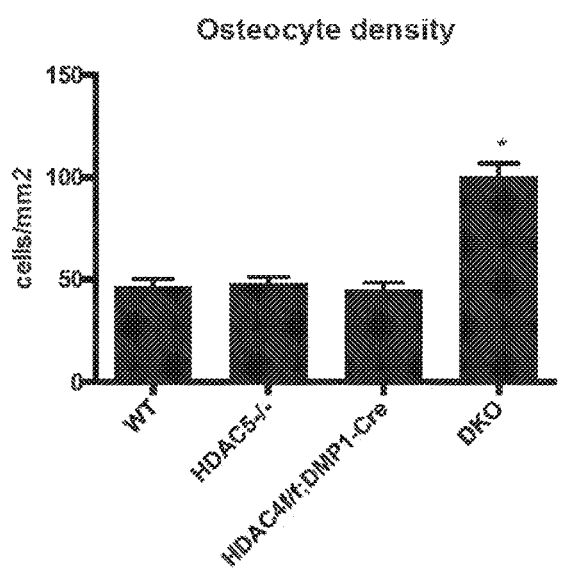
Figure 1C:
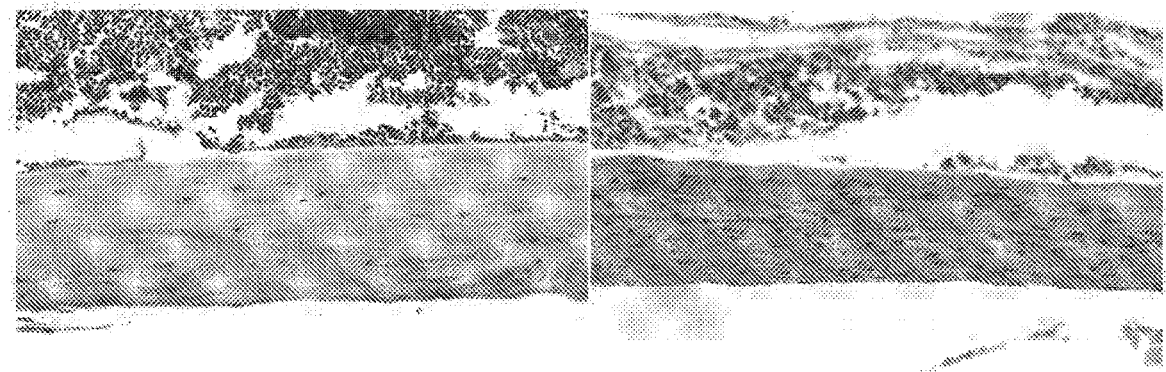

With evidence that HDAC5 control of SOST is physiologically important, it came into question if other class IIa HDACs function in osteocytes. It has previously been reported that HDAC5−/− mice display mild trabecular osteopenia (18) and (26). For these studies, analyses were extended to include the closely related family member HDAC4 for two reasons. First, endogenous MEF2C immunoprecipitates from Ocy454 cells contained HDAC4 in addition to HDAC5 (FIG. 1A and (18)). Second, while no obvious skeletal phenotype was observed when HDAC4 was deleted from osteocytes using DMP1-Cre (27), compound deletion of both HDAC4 and HDAC5 led to a skeletal phenotype not observed in either single mutant strain, characterized by severe trabecular osteopenia (Table 1 and FIG. 10F for results of static and dynamic histomorphometry results), increased osteocyte density (FIGS. 1B and 1C), disorganized, "woven" cortical bone (FIG. 1D), failure to respond to sclerostin antibody (FIG. 10D), and reduced endocortical bone formation (FIG. 10E). As previously reported, mice lacking HDAC5 alone show mild cancellous osteopenia and reduced markers of bone formation by histomorphometry (18).

cell line to demonstrate that mutation of these serines to alanine led to PTH-independent nuclear import (31). PTH-induced HDAC4/5 dephosphorylation and nuclear translocation requires cAMP signaling, as evidenced by the fact that these events did not occur in cells lacking Gsα via CRISPR/Cas9-mediated genome editing (FIGS. 2C and 2D and FIGS. 11B to 11E). As previously described (17, 32, 33), Gsα deficiency significantly increases sclerostin production by osteocytes. However, reducing MEF2C levels via shRNA or by over-expressing a constitutively nuclear super-repressor form of HDAC5 rescued this phenotype (FIG. 11F to

TABLE 1

Tibial histomorphometry results for 8 week old female mice of the indicated genotype.

|  | WT (n = 8) | | HDAC5-/- (n = 9) | | HDAC4f/f;DMP1-Cre (n = 8) | | DKO (n = 9) | |
| --- | --- | --- | --- | --- | --- | --- | --- | --- |
|  | value | s.e.m. | value | s.e.m. | value | s.e.m. | value | s.e.m. |
| BV/TV (%) | 8.12 | 0.880 | 5.84 | 0.447 | 6.72 | 0.717 | 3.45 | 0.707 |
| Tb.Th (μm) | 34 | 1.152 | 28.9 | 1.567 | 30.1 | 1.240 | *20.5* | 0.993 |
| Tb.N (/mm) | 2.36 | 0.201 | 2.01 | 0.093 | 2.2 | 0.201 | 1.6 | 0.263 |
| Tb.Sp (μm) | 414 | 40.636 | 487 | 24.333 | 464 | 65.724 | 804 | 166.333 |
| MAR (μm/day) | 1.96 | 0.085 | 1.25 | 0.087 | 1.74 | 0.159 | 0.96 | 0.010 |
| MS/BS (%) | 50.3 | 1.177 | 41.6 | 2.567 | 42.8 | 2.915 | 35.4 | 0.590 |
| BFR/BV (%/year) | 2257 | 56.890 | 1462 | 102.667 | 1848 | 203.534 | 1293 | 66.000 |
| BFR/BS (μm3/μm2/year) | 361 | 21.201 | 193 | 23.667 | 273 | 30.035 | 125 | 2.467 |
| N.Ob/B.Pm (/mm) | 13.6 | 0.763 | 10.4 | 0.887 | 14.1 | 0.512 | 11.9 | 0.813 |
| Ob.S/B.Pm (%) | 21.1 | 1.389 | 14.2 | 0.900 | 19.6 | 0.710 | 14.9 | 1.063 |
| OS/BS (%) | 14.2 | 2.039 | 7.34 | 0.840 | 14.1 | 1.852 | 3.92 | 0.623 |
| O.Th (μm) | 4.04 | 0.198 | 3.4 | 0.173 | 3.92 | 0.230 | 2.94 | 0.190 |
| N.OC/B/Pm (N.Oc/B.Pm.) (/mm) | 4.35 | 0.360 | 4.87 | 0.413 | 5.51 | 0.332 | 6.57 | 0.790 |
| Oc.S/B.Pm (%) | 13.6 | 0.866 | 14.2 | 1.070 | 15.1 | 0.965 | 18 | 2.017 |
| ES/BS (%) | 3.3 | 0.442 | 2.99 | 0.217 | 4.26 | 0.431 | 3.54 | 0.650 |

For each parameter, the value is shown followed by s.e.m.
Statistical analysis was performed by one-way ANOVA followed by Tukey's posthoc t test.
Values in bold indicate p < 0.05 comparing WT and the strain of interest.
Values in *italics* indicates p < 0.05 comparing HDAC5-/- and DKO groups.

"MAR" denotes mineral apposition rate, "MS/BS" denotes mineralizing surface/bone surface. "BFR/BS" denotes bone formation rate/bone surface. "BFR/BV" denotes bone formation rate/bone volume. "N.Ob/B.Pm" denotes number of osteoblasts per bone perimeter. "N.Oc/B.Pm" denotes number of osteoclasts per bone perimeter. "OS/BS" denotes osteoid surface/bone surface. "O.Th" denotes osteoid thickness. "ES/BS" denotes eroded surface per bone surface. "Ob.S" denotes osteoblast surface. "Oc.S" denotes osteoclast surface.

PTH Signals Through HDAC4 and HDAC5 to Suppress SOST

It was next asked whether PTH, a known suppressor of SOST expression (9), worked through HDAC4, HDAC5, or both. PTH treatment of Ocy454 cells caused translocation from the cytosol to the nucleus of both HDAC4 and HDAC5 (FIG. 2A). When phosphorylated, class IIa HDACs are predominantly cytoplasmic through retention by 14-3-3 proteins (19). When dephosphorylated, class IIa HDACs translocate to the nucleus where they potently inhibit MEF2-driven gene expression in muscle (28, 29). In neurons, HDAC5 nuclear import is additionally inhibited by CDK5-mediated phosphorylation at S279 (30). PTH signaling reduced phosphorylation of HDAC4 at S246/S632 and, to a lesser extent, HDAC5 at S259/S279 (FIGS. 2B and 11A). Others have over-expressed HDAC5 in a rat osteosarcoma 11I), consistent with the model that Gsα deficiency increases sclerostin production via a gain-of-function MEF2C phenotype.

Figure 2D:
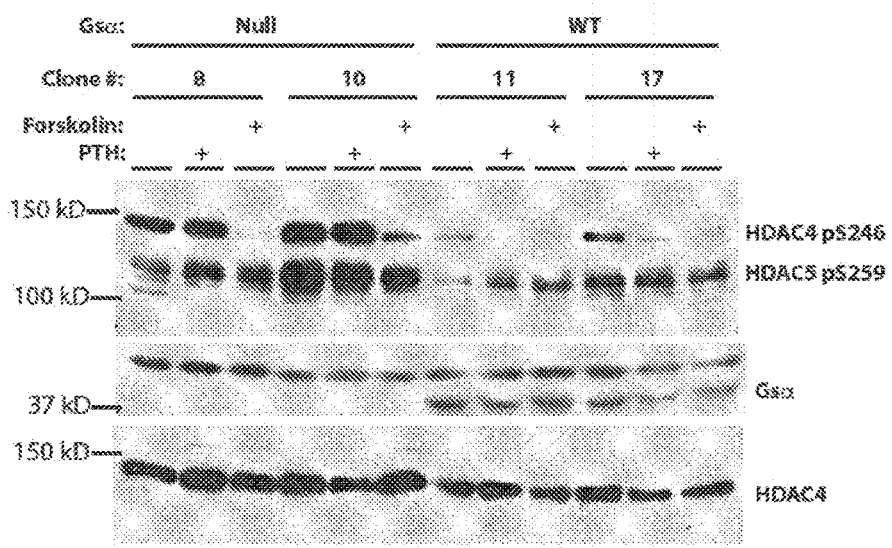
Figure 2E:
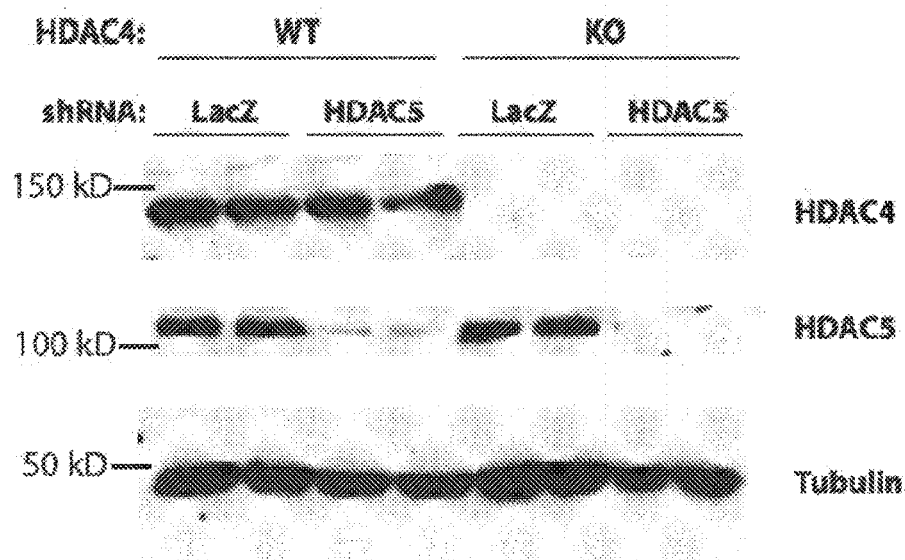

To determine the roles of HDAC4/5 in mediating PTH actions, osteocytes lacking HDAC4 (via CRISPR/Cas9-mediated deletion, FIGS. 12A to 12E), HDAC5 (via lentiviral-mediated shRNA), or both (FIG. 2E) were generated. While cells lacking HDAC4 or HDAC5 alone showed normal suppression of SOST expression in response to PTH, deletion of both HDAC4 and HDAC5 abolished PTH-induced SOST down-regulation (FIG. 2F, left). Importantly, HDAC4/5-deficient cells showed preserved PTH-induced RANKL up-regulation (FIG. 2F, right). Chromatin IP revealed that PTH signaling reduces MEF2C binding to the +45 kB downstream SOST enhancer (FIG. 2G); this occurs rapidly, at time points prior to observed reductions in MEF2C mRNA levels (FIG. 12F and (34, 35)). HDAC4/5-deficient cells showed increased MEF2C binding at baseline, and failed to reduce MEF2C SOST enhancer occupancy in response to PTH (FIG. 2H).

To determine the relevance of HDAC4/5 in mediating PTH actions in vivo, HDAC4/5-deficient mice were treated with PTH, and acute effects were measured 90 minutes later. While bone RANKL levels increased comparably across all four genotypes (WT, HDAC5-/-, HDAC4f/f;DMP1-Cre, and HDAC4f/f;HDAC5-/-;DMP1-Cre), HDAC4/5-deficient mice were unique in that SOST levels failed to decrease following PTH treatment (FIGS. 3A and 3B). At the protein level, PTH administration significantly decreased the numbers of sclerostin-immunoreactive cortical osteocytes in all genotypes tested except in HDAC4/5-deficient animals (FIGS. 3C and 3D). Taken together, these results indicate that HDAC4 and HDAC5 are downstream of PTH receptor signaling, and are required for PTH-mediated SOST suppression, both in vitro and in vivo.

Figure 13A:
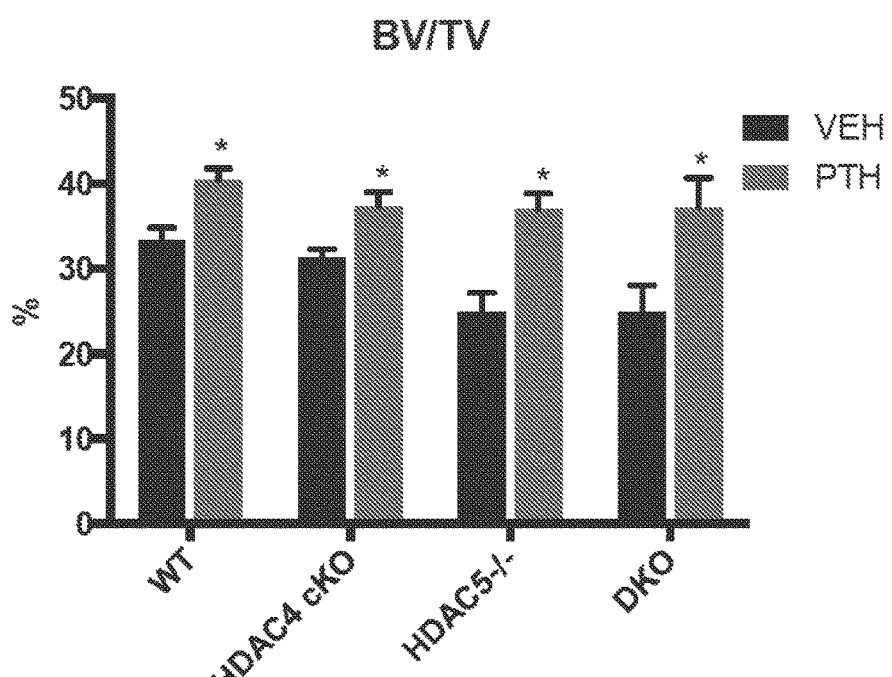

While SOST is a well-studied. PTH target genes, it represents a small portion of the portion of transcriptome regulated by parathyroid hormone (FIG. 6A). Underscoring this point, once daily intermittent PTH treatment leads to comparable gains in trabecular bone density in mice lacking HDAC4 in osteocytes, HDAC5, or both (FIG. 13A). Therefore, although class II HDACs are required for acute PTH-induced changes in SOST expression, other signaling arms and target genes downstream of the PTH receptor may exist that are important for the pharmacologic effects of this hormone.

Figure 13B:
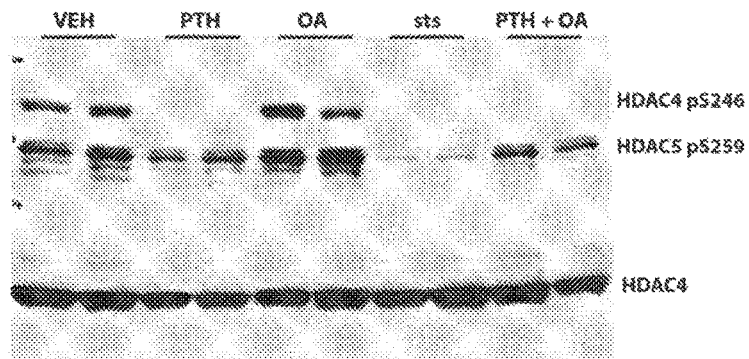
Figure 13C:
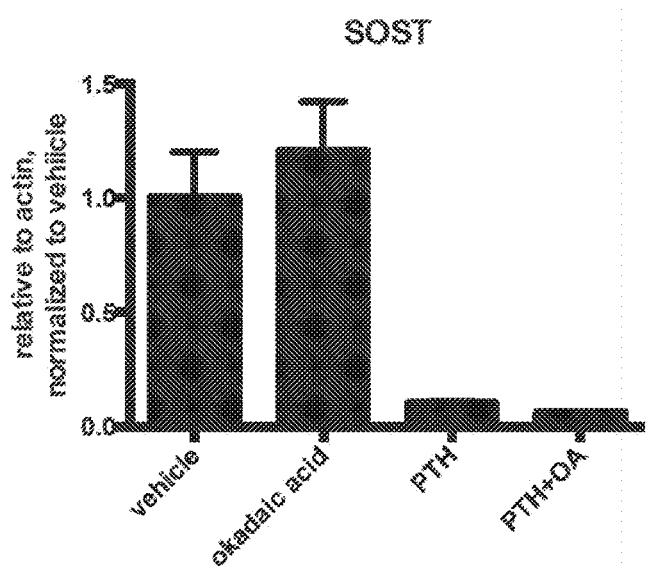
Figure 13D:
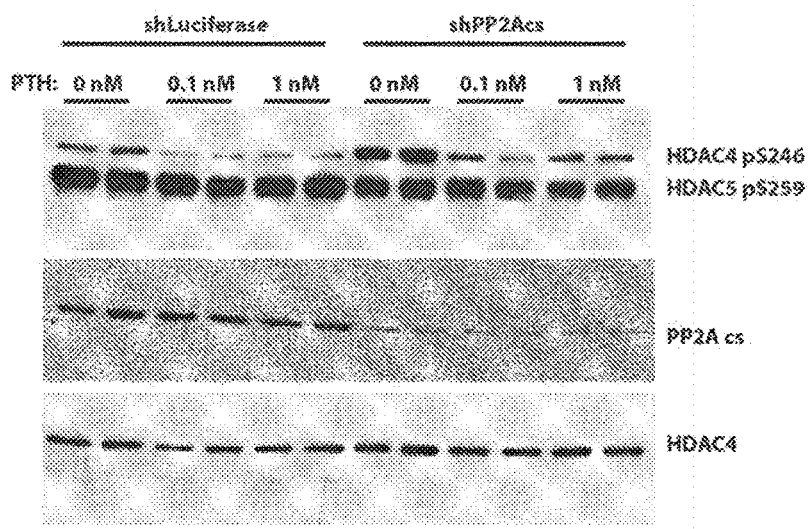
Figure 13E:
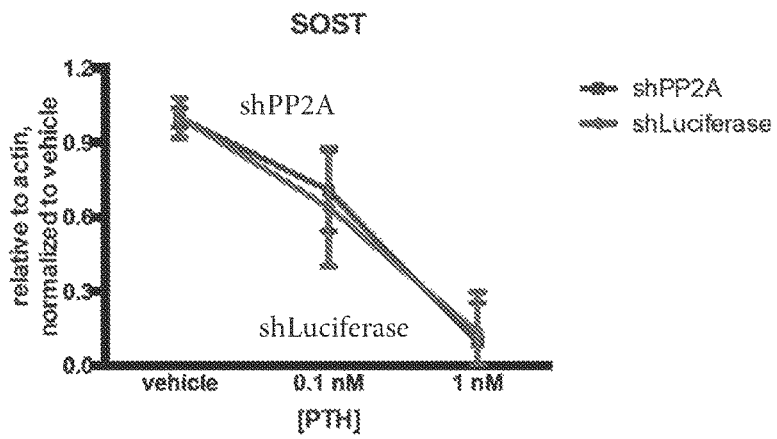
Figure 13F:
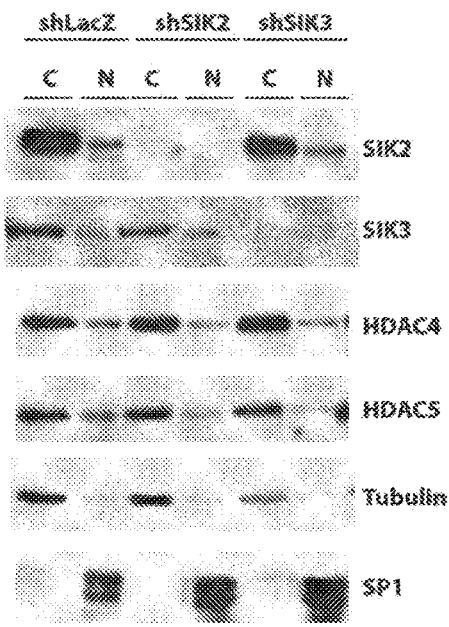

SIK2 is Inhibited by PTH, and Required for PTH-Mediated Decreased HDAC4/5 Phosphorylation and Gene Regulation Next, the signaling mechanisms used between activation of the PTH receptor and HDAC4/5 dephosphorylation were addressed. In chondrocytes in vitro, PTHrP drives HDAC4 into the nucleus via PP2A-mediated dephosphorylation, which can be blocked by okadaic acid (36). Surprisingly, okadaic acid did not block PTH-mediated decreased HDAC4/5 phosphorylation or SOST suppression in Ocy454 cells (FIGS. 13B and 13C). Similarly, PTH-induced decreases in HDAC4/5 phosphorylation and SOST suppression were intact when PP2A catalytic subunit levels were reduced via shRNA (FIGS. 13D and 13E). Okadaic acid and PP2A shRNA efficacy was confirmed in these experiments based on observed increases in HDAC4 S246 phosphorylation (FIGS. 13B and 13D). Taken together, these results suggest that, unlike in chondrocytes, in osteocytes PTH-stimulated decreased phosphorylation of HDAC4/5 is not mediated by activation of PP2A.

To explore candidate kinases whose activity might mediate the actions of PTH on HDAC4/5, salt inducible kinases (SIKs), AMPK family members reported to function as class IIa HDAC N-terminal kinases (22, 37) were examined. Subcellular fractionation experiments revealed that both SIK2 and SIK3 proteins are predominantly cytoplasmic in osteocytes (FIG. 13E). Combined silencing of both SIK2 and SIK3 in Ocy454 cells significantly decreased HDAC4/5 N-terminal phosphorylation (FIG. 4A).

Figure 4H:
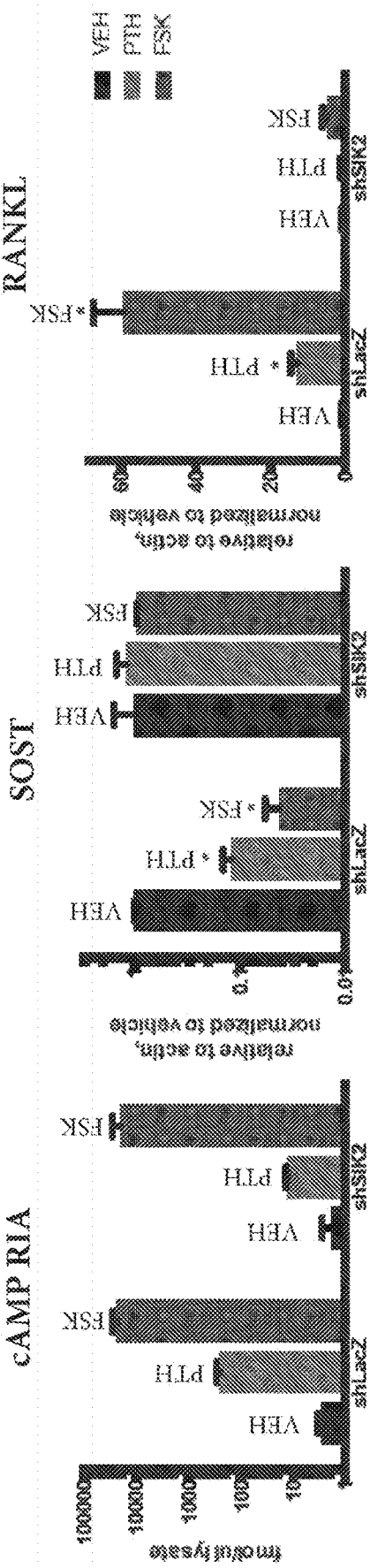

Cyclic AMP signaling in adipocytes and hepatocytes inhibits SIK2 activity via protein kinase A (PKA)-mediated phosphorylation, which in turn sequesters SIK2 from its substrates (38-40). PTH signaling in osteocytes triggered SIK2 phosphorylation at S343, S358, and T484 (FIG. 4B). PKA-mediated SIK3 phosphorylation was not triggered by PTH signaling (FIG. 4B). Notably, PTH-stimulated SIK2 S358 phosphorylation occurred rapidly, faster than the fall in HDAC4/5 phosphorylation levels (FIG. 4C). Importantly, SIK2-silenced cells showed normal up-regulation of the PTH target gene CITED1 (41) (FIG. 4D). In contrast, PTH-induced decreases in HDAC4/5 phosphorylation (FIG. 4E) and SOST suppression (FIG. 4F) did not occur in SIK2-silenced cells. Interestingly, PTH-induced RANKL upregulation, an HDAC4/5-independent phenomenon (FIG. 2F and FIG. 3A) also did not occur in SIK2-deficient osteocytes (FIG. 4G), suggesting that another SIK substrate may be involved in PTH-mediated RANKL gene induction. SIK3 deficient cells showed normal PTH responses (FIGS. 4D, 4F and 4G), as predicted by the fact that this protein is not phosphorylated in response to PTH signaling Cyclic AMP responses to PTH were slightly blunted in SIK2-silenced Ocy454 cells but were clearly present at PTH levels above 4 nM (FIG. 13F), However, forskolin-induced cAMP up-regulation was normal in SIK2 deficient cells, yet this agent failed to regulate SOST or RANKL expression in the absence of SIK2 (FIG. 4H).

Figure 4I:
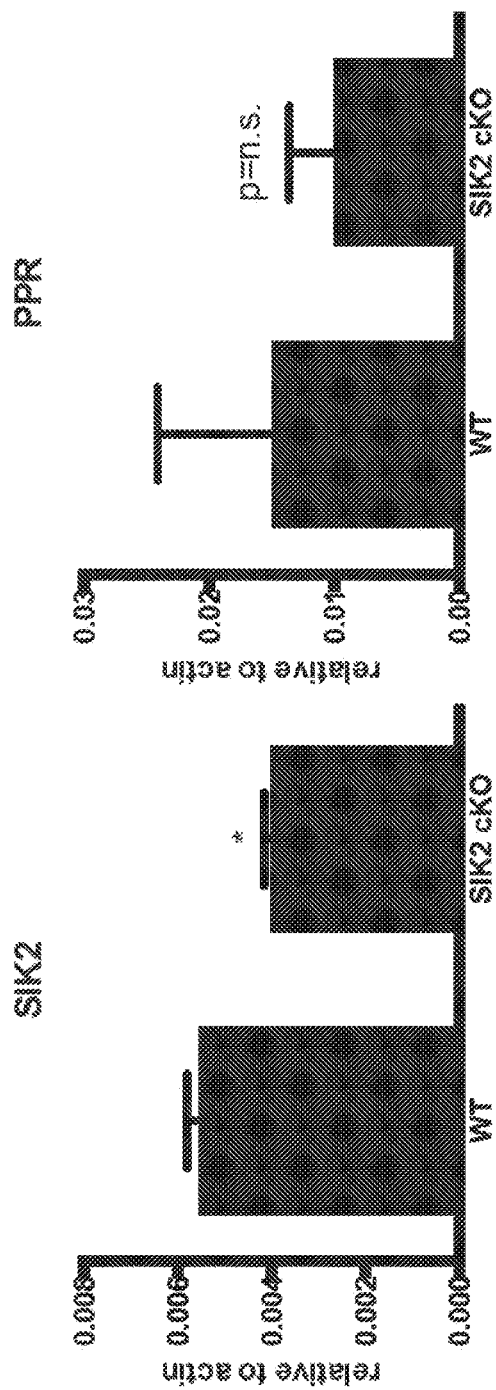
Figure 4I:
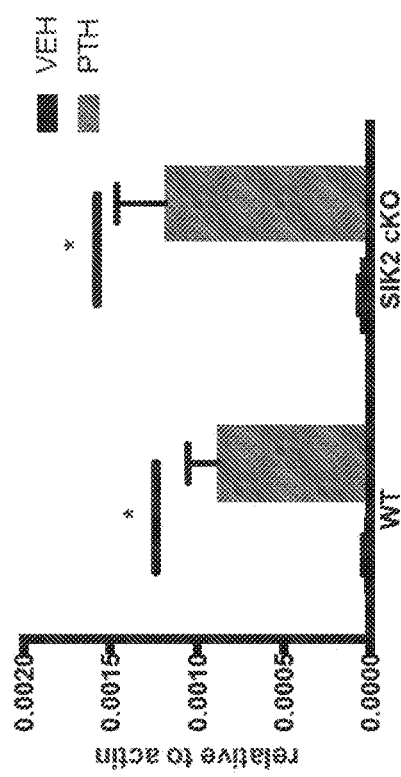

To determine the relevance of SIK2 in mediating PTH actions in vivo, mice lacking SIK2 in DMP1-expressing cells (including osteocytes) were treated with PTH, and acute effects were measured in bone 120 minutes later. FIG. 4I shows that DMP1-Cre deletion of SIK2 led to a significant reduction in SIK2, but not PTH receptor, mRNA levels in bone. Similar to the results in Ocy454 cells, PTH-induced Cited1 up-regulation was preserved in SIK2$^{OcyKO}$ mice (FIG. 4J). However, PTH-induced SOST and RANKL gene regulation did not occur in the absence of SIK2 (FIG. 4K).

Figure 13G:
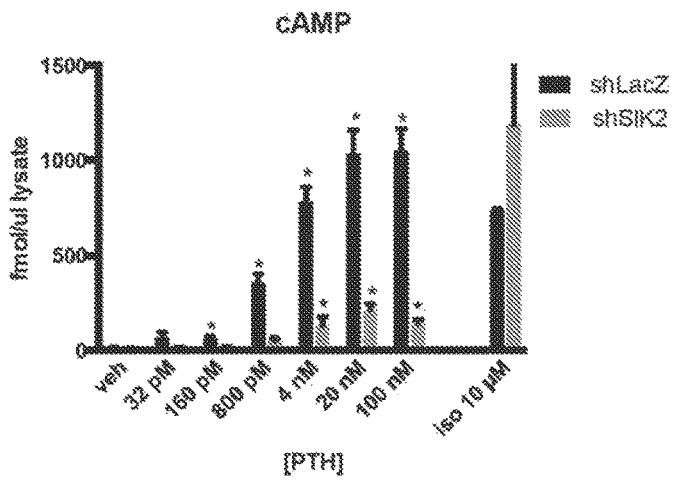
Figure 13H:
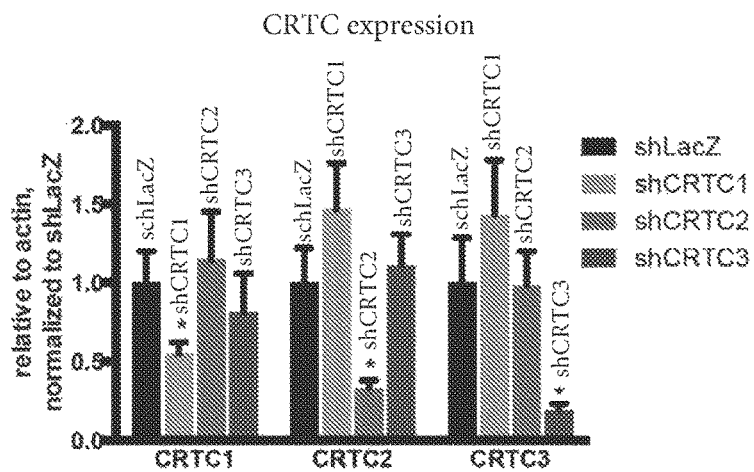
Figure 13I:
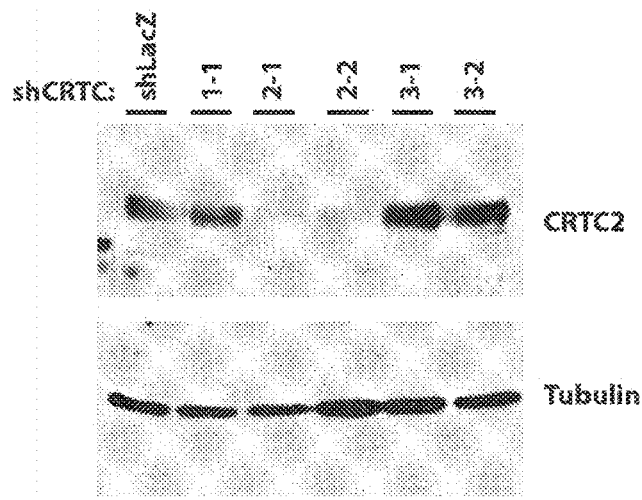
Figure 13J:
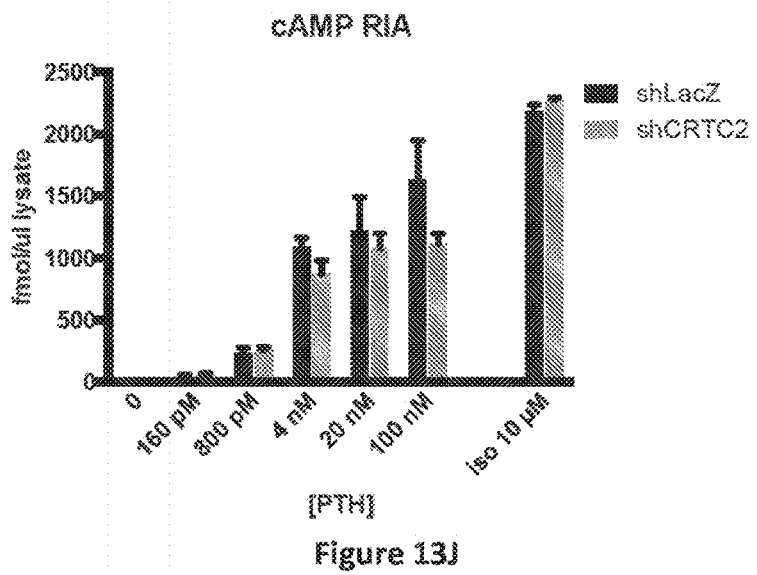

RANKL is a known PTH target gene; previous studies have suggested an important role for CREB, through binding to an enhancer 75 kB upstream of the transcription start site (13-15, 42, 43). While CREB itself is not a known SIK substrate, the CRTC CREB coactivator proteins are (21). All three CRTC proteins are expressed in osteocytes; therefore, levels of each were reduced individually using shRNA. CRTC2 silencing was sufficient to block PTH-induced RANKL up-regulation (FIG. 4L). FIG. 13G to 13I shows that PTH-induced cAMP generation was normal in CRTC2-deficient cells. PTH promoted CRTC2 nuclear translocation in a Gsα-dependent manner (FIG. 2C), and CRTC2 inducibly associated with the –75 kB "D5" RANKL enhancer (44) following PTH treatment (FIG. 4M). In summary, these results demonstrate that two key SIK substrates, HDAC4/5 and CRTC2, play major roles in PTH-mediated regulation of SOST and RANKL expression, respectively.

Small Molecule SIK Inhibitors Regulate SOST and RANKL Expression in Osteocytes

Figure 5D:
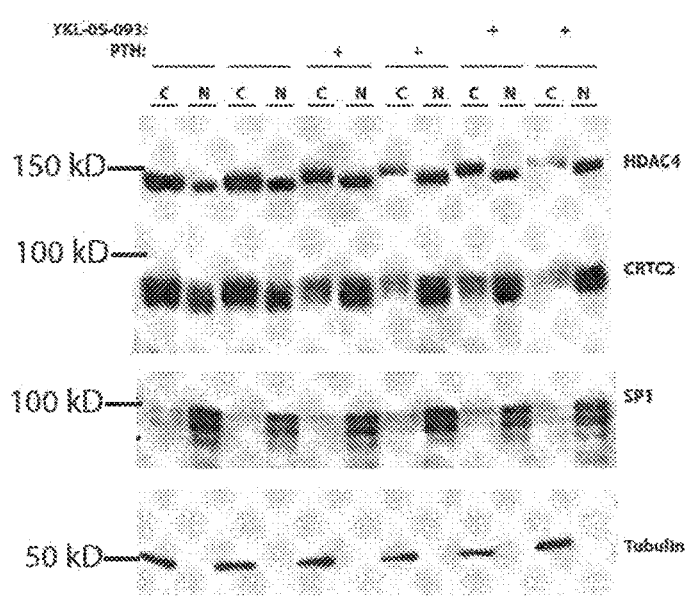
Figure 5D:
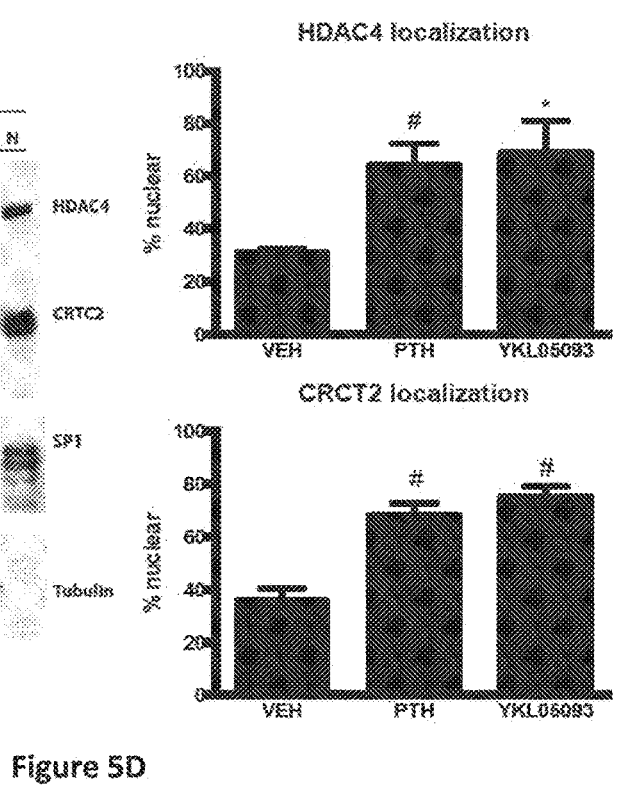

Gene ablation studies suggested that SIK inhibition may be needed for PTH to regulate SOST and RANKL expression, and PTH signaling may lead to PKA-mediated SIK2 inhibition. Therefore, it was asked whether acute inhibition of SIK kinase activity in otherwise normal cells or mice would be sufficient to mimic these actions of PTH. HG-9-91-01 is a small molecule kinase inhibitor with demonstrated biologic activity against SIKs in cultured macrophages, dendritic cells, and hepatocytes (39, 40, 45, 46). However, HG-9-91-01 is not SIK-specific and is not suitable for in vivo use; therefore, analogs were screened for based on the goals of improved specificity and pharmacokinetics. These efforts ultimately led to the identification of YKL-04-114 and its closely related analog YKL-05-093 (FIG. 5A). The $K_d$ of YKL-05-093 for SIK2 is 7.1 nM, and its activity against a panel of 96 recombinant kinases is shown in Table 2 (here SIK refers to SIK1 and QSK refers to SIK3) and shown graphically in FIG. 14A. YKL-04-114 treatment of Ocy454 cells led to rapid, dose-dependent decreases in HDAC4/5 phosphorylation (FIGS. 5B and 5C), and nuclear translocation of HDAC4 and CRTC2 (FIG. 5D). YKL-04-114 and YKL-05-093 caused rapid and potent SOST suppression and RANKL up-regulation (FIG. 5E) without increasing cAMP levels (FIG. 14B). Optimal efficacy at the level of HDAC4/5 dephosphorylation (~1 µM, FIG. 5C) and gene expression (~0.5 µM, FIG. 5E) occurred at comparable doses.

TABLE 2

Results of YKL-05-093 profiling against 96 recombinant kinases

| Gene Symbol | % of control activity at 71 nM |
| --- | --- |
| ABL1 | 0.2 |
| ACVR1B | 50 |
| ADCK3 | 93 |
| AKT1 | 92 |
| ALK | 23 |
| AMPK-alpha1 | 94 |
| ARK5 | 77 |
| AURKA | 12 |
| AXL | 68 |
| BMPR2 | 87 |
| BRAF | 66 |
| BRSK1 | 74 |
| BTK | 0.45 |
| CDK11 | 88 |
| CDK2 | 99 |
| CDK3 | 80 |
| CDK7 | 85 |
| CDK9 | 88 |
| CHEK1 | 42 |
| CSF1R | 0.85 |
| CSNK1D | 98 |
| CSNK1G2 | 100 |
| DCAMKL1 | 89 |
| DYRK1B | 93 |
| EGFR | 5.9 |
| EPHA2 | 7.1 |
| ERBB2 | 3.5 |
| ERBB4 | 6.1 |
| ERK1 | 100 |
| FAK | 90 |
| FGFR2 | 8.9 |
| FGFR3 | 24 |
| FLT3 | 20 |
| GSK3B | 68 |
| HCK | 1.2 |
| HIPK2 | 100 |
| IGF1R | 100 |
| IKK-alpha | 93 |
| IKK-beta | 84 |
| INSR | 56 |
| JAK2 | 13 |
| JNK1 | 97 |
| JNK2 | 89 |
| KIT | 1.8 |
| LCK | 0.75 |
| LKB1 | 85 |
| MAP3K4 | 60 |
| MAPKAPK2 | 85 |
| MARK1 | 84 |
| MARK3 | 40 |
| MEK1 | 20 |
| MEK2 | 12 |
| MELK | 36 |
| MET | 92 |
| MKNK1 | 76 |
| MLK1 | 12 |
| p38-alpha | 0.95 |
| p38-beta | 47 |
| PAK1 | 6.6 |
| PAK2 | 75 |
| PAK4 | 88 |
| PCTK1 | 91 |
| PDGFRA | 11 |
| PDGFRB | 0.35 |
| PDPK1 | 55 |
| PIK3C2B | 100 |
| PIK3CA | 84 |
| P1K3CG | 80 |
| PIM1 | 89 |
| PIM2 | 97 |
| PIM3 | 84 |
| PKAC-alpha | 100 |
| PLK1 | 100 |
| PLK3 | 90 |
| PRKCE | 92 |
| QSK | 5.3 |
| RAF1 | 100 |
| RET | 3.6 |
| RIOK-2 | 77 |
| RIPK2 | 16 |
| ROCK2 | 70 |
| RSK2 | 51 |
| SIK | 0.6 |
| SIK2 | 10 |
| SNARK | 6 |
| SRC | 0 |
| SRPK3 | 88 |
| TGFBR1 | 90 |
| TIE2 | 32 |
| TRKA | 74 |
| TSSK1B | 83 |
| TYK2 | 49 |
| ULK2 | 31 |
| VEGFR2 | 26 |
| YANK3 | 95 |
| ZAP70 | 52 |

Figure 5H:
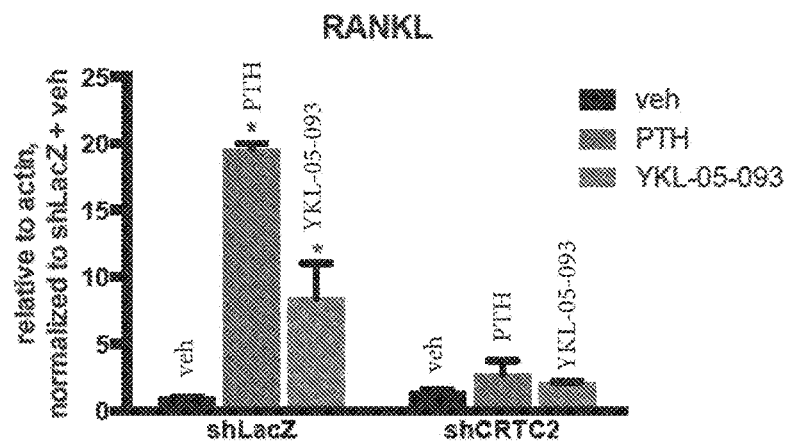

Importantly, treatment with YKL-05-093 did not decrease HDAC4 S246 phosphorylation or cause SOST suppression in osteocytes lacking SIK2 and SIK3 (FIGS. 5F to 5G). In addition, PTH and YKL-05-093-mediated stimulation of RANKL expression was abrogated in cells lacking CRTC2 (FIG. 5H). So although YKL-05-093 does target other kinases in vitro, its cellular actions studied here depend on the presence of SIK2 and SIK3.

Figure 5I:
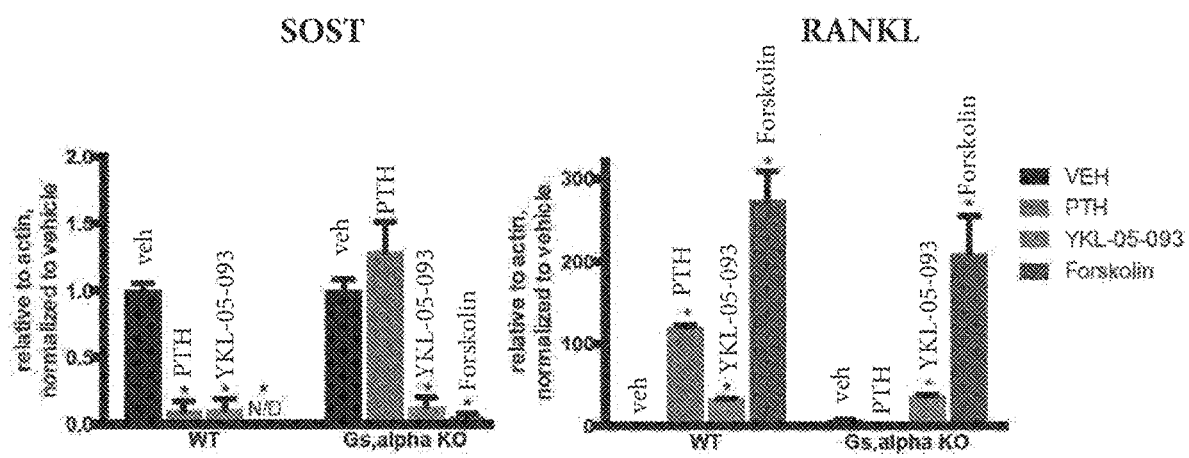
Figure 5J:
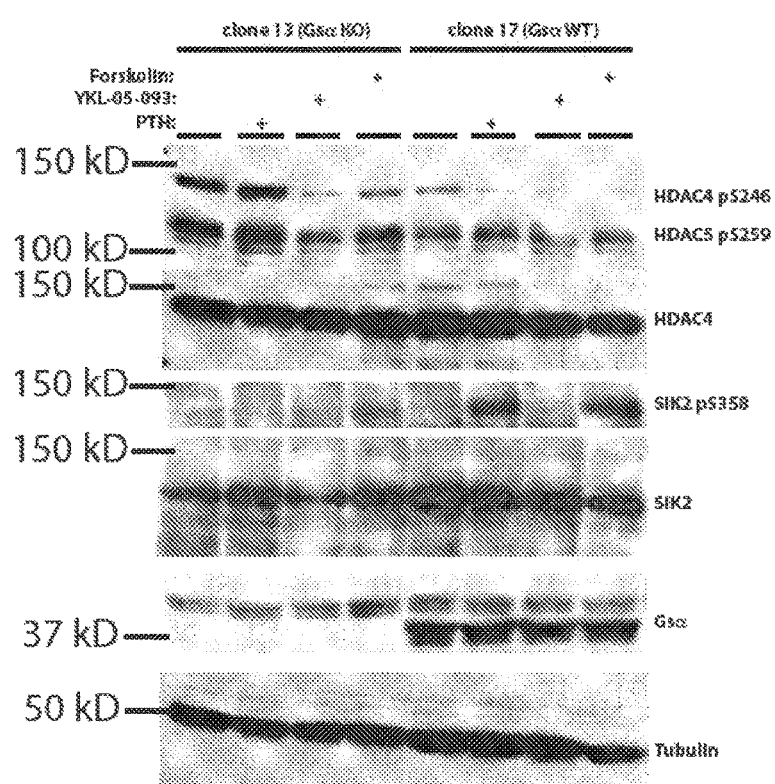

Based on the model that YKL-05-093 functions as a SIK inhibitor downstream of PTH-stimulated cAMP generation, one would predict that the inhibitor would regulate gene expression in Gsα-deficient osteocytes. Indeed, YKL-05-093 treatment of Gsα-deficient Ocy454 caused SOST suppression and RANKL up-regulation with effects similar to forskolin, except, as expected based on its inability to increase cellular cAMP levels (FIG. 14B), YKL-05-093 did not increase SIK2 S358 phosphorylation (FIGS. 5I to 5J).

The Ocy454 osteocyte cell line was treated for 90 minutes with the indicated compound at 10 uM dose (FIG. 17). Phospho-HDAC4 S246 levels were monitored by immunoblotting (top band) compared to DMSO control. Several compounds reduce HDAC4 S246 phosphorylation, but compound 3-9 (YKL-04-114) showed the most clear results across multiple replicates. Table X shows the compounds tested in FIG. 17.

TABLE 21

Compounds tested in FIG. 17

| Compound Number recited in FIG. 17 | Compound |
| --- | --- |
| 3 | HG-11-136-01 |
| ?3 | HG-11-136-01 |
| 3-1 | YKL-04-103 |
| 3-2 | YKL-04-104 |
| 3-3 | YKL-04-105 |
| 3-4 | YKL-04-106 |
| 3-5 | YKL-04-107 |
| 3-6 | YKL-04-108 |
| 3-7 | YKL-04-112 |
| 3-8 | YKL-04-113 |
| 3-9 | YKL-04-114 |
| 3-10 | YKL-04-114 |

TABLE 21-continued

Compounds tested in FIG. 17

| Compound Number recited in FIG. 17 | Compound |
|---|---|
| 3-11 | YKL-04-118 |
| 3-12 | YKL-04-125 |
| 3-13 | YKL-04-136-1 |
| 3-14 | YKL-04-136-2 |
| 3-15 | YKL-04-136-3 |
| 3-16 | YKL-04-136-4 |
| 3-17 | YKL-04-136-5 |
| 3-18 | YKL-04-136-6 |
| 3-19 | YKL-04-136-7 |
| 3-20 | YKL-04-136-8 |
| 3-21 | YKL-04-136-9 |
| 3-22 | YKL-04-136-10 |
| 3-23 | YKL-04-136-11 |

In FIG. 18, analogs of YKL-04-114 were synthesized and tested in a similar assay as in FIG. 17. YKL-05-093 showed clear activity with respect to reducing HDAC4 S246 levels Analogs of YKL-05-093 were tested in multiple experiments (FIG. 19). Among the tested compounds in FIG. 19, YKL-05-093 was the compound that most reproducibly led to reduced HDAC4 S246 phosphorylation.

FIG. 20 shows additional data showing the activity of YKL-05-093 and some analogs thereof in HDAC4 S246 phosphorylation assays.

In FIG. 21, Ocy454 cells (osteocyte cell line, also known at 6-9 cells) were cultured at 37° C. for 2 weeks to permit osteocyte differentiation. The cells were then treated with the indicated compound (0.5 µM) for 3.5 hours, and gene expression was analyzed by RT-qPCR. SOST expression was reduced by the indicated compounds. RANKL expression was increased by the indicated compounds. YKL-04-114 and YKL-05-093 were most active in these experiments at reducing SOST and increasing RANKL amongst the indicated compounds. These effects did not occur in Ocy454 cells lacking SIK2 and SIK3. Therefore, these changes in gene expression may be due to on-target effects of the indicated compound.

The experiments of FIG. 22A are similar to the experiments as shown in FIG. 21, using additional analogs of YKL-05-093. FIG. 22B shows SIK2 $IC_{50}$ data generated from an in vitro kinase assay.

FIG. 23 is a plot of the data from FIGS. 22A and 22B showing the SIK2 $IC_{50}$ on the x-axis and the effects of RANKL and SOST on the y-axis. The relationship may be affected by factors like poor cellular penetration of some of the compounds that potently inhibit SIK2 in a pure in vitro assay.

Small Molecule SIK Inhibitors Mimic PTH Action In Vitro

The ability of YKL-05-093 to mimic the effects of PTH with respect to SOST and RANKL gene regulation supports the hypothesis that the actions of YKL-05-093 might mimic the effects of PTH on many genes. Therefore, RNA-seq was performed on Ocy454 cells treated for four hours with vehicle, PTH (1 nM), or YKL-05-093 (0.5 µM) to determine the overlap in global gene regulation by these two agents. 446 genes were significantly (>2 fold, FDR<0.05) regulated by PTH, and 257 genes were significantly regulated by YKL-05-093. Of the 446 PTH-regulated genes, 142 (32%) were co-regulated in the same direction by YKL-05-093 (FIGS. 6A and 6B and Table 3 for differentially expressed genes, and Table 4 for all RNA-seq data). This significant overlap was not due to random chance (FIGS. 15A and 15B). Gene ontology analysis for the genes regulated by both PTH and YKL-05-093 is shown in FIGS. 15C and 15D: many of the co-regulated genes fit into categories of interest such as "ossification" and "mesenchyme development".

TABLE 3

Results of YKL-05-093 profiling against 96 recombinant kinases

| Gene Symbol | % of control activity at 71 nM |
|---|---|
| ABL1 | 0.2 |
| ACVR1B | 50 |
| ADCK3 | 93 |
| AKT1 | 92 |
| ALK | 23 |
| AMPK-alpha1 | 94 |
| ARK5 | 77 |
| AURKA | 12 |
| AXL | 68 |
| BMPR2 | 87 |
| BRAF | 66 |
| BRSK1 | 74 |
| BTK | 0.45 |
| CDK11 | 88 |
| CDK2 | 99 |
| CDK3 | 80 |
| CDK7 | 85 |
| CDK9 | 88 |
| CHEK1 | 42 |
| CSF1R | 0.85 |
| CSNK1D | 98 |
| CSNK1G2 | 100 |
| DCAMKL1 | 89 |
| DYRK1B | 93 |
| EGFR | 5.9 |
| EPHA2 | 7.1 |
| ERBB2 | 3.5 |
| ERBB4 | 6.1 |
| ERK1 | 100 |
| FAK | 90 |
| FGFR2 | 8.9 |
| FGFR3 | 24 |
| FLT3 | 20 |
| GSK3B | 68 |
| HCK | 1.2 |
| HIPK2 | 100 |
| IGF1R | 100 |
| IKK-alpha | 93 |
| IKK-beta | 84 |
| INSR | 56 |
| JAK2 | 13 |
| JNK1 | 97 |
| JNK2 | 89 |
| KIT | 1.8 |
| LCK | 0.75 |
| LKB1 | 85 |
| MAP3K4 | 60 |
| MAPKAPK2 | 85 |
| MARK1 | 84 |
| MARK3 | 40 |
| MEK1 | 20 |
| MEK2 | 12 |
| MELK | 36 |
| MET | 92 |
| MKNK1 | 76 |
| MLK1 | 12 |
| p38-alpha | 0.95 |
| p38-beta | 47 |
| PAK1 | 6.6 |
| PAK2 | 75 |
| PAK4 | 88 |
| PCTK1 | 91 |
| PDGFRA | 11 |
| PDGFRB | 0.35 |
| PDPK1 | 55 |
| PIK3C2B | 100 |
| PIK3CA | 84 |
| PIK3CG | 80 |
| PIM1 | 89 |
| PIM2 | 97 |

TABLE 3-continued

Results of YKL-05-093 profiling against 96 recombinant kinases

| Gene Symbol | % of control activity at 71 nM |
|---|---|
| PIM3 | 84 |
| PKAC-alpha | 100 |
| PLK1 | 100 |
| PLK3 | 90 |
| PRKCE | 92 |
| QSK | 5.3 |
| RAF1 | 100 |
| RET | 3.6 |
| RIOK2 | 77 |
| RIPK2 | 16 |
| ROCK2 | 70 |
| RSK2 | 51 |
| SIK | 0.6 |
| SIK2 | 10 |
| SNARK | 6 |
| SRC | 0 |
| SRPK3 | 88 |
| TGFBR1 | 90 |
| TIE2 | 32 |
| TRKA | 74 |
| TSSK1B | 83 |
| TYK2 | 49 |
| ULK2 | 31 |
| VEGFR2 | 26 |
| YANK3 | 95 |
| ZAP70 | 52 |

TABLE 4

All RBA-seq data

| Up with PTH only | Up with YKL-05-093 alone | Up with both PTH and YKL-05-093 | Down with PTH only | Down with YKL-05-093 only | Down with both PTH and YKL-05-093 |
|---|---|---|---|---|---|
| 2310043M15Rik | 1700023H06Rik | Ackr3 | 1700001L05Rik | Arc | 6330403L08Rik |
| Abtb1 | 1700023L04Rik | Acsl3 | 2310022B05Rik | Arrdc4 | Adra1d |
| Aldh3a1 | A930018M24Rik | Adrb2 | 2700038G22Rik | Atoh8 | Cd200 |
| Ankrd44 | Adamts1 | Alx3 | 9930013L23Rik | Bahcc1 | Chst15 |
| Arl4c | Adck3 | Arl4d | Abi2 | Bcl2 | Cxcl12 |
| Baalc | Adrb1 | Arrdc3 | Adamts18 | Ccl2 | Cyp26b1 |
| Batf | Aim1 | Avpi1 | Ahrr | Ccl7 | Dlk2 |
| Bglap | Apbb1 | BB557941 | Akap6 | Csf1 | Egr2 |
| Bglap2 | AU021092 | C2cd4c | Ankrd34a | Ctgf | Enc1 |
| C1qtnf1 | Bmf | Cebpd | Ano6 | Dlx2 | Esm1 |
| Camk4 | Bmp6 | Col13a1 | Apin | Dlx5 | F3 |
| Ccdc109b | Btbd17 | Crem | Bcar3 | Dlx6 | Fam198b |
| Ccdc152 | C130050O18Rik | Crispld2 | Bmp2 | Dmp1 | Fjx1 |
| Cda | Cd24a | Cxcl1 | Bok | Dusp4 | Fzd5 |
| Cebpb | Col11a2 | Enpp6 | Car8 | Dusp6 | Fzd8 |
| Ch25h | Dhrs3 | Eya2 | Cd2ap | Egr1 | Gm10715 |
| Chst12 | Dusp1 | Fam167a | Cdk5r1 | Eps8 | Gm10717 |
| Cited1 | Fbxo32 | Fam20a | Cdo1 | Etv5 | Gm10718 |
| Clec2d | Fosl2 | Fos | Chst3 | Gcnt4 | Gm10800 |
| Col2a1 | Gm11837 | Gadd45a | Chsy1 | Gm11168 | Gm10801 |
| Cyp1b1 | Gm22314 | Gja1 | Cmya5 | Gm16516 | Gm13186 |
| Cyp26a1 | Gm22633 | Glis1 | Deptor | Gm23296 | Gm13493 |
| Ddc | Gm24119 | Gm22220 | Dixdc1 | Gm25047 | Gm21738 |
| Dio3 | Gm25395 | Gm22288 | Dlx3 | Gm26982 | Gm26507 |
| Dio3os | Gm9949 | Gm22421 | Dtx4 | Gm3200 | Gm26870 |
| Dnajc12 | Gpr133 | Gm22623 | Dusp7 | Gm9987 | Gm5763 |
| Dpt | Gprc5c | Gm22628 | Eepd1 | Hey1 | Gpr176 |
| Efnb2 | Grhl3 | Gm23287 | Ell2 | Hmga2 | Gprin3 |
| Emb | Hgf | Gm23445 | Fam101b | Hoxc12 | Hdac9 |
| Fam134b | Hrc | Gm23927 | Fam102a | Hoxc13 | Id3 |
| Fam169b | Inhbb | Gm23947 | Fam13c | Id1 | Il17rd |
| Fam198a | Kctd7 | Gm23966 | Fam180a | Id2 | Klf5 |
| Fam69c | Kdr | Gm23971 | Fam217b | Irf5 | Lfng |
| Fas | Krt80 | Gm24204 | Fam43a | Klhdc8a | Lmcd1 |
| Fbxo31 | Mn1 | Gm24316 | Farp2 | Krtap1-5 | Nuak1 |
| Flrt2 | Ncf1 | Gm24447 | Fgd3 | Mical2 | Pdgfa |
| Foxf1 | Nfil3 | Gm24620 | Fhod1 | Nfkbie | Rasl11a |
| Fxyd5 | Nr4a3 | Gm24917 | Foxd1 | Pcdh10 | Rgs3 |
| Fzd1 | Pdzrn3 | Gm24968 | Gadd45g | Pdp1 | Shisa2 |
| Gfra1 | Per1 | Gm25101 | Gcnt1 | Prkg2 | Spry1 |
| Gm10327 | Plekha5 | Gm25514 | Gli1 | Ptprj | Tbx2 |
| Gm10638 | Ptgfr | Gm25682 | Gm10136 | Rin1 | Thbs1 |
| Gm13705 | Rftn1 | Gm26072 | Gm10602 | Rnf150 | Tiam2 |
| Gm16062 | Rhpn2 | Gm26323 | Gm10722 | Rspo3 | Tmem229b |
| Gm22265 | Serpinb6b | Gm26324 | Gm11944 | Sacs | Vgll3 |
| Gm22307 | Sik1 | Gm26331 | Gm129 | Serpina3f | |
| Gm22488 | Sox4 | Gng4 | Gm15663 | Serpina3g | |

TABLE 4-continued

All RBA-seq data

| Up with PTH only | Up with YKL-05-093 alone | Up with both PTH and YKL-05-093 | Down with PTH only | Down with YKL-05-093 only | Down with both PTH and YKL-05-093 |
|---|---|---|---|---|---|
| Gm22513 | Spon2 | Has2 | Gm16185 | Skil | |
| Gm22661 | Ston2 | Hdac4 | Gm17045 | Smad7 | |
| Gm22980 | Tcp11l2 | Igf1 | Grn17275 | Smad9 | |
| Gm22997 | Tmie | Il1rl1 | Gm20471 | Snai2 | |
| Gm23008 | Usp2 | Il6 | Gm20655 | Socs1 | |
| Gm23137 | Utp14b | Kcne4 | Gm23388 | Socs5 | |
| Gm23140 | Wnt7b | Kcnj2 | Gm6478 | Spred1 | |
| Gm23143 | Xylt1 | Kcnk10 | Gm6578 | Spry4 | |
| Gm23153 | Ypel1 | Limch1 | Gm9869 | Synj2 | |
| Gm23201 | | Lpcat2 | Hoxa4 | Imem2 | |
| Gm23240 | | Lrrc17 | Hps3 | Tnfaip3 | |
| Gm23511 | | Mcam | Hspb7 | Tnfrsf12a | |
| Gm23523 | | Metazoa_SRP | Ihh | | |
| Gm23686 | | Mrgprf | Inhba | | |
| Gm24207 | | mt-Co3 | Insc | | |
| Gm24299 | | mt-Tl1 | Irx1 | | |
| Gm24305 | | mt-Tm | Irx3 | | |
| Gm24317 | | N4bp2l1 | Irx5 | | |
| Gm24407 | | Ncald | Kcnb1 | | |
| Gm24438 | | Nr4a1 | KCTD12 | | |
| Gm24449 | | Nr4a2 | Kif21b | | |
| Gm24494 | | Nrp1 | Klf4 | | |
| Gm24596 | | Pde4b | Klhl30 | | |
| Gm25099 | | Pde4d | Krt12 | | |
| Gm25107 | | Phex | Lbh | | |
| Gm25135 | | Pim1 | Lifr | | |
| Gm25189 | | Plau | Lmo7 | | |
| Gm25327 | | Prex1 | Lmod1 | | |
| Gm25380 | | Rasl10b | Lpar3 | | |
| Gm25414 | | Rgs2 | Lyst | | |
| Gm25681 | | Rnf122 | Mars2 | | |
| Gm25739 | | Rprl2 | Mef2c | | |
| Gm25781 | | S1pr1 | Mgat5 | | |
| Gm25793 | | Scg2 | Mtus2 | | |
| Gm25970 | | Serpinb1a | Murc | | |
| Gm26104 | | Shc2 | Ndnf | | |
| Gm26107 | | Slc7a7 | Neurl2 | | |
| Gm26202 | | Slpi | Nexn | | |
| Gm6872 | | Snai1 | Nhsl1 | | |
| Gm9889 | | Snora15 | P2rx5 | | |
| Got1 | | Tmem100 | Pak3 | | |
| Gpr153 | | Tnfrst9 | Panx3 | | |
| Grem2 | | Tnfsf11 | Pawr | | |
| Hopx | | Trib2 | Phospho1 | | |
| Ifngr1 | | Trp53inp1 | Pitx2 | | |
| Il4ra | | Tsc22d3 | Polr3e | | |
| Irak3 | | Tspan11 | Pparg | | |
| Itga11 | | Vdr | Ppm1e | | |
| Itga9 | | Wnt4 | Rassf3 | | |
| Itgb3 | | Ypel3 | Rcan2 | | |
| Kremen1 | | | Rcor2 | | |
| Krt31 | | | Rnf144b | | |
| Krt33b | | | Rnf43 | | |
| Ksr1 | | | Rpgrip1l | | |
| Lef1 | | | Rtn4rl1 | | |
| Lif | | | Runx1 | | |
| Lrp8 | | | Runx2 | | |
| Ly6a | | | Sap30 | | |
| Ly6c1 | | | Satb2 | | |
| Megf10 | | | Scn3a | | |
| Mgp | | | Serpine1 | | |
| Mir3068 | | | Slc22a23 | | |
| Mir5136 | | | Slc25a13 | | |
| Mir677 | | | Slc40a1 | | |
| Mmp13 | | | Slc8a3 | | |
| mt-Atp6 | | | Smpd3 | | |
| mt-Tv | | | Smtnl2 | | |
| mt-Tw | | | Sncaip | | |
| Nap1l5 | | | Snta1 | | |
| Net1 | | | Snx7 | | |
| Notum | | | Sp7 | | |

TABLE 4-continued

All RBA-seq data

| Up with PTH only | Up with YKL-05-093 alone | Up with both PTH and YKL-05-093 | Down with PTH only | Down with YKL-05-093 only | Down with both PTH and YKL-05-093 |
|---|---|---|---|---|---|
| Osmr | | | Stc2 | | |
| Parvb | | | Swap70 | | |
| Pdk4 | | | Tbc1d4 | | |
| Pdpn | | | Tcf7 | | |
| Pgpep1l | | | Tmeff1 | | |
| Pitpnc1 | | | Tmem119 | | |
| Pkdcc | | | Tmtc2 | | |
| Plaur | | | Tnfrsf11b | | |
| Plxna2 | | | Tnik | | |
| Ppap2b | | | Trmt61a | | |
| Ppfibp2 | | | Wisp1 | | |
| Prr5 | | | Wnt10b | | |
| Ptp4a1 | | | Zbtb16 | | |
| Rnu12 | | | Zfp296 | | |
| Rnu73b | | | | | |
| Rny3 | | | | | |
| Rprl3 | | | | | |
| Scarna17 | | | | | |
| Sfrp1 | | | | | |
| Sfrp4 | | | | | |
| Slc1a3 | | | | | |
| Slc37a2 | | | | | |
| Slc43a2 | | | | | |
| Smim3 | | | | | |
| Snora28 | | | | | |
| Snora36b | | | | | |
| Snora47 | | | | | |
| Snora62 | | | | | |
| Snord100 | | | | | |
| Snord104 | | | | | |
| Snord110 | | | | | |
| Snord19 | | | | | |
| Snord35b | | | | | |
| Snord49a | | | | | |
| Snord49b | | | | | |
| Snord61 | | | | | |
| Snord65 | | | | | |
| Snord71 | | | | | |
| Snord82 | | | | | |
| Snord85 | | | | | |
| Soga2 | | | | | |
| Stat3 | | | | | |
| Tgfa | | | | | |
| Tll1 | | | | | |
| Tnfaip6 | | | | | |
| Tnfrsf19 | | | | | |
| Vit | | | | | |
| Wdr45 | | | | | |
| Wif1 | | | | | |
| Wisp2 | | | | | |
| Wnt9a | | | | | |
| Zfp52 | | | | | |
| Zfp791 | | | | | |
| Zhx2 | | | | | |

Differentially-expressed genes: >2-fold, FDR < 0.05.

Overall, six clusters of differentially-expressed genes were identified: those up-regulated by PTH alone (172 genes), YKL-05-093 alone (56 genes), and both PTH and YKL-05-093 (97 genes), and those down-regulated by PTH alone (132 genes), YKL-05-093 alone (59 genes), and both PTH and YKL-05-093 (45 genes). The appropriateness of gene categorization was assessed for selected genes from each of these 6 clusters (FAM69C, ADAMTS1, WNT4, KLHL30, DUSP6, and CD200, respectively) by RT-qPCR from independently generated samples (FIGS. 6C to 6H). While YKL-05-093 regulation of many of its target genes not co-regulated by PTH did occur in cells lacking SIK2 and SIK3 (FIG. 15E), regulation of WNT4 and CD200 (genes co-regulated by both PTH and YKL-05-093) by YKL-05-093 did not occur in SIK2/3 deficient cells (FIGS. 6I and 6J). In total, 13/19 genes measured showed SIK2/3-dependent regulation by YKL-05-093, while 6/19 genes measured showed regulation by YKL-05-093 independent of the presence of SIK2/3 (FIGS. 6I to 6J and 15E). Taken together, these results demonstrate that a major arm of PTH signaling in Ocy454 cells can be mimicked by SIK inhibition.

YKL-05-093 Mimics PTH Actions In Vivo

While YKL-04-114 and YKL-05-093 had comparable activity in vitro, YKL-05-093 showed somewhat improved stability when exposed to murine hepatic microsomes in vitro (FIG. 16). Therefore, mice were treated with YKL-05-093 and effects on gene expression in bone were assessed 2 hours later. Similar to acute PTH administration (FIGS. 3A to 3D), intraperitoneal YKL-05-093 administration led to dose-dependent SOST suppression and RANKL up-regulation in osteocyte-enriched bone RNA (FIGS. 7A and 7B). This was accompanied by reductions in sclerostin protein levels measured by immunohistochemistry (FIG. 7C). Finally, expression of genes identified by RNA-Seq as co-regulated by PTH and YKL-05-093 in vitro were measured: as shown in FIGS. 7D to 7I, in vivo 20 µmol/kg YKL-05-093 treatment leads to significant regulation of VDR, WNT4, NR4A2, NUAK1, PDGFA, and CD200 expression in the directions predicted from the in vitro experiments. Therefore, acute YKL-05-093 treatment in vitro and in vivo engages a program of gene expression quite similar to one used by parathyroid hormone, thus identifying SIK inhibition as an important mechanism used by PTH to regulate gene expression in osteocytes.

Small Molecule SIK Inhibitors Boost Bone Formation and Bone Mass In Vivo

YKL-05-099 (25) was also tested. Developed in parallel efforts to design SIK inhibitors suitable for in vivo use, YKL-05-099 is well-tolerated and achieves free serum concentrations above its $IC_{50}$ for SIK2 (34 nM) for >16 hours (25).

First, in vitro experiments were performed to characterize the effects of YKL-05-099 in Ocy454 cells. In these experiments, YKL-05-099 was compared side-by-side with YKL-05-093. As expected, YKL-05-099 leads to dose-dependent reduction in HDAC4 S246 phosphorylation (FIG. 8A). Furthermore, YKL-05-099 treatment causes SOST down-regulation and RANKL up-regulation in a SIK2/3-dependent manner (FIG. 8B). Like YKL-05-093, acute intraperitoneal administration of YKL-05-099 in vivo leads to SOST down-regulation and RANKL up-regulation (FIG. 8C).

Male mice were then treated with vehicle or YKL-05-099 (6 mg/kg) once daily via intraperitoneal injection for 2 weeks. Bone RNA from these animals revealed that RANKL levels were increased and there was a trend towards reduced SOST (FIG. 8D). In addition, osteoblast marker genes (osteocalcin and COL1A1) were significantly increased by YKL-05-099 treatment, suggesting possible positive effects on osteoblastic bone anabolism (FIG. 8D). To determine effects on bone mass and cellular composition/activity, static and dynamic histomorphometry were performed. Indeed, once daily YKL-05-099 treatment increased cancellous bone mass (FIG. 8E) and osteoid surface (FIG. 8F), suggesting accelerated bone formation. Dynamic histomorphometry revealed that YKL-05-099 led increased mineralizing surface, a trend towards increased matrix apposition rate, and increased bone formation rate (FIGS. 8G to 8I and 8L). At the cellular level, YKL-05-099 treatment increased osteoblast numbers (FIGS. 8J and 8M) and reduced osteoclast numbers (FIG. 8K). Other than the observed reduction in osteoclast numbers, these findings are quite similar to the effects of once daily PTH treatment.

Discussion

PTH is currently the only approved osteoporosis therapy that promotes new bone formation. While its effects on target cells in bone are broad, major target genes in osteocytes responsible for its ability to increase both bone formation and resorption are SOST and RANKL, respectively. Here, it was demonstrated that SIKs may act as gatekeepers to regulate a major arm of PTH signaling in osteocytes, including (but not limited to) these two important target genes. Tonic SIK activity may lead to constitutive phosphorylation and cytoplasmic localization of HDAC4/5 and CRTC2. Activation of protein kinase A, as may occur with activation of the PTH receptor (8), may lead to multisite phosphorylation on SIK2, modifications that inhibit its cellular activity (38, 40). This inhibition may reduce tonic HDAC4/5 and CRTC2 phosphorylation, which in turn leads to their nuclear localization and action on respective target genes (FIG. 9).

HDAC4/5 are required for PTH-stimulated SOST repression in osteocytes, through effects on MEF2C binding to the +45 kB SOST enhancer. Previous overexpression studies have suggested that PTH signaling impinges on the upstream SOST enhancer (31, 51, 52): here, it is shown that HDAC4/5 are required for this effect using loss of function approaches in vitro and in vivo. At later time points, PTH treatment reduces in MEF2C mRNA levels (34, 35, 53), in addition to the post-translational effects on DNA binding observed here earlier (FIG. 2G). Similarly, PTH induces both the rapid nuclear translocation of HDAC4 and, at later time points, increases in HDAC4 mRNA (FIGS. 6A to 6J and (54)). It is interesting that PTH signaling has evolved two complementary mechanisms to inhibit MEF2C activity: HDAC4/5-mediated inhibition of binding of MEF2C to target genes and inhibition of transcription of the MEF2C gene. Since MEF2C autoregulation is known to occur (55), future studies will focus on whether class IIa HDACs regulate MEF2C-driven expression of MEF2C itself, and other targets of MEF2C in osteocytes (56, 57).

HDAC4/5 "DKO" mice display several phenotypes not present in either single knockout strain (FIGS. 10A to 10E). Notably, sclerostin transgenic mice (58, 59) do not display woven bone and increased osteocyte density, and sclerostin antibody did not increase bone mineral density (BMD) in DKO animals. Therefore, class IIa HDACs control expression of additional genes in osteocytes that potently regulate skeletal biology. In addition, as evidenced by the fact that HDAC4/5 "DKO" mice show a preserved bone anabolic effect of intermittent PTH treatment (FIG. 13A), class II HDAC/SOST-independent pathways that mediate the pharmacologic effects of parathyroid hormone must exist.

Interesting parallels and distinct differences are noted between PTH-mediated SOST suppression in osteocytes and PTHrP-mediated suppression of expression of the Collagen X gene in growth plate chondrocytes (36). While both pathways may utilize a class IIa HDAC/MEF2 mechanism of action, the signaling events required for HDAC4 nuclear translocation may differ. PTH signaling in osteocytes may involve inhibition of STK activity, while in chondrocytes, PTHrP signaling may activate the cAMP-dependent phosphatase PP2A. That being said, a role for SIKs in PTHrP signaling in chondrocytes cannot be excluded given the fact that SIK3-deficiency (23) appears to phenocopy the effects of PTHrP overexpression (60).The experiments with okadaic acid and PP2A shRNA (FIGS. 13A to 13D) argue against a major role for PP2A in mediating PTH signaling in osteocytes. Because the inhibition of HDAC4/5 phosphorylation in response to PTH was shown to be substantial, any further action of PTH on PP2A or other phosphatases would be likely to have a modest effect on overall phosphorylation levels.

PTH signaling to regulate RANKL expression in osteoblasts and osteocytes has been studied extensively over the past decade. Many investigators have demonstrated a role for a cAMP/CREB pathway via the gene's upstream enhancers (14, 42, 44, 61). Herein it is shown an additional requirement for the presence of a CREB co-activator, CRTC2, for PTH-induced RANKL gene regulation. It is of interest that PTH action may require two pathways, one involving a direct PKA target (CREB) and another that uses PKA-mediated SIK inhibition. Since SIK inhibition, through suppression of SOST expression, can also increase bone formation, one can speculate that this use of the SIK pathway may force PTH action to link bone resorption and bone formation.

A recent report has suggested that, in osteoblasts, PTH signaling promotes proteasomal degradation of HDAC4 which in turn allows MEF2C-driven activation of the RANKL promoter (26). No changes in HDAC4/5 levels are observed after PTH treatment, which may be explained by the differing time courses and cell types used. PTH may induce RANKL expression via its −75 kB enhancer through SIK-dependent CRTC2 nuclear translocation.

The use of SIK inhibitors uniquely allows us to examine the acute effects of changes in SIK enzyme activity in cells and mice. These experiments show that the effects of SIK inhibition are rapid enough to mediate the effects of PTH on SOST and RANKL expression. In this way, though the inhibitors are less specific than gene knockout or shRNA-mediated expression knockdown, they may complement the data derived from the genetic studies. While YKL-05-093 and YKL-05-099 do inhibit kinases other than SIKs when tested in vitro, many of its effects in Ocy454 cells were not observed when SIK2/3 proteins were absent.

The role of SIK2 and SIK3 (the predominant SIKs expressed in osteocytes) in bone biology in vivo remains incompletely understood. Global. SIK2 knockout mice have been described to display phenotypes in melanocytes (62), neurons after ischemic injury (63), cardiomyocytes during hypertrophy (64), and in lipid homeostasis (65). Conditional SIK2 mutant alleles have been described as well (40, 66) to further study the role of this kinase in hepatocytes and in the pancreas. Global SIK2 knockout mice have no reported skeletal phenotype to date. SIK2 has been deleted from DMP1-Cre expressing cells and it has been observed that this gene may be required for the acute response of osteocytes to PTH. A detailed description of the global bone phenotype of the SIK2$^{OcyKO}$ strain remains to be determined. Global SIK3 deficient mice display a dramatic growth plate phenotype (23) that confounds study of osteocyte biology in vivo. A conditional SIK3 allele has been reported, and deletion in chondrocytes shows the cell-intrinsic role for SIK3 in these cells (67).

SIK inhibition downstream of cAMP signaling has long been appreciated to occur (38, 45, 46, 68), but the relative contribution of SIK inhibition to overall changes in gene expression due to Gsα-coupled GPCR signaling has not previously been explored. Remarkably, 32% of genes regulated by PTH in osteocytes were co-regulated by YKL-05-093. While it is likely that many of these genes (like SOST and RANKL) are regulated in turn by HDAC4/5 and CRTC2, undoubtedly additional SIK2/3 substrates may be responsible for these widespread effects.

Recently, pterosin B was reported as a small molecule inhibitor of SIK3 with in vivo activity in a SIK3-dependent murine osteoarthritis model (67). Interestingly, this small molecule leads to ubiquitin-dependent SIK3 degradation, and therefore acts in a manner distinct to that of YKL-05-093 and YKL-05-099 which function as kinase inhibitors (25). While SIK2 deficiency was sufficient to abrogate responses to parathyroid hormone in vitro and in vivo (FIGS. 4A to 4M), combined SIK2 and SIK3 deficiency was required to blunt effects of YKL-05-093 and YKL-05-099. This is consistent was potential redundancy between these two kinases (40), and the fact that both inhibitors potently target SIK3 in addition to SIK2.

In many regards, YKL-05-099 treatment mimics the effects of once-daily PTH treatment in vivo. However, one notable exception is present. PTH treatment increases osteoclastic bone resorption, in part due to PTH-induced RANKL up-regulation (13). Although YKL-05-099 potently increases RANKL levels in bone (FIG. 8D), osteoclast numbers are actually decreased by this treatment (FIG. 8J). In addition to targeting SIK2, YKL-05-099 is known to inhibit the tyrosine kinase Src (25). Src deficiency leads to osteoclast defects and osteopetrosis (69). Therefore, combined SIK and Src inhibition may lead to the desirable therapeutic combination (16) of increased bone formation and reduced bone resorption. More detailed assessment of the long-term safety profile of YKL-05-099 will be required to determine if its profile of kinase inhibition will be well-tolerated over time.

Recombinant PTH is the only current osteoanabolic therapy approved for osteoporosis treatment. The data show that distinct signaling modules existed downstream of PTH receptor signaling, including a major arm involving SIK inhibition. SIK inhibition may be sufficient to reduce sclerostin levels and to mimic many of the other effects of PTH in osteocytes at the level of gene expression. Furthermore, in vivo SIK inhibition with YKL-05-099 boosted osteoblast numbers, osteoblast activity, and trabecular bone mass. Inhibitors of SIK action may provide a novel approach to mimic PTH action to stimulate bone anabolism.

Methods

Animal Studies

All animals were housed in the Center for Comparative Medicine at the Massachusetts General Hospital, and all experiments were approved by the hospital's Subcommittee on Research Animal Care. HDAC5-null mice (70) and HDAC4 f/f mice (71) were generously provided by Dr. Eric Olson (University of Texas Southwestern Medical Center, Dallas, Tex.) and were backcrossed to C57B/6 mice for at least 6 generations. DMP1-Cre mice (27) were generously provided by Dr. Jian (Jerry) Feng (Texas A&M University, Baylor College of Dentistry, Dallas, Tex.). "DKO" HDAC4/5 mice were of the following genotype: HDAC4f/f;HDAC5−/−;DMP1-Cre. SIK2 f/f mice were as described (40), and were bred to DMP1-Cre animals to generate SIK2$^{OcyKO}$ mice. ES cells carrying the targeted SOST allele Sost$^{tm1(KOMP)Vlcg}$, in which the SOST coding sequence has been replaced by LacZ and foxed Neo cassette, were obtained from the Knockout Mouse Project (KOMP) Repository. Clone VG10069-BE8 was injected into blastocysts, and the resulting SOST+/− mice were crossed to HDAC5 mutant animals to generate compound heterozygous mice. In all instances, skeletal phenotypes were evaluated in 8 week-old sex-matched littermates. For acute effects of PTH on bone gene expression, animals were treated with PTH (1-34, 300 µg/kg, subcutaneous administration) and then sacrificed 90 minutes later. For acute effects of YKL-05-093 on bone gene expression, animals were treated with the indicated doses of compound (dissolved in PBS+25 mM HCl) or solvent via intraperitoneal injections, and sacrificed 2 hours later. Experiments with YKL-05-099 were performed in a similar fashion: compound was dissolved in PBS+25 mM HCl and injected I.P. once daily five times per week for a total of 10 injections. For in vivo sclerostin antibody treatment, mice were treated twice weekly with sclerostin antibody (50 mg/kg, subcutaneous administration, generously provided by Dr. Michael Ominsky, Amgen) for 6 weeks. Power calculations were performed based on pilot experiments in which standard deviations and magnitudes of effect sizes were estimated. For experiments in which mice were treated with either vehicle or PTH (or YKL-05-093), mice were assigned to alternating treatment groups in consecutive order.

Antibodies and Compounds

Antibodies against phospho-HDAC4/5/7 S246/259/155 (3443), phospho-HDAC4 S632 (3424), MEF2C (5030), tubulin (2146), phospho-PKA substrate (9624), and PP2Acs (2259) were purchased from Cell Signaling Technology (Danvers, Mass.). HDAC4 (ab 12172) and GFP (ab6556) antibodies were from Abcam (Cambridge, Mass.). FLAG antibody (F1804) was from Sigma (St. Louis, Mo.). CRTC2 (ST1099) and SP1 (07-645) antibodies were from EMD Millipore (Darmstadt, Germany). Gs,alpha antibody (C-18) was from Santa Cruz Biotechnology (Santa Cruz, Calif.). Phospho-HDAC5 S279 (30) antibody was a generous gift from Dr. Chris Cowan (McLean Hospital, Belmont, Mass.). Antibodies recognizing phosphorylated and total forms of SIK2 and SIK3 were as described (39, 40). The phospho-SIK3 (T469) antibody was generated by YenZym Antibodies by immunizing rabbits with mouse SIK3 peptide (Res 463-476 of mouse SIK3 (www.kinase.com): *CLSMRRH-pT-VGVADPR (SEQ ID NO: 5), a terminal cysteine (*C) was added to the peptide sequence to allow peptide conjugation to carrier proteins and "p" denotes the phosphorylated residue). For sclerostin immunohistochemistry, biotinylated anti-sclerostin antibody (BAF1589) was purchased from R+D (Minneapolis, Minn.). Synthetic human PTH(1-34) was synthesized by Dr. Ashok Khatri (peptide/protein core facility, MGH). Forskolin (F6886), staurosporine (S5921), and okadaic acid (O113) were from Sigma. Oligonucleotides were synthesized by the DNA synthesis group of the CCIB DNA Core Facility at MGH (Boston, Mass.).

Cell Culture

For all experiments, a single cell subclone of Ocy454 cells (17, 18) was used. Cells were passages in alpha-MEM supplemented with 10% heat-inactivated fetal bovine serum and 1% antibiotics (penicillin/streptomycin, Fungizone) at 33° C. with 5% CO2. Cells were plated at 50,000 cells/ml and allowed to reach confluency at 33° C. (typically in 2-3 days). At this point, cells were transferred to 37° C. for subsequent analysis. For immunoblotting, cells were always analyzed after culture at 37° C. for 7 days. For gene expression analysis, cells were analyzed after culture at 37° C. for 14 days. Mycoplasma contamination was ruled out by PCR. Cells were routinely assayed for SOST expression at 37° C. and examined for osteocytic morphology.

shRNA Infections and CRISPR/Cas9-Mediated Gene Deletion

See Tables 5 and 6 for all shRNA and sgRNA targeting sequences used. For shRNA, lentiviruses were produced in 293T cells in a pLKO.1-puro (Addgene, plasmid 8453) backbone. Viral packaging was performed in 293T cells using standard protocols (www.broadinstitute.org/rnai/public/resources/protocols). For experiments with SIK2/SIK3 double knockdown, one shRNA was transferred into a blasticidin resistance-conferring backbone (Addgene, plasmid 26655). Cells were exposed to lentiviral particles (MOI=1) overnight at 33° C. In the presence of polybrene (5 µg/ml). Media was then changed and puromycin (2 µg/ml) and/or blasticidin (4 µg/ml) was added. Cells were maintained in selection medium throughout the duration of the experiment. HDAC5 S/A cDNA was introduced via lentivirus as described (18).

TABLE 5 shRNA target sequences

| | | |
|---|---|---|
| HDAC5 | CATCGCTGAGAACGGCTTTAC | 6 |
| GNAS | TCGGGATGAGTTTCTGAGAAT | 7 |
| LacZ | CCAACGTGACCTATCCCATTA | 8 |
| SIK2 | CTTGTTGGTGGAACGTCTAAA | 9 |
| SIK3 | CGCACGGAAGTTATGGAAGAT | 10 |
| MEF2C | CCCTATGAATCTAGGAATGAA | 11 |
| CRTC1 | ATAGGTCACCTGTCCGATAAT | 12 |
| CRTC2 | CAAGGTGTAGAGGGAAATCTT | 13 |
| CRTC3 | GACAATGTAGCACTGAATTAA | 14 |

TABLE 6 sgRNA target sequences

| | | |
|---|---|---|
| HDAC4 #1 | TGACGTGTAGAGAGGAAGTG | 15 |
| HDAC4 #2 | ACTTACCCATACCAGTAGCG | 16 |
| GNAS #1 | CCTCGGCAACAGTAAGACCG | 17 |
| GNAS #2 | GATCCTCATCTGCTTCACAA | 18 |

For sgRNA experiments, first Ocy454 cells were stably transduced with a hygromycin resistance-conferring Cas9-expressing lentivirus to ensure no effects on sclerostin secretion. Sclerostin ELISAs were performed exactly as described in (18). For subsequent experiments, sgRNA sequences were subcloned into PX458 (a gift from Feng Zhang, Addgene plasmid 48138 (72)), a plasmid that co-expressed an sgRNA, Cas9, and eGFP. Ocy454 cells were transfected with this plasmid using Fugene HD (Promega, Madison, Wis.) (1 µg plasmid per well of a 6 well plate). 48 hours later, eGFP$^{hi}$ cells were recovered by FACS-based sorting and plated in 96 well plates at 1 cell per well. Media was changed once weekly, and 3 weeks later colonies were identified by visual inspection. Colonies were then expanded and analyzed for loss of target protein expression by immunoblotting. For HDAC4 and Gsα targeting experiments, at least 3 independent clones (deriving from 2 independent sgRNA sequences) were analyzed and showed similar results. Allele-specific sequencing in mutant clones was performed by amplifying the genomic region of interest surrounding the targeted site by PCR. PCR products were then TOPO-TA cloned, and multiple bacterial colonies sequenced using T7 sequencing primer.

Real-Time Quantitative PCR

Total RNA was extracted from cultured cells using RNeasy (Qiagen, Venlo, Netherlands) following the manufacturer's instructions. For long bone RNA isolation, mice were sacrificed and both femurs were rapidly dissected on ice. Soft tissue was removed and epiphyses cut. Bone marrow cells were then removed by serial flushing with ice-cold PBS. TRIzol (Life Technologies) was added and sampled were frozen at −80 C and then homogenized. RNA was then extracted per the manufacturer's instructions, and further purified on RNeasy microcolumns prior to cDNA synthesis. RNA with A260/280 ratio<1.7 was not used for downstream analysis. For cDNA synthesis, 1 µg RNA was used in synthesis reactions according to the instructions of the manufacturer (Primescript RT, Takara). SYBR Green-based qPCR detection was performed using FastStart Universal SYBR Green (Roche, Basel, Switzerland) on a StepOne Plus (Applied Biosystems, Carlsbad, Calif.) thermocycler. All PCR primer sequences are listed in Tables 7 and 8.

TABLE 7

RT-qPCR primer pairs

| | Forward primer | SEQ ID NO: | Reverse primer | SEQ ID NO: |
|---|---|---|---|---|
| SOST | GCCTCATCTGCCTACTTGTG | 19 | CTGTGGCATCATTCCTGAAG | 37 |
| RANKL | GCTGGGCCAAGATCTCTAAC | 20 | GTAGGTACGCTTCCCGATGT | 38 |
| β-actin | CCTCTATGCCAACACAGTGC | 21 | ACATCTGCTGGAAGGTGGAC | 39 |
| CITED1 | CCAACCTTGGAGTGAAGGAT | 22 | CCAGAGGAGCTAGTGGGAAC | 40 |
| CRTC1 | TCTGCAGACCAGGAGAACAC | 23 | GTGGATGTTGGTGAGGTCAG | 41 |
| CRTC2 | CCATAGTCACCCATCACTGC | 24 | GCACTCAGGACAGGAGATGA | 42 |
| CRTC3 | ATGGGTTTCTGTGATGGTGA | 25 | ACAGGGACTGGATCTCCTTG | 43 |
| FAM69C | TATTAGCCACATTGCCCTCA | 26 | ATGGCGAAGTTCTCAGGTTT | 44 |

TABLE 7-continued

RT-qPCR primer pairs

| | Forward primer | SEQ ID NO: | Reverse primer | SEQ ID NO: |
|---|---|---|---|---|
| ADAMTS1 | GAAACCATGCTCGTAGCTGA | 27 | AATTCCTAATGCTGGGATGC | 45 |
| WNT4 | GGCCTTTGTATACGCCATCT | 28 | CACAGCCACACTTCTCCAGT | 46 |
| KLHL30 | AGGTGCAATCTCAACACAGC | 29 | GTAGGCCTCCATCTCCACAT | 47 |
| DUSP6 | CATGCAGAAGCTCAACCTGT | 30 | AGGGTCCTTTCGAAGTCAAG | 48 |
| CD200 | GAGCTGGGACTCTGGAACTC | 31 | GAGGGTAAGGCAAGCTGTTC | 49 |
| VDR | ACACTGCAGACCTACATCCG | 32 | AGCCAGCTTCTGGATCATCT | 50 |
| NR4A2 | ATCTCCTGACCGGCTCTATG | 33 | TGGGTTGGACCTGTATGCTA | 51 |
| NUAK1 | GTGGATGCTGATGGTGAATC | 34 | TGCCAAGAGTGGAGACTCAG | 52 |
| PDGFA | CGAAGTCAGATCCACAGCAT | 35 | GGGCTCTCAGACTTGTCTCC | 53 |
| MEF2C | ATCAGCAGGCAAAGATTGTG | 36 | CTGTTATGGCTGGACACTGG | 54 |

TABLE 8

Primer pairs for ChIP qPCR (RANKL nomenclature is per Onal et al., 2015)

| | Forward primer | SEQ ID NO: | Reverse primer | SEQ ID NO: |
|---|---|---|---|---|
| SOST + 45 kB | GAGCCTGGTCTCATTTGTTG | 55 | CCTCTCTAGGATGGCAGCAT | 67 |
| SOST promoter | CGCTGTGGTATGCTAACTGG | 56 | CTTACAAGTCGAGGCAGGTG | 68 |
| MEOX promoter | CCTCTGGGCAATTTGTCTCT | 57 | CTCCAGGGATTGAGAGAAGG | 69 |
| RANKL D2 | CTTGGAAGGACTCCAGGAAA | 58 | CCTTTCTCAGAGCACACTGG | 70 |
| RANKL D3 | AAATCCCATTTGCTTTCCAG | 59 | GAGCTGTGTCCTAGAAGAATTGTC | 71 |
| RANKL D4 | TGGGAGACTCAGTTGTTGCT | 60 | TGTTGTTGGTTCGTTGTCCT | 72 |
| RANKL D5 | GATGGAGTCAGGATGCACAG | 61 | GAGCCCTGAGAACAGTGTGA | 73 |
| RANKL D6 | GAAGAGAACATTGCTGGTTGC | 62 | TAAGGATGCTTTCCCAGCTC | 74 |
| RANKL D7 | CACCTGTAATTCTAGCACGCA | 63 | TCACGCTCCTCTCAAATTCA | 75 |
| RANKL T1 | TGGTCCAGGTCAAGCAATAA | 64 | GGCAACACAAACCTCCTGTA | 76 |

TABLE 8-continued

Primer pairs for ChIP qPCR (RANKL nomenclature is per Onal et al., 2015)

| | Forward primer | SEQ ID NO: | Reverse primer | SEQ ID NO: |
|---|---|---|---|---|
| RANKL T2 | CCTCTGGGAGCAAATGAGAG | 65 | GGTGCATCTGTGGATGGTAA | 77 |
| RANKL T3 | CCTTGAATTCTTTGGACTGGA | 66 | TACACTGTCCTTTCCTTGCG | 78 |

Immunoprecipitation and Immunoblotting

Whole cell lysates were prepared using TNT buffer (20 mM Tris-HCl pH 8, 200 mM NaCl, 0.5% Triton X-100 supplemented with 1 mM DTT, 1 mM NaF, and protease inhibitors (Pierce, catalog #88266). This lysis buffer was used for all experiments except those in which SIK2 and SIK3 phosphorylation was measured using phospho-specific antibodies: for those experiments, cells were lysed in buffer containing 50 mM Tris-HCl pH 7.5, 270 mM sucrose, 1 mM EDTA, 1 mM EGTA, and protease/phosphatase inhibitors. MEF2C (18) and SIK3 (39, 40) immunoprecipitations were performed as described. Subcellular fractionation was performed using commercially-available kit (Thermo Scientific, product number 78840) following the manufacturer's instructions. Lysates (15-20 µg cellular protein) were separated by SDS-PAGE and proteins were transferred to nitrocellulose. Membranes were blocked with 5% milk in TBST, and incubated with primary antibody overnight at 4° C. The next day, membranes were washed, incubated with appropriate horseradish peroxidase (HRP)-coupled secondary antibodies, and signals detected with enhanced chemiluminescence (ECL, Pierce). All immunoblots were repeated twice with comparable results obtained.

Histology, Immunohistochemistry, and Analysis

Formalin-fixed paraffin-embedded decalcified tibia sections from 8 week-old mice were obtained. Sirius red staining was performed following standard procedures (73) using Sirius red and picric acid obtained from Sigma. Sections were visualized under polarized light. Hematoxylin and eosin (H+E) staining was performed on some sections using standard protocols, and osteocyte density was assessed on cortical bone osteocytes in a medium power field 3 min below the tibial growth plate. For anti-sclerostin immunohistochemistry, antigen retrieval was performed using proteinase K (20 µg/ml) for 15 minutes. Indogenous peroxidases were quenched, and slides were blocked in TNB buffer (Perkin Elmer), then stained with anti-sclerostin antibody at a concentration of 1:200 for one hour at room temperature. Sections were washed, incubated with HRP-coupled secondary antibodies, signals amplified using tyramide signal amplification (TSA), and HRP detection was performed using 3,3'-diaminobenzidine (DAB, Vector) for 2-3 minutes. Slides were briefly counterstained with hematoxylin prior to mounting. Quantification of sclerostin positive osteocytes was performed on a blinded basis. All photomicrographs were taken 3 mm below the growth plate on the lateral side of the tibia. All osteocytes were counted and then scored as either sclerostin-positive or negative. Sections from at least 4 mice per experimental group were analyzed. Quantification of immunostaining was done based on coded sample numbers in a completely blinded manner. Representative photomicrographs are displayed next to quantification in data figures.

Chromatin Immunoprecipitations

ChIP assay was performed using a kit (EZ-Chip, Millipore, 17-371, Billerica, Mass.) according to the manufacturer's instructions. Briefly, cells were grown at 37° C. for 7 days, followed by PTH treatment (25-50 nM) for the indicated times. Cells were then cross-linked with 1% formaldehyde for 10 minutes and then quenched with 0.125M glycine. Cells were lysed and sonicated with 10 pulses for 30 seconds each to fragment DNA to 200-800 bp fragments. DNA-protein complexes were precipitated using 1.5 µg antibodies (MEF2C, CRTC2, or control rabbit IgG) overnight at 4° C. Immune complexes were precipitated, DNA was purified, and real-time PCR was conducted using primer sets (Tables 5 through 8) to detect the +45 kB SOST enhancer and upstream RANKL enhancers. Data are expressed as relative enrichment for each antibody (above control IgG) for each primer set. Data shown represent triplicate biological repeats within experiments, and each experiment was performed at least twice.

cAMP Radioimmunoassays

Cells, in 96 well plates, were treated with indicated ligands for 20 minutes at room temperature in the presence of the phosphodiesterase inhibitor 3-isobutyl-1-methylxanthine (IBMX, Sigma I5879, 2 mM). The medium was then removed and cells were lysed in 50 mM HCl and transferred to −80 C. Thawed lysates were diluted 1:5 with dH2O, and an 10 µl aliquot was assessed for cAMP content by radioimmunoassay using $^{125}$I-cAMP analog as a tracer and unlabeled cAMP to generate a standard curve.

RNA-Sequencing

Total RNA was subjected to rRNA depletion using RiboZero kit (Illumina) followed by NGS library construction using NEBNext Ultra Directional RNA Library Prep Kit for Illumina (New England Biolabs). Experimental duplicates were performed for each condition. Sequencing was performed on Illumina HiSeq 2500 instrument, resulting in an average of 33 million pairs of 50 bp reads per sample. Sequencing reads were mapped to the mouse reference genome (mm10/GRCm38) using STAR (bioinformatics.oxfordjournals.org/content/early/2012/10/25/bioinformatics.bts635). Gene expression counts were calculated using HTSeq v.0.6.0 (www.huber.embl.de/users/anders/HTSeq/doc/overview.html) based on a current Ensembl annotation file for mm10/GRCm38 (release 75). Differential expression analysis was performed using EgdeR package based on the criteria of >2-fold change in expression value versus control and false discovery rates (FDR)<0.05. Venn diagrams from gene set analysis were generated using genes with >1.5 fold change in expression values and FDR<0.05. Significance testing for gene set overlap was performed according to a standard hypergeometric distribution, p-values<$2.2*10^{-16}$. The accession number for the RNA-seq dataset reporter in this paper is GEO: GSE76932 (www.ncbi.nlm.nih.gov/geo/query/acc.cgi?acc=GSE76932).

ScanEDGE kinase assays paneling specificity across a panel of 96 representative kinases were performed by DiscoverX (Fremont, Calif.). For most assays, kinase-tagged T7 phage strains were grown in parallel in 24-well blocks in an *E. coli* host derived from the BL21 strain. Bacteria were grown to log phase and infected with T7 phage from frozen stock (MOI=0.4) and incubated with shaking at 32° C. until lysis (90-150 minutes). The lysates were centrifuged (6000× g) and filtered (0.2 µm) to remove cell debris. The remaining kinases were produced in HEK-293 cells and subsequently tagged with DNA for qpCR detection. Streptavidin coated magnetic beads were treated with biotinylated small molecule ligands for 30 minutes at room temperature to generate affinity resins for kinase assays. The liganded beads were blocked with excess biotin and washing with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384 well plates in a final volume of 40 µl. The assay plates were incubated at room temperature with shaking for 1 hour and the affinity beads were washed with wash buffer (1×PBS, 0.05% Tween 20). The beads were then resuspended in elution buffer (1×PBS, 0.05% Tween. 20, 0.5 µM of the non-biotinylated affinity ligand) and incubated at room temperature with shaking for 30 minutes. The kinase concentration in the eluates was measured by qPCR. YKL-05-093 was screened in this assay at 71 nM (ten times its Kd for SIK2), and results are reported as "% control", where lower numbers indicate stronger hits.

Micro-CT

Assessment of bone morphology and microarchitecture was performed with high-resolution microcomputed tomography (µCT40; Scanco Medical, Brüttisellen, Switzerland). In brief, the distal femoral metaphysis and mid-diaphysis were scanned using 70 kVp peak x-ray tube potential, 113 mAs x-ray tube current, 200 ms integration time, and 10-µm isotropic voxel size. Cancellous bone was assessed in the distal metaphysis and cortical bone was assessed in the mid-diaphysis. The femoral metaphysis region began 1700 µm proximal to the distal growth plate and extended 1500 µm distally. Cancellous bone was separated from cortical bone with a semiautomated contouring program. For the cancellous bone region, bone volume fraction (BV/TV, %), trabecular thickness (Tb.Th, mm), trabecular separation (Tb.Sp, mm), trabecular number (Tb.N, 1/mm), connectivity density (Conn.D or ConnD, 1/mm$^3$), and structure model index (SMI) were assessed. Transverse CT slices were also acquired in a 500 µm long region at the femoral mid-diaphysis to assess total cross-sectional area, cortical bone area, and medullary area (Tt.Ar, Ct.Ar, and Ma.Ar, respectively, all mm$^2$); bone area fraction (Ct.Ar/Tt.Ar, %), cortical thickness (Ct.Th, mm), porosity (Ct.Po, %) and minimum ($I_{min}$, mm$^4$), maximum ($I_{max}$, mm$^4$), and polar (J, mm$^4$) moments of inertia. Bone was segmented from soft tissue using the same threshold, 300 mg HA/cm$^3$ for trabecular and 733 mg HA/cm$^3$ for cortical bone. Scanning and analyses adhered to the guidelines for the use of micro-CT for the assessment of bone architecture in rodents (74). For the primary spongiosa region (where intermittent PTH treatment has its predominant effect) analyzed in. FIG. 13A, coronal CT slices were evaluated in a 500 µm (50 slices) region located centrally in the bone. The region of interest began 1000 µm superior to the epiphysis and included all primary spongiosa and the medullary cavity. The primary spongiosa bone region was identified by semi-manually contouring the region of interest. Images were thresholded using an adaptive-iterative algorithm. The average adaptive-iterative threshold of control mice (WT, vehicle treated) for the region of interest (299 mgHA/cm$^3$) were then used to segment bone from soft tissue for all distal femur images. Micro-CT analysis was done based on sample numbers in a completely blinded manner.

Histomorphometry

Right tibia from 8-week-old mice were subjected to bone histomorphometric analysis. The mice were injected 20 mg/kg body weight of calcein and 40 mg/kg body weight of demeclocycline on 7 and 2 days before necropsy, respectively. The tibia was dissected and fixed in 70% ethanol for 3 days. Fixed bones were dehydrated in graded ethanol, then infiltrated and embedded in methylmethacrylate without demineralization. Undecalcified 4-µm-thick longitudinal sections were obtained using microtome (RM2255, Leica Biosystems, IL, USA). Sections were left unstained for dynamic parameters measurement, and consecutive sections were stained with tartrate-resistant acid phosphatase and counterstained with toluidine blue for measurement of cellular parameters. A standard dynamic bone histomorphometric analysis of the tibial metaphysis was done using the Osteomeasure analyzing system (Osteometrics Inc., Decatur, Ga., USA). Measurements were performed in the area of secondary spongiosa, 200 µm below the proximal growth plate. The observer was blinded to the experimental genotype at the time of measurement. The structural, dynamic and cellular parameters were calculated and expressed according to the standardized nomenclature (75).

Example 3. Additional Biological Assays

In Example 3, "YKL" refers to YKL-05-099, and the experimental conditions are described herein or as described in Example 2. Exemplary results of Example 3 are shown in FIGS. 24 to 37D.

YKL-05-099 Uncouples Bone Formation and Resorption by Blocking M-CSF-Driven Osteoclastogenesis It was recently reported that PTH signaling in osteocytes blocks the activity of the kinase, salt inducible kinase 2 (SIK2). Treatment of mice with YKL-05-099 once daily (single dose, 6 mg/kg) for 2 weeks led to effects similar to those of intermittent PTH: increased osteoblast numbers, increased bone formation, and increased bone mass. However, unlike PTH, YKL-05-099 treatment led to reductions in osteoclast numbers despite increased levels of RANKL. The goal of the current study is to understand how YKL-05-099 regulates osteoclast differentiation.

8-week-old male C57B/6 mice were treated with vehicle or different doses of YKL-05-099 (2 mg/kg, 6 mg/kg, 18 mg/kg) once daily for two weeks. Static and dynamic histomorphometry was performed (see FIG. 24). Previous results of in vitro kinase profiling (DiscoverX) for YKL-05-099 were examined (see FIG. 27). Murine bone marrow-derived macrophages were differentiated into osteoclasts in the presence of 10 different doses of YKL-05-099 (see FIG. 25). Effects on osteoclast differentiation were assessed by TRAP secretion assays and counting multi-nucleated TRAP-positive cells (see FIG. 26). M-CSF signaling in primary macrophages, was assessed by immunoblotting for MCSF-receptor Y723 phosphorylation and ERK1/2 phosphorylation (see FIG. 27).

Compared to vehicle-treated mice, YKL-05-099 treatment caused dose-dependent increases in trabecular bone volume (veh 10.3±1.9 vs 18 mg/kg 16.3±2.0, p<0.01), increases in Ob.S/BS (veh 11.9±0.8 vs 18 mg/kg 16.8±1.3, p<0.01), and reductions in Oc.S/BS (veh 2.79±0.8 vs 18 mg/kg 1.59±0.4, p<0.05). It was hypothesized that YKL-05-099 might directly block osteoclastogenesis. M-CSF+RANKL-primed osteoclastogenesis was inhibited by YKL-05-099 treatment in vitro with an $IC_{50}$ of 52 nM. In addition to SIK2, DiscoverX profiling data indicated that this compound could also target the M-CSF receptor. Acute YKL-05-099 pre-treatment (15 µM) of bone marrow-derived macrophages blocked M-CSF-induced M-CSF receptor Y723 auto-phosphorylation and downstream ERK phosphorylation.

YKL-05-099 may target bone formation and bone resorption by two distinct mechanisms. In osteocytes, this compound may block SIK2 and may boost bone formation, in part, by reducing sclerostin production. In pre-osteoclasts, this compound may block M-CSF receptor signaling. By boosting bone formation and inhibiting bone resorption, YKL-05-099 represents a promising osteoporosis treatment strategy.

The Small Molecule SIK Inhibitor YKL-05-099 Increases Trabecular Bone Mass and Bone Formation in Hypogonadal Female Mice Whether YKL-05-099 boosts bone mass in oophorectomized (OVX) animals remains unknown. Furthermore, side-by-side comparison of PTH and YKL-05-099 treatment in vivo has not been performed. Here, it is determined if YKL-05-099 increases bone mass in OVX mice, and compared the skeletal effects of these two bone anabolic agents.

48 female C57B/6 mice were subjected to sham surgery (SHAM; n=24) or oophorectomy (n=24) at 12 weeks of age. 8 weeks later, the mice were treated with either vehicle (n=8), YKL-05-099 (i.p., 18 mg/kg, n=8), or PTH (s.c., 1-34 (amino acids 1-34 of PTH), 100 mcg/kg, n=8) once per day for 4 weeks. The mice were assessed by micro-CT (µ-CT) of the femur and L5 vertebrae, and static/dynamic histomorphometry of the tibia. Exemplary results are shown in FIGS. 29A to 35.

Neither PTH nor YKL-05-099 altered growth or peripheral blood counts. OVX reduced trabecular BMD (Tb.BMD) in the distal femur (sham/veh vs OVX/veh p=0.041 (see FIG. 30) and L5 vertebrae (p=0.00043), and reduced trabecular L5 BV./TV (p=0.00089) (see FIG. 31A). In OVX mice, PTH and YKL-05-099 treatment increased trabecular bone mass at both skeletal sites (for example, distal femur Tb.BMD p=0.0047 veh vs PTH, p=0.00036 veh vs YKL) (see FIG. 31B). Both PTH and YKL-05-099 increased osteoblast numbers (see FIG. 32A) and bone formation rate (see FIG. 33C) in OVX mice. Treatment effects of PTH and YKL-05-099 differed in two significant regards. First, while PTH tended to increase osteoclast activity, YKL-05-099 reduced eroded surfaces (see FIG. 32C, p=0.41 veh vs PTH, p=0.0129 veh vs YKL). Second, while PTH increased amounts of non-mineralized osteoid, YKL-05-099 did not (see FIG. 33D, p=0.00071 veh vs PTH, p=0.64 veh vs YKL).

Figure 33A:
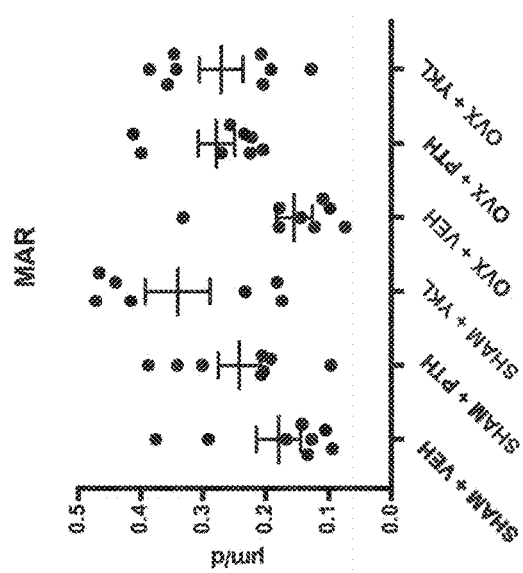
Figure 33B:
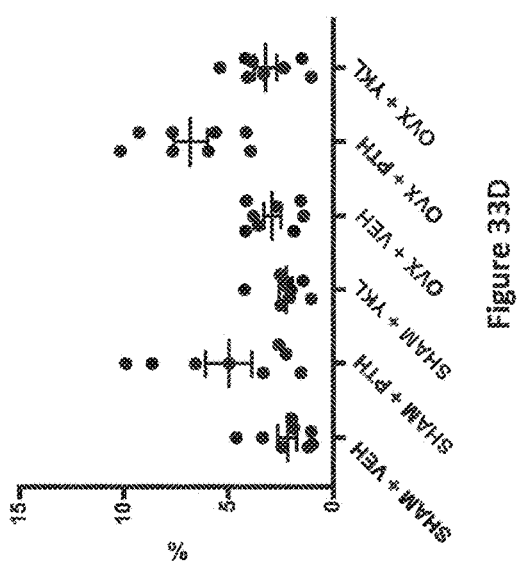
Figure 33C:
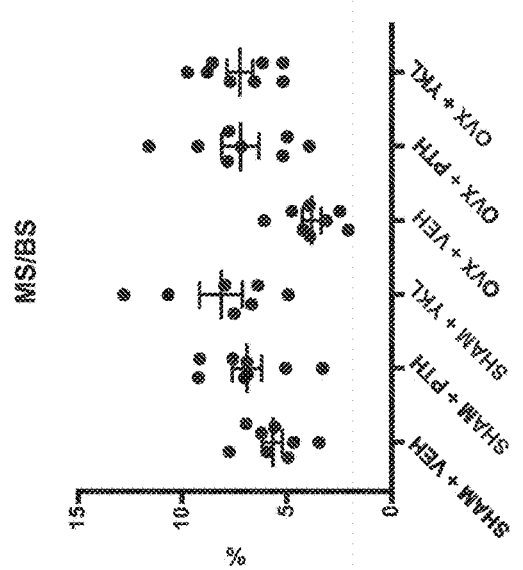
Figure 33D:
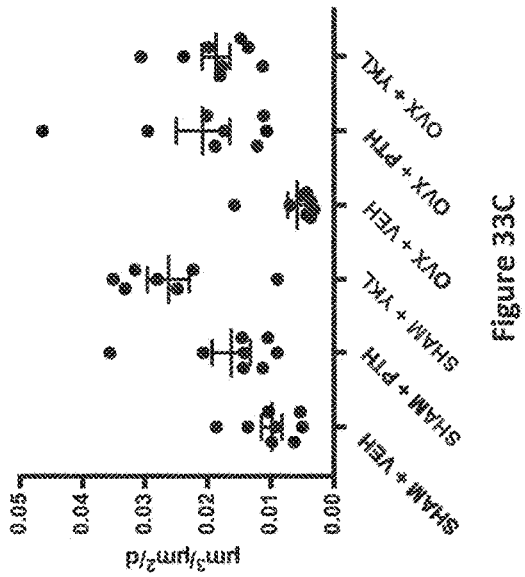

In OVX mice, both YKL-05-099 and PTH increased trabecular bone mass (see FIG. 30) and bone formation (see FIG. 33C). Potential therapeutic advantages of YKL-05-099 may include its ability to reduce bone resorption and promote efficient osteoid mineralization.

Summary of OVX Results: YXL vs PTH

OVX reduced BMD in the femur and reduced BMD and BV/TV in spine. PTH and YKL both increased bone mass/density in OVX mice. Both PTH and YKL increased osteoblast numbers and bone formation rate in OVX mice. YKL reduced osteoclasts, which is a direct anti-resorptive effect of YKL, and PTH increased osteoclasts. PTH increased osteoid but YKL did not. YKL may promote mineralization. YKL may also reduce marrow adipocytes.

In Vivo Toxicity Experiments

In a 4 week treatment (weeks 20-24) 16 mice treated with vehicle, PTH, or YKL-05-099. There was normal weight gain in all groups. Blood was obtained for the complete blood count (CBC) measurement, and serum was obtained for the glucose, blood urea nitrogen (BUN), cholesterol, triglycerides, ALT, Creatine kinase (CK), amylase, and total protein measurements. Exemplary results are shown in FIGS. 36A to 37D. There were no effects of sham versus OVX on any of these parameters, so the data were analyzed with respect to drug (PTH or YKL-05-099) treatment. "WBC" refers to "white blood cell". "Hgb" refers to "hemoglobin". "Plt" refers to "platelet". "V vs Y" refers to "Vehicle vs. YKL-05-099." The hematology data showed no signal (see FIGS. 36A to 36D), suggesting that PTH and YKL-05-099 are not toxic under the test conditions. Serum toxicology data showed increased glucose and BUN (see FIGS. 37A to 37D).

REFERENCES

1. Harvey N, Dennison E, Cooper C. Osteoporosis: impact on health and economics. Nature reviews Rheumatology. 2010 February; 6(2):99-105. PubMed PMID: 20125177.
2. Bonewald L F. The amazing osteocyte. Journal of bone and mineral research: the official journal of the American Society for Bone and Mineral Research. 2011 February; 26(2):229-38. PubMed PMID: 21254230. Pubmed Central PMCID: 3179345.
3. Nakashima T, Hayashi M, Fukunaga T, Kurata K, Oh-Horn M, Feng J Q, et al. Evidence for osteocyte regulation of bone homeostasis through RANKL expression. Nature medicine. 2011 October; 17(10):1231-4. PubMed PMID: 21909105.
4. Xiong J, Onal M, Jilka R L, Weinstein R S, Manolagas S C, O'Brien C A. Matrix-embedded cells control osteoclast formation. Nature medicine. 2011 October; 17(10):1235-41. PubMed PMID: 21909103. Pubmed Central PMCID: 3192296.
5. Cummings S R, San Martin J, McClung M R, Skis E S, Eastell R, Reid I R, et al. Denosumab for prevention of fractures in postmenopausal women with osteoporosis. The New England journal of medicine. 2009 Aug. 20; 361(8):756-65. PubMed PMID: 19671655.
6. Baron R, Kneissel. M. WNT signaling in bone homeostasis and disease: from human mutations to treatments. Nature medicine. 2013 February; 19(2):179-92. PubMed PMID: 23389618.
7. McClung M R, Grauer A, Boonen S, Bolognese M A, Brown J P, Diez-Perez A, et al. Romosozumab in postmenopausal women with low bone mineral density. The New England journal of medicine. 2014 Jan. 30; 370(5): 412-20. PubMed PMID: 24382002.
8. Cheloha R W, Gellman S H, Vilardaga J P, Gardena T J. PTH receptor-1 signalling-mechanistic insights and therapeutic prospects. Nature reviews Endocrinology. 2015 December; 11(12):712-24. PubMed PMID: 26303600. Pubmed Central PMCID: 4651712.

9. Keller H, Kneissel M. SOST is a target gene for PTH in bone. Bone. 2005 August; 37(2):148-58. PubMed PMID: 15946907.
10. Rhee Y, Allen M R, Condon K, Lezcano V, Ronda A C, Galli C, et al. PTH receptor signaling in osteocytes governs periosteal bone formation and intracortical remodeling. Journal of bone and mineral research: the official journal of the American. Society for Bone and Mineral Research. 2011 May; 26(5):1035-46. PubMed PMID: 21140374. Pubmed Central PMCID: 3179307.
11. Kramer I, Loots G G, Studer A, Keller H, Kneissel M. Parathyroid hormone (PTH)-induced bone gain is blunted in SOST overexpressing and deficient mice. Journal of bone and mineral research: the official journal of the American Society for Bone and Mineral Research. 2010 February; 25(2):178-89. PubMed PMID: 19594304. Pubmed Central PMCID: 3153379.
12. Saini V, Marengi D A, Barry K J, Fulzele K S, Heiden E, Liu X, et al. Parathyroid hormone (PTH)/PTH-related peptide type 1 receptor (PPR) signaling in osteocytes regulates anabolic and catabolic skeletal responses to PTH. The Journal of biological chemistry. 2013 Jul. 12; 288(28):20122-34. PubMed PMID: 23729679. Pubmed Central PMCID: 3711281.
13. Fu Q, Jilka R L, Manolagas S C, O'Brien C A. Parathyroid hormone stimulates receptor activator of NFkappa B ligand and inhibits osteoprotegerin expression via protein kinase A activation of cAMP-response element-binding protein. The Journal of biological chemistry. 2002 Dec. 13; 277(50):48868-75. PubMed PMID: 12364326.
14. Fu Q, Manolagas S C, O'Brien C A. Parathyroid hormone controls receptor activator of NF-kappaB ligand gene expression via a distant transcriptional enhancer. Mol Cell Biol. 2006 September; 26(17):6453-68. PubMed PMID: 16914731. Pubmed. Central PMCID: 1592840.
15. Kim S, Yamazaki M, Shevde N K, Pike S W. Transcriptional control of receptor activator of nuclear factor-kappaB ligand by the protein kinase A activator forskolin and the transmembrane glycoprotein 130-activating cytokine, oncostatin M, is exerted through multiple distal enhancers. Molecular endocrinology. 2007 January; 21(1):197-214. PubMed PMID: 17053039.
16. Tsai J N, Uihlein A V, Lee H, Kumbhani R, Siwila-Sackman E, McKay E A, et al. Teriparatide and denosumab, alone or combined, in women with postmenopausal osteoporosis: the DATA study randomised trial. Lancet. 2013 Jul. 6; 382(9886):50-6. PubMed PMID: 23683600. Pubmed Central PMCID: 4083737.
17. Spatz J M, Wein M N, Gooi J H, Qu Y, Garr J L, Liu S, et al. The Wnt Inhibitor Sclerostin Is Up-regulated by Mechanical Unloading in Osteocytes in vitro. The Journal of biological chemistry. 2015 Jul. 3; 290(27):16744-58. PubMed PMID: 25953900. Pubmed Central PMCID: 4505423.
18. Wein M N, Spatz S, Nishimori S, Doench J, Root D, Babij P, et al. HDAC5 controls MEF2C-driven sclerostin expression in osteocytes. Journal of bone and mineral research: the official journal of the American Society for Bone and Mineral Research. 2015 March; 30(3):400-11. PubMed PMID: 25271055. Pubmed Central PMCID: 4342334.
19. Haberland M, Montgomery R L, Olson E N. The many roles of histone deacetylases in development and physiology: implications for disease and therapy. Nature reviews Genetics. 2009 January; 10(1):32-42. PubMed PMID: 19065135. Pubmed. Central PMCID: 3215088.
20. Parra M, Verdin E. Regulatory signal transduction pathways for class IIa histone deacetylases. Current opinion in pharmacology. 2010 August; 10(4):454-60. PubMed PMID: 20447866.
21. Altarejos J Y, Montminy M. CREB and the CRTC co-activators: sensors for hormonal and metabolic signals. Nature reviews Molecular cell biology. 2011 March; 12(3):141-51. PubMed PMID: 21346730. Pubmed. Central PMCID: 4324555.
22. Berdeaux R, Goebel N, Banaszynski L, Takemori H, Wandless T, Shelton G D, et al. SIK1 is a class II HDAC kinase that promotes survival of skeletal myocytes. Nature medicine. 2007 May; 13(5):597-603. PubMed PMID: 17468767.
23. Sasagawa S, Takemori H, Uebi T, Ikegami D, Hiramatsu K, Ikegawa S, et al. SIK3 is essential for chondrocyte hypertrophy during skeletal development in mice. Development. 2012 March; 139(6):1153-63. PubMed PMID: 22318228.
24. Walkinshaw D R, Weist R, Kim G W, You L, Xiao L, Nie J, et al. The tumor suppressor kinase LKB1 activates the downstream kinases SIK2 and SIK3 to stimulate nuclear export of class IIa histone deacetylases. The Journal of biological chemistry. 2013 Mar. 29; 288(13):9345-62. PubMed PMID: 23393134. Pubmed Central PMCID: 3611005.
25. Sundberg T B, Liang Y, Wu H, Choi H G, Kim N D, Sim T, et al. Development of Chemical Probes for Investigation of Salt-Inducible Kinase Function in Vivo. ACS chemical biology. 2016 Jun. 6. PubMed PMID: 27224444.
26. Obri A, Makinistoglu M P, Zhang H, Karsenty G. HDAC4 integrates PTH and sympathetic signaling in osteoblasts. The Journal of cell biology. 2014 Jun. 23; 205(6):771-80. PubMed PMID: 24934156. Pubmed Central PMCID: 4068141.
27. Lu Y, Xie Y, Zhang S, Dusevich V, Bonewald L F, Feng J Q. DMP1-targeted Cre expression in odontoblasts and osteocytes. Journal of dental research. 2007 April; 86(4): 320-5. PubMed PMID: 17384025.
28. McKinsey T A, Zhang C L, Lu J, Olson E N. Signal-dependent nuclear export of a histone deacetylase regulates muscle differentiation. Nature. 2000 Nov. 2; 408 (6808):106-11. PubMed. PMID: 11081517. Pubmed Central PMCID: 4459600.
29. Grozinger C M, Schreiber S L. Regulation of histone deacetylase 4 and 5 and transcriptional activity by 14-3-3-dependent cellular localization. Proceedings of the National Academy of Sciences of the United States of America. 2000 Jul. 5; 97(14):7835-40. PubMed PMID: 10869435. Pubmed Central PMCID: 16631.
30. Taniguchi M, Carreira M B, Smith L N, Zirlin B C, Neve R L, Cowan C W. Histone deacetylase 5 limits cocaine reward through cAMP-induced nuclear import. Neuron. 2012 Jan. 12; 73(1):108-20. PubMed. PMID: 22243750. Pubmed Central PMCID: 3259532.
31. Baertschi S, Baur N, Lueders-Lefevre V, Voshol J, Keller H. Class I and IIa histone deacetylases have opposite effects on sclerostin gene regulation. The Journal of biological chemistry. 2014 Sep. 5; 289(36):24995-5009. PubMed PMID: 25012661. Pubmed Central PMCID: 4155667.
32. Wu J Y, Aarnisalo P, Bastepe M, Sinha P, Fulzele K, Selig M K, et al. Gsalpha enhances commitment of mesenchymal progenitors to the osteoblast lineage but restrains osteoblast differentiation in mice. The Journal of clinical 33. Fulzele K, Krause D S, Panaroni C, Saini V, Barry K J, Liu X, et al. Myelopoiesis is regulated by osteocytes through Gsalpha-dependent signaling. Blood. 2013 Feb. 7; 121(6):930-9. PubMed PMID: 23160461. Pubmed Central PMCID: 3567340.
34. Bonnet N, Conway S J, Ferrari S L. Regulation of beta catenin signaling and parathyroid hormone anabolic effects in bone by the matricellular protein periostin. Proceedings of the National Academy of Sciences of the United States of America. 2012 Sep. 11; 109(37):15048-53. PubMed PMID: 22927401. Pubmed Central PMCID: 3443161.
35. Saidak Z, Le Henaff C, Azzi S, Marty C, Marie P J. Low-dose PTH increases osteoblast activity via decreased Mef2c/Sost in senescent osteopenic mice. The Journal of endocrinology. 2014 October; 223(1):25-33. PubMed PMID: 25056116.
36. Kozhemyakina E, Cohen T, Yao T P, Lassar A B. Parathyroid hormone-related peptide represses chondrocyte hypertrophy through a protein phosphatase 2A/histone deacetylase 4/MEF2 pathway. Mol Cell. Biol. 2009 November; 29(21):5751-62. PubMed PMID: 19704004. Pubmed Central PMCID: 2772746.
37. Wang B, Moya N, Niessen S, Hoover H, Mihaylova M M, Shaw R J, et al. A hormone-dependent module regulating energy balance. Cell. 2011 May 13; 145(4):596-606. PubMed PMID: 21565616. Pubmed Central PMCID: 3129781.
38. Henriksson E, Jones H A, Patel K, Peggie M, Morrice N, Sakamoto K, et al. The AMPK-related kinase SIK2 is regulated by cAMP via phosphorylation at Ser358 in adipocytes. The Biochemical journal. 2012 Jun. 15; 444(3):503-14. PubMed PMID: 22462548. Pubmed Central PMCID: 3631101.
39. Henriksson E, Sall J, Gormand A, Wasserstrom S, Morrice N A, Fritzen A M, et al. SIK2 regulates CRTCs, HDAC4 and glucose uptake in adipocytes. Journal of cell science. 2015 Feb. 1; 128(3):472-86. PubMed PMID: 25472719. Pubmed Central PMCID: 4311129.
40. Patel K, Foretz M, Marion A, Campbell D G, Gourlay R, Boudaba N, et al. The LKB1-salt-inducible kinase pathway functions as a key gluconeogenic suppressor in the liver. Nature communications. 2014; 5:4535. PubMed PMID: 25088745. Pubmed Central PMCID: 4143937.
41. Yang D, Guo J, Divieti P, Shioda T, Bringhurst F R. CBR/p300-interacting protein CITED1 modulates parathyroid hormone regulation of osteoblastic differentiation. Endocrinology. 2008 April; 149(4):1728-35. PubMed. PMID: 18187554. Pubmed Central PMCID: 2276703.
42. Galli C, Zella L A, Fretz J A, Fu Q, Pike J W, Weinstein R S, et al. Targeted deletion of a distant transcriptional enhancer of the receptor activator of nuclear factor-kappaB ligand gene reduces bone remodeling and increases bone mass. Endocrinology. 2008 January; 149(1):146-53. PubMed PMFD: 17932217. Pubmed Central PMCID: 2194617.
43. Kim S, Yamazaki M, Zella L A, Shevde N K, Pike J W. Activation of receptor activator of NF-kappaB ligand gene expression by 1,25-dihydroxyvitamin D3 is mediated through multiple long-range enhancers. Mol Cell Biol. 2006 September; 26(17):6469-86. PubMed PMID: 16914732. Pubmed Central PMCID: 1592822.
44. Onal M, St John H C, Danielson A L, Pike J W. Deletion of the Distal Tnfsf1 1 RL-D2 Enhancer that Contributes to PTH-Mediated RANKL Expression in Osteoblast Lineage Cells Results in a High Bone Mass Phenotype in Mice. Journal of bone and mineral research: the official journal of the American Society for Bone and Mineral Research. 2015 Aug. 31. PubMed PMID: 26332516.
45. Clark K, MacKenzie K F, Petkevicius K, Kristariyanto Y, Zhang J, Choi H G, et al. Phosphorylation of CRTC3 by the salt-inducible kinases controls the interconversion of classically activated and regulatory macrophages. Proceedings of the National Academy of Sciences of the United States of America. 2012 Oct. 16; 109(42):16986-91. PubMed PMID: 23033494. Pubmed Central PMCID: 3479463.
46. Sundberg T B, Choi H G, Song J H, Russell C N, Hussain M M, Graham D B, et al. Small-molecule screening identifies inhibition of salt-inducible kinases as a therapeutic strategy to enhance immunoregulatory functions of dendritic cells. Proceedings of the National Academy of Sciences of the United States of America. 2014 Aug. 26; 111(34):12468-73. PubMed PMID: 25114223. Pubmed Central PMCID: 4151730.
47. Kronenberg H M. Developmental regulation of the growth plate. Nature. 2003 May 15; 423(6937):332-6. PubMed PMID: 12748651.
48. Bergwitz C, Juppner H. Regulation of phosphate homeostasis by PTH, vitamin D, and FGF23. Annual review of medicine. 2010; 61:91-104. PubMed. PMID: 20059333.
49. Pacifici R. Role of T cells in the modulation of PTH action: physiological and clinical significance. Indocrine. 2013 December; 44(3):576-82. PubMed. PMID: 23729167. Pubmed Central PMCID: 3815684.
50. Kir S, White J P, Kleiner S, Kazak L, Cohen P, Baracos V E, et al. Tumour-derived PTH-related protein triggers adipose tissue browning and cancer cachexia. Nature. 2014 Sep. 4; 513(7516):100-4. PubMed PMID: 25043053. Pubmed Central PMCID: 4224962.
51. Leupin O, Kramer I, Collette N M, Loots G G, Natt F, Kneissel M, et al. Control of the SOST bone enhancer by PTFE using MEF2 transcription factors. Journal of bone and mineral research: the official journal of the American Society for Bone and Mineral Research. 2007 December; 22(12):1957-67. PubMed. PMID: 17696759. Pubmed Central PMCID: 2882185.
52. St John H C, Hansen S J, Pike J W. Analysis of SOST expression using large minigenes reveals the MEF2C binding site in the evolutionarily conserved region (ECR5) enhancer mediates forskolin, but not 1,25-dihydroxyvitamin D or TGFbeta responsiveness. The journal of steroid biochemistry and molecular biology. 2015 Sep. 7. PubMed PMID: 26361013.
53. Li C, Wang W, Xie L, Luo X, Cao X, Wan M. Lipoprotein receptor-related protein 6 is required for parathyroid hormone-induced Sost suppression. Annals of the New York Academy of Sciences. 2015 Apr. 2. PubMed PMID: 25847683. Pubmed Central PMCID: 4592361.
54. Shimizu E, Selvamurugan N, Westendorf J J, Olson E N, Partridge N C. HDAC4 represses matrix metalloproteinase-13 transcription in osteoblastic cells, and parathyroid hormone controls this repression. The Journal of biological chemistry. 2010 Mar. 26; 285(13):9616-26. PubMed PMID: 20097749. Pubmed Central PMCID: 2843211.
55. Haberland M, Arnold M A, McAnally J, Phan D, Kim Y, Olson E N. Regulation of HDAC9 gene expression by MEF2 establishes a negative-feedback loop in the transcriptional circuitry of muscle differentiation. Mol Cell 56. Kramer I, Baertschi S, Halleux C, Keller H, Kneissel M. Mef2c deletion in osteocytes results in increased bone mass. Journal of bone and mineral research: the official journal of the American Society for Bone and Mineral Research. 2012 February; 27(2):360-73. PubMed PMID: 22161640.
57. Collette N M, Genetos D C, Economides A N, Xie L, Shahnazari M, Yao W, et al. Targeted deletion of Sost distal enhancer increases bone formation and bone mass. Proceedings of the National Academy of Sciences of the United States of America. 2012 Aug. 28; 109(35):14092-7. PubMed PMID: 22886088. Pubmed Central PMCID: 3435175.
58. Loots G G, Kneissel M, Keller H, Baptist M, Chang J, Collette N M, et al. Genomic deletion of a long-range bone enhancer misregulates sclerostin in Van Buchem disease. Genome research. 2005 July; 15(7):928-35. PubMed. PMID: 15965026. Pubmed Central PMCID: 1172036.
59. Tu X, Rhee Y, Condon K W, Bivi N, Allen M R, Dwyer D, et al. Sost downregulation and local Wnt signaling are required for the osteogenic response to mechanical loading. Bone. 2012 January; 50(1):209-17. PubMed PMID: 22075208. Pubmed Central PMCID: 3246572.
60. Weir E C, Philbrick W M, Amling M, Neff L A, Baron R, Broadus A E. Targeted overexpression of parathyroid hormone-related peptide in chondrocytes causes chondrodysplasia and delayed endochondral bone formation. Proceedings of the National Academy of Sciences of the United States of America. 1996 Sep. 17; 93(19):10240-5. PubMed PMID: 8816783. Pubmed Central PMCID: 38368.
61. Martowicz M L, Meyer M B, Pike J W. The mouse RANKL gene locus is defined by a broad pattern of histone H4 acetylation and regulated through distinct distal enhancers. Journal of cellular biochemistry. 2011 August; 112(8):2030-45. PubMed. PMID: 21465526. Pubmed Central PMCID: 3135786.
62. Horike N, Kumagai A, Shimono Y, Onishi T, Itoh Y, Sasaki T, et al. Downregulation of SIK2 expression promotes the melanogenic program in mice. Pigment cell & melanoma research. 2010 December; 23(6):809-19. PubMed. PMID: 20819186.
63. Sasaki T, Takemori H, Yagita Y, Terasaki Y, Uebi T, Horike N, et al. SIK2 is a key regulator for neuronal survival after ischemia via TORC1-CREB. Neuron. 2011 Jan. 13; 69(1):106-19. PubMed PMID: 21220102.
64. Popov S, Takemori H, Tokudome T, Mao Y, Otani K, Mochizuki N, et al. Lack of salt-inducible kinase 2 (SIK2) prevents the development of cardiac hypertrophy in response to chronic high-salt intake. PloS one. 2014; 9(4):e95771. PubMed PMID: 24752134. Pubmed Central PMCID: 3994160.
65. Park J, Yoon Y S, Han H S, Kim Y H, Ogawa Y, Park K G, et al. SIK2 is critical in the regulation of lipid homeostasis and adipogenesis in vivo. Diabetes. 2014 November; 63(11):3659-73. PubMed PMID: 24898145.
66. Sakamaki J, Fu A, Reeks C, Baird S, Depatie C, Al Azzabi M, et al. Role of the SIK2-p35-PJA2 complex in pancreatic beta-cell functional compensation. Nature cell biology. 2014 March; 16(3):234-44. PubMed PMID: 24561619. Pubmed Central PMCID: 4107453.
67. Yahara Y, Takemori H, Okada M, Kosai A, Yamashita A, Kobayashi T, et al. Pterosin B prevents chondrocyte hypertrophy and osteoarthritis in mice by inhibiting Sik3. Nature communications. 2016; 7:10959. PubMed PMID: 27009967.
68. Screaton R A, Conkright M D, Katoh Y, Best J L, Canettieri G, Jeffries S, et al. The CREB coactivator TORC2 functions as a calcium- and cAMP-sensitive coincidence detector. Cell. 2004 Oct. 1; 119(1):61-74. PubMed PMID: 15454081.
69. Soriano P, Montgomery C, Geske R, Bradley A. Targeted disruption of the c-src proto-oncogene leads to osteopetrosis in mice. Cell. 1991 Feb. 22; 64(4):693-702. PubMed PMID: 1997203.
70. Chang S, McKinsey T A, Zhang C L, Richardson J A, Hill J A, Olson E N. Histone deacetylases 5 and 9 govern responsiveness of the heart to a subset of stress signals and play redundant roles in heart development. Mol Cell Biol. 2004 October; 24(19):8467-76. PubMed PMID: 15367668. Pubmed Central PMCID: 516756.
71. Kim M S, Akhtar M W, Adachi M, Mahgoub M, Bassel-Duby R, Kavalali E T, et al. An essential role for histone deacetylase 4 in synaptic plasticity and memory formation. The Journal of neuroscience: the official journal of the Society for Neuroscience. 2012 Aug. 8; 32(32): 10879-86. PubMed PMID: 22875922. Pubmed Central PMCID: 3480333.
72. Ran F A, Hsu P D, Wright J, Agarwala V, Scott D A, Zhang F. Genome engineering using the CRISPR-Cas9 system. Nature protocols. 2013 November; 8(11):2281-308. PubMed PMID: 24157548. Pubmed Central PMCID: 3969860.
73. Junqueira L C, Bignolas G, Brentani R R. Picrosirius staining plus polarization microscopy, a specific method for collagen detection in tissue sections. The Histochemical journal. 1979 July; 11(4):447-55. PubMed PMID: 91593.
74. Bouxsein M L, Boyd S K, Christiansen B A, Guldberg R E, Jepsen K J, Muller R. Guidelines for assessment of bone microstructure in rodents using micro-computed tomography. Journal of bone and mineral research: the official journal of the American Society for Bone and Mineral Research. 2010 July; 25(7):1468-86. PubMed PMID: 20533309.
75. Dempster D W, Compston J E, Drezner M K, Glorieux F H, Kanis J A, Malluche H, et al. Standardized nomenclature, symbols, and units for bone histomorphometry: a 2012 update of the report of the ASBMR Histomorphometry Nomenclature Committee. Journal of bone and mineral research: the official journal of the American Society for Bone and Mineral Research. 2013 January; 28(1):2-17. PubMed PMID: 23197339. Pubmed Central PMCID: 3672237.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

In Claim 24, at Column 329, Lines 33-45, the formula: 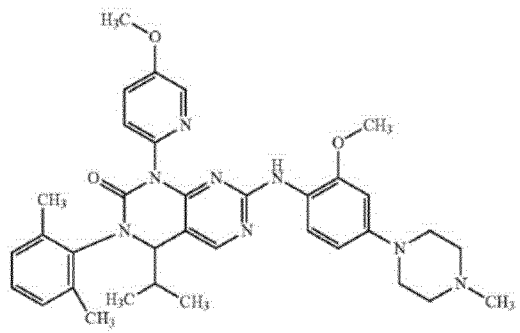

Should be replaced with the formula: 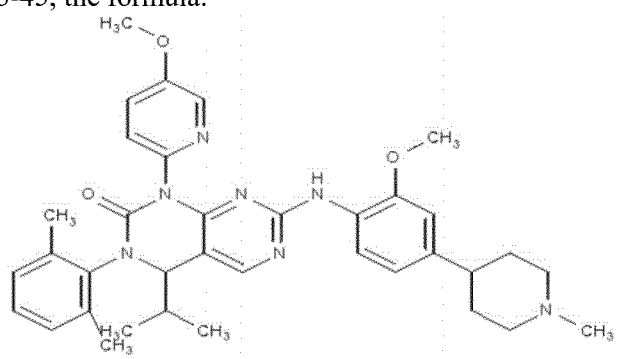

What is claimed is:

1. A method of treating osteoporosis in a subject in need thereof comprising administering to the subject in need thereof a therapeutically effective amount of a compound of Formula (I):

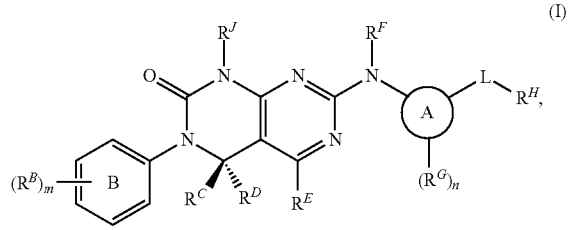

or a pharmaceutically acceptable salt, solvate, hydrate, polymorph, co-crystal, tautomer, stereoisomer, isotopically labeled derivative, or prodrug thereof, wherein:

$R^A$ is substituted or unsubstituted alkenyl, substituted or unsubstituted alkynyl,

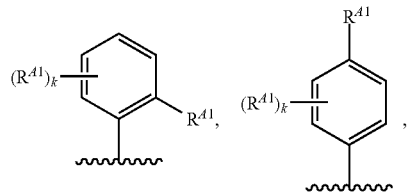

substituted or unsubstituted heteroaryl, or substituted or unsubstituted heterocyclyl, provided that the substituted or unsubstituted heterocyclyl is not substituted or unsubstituted 3-pyrrolidinyl:

each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$N^bC$(=O)$R^a$, —$NR^bC$(=O)$OR^a$, —$NR^bC$(=O)N($R^b$)$_2$, —OC(=O)$R^a$, —OC(=O)$OR^a$, or —OC(=O)N($R^b$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted, $C_{1-6}$ alkyl, or a nitrogen protecting group, or two instances of $R^b$ are taken together with their intervening atoms to form a substituted or unsubstituted heterocyclic or substituted or unsubstituted heteroaryl ring;

k is 0, 1, 2, 3, or 4;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —C(=$NR^b$)$R^a$, —C(=$NR^b$)$OR^a$, —C(=$NR^b$)N($R^b$)$_2$, —C(=O)$R^a$, —C(=O)$OR^a$, —C(=O)N($R^b$)$_2$, —$NO_2$, —$NR^bC$(=O)$R^a$, —$NR^bC$(=O)$OR^a$, —$NR^bC$(=O)N($R^b$)$_2$, —OC(=O)$R^a$, —OC(=O)$OR^a$, or —OC(=O)N($R^b$)$_2$;

m is 0, 1, 2, 3, 4, or 5;

$R^C$ is hydrogen, halogen, or substituted or unsubstituted, $C_{1-6}$ alkyl;

$R^D$ is hydrogen, halogen, or substituted or unsubstituted, $C_{1-6}$ alkyl;

$R^E$ is hydrogen, halogen, or substituted or unsubstituted, $C_{1-6}$ alkyl;

$R^F$ is hydrogen, substituted or unsubstituted, $C_{1-6}$ alkyl, or a nitrogen protecting group;

Ring A is substituted or unsubstituted phenyl; substituted or unsubstituted, polycyclic aryl; substituted or unsubstituted, 5- or 6-membered, monocyclic heteroaryl; or substituted or unsubstituted, polycyclic heteroaryl;

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, —$SR^a$, —CN, —SCN, —$C(=NR^b)R^a$, —$C(=NR^b)OR^a$, —$C(=NR^b)N(R^b)_2$, —$C(=O)R^a$, —$C(=O)OR^a$, —$C(=O)N(R^b)_2$, —$NO_2$, —$NC(=O)R^a$, —$NR^bC(=O)OR^a$, —$NR^bC(=O)N(R^b)_2$, —$OC(=O)R^a$, —$OC(=O)OR^a$, or —$OC(=O)N(R^b)_2$;

n is 0, 1, 2, 3, or 4, as valency permits;

L is a bond or a substituted or unsubstituted, $C_{1-6}$ hydrocarbon chain, optionally wherein one or more chain atoms of the hydrocarbon chain are independently replaced with —$C(=O)$—, —O—, —S—, —$NR^b$—, —N=, or =N—; and $R^H$ is substituted or unsubstituted, $C_{1-6}$ alkyl, substituted or unsubstituted heterocyclyl, —OH, or —$N(R^c)_2$, wherein each instance of $R^c$ is independently hydrogen, substituted or unsubstituted, $C_{1-6}$ alkyl, or a nitrogen protecting group, or optionally two instances of $R^c$ are taken together with their intervening atoms to form a substituted or unsubstituted heterocyclic or substituted or unsubstituted heteroaryl ring;

each carbon atom substituent is independently selected from halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^b)_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$, —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NNR$^{bb}$C(=O)$R^{aa}$, =NNR$^{bb}$C(=O)O$R^{aa}$, =NNR$^{bb}$S(=O)$R^{aa}$, =N$R^{bb}$, or =NOR$^{cc}$;

each instance of $R^{aa}$ is independently selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is independently selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(R^{aa})_2$, —$P(=O)(OR^{cc})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is independently selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynvl, $C_{3-10}$ carbocyclyl, 3-14 membered heterocyclyl, C6-14 aryl, and 5-14 membered heteroaryl, or two $R^{cc}$ groups are joined to form a 3-14 membered heterocyclyl or 5-14 membered heteroaryl ring, wherein each alkyl, alkenyl, alkynvl, heteroalkyl, heteroalkenyl, heteroalkynyl, carbocyclyl, heterocycyl, aryl, and heteroaryl is independently substituted with 0, 1, 2, 3, 4, or 5 $R^{dd}$ groups;

each instance of $R^{dd}$ is independently selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —$C(=O)R^{ee}$, —$CO_2H$, —$CO_2R^{ee}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)(OR^{ee})_2$, —$P(=O)(R^{ee})_2$, —$OP(=O)(R^{ee})_2$, —$OP(=O)(OR^{ee})_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents are joined to form =O or =S;

each instance of $R^{ee}$ is independently selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is independently selected from hydrogen, $C_{1-4}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^9$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O(C$_{1-6}$ alkyl), —OCO$_2$(C$_{1-6}$ alkyl), —C(=O)NH$_2$, —C(=O)N(C$_{1-6}$ alkyl)h, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl), —OSi(C$_{1-6}$ alkyl)$_3$ —C(=S)N (C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)h, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, or 5-10 membered heteroaryl; or two geminal R$^{gg}$ substituents are joined to form =O or =S;

X$^-$ is a counterion;

each nitrogen atom substituent is independently selected from nitrogen protecting groups, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N (R$^{cc}$)$_2$, —SO$_2$R$^{cc}$, —SO$_2$OR$^{cc}$, —SOR$^{aa}$, —C(=S)N (R$^{cc}$), —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each nitrogen protecting group is independently selected from —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N (R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S) SR$^{cc}$, C$_{1-10}$ alkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy) propanamide, 4-chlorobutanamide, 3-methyl-3-nitrobutanamide, o-nitrocinnamide, N-acetylmethionine derivative, o nitrobenzamide, and o-(benzoyloxymethyl)benzamide; methyl carbamate, ethyl carbamate, 9-fluorenylmethyl carbamate (Fmoc), 9-(2-sulfo)fluorenylmethyl carbamate, 9-(2,7-dibromo) fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonyl ethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-43,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate; p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide; and phenothiazinyl-(10)-acyl derivative, N'-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF)N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys);

each oxygen protecting group is independently selected from —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{aa})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR)_3{}^{+*}X^-$, —$P(=O)(R^{aa})_2$, —$P(=O)(OR^{cc})_2$, and —$P(=O)(N(R^{bb})_2)_2$; and methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenymethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-P-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl) ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy) ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts); and each sulfur protecting group is independently selected from —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$.

2. The method of claim 1, wherein $R^A$ is

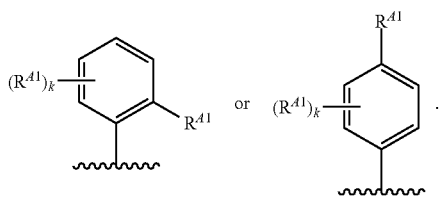

3. The method of claim 1, wherein $R^A$ is

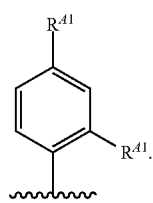

4. The method of claim 1, wherein $R^A$ is

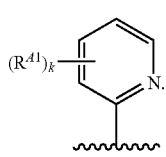

5. The method of claim 1, wherein $R^A$ is

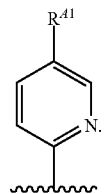

6. The method of claim 1, wherein $R^A$ is substituted or unsubstituted heterocyclyl, provided that the substituted or unsubstituted heterocyclyl is not substituted or unsubstituted 3-pyrrolidinyl.

7. The method of claim 1, wherein $R^A$ is substituted or unsubstituted tetrahydropyranyl.

8. The method of claim 1, wherein at least one instance of $R^B$ is halogen or substituted or unsubstituted, $C_{1-6}$ alkyl.

9. The method of claim 1, wherein Ring A is phenyl.

10. The method of claim 1, wherein Ring A is pyrazolyl or pyridinyl.

11. The method of claim 1, wherein L is a bond.

12. The method of claim 1, wherein L is an unsubstituted $C_{1-3}$ hydrocarbon chain, optionally wherein one chain atom of the hydrocarbon chain is replaced with —O— or —$NR^b$—.

13. The method of claim 1, wherein $R^H$ is substituted or unsubstituted heterocyclyl.

14. The method of claim 1, wherein $R^H$ is substituted or unsubstituted tetrahydropyranyl, substituted or unsubstituted piperidinyl, substituted or unsubstituted morpholinyl, or substituted or unsubstituted piperazinyl.

15. The method of claim 1, wherein $R^H$ is substituted or unsubstituted, $C_{1-6}$alkyl.

16. The method of claim 1, wherein $R^H$ is —OH or —$N(R^c)_2$.

17. The method of claim 16, wherein each instance of $R^c$ is substituted or unsubstituted, $C_{1-6}$ alkyl.

18. The method of claim 1, wherein $R^C$ is hydrogen.

19. The method of claim 1, wherein $R^D$ is hydrogen.

20. The method of claim 1, wherein $R^E$ is hydrogen.

21. The method of claim 1, wherein $R^F$ is hydrogen.

22. The method of claim 1, wherein at least one instance of $R^G$ is substituted or unsubstituted, $C_{1-3}$ alkyl, halogen, or —$OR^a$, wherein $R^a$ is substituted or unsubstituted, $C_{1-6}$ alkyl.

23. The method of claim 1, wherein at least one instance of $R^G$ is substituted or unsubstituted morpholinyl, or substituted or unsubstituted piperazinyl.

24. The method of claim 1, wherein the compound is of the formula:

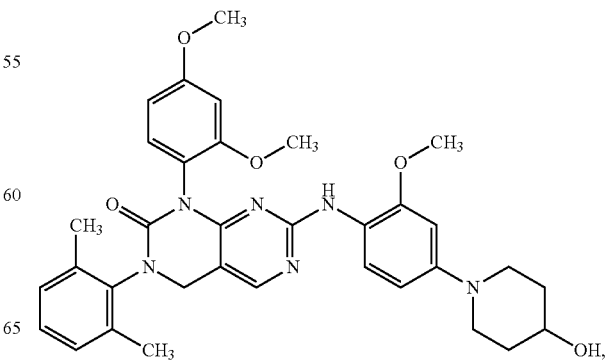

309
-continued
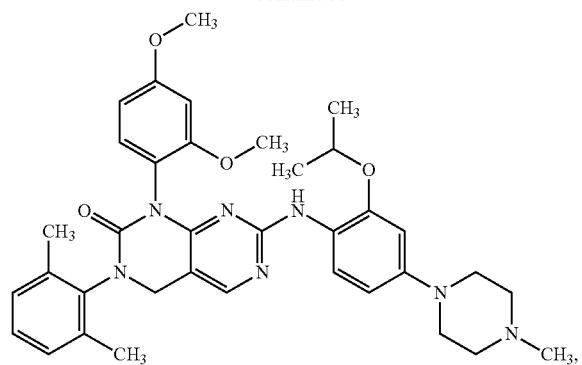
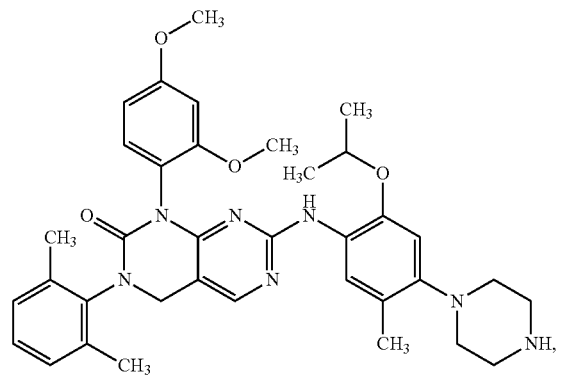
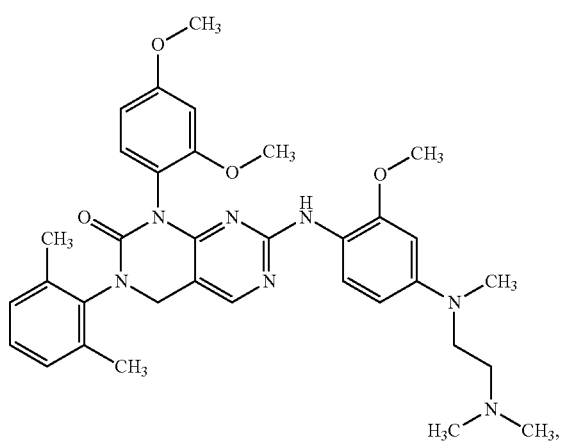
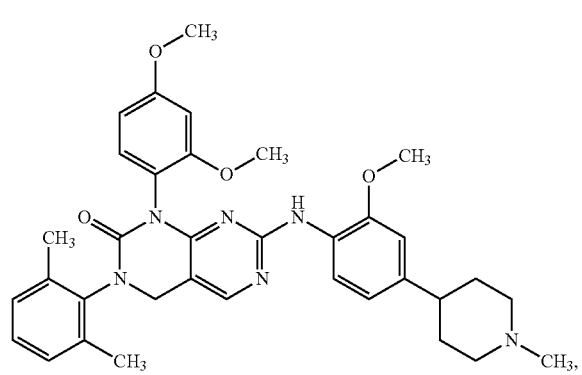
310
-continued
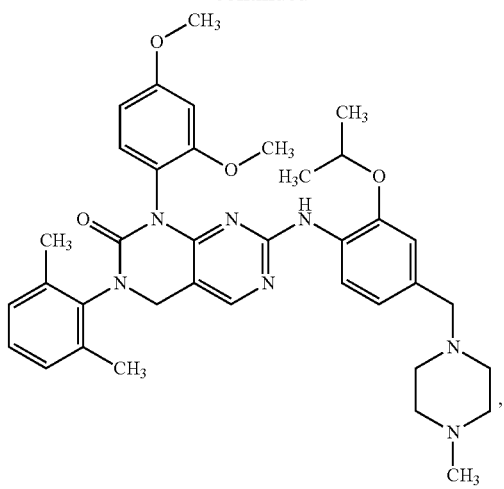
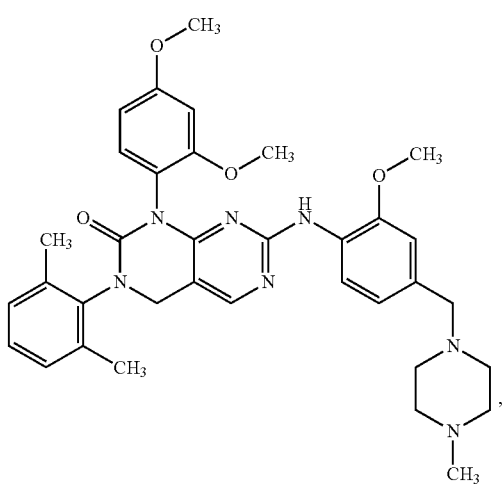
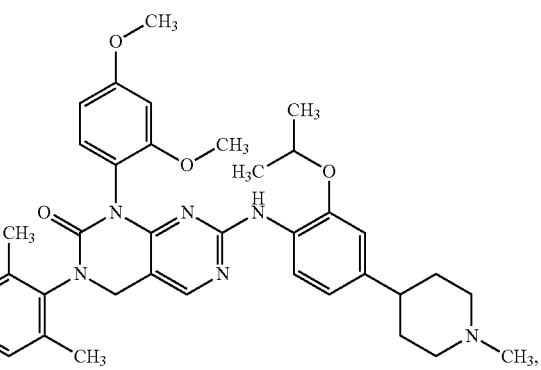
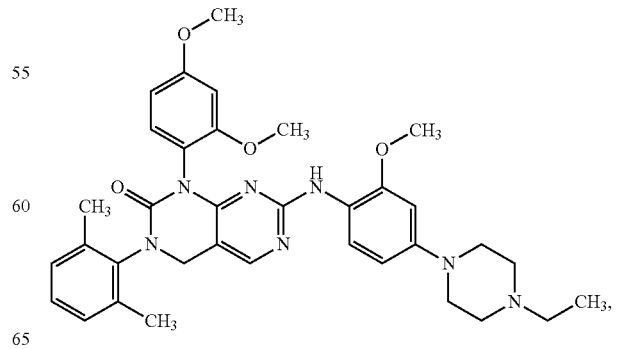

311
-continued
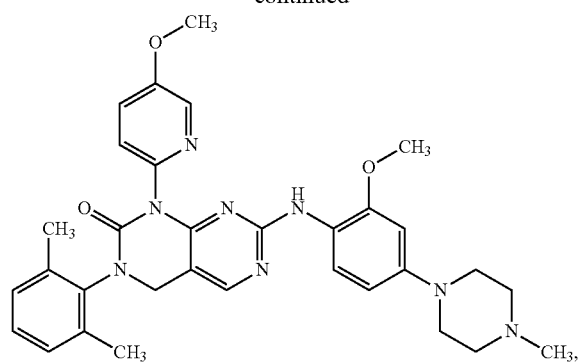
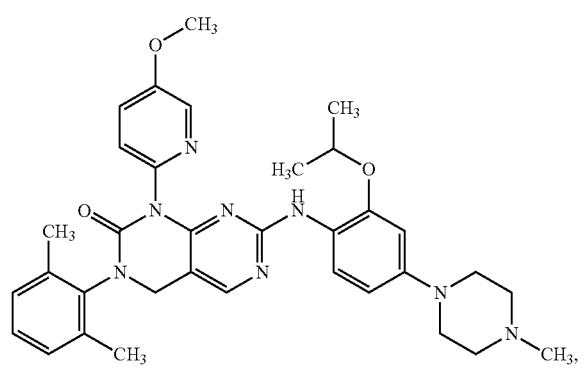
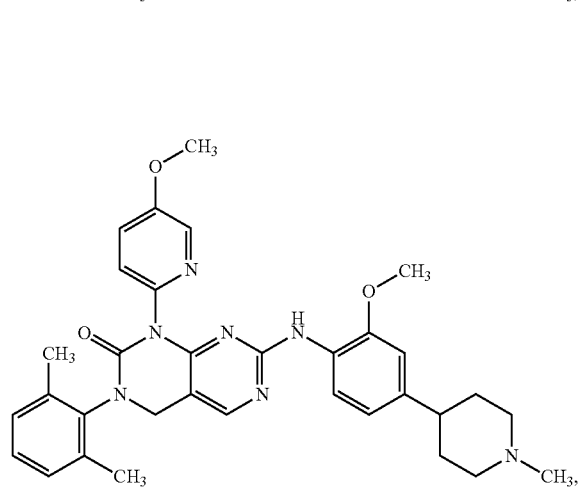
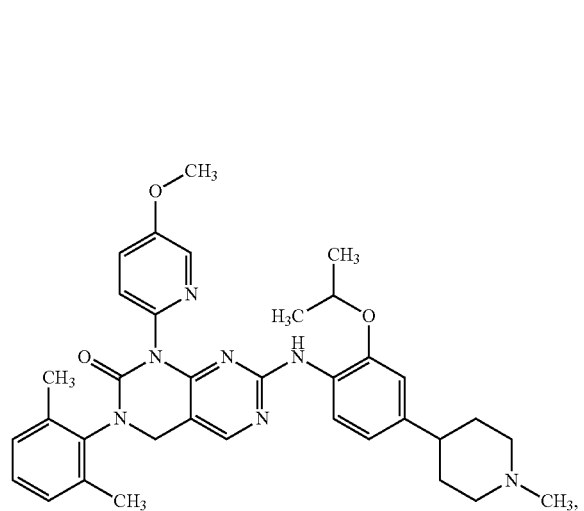
312
-continued
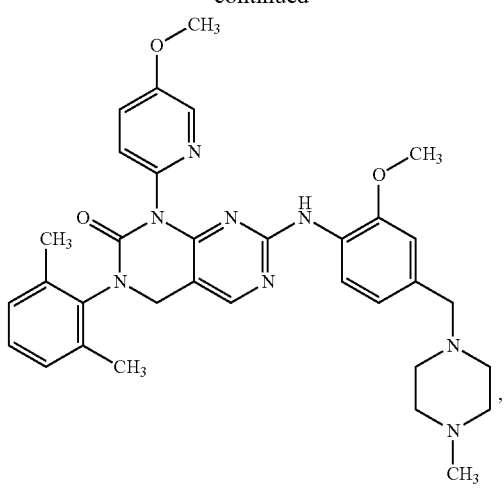
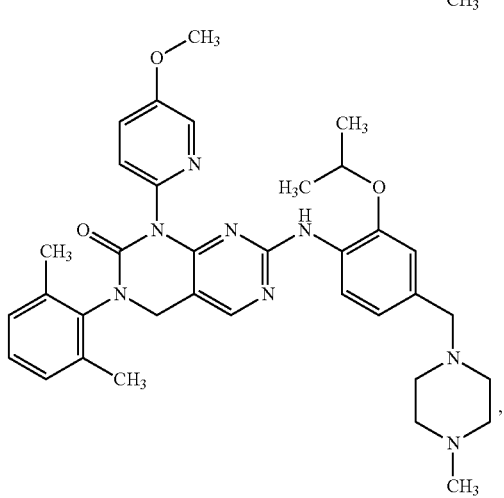
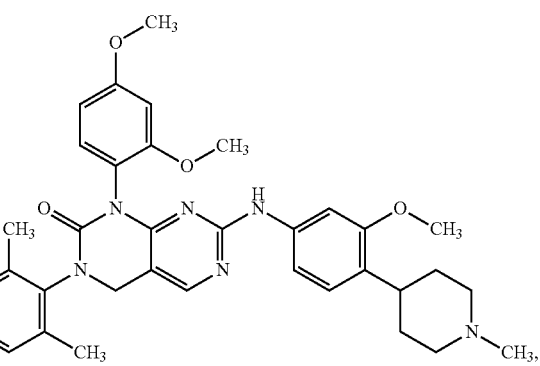

313
-continued
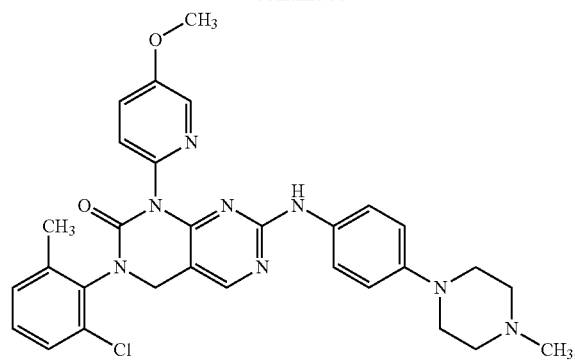
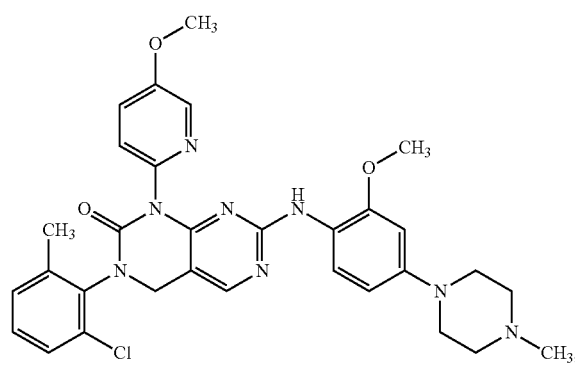
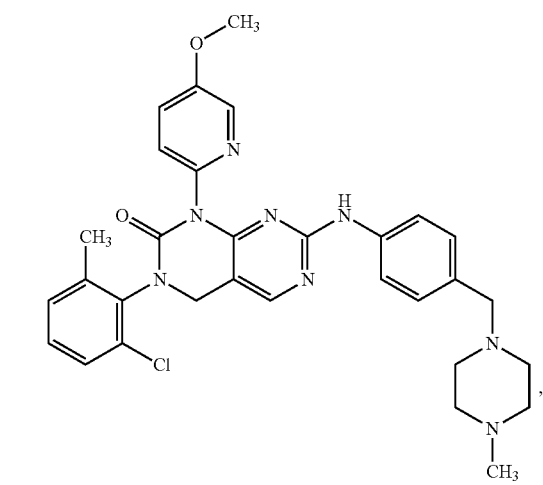
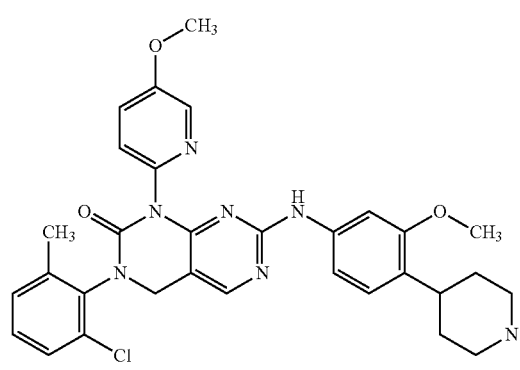
314
-continued
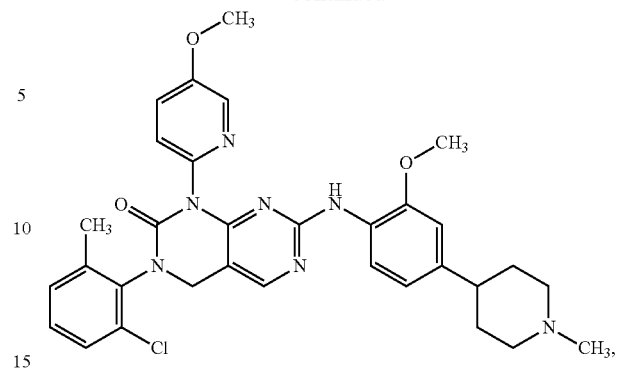
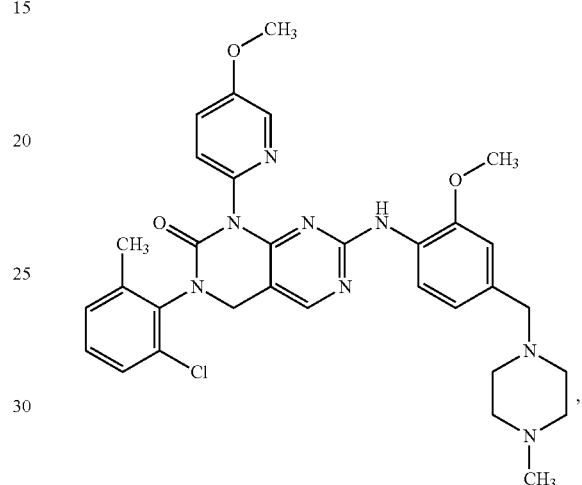
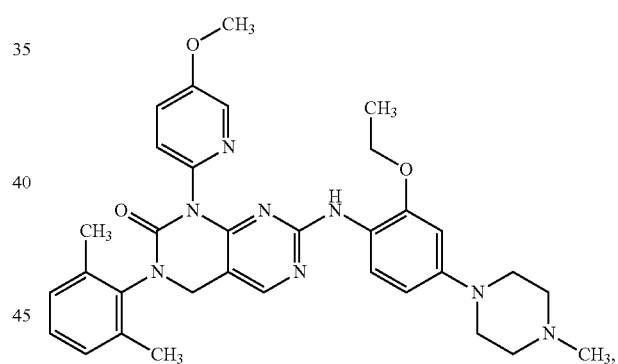
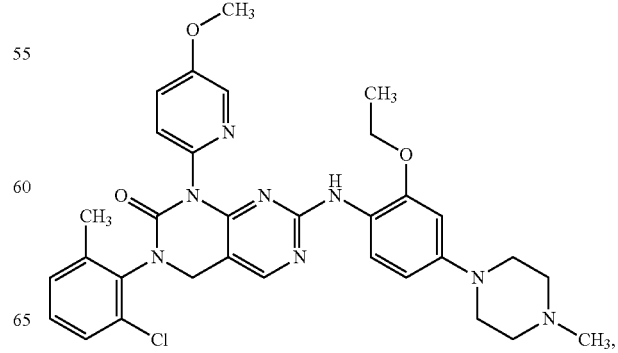

315
-continued
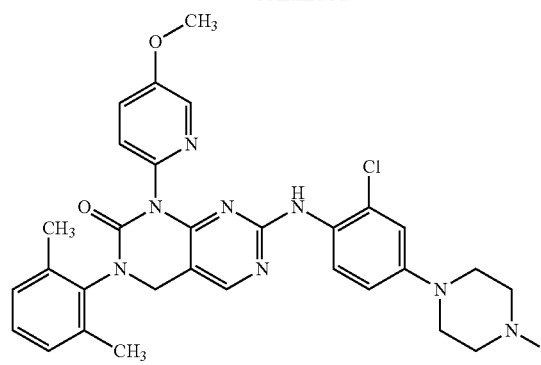
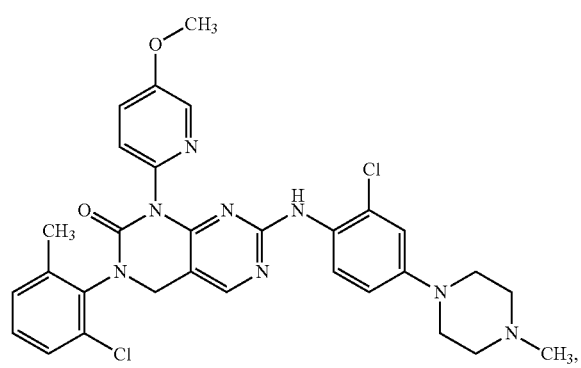
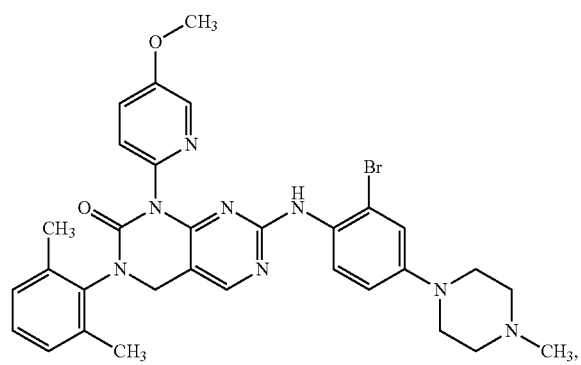
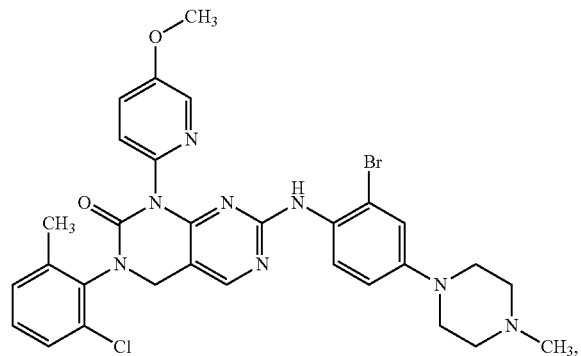
316
-continued
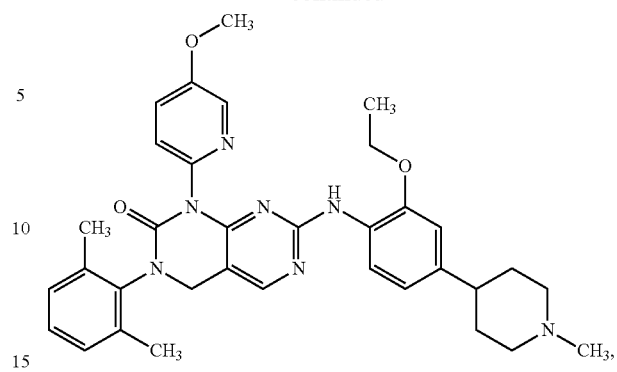
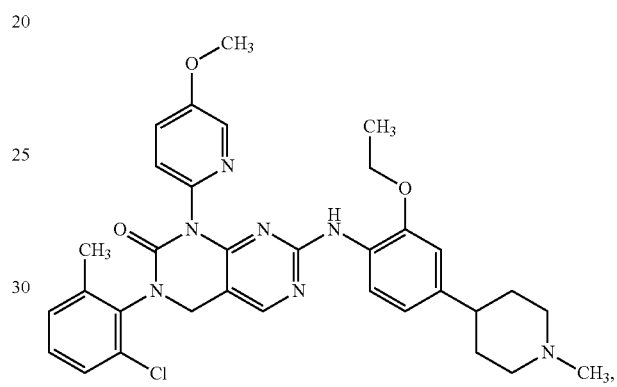
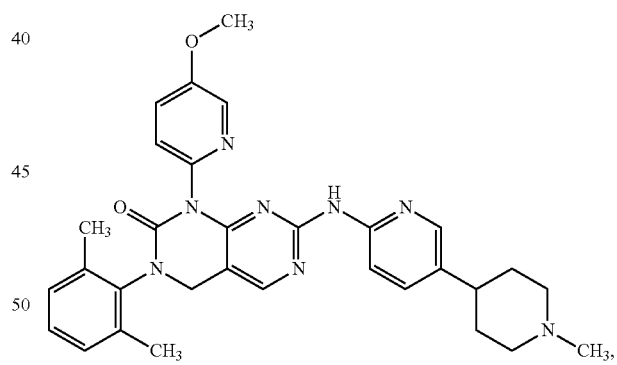
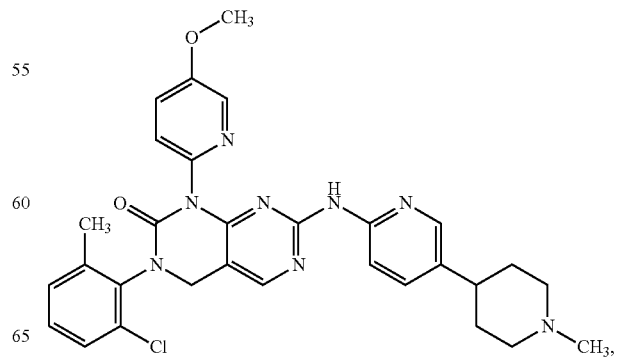

317
-continued
318
-continued
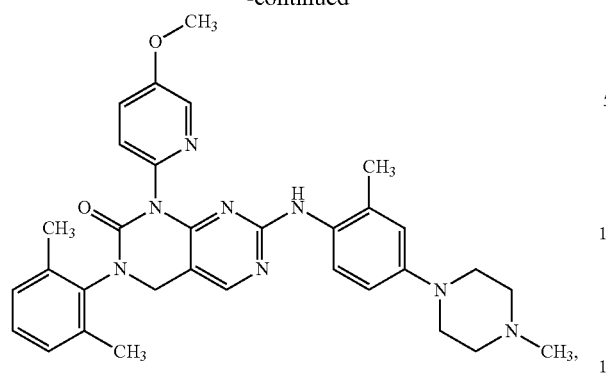
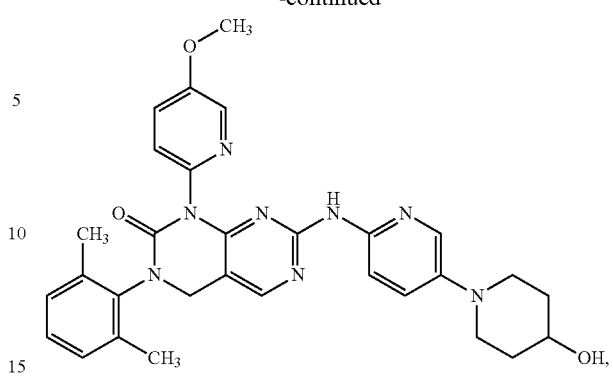
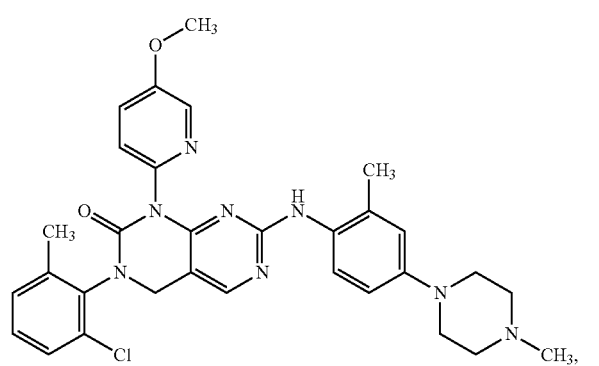
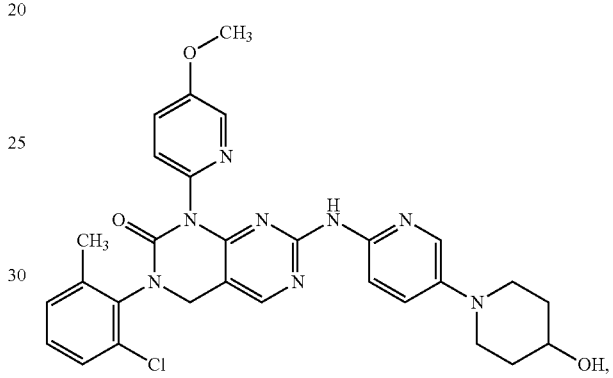
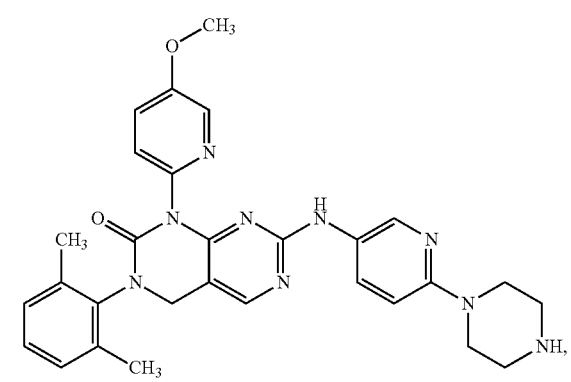
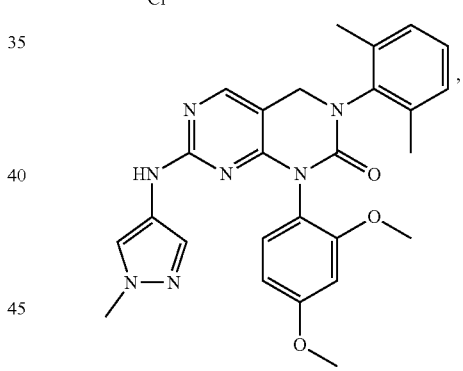
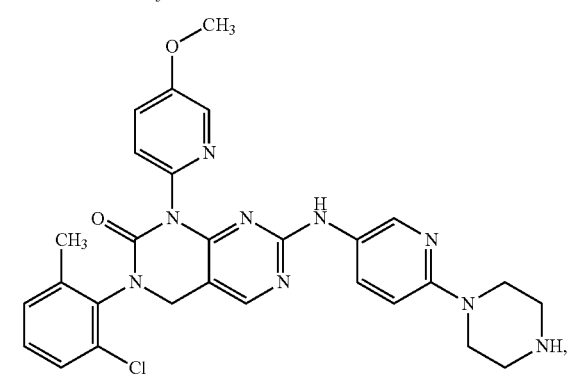
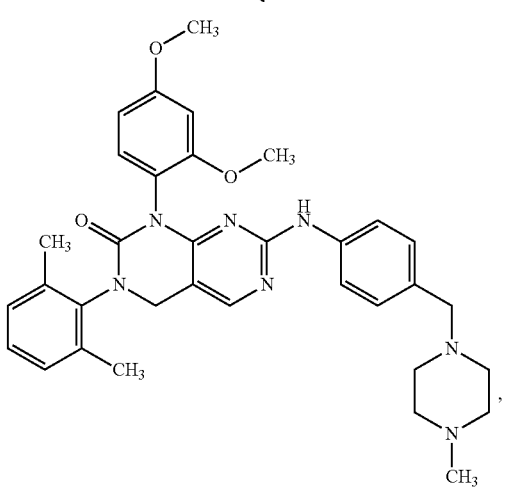

319
-continued
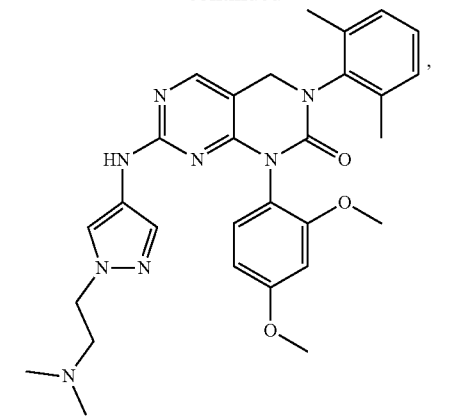
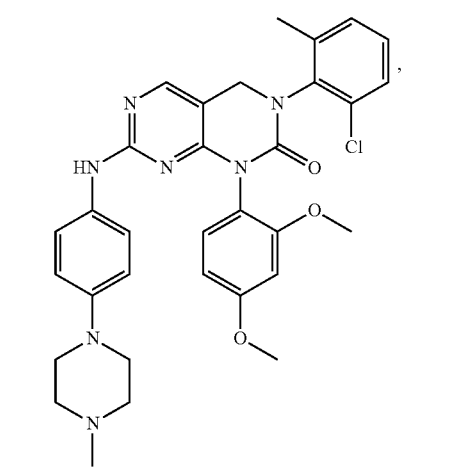
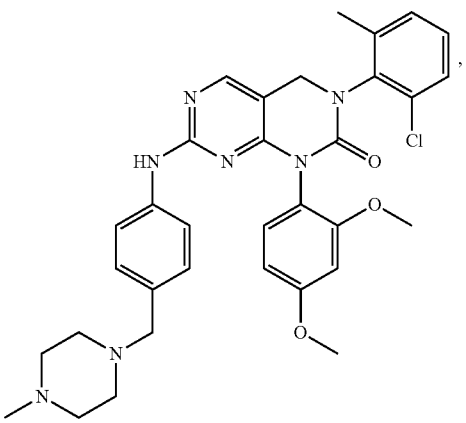
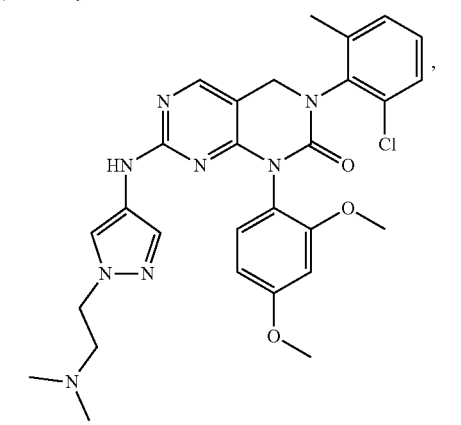
320
-continued
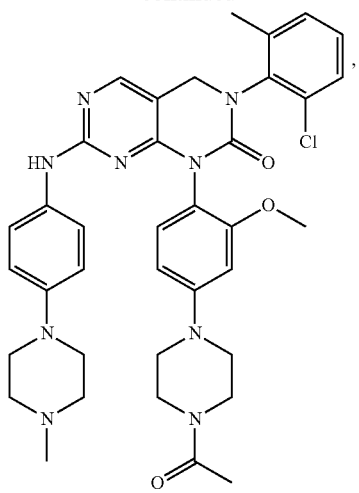

321
-continued
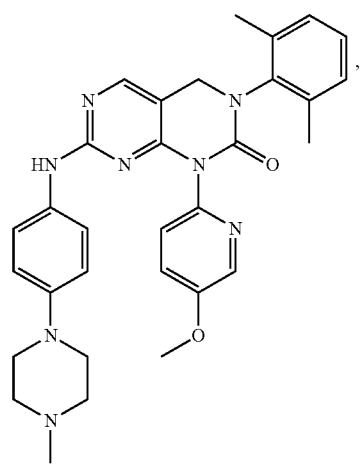
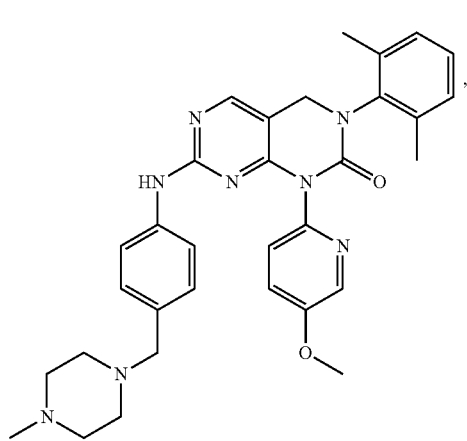
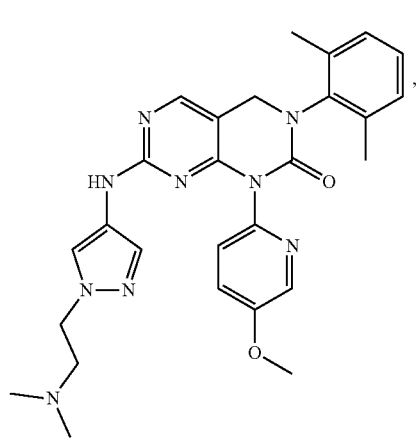
322
-continued
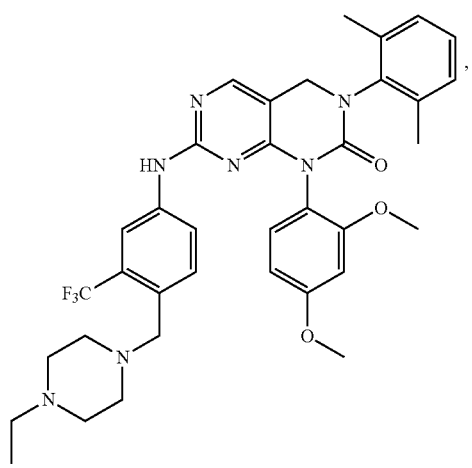
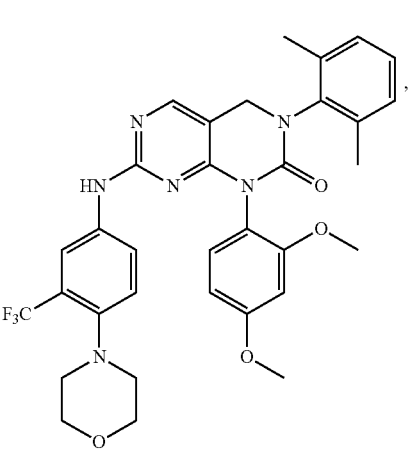
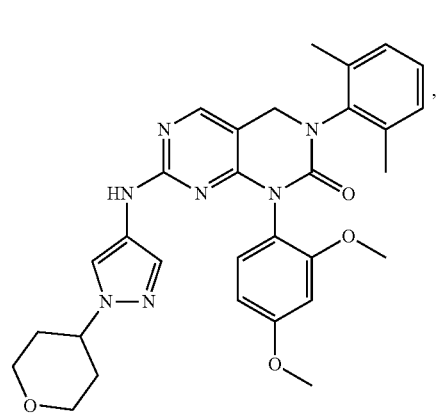

323
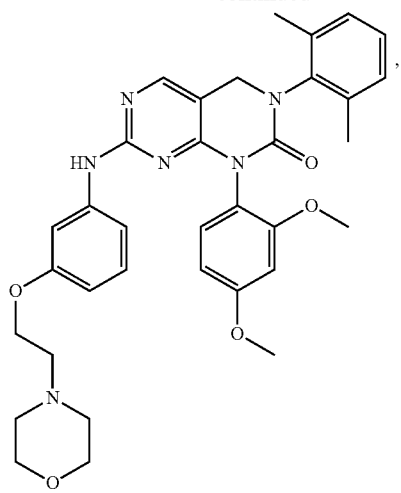
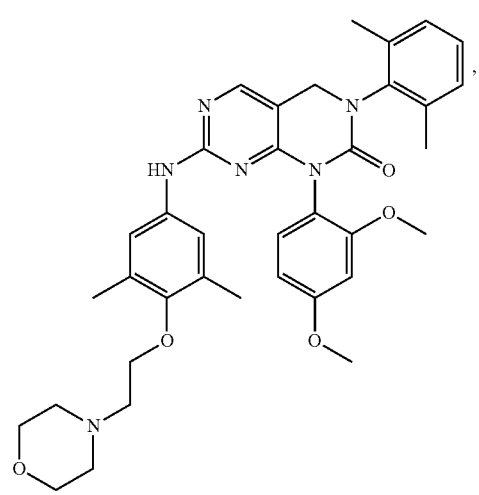
(YKL-04-108)
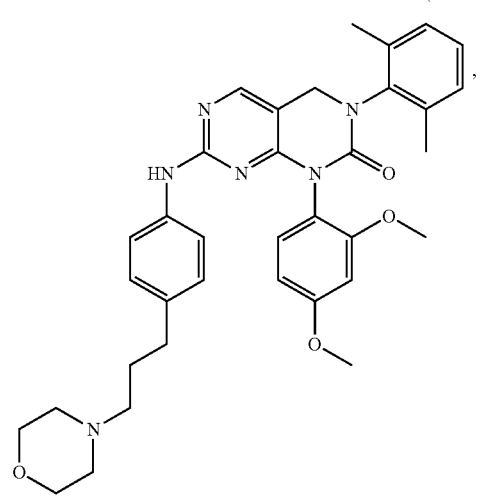
324
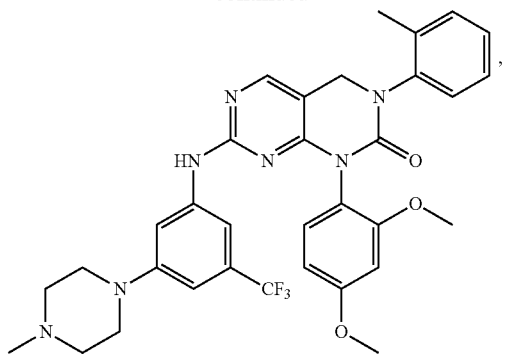
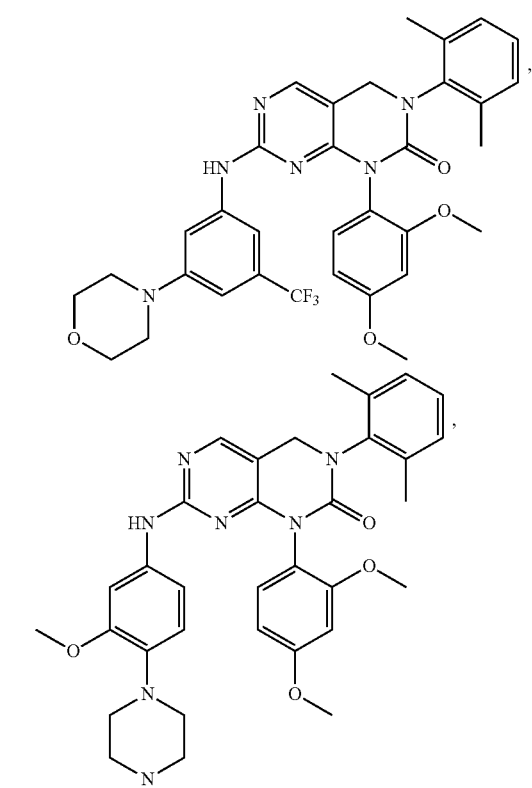
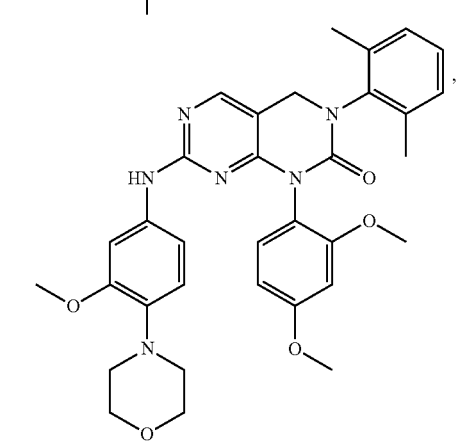

325
-continued
326
-continued
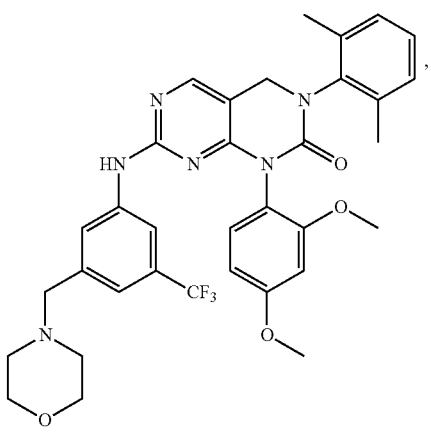
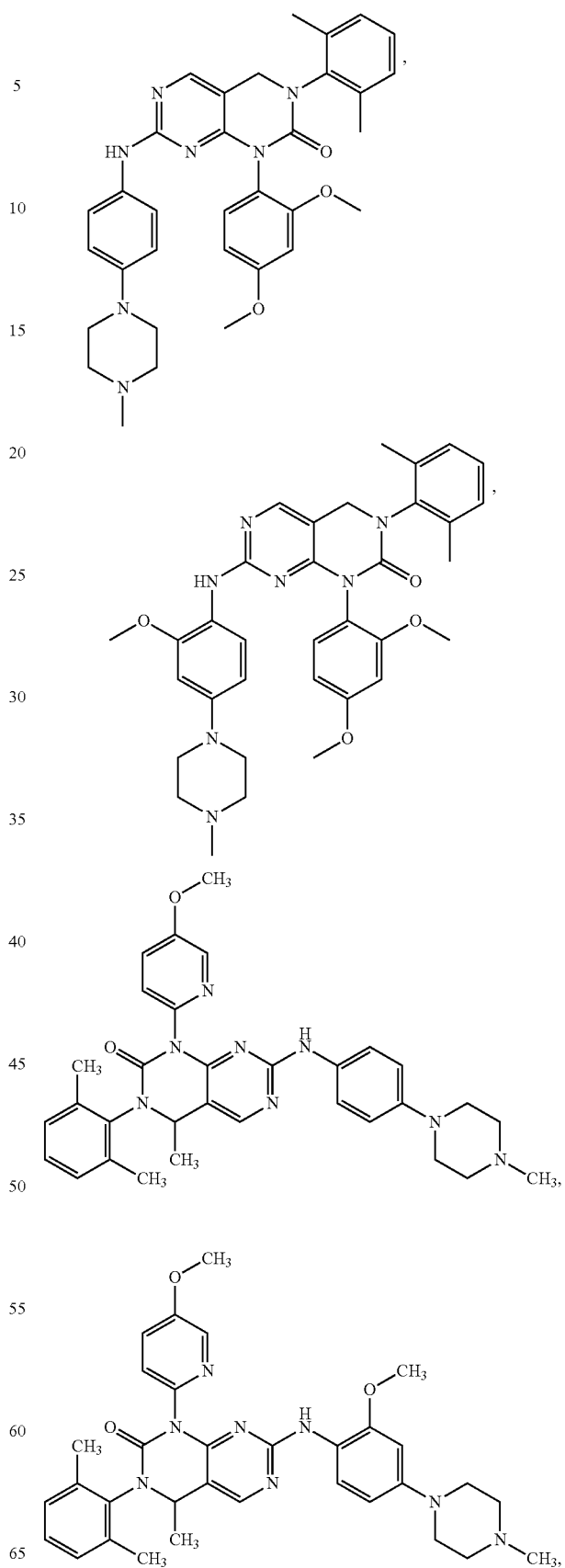

327
-continued
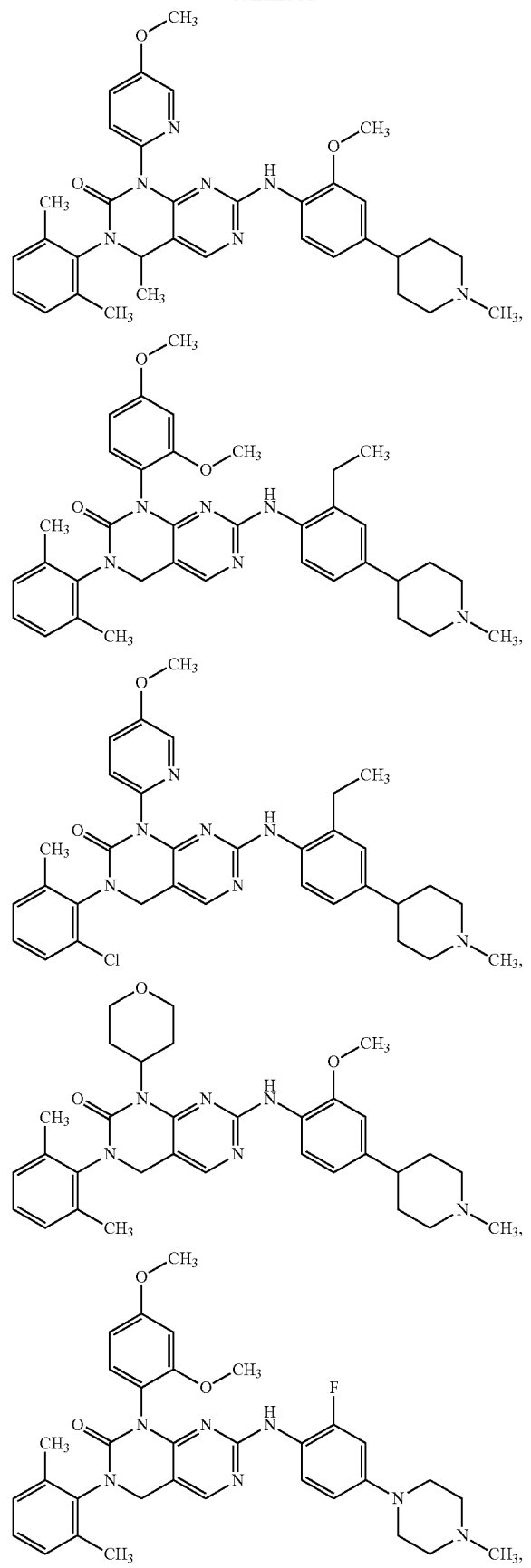
328
-continued
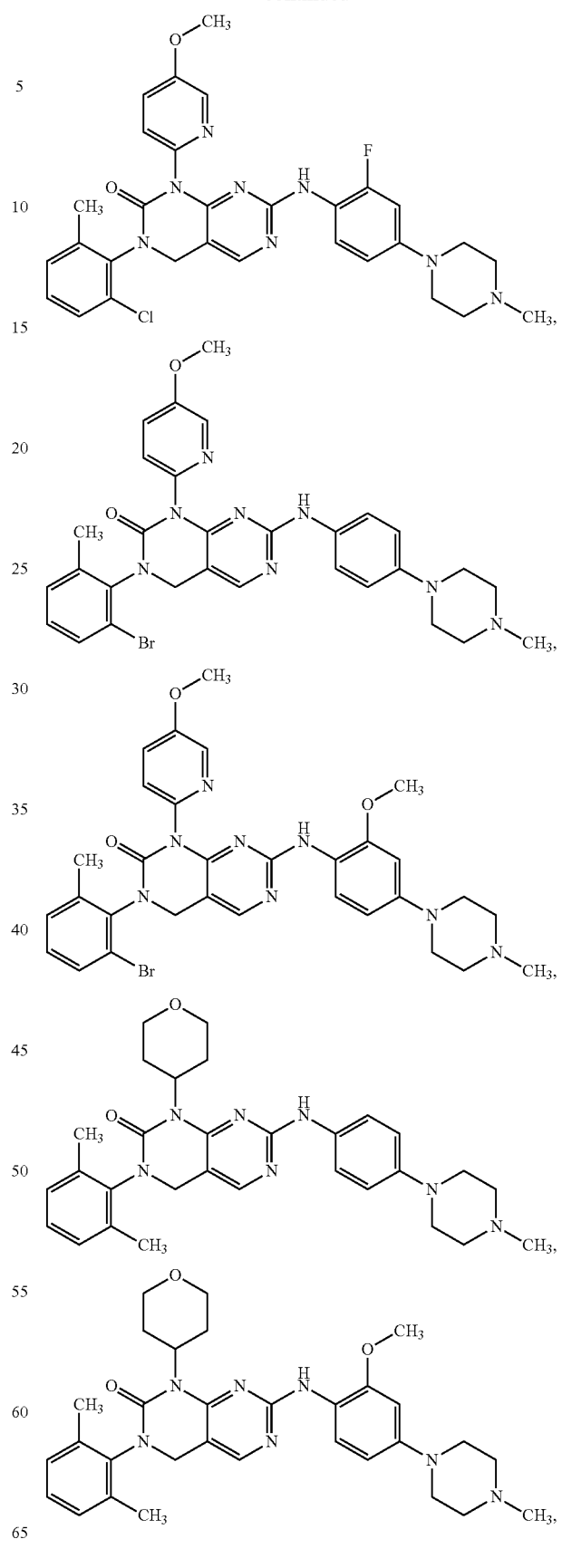

329
-continued
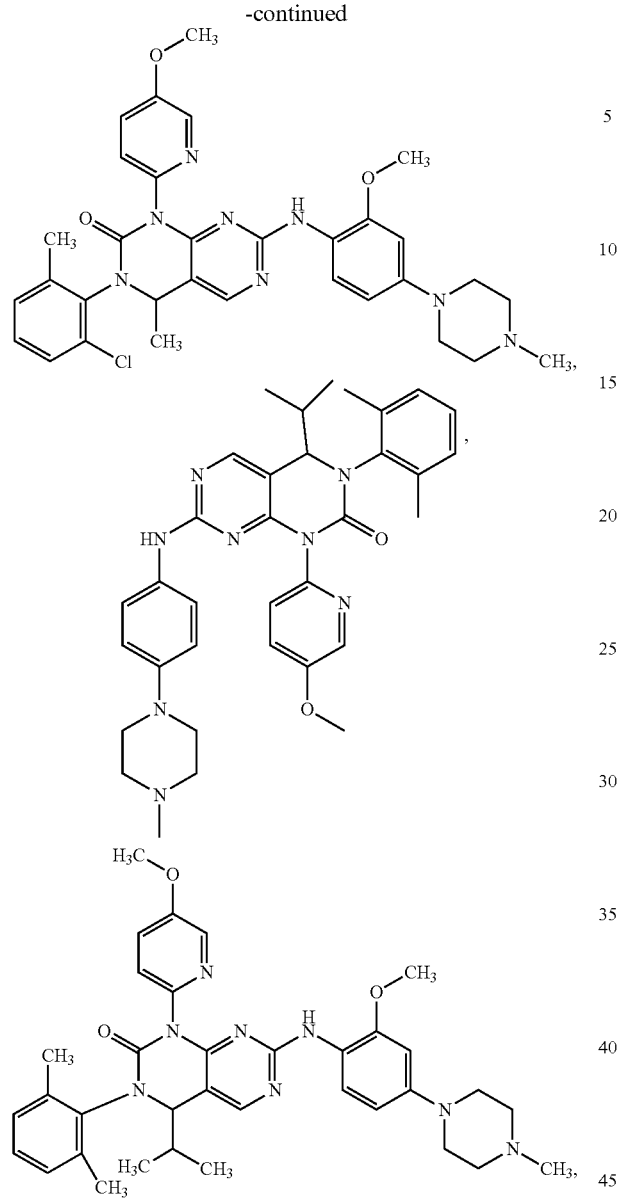
330
-continued
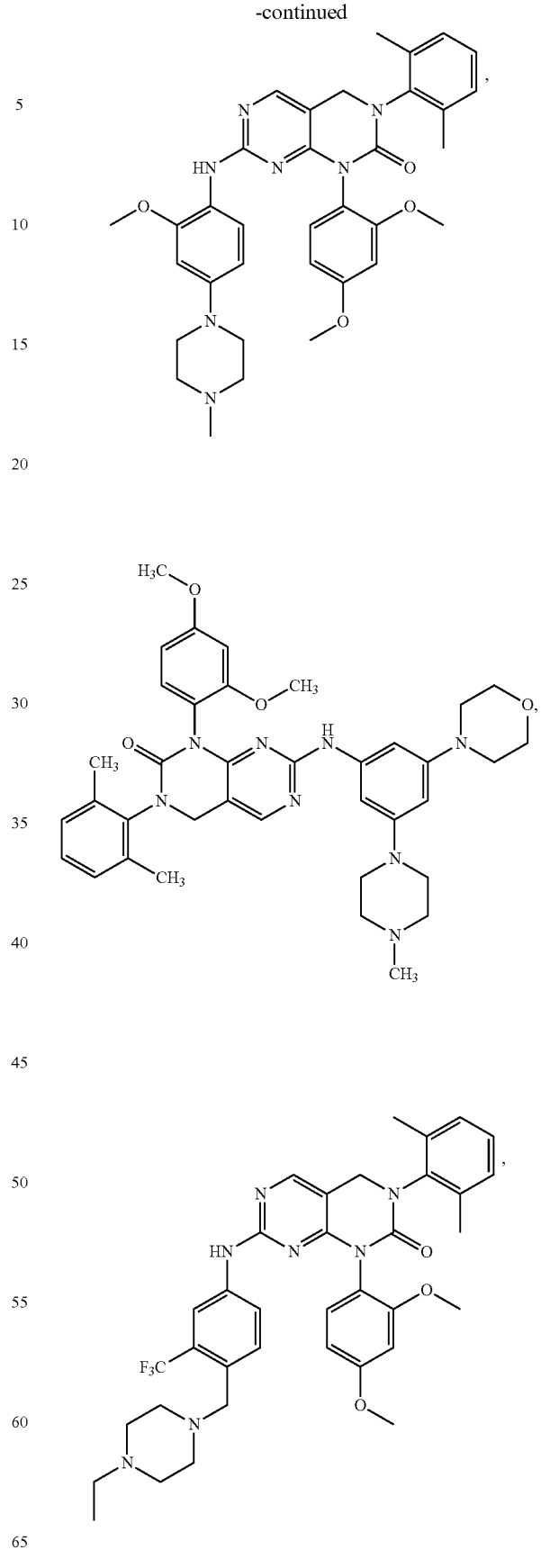

331
-continued
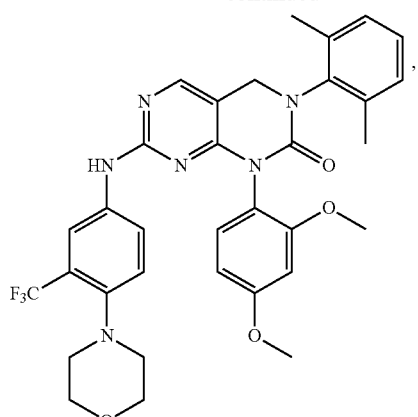
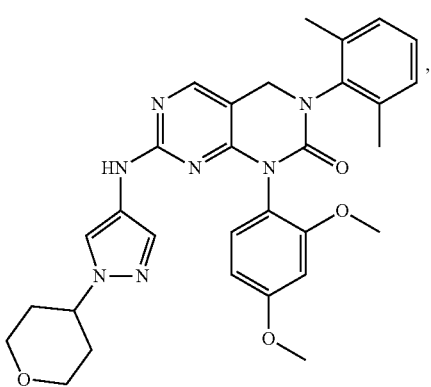
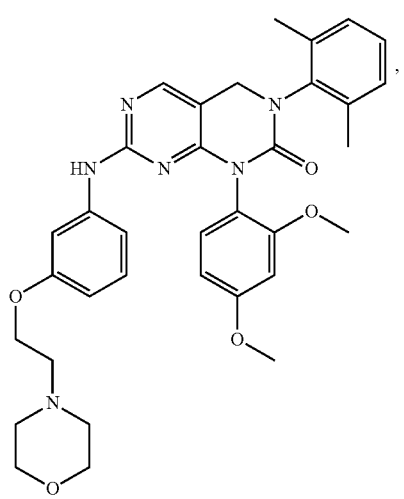
332
-continued
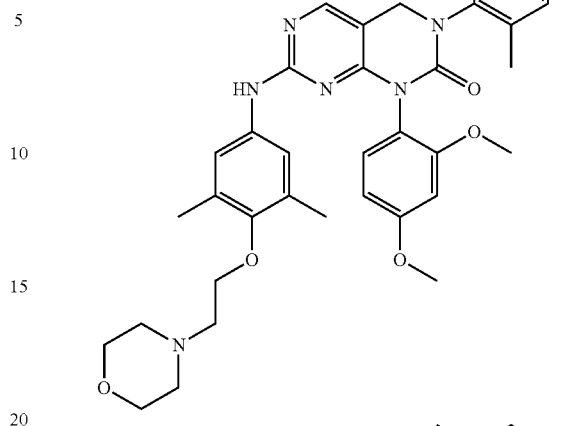
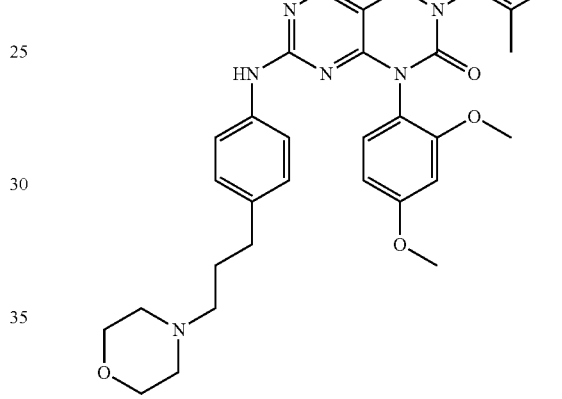
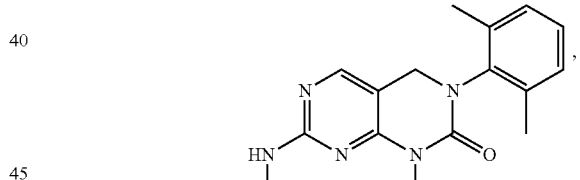
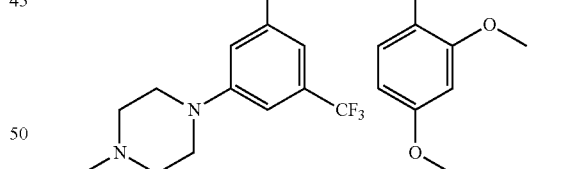
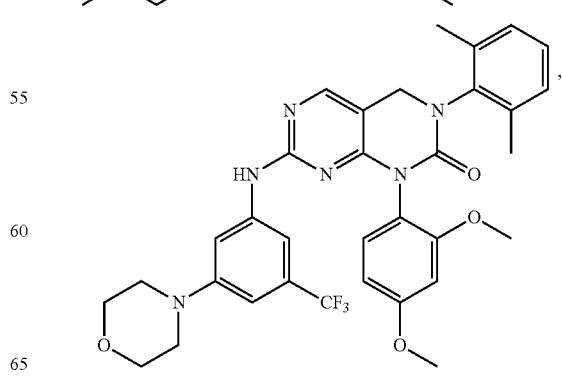

333
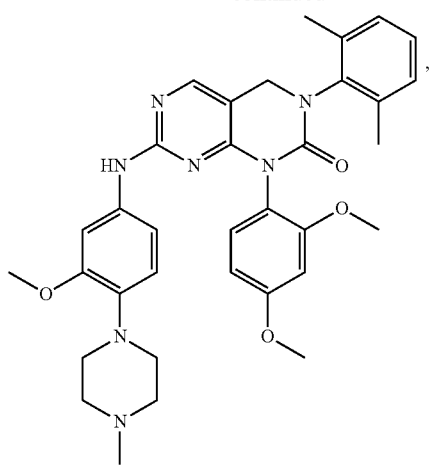
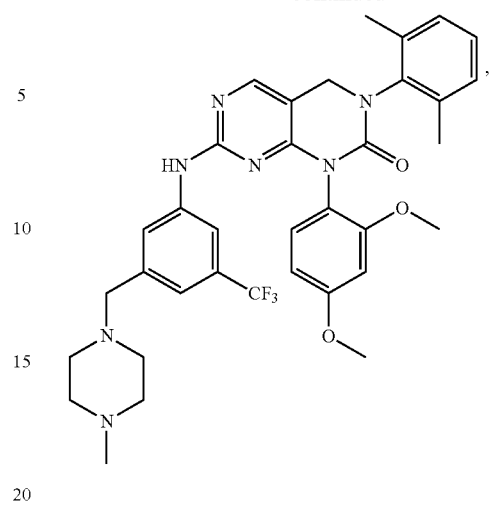
334
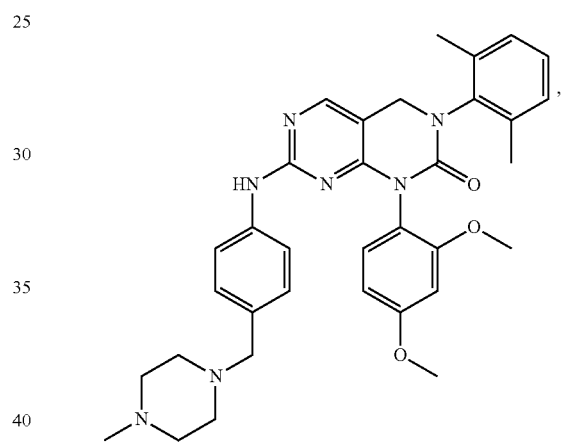
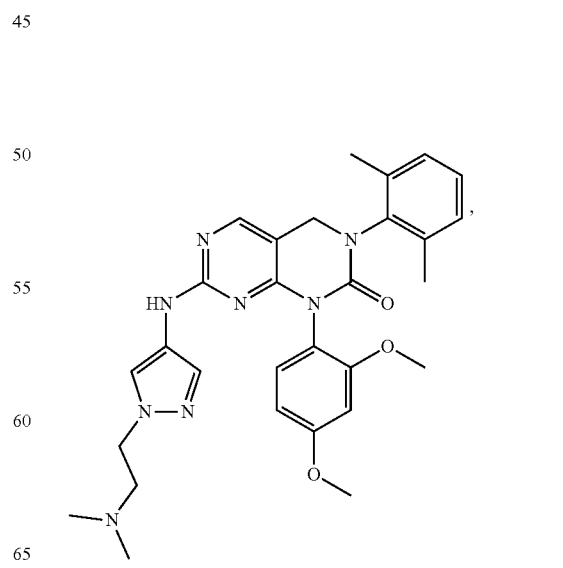

335
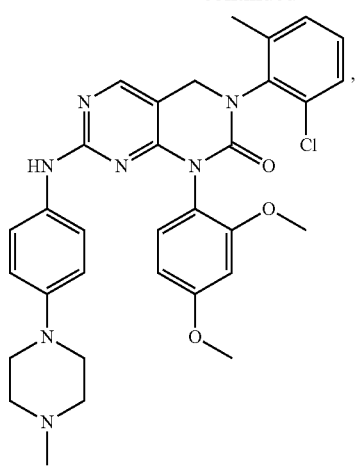
336
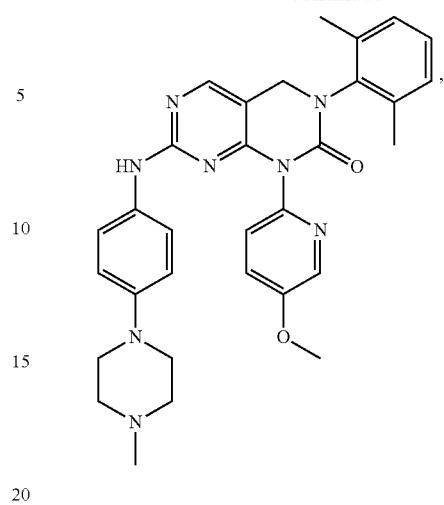
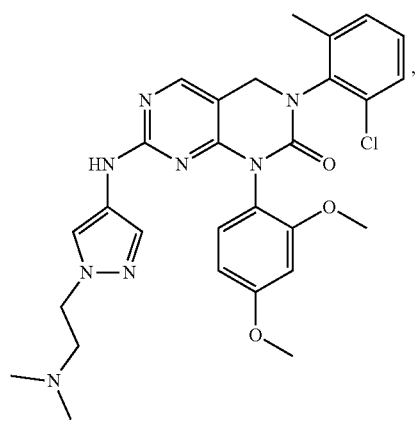
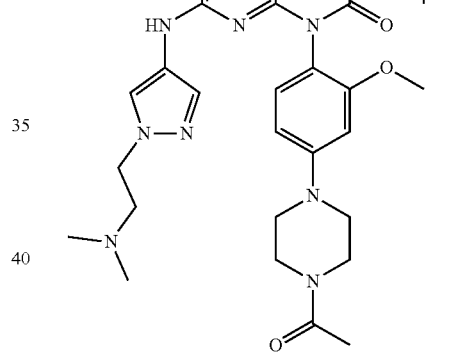
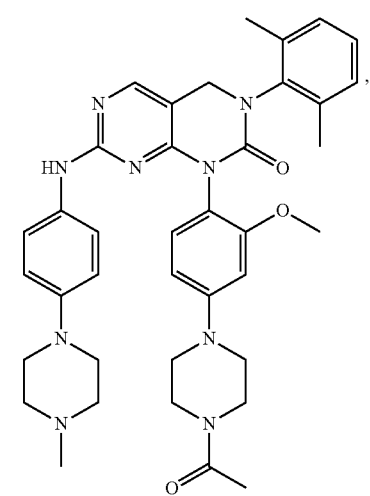
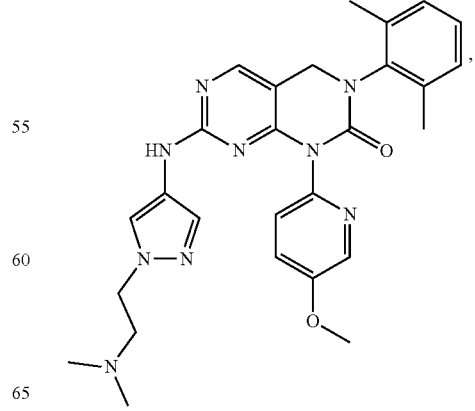

337
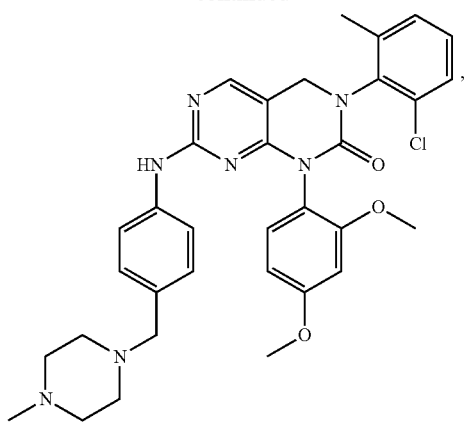
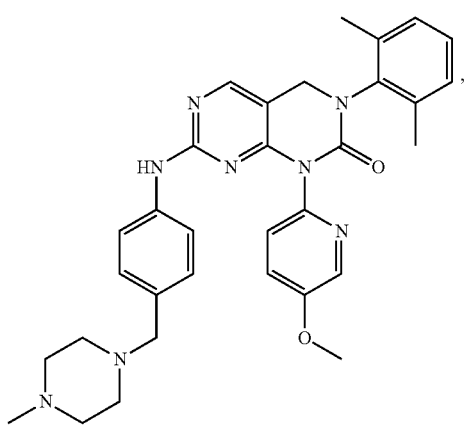
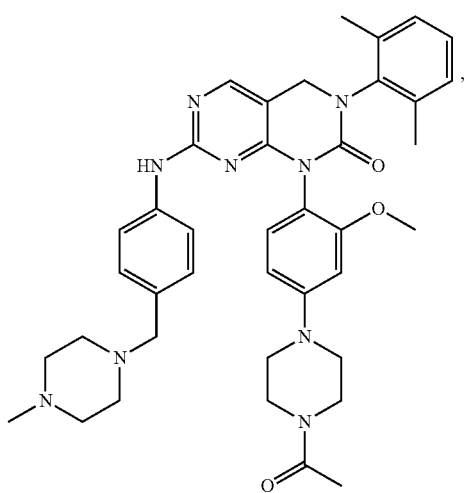
338
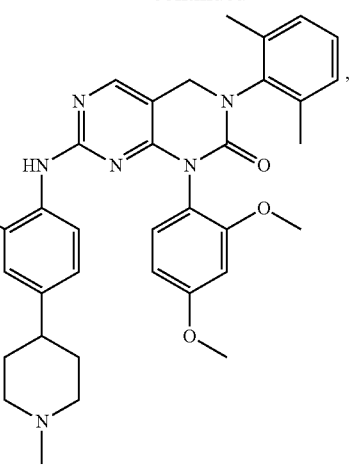
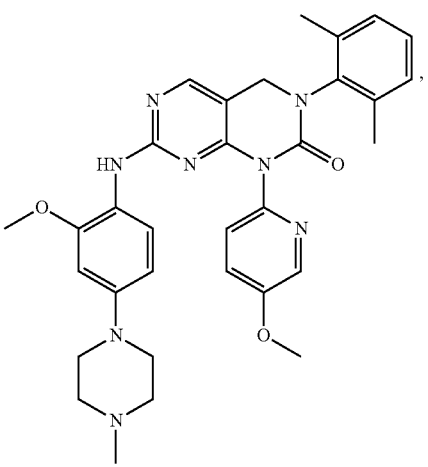
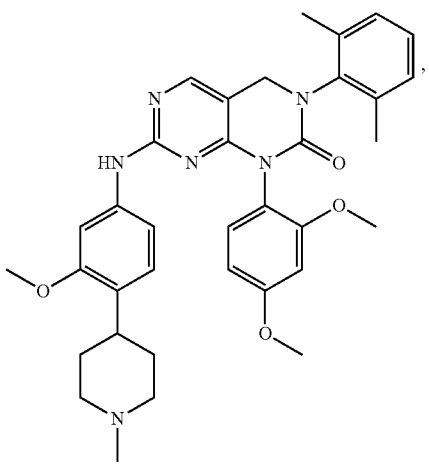

339
-continued
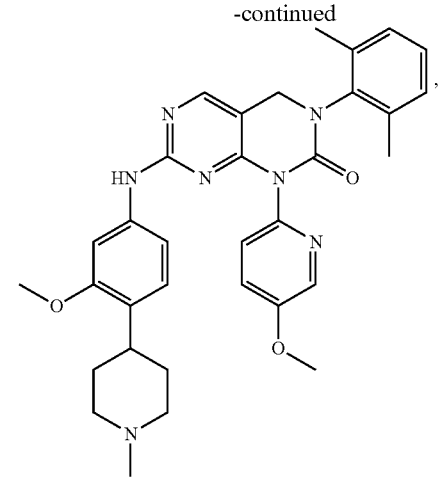
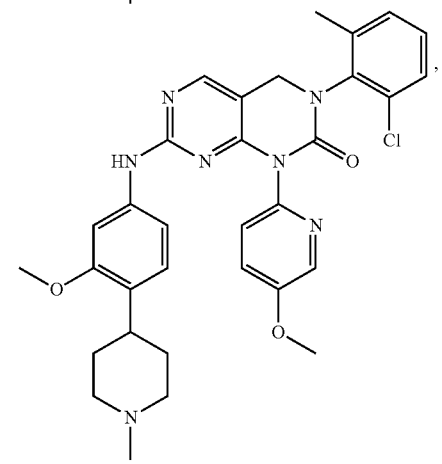
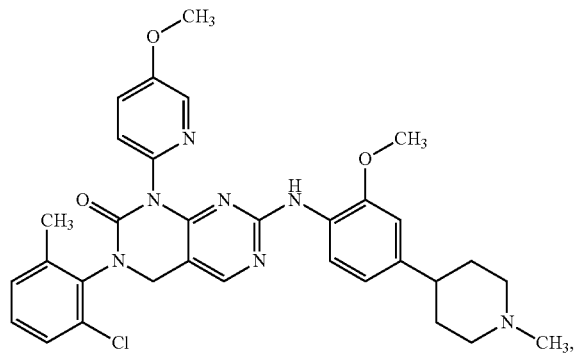
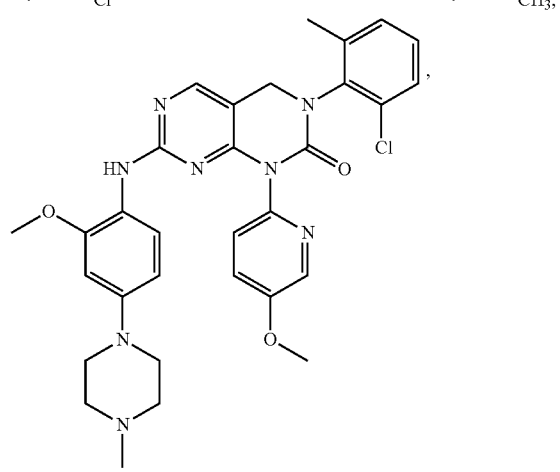
340
-continued
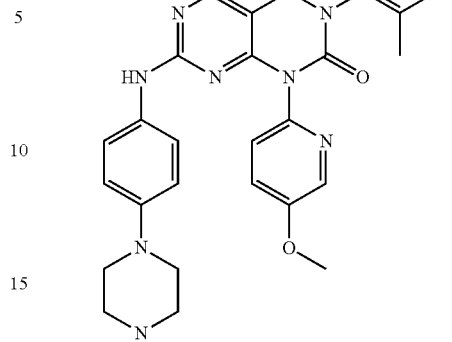
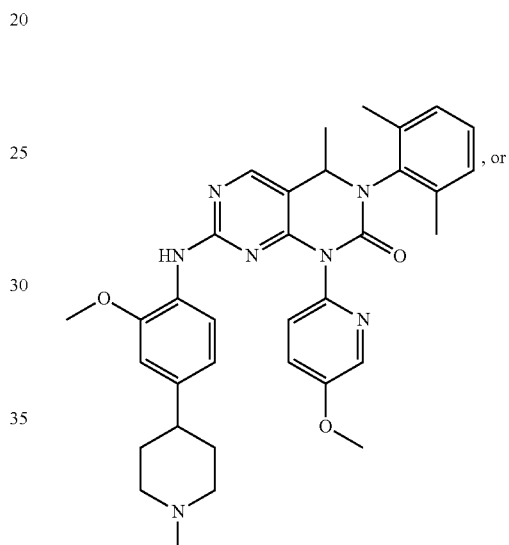
, or
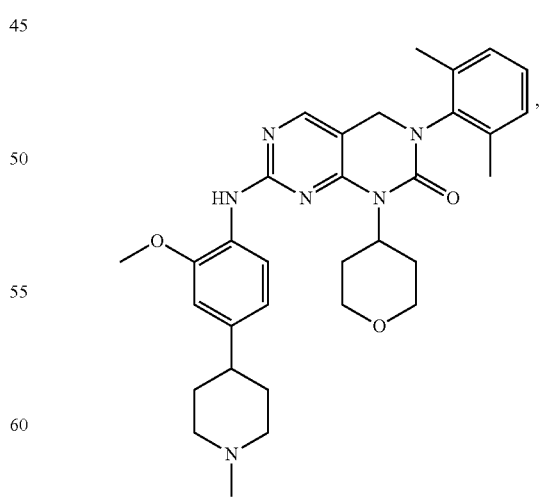
or a pharmaceutically acceptable salt thereof.
25. The method of claim 1, wherein the compound is of the formula:

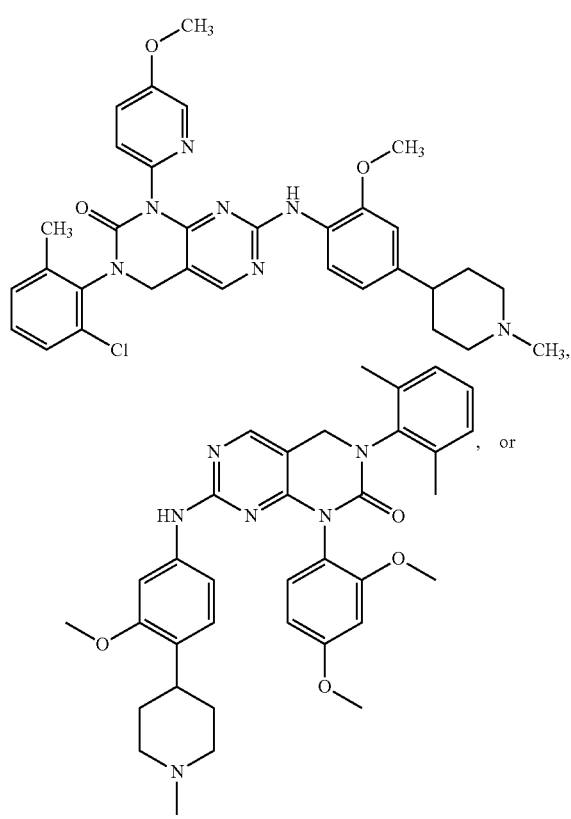
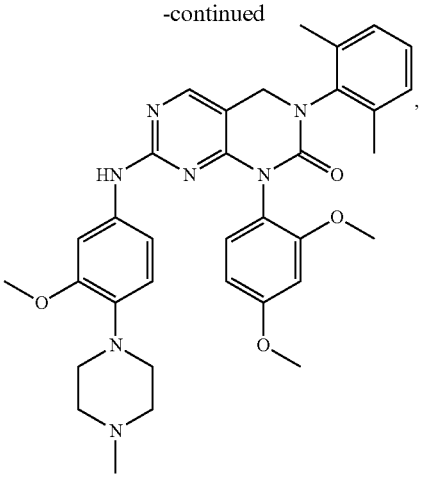
or a pharmaceutically acceptable salt thereof.
26. The method of claim 1 comprising administering to the subject in need thereof a therapeutically effective amount of a compound of Formula (I), or a pharmaceutically acceptable salt thereof.
27. The method of claim 1, wherein the subject is a human.
* * * * *

UNITED STATES PATENT AND TRADEMARK OFFICE
CERTIFICATE OF CORRECTION

| | | |
|---|---|---|
| PATENT NO. | : 11,241,435 B2 | Page 1 of 3 |
| APPLICATION NO. | : 16/333546 | |
| DATED | : February 8, 2022 | |
| INVENTOR(S) | : Marc Wein et al. | |

It is certified that error appears in the above-identified patent and that said Letters Patent is hereby corrected as shown below:

In the Claims

In Claim 1, at Column 299, Lines 57-65, the formula:

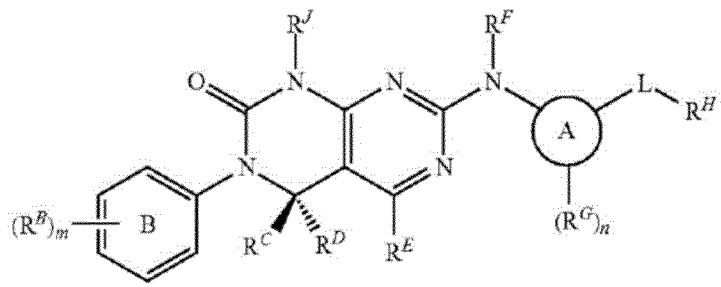

Should be replaced with the formula:

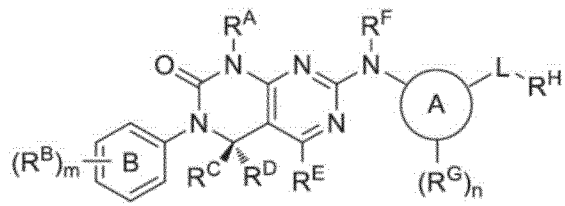

.

Signed and Sealed this
Fifth Day of July, 2022

Katherine Kelly Vidal
*Director of the United States Patent and Trademark Office*

In Claim 24, at Column 320, Lines 1-20, the formula:
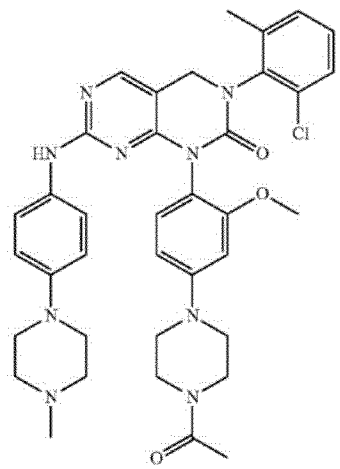
Should be replaced with the formula:
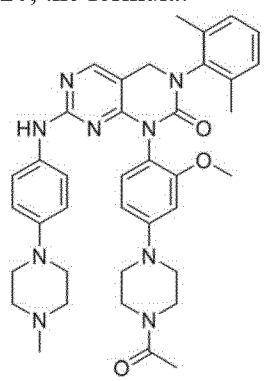
In Claim 24, at Column 323, Line 47, the text "(YKL-04-108)" should be removed.
In Claim 24, at Column 329, Lines 15-32, the formula:
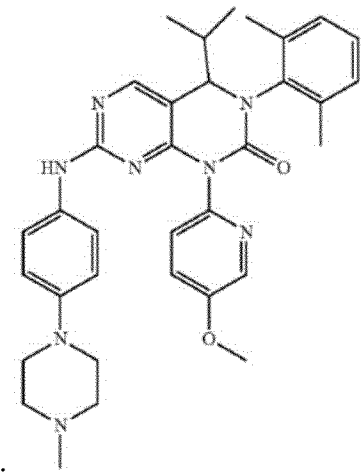

CERTIFICATE OF CORRECTION (continued)
U.S. Pat. No. 11,241,435 B2

Page 3 of 3

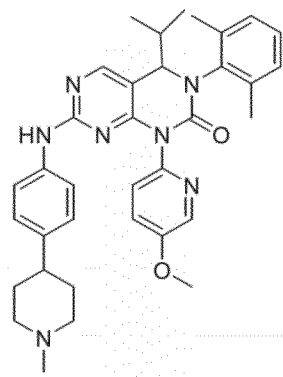

Should be replaced with the formula: